US011491220B2

(12) United States Patent
Geurtsen et al.

(10) Patent No.: US 11,491,220 B2
(45) Date of Patent: Nov. 8, 2022

(54) **METHODS OF PRODUCING BIOCONJUGATES OF *E. COLI* O-ANTIGEN POLYSACCHARIDES, COMPOSITIONS THEREOF, AND METHODS OF USE THEREOF**

(71) Applicants: Janssen Pharmaceuticals, Inc., Titusville, NJ (US); GlaxoSmithKline Biologicals S.A., Rixensart (BE)

(72) Inventors: Jeroen Geurtsen, Vleuten (NL); Pieter Jan Burghout, Pijnacker (NL); Eveline Marleen Weerdenburg, Uithoorn (NL); Jan Theunis Poolman, Haarlem (NL); Kellen Cristhina Fae, Oegstgeest (NL); Patricia Ibarra Yon, Solothurn (CH); Darren Robert Abbanat, Cornwal, NY (US); Stefan Jochen Kemmler, Zurich (CH); Michael Thomas Kowarik, Zurich (CH); Manuela Mally, Watt (CH); Veronica Gambillara Fonck, Meilen (CH); Martin Edward Braun, Cham (CH); Maria Paula Carranza Sandmeier, Rudolfstetten (CH)

(73) Assignees: Janssen Pharmaceuticals, Inc., Titusville, NJ (US); GlaxoSmithKline Biologal S.A.

( * ) Notice: Subject to any disclaimer, the term of this patent is extended or adjusted under 35 U.S.C. 154(b) by 0 days.

(21) Appl. No.: 16/822,403

(22) Filed: Mar. 18, 2020

(65) Prior Publication Data

US 2020/0353073 A1 Nov. 12, 2020

Related U.S. Application Data

(60) Provisional application No. 62/819,762, filed on Mar. 18, 2019.

(51) Int. Cl.

| | |
|---|---|
| ***A61K 39/095*** | (2006.01) |
| ***A61K 39/085*** | (2006.01) |
| ***A61K 39/102*** | (2006.01) |
| ***A61K 39/104*** | (2006.01) |
| ***A61K 39/09*** | (2006.01) |
| ***A61K 39/02*** | (2006.01) |
| ***A61K 47/64*** | (2017.01) |
| ***A61K 39/00*** | (2006.01) |
| ***A61K 39/385*** | (2006.01) |
| ***A61K 39/108*** | (2006.01) |

(52) U.S. Cl.

CPC ........ *A61K 39/385* (2013.01); *A61K 39/0258* (2013.01); *A61K 39/085* (2013.01); *A61K 39/092* (2013.01); *A61K 39/095* (2013.01); *A61K 39/102* (2013.01); *A61K 39/104* (2013.01); *A61K 39/107* (2013.01); *A61K 47/646* (2017.08); *A61K 2039/6037* (2013.01); *A61K 2039/62* (2013.01)

(58) Field of Classification Search

None

See application file for complete search history.

(56) References Cited

U.S. PATENT DOCUMENTS

| | | | |
|---|---|---|---|
| 3,700,612 | A | 10/1972 | Fath |
| 5,057,540 | A | 10/1991 | Kensil |
| 5,370,872 | A | 12/1994 | Cryz |
| 9,700,612 | B2 | 7/2017 | Kowarik |
| 10,150,952 | B2 | 12/2018 | Haas |
| 10,159,751 | B2 | 12/2018 | Labovitiadi |
| 10,441,647 | B2 | 10/2019 | Kowarik et al. |
| 10,525,145 | B2 | 1/2020 | Labovitiadi et al. |
| 10,577,592 | B2 | 3/2020 | Haas |
| 10,583,185 | B2 | 3/2020 | Poolman et al. |
| 10,844,098 | B2 | 11/2020 | Wu et al. |
| 10,940,192 | B2 | 3/2021 | Kowarik et al. |
| 11,015,177 | B2 | 5/2021 | Haas |
| 11,033,633 | B2 | 6/2021 | Labovitiadi et al. |
| 2014/0038296 | A1 | 2/2014 | Palsson |
| 2015/0238588 | A1 | 8/2015 | Kowarik |
| 2018/0002679 | A1 | 1/2018 | Haas |
| 2019/0078064 | A1 | 3/2019 | Haas |

(Continued)

FOREIGN PATENT DOCUMENTS

| | | |
|---|---|---|
| CN | 101983070 | 3/2011 |
| GB | 2220211 | 1/1990 |

(Continued)

OTHER PUBLICATIONS

Van Den Dobbelsteen et al.,"Immunogenicity and safety of tetravalent *Escherichia coli* O-antigen bioconjugate vaccine in animal models," Vaccine, vol. 34, No. 35, pp. 4152-4160 (2016).

(Continued)

*Primary Examiner* — Sarvamangala Devi

(74) *Attorney, Agent, or Firm* — Ice Miller LLP

(57) ABSTRACT

Methods of producing bioconjugates of O-antigen polysaccharides covalently linked to a carrier protein using recombinant host cells are provided. The recombinant host cells used in the methods described herein encode a particular oligosaccharyl transferase enzyme depending on the O-antigen polysaccharide bioconjugate to be produced. The oligosaccharyl transferase enzymes can be PglB oligosaccharyl transferase or variants thereof. Also provided are compositions containing the bioconjugates, and methods of using the bioconjugates and compositions described herein to vaccinate a subject against extra-intestinal pathogenic *E. coli*. (ExPEC).

6 Claims, 12 Drawing Sheets

Specification includes a Sequence Listing.

(56) References Cited

U.S. PATENT DOCUMENTS

| | | | |
|---|---|---|---|
| 2020/0181586 A1 | 6/2020 | Haas |
| 2020/0316184 A1 | 10/2020 | Geurtsen et al. |
| 2021/0004617 A1 | 1/2021 | Gouraud et al. |
| 2021/0154286 A1 | 5/2021 | Kowarik et al. |
| 2022/0088165 A1 | 3/2022 | Poolman et al. |

FOREIGN PATENT DOCUMENTS

| | | | |
|---|---|---|---|
| GB | 2220211 A | 1/1990 |
| JP | 2011514155 | 5/2011 |
| JP | 2017507178 | 3/2017 |
| WO | 2003074687 A1 | 9/2003 |
| WO | 2006119987 A2 | 11/2006 |
| WO | 2007109812 A2 | 9/2007 |
| WO | 2007109813 A1 | 9/2007 |
| WO | 2009089396 A2 | 7/2009 |
| WO | 2009104074 A2 | 8/2009 |
| WO | 2011062615 | 5/2011 |
| WO | 2012078482 A1 | 6/2012 |
| WO | 2013034664 A1 | 3/2013 |
| WO | 2014037585 A1 | 3/2014 |
| WO | 2014057109 A1 | 4/2014 |
| WO | 2014102265 A1 | 7/2014 |
| WO | 2014111516 A1 | 7/2014 |
| WO | 2015052344 | 4/2015 |
| WO | 2015/082571 | 6/2015 |
| WO | 2015/124769 | 8/2015 |
| WO | 2015117711 A1 | 8/2015 |
| WO | 2015124769 A1 | 8/2015 |
| WO | 2015/158403 | 10/2015 |
| WO | 2016/082597 | 6/2016 |
| WO | 2016107818 A1 | 7/2016 |
| WO | 2016107819 A1 | 7/2016 |
| WO | 2017035181 A1 | 3/2017 |
| WO | 2017/067964 | 4/2017 |
| WO | 2017/216286 | 12/2017 |
| WO | 2018/077853 | 5/2018 |

OTHER PUBLICATIONS

Cryz Jr. et al., "Synthesis and Characterization of *Escherichia coli* O18 O-Polysaccharide Conjugate Vaccines," Infection and Immunity, vol. 58, No. 2, pp. 373-377 (1990).

Ihssen et al., "Production of glycoprotein vaccines in *Escherichia coli*," Microbial Cell Factories, vol. 9, No. 61, pp. 1-13 (2010).

Poolman et al., "Extraintestinal Pathogenic *Escherichia coli*, a Common Human Pathogen: Challenges for Vaccine Development and Progress in the Field," Journal of Infectious Diseases, vol. 213, pp. 6-13 (2016).

Jiang et al., "Tungsten-Induced Protein Aggregation: Solution Behavior," Wiley InterScience, vol. 98, No. 12, pp. 4695-4710 (2009).

Seidl et al., "Tungsten-Induced Denaturation and Aggregation of Epoetin Alfa During Primary Packaging as a Cause of Immunogenicity," Pharm. Res., vol. 29, pp. 1454-1467 (2012).

"Typhoid Vi Polysaccharide Vaccine Typhim VI," Sanofi Pasteur Inc., vol. 3., pp. 1-26 (Mar. 2014).

Stenutz R et al., "The structures of *Escherichia coli* O-polysaccharide antigens.", FEMS Microbiol Rev. May 2006;30(3):382-403.

V. Szijarto et al., "Diagnostic Potential of Monoclonal Antibodies Specific to the Unique O-Antigen of Multidrug-Resistant Epidemic *Escherichia coli* Clone ST131-025b:H4", Clinical and Vaccine Immunology, (Apr. 30, 2014), vol. 21, No. 7, doi:10.1128/CVI.00685-13, ISSN 1556-6811, pp. 930-939, XP055179667.

Rogers B.A. et al., "*Escherichia coli* O25b-ST131: a pandemic, multiresistant, community-associated strain", Journal of Antimicrobial Chemotherapy, 2011, vol. 66, No. 1, pp. 1-14.

Pitout et al., "Extraintestinal Pathogenic *Escherichia Coli*: An Update on Antimicrobial Resistance, Laboratory Diagnosis and Treatment," Expert Rev. Anti. Infect. Then, vol. 10, No. 10, pp. 1165-1176 (2012).

Mario F Feldman et al., "Engineering N-linked protein glycosylation with diverse O antigen lipopolysaccharide structures in *Escherichia coli*", Proceedings of the National Academy of Sciences, vol. 102, No. 8, pp. 3016-3021, (Feb. 9, 2005).

Fratamico et al., "*Escherichia coli* serogroup O2 and O28ac O-antigen gene cluster sequences and detection of pathogenic *Escherichia coil* O2 and O28ac by PCR," Canadian Journal of Microbiology, vol. 56, No. 4, pp. 308-316 (2010).

Jann et al., "Structural Comparison of the O6 Specific Polysaccharides From *Escherichia coli* O6:K2:H1, *Escherichia coli* O6:K13:H1, and *Escherichia coli* O6:K54:H10," Carbohydrate Research, vol. 263, No. 2, pp. 217-225 (1994).

Jansson et al., "Structural studies of the *Escherichia coli* O-antigen 6," Carbohydrate Research, vol. 131, No. 2, pp. 277-283 (1984).

Wacker et al., "N-linked glycosylation in Campylobacter jejuni and its functional transfer into *Escherichia coli*," Science, vol. 298, No. 5599, pp. 1790-1793 (2002).

Debroy et al., "Detection of O antigens in *Escherichia coli*," Animal Health Research Reviews, vol. 12, No. 2, pp. 169-185 (2011).

Datsenko et al., "One-step inactivation of chromosomal genes in *Escherichia coli* K-12 using PCR products," PNAS, vol. 97, No. 12, pp. 6640-6645 (2000).

Blanco et al., "Virulence factors and O groups of *Escherichia coli* isolates from patients with acute pyelonephritis, cystitis and asymptomatic bacteriuria," Eur. J. Epidemiol., vol. 12, No. 2, pp. 191-198 (1996).

Molina-Lopez et al., "Drug resistance, serotypes, and phylogenetic groups among uropathogenic *Escherichia coli* including O25-ST131 in Mexico City," J Infect Dev Ctries, vol. 5, No. 12, pp. 840-849 (2011).

Terai et al., "*Escherichia coli* Virulence Factors and Serotypes in Acute Bacterial Prostatitis," Int. Journal of Urology, vol. 4, No. 3, pp. 289-294 (1997).

Kenne et al., "Structural studies of the *Escherichia coli* O-antigen 25," Carbohydrate Research, vol. 122, No. 2, pp. 249-256 (1983).

Fundin et al., "NMR analysis of the O-antigen polysaccharide from *Escherichia coli* strain F171," Magnetic Resonance in Chemistry, vol. 41, No. 3, pp. 202-205 (2003).

Johnson et al., "*Escherichia coli* sequence type ST131 as an emerging fluoroquinolone-resistant uropathogen among renal transplant recipients," Antimicrob Agents Chemother. vol. 54, No. 1, pp. 546-550 (2010).

Banerjee et al., "A new clone sweeps clean: the enigmatic emergence of *Escherichia coli* sequence type 131," Antimicrob Agents Chemother. vol. 58, No. 9, pp. 4997-5004 (2014).

Lukac et al., "Toxoid of Pseudomonas aeruginosa exotoxin A generated by deletion of an active-site residue," Infect Immun, vol. 56, No. 12, pp. 3095-3098 (1988).

Szijarto et al. "The rapidly emerging ESBL-producing *Escherichia coil* O25-ST131 clone carries LPS core synthesis genes of the K-12 type," FEMS Microbiol. Lett., vol. 332, pp. 131-136 (2012).

Clermont et al.,"The CTX-M-15-producing *Escherichia coli* diffusing clone belongs to a highly virulent B2 phylogenetic subgroup," J. Antimicrob. Chemother., vol. 61, No. 5, pp. 1024-1028 (2008).

Blanco et al.,"Molecular epidemiology of *Escherichia coli* producing extended-spectrum {beta}-lactamases in Lugo (Spain): dissemination of clone O25b:H4-ST131 producing CTX-M-15," J. Antimicrob. Chemother., vol. 63, pp. 1135-1141 (2009).

Phan et al., "The serum resistome of a globally disseminated multidrug resistant uropathogenic *Escherichia coil* clone," PLOS Genetics, vol. 9, No. 10, pp. 1-18 (2013).

Stevenson et al., "Structure of the O antigen of *Escherichia coli* K-12 and the sequence of its rfb gene cluster," J. Bacteriol., vol. 176, No. 13, pp. 4144-4156 (1994).

Amor et al., "Distribution of core oligosaccharide types in lipopolysaccharides from *Escherichia coli*," Infect. Immun., vol. 68, No. 3, pp. 1116-1124 (2000).

Jansson et al., "Structural studies of the O-specific side-chains of the *Escherichia coli* O2 lipopolysaccharide," Carbohydrate Res., vol. 161, pp. 273-279 (1987).

A. Cross et al., "Safety And Immunogenicity Of A Polyvalent *Escherichia coli* Vaccine In Human Volunteers", Journal of Infec-

(56) References Cited

OTHER PUBLICATIONS tious Diseases. JID, Chicago, IL., (Oct. 1, 1994), vol. 170, No. 4, doi:10.1093/infdis/170.4.834, ISSN 0022-1899, pp. 834-840, XP055311603.
Cryz S J et al., "Synthesis and characterization of a polyvalent *Escherichia coli* O-polysaccharide-toxin A conjugate vaccine", Vaccine, Elsevier Ltd, GB, (Jan. 1, 1995), vol. 13, No. 5, doi:10.1016/0264-4108X(94)00009-C, ISSN 0264-41 OX, pp. 449-453, XP004057719.
Int'l Search Report and Written Opinion dated Jun. 15, 2015 in Int'l Application No. PCT/EP2015/053739.
Int'l Search Report and Written Opinion dated Oct. 27, 2016 in Int'l Application No. PCT/US2016/048278.
Jadhav et al., "Virulence characteristics and genetic affinities of multiple drug resistant uropathogenic *Escherichia coli* from a Semi Urban Locality in India," PLOS One, vol. 6, No. 3, (2011).
Mora et al, "Emergence of clonal groups O1:HNM-D-ST59, O15:H1-D-ST393, O20:H34/HNM-D-ST354, O25b:H4-B2-ST131 and ONT:H21,42-B1-ST101 among CTX-M-14-producing *Escherichia coli* clinical isolates in Galicia, northwest Spain," International J. of Antimicrob. Agents, vol. 37, No. 1, pp. 16-21 (2011).
Clermont et al., "Rapid Detection of the O25b-ST131 clone of *Escherichia coil* encompassing the CTX-M-15- producing strains," Journal of Antimicrobial Chemotherapy, vol. 64, No. 2, pp. 274-277 (2009).
Glover et al., "Chemoenzymatic synthesis of Glycopeptides with PglB, a bacterial oligosaccharyl transferase from Campylobacter jejuni," Chemistry and Biology, Current Biology, vol. 12, No. 12, pp. 1311-1316 (2005).
Laurentin et al., "A Microtiter Modification of the anthrone-sulfuric acid colorimetric assay for glucose-based carbohydrates", Analytical Biochemistry, 315, pp. 143-145, 2003.
Russo et al., "A killed, genetically engineered derivative of a wild-type extraintestinal pathogenic *E coli* strain is a caccine candidate", Elsevier, Vaccine 25, pp. 3859-3870, 2007.
Russo et al., "Medical and Exonomic impact of extraintestinal infections due to *Escherichia coli*: focus on an Increasingly important endemic problem", Elsevier, Microbes and Infection 5, pp. 449-456, 2003.
Kohler et al., "What defines extraintestinal pathogenic *Escherichia coli*", Elsevier, International journal of Medical Microbiology 301, pp. 642-647, 2011.
Ho et al., Preclinical Laboratory Evaluation of a Bivalent *Staphylococcus aureus* Saccharide-Exotoxin A Protein Conjugate Vaccine, Human vaccines, 2:3, pp. 89-98, May/Jun. 2006.
Lipsitch, "Bacterial vaccines and Serotype Replacement: Lessons from Haemophilus Influenzae and Prospects for *Streptococcus pneumoniae*", Emerging Infectious Diseases, vol. 5, No. 3, May/Jun. 1999.
Schito et al., "The ARESC study: an international survey on the antimicrobial resistance of pathogens involved in uncomplicated urinary tract infections", Elsevier, International Journal of Antimicrobial Agents 34, pp. 407-413, 2009.
Foxman, "Epidemiology of Urinary Tract Infections: Incidence, morbidity, and Economic Costs", The American Journal of Medicine, vol. 113(1A), 5S-13S, Jul. 2002.
Johnson et al., Extraintestinal Pathogenic *Escherichi coli*: "The other bad *E coli*", J Lab Clin Med., 139(3), pp. 155-162, 2002.
Kim et al., "Efficiency of a pneumococal Opsonophagocytic Killing Assay Improved by Multiplexing and by Colloring Colonies", Clinical and Dianostic laboratory Immunology, pp. 616-621, Jul. 2003.
Int'l Search Report and Written Opinion dated Jul. 20, 2017 in Int'l Application No. PCT/US2016/048278.
Int'l Preminary Report on Patentability dated Feb. 14, 2019 in Int'l Application No. PCT/EP2017/077123.
Written Opinion dated Dec. 21, 2018 in Int'l Application No. PCT/EP2017/077123.
Written Opinion of the International Preliminary Examining Authority dated Sep. 11, 2018 in PCT/EP2017/077123.
Written opinion of the Int'l Searching Authority dated Jan. 24, 2018 in Int'l Application No. PCT/EP2017/077123.
Int'l Search Report dated Jan. 24, 2018 in Int'l Application No. PCT/EP2017/077123.
Stoute et al., "A Preliminary Evaluation of a Recombinant Circumsporozoite Protein Vaccine Against Plasmodium Falciparum Malaria," New England Journal of Medicine, vol. 336, pp. 86-91 (1997).
Extended Search Report dated Apr. 12, 2017 in EP Application No. 16195256.9.
Frenck, et al., "Safety and Immunogenicity of a vaccine for extra-intestinal pathogenic *Escherichia coli* (ESTELLA): a phase 2 randomised controlled trial," Lancet Infect. Dis. vol. 1, No. 6, pp. 631-640 (2019).
International Search Report and Written Opinion for App. No. PCT/US2020/023415, dated Jun. 12, 2020, 21 pages.
Bowie et al. (Science, 1990, 247:1306-1310).
Burgess et al. (J. Cell Biol. 111:2129-2138, 1990).
Lazar et al. (Mol. Cell. Biol., 8:1247-1252, 1988).
Abbanat et al., "Development and Qualification of an Opsonophagocytic Killing Assay To Assess Immunogenicity of a Bioconjugated *Escherichia coli*Vaccine," Clin Vaccine Immunol 24:e00123-17. https://doi.org/10.1128/CVI.00123-17.
DebRoy et al., "Comparison of O-Antigen Gene Clusters of All O-Serogroups of *Escherichia coli*and Proposal for Adopting a New Nomenclature for O-Typing," PLoS ONE 11(1): e0147434. doi:10.1371/journal.pone.0147434, 2016.
DebRoy et al., "Correction: Comparison of O-Antigen Gene Clusters of All O-Serogroups of *Escherichia coli*and Proposal for Adopting a New Nomenclature for O-Typing," PLoS ONE 11(4): e0154551. doi:10.1371/journal.pone.0154551, 2016.
Frenck et al., "Long-term Immunogenicity and Safety of ExPEC4V Vaccine Against Extraintestinal Pathogenic *Escherichia coli*Disease in Healthy Participants," Abstract 5587, ASM Microbe, 2018.
Hayashi et al., "Highly accurate genome sequences of *Escherichia coli*K-12 strains MG1655 and W3110," Molecular Systems Biology Feb. 21, 2006; doi:10.1038/msb4100049.
Huttner et al., "Safety, immunogenicity, and preliminary clinical efficacy of a vaccine against extraintestinal pathogenic *Escherichia coli*in women with a history of recurrent urinary tract infection: a randomised, single-blind, placebo-controlled phase 1b trial," 2017, Lancet Infect Dis, http://dx.doi.org/10.1016/S1473-3099(17)30108-1.
Iguchi et al., "A complete view of the genetic diversity of the *Escherichia coli*O-antigen biosynthesis gene cluster," DNA Research, 2015, 22(1), 101-107.
Ireton et al., "Adjuvants containing natural and synthetic Toll-like receptor 4 ligands," 2013, Expert Rev Vaccines 12: 793-807.
Jann et al., "Structural comparison of the 04-specific polysaccharides from *E. coli*O4:K6 and *E. coli* O4:K52," Carbohydrate Research, 248:241-250, 1993.
Jansson et al., "Structural Studies of the O-Antigen Polysaccharide of *Escherichia coli*O4," Carbohydrate Research, 134:283-291, 1984.
Pawlowski et al., "Preparation of pneumococcal capsular polysaccharide-protein conjugate vaccines utilizing new fragmentation and conjugation technologies," Vaccine 18 (2000) 1873-1885.
Poolman et al., "The history of pneumococcal conjugate vaccine development: dose selection," Expert Rev. Vaccines 12(12), 1379-1394 (2013).
Reed et al., "Key roles of adjuvants in modern vaccines," Nature Medicine, 19(12): 1597-1608, 2013.
Robbins et al., "Synthesis, characterization, and immunogenicity in mice of Shigella sonnei O-specific oligosaccharide-core-protein conjugates," PNAS, 106(19):7974-7978, 2009.
Wacker et al., "Substrate specificity of bacterial oligosaccharyltransferase suggests a common transfer mechanism for the bacterial and eukaryotic systems," PNAS, 103(18):7088-7093, 2006.
Zhu et al., "QS-21: A Potent Vaccine Adjuvant," Nat Prod Chem Res, 3(4):1000e113, 2016.
Saade et al., "Characertization of *Escherichia coli*isolates potentially covered by ExPEC4V and ExPECIOV, that were collected from post-transrectal ultrasound-guided prostate needle biopsy," Vaccine, vol. 38, No. 33, 2020, pp. 5100-5104.

Gel 1:

| Lane | Sample Name | gtrS | Amount loaded (µl) |
|---|---|---|---|
| 1 | Marker | NA | 5.0 |
| 2 | A2625 | Negative | 4.0 |
| 3 | Y1382 | Positive | 3.8 |
| 4 | stGVXN4988 | Negative | 4.2 |
| 5 | E551 | Positive | 3.9 |
| 6 | OC24784 | Negative | 4.5 |
| 7 | OC24334 | Positive | 4.1 |
| 8 | OC24787 | Negative | 4.2 |
| 9 | stGVXN4983 | Positive | 3.9 |
| 10 | OC9487 neg. control | NA | 4.1 |
| 11 | Marker | NA | 5.0 |
| 12 | EMPTY | - | - |

Gel 2:

| Lane | Sample Name | gtrS | Amount loaded (µl) |
|---|---|---|---|
| 1 | Marker | NA | 5.0 |
| 2 | stGVXN4994 | Positive | 4.0 |
| 3 | OC24788 | Negative | 4.2 |
| 4 | OC24794 | Positive | 3.9 |
| 5 | OC9487 neg. control | Reduced | 4.1 |
| 6 | Marker | NA | 5.0 |

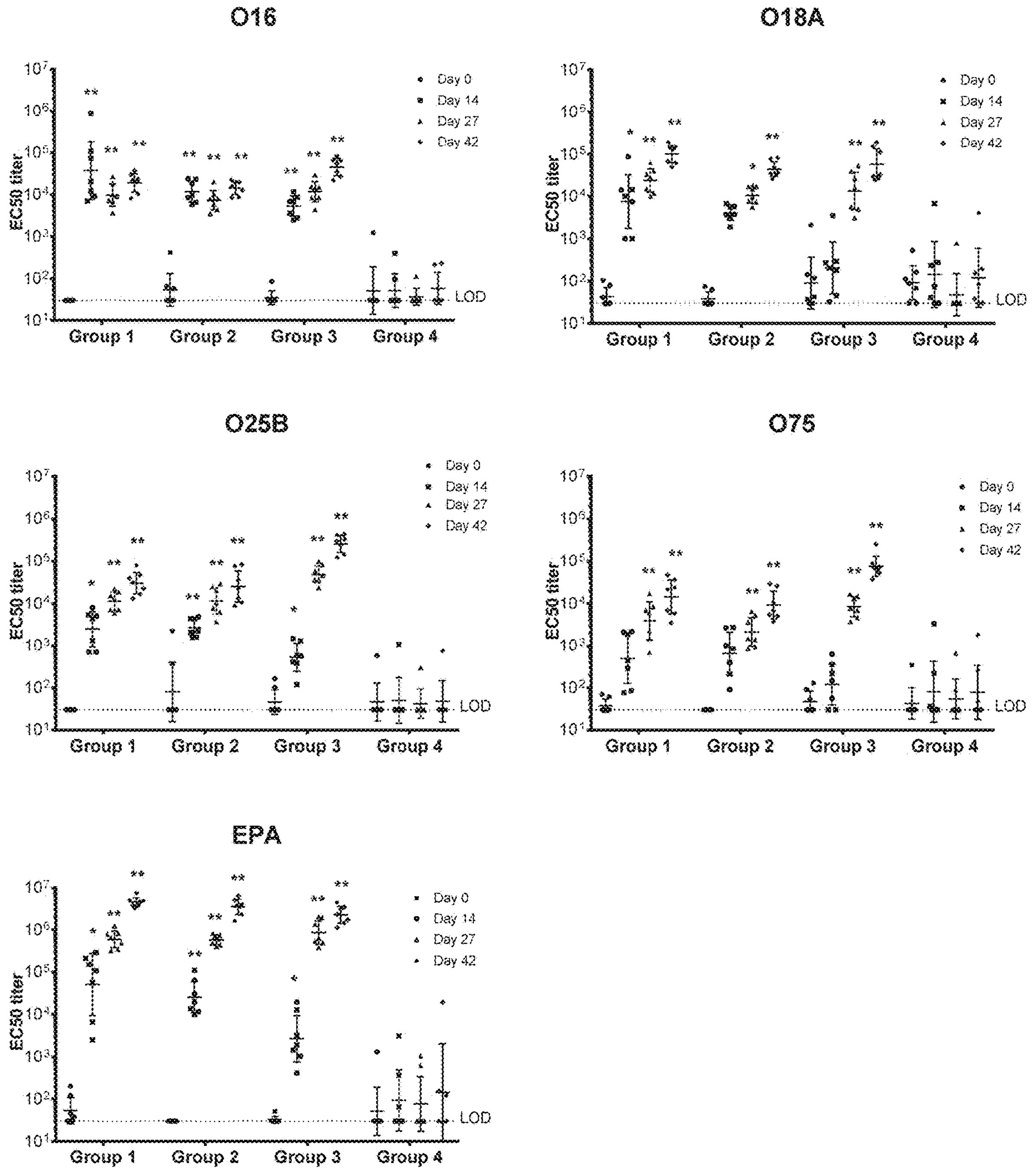
Fig. 8 - continued

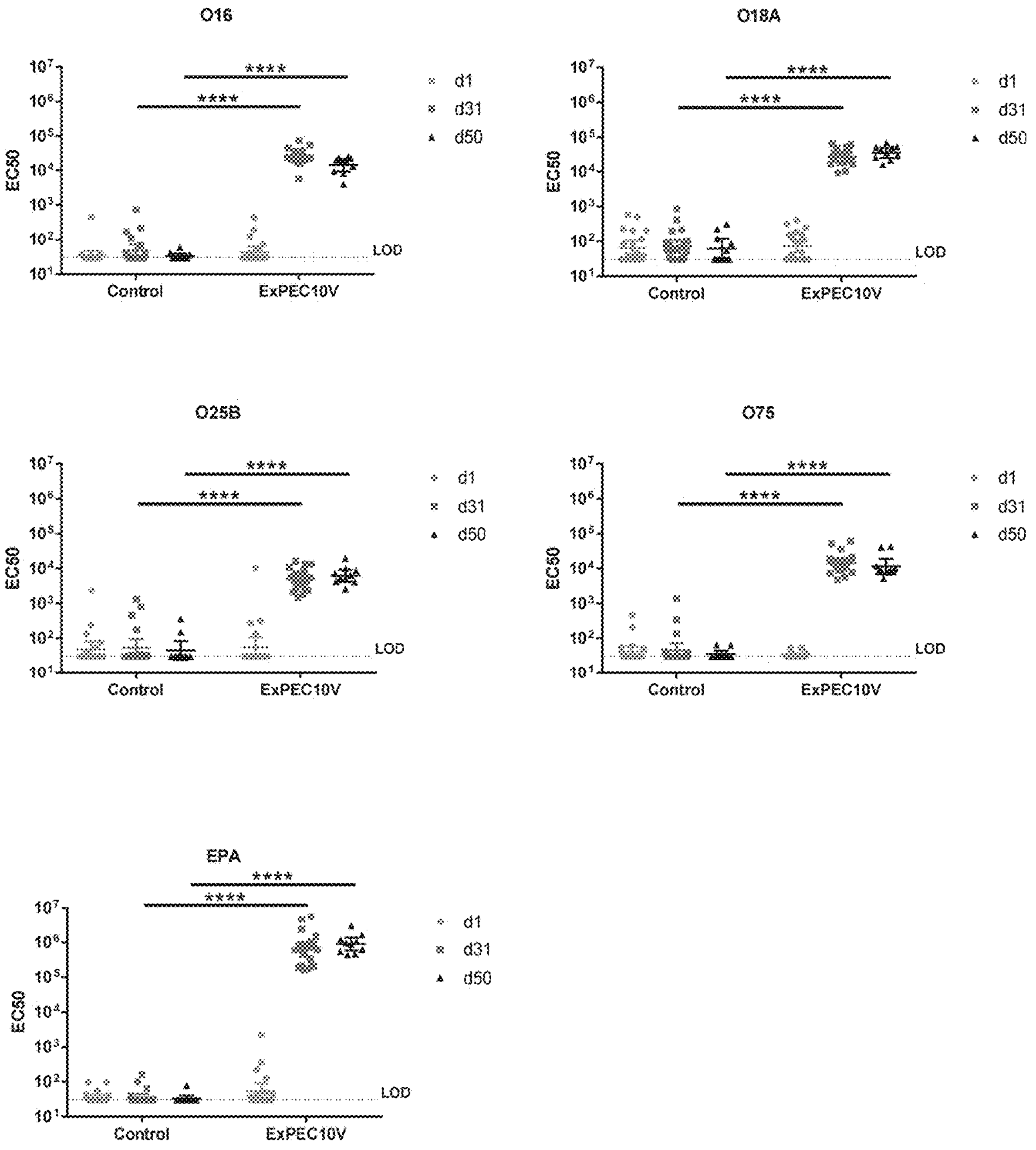
Fig. 9 - continued

METHODS OF PRODUCING BIOCONJUGATES OF *E. COLI* O-ANTIGEN POLYSACCHARIDES, COMPOSITIONS THEREOF, AND METHODS OF USE THEREOF

CROSS REFERENCE TO RELATED APPLICATION

This application claims priority to U.S. Provisional Application No. 62/819,762 filed on Mar. 18, 2019, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "004852_11653_Sequence_Listing", creation date of Mar. 18, 2020, and having a size of 199 KB. The sequence listing submitted via EFS-Web is part of the specification and is herein incorporated by reference in its entirety.

BACKGROUND OF THE INVENTION

Extraintestinal pathogenic *Escherichia coli* (ExPEC) strains are normally harmless inhabitants of the human gastrointestinal tract, alongside commensal *E. coli* strains. ExPEC isolates cannot readily be distinguished from commensal isolates by serotype, although many clonal lineages are dominated by ExPEC, as defined by O-antigen, capsule and flagellar antigen serotypes (abbreviated as O:K:H, for example O25:K1:H4). In contrast to commensal *E. coli*, ExPEC strains express a broad array of virulence factors enabling them to colonize the gastrointestinal tract, as well as to cause a wide range of extraintestinal infections, which are associated with a significant healthcare cost burden due to hospitalization and death. Neonates, the elderly, and immunocompromised patients are particularly susceptible to ExPEC infection, including invasive ExPEC disease (IED).

ExPEC strains are the most common cause of urinary tract infections (UTI) and important contributors to surgical site infections and neonatal meningitis. The strains are also associated with abdominal and pelvic infections and nosocomial pneumonia, and are occasionally involved in other extraintestinal infections, such as osteomyelitis, cellulitis, and wound infections. All these primary sites of infection can result in ExPEC bacteremia. ExPEC is the most common cause of community-onset bacteremia and a major causative pathogen in nosocomial bacteremia and is found in about 17% to 37% of clinically significant blood isolates. Patients with an ExPEC-positive blood culture typically suffer sepsis syndrome, severe sepsis, or septic shock. Increasing resistance of ExPEC against first-line antibiotics including the cephalosporins, fluoroquinolones, and trimethoprim/sulfamethoxazole has been observed. The emergence and rapid global dissemination of ExPEC sequence type 131 (ST131) is considered a main driver of increased drug resistance, including multi-drug resistance. This clone is found in 12.5% to 30% of all ExPEC clinical isolates, exhibits mostly serotype O25b:H4, and shows high levels of resistance to fluoroquinolones, which is often accompanied by trimethoprim/sulfamethoxazole resistance and extended-spectrum beta-lactamases conferring resistance to cephalosporins.

The O-antigen comprises the immunodominant component of the cell wall lipopolysaccharide (LPS) in Gram-negative bacteria, including *E. coli*. There are currently >180 serologically unique *E. coli* O-antigens identified, with the vast majority of ExPEC isolates classified within less than 20 O-antigen serotypes. Full-length *E. coli* O-antigens are typically comprised of about 10 to 25 repeating sugar units attached to the highly conserved LPS core structure, with each component synthesized separately by enzymes encoded predominantly in the rfb and rfa gene clusters, respectively. Following polymerization of the O-antigen, the O-antigen polysaccharide backbone may be modified, typically through the addition of acetyl or glucose residues. These modifications effectively increase serotype diversity by creating antigenically distinct serotypes that share a common polysaccharide backbone, but differ in side branches. Genes encoding O-antigen modifying enzymes typically reside outside of the rfb cluster on the chromosome, and in some cases, these genes are found within lysogenic bacteriophages.

ExPEC isolates belonging to the O4 serogroup have been commonly identified in contemporary surveillance studies of U.S. and EU blood isolates. The structure of the O4 polysaccharide was determined as →2) α-L-Rha (1→6) α-D-Glc (1→3) α-L-FucNAc (1→3) β-D-GlcNAc (1→from an *E. coli* O4:K52 strain (Jann et al., *Carbohydr. Res*. (1993) v. 248, pp. 241-250). A distinct form of the O4 polysaccharide structure was determined for O4:K3, O4:K6 and O4:K12 strains, in which the structure above was modified by the addition of an α-D-Glc (1→3) linked to the rhamnose residue of the polysaccharide (Jann et al., 1993, supra), this form of the polysaccharide referred to herein below as 'glucosylated O4'. The enzymes responsible for the O-antigen modification within *E. coli* O4 strains were not identified.

Efforts toward the development of a vaccine to prevent ExPEC infections have focused on O-antigen polysaccharide conjugates. A 12-valent O-antigen conjugate vaccine was synthesized through extraction and purification of O-antigen polysaccharide and chemical conjugation to detoxified *Pseudomonas aeruginosa* exotoxin A and tested for safety and immunogenicity in a Phase 1 clinical study (Cross et al., *J. Infect. Dis*. (1994) v. 170, pp. 834-40). This candidate vaccine was never licensed for clinical use. A bioconjugation system in *E. coli* has been developed recently, in which the polysaccharide antigen and the carrier protein are both synthesized in vivo and subsequently conjugated in vivo through the activities of the oligosaccharyl transferase PglB, a *Campylobacter jejuni* enzyme, expressed in *E. coli* (Wacker et al., *Proc. Nat. Acad. Sci*. (2006) v. 103, pp. 7088-93). This N-linked protein glycosylation system is capable of the transfer of diverse polysaccharides to a carrier protein, allowing for straightforward methods to purify the conjugate.

Bioconjugation has been used successfully to produce conjugate polysaccharide for an *E. coli* four-valent O-antigen candidate vaccine (Poolman and Wacker, *J. Infect. Dis*. (2016) v. 213(1), pp. 6-13). However, the development of a successful ExPEC vaccine requires coverage of predominant serotypes, and the presence of further O-antigen modifications in subsets of ExPEC isolates presents a further challenge in covering isolates displaying unmodified and modified LPS. Moreover, efficiency of production of the multiple components for more complex vaccine compositions covering multiple serotypes becomes increasingly important, and hence there remains a need for improvements in production of individual bioconjugates of specific O-antigens.

BRIEF SUMMARY OF THE INVENTION

In view of increasing antibiotic resistance among ExPEC isolates and the presence of further O-antigen modifications among predominant O-serotypes, there is a need for improved prophylactic and therapeutic treatments for these infections. The invention satisfies this need by defining the genetic composition of contemporary clinical isolates, including identifying the genes encoding O-antigen modifying enzymes, thus allowing for the engineering of recombinant host cells capable of synthesizing bioconjugates of the O-antigens including bioconjugates comprising selected O-antigen modifications. In addition, in one aspect of the invention, host cells and methods for improved production of bioconjugates of specific O-antigens by using variants of oligosaccharyltransferase (OST) are provided, based on advantages of use of certain OST variants for bioconjugates of certain *E. coli* O-antigens in an unpredictable serotype-dependent manner. Use of such OST variants may in certain cases also affect the glycosylation pattern of the bioconjugate, e.g. by increasing the relative number of glycans coupled to the carrier protein as compared to bioconjugates produced using wild-type or other variants of the OST, and hence novel bioconjugates produced by such methods are also provided as an aspect of the invention.

In one aspect, provided is a method of preparing a bioconjugate of an *E. coli* $O_x$ antigen polysaccharide covalently linked to a carrier protein, the method comprising:

(i) providing a recombinant host cell comprising:
- a. a nucleotide sequence of an rfb gene cluster for the $O_x$-antigen polysaccharide;
- b. a nucleotide sequence encoding the carrier protein comprising at least one glycosylation site comprising a glycosylation consensus sequence having SEQ ID NO: 1, preferably having SEQ ID NO: 2; and
- c. a nucleotide sequence encoding an oligosaccharyl transferase $PglB_y$; and (ii) culturing the recombinant host cell under conditions for production of the bioconjugate, wherein:

when the $O_x$-antigen is O1A antigen polysaccharide, the $PglB_y$ comprises the amino acid mutations of N311V, K482R, D483H, and A669V;

when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8 respectively, wherein the translocase is capable of translocating bactoprenol linked glucose and the glycosyltransferase is capable of glucosylating bactoprenol;

when the $O_x$-antigen is O6A antigen polysaccharide, the $PglB_y$ comprises the amino acid mutations of N311V, K482R, D483H, and A669V;

when the $O_x$-antigen is O8 antigen polysaccharide, the $PglB_y$ comprises no amino acid mutations at positions 77, 80, 287, 289, 311, 482, 483 and 669;

when the $O_x$-antigen is O15 antigen polysaccharide, the $PglB_y$ comprises the amino acid mutations of N311V, K482R, D483H, and A669V;

when the $O_x$-antigen is O16 antigen polysaccharide, the $PglB_y$ comprises the amino acid mutations of Y77H, S80R, Q287P, K289R, and N311V;

when the $O_x$-antigen is O18A antigen polysaccharide, the $PglB_y$ comprises no amino acid mutations at positions 77, 80, 287, 289, 311, 482, 483 and 669; and when the $O_x$-antigen is O75 antigen polysaccharide, the $PglB_y$ comprises the amino acid mutation of N311V, wherein in each case the amino acid mutations are relative to the wild-type PglB having the amino acid sequence of SEQ ID NO: 6, wherein the O1A, glucosylated O4, O6A, O8, O15, O16, O8A, and O75 antigen polysaccharides have the structures of Formulas (O1A), (O4-Glc+), (O6A), (O8), (O15), (O16), (O18A), and (O75), respectively, as shown in Table 1, and each n is independently an integer of 1 to 100, preferably 3 to 50, e.g. 5 to 40, e.g. 7 to 25, e.g. 10 to 20.

In one embodiment, the $O_x$-antigen is O1A antigen polysaccharide, the $PglB_y$ comprises the amino acid mutations of N311V, K482R, D483H, and A669V relative to wild-type PglB having the amino acid sequence of SEQ ID NO: 6.

In one embodiment, the $O_x$-antigen is glucosylated O4 antigen polysaccharide, and the $PglB_y$ comprises the amino acid mutation N311V relative to wild-type PglB having the amino acid sequence of SEQ ID NO: 6. In one embodiment, the $O_x$-antigen is glucosylated O4 antigen polysaccharide, and the $PglB_y$ comprises the amino acid mutations Y77H and N311V relative to wild-type PglB having the amino acid sequence of SEQ ID NO: 6. In embodiments wherein the $O_x$-antigen is glucosylated O4 antigen polysaccharide, the recombinant host cell preferably further comprises a sequence encoding a GtrS having at least 80% identity to SEQ ID NO: 4, and nucleotide sequences encoding a GtrA and a GtrB having at least 80% sequence identity to SEQ ID NOs: 7 and 8 respectively.

In one embodiment, the $O_x$-antigen is O6A antigen polysaccharide, the $PglB_y$ comprises the amino acid mutations of N311V, K482R, D483H, and A669V relative to wild-type PglB having the amino acid sequence of SEQ ID NO: 6.

In one embodiment, the $O_x$-antigen is O8 antigen polysaccharide, the $PglB_y$ comprises no amino acid mutations at positions 77, 80, 287, 289, 311, 482, 483 and 669 relative to wild-type PglB having the amino acid sequence of SEQ ID NO: 6.

In one embodiment, the $O_x$-antigen is O15 antigen polysaccharide, the $PglB_y$ comprises the amino acid mutations of N311V, K482R, D483H, and A669V relative to wild-type PglB having the amino acid sequence of SEQ ID NO: 6.

In one embodiment, the $O_x$-antigen is O16 antigen polysaccharide, the $PglB_y$ comprises the amino acid mutations of Y77H, S80R, Q287P, K289R, and N311V relative to wild-type PglB having the amino acid sequence of SEQ ID NO: 6.

In one embodiment, the $O_x$-antigen is O18A antigen polysaccharide, the $PglB_y$ comprises no amino acid mutations at positions 77, 80, 287, 289, 311, 482, 483 and 669 relative to wild-type PglB having the amino acid sequence of SEQ ID NO: 6, and preferably comprises the amino acid sequence of SEQ ID NO: 6.

In one embodiment, the $O_x$-antigen is O75 antigen polysaccharide, the $PglB_y$ comprises the amino acid mutation of N311V relative to wild-type PglB having the amino acid sequence of SEQ ID NO: 6.

In a particular aspect, provided is a method of preparing a bioconjugate of an *E. coli* $O_x$-antigen polysaccharide covalently linked to a carrier protein, the method comprising:

(i) providing a recombinant host cell comprising:
  a. a nucleotide sequence of an rfb gene cluster for the $O_x$-antigen polysaccharide;
  b. a nucleotide sequence encoding the carrier protein comprising at least one glycosylation site comprising a glycosylation consensus sequence having SEQ ID NO: 1, preferably having SEQ ID NO: 2; and
  c. a nucleotide sequence encoding an oligosaccharyl transferase $PglB_y$; and
(ii) culturing the recombinant host cell under conditions for production of the bioconjugate,
wherein the $PglB_y$ comprises the amino acid mutation N311V relative to the wild-type PglB having the amino acid sequence of SEQ ID NO: 6,
wherein the $O_x$-antigen is O1A antigen polysaccharide, glucosylated O4 antigen polysaccharide, O6A antigen polysaccharide, O15 antigen polysaccharide, O16 antigen polysaccharide, or O75 antigen polysaccharide, and when the $O_x$-antigen is glucosylated O4 antigen polysaccharide, the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8, respectively, wherein the translocase is capable of translocating bactoprenol linked glucose and the glycosyltransferase is capable of glucosylating bactoprenol, and wherein the O1A, glucosylated O4, O6A, O15, O16, and O75 antigen polysaccharides have the structures of Formulas (O1A), (O4-Glc+), (O6A), (O15), (O16), and (O75), respectively, as shown in Table 1, and each n is independently an integer of 1 to 100, preferably 3 to 50, e.g. 5 to 40, e.g. 7 to 25, e.g. 10 to 20.

In certain embodiments, the method further comprises isolating the bioconjugate from the recombinant host cell.

In certain embodiments, the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae.*

In certain embodiments, the carrier protein is detoxified exotoxin A of *Pseudomonas aeruginosa* (EPA). Preferably, the EPA carrier protein comprises 1-10, preferably 2-4, more preferably 4, glycosylation sites. In certain embodiments, each glycosylation site comprises a glycosylation consensus sequence having SEQ ID NO: 2. In a particular embodiment, the EPA carrier protein comprises SEQ ID NO: 3.

In certain embodiments, the recombinant host cell is an *E. coli* cell, e.g., an *E. coli* K-12 strain, such as strain W3110.

In another aspect, provided is a bioconjugate produced by a method of preparing a bioconjugate of an $O_x$ antigen polysaccharide covalently linked to a carrier protein as described herein.

In another aspect, provided is a composition comprising such a bioconjugate. In some embodiments, a composition comprises at least 2, preferably at least 3, more preferably at least 5, still more preferably at least 7 of such bioconjugates.

In certain embodiments, a composition according to the invention comprises a bioconjugate of *E. coli* glucosylated O4 antigen polysaccharide covalently linked to a carrier protein, wherein the glucosylated O4 antigen polysaccharide has the structure of Formula (O4-Glc+) as shown in Table 1, and n is an integer of 1 to 100, preferably 3 to 50, e.g. 5 to 40, e.g. 7 to 25, e.g. 10 to 20. In certain embodiments, a composition according to the invention further comprises at least a bioconjugate of *E. coli* O25B antigen polysaccharide covalently linked to a carrier protein, wherein the O25B antigen polysaccharide has the structure of Formula (O25B) as shown in Table 1, and n is an integer of 1 to 100, preferably 3 to 50, e.g. 5 to 40, e.g. 7 to 25, e.g. 10 to 20. In certain embodiments, a composition according to the invention further comprises at least a bioconjugate of *E. coli* O2 antigen polysaccharide covalently linked to a carrier protein, wherein the O2 antigen polysaccharide has the structure of Formula (O2) as shown in Table 1, and n is an integer of 1 to 100, preferably 3 to 50, e.g. 5 to 40, e.g. 7 to 25, e.g. 10 to 20.

In certain embodiments, a composition of the invention comprises: (i) bioconjugate of *E. coli* O1A antigen polysaccharide covalently coupled to a carrier protein, (ii) bioconjugate of *E. coli* O2 antigen polysaccharide covalently coupled to a carrier protein, (iii) bioconjugate of *E. coli* glucosylated O4 antigen polysaccharide covalently coupled to a carrier protein, (iv) bioconjugate of *E. coli* O6A antigen polysaccharide covalently coupled to a carrier protein, (v) bioconjugate of *E. coli* O8 antigen polysaccharide covalently coupled to a carrier protein, (vi) bioconjugate of *E. coli* O15 antigen polysaccharide covalently coupled to a carrier protein, (vii) bioconjugate of *E. coli* O16 antigen polysaccharide covalently coupled to a carrier protein, (viii) bioconjugate of *E. coli* O25B antigen polysaccharide covalently coupled to a carrier protein, and (ix) bioconjugate of *E. coli* O75 antigen polysaccharide covalently coupled to a carrier protein, wherein the O1A, O2, glucosylated O4, O6A, O8, O15, O16, O25B, and O75 antigen polysaccharides have the structures of Formulas (O1A), (O2), (O4-Glc+), (O6A), (O8), (O15), (O16), (O25B), and (O75), respectively, as shown in Table 1, and each n is independently an integer of 1 to 100, preferably 3 to 50, e.g. 5 to 40, e.g. 7 to 25, e.g. 10 to 20. In certain embodiments, such a composition further comprises: (x) bioconjugate of *E. coli* O18A antigen polysaccharide covalently coupled to a carrier protein, wherein the O18A antigen polysaccharide has the structure of Formula (O18A) as shown in Table 1, and n is an integer of 1 to 100, preferably 3 to 50, e.g. 5 to 40, e.g. 7 to 25, e.g. 10 to 20. In certain embodiments, a composition of the invention is an immunogenic composition.

In other aspects, provided is a method of vaccination a subject against extra-intestinal pathogenic *E. coli* (ExPEC), comprising administering to the subject such a bioconjugate or composition as described herein. In yet other aspects, provided is such bioconjugate or composition as described herein for use in vaccination against extra-intestinal pathogenic *E. coli* (ExPEC).

In other aspects, provided are recombinant host cells for preparing a bioconjugate of an *E. coli* $O_x$ antigen polysaccharide covalently linked to a carrier protein, the recombinant host cell comprising:

(a) a nucleotide sequence of an rfb gene cluster for the $O_x$-antigen polysaccharide;

(b) a nucleotide sequence encoding the carrier protein comprising at least one glycosylation site comprising a glycosylation consensus sequence having SEQ ID NO: 1, preferably having SEQ ID NO: 2; and (c) a nucleotide sequence encoding an oligosaccharyl transferase $PglB_y$, wherein:

when the $O_x$-antigen is O1A antigen polysaccharide, the $PglB_y$ comprises the amino acid mutations of N311V, K482R, D483H, and A669V;

when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8 respectively, wherein the translocase is capable of translocating bactoprenol linked glucose and the glycosyltransferase is capable of glucosylating bactoprenol;

when the $O_x$-antigen is O6A antigen polysaccharide, the $PglB_y$ comprises the amino acid mutations of N311V, K482R, D483H, and A669V;

when the $O_x$-antigen is O6A antigen polysaccharide, the $PglB_y$ comprises the amino acid mutations of N311V, K482R, D483H, and A669V;

when the $O_x$-antigen is O15 antigen polysaccharide, the $PglB_y$ comprises the amino acid mutations of N311V, K482R, D483H, and A669V;

when the $O_x$-antigen is O16 antigen polysaccharide, the $PglB_y$ comprises the amino acid mutations of Y77H, S80R, Q287P, K289R, and N311V;

when the $O_x$-antigen is O18A antigen polysaccharide, the $PglB_y$ comprises no amino acid mutations at positions 77, 80, 287, 289, 311, 482, 483 and 669; and when the $O_x$-antigen is O75 antigen polysaccharide, the $PglB_y$ comprises the amino acid mutation of N311V, wherein in each case the amino acid mutations are relative to the wild-type PglB having the amino acid sequence of SEQ ID NO: 6, and wherein the O1A, glucosylated O4, O6A, O8, O15, O16, O18A, and O75 antigen polysaccharides have the structures of Formulas (O1A), (O4-Glc+), (O6A), (O8), (O15), (O16), (O18A), and (O75), respectively, as shown in Table 1, and each n is independently an integer of 1 to 100, preferably 3 to 50, e.g. 5 to 40, e.g. 7 to 25, e.g. 10 to 20.

In certain embodiments, such host cells are provided wherein the $O_x$-antigen is O1A antigen polysaccharide, and the $PglB_y$ comprises the amino acid mutations of N311V, K482R, D483H, and A669V relative to wild-type PglB having the amino acid sequence of SEQ ID NO: 6.

In certain embodiments, recombinant host cells of the invention are provided wherein the $O_x$-antigen is glucosylated O4 antigen polysaccharide, and the $PglB_y$ comprises the amino acid mutation N311V relative to wild-type PglB having the amino acid sequence of SEQ ID NO: 6. In certain embodiments, recombinant host cells of the invention are provided wherein the $O_x$-antigen is glucosylated O4 antigen polysaccharide, and the $PglB_y$ comprises the amino acid mutations Y77H and N311V relative to wild-type PglB having the amino acid sequence of SEQ ID NO: 6. In certain embodiments wherein the $O_x$-antigen is glucosylated O4 antigen polysaccharide, the recombinant host cell further comprises a sequence encoding a GtrS having the amino acid sequence of SEQ ID NO: 4, and nucleotide sequences encoding a GtrA and a GtrB having the amino acid sequences of SEQ ID NOs: 7 and 8, respectively.

In certain embodiments, recombinant host cells of the invention are provided wherein the $O_x$-antigen is O6A antigen polysaccharide, and the $PglB_y$ comprises the amino acid mutations of N311V, K482R, D483H, and A669V relative to wild-type PglB having the amino acid sequence of SEQ ID NO: 6.

In certain embodiments, recombinant host cells of the invention are provided wherein the $O_x$-antigen is O8 antigen polysaccharide, the $PglB_y$ comprises no amino acid mutations at positions 77, 80, 287, 289, 311, 482, 483 and 669 relative to wild-type PglB having the amino acid sequence of SEQ ID NO: 6.

In certain embodiments, recombinant host cells of the invention are provided wherein the $O_x$-antigen is O15 antigen polysaccharide, the $PglB_y$ comprises the amino acid mutations of N311V, K482R, D483H, and A669V relative to wild-type PglB having the amino acid sequence of SEQ ID NO: 6.

In certain embodiments, recombinant host cells of the invention are provided wherein the $O_x$-antigen is O16 antigen polysaccharide, the $PglB_y$ comprises the amino acid mutations of Y77H, S80R, Q287P, K289R, and N311V relative to wild-type PglB having the amino acid sequence of SEQ ID NO: 6.

In certain embodiments, recombinant host cells of the invention are provided wherein the $O_x$-antigen is O18A antigen polysaccharide, the $PglB_y$ comprises no amino acid mutations at positions 77, 80, 287, 289, 311, 482, 483 and 669 relative to wild-type PglB having the amino acid sequence of SEQ ID NO: 6.

In certain embodiments, recombinant host cells of the invention are provided wherein the $O_x$-antigen is O75 antigen polysaccharide, the $PglB_y$ comprises the amino acid mutation of N311V relative to wild-type PglB having the amino acid sequence of SEQ ID NO: 6.

In certain embodiments, recombinant host cells of the invention are provided wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In certain embodiments, recombinant host cells of the invention are provided wherein the carrier protein is detoxified exotoxin A of *Pseudomonas aeruginosa* (EPA). In certain embodiments thereof, the EPA carrier protein comprises 1-10, preferably 2-4, more preferably 4, of the glycosylation sites. In certain embodiments, each glycosylation site comprises a glycosylation consensus sequence having SEQ ID NO: 2. In certain embodiments, the EPA carrier protein comprises SEQ ID NO: 3.

In certain embodiments, recombinant host cells of the invention are provided wherein the recombinant host cell is an *E. coli* cell, e.g. an *E. coli* K-12 strain, such as strain W3110.

In certain embodiments for the host cells and methods for preparing a bioconjugate of an *E. coli* glucosylated O4 antigen polysaccharide covalently linked to a carrier protein according to the invention, the rfb gene cluster for the *E. coli* O4 antigen polysaccharide comprises a sequence that encodes the enzymes that create the *E. coli* O4 antigen polysaccharide (Formula (O4-Glc−) in Table 1) and is at least 80%, e.g. at least 90%, e.g. at least 95%, e.g. at least 98% identical to SEQ ID NO: 9. In certain embodiments the rfb gene cluster comprises SEQ ID NO: 9.

In certain embodiments for the host cells and methods for preparing a bioconjugate of an *E. coli* glucosylated O4 antigen polysaccharide covalently linked to a carrier protein according to the invention, the glucosyl transferase that is capable of modifying the *E. coli* O4 antigen polysaccharide to produce the *E. coli* glucosylated O4 antigen polysaccharide has an amino acid sequence that has at least 90%, preferably at least 95%, preferably at least 98% sequence identity to SEQ ID NO: 4. In certain embodiments, the glucosyl transferase comprises SEQ ID NO: 4.

In certain embodiments for the host cells and methods for preparing a bioconjugate of an *E. coli* glucosylated O4 antigen polysaccharide covalently linked to a carrier protein according to the invention, the translocase is capable of translocating bactoprenol-linked glucose and has at least 90%, preferably at least 95%, preferably at least 98% sequence identity to SEQ ID NO: 7. In certain embodiments, the translocase comprises SEQ ID NO: 7.

In certain embodiments for the host cells and methods for preparing a bioconjugate of an *E. coli* glucosylated O4 antigen polysaccharide covalently linked to a carrier protein according to the invention, the glycosyltransferase is capable of glucosylating bactoprenol and has at least 90%, preferably at least 95%, preferably at least 98% sequence identity to SEQ ID NO: 8. In certain embodiments, the glycosyltransferase comprises SEQ ID NO: 8.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

In the drawings:

FIG. 4A shows serum antibody levels measured by ELISA at day 0, 14 and 42 post-immunization; individual titers (log 10 EC50 titer) and GMT 95% CI are shown; the grey dotted line indicates the threshold above which the dilution curves of the samples have a 4PL fitting; FIG. 4B shows the results of the opsonophagocytic (OPK) assay to determine the functionality of the antibodies in serum samples obtained at day 42 post-immunization with glucosylated O4 (O4-Glc+)-EPA bioconjugate (4.0 μg); Wilcoxon rank sum test and Bonferroni correction; *P≤0.05, ***P≤0.0001;

FIG. 10 shows the overall study design for a phase 1/2a clinical trial with ExPEC10V vaccine in humans.

DETAILED DESCRIPTION OF THE INVENTION

Figure 1:
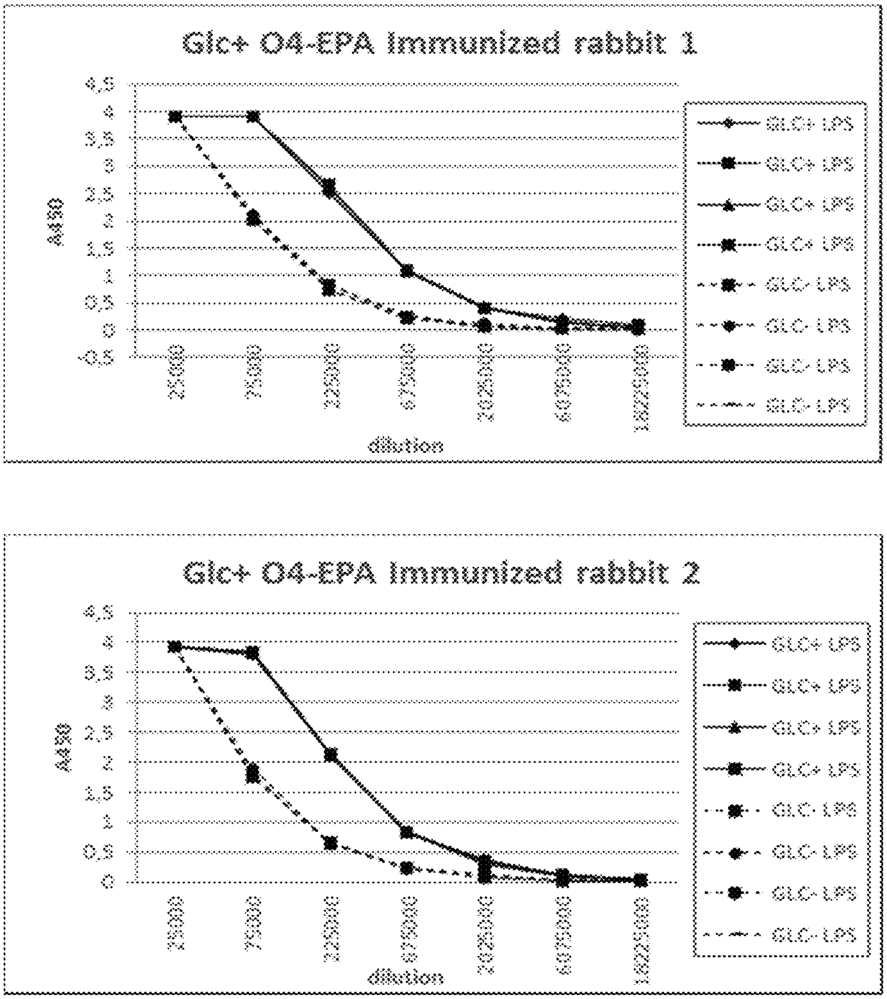
FIG. 1 shows ELISA IgG titers against unmodified (GLC−) or glucose-modified (GLC+) O4 LPS in sera from two rabbits immunized with Glc-modified O4 polysaccharide bioconjugate as described in Example 4; ELISA titers were determined in quadruplicate.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series.

Those skilled in the art will recognize or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The identification of an O-antigen structural modification, namely glucose branching, within the *E. coli* O4 serotype (Jann et al., 1993) presents a challenge to the discovery and development of a glycoconjugate vaccine targeting bacterial isolates within this serotype. The proportion of clinical contemporary O4 isolates expressing the unmodified (not having a glucose side-branch) and modified (having a glucose side-branch) forms of the O4 O-antigen is unknown. Obtaining information on this characteristic is critical for selecting the relevant antigenic structure. In addition, the extent to which vaccine induced antibodies elicited to one form of the O4 polysaccharide will cross-react with the other form has not been determined. Purification of O-antigen free from lipid A and subsequent chemical conjugation to a carrier protein is a lengthy and laborious process. Additionally, the purification, lipid A detoxification and chemical conjugation processes can result in loss of epitopes, antigen heterogeneity and reduced immunogenicity of the conjugated polysaccharide. Synthesis of glycoconjugates by bioconjugation can overcome these limitations of classical purification and chemical conjugation, but the in vivo synthesis of glucose-branched O4 O-antigen requires the activity of a polysaccharide branching enzyme, which lies outside of the rfb gene cluster. To date, the O-antigen modifying enzyme responsible for glucose-branching in O4 *E. coli* strains has not been identified. Cloning the O4 rfb gene cluster into the bioconjugation *E. coli* strain expressing PglB will not be sufficient to synthesize the glucose-branched O4 glycoconjugate, but rather would only produce non-glucose-branched O4 bioconjugates (the structure of the glycan thereof is shown in Formula (O4) in Table 1). As used herein, the terms "glucosylated O4", "glucose-branched O4", "O4 Glc+" and "Glc+O4" O-antigen refer to O4 O-antigen with a glucose side-branch, and the structure thereof is shown in formula (O4-Glc+) in Table 1.

Disclosed herein is the gene encoding the O-antigen modifying enzyme responsible for glucose branching of the *E. coli* O4 antigen polysaccharide. Also disclosed herein are host cells, e.g., recombinantly engineered host cells comprising nucleic acid encoding enzymes capable of producing bioconjugates comprising the glucosylated O4 antigen polysaccharide covalently bound to a carrier protein in vivo. Such host cells can be used to generate bioconjugates comprising the glucosylated O4 antigen linked to a carrier protein, which can be used in, e.g., the formulation of therapeutic and/or prophylactic compositions (e.g., vaccines). Further provided herein are compositions comprising bioconjugates of the glucosylated O4 antigen polysaccharide, alone or in combination with other *E. coli* antigens (e.g., O1, O2, O6, O8, O15, O16, O18, O25, and/or O75 antigen polysaccharides and subserotypes thereof). The compositions can be used in prophylactic and/or therapeutic methods, e.g., vaccination of hosts against infection with *E. coli*, and are useful in the generation of antibodies, which can be used, e.g., in therapeutic methods such as for immunization of subjects.

As used here, the terms "O-antigen," "O-antigen polysaccharide," "O-antigen saccharide," and "OPS" refer to the O-antigen of Gram-negative bacteria. Typically, an O-antigen is a polymer of immunogenic repeating polysaccharide units. In a particular embodiment, the terms "O-antigen," "O-antigen polysaccharide," and "OPS" refer to the O-antigen of *Escherichia coli*. Different serotypes of *E. coli* express different O-antigens. In *E. coli*, the gene products involved in O-antigen biogenesis are encoded by the rfb gene cluster.

As used herein, "rfb cluster" and "rfb gene cluster" refer to a gene cluster that encodes enzymatic machinery capable of synthesizing an O-antigen backbone structure. The term rfb cluster can apply to any O-antigen biosynthetic cluster, and preferably refers to a gene cluster from the genus *Escherichia*, particularly *E. coli*.

As used herein, the term "O1A" refers to the O1A antigen of *E. coli* (a subserotype of *E. coli* serotype O1). The term "O2" refers to the O2 antigen of *E. coli* (*E. coli* serotype O2). The term "O6A" refers to the O6A antigen of *E. coli* (a subserotype of *E. coli* serotype O6). The term "O8" refers to the O8 antigen of *E. coli* (*E. coli* serotype O8). The term "O15" refers to the O15 antigen of *E. coli* (*E. coli* serotype O15). The term "O16" refers to the O16 antigen of *E. coli* (*E. coli* serotype O16). The term "O18A" refers to the O18A antigen of *E. coli* (a subserotype of *E. coli* serotype O18). The term "O25B" refers to the O25B antigen from *E. coli* (a subserotype of *E. coli* serotype O25). The term "O75" refers to the O75 antigen of *E. coli* (*E. coli* serotype O75).

The structures of *E. coli* O-antigen polysaccharides referred to throughout this application are shown below in Table 1. A single repeating unit for each *E. coli* O-antigen polysaccharide is shown.

TABLE 1

Structures of *E. coli* O-antigen Polysaccharides

| *E. coli* O-antigen Polysaccharide | Structure of Repeating Unit[1] |
|---|---|
| Non-glucosylated O4 antigen polysaccharide (O4-Glc−) | [→2)-α-L-Rhap-(1→6)-α-D-Glcp-(1→3)-α-L-FucpNAc-(1→3)-β-D-GlcpNAc-(1→]$_n$ |
| Glucosylated O4 antigen polysaccharide (O4-Glc+) | α-D-Glcp<br>1<br>↓<br>3<br>[→2)-α-L-Rhap-(1→6)-α-D-Glcp-(1→3)-α-L-FucpNAc-(1→3)-β-D-GlcpNAc-(1→]$_n$ |
| O1A antigen polysaccharide (O1A) | [→3)-α-L-Rhap-(1→3)-α-L-Rhap-(1→3)-β-L-Rhap-(1→4)-β-D-GlcpNAc-(1→]$_n$<br>2<br>↑<br>1<br>β-D-ManpNAc |
| O2 antigen polysaccharide (O2) | [→3)-α-L-Rhap-(1→2)-α-L-Rhap-(1→3)-β-L-Rhap-(1→4)-β-D-GlcpNAc-(1→]$_n$<br>2<br>↑<br>1<br>α-D-Fucp3NAc |
| O6A antigen polysaccharide (O6) | [→4)-α-D-GalpNAc-(1→3)-β-D-Manp-(1→4)-β-D-Manp-(1→3)-α-D-GlcpNAc-(1→]$_n$<br>2<br>↑<br>1<br>β-D-Glcp |
| O8 antigen polysaccharide (O8) | α-D-Manp3Me-(1→[3)-β-D-Manp-(1→2)-α-D-Manp-(1→2)-α-D-Manp-(1→]$_n$ |
| O15 antigen polysaccharide (O15) | [→2)-β-D-Galp-(1→3)-α-L-FucpNAc-(1→3)-β-D-GlcpNAc-(1→]$_n$ |
| O16 antigen polysaccharide (O16) | [→2)-β-D-Galf-(1→6)-α-D-Glcp-(1→3)-α-L-Rhap-(1→3)-α-D-GlcpNAc-(1→]$_n$<br>2<br>↑<br>Ac |
| O18A antigen polysaccharide (O18A) | [→2)-α-L-Rhap-(1→6)-α-D-Glcp-(1→4)-α-D-Galp-(1→3)-α-D-GlcpNAc-(1→]$_n$<br>3<br>↑<br>1<br>β-D-GlcpNAc |

TABLE 1-continued

| Structures of *E. coli* O-antigen Polysaccharides | |
|---|---|
| *E. coli* O-antigen Polysaccharide | Structure of Repeating Unit[1] |
| O25B antigen polysaccharide (O25B) | β-D-Glcp<br>1<br>↓<br>6<br>[→4)-α-D-Glcp-(1→3)-α-L-Rhap-(1→3)-β-D-GlcpNAc-(1→]$_n$<br>3 2<br>↑ ↑<br>1 Ac<br>α-L-Rhap |
| O75 antigen polysaccharide (O75) | β-D-Manp<br>1<br>↓<br>4<br>[→3)-α-D-Galp-(1→4)-α-L-Rhap-(1→3)-β-D-GlcpNAc-(1→]$_n$ |

[1]Each n is independently an integer of 1 to 100, such as 1-50, 1-40, 1-30, 1-20, and 1-10, 3-50, 3-40, e.g. at least 5, such as 5-40, e.g. 7-30, e.g. 7 to 25, e.g. 10 to 20, but in some instances can be 1-2.

All monosaccharides described herein have their common meaning known in the art. Monosaccharides can have the D or L configuration. If D or L is not specified, the sugar is understood to have the D configuration. Monosaccharides are typically referred to by abbreviations commonly known and used in the art. For example, Glc refers to glucose; D-Glc refers to D-glucose; and L-Glc refers to L-glucose. Other common abbreviations for monosaccharides include: Rha, rhamnose; GlcNAc, N-acetylglucosamine; GalNAc, N-acetylgalactosamine; Fuc, fucose; Man, mannose; Man3Me, 3-O-methyl-mannose; Gal, galactose; FucNAc, N-acetylfucosamine; and Rib, ribose. The suffix "f" refers to furanose and the suffix "p" refers to pyranose.

The terms "RU," "repeat unit," and "repeating unit" as used with respect to an O-antigen refer to the biological repeat unit (BRU) of an O-antigen as it is synthesized in vivo by cellular machinery (e.g., glycosyltransferases). The number of RUs of an O-antigen may vary per serotype, and in embodiments of the invention typically varies from about 1-100 RUs, preferably about 1 to 50 RUs, such as 1-50 RUs, 1-40 RUs, 1-30 RUs, 1-20 RUs, and 1-10 RUs, and more preferably at least 3 RUs, at least 4 RUs, at least 5 RUs, such as 3-50 RUs, preferably 5-40 RUs, e.g. 7-25 RUs, e.g. 10-20 RUs. However, in some instances, the number of RUs of an O-antigen can be 1-2. The structure of each O-antigen that is specifically described herein is shown containing one RU with the variable "n" designating the number of RUs. In each O-antigen polysaccharide in a bioconjugate of the invention, n is independently an integer of 1-100, such as 1-50, 1-40, 1-30, 1-20, 1-10, preferably at least 3, more preferably at least 5, such as 3-50, preferably 5-40 (e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40), but in some instances can be 1-2. In some embodiments n is indepently an integer of about 7-25, e.g. about 10-20. The values may vary between individual O-antigen polysaccharides in a composition, and are provided here as average values, i.e. if a bioconjugate is described herein as having an n that is independently an integer of 5-40, the composition contains a majority of O-antigen polysaccharides with 5-40 repeat units, but may also contain some O-antigen polysaccharides that have less than 5 repeat units or more than 40 repeat units.

The term "glycoconjugate" refers to a sugar or saccharide antigen (e.g., oligo- and polysaccharide)-protein conjugate linked to another chemical species, including but not limited to proteins, peptides, lipids, etc. Glycoconjugates can be prepared chemically, e.g., by chemical (synthetic) linkage of the protein and sugar or saccharide antigen. The term glycoconjugate also includes bioconjugates.

The term "bioconjugate" refers to a conjugate between a protein (e.g., a carrier protein) and a sugar or saccharide antigen (e.g., oligo- and polysaccharide) prepared in a host cell background, preferably a bacterial host cell, e.g. an *E. coli* host cell, wherein host cell machinery links the antigen to the protein (e.g., N-links). Preferably, the term "bioconjugate" refers to a conjugate between a protein (e.g., carrier protein) and an O-antigen, preferably an *E. coli* O-antigen (e.g., O1A, O2, glucosylated O4, O6A, O8, O15, O16, O18A, O25B, O75, etc.) prepared in a host cell background, wherein host cell machinery links the antigen to the protein (e.g., N-links). Because bioconjugates are prepared in host cells by host cell machinery, the antigen and protein are covalently linked via a glycosidic linkage or bond in a bioconjugate. Bioconjugates can be prepared in recombinant host cells engineered to express the cellular machinery needed to synthesize the O-antigen and/or link the O-antigen to the target protein. Bioconjugates, as described herein, have advantageous properties over chemically prepared glycoconjugates where the glycans are purified from bacterial cell walls and subsequently chemically coupled to a carrier protein, e.g., bioconjugates require fewer chemicals in manufacture and are more consistent in terms of the final product generated, and contain less or no free (i.e. unbound to carrier protein) glycan. Thus, in typical embodiments, bioconjugates are preferred over chemically produced glycoconjugates.

The term "about," when used in conjunction with a number, refers to any number within ±1, ±5 or ±10% of the referenced number.

The term "percent (%) sequence identity" or "% identity" describes the number of matches ("hits") of identical amino acids of two or more aligned amino acid sequences as compared to the number of amino acid residues making up the overall length of the amino acid sequences. In other terms, using an alignment, for two or more sequences the percentage of amino acid residues that are the same (e.g. 90%, 95%, 97% or 98% identity) may be determined, when the sequences are compared and aligned for maximum correspondence as measured using a sequence comparison algorithm as known in the art, or when manually aligned and visually inspected. The sequences which are compared to determine sequence identity may thus differ by substitution(s), addition(s) or deletion(s) of amino acids. Suitable programs for aligning protein sequences are known to the skilled person. The percentage sequence identity of protein sequences can, for example, be determined with programs such as CLUSTALW, Clustal Omega, FASTA or BLAST, e.g using the NCBI BLAST algorithm (Altschul S F, et al (1997), Nucleic Acids Res. 25:3389-3402).

For example, for amino acid sequences, sequence identity and/or similarity can be determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J. Mol. Biol. 48:443, the search for similarity method of Pearson and Lipman, 1988, Proc. Nat. Acad. Sci. U.S.A. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al, 1984, Nucl. Acid Res. 12:387-395, preferably using the default settings, or by inspection. In certain embodiments, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

Another example of a useful algorithm is the BLAST algorithm, described in: Altschul et al, 1990, J. Mol. Biol. 215:403-410; Altschul et al, 1997, Nucleic Acids Res. 25:3389-3402; and Karin et al, 1993, Proc. Natl. Acad. Sci. U.S.A. 90:5873-5787. A particularly useful BLAST program is the WU-BLAST-2 program which was obtained from Altschul et al, 1996, Methods in Enzymology 266:460-480. WU-BLAST-2 uses several search parameters, most of which are set to the default values.

An additional useful algorithm is gapped BLAST as reported by Altschul et al, 1993, Nucl. Acids Res. 25:3389-3402.

The term "Invasive Extraintestinal pathogenic *Escherichia coli* (ExPEC) disease (IED)" is defined herein as an acute illness consistent with systemic bacterial infection, which is microbiologically confirmed either by the isolation and identification of *E. coli* from blood or other normally sterile body sites, or by the isolation and identification of *E. coli* from urine in a patient with presence of signs and symptoms of invasive disease (systemic inflammatory response syndrome (SIRS), sepsis or septic shock) and no other identifiable source of infection.

Bioconjugates of *E. coli* Glucosylated O4 Antigen Polysaccharides

In one aspect, provided herein is a bioconjugate of an *E. coli* glucosylated O4 antigen polysaccharide covalently linked to a carrier protein. As used herein, the term "O4" refers to the O4 antigen from *E. coli* (*E. coli* serotype O4). O-antigen structural modification is known to exist within the *E. coli* O4 serotype. In particular, some O4 serotypes express a modified O-antigen having a branched glucose unit. As used herein, "glucosylated O4 antigen," "glucosylated O4 antigen polysaccharide, "O4-Glc+ antigen polysaccharide," and "O4-Glc+ antigen" refer to an O4 antigen (e.g., *E. coli* O4 antigen) having a glucose branch, in which D-glucose is linked to L-rhamnose in the repeating unit L-Rha→D-Glc→L-FucNAc→D-GlcNAc. In a particular embodiment, an *E. coli* glucosylated O4 antigen polysaccharide comprises the structure of formula (O4-Glc+), as shown in Table 1, wherein n is an integer of 1 to 100. In preferred embodiments, n is an integer of 3 to 50, e.g. 5 to 40, e.g. 7 to 25, e.g. 10 to 20.

*E. coli* O4 strains, independent of glucose branching status, carry a substantially identical rfb gene cluster encoding the genes responsible for production of the O4 antigen polysaccharide. However, in vivo synthesis of the modified O4 antigen having glucose branching requires the activity of a polysaccharide branching enzyme, which lies outside of the rfb gene cluster. To the best of the knowledge of the inventors, the identity of the polysaccharide branching enzyme responsible for glucose modification of the O4 antigen has remained unknown to date. Here, the inventors discovered the sequence of the polysaccharide branching enzyme responsible for glucose modification of the O4 antigen. Identification of this enzyme enables production of bioconjugates of the modified O4 antigen polysaccharide having glucose branching. The glucose modified form of the O4 antigen polysaccharide is present in predominant serotypes and can thus be used to provide an improved immune response, e.g for prophylactic or therapeutic use.

In particular, provided herein is the sequence of a gtrS gene encoding a glucosyltransferase enzyme specific for *E. coli* serotype O4 that glucosylates the O4 antigen. In general, the gtrA, gtrB, and gtrS genes encodes the enzymes responsible for O-antigen glucosylation. While the gtrA and gtrB genes in different serotypes are highly homologous and interchangeable, the gtrS gene encodes a serotype specific O-antigen glucosyl transferase. The gtrS gene of *E. coli* serotype O4 encodes the GtrS enzyme that modifies the O4 antigen by introducing glucose branching. Characterization of contemporary clinical *E. coli* isolates of the O4 serotype revealed the presence of gtrS in 78% of tested isolates, indicating that *E. coli* O4 antigen polysaccharide modified with the addition of a glucose residue is predominant in current infecting isolates.

In one embodiment, provided herein is a nucleic acid of a gtrS gene from *E. coli* serotype O4 encoding a GtrS glucosyltransferase comprising the amino acid sequence of SEQ ID NO: 4. In another embodiment, a gtrS nucleic acid encodes a GtrS protein from *E. coli* serotype O4 that is about 80%, 85%, 90%, 95%, 96%, 97%, 98%, 99%, or 100% identical to the amino acid sequence of SEQ ID NO: 4, preferably 98%, 99%, or 100% identical to the amino acid sequence of SEQ ID NO: 4. A GtrS protein that is at least 80% identical to the amino acid sequence of SEQ ID NO: 4 is capable of specifically glucosylating the *E. coli* O4 antigen polysaccharide to obtain a glucosylated O4 antigen having the structure of Formula (O4-Glc+) as shown in Table 1. One of ordinary skill in the art will be able to make mutated forms of the GtrS protein of SEQ ID NO: 4 having at least 80% sequence identity to SEQ ID NO: 4, and test such sequences for glucosylation activity of the *E. coli* O4 antigen in view of the present disclosure. Recombinant host cells comprising nucleic acid sequence encoding the glucosyl transferase gtrS gene of *E. coli* serotype O4, and use of the recombinant host cells in production of the glucose modified O4 antigen polysaccharides and bioconjugates thereof are described in greater detail below.

Sequences for gtrA and gtrB encoded proteins, which function as bactoprenol-linked glucose translocase (GtrA, flips the bactoprenol-linked glucose over the inner membrane to the periplasm) and bactoprenol glucosyl transferase (GtrB, links glucose to bactoprenol), respectively, may comprise amino acid sequences that are at least about 80% identical to SEQ ID NOs: 7 and 8, respectively. In certain embodiments, nucleic acid sequences encoding GtrA and GtrB proteins that are at least about 80%, 85%, 90%, 95%, 96%, 97%, 98%, 99%, or 100% identical to SEQ ID NOs: 7 and 8, respectively, and having bactoprenol-linked glucose translocase and bactoprenol glucosyl transferase activity, respectively, are also present in the host cells of the invention, that further comprise an O4-specific rfb locus, the O4-specific GtrS encoding sequence described above, an oligosaccharyl transferase as described herein, and a sequence encoding a carrier protein having one or more glycosylation consensus sequences as described herein, to produce bioconjugates of *E. coli* glucosylated O4 serotype (comprising glycan structure of Formula (O4-Glc+) in Table 1).

Bioconjugates of an *E. coli* glucosylated O4 antigen polysaccharide provided herein are covalently linked to a carrier protein, preferably by a glycosidic linkage. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Bioconjugation with various different carrier proteins containing the required consensus glycosylation sequence has been described, showing that a wide range of proteins can be glycosylated using this technology (see, e.g. WO 06/119987, WO 2015/124769, WO 2015/158403, WO 2015/82571, WO 2017/216286, and WO 2017/67964, together showing a wide variety of carrier proteins that were successfully used in bioconjugation).

In certain embodiments a carrier protein is modified, e.g., modified in such a way that the protein is less toxic and/or more susceptible to glycosylation. In a specific embodiment, the carrier proteins used herein are modified such that the number of glycosylation sites in the carrier proteins is maximized in a manner that allows for lower concentrations of the protein to be administered, e.g., in an immunogenic composition, particularly in its bioconjugate form.

Thus, in certain embodiments, the carrier proteins described herein are modified to include 1, 2, 3, 4, 5, 6, 7, 8, 9, 10 or more glycosylation sites than would normally be associated with the carrier protein (e.g., relative to the number of glycosylation sites associated with the carrier protein in its native/natural, i.e., "wild-type" state). Introduction of glycosylation sites into a carrier protein can be accomplished by insertion of a glycosylation consensus sequence anywhere in the primary structure of the protein by, e.g., adding new amino acids to the primary structure of the protein such that a glycosylation site is added in full or in part, or by mutating existing amino acids in the protein in order to generate a glycosylation site. One of ordinary skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In some embodiments, a glycosylation consensus sequence can be extended by addition of lysine residues for more efficient glycosylation.

Exemplary examples of glycosylation consensus sequences that can be inserted into or generated in a carrier protein include Asn-X-Ser(Thr), wherein X can be any amino acid except Pro (SEQ ID NO: 1); and Asp(Glu)-X-Asn-Z-Ser(Thr), wherein X and Z are independently selected from any amino acid except Pro (SEQ ID NO: 2).

In some embodiments, the *E. coli* glucosylated O4 antigen polysaccharide is covalently linked to an asparagine (Asn) residue in the carrier protein (e.g., N-linked), wherein the Asn residue is present in a glycosylation site comprising a glycosylation consensus sequence having SEQ ID NO: 1, more preferably having SEQ ID NO: 2. Typically, a carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequences having the amino acid sequence of SEQ ID NO: 1, and more preferably the amino acid sequence of SEQ ID NO: 2.

In particular embodiments, a carrier protein is a detoxified Exotoxin A of *P. aeruginosa*. For EPA, various detoxified protein variants have been described in literature and could be used as carrier proteins. For example, detoxification can be achieved by mutating and deleting the catalytically essential residues L552V and ΔE553 according to Lukac et al., 1988, *Infect Immun,* 56: 3095-3098, and Ho et al., 2006, *Hum Vaccin,* 2:89-98. As used herein, "EPA" refers to a detoxified Exotoxin A of *P. aeruginosa*. In those embodiments, wherein the carrier protein is EPA, an *E. coli* glucosylated O4 antigen polysaccharide can be covalently linked to an Asn residue in a glycosylation site comprising a glycosylation consensus sequence having SEQ ID NO: 1, and preferably covalently linked to an Asn residue in a glycosylation site comprising a glycosylation consensus sequence having SEQ ID NO: 2. Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably the amino acid sequence of SEQ ID NO: 2.

In some embodiments, the EPA carrier protein comprises four glycosylation sites each comprising a glycosylation consensus sequence, for instance a glycosylation site comprising a glycosylation consensus sequence having SEQ ID NO: 2. As used herein, "EPA-4 carrier protein" and "EPA-4" refer to a detoxified Exotoxin A of *P. aeruginosa* carrier protein comprising four glycosylation sites each comprising a glycosylation consensus sequences having SEQ ID NO: 2. An exemplary preferred example of an EPA-4 carrier protein is EPA carrier protein comprising the amino acid sequence of SEQ ID NO: 3.

Compositions

In another aspect, provided herein is a composition comprising a bioconjugate of an *E. coli* glucosylated O4 antigen polysaccharide covalently linked to a carrier protein. The compositions provided herein can include any bioconjugate of an *E. coli* glucosylated O4 antigen polysaccharide covalently linked to a carrier protein (e.g., EPA) described herein.

In some embodiments, a composition is an immunogenic composition. As used herein, an "immunogenic composition" refers to a composition that can elicit an immune response in a host or subject to whom the composition is administered. Immunogenic compositions can further comprise a pharmaceutically acceptable carrier. In some embodiments, a composition is a pharmaceutical composition further comprising a pharmaceutically acceptable carrier. As used herein, a "pharmaceutically acceptable carrier" refers to a diluent, adjuvant, excipient or vehicle with which a composition is administered, and that is non-toxic and should not interfere with the efficacy of the active ingredient. For example, saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable pharmaceutically acceptable carriers are described in "Remington's Pharmaceutical Sciences" by E. W. Martin.

In one embodiment, a composition of the invention comprises the bioconjugates of the invention in a Tris-buffered saline (TBS) pH 7.4 (e.g. containing Tris, NaCl and KCl, e.g. at 25 mM, 137 mM and 2.7 mM, respectively). In other embodiments, the compositions of the invention comprise bioconjugates of the invention in about 10 mM $KH_2PO_4$/$Na_2HPO_4$ buffer at pH of about 7.0, about 5% (w/v) sorbitol, about 10 mM methionine, and about 0.02% (w/v) polysorbate 80. In other embodiments, the compositions of the invention comprise bioconjugates of the invention in about 10 mM $KH_2PO_4$/$Na_2HPO_4$ buffer at pH of about 7.0, about 8% (w/v) sucrose, about 1 mM EDTA, and about 0.02% (w/v) polysorbate 80 (see e.g. WO 2018/077853 for suitable buffers for bioconjugates of *E. coli* O-antigens covalently bound to EPA carrier protein).

In some embodiments, the compositions described herein are monovalent formulations, and contain one *E. coli* O-antigen polysaccharide, e.g., in isolated form or as part of a glycoconjugate or bioconjugate, such as the *E. coli* glucosylated O4 antigen polysaccharide. Also provided herein are compositions (e.g., pharmaceutical and/or immunogenic compositions) that are multivalent compositions, e.g., bivalent, trivalent, tetravalent, etc. compositions. For example, a multivalent composition comprises more than one antigen, such as an *E. coli* O-antigen, glycoconjugate, or bioconjugate thereof. In particular embodiments, multivalent compositions provided herein comprise a bioconjugate of an *E. coli* glucosylated O4 antigen polysaccharide, and at least one additional antigen.

In one embodiment, a composition (e.g., pharmaceutical and/or immunogenic composition) is a monovalent composition comprising a biconjugate of an *E. coli* glucosylated O4 antigen polysaccharide covalently linked to a carrier protein as described herein.

In another embodiment, a composition (e.g., pharmaceutical and/or immunogenic composition) is a multivalent composition comprising an *E. coli* glucosylated O4 antigen polysaccharide covalently linked to a carrier protein as described herein, and at least one additional antigen.

In some embodiments, the additional antigen is antigen saccharide or polysaccharide, more preferably an *E. coli* O-antigen polysaccharide, such as *E. coli* O-antigens of one or more of the O1, O2, O6, O8, O15, O16, O18, O25, and O75 serotypes and subserotypes thereof. In some embodiments, each of the additional *E. coli* O-antigen polysaccharides is a glycoconjugate, meaning that the *E. coli* O-antigen polysaccharide is covalently linked to another chemical species, e.g., protein, peptide, lipid, etc., most preferably a carrier protein, such as by chemical or enzymatic methods. In preferred embodiments, each of the additional *E. coli* O-antigen polysaccharides is a bioconjugate in which the O-antigen polysaccharide is covalently linked to, e.g. a carrier protein, via a glycosidic bond enzymatically by host cell machinery. Compositions provided herein in certain embodiments can comprise 1-20 additional glycoconjugates, more preferably bioconjugates of *E. coli* O-antigen polysaccharides, such as 1, 2, 3, 4, 5, 6, 7, 8, 9, 10, 11, 12, 13, 14, 15, 16, 17, 18, 19 or 20 additional glycoconjugates or preferably bioconjugates of *E. coli* O-antigen polysaccharides. Other antigens can be included in the compositions provided herein, such as peptide, protein, or lipid antigens, etc.

In some embodiments, a composition (e.g., pharmaceutical and/or immunogenic composition) comprises a bioconjugate of an *E. coli* glucosylated O4 antigen polysaccharide, and at least one additional antigen polysaccharide selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide. Preferably, each of the additional O-antigen polysaccharides is covalently linked to a carrier protein, and is more preferably a bioconjugate.

In one embodiment, an O1A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O1A antigen polysaccharide comprises the structure of formula (O1A) as shown in Table 1, wherein n is an integer of 1-100, preferably 3-50, e.g. 5-40, e.g. 7 to 25, e.g. 10 to 20. Preferably, the O1A antigen polysaccharide is part of a bioconjugate and is covalently linked to a carrier protein, e.g., EPA.

In one embodiment, an O2 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O2 antigen polysaccharide comprises the structure of formula (O2) as shown in Table 1, wherein n is an integer of 1-100, preferably 3-50, e.g. 5-40, e.g. 7 to 25, e.g. 10 to 20. Preferably, the O2 antigen polysaccharide is part of a bioconjugate and is covalently linked to a carrier protein, e.g., EPA.

In one embodiment, an O6A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O6A antigen polysaccharide comprises the structure of formula (O6A) as shown in Table 1, wherein n is an integer of 1-100, preferably 3-50, e.g. 5-40, e.g. 7 to 25, e.g. 10 to 20. Preferably, the O6A antigen polysaccharide is part of a bioconjugate and is covalently linked to a carrier protein, e.g., EPA.

In one embodiment, an O8 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O8 antigen polysaccharide comprises the structure of formula (O8) as shown in Table 1, wherein n is an integer of 1-100, preferably 3-50, e.g. 5-40, e.g. 7 to 25, e.g. 10 to 20. Preferably, the O8 antigen polysaccharide is part of a bioconjugate and is covalently linked to a carrier protein, e.g., EPA.

In one embodiment, an O15 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O15 antigen polysaccharide comprises the structure of formula (O15) as shown in Table 1, wherein n is an integer of 1-100, preferably 3-50, e.g. 5-40, e.g. 7 to 25, e.g. 10 to 20. Preferably, the O15 antigen polysaccharide is part of a bioconjugate and is covalently linked to a carrier protein, e.g., EPA.

In one embodiment, an O16 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O16 antigen polysaccharide comprises the structure of formula (O16) as shown in Table 1, wherein n is an integer of 1-100, preferably 3-50, e.g. 5-40, e.g. 7 to 25, e.g. 10 to 20. Preferably, the O16 antigen polysaccharide is part of a bioconjugate and is covalently linked to a carrier protein, e.g., EPA.

In one embodiment, an O18A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O18A antigen polysaccharide comprises the structure of formula (O18A) as shown in Table 1, wherein n is an integer of 1-100, preferably 3-50, e.g. 5-40, e.g. 7 to 25, e.g. 10 to 20. Preferably, the O18A antigen polysaccharide is part of a bioconjugate and is covalently linked to a carrier protein, e.g., EPA.

In one embodiment, an O25B antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O25B antigen polysaccharide comprises the structure of formula (O25B) as shown in Table 1, wherein n is an integer of 1-100, preferably 3-50, e.g. 5-40, e.g. 7 to 25, e.g. 10 to 20. Preferably, the O25B antigen polysaccharide is part of a bioconjugate and is covalently linked to a carrier protein, e.g., EPA.

In one embodiment, an O75 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O75 antigen polysaccharide comprises the structure of formula (O75) as shown in Table 1, wherein n is an integer of 1-100, preferably 3-50, e.g. 5-40, e.g. 7 to 25, e.g. 10 to 20. Preferably, the O75 antigen polysaccharide is part of a bioconjugate and is covalently linked to a carrier protein, e.g., EPA.

In another embodiment, a composition (e.g., a pharmaceutical and/or immunogenic composition) comprises at least the *E. coli* O1A, O2, glucosylated O4, O6A and O25B antigen polysaccharides, preferably bioconjugates of the O1A, O2, glucosylated O4, O6A and O25B antigen polysaccharides covalently linked to a carrier protein, e.g., EPA (i.e., a pentavalent composition).

In a preferred embodiment, a composition (e.g., a pharmaceutical and/or immunogenic composition) comprises at least the *E. coli* O1A, O2, glucosylated O4, O6A, O8, O15, O16, O25B and O75 antigen polysaccharides, preferably bioconjugates of the O1A, O2, glucosylated O4, O6A, O8, O15, O16, O25B and O75 antigen polysaccharides covalently linked to a carrier protein, e.g., EPA (i.e., a 9-valent composition).

In another preferred embodiment, a composition (e.g., a pharmaceutical and/or immunogenic composition) comprises at least the *E. coli* O1A, O2, glucosylated O4, O6A, O8, O15, O16, O18A, O25B and O75 antigen polysaccharides, preferably bioconjugates of the O1A, O2, glucosylated O4, O6A, O8, O15, O16, O18A, O25B and O75 antigen polysaccharides covalently linked to a carrier protein, e.g., EPA (i.e., a 10-valent composition).

Also contemplated herein are compositions which optionally further comprise additional O-antigens (e.g., in isolated form, or as part of a glycoconjugate or bioconjugate) from other *E. coli* serotypes.

In some embodiments, each of the additional *E. coli* O1A, O2, O6A, O8, O15, O16, O18A, O25B, and/or O75 antigen polysaccharides is covalently linked to a carrier protein. The O-antigen polysaccharide can be linked to a carrier protein by chemical or other synthetic methods, or the O-antigen polysaccharide can be part of a bioconjugate, and is preferably part of a bioconjugate. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Preferably, the carrier protein is EPA.

In some embodiments, each of the additional *E. coli* O1A, O2, O6A, O8, O15, O16, O18A, O25B, and/or O75 antigen polysaccharides, particularly when part of a bioconjugate, is covalently linked to an asparagine (Asn) residue in the carrier protein, wherein the Asn residue is present in a glycosylation site comprising a glycosylation consensus sequence Asn-X-Ser(Thr), wherein X can be any amino acid except Pro (SEQ ID NO: 1), preferably wherein the Asn residue is present in a glycosylation site comprising a glycosylation consensus sequence Asp(Glu)-X-Asn-Z-Ser (Thr), wherein X and Z are independently selected from any amino acid except Pro (SEQ ID NO: 2). The carrier protein can comprise 1-10 glycosylation sites, preferably 2 to 4 glycosylation sites, most preferably 4 glycosylation sites, each comprising a glycosylation consensus sequence. In a particular embodiment, the carrier protein is EPA-4 carrier protein, for instance EPA-4 carrier protein comprising the amino acid sequence of SEQ ID NO: 3.

In a particular embodiment, provided herein is a composition (e.g., pharmaceutical and/or immunogenic composition) comprising: (i) a bioconjugate of an *E. coli* glucosylated O4 antigen polysaccharide covalently linked to a detoxified Exotoxin A of *P. aeruginosa* carrier protein comprising SEQ ID NO: 3 (EPA-4 carrier protein), wherein the *E. coli* glucosylated O4 antigen polysaccharide comprises the structure of Formula (O4-Glc+); (ii) a bioconjugate of an *E. coli* O1A antigen polysaccharide covalently linked to an EPA-4 carrier protein, wherein the *E. coli* O1A antigen polysaccharide comprises the structure of Formula (O1A); (iii) a bioconjugate of an *E. coli* O2 antigen polysaccharide covalently linked to an EPA-4 carrier protein, wherein the *E. coli* O2 antigen polysaccharide comprises the structure of Formula (O2); (iv) a bioconjugate of an *E. coli* O6A antigen polysaccharide covalently linked to an EPA-4 carrier protein, wherein the *E. coli* O6A antigen polysaccharide comprises the structure of Formula (O6A); (v) a bioconjugate of an *E. coli* O8 antigen polysaccharide covalently linked to an EPA-4 carrier protein, wherein the *E. coli* O8 antigen polysaccharide comprises the structure of Formula (O8); (vi) a bioconjugate of an *E. coli* O15 antigen polysaccharide covalently linked to an EPA-4 carrier protein, wherein the *E. coli* O15 antigen polysaccharide comprises the structure of Formula (O15); (vii) a bioconjugate of an *E. coli* O16 antigen polysaccharide covalently linked to an EPA-4 carrier protein, wherein the *E. coli* O16 antigen polysaccharide comprises the structure of Formula (O16); (viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* O75 antigen polysaccharide covalently linked to an EPA-4 carrier protein, wherein the *E. coli* O75 antigen polysaccharide comprises the structure of Formula (O75), wherein each of the Formulas is provided in Table 1, and for each of the Formulas independently n is an integer of 1 to 100, e.g. 1 to 50, preferably 3 to 50, e.g. 5 to 40.

In a particular embodiment, said composition (e.g. pharmaceutical and/or immunogenic composition) further comprises: (x) a bioconjugate of an *E. coli* O18A antigen polysaccharide covalently linked to an EPA-4 carrier protein, wherein the *E. coli* O18A antigen polysaccharide comprises the structure of Formula (O18A) as shown in Table 1, wherein n for this structure is an integer of 1 to 100, e.g. 1 to 50, preferably 3 to 50, e.g. 5 to 40.

In some embodiments, a composition provided herein comprises a biconjugate of an *E. coli* glucosylated O4 antigen polysaccharide, and at least a bioconjugate of an *E. coli* O25B antigen polysaccharide, wherein the bioconjugate of the *E. coli* O25B antigen polysaccharide is present in the composition at a concentration that is about 1.5 to 6 times, e.g. about 2 to 4 times higher, such as 1.5, 2, 3, 4, 5 or 6 times higher than the concentration of any of the other bioconjugates present in the composition.

In particular embodiments, a composition comprises bioconjugates of *E. coli* O1A, O2, glucosylated O4, O6A, O8, O15, O16, O25B, and O75 antigen polysaccharides, wherein the bioconjugates of O1A:O2:glucosylated O4:O6A:O8:O15:O16:O25B:O75 are present in a ratio (by weight of O-antigen polysaccharide) of 1:1:1:1:1:1:1:2:1, or 2:1:1:2:1:1:1:4:1.

In particular embodiments, a composition comprises bioconjugates of *E. coli* O1A, O2, glucosylated O4, O6A, O8, O15, O16, O18A, O25B, and O75 antigen polysaccharides, wherein the bioconjugates of O1A:O2:glucosylated O4:O6A:O8:O15:O16:O18A:O25B:O75 are present in a ratio (by weight of O-antigen polysaccharide) of 1:1:1:1:1: 1:1:1:2:1, or 2:1:1:2:1:1:1:1:4:1.

In some embodiments, a composition provided herein comprises a bioconjugate of an *E. coli* glucosylated O4 antigen polysaccharide, and at least a bioconjugate of an *E. coli* O25B antigen polysaccharide, wherein the bioconjugate of the *E. coli* O25B antigen polysaccharide is present in the composition at a concentration of 2 to 50 μg/mL, preferably 8 to 40 μg/mL, more preferably 16-32 μg/mL, such as 16, 18, 20, 22, 24, 26, 28, 30, or 32 μg/mL. In such embodiments, the concentration of the bioconjugate of the *E. coli* O25B antigen polysaccharide is preferably about 1.5 to 6 times, e.g., about 2 to 4 times higher, such as 1.5, 2, 3, 4, 5, or 6 times higher than the concentration of any of the other bioconjugates present in the composition.

In certain embodiments, the compositions described herein (e.g., pharmaceutical and/or immunogenic compositions) comprise, or are administered in combination with, an adjuvant. The adjuvant for administration in combination with a composition described herein may be administered before (e.g. within 72 hours, 48 hours, 24 hours, 12 hours, 6 hours, 2 hours, 1 hour, 10 minutes), concomitantly with, or after (e.g. within 72 hours, 48 hours, 24 hours, 12 hours, 6 hours, 2 hours, 1 hour, 10 minutes) administration of said composition. As used herein, the term "adjuvant" refers to a compound that when administered in conjunction with or as part of a composition described herein augments, enhances and/or boosts the immune response to an *E. coli* O-antigen polysaccharide in a bioconjugate, but when the adjuvant compound is administered alone does not generate an immune response to the *E. coli* O-antigen polysaccharide in the bioconjugate. In some embodiments, the adjuvant enhances an immune response to an *E. coli* O-antigen polysaccharide in a bioconjugate thereof and does not produce an allergy or other adverse reaction. Adjuvants can enhance an immune response by several mechanisms including, e.g., lymphocyte recruitment, stimulation of B and/or T cells, and stimulation of macrophages.

Examples of suitable adjuvants include, but are not limited to, aluminum salts (alum) (such as aluminum hydroxide, aluminum phosphate, aluminum sulfate and aluminum oxide, including nanoparticles comprising alum or nanoalum formulations), calcium phosphate, monophosphoryl lipid A (MPL) or 3-de-O-acylated monophosphoryl lipid A (3D-MPL) (see e.g., United Kingdom Patent GB2220211, EP0971739, EP1194166, U.S. Pat. No. 6,491,919), AS01, AS02, AS03 and AS04 (all GlaxoSmithKline; see e.g. EP1126876, U.S. Pat. No. 7,357,936 for AS04, EP0671948, EP0761231, U.S. Pat. No. 5,750,110 for AS02), MF59 (Novartis), imidazopyridine compounds (see WO2007/109812), imidazoquinoxaline compounds (see WO2007/109813), delta-inulin, STING-activating synthetic cyclic-dinucleotides (e.g. US20150056224), combinations of lecithin and carbomer homopolymers (e.g. U.S. Pat. No. 6,676,958), and saponins, such as QuilA and QS21 (see e.g. Zhu D and W Tuo, 2016, Nat Prod Chem Res 3: e113 (doi:10.4172/2329-6836.1000e113), Matrix M, Iscoms, Iscomatrix, etc, optionally in combination with QS7 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Further examples of adjuvants are liposomes containing immune stimulants such as MPL and QS21 such as in AS01E and AS01B (e.g. US 2011/0206758). Other examples of adjuvants are CpG (Bioworld Today, Nov. 15, 1998) and imidazoquinolines (such as imiquimod and R848). See, e.g., Reed G, et al., 2013, *Nature Med,* 19: 1597-1608. In certain embodiments, the adjuvant contains a toll-like receptor 4 (TLR4) agonist. TLR4 agonists are well known in the art, see e.g. Ireton G C and S G Reed, 2013, Expert Rev Vaccines 12: 793-807. In certain embodiments, the adjuvant comprises a TLR4 agonist comprising lipid A, or an analog or derivative thereof, such as MPL, 3D-MPL, RC529 (e.g. EP1385541), PET-lipid A, GLA (glycopyranosyl lipid adjuvant, a synthetic disaccharide glycolipid; e.g. US20100310602, U.S. Pat. No. 8,722,064), SLA (e.g. Carter D et al, 2016, Clin Transl Immunology 5: e108 (doi: 10.1038/cti.2016.63), which describes a structure-function approach to optimize TLR4 ligands for human vaccines), PHAD (phosphorylated hexaacyl disaccharide), 3D-PHAD (the structure of which is the same as that of GLA), 3D-(6-acyl)-PHAD (3D(6A)-PHAD) (PHAD, 3D-PHAD, and 3D(6A)PHAD are synthetic lipid A variants, see e.g. avantilipids.com/divisions/adjuvants, which also provide structures of these molecules), E6020 (CAS Number 287180-63-6), ONO4007, OM-174, and the like.

In certain embodiments, the compositions described herein do not comprise, and are not administered in combination with, an adjuvant.

In certain embodiments, the compositions described herein are formulated to be suitable for the intended route of administration to a subject. For example, the compositions (e.g., pharmaceutical and/or immunogenic) described herein can be formulated for subcutaneous, parenteral, oral, sublingual, buccal, intradermal, transdermal, colorectal, intraperitoneal, rectal administration, intravenous, intranasal, intratracheal, intramuscular, topical, transdermal, or intradermal administration. In a specific embodiment, a composition provided herein (e.g., pharmaceutical and/or immunogenic) is formulated for intramuscular injection.

Methods of Use

Bioconjugates and compositions provided herein can be used to induce antibodies against an *E. coli* glucosylated O4 antigen in a subject, and to vaccinate a subject against *E. coli* in particular extra-intestinal pathogenic *E. coli* (ExPEC). As used herein, "subject" means any animal, preferably a mammal, to whom will be or has been administered a bioconjugate or composition provided herein. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc. In certain embodiments, a subject is a human. A human subject may be of any age. In certain embodiments, a subject is a human of about two months to about 18 years old, e.g. of 1 year to 18 years old. In certain embodiments, a subject is a human of at least 18 years old. In certain embodiments, a subject is a human of 15 to 50 years old, e.g. 18 to 45 years old, e.g. 20 to 40 years old. In certain embodiments, a subject is a human male. In certain embodiments, a subject is a human female. In certain embodiments, a subject is immunocompromised. In certain embodiments, a subject is a human of at least 50 years, at least 55 years, at least 60 years, at least 65 years old. In certain embodiments, a subject is a human that is not older than 100 years, not older than 95 years, not older than 90 years, not older than 85 years, not older than 80 years, or not older than 75 years. In certain embodiments, a subject is a human of at least 60 years old, and not older than 85 years old. In certain embodiments, a subject is a human in stable health. In certain embodiments, a subject is a human adult of at least 60 and not more than 85 years old in stable health. In certain embodiments, a subject is a human that has a history of a urinary tract infection (UTI, i.e. a bacterial infection in the urethra, bladder, ureters, and/or kidneys), i.e. having had at least one UTI episode in his or her life. In certain embodiments, a subject is a human that has a history of UTI in the past twenty, fifteen, twelve, ten, nine, eight, seven, six, five, four, three, two or one years. In certain embodiments, a subject is a human that has a history of UTI in the past two years. In certain embodiments, a subject is a human subject that has a history of recurrent UTI, i.e. having had at least two UTIs in six months or at least three UTIs in one year. In certain embodiments, a subject is a human subject that has a history of recurrent UTI in the past two years. In certain embodiments, a subject is a human of 60 years or older in stable health. In certain embodiments, a subject is a human of 60 years or older that has a history of UTI in the past two years. In certain embodiments, a subject is a human of at least 60 years and less than 75 years old that has a history of UTI in the past two years. In certain embodiments, a subject is a human subject of 75 years or older that has a history of UTI in the past two years. In certain embodiments, a subject is a patient scheduled for undergoing elective urogenital and/or abdominal procedures or surgeries, e.g. transrectal ultrasound-guided prostate needle biopsy (TRUS-PNB).

In one aspect, provided herein is a method of inducing antibodies against an *E. coli* glucosylated O4 antigen in a subject, comprising administering to the subject any of the bioconjugates of an *E. coli* glucosylated O4 antigen covalently linked to a carrier protein described herein, or a composition comprising a bioconjugate of an *E. coli* glucosylated O4 antigen covalently linked to a protein, alone or further in combination with other *E. coli* O-antigen polysaccharides or glycoconjugates or bioconjugates thereof.

In certain embodiments, the antibodies induced, elicited or identified against an *E. coli* glucosylated O4 antigen have opsonophagocytic activity. In particular embodiments, the antibodies induced, elicited or identified are cross-reactive antibodies capable of mediating opsonophagocytic killing of both *E. coli* glucosylated and non-glucosylated O4 strains.

In certain embodiments, the antibodies induced, elicited or identified against an *E. coli* glucosylated O4 antigen specifically recognize unmodified and glucose modified O4 antigen polysaccharide. In certain embodiments, the antibodies induced, elicited or identified against an *E. coli* glucosylated O4 antigen specifically recognize *E. coli* of the O4 serotype. In certain embodiments, the antibodies induced by a bioconjugate of an *E. coli* glucosylated O4 antigen bind preferentially to glucosylated O4 antigen as compared to non-glucosylated O4 antigen.

Antibodies induced by the bioconjugates and compositions described herein can include immunoglobulin molecules and immunologically active portions of immunoglobulin molecules, i.e., molecules that contain an antigen binding site that specifically binds to an *E. coli* O-antigen polysaccharide, e.g., glucosylated O4 antigen polysaccharide.

Antibodies induced, elicited or identified using the bioconjugates or compositions provided herein can be used to monitor the efficacy of a therapy and/or disease progression. Any immunoassay system known in the art can be used for this purpose including, but not limited to, competitive and noncompetitive assay systems using techniques such as radioimmunoassays, ELISA (enzyme linked immunosorbent assays), electrochemiluminescence (ECL)-based immunoassays, "sandwich" immunoassays, precipitin reactions, gel diffusion precipitin reactions, immunodiffusion assays, immunoradiometric assays, fluorescent immunoassays, protein A immunoassays and immunoelectrophoresis assays. Several of these assays, e.g. ECL-based immunoassays, can be done in multiplex format, and typically multiplex assay formats are preferred.

Antibodies induced, elicited or identified using a bioconjugate of an *E. coli* glucosylated O4 antigen polysaccharide can be used to detect *E. coli* O4 strains, particularly glucosylated O4 strains, for example, from a plurality of *E. coli* strains and/or to diagnose an infection by an *E. coli* O4 or glucosylated O4 strain.

In another aspect, provided herein is a method of vaccinating a subject against *E. coli* (e.g. extra-intestinal pathogenic *E. coli*, ExPEC), comprising administering to the subject any of the bioconjugates of an *E. coli* glucosylated O4 antigen covalently linked to a carrier protein described herein, or a composition comprising a bioconjugate of an *E. coli* glucosylated O4 antigen covalent linked to a carrier protein, alone or further in combination with other *E. coli* O-antigens or glycoconjugates or bioconjugates thereof. One skilled in the art will understand that the subject will be vaccinated against *E. coli* strains whose O antigens or glycoconjugates or bioconjugates thereof are present in the composition administered. For example, administration of a composition comprising O1A, O2, glucosylated O4, O6A, and O25B antigen polysaccharides can be used to a vaccinate a subject against *E. coli* serotypes O1A, O2, O4, O6A, and O25B.

In certain embodiments, vaccination is for preventing an invasive ExPEC disease (IED), e.g., urosepsis, bacteremia, sepsis, etc. In certain embodiments, vaccination is to prevent or reduce the occurrence or severity of urinary tract infections. In certain embodiments, an IED can be hospital-acquired, e.g. in patients undergoing urogenital and/or abdominal procedures or surgeries. In certain embodiments, an IED can be healthcare-associated, e.g. in patients receiving health care for another condition, for instance via central lines, catheters, etc, e.g. in a hospital, ambulatory surgical center end-stage renal disease facility, long-term care facility, etc. In certain embodiments, the IED can be community-acquired, e.g. in a patient that was not recently exposed to healthcare risks.

In another aspect, provided herein is a method of inducing an immune response against *E. coli* (e.g., ExPEC) in a subject, comprising administering to the subject any of the bioconjugates of an *E. coli* glucosylated O4 antigen covalently linked to a carrier protein described herein, or a composition comprising a bioconjugate of an *E. coli* glucosylated O4 antigen covalently linked to a carrier protein, alone or further in combination with other *E. coli* O-antigens or glycoconjugates or bioconjugates thereof. In one embodiment, the subject has an *E. coli* (e.g., ExPEC) infection at the time of administration. In a preferred embodiment, the subject does not have an *E. coli* (e.g., ExPEC) infection at the time of administration.

In certain embodiments, the compositions and bioconjugates described herein can be administered to a subject to induce an immune response that includes the production of antibodies, preferably antibodies having opsonophagocytic activity. Such antibodies can be isolated using techniques known to one of skill in the art (e.g., immunoaffinity chromatography, centrifugation, precipitation, etc.).

The ability of the bioconjugates and compositions described herein to generate an immune response in a subject can be assessed using any approach known to those of skill in the art or described herein. In some embodiments, the ability of a bioconjugate to generate an immune response in a subject can be assessed by immunizing a subject (e.g., a mouse, rat, rabbit, or monkey) or set of subjects with a bioconjugate described herein and immunizing an additional subject (e.g., a mouse, rat, rabbit, or monkey) or set of subjects with a control (PBS). The subjects or set of subjects can subsequently be challenged with ExPEC and the ability of the ExPEC to cause disease (e.g., UTI, bacteremia, or other disease) in the subjects or set of subjects can be determined. Those skilled in the art will recognize that if the subject or set of subjects immunized with the control suffer(s) from disease subsequent to challenge with the ExPEC but the subject or set of subjects immunized with a bioconjugate(s) or composition thereof described herein suffer less from or do not suffer from disease, then the bioconjugate is able to generate an immune response in a subject. The ability of a bioconjugate(s) or composition thereof described herein to induce antiserum that cross-reacts with an O antigen from ExPEC can be tested by, e.g., an immunoassay, such as an ELISA (see e.g., Van den Dobbelsteen et al, 2016, Vaccine 34: 4152-4160), or an ECL-based immunoassay.

For example, the ability of the bioconjugates described herein to generate an immune response in a subject can be assessed using a serum bactericidal assay (SBA) or opsonophagocytic killing assay (OPK assay, or OPKA), which represents an established and accepted method that has been used to obtain approval of glycoconjugate-based vaccines. Such assays are well-known in the art and, briefly, comprise the steps of generating and isolating antibodies against a target of interest (e.g., an O antigen polysaccharide, e.g., *E. coli* glucosylated O4 antigen polysaccharide) by administering to a subject (e.g., a mouse, rat, rabbit, or monkey) a compound that elicits such antibodies. Subsequently, the bactericidal capacity of the antibodies can be assessed by, e.g., culturing the bacteria in question (e.g., *E. coli* of the relevant serotype) in the presence of the antibodies and complement and—depending on the assay—neutrophilic cells and assaying the ability of the antibodies to mediate killing and/or neutralization of the bacteria, e.g., using standard microbiological approaches. For an example of OPK assay for *E. coli* bioconjugate vaccines, see e.g. Abbanat et al, 2017, Clin. Vaccine Immunol. 24: e00123-17. An OPK assay can be performed in monoplex or multiplex format, of which multiplex format (e.g. testing multiple serotypes at the same time) is typically preferred. A multiplex OPK assay is sometimes referred to herein as 'MOPA'.

In some embodiments, the methods described herein comprise administering an effective amount of bioconjugates of an *E. coli* glucosylated O4 antigen covalently linked to a carrier protein described herein, or a composition comprising a bioconjugate of an *E. coli* glucosylated O4 antigen covalently linked to a carrier protein, alone or further in combination with other *E. coli* O-antigens or glycoconjugates or bioconjugates thereof. In one embodiment, an "effective amount" is an amount that vaccinates a subject against *E. coli* (e.g., ExPEC). In another embodiment, an "effective amount" is an amount that induces an immune response against *E. coli* (e.g., ExPEC) in a subject, such as an immune response including the production of antibodies, preferably antibodies having opsonophagocytic activity.

In particular embodiments, wherein a composition provided herein comprises a bioconjugate of an *E. coli* glucosylated O4 antigen polysaccharide and at least a bioconjugate of an *E. coli* O25B antigen polysaccharide, an effective amount of the *E. coli* O25B antigen polysaccharide is about 1.5 to 6 times, e.g. about 2 to 4 times higher, such as 1.5, 2, 3, 4, 5 or 6 times higher than the concentration of any of the other bioconjugates present in the composition. In such embodiments, an effective amount of the *E. coli* O25B antigen polysaccharide is for instance about 5 to 18 μg per administration, such as 5, 6, 7, 8, 9, 10, 11, 12, 13, 14, 15, 16, 17, 18 μg per administration.

In certain embodiments, a bioconjugate or composition according to the invention is administered to a subject once. In certain embodiments, a bioconjugate or composition according to the invention is administered to a subject more than once, e.g. in a prime-boost regimen. In certain embodiments, the time between two administrations is at least two weeks, at least one month, at least two months, at least three months, at least six months, at least one year, at least two years, at least five years, at least ten years, or at least fifteen years. In humans, a desired immune response can typically be generated by a single administration of a bioconjugate or composition according to the invention. In certain embodiments, a repeat administration after for instance ten years is provided.

Host Cells

Provided herein are host cells, e.g., prokaryotic host cells, capable of producing *E. coli* O antigens and bioconjugates comprising such *E. coli* O antigens. The host cells provided herein preferably are modified to comprise (e.g., through genetic engineering) one or more of the nucleic acids encoding host cell machinery (e.g., glycosyltransferases) used to produce *E. coli* O-antigen polysaccharides and/or bioconjugates thereof.

Any host cells known to those of skill in the art can be used to produce the *E. coli* O antigen polysaccharides described herein (e.g., *E. coli* glucosylated O4 antigen polysaccharide) and bioconjugates comprising the *E. coli* O antigen polysaccharides described herein (e.g., a bioconjugate of *E. coli* glucosylated O4 antigen polysaccharide) including archaea, prokaryotic host cells, and eukaryotic host cells. In a preferred embodiment, a host cell is a prokaryotic host cell. Exemplary prokaryotic host cells for use in production of the *E. coli* O antigen polysaccharides described herein and bioconjugates comprising the *E. coli* O antigen polysaccharides described herein include, but are not limited to, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species.

In a specific embodiment, the host cell used to produce the *E. coli* O antigen polysaccharides described herein and bioconjugates comprising the *E. coli* O antigen polysaccharides described herein is a prokaryotic host cell, and is preferably *E. coli.*

In certain embodiments, the host cells used to produce the *E. coli* O antigen polysaccharides and bioconjugates described herein are engineered to comprise heterologous nucleic acids, e.g., heterologous nucleic acids comprising rfb gene clusters of a desired O antigen serotype, heterologous nucleic acids that encode one or more carrier proteins and/or glycosyltransferases. In a specific embodiment, heterologous rfb genes, and/or heterologous nucleic acids that encode proteins involved in glycosylation pathways (e.g., prokaryotic and/or eukaryotic glycosylation pathways) can be introduced into the host cells described herein. Such nucleic acids can encode proteins including, but not limited to, oligosaccharyl transferases and/or glycosyltransferases.

Sequences of various genes and gene clusters encoding glycosyltransferases useful in making recombinant host cells that can, e.g., be used to prepare *E. coli* O antigen polysaccharides and bioconjugates thereof are described herein. Those skilled in the art will appreciate that due to the degeneracy of the genetic code, a protein having a specific amino acid sequence can be encoded by multiple different nucleic acids. Thus, those skilled in the art will understand that a nucleic acid provided herein can be altered in such a way that its sequence differs from a sequence provided herein, without affecting the amino acid sequence of the protein encoded by the nucleic acid.

Provided herein are host cells (e.g., recombinant host cells) for producing a bioconjugate of an *E. coli* glucosylated O4 antigen polysaccharide, O1A antigen polysaccharide, O2 antigen polysaccharide, O6A antigen polysaccharide, O8 antigen polysaccharide, O15 antigen polysaccharide, O16 antigen polysaccharide, O18A antigen polysaccharide, O25B antigen polysaccharide, or O75 antigen polysaccharide. The host cells provided herein comprise nucleic acids encoding enzymes (e.g., glycosyltransferases) capable of producing the *E. coli* O antigen polysaccharide. The host cells provided herein can naturally express nucleic acids capable of producing an O antigen of interest, or the host cells can be made to express such nucleic acids. In certain embodiments the nucleic acids are heterologous to the host cells and introduced into the host cells using genetic approaches known in the art. For example, the nucleic acids can be introduced into the host cell by genetic manipulation (e.g., the gene cluster is expressed on a plasmid or plasmids or integrated into the host cell genome (see, e.g., International Patent Application Publications WO 2014/037585, WO 2014/057109, WO 2015/052344).

In one embodiment, provided herein is a host cell (e.g., recombinant host cell) capable of producing a bioconjugate of an *E. coli* glucosylated O4 antigen polysaccharide covalently linked to a carrier protein. Such a host cell comprises, preferably by engineering a precursor cell, a nucleic acid sequence encoding a gtrS gene, which, to the best of the knowledge of the inventors, was identified herein for the first time as encoding a polysaccharide branching enzyme capable of transferring glucose to the *E. coli* O4 antigen (i.e., a glucosyltransferase specific to the *E. coli* O4 antigen polysaccharide), and particularly to L-Rha via an α-1,3-glycosidic linkage. An example of an amino acid sequence of such branching enzyme is provided in SEQ ID NO: 4. Other examples comprise amino acid sequences that are at least 80% identical thereto. Exemplary examples of nucleic acid sequence encoding gtrS genes specific to the *E. coli* O4 antigen polysaccharide include, but are not limited to, SEQ ID NO: 5, or degenerate nucleic acid sequences thereto that encode SEQ ID NO: 4, or nucleic acid sequences that encode functional O4-specific GtrS enzymes that have at least 80% identity to SEQ ID NO: 4.

In a specific embodiment, a host cell (e.g., recombinant host cell) capable of producing a bioconjugate of an *E. coli* glucosylated O4 antigen polysaccharide covalently linked to a carrier protein, comprises a nucleotide sequence encoding a glucosyl transferase having at least 80% sequence identity to SEQ ID NO: 4, such as about 80%, 85%, 90%, 91%, 92%, 93%, 94%, 95%, 95%, 97%, 98%, 99%, or 100% sequence identity to SEQ ID NO: 4. In view of the redundancy in the genetic code, one of ordinary skill in the art can make variants of nucleic encoding the amino acid sequences of glucosyl transferases, e.g., using codon optimized sequences, if desired.

In certain embodiments, a host cell (e.g., recombinant host cell) capable of producing a bioconjugate of an *E. coli* glucosylated O4 antigen polysaccharide covalently linked to a carrier protein, comprising a nucleotide sequence encoding a glucosyl transferase (GtrS) having at least 80% sequence identity to SEQ ID NO: 4, further comprises a nucleotide sequence encoding a bactoprenol-linked glucose translocase (GtrA) having at least 80% sequence identity to SEQ ID NO: 7, and a nucleotide sequence encoding a bactoprenol glucosyl transferase (GtrB) having at least 80% sequence identity to SEQ ID NO: 8. In certain embodiments, said nucleic acid sequences encode GtrA and GtrB proteins that are at least about 80%, 85%, 90%, 95%, 96%, 97%, 98%, 99%, or 100% identical to SEQ ID NOs: 7 and 8, respectively, and have bactoprenol-linked glucose translocase (SEQ ID NO: 7) and bactoprenol glucosyl transferase (SEQ ID NO: 8) activity, respectively. In view of the redundancy in the genetic code, one of ordinary skill in the art can make variants of nucleic encoding the amino acid sequences of bactoprenol-linked glucose translocases and of bactoprenol glucosyl transferases, e.g., using codon optimized sequences, if desired.

A host cell (e.g., recombinant host cell) capable of producing a bioconjugate of an *E. coli* glucosylated O4 antigen polysaccharide covalently linked to a carrier protein provided herein further comprises a nucleotide sequence of an rfb gene cluster for the *E. coli* O4 antigen polysaccharide. An example of an rfb gene cluster useful for production of the *E. coli* O4 antigen polysaccharide is provided herein as SEQ ID NO: 9. Another example can be found in GenBank, locus AY568960. Degenerate nucleic acid sequences encoding the same enzymes as encoded by this sequence, or sequences that encode enzymes that are at least 80% identical, preferably at least 85%, 90%, 91%, 92%, 93%, 94%, 95%, 96%, 97%, 98%, 99% identical, can also be used.

In a specific embodiment, provided herein is a host cell (e.g., a recombinant host cell, preferably a recombinant prokaryotic host cell, preferably a recombinant *E. coli* host cell) that produces glucosylated O4 antigen polysaccharide, wherein the host cell comprises gtrS, an rfb gene cluster for the *E. coli* O4 antigen polysaccharide, and nucleic acid encoding a carrier protein. Such host cells can be engineered using recombinant approaches to comprise one or more plasmids comprising the gtrS gene, the rfb gene cluster, and/or nucleic acid encoding a carrier protein, or to comprise some or all of the relevant genes such as gtrS, the rfb cluster and/or the nucleic acid encoding the carrier protein integrated into the host cell genome. In certain embodiments, the genes or gene clusters have been integrated into the genome of the host cell using homologous recombination. An advantage of integration of genes into the genome of the host cell is stability in the absence of antibiotic selection.

In another specific embodiment, provided herein is a host cell (e.g., a recombinant host cell, preferably a recombinant prokaryotic host cell) that produces glucosylated O4 antigen polysaccharide, wherein the host cell comprises GtrS (glucosyltransferase), as well as the enzymes encoded by the O4 rfb cluster. In certain embodiments, some or all of the aforementioned enzymes are heterologous to the host cell.

In other specific embodiments, provided herein is a host cell (e.g. a recombinant host cell, preferably a recombinant prokaryotic host cell) that produces *E. coli* glucosylated O4 antigen polysaccharide, preferably a bioconjugate of *E. coli* glucosylated O4 antigen polysaccharide, wherein the host cell further comprises a nucleotide sequence encoding an oligosaccharyl transferase and/or a nucleotide sequence encoding a carrier protein. In one specific embodiment, the oligosaccharyl transferase is heterologous to the host cell. In another specific embodiment, the carrier protein is heterologous to the host cell. Preferably, the host cell comprises a heterologous nucleotide sequence encoding a glucosyl transferase having at least 80% sequence identity to SEQ ID NO: 4. In preferred embodiments, the rfb genes of the O4 cluster are heterologous to the host cell. Preferably the sequence encoding the enzyme that is capable of introducing the branched glucose side chain to the O4 antigen, i.e. the gtrS gene (encoding a glucosyl transferase having at least 80% sequence identity to SEQ ID NO:4) is heterologous to the host cell. A nucleic acid is heterologous to the host cell if the same sequence is not naturally present in said host cell. Heterologous nucleic acid can for instance be introduced in a parent cell by genetic engineering, e.g by transformation (e.g. chemical transformation or electroporation) and/or recombination. In certain embodiments, heterologous nucleic acid such as a desired rfb locus, gtrS coding sequence, carrier protein encoding sequence, and/or glycosyltransferase encoding sequence are integrated into the genome of the host cell, preferably a bacterial host cell, preferably an *E. coli* host cell. In preferred embodiments, the endogenous rfb locus and if applicable gtrS coding sequence have been inactivated, preferably deleted from the genome of the recombinant host cell as compared to a predecessor thereof, and preferably these are replaced by the desired heterologous rfb locus, and if applicable desired gtrS coding sequence, respectively. In certain embodiments the host cell is a K-12 of *E. coli* (as a non-limiting example, *E. coli* strain W3110 is a K-12 strain), or a B strain of *E. coli* (as a non-limiting example, *E. coli* strain BL21 is a B strain), or any other well-defined strain of *E. coli*, e.g. laboratory strains or production strains, in contrast to primary wild-type isolates. In preferred embodiments, the host cell is derived from *E. coli* that does not express O4 antigen or glucosylated O4 antigen, by introduction into such *E. coli* of the O4 rfb locus and the gtrS gene encoding a glucosyl transferase having at least 80% sequence identity to SEQ ID NO:4. Advantages of using well-characterized strains, such as *E. coli* K-12 or *E. coli* B, as precursors for host cells is the possibility to use a similar production process for different O-antigen bioconjugates, since the characteristics of the production strain are well-defined. Even though bioconjugates of different O-antigens will behave differently and expression processes can be optimized per production strain, at least the basic process for production of O-antigen bioconjugates will be more predictable using such well-defined precursor strains than when unknown strains such as wild-type isolates are used as precursors for production of host strains. This way, experience with production of earlier described *E. coli* O-antigen bioconjugates such as O1A, O2, O6A and O25B bioconjugates as described in for instance WO 2015/124769 and WO 2017/035181 can be used as basis to design production of other *E. coli* O-antigen bioconjugates. Unlike gtrS, the gtrA and gtrB genes are not serotype-specific, and in certain embodiments these are homologous to the host cell (e.g. *E. coli* K12 strain W3110 includes gtrA and gtrB genes that are capable of functioning together with the O4-serotype specific recombinantly introduced gtrS gene encoding a glucosyl transferase of SEQ ID NO: 4 or a glucosyl transferase that is at least 80% identical thereto, replacing the endogenous gtrS gene). In other embodiments, one or both of gtrA and gtrB genes (encoding GtrA and GtrB proteins that are at least about 80% identical to SEQ ID NOs: 7 and 8, respectively, and having bactoprenol-linked glucose translocase and bactoprenol glucosyl transferase activity respectively, are also recombinantly introduced in the host cell, for instance in case the host cell does not have endogenous gtrA and/or gtrB genes.

Also provided herein are host cells (e.g., recombinant host cells) capable of producing a bioconjugate of an *E. coli* O1A, O2, O6A, O8, O15, O16, O18A, O25B, or O75 antigen polysaccharide covalently linked to a carrier protein. Such host cells (e.g., recombinant host cells) comprise nucleotide sequence of an rfb gene cluster specific to the O-antigen polysaccharide. The rfb gene clusters can be isolated from wild-type *E. coli* strains, and combined with nucleic acids encoding an oligosaccharyl transferase (e.g., PglB) and carrier protein (e.g., EPA) within one host cell to obtain a recombinant host cell that produces the *E. coli* O-antigen of interest or bioconjugate thereof. For example, such host cells can be engineered using recombinant approaches to comprise one or more plasmids comprising the rfb gene cluster, oligosaccharyl transferase (e.g., PglB) and carrier protein (e.g., EPA) using bioconjugation technology such as that described in WO 2014/037585, WO 2009/104074, and WO 2009/089396. Preferably the host cells comprise the rfb gene clusters integrated into their genome. The nucleic acids encoding oligosaccharyl transferase, carrier protein, and where applicable gtrS gene, are in certain embodiments also integrated into the genome of the host cell. Heterologous or homologous gtrA and gtrB genes are in certain embodiments also integrated into the genome of the host cell.

Preparation of bioconjugates for O1A, O2, O6A and O25B antigens has been described in detail in WO 2015/124769 and WO 2017/035181. Exemplary gene clusters for each *E. coli* O antigen (rfb loci) have been described in Iguchi A, et al, DNA Research, 2014, 1-7 (doi: 10.1093/dnares/dsu043), and in DebRoy C, et al, PLoS One. 2016, 11(1):e0147434 (doi: 10.1371/journal.pone.0147434; correction in: Plos One. 2016, 11(4):e0154551, doi: 10.1371/journal.pone.0154551). Nucleic acid sequences for the rfb clusters and amino acid sequences for proteins encoded therein can also be found in public databases, such as GenBank. Exemplary sequences for rfb clusters that can be used in production strains for bioconjugates with polysaccharide antigens of the serotypes disclosed herein, are also provided in SEQ ID NOs: 9 and 11-19. Thus, for each of the desired bioconjugates mentioned above, the respective rfb cluster can be introduced into a host cell, to obtain host cells with the specific rfb cluster for the desired O-antigen, as well as containing nucleic acid encoding oligosaccharyltransferase and carrier protein. For reasons indicated above, preferably the host cells are recombinant host cells, and preferably are derived from strains with relatively well-known characteristics, such as *E. coli* laboratory or production strains, e.g. *E. coli* K12 or *E. coli* BL21, etc. Preferably, the rfb clusters are heterologous to the host cell, e.g. introduced into a precursor cell of the host cell, and preferably integrated into the genome thereof. Preferably an original rfb gene cluster, if such was present in a precursor cell, has been replaced by the rfb gene cluster for the O-antigen of interest in the host cell, to enable production of bioconjugate of the O-antigen of interest. Preferably the oligosaccharyltransferase is heterologous to the host cell, and in certain embodiments nucleic acid encoding such oligosaccharyltransferase is integrated into the genome of the host cell.

Any of the host cells provided herein (e.g., recombinant host cells, preferably recombinant prokaryotic host cells) comprise nucleic acids encoding additional enzymes active in the N-glycosylation of proteins, e.g., the host cell provided herein can further comprise a nucleic acid encoding an oligosaccharyl transferase or nucleic acids encoding other glycosyltransferases.

The host cells provided herein comprise a nucleic acid that encodes an oligosaccharyl transferase. Oligosaccharyl transferases transfer lipid-linked oligosaccharides to asparagine residues of nascent polypeptide chains that comprise an N-glycosylation consensus motif. The nucleic acid that encodes an oligosaccharyl transferase can be native to the host cell, or can be introduced into the host cell using genetic approaches. In preferred embodiments, the oligosaccharyl transferase is heterologous to the host cell. *E. coli* does not naturally comprise an oligosaccharyl transferase, and hence if *E. coli* is used as a host cell for production of bioconjugates, a heterologous oligosaccharyl transferase is comprised in such host cell, e.g. upon introduction by genetic engineering. The oligosaccharyl transferase can be from any source known in the art in view of the present disclosure.

In certain embodiments, an alternative to an oligosaccharyl transferase with N-glycosyltransferase activity, such as an O-glycosyltransferase, e.g. as a non-limiting example PglL, can be used, in conjunction with its own, different, glycosylation consensus sequence in the carrier protein, as for instance described in WO 2016/82597. Other glycosyltransferases, such as O-glycosyltransferases, can thus also be used as an oligosaccharyltransferase according to the invention.

In certain preferred embodiments, the oligosaccharyl transferase is an oligosaccharyl transferase from *Campylobacter*. For example, in one embodiment, the oligosaccharyl transferase is an oligosaccharyl transferase from *Campylobacter jejuni* (i.e., pglB; see, e.g., Wacker et al., 2002, *Science* 298:1790-1793; see also, e.g., NCBI Gene ID: 3231775, UniProt Accession No. O86154). In another embodiment, the oligosaccharyl transferase is an oligosaccharyl transferase from *Campylobacter lari* (see, e.g., NCBI Gene ID: 7410986).

In specific embodiments, the oligosaccharyl transferase is PglB oligosaccharyl transferase from *Campylobacter jejuni*, including the natural (wild-type) protein or any variant thereof, such as those described in International Patent Application Publications WO 2016/107818 and WO 2016/107819. PglB can transfer lipid-linked oligosaccharides to asparagine residues in the consensus sequences SEQ ID NO: 1 and SEQ ID NO: 2. In particular embodiments, the PglB oligosaccharyl transferase comprises SEQ ID NO: 6, or a variant thereof. In certain embodiments one or more endogenous glycosylation consensus sequences in a wild-type PglB have been mutated to avoid PglB autoglycosylation, e.g. SEQ ID NO: 6 comprising the mutation N534Q. Examples of variant PglB oligosaccharyl transferases suitable for use in the recombinant host cells provided herein include the PglB oligosaccharyl transferase of SEQ ID NO: 6 comprising at least one mutation selected from the group consisting of N311V, K482R, D483H, A669V, Y77H, S80R, Q287P, and K289R. In one particular embodiment, a variant PglB oligosaccharyl transferase has SEQ ID NO: 6 comprising the mutation N311V. In another particular embodiment, a variant PglB oligosaccharyl transferase has SEQ ID NO: 6 comprising the mutations Y77H and N311V. In another particular embodiment, a variant PglB oligosaccharyl transferase has SEQ ID NO: 6 comprising the mutations N311V, K482R, D483H, and A669V. In another particular embodiment, a variant PglB oligosaccharyl transferase has SEQ ID NO: 6 comprising the mutations Y77H, S80R, Q287P, K289R, and N311V. It was found and described herein that certain PglB oligosaccharyl transferase variants give surprisingly improved yields in production of *E. coli* O-antigen bioconjugates of specific serotypes. The improved or optimal PglB variant for a given *E. coli* O-antigen was not predictable. The invention in certain aspects therefore also provides methods for producing bioconjugates of specific *E. coli* O-antigens, using specific PglB variants as the oligosaccharyl transferase. Further variants of PglB that are at least 80%, 85%, 90%, 91%, 92%, 93%, 94%, 95%, 96%, 97%, 98%, 99% identical to SEQ ID NO: 6 and still have oligosaccharyl transferase activity, preferably having one or more of the specific amino acids on the indicated positions disclosed in combination herein (e.g. 77Y, 80S, 287Q, 289K, 311N, 482K, 483D, 669A; or 311V; or 311V, 482R, 483H, 669V; or 77H, 80R, 287P, 289R, 311V; or 77H, 311V; etc) can also be used for production of bioconjugates.

In a specific embodiment, a host cell (e.g., recombinant host cell) capable of producing a bioconjugate of an *E. coli* glucosylated O4 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V, or more preferably SEQ ID NO: 6 comprising the mutations Y77H and N311V.

In other specific embodiments, a host cell (e.g., recombinant host cell) capable of producing a bioconjugate of an *E. coli* O1A, O6A, or O15 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations N311V, K482R, D483H, and A669V.

In a specific embodiment, a host cell (e.g., recombinant host cell) capable of producing a bioconjugate of an *E. coli* O16 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations Y77H, S80R, Q287P, K289R, and N311V.

In a specific embodiment, a host cell (e.g., recombinant host cell) capable of producing a bioconjugate of an *E. coli* O75 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V.

In a specific embodiment, a host cell (e.g., recombinant host cell) capable of producing a bioconjugate of an *E. coli* O8, O18A, O25B, or O2 antigen polysaccharide covalently linked to a carrier protein further comprises a nucleotide sequence encoding PglB oligosaccharyl transferase from *Campylobacter jejuni* having the amino acid sequence of SEQ ID NO: 6, preferably wherein SEQ ID NO: 6 comprises no amino acid mutations at positions 77, 80, 287, 289, 311, 482, 483, and 669.

In some embodiments, any of the host cells provided herein comprise a nucleic acid encoding a carrier protein, e.g., a protein to which the O-antigen polysaccharide(s) produced by the host cell glycosylation machinery can be attached to form a bioconjugate. The host cell can comprise a nucleic acid encoding any carrier protein known to those skilled in the art in view of the present disclosure including, but not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae.*

In preferred embodiments, a host cell further comprises a nucleic acid encoding detoxified Exotoxin A of *P. aeruginosa* (EPA). Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably having the amino acid sequence of SEQ ID NO: 2. In a specific embodiment, a host cell further comprises a nucleic acid encoding EPA-4 carrier protein comprising SEQ ID NO: 3.

In certain embodiments, the carrier proteins used in the generation of the bioconjugates by the host cells described herein comprise a "tag," i.e., a sequence of amino acids that allows for the isolation and/or identification of the carrier protein. For example, adding a tag to a carrier protein can be useful in the purification of that protein and, hence, the purification of conjugate vaccines comprising the tagged carrier protein. Exemplary tags that can be used herein include, without limitation, histidine (HIS) tags (e.g., hexa-histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified. In other embodiments, the carrier protein does not comprise a tag.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia carotovorans* pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI). In one embodiment, the signal sequence comprises SEQ ID NO: 10. A signal sequence may be cleaved off after translocation of the protein to the periplasm and may thus no longer be present in the final carrier protein of a bioconjugate.

In certain embodiments, additional modifications can be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein). In certain embodiments, when nucleic acids are deleted from the genome of the host cells provided herein, they are replaced by a desirable sequence, e.g., a sequence that is useful for production of an O antigen polysaccharide or bioconjugate thereof.

Exemplary genes or gene clusters that can be deleted in host cells (and, in some cases, replaced with other desired nucleic acid sequences) include genes or gene clusters of host cells involved in glycolipid biosynthesis, such as waaL (see, e.g., Feldman et al., 2005, *PNAS USA* 102:3016-3021), the lipid A core biosynthesis cluster (waa), galactose cluster (gal), arabinose cluster (ara), colonic acid cluster (wc), capsular polysaccharide cluster, undecaprenol-p biosynthesis genes (e.g. uppS, uppP), und-P recycling genes, metabolic enzymes involved in nucleotide activated sugar biosynthesis, enterobacterial common antigen cluster (eca), and prophage O antigen modification clusters like the gtrABS cluster or regions thereof. In a specific embodiment, the host cells described herein are modified such that they do not produce any O antigen polysaccharide other than a desired O antigen polysaccharide, e.g., glucosylated O4 antigen polysaccharide.

In a specific embodiment, the waaL gene is deleted or functionally inactivated from the genome of a host cell (e.g., recombinant host cell) provided herein. The terms "waaL" and "waaL gene" refer to the O-antigen ligase gene encoding a membrane bound enzyme with an active site located in the periplasm. The encoded enzyme transfers undecaprenylphosphate (UPP)-bound O antigen to the lipid A core, forming lipopolysaccharide. Deletion or disruption of the endogenous waaL gene (e.g., ΔwaaL strains) disrupts transfer of the O-antigen to lipid A, and can instead enhance transfer of the O-antigen to another biomolecule, such as a carrier protein.

In another specific embodiment, one or more of the waaL gene, gtrA gene, gtrB gene, gtrS gene, and the rfb gene cluster is deleted or functionally inactivated from the original genome of a prokaryotic host cell provided herein.

In one embodiment, a host cell used herein is *E. coli* that produces a bioconjugate of glucosylated O4 antigen polysaccharide, wherein the waaL gene is deleted or functionally inactivated from the genome of the host cell, and a gtrS gene specific to *E. coli* O4 antigen polysaccharide is inserted. In certain embodiments for production strains for bioconjugates of the glucosylated O4 O-antigen, a gtrS gene encoding a glucosyl transferase having at least 80% sequence identity to SEQ ID NO:4 is inserted in the place of a gtrS gene of the parent strain, so as to replace the gtrS gene in that parent strain with the one that is responsible for glucosylation of the O4 antigen. An example of such a parent strain is *E. coli* K-12 strain W3110. The gtrA and gtrB genes can be homologous to the parent strain, or alternatively one or both of these genes can be heterologous to the parent strain. Typically, and unlike the gtrS gene, these gtrA and gtrB genes are not specific for the O-antigen structure.

Also provided herein are methods of making recombinant host cells. Recombinant host cells produced by the methods described herein can be used to produce bioconjugates of *E. coli* O antigens. The methods comprise introducing one or more recombinant nucleic acid molecules into a cell to produce the recombinant host cell. Typically, the recombinant nucleic acid molecules are heterologous. Any method known in the art in view of the present disclosure can be used to introduce recombinant nucleic acid molecules into a host cell. Recombinant nucleic acids can be introduced into the host cells described herein using any methods known to those of ordinary skill in the art, e.g., electroporation, chemical transformation, by heat shock, natural transformation, phage transduction, and conjugation. In specific embodiments, recombinant nucleic acids are introduced into the host cells described herein using a plasmid. For example, the heterologous nucleic acids can be expressed in the host cells by a plasmid (e.g., an expression vector). In another specific embodiment, heterologous nucleic acids are introduced into the host cells described herein using the method of insertion into the genome as for instance described in International Patent Application Publication WO 2014/037585, WO 2014/057109, or WO 2015/052344.

In one embodiment, a method of making a recombinant host cell for producing a bioconjugate of an *E. coli* glucosylated O4 antigen polysaccharide covalently linked to a carrier protein comprises introducing one or more recombinant nucleic acid molecules into a cell, preferably an *E. coli* cell, to produce the recombinant host cell. In such embodiments, the recombinant nucleic acid molecules introduced into the cell include (i) a nucleotide sequence of an rfb gene cluster for the *E. coli* O4 antigen polysaccharide; (ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide; (iii) a nucleotide sequence encoding a carrier protein; and (iv) a nucleotide sequence encoding an oligosaccharyl transferase capable of covalently linking the *E. coli* glucosylated O4 antigen polysaccharide to the carrier protein to produce the bioconjugate. In preferred embodiments, the nucleotide sequence encoding a glucosyl transferase having at least 80% sequence identity to SEQ ID NO: 4 replaces the endogenous gtrS gene. Deleting the endogenous gtrS has the advantage that it will not interfere with generation of the glucosylated O4 antigen polysaccharide structure. In certain embodiments, the nucleotide sequence of the rfb gene cluster for the *E. coli* O4 antigen polysaccharide replaces the endogenous rfb gene cluster of the parent strain that is used to make the recombinant host cell. If the cell does not yet encode gtrA and/or gtrB genes, nucleotide sequences encoding a translocase (gtrA) and a glycosyltransferase (gtrB), having at least 80% identity to SEQ ID NOs: 7 and 8, respectively, can be introduced into the cell. If the cell already encodes gtrA and gtrB genes (such as for instance the case in *E. coli* K-12 strain W3110), there is no need to introduce or change these genes.

In a specific embodiment, the glucosyl transferase (gtrS specific for adding glucose branch to O4 antigen) has SEQ ID NO: 4.

In a specific embodiment, the oligosaccharyl transferase is PglB from *C. jejuni*. In one such embodiment, the oligosaccharyl transferase comprises the amino acid sequence of SEQ ID NO: 6. In another such embodiment, the oligosaccharyl transferase comprises the amino acid sequence of SEQ ID NO: 6 comprising the mutation N311V. In another such embodiment, the oligosaccharyl transferase comprises the amino acid sequence of SEQ ID NO: 6 comprising the mutations Y77H and N311V.

In another specific embodiment, the carrier protein comprises at least one glycosylation site comprising a glycosylation consensus sequence having SEQ ID NO: 1, preferably SEQ ID NO: 2. In another specific embodiment, the carrier protein is EPA, preferably EPA-4, such as EPA-4 comprising SEQ ID NO: 3.

*E. coli* strains that are used routinely in molecular biology as both a tool and a model organism can for instance be used as parents for host cells in certain embodiments according to the invention. Non-limiting examples include *E. coli* K12 strains (for example, such as W1485, W2637, W3110, MG1655, DH1, DH5α, DH10, etc.), B strains (e.g. BL-21, REL606, etc.), C strains, or W strains. In one particular embodiment, the host strain is derived from parent strain W3110. This strain can for instance be obtained from the *E. coli* Genetic Stock Center at Yale. For more information on *E. coli*, see e.g. Ecoliwiki.net.

Methods of Producing Conjugates and Bioconjugates

Also provided are methods of producing glycoconjugates of the *E. coli* O antigen polysaccharides described herein. Glycoconjugates, including bioconjugates, can be prepared in vitro or in vivo, e.g., using the recombinant host cells described herein for production.

In some embodiments, glycoconjugates can be prepared by chemical synthesis, i.e., prepared outside of host cells (in vitro). For example, an *E. coli* O antigen polysaccharide can be conjugated to carrier proteins using methods known to those of ordinary skill in the art, including by means of using activation reactive groups in the polysaccharide/oligosaccharide as well as the carrier protein. See, e.g., Pawlowski et al., 2000, *Vaccine* 18:1873-1885; and Robbins, et al., 2009, *Proc Natl Acad Sci USA* 106:7974-7978), the disclosures of which are herein incorporated by reference. Such approaches comprise extraction of antigenic polysaccharides/oligosaccharides from host cells, purifying the polysaccharides/oligosaccharides, chemically activating the polysaccharides/oligosaccharides, and conjugating the polysaccharides/oligosaccharides to a carrier protein.

In some embodiments, the host cells described herein can be used to produce bioconjugates comprising an *E. coli* O antigen polysaccharide covalently linked to a carrier protein. Methods of producing such bioconjugates using host cells are known in the art. See, e.g., WO 2003/074687 and WO 2006/119987. Such methods comprise culturing any of the recombinant host cells described herein under conditions for production of the bioconjugate. Bioconjugates can be isolated, separated, and/or purified from recombinant host cells using any method known in the art in view of the present disclosure. For example, bioconjugates can be purified by any method known in the art for purification of a protein, for instance, by chromatography (e.g., ion exchange, anionic exchange, affinity, and sizing column chromatography), centrifugation, differential solubility, or by any other standard technique for the purification of proteins. See, e.g., methods described in WO 2009/104074. Further, the bioconjugates can be fused to heterologous polypeptide sequences to facilitate purification. The actual conditions used to purify a particular bioconjugate will depend, in part, on factors such as net charge, hydrophobicity, and/or hydrophilicity of the bioconjugate, and will be apparent to those skilled in the art. Preparation of bioconjugates for O1A, O2, O6A, and O25B, as well as vaccine compositions comprising these, have for instance been described in WO 2015/124769 and in WO 2017/035181.

Also provided are bioconjugates produced by the methods described herein, i.e., using the recombinant host cells described herein.

In some embodiments, a method of preparing a bioconjugate of an *E. coli* O-antigen polysaccharide covalently linked to a carrier protein comprises: (i) providing a recombinant host cell comprising (a) nucleotide sequence of an rfb gene cluster for the O-antigen polysaccharide; (b) a nucleotide sequence encoding a carrier protein, preferably EPA, comprising at least one glycosylation site comprising a glycosylation consensus sequence having SEQ ID NO: 1, preferably SEQ ID NO: 2, and more preferably comprising four glycosylation sites each comprising a glycosylation consensus sequence having SEQ ID NO: 2; and (c) nucleotide sequence encoding an oligosaccharyl transferase, for instance PglB oligosaccharyl transferase or variant thereof.

In certain embodiments, *E. coli* O-antigen polysaccharides produced using the recombinant host cells described herein are covalently bound to the carrier protein at a particular polysaccharide to protein ratio by weight (w/w). This ratio of amount of O-antigen polysaccharide by weight covalently bound to the carrier protein by weight is referred to as the "glycan/protein ratio" or "polysaccharide/protein ratio" or "PS/protein ratio". In some embodiments, the O-antigen polysaccharide is covalently bound to the carrier protein at a polysaccharide to protein (w/w) ratio of about 1:20 to 20:1, preferably 1:10 to 10:1, more preferably 1:3 to 3:1. In certain non-limiting embodiments for bioconjugates described herein, glycan/protein ratio is about 0.1 to 0.5, such as 0.1, 0.15, 0.2, 0.25, 0.3, 0.35, 0.4, 0.45, or 0.5. In such embodiments, the weight ratio of the O-antigen polysaccharide:protein is about 1:10 to 1:2, such as 1:10:1:9:1:8, 1:7, 1:6, 1:5, 1:4, 1:3, or 1:2, depending on the particular O-antigen serotype. In certain embodiments the glycan/protein ratio is from about 0.15 to about 0.45. In general, a higher glycan/protein ratio of O-antigen polysaccharide to carrier protein is preferred, because a high amount of carrier protein can lead to immunological interference in some instances. Also, a higher glycan/protein ratio would help getting sufficient O-antigen polysaccharide dosed in the form of bioconjugate, while keeping the amount of carrier protein relatively low, which is especially beneficial for multivalent compositions where multiple serotypes are to be covered by the composition, e.g. compositions comprising bioconjugates from at least 4 different O-antigens, at least 5 different O-antigens, at least 6 different O-antigens, at least 7 different O-antigens, at least 8 different O-antigens, at least 9 different O-antigens, at least 10 different O-antigens, etc.

A glycan/protein ratio of a conjugate according to the invention can be determined by determining the protein amount and the glycan amount. Protein amount can be determined by measurement of UV absorbance at 280 nm (A280). Glycan amount can be determined based on ion chromatography with pulsed amperometric detection (IC-PAD) of a sugar in the repeat unit (e.g. of Man for O8 in Table 1, and of GlcNAc for the other glycans in Table 1), after which the structural information of the repeat unit can be used to calculate the total glycan amount (e.g. the repeat unit of O1A has a molar mass of 845 Da and one mole of such a repeat unit contains one mole of GlcNAc, enabling calculation of the total glycan amount when the amount of GlcNAc has been determined by IC-PAD).

In some embodiments, a bioconjugate of an *E. coli* O25B antigen polysaccharide covalently linked to a carrier protein produced using a recombinant host cell according to the cells and methods described herein has a certain degree of acetylation at position 2 of the L-Rh sugar. The degree of O-acetylation of O25B antigen polysaccharide in a bioconjugate is preferably at least 30%, preferably at least 50%, such as at least 50%, 55%, 60%, 65%, 70%, 75%, 80%, 85%, 90%, 95%, or 100%.

Similarly, the degree of O-acetylation of an *E. coli* O16 antigen polysaccharide in a bioconjugate is preferably at least 30%, preferably at least 50%, such as at least 50%, 55%, 60%, 65%, 70%, 75%, 80%, 85%, 90%, 95%, or 100%.

In specific embodiments, a method of preparing a bioconjugate of an O-antigen polysaccharide comprises providing a recombinant host cell comprising nucleic acid sequence encoding a particular oligosaccharyl transferase enzyme, particularly a PglB oligosaccharyl transferase or variant thereof, depending on the O-antigen polysaccharide bioconjugate to be produced. The particular oligosaccharyl transferase enzyme variant may impact the yield of bioconjugate produced by the host cell. Typically, a higher yield is preferred, since the yield will impact the costs for producing a specific bioconjugate, which is especially important for multivalent compositions comprising several different bioconjugates. In some embodiments, the method further comprises isolating the bioconjugate from the recombinant host cell.

In one particular embodiment, when the O-antigen is O1A, O6A, or O15 antigen polysaccharide, the PglB oligosaccharyl transferase comprises the amino acid mutations of N311V, K482R, D483H, and A669V, wherein the amino acid mutations are relative to the wild-type PglB having the amino acid sequence of SEQ ID NO: 6.

In another particular embodiment, when the O-antigen is glucosylated O4 antigen polysaccharide, the PglB oligosaccharyl transferase comprises the amino acid mutation N311V, or the amino acid mutations of Y77H and N311V, wherein the amino acid mutations are relative to the wild-type PglB having the amino acid sequence of SEQ ID NO: 6.

In another particular, embodiment, when the O-antigen is O16 antigen polysaccharide, the PglB oligosaccharyl transferase comprises the amino acid mutations of Y77H, S80R, Q287P, K289R, and N311V, wherein the amino acid mutations are relative to the wild-type PglB having the amino acid sequence of SEQ ID NO: 6.

In another particular embodiment, when the O-antigen is O75 antigen polysaccharide, the PglB oligosaccharyl transferase comprises the amino acid mutation of N311V, wherein the amino acid mutations are relative to the wild-type PglB having the amino acid sequence of SEQ ID NO: 6.

In another particular embodiment, when the O-antigen is O8, O18A, O25B, or O2 antigen polysaccharide, the PglB oligosaccharyl transferase comprises the amino acid sequence of SEQ ID NO: 6, wherein SEQ ID NO: 6 comprises no amino acid mutations at positions 77, 80, 287, 289, 311, 482, 483, and 669. In certain embodiments thereof, the PglB oligosaccharyl transferase comprises the amino acid sequence of SEQ ID NO: 6.

In some embodiments, the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae.*

In certain embodiments, the carrier protein is detoxified exotoxin A of *Pseuodomonas aeruginosa* (EPA). Preferably, the EPA carrier protein comprises 1-10, preferably 2-4, more preferably 4 glycosylation sites. Preferably, each glycosylation site comprises a glycosylation consensus sequence having the amino acid sequence of SEQ ID NO: 2. In a specific embodiment, a host cell comprises a nucleic acid encoding EPA-4 carrier protein comprising SEQ ID NO: 3.

In certain embodiments, the recombinant host cell is an *E. coli* cell, e.g., an *E. coli* K-12 strain, such as strain W3110.

Also provided herein are bioconjugates of O-antigen polysaccharides produced using recombinant host cells encoding the oligosaccharyl transferase enzymes per the O-antigen/PglB oligosaccharyl transferase pairings indicated above. Also provided are compositions comprising such bioconjugates. In certain embodiments, a composition comprises at least 2, preferably at least 3, more preferably at least 5, still more preferably at least 7 of such bioconjugates.

In some embodiments, bioconjugates of O-antigen polysaccharides produced by recombinant host cells encoding the oligosaccharyl transferase enzymes per the O-antigen/PglB oligosaccharyl transferase pairings indicated above preferably have one or more of the preferred attributes described herein, e.g., glycan/protein ratio and/or amount or ratio of multi-glycosylated carrier protein.

EMBODIMENTS

Embodiment 1 is a method of preparing a bioconjugate of an *E. coli* $O_x$ antigen polysaccharide covalently linked to a carrier protein, the method comprising:

(i) providing a recombinant host cell comprising:

a. a nucleotide sequence of an rfb gene cluster for the $O_x$-antigen polysaccharide;

b. a nucleotide sequence encoding the carrier protein comprising at least one glycosylation site comprising a glycosylation consensus sequence having SEQ ID NO: 1, preferably having SEQ ID NO: 2; and c. a nucleotide sequence encoding an oligosaccharyl transferase $PglB_y$; and (ii) culturing the recombinant host cell under conditions for production of the bioconjugate; wherein:

when the $O_x$-antigen is O1A antigen polysaccharide, the $PglB_y$ comprises the amino acid mutations of N311V, K482R, D483H, and A669V;

when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8 respectively, wherein the translocase is capable of translocating bactoprenol linked glucose and the glycosyltransferase is capable of glucosylating bactoprenol;

when the $O_x$-antigen is O6A antigen polysaccharide, the $PglB_y$ comprises the amino acid mutations of N311V, K482R, D483H, and A669V;

when the $O_x$-antigen is O8 antigen polysaccharide, the $PglB_y$ comprises no amino acid mutations at positions 77, 80, 287, 289, 311, 482, 483 and 669;

when the $O_x$-antigen is O15 antigen polysaccharide, the $PglB_y$ comprises the amino acid mutations of N311V, K482R, D483H, and A669V;

when the $O_x$-antigen is O16 antigen polysaccharide, the $PglB_y$ comprises the amino acid mutations of Y77H, S80R, Q287P, K289R, and N311V;

when the $O_x$-antigen is O18A antigen polysaccharide, the $PglB_y$ comprises no amino acid mutations at positions 77, 80, 287, 289, 311, 482, 483 and 669; and when the $O_x$-antigen is O75 antigen polysaccharide, the $PglB_y$ comprises the amino acid mutation of N311V;

wherein in each case the amino acid mutations are relative to the wild-type PglB having the amino acid sequence of SEQ ID NO: 6, and wherein the O1A, glucosylated O4, O6A, O8, O15, O16, O18A, and O75 antigen polysaccharides have the structures of Formulas (O1A), (O4-Glc+), (O6A), (O8), (O15), (O16), (O18A), and (O75), respectively, as shown in Table 1, and each n is independently an integer of 1 to 100, preferably 3 to 50, e.g. 5 to 40, e.g. 7 to 25, e.g. 10 to 20.

Embodiment 2 is the method of embodiment 1, wherein the $O_x$-antigen is O1A antigen polysaccharide, and the $PglB_y$ comprises the amino acid mutations of N311V, K482R, D483H, and A669V relative to wild-type PglB having the amino acid sequence of SEQ ID NO: 6.

Embodiment 3 is the method of embodiment 1, wherein the $O_x$-antigen is glucosylated O4 antigen polysaccharide, and the $PglB_y$ comprises the amino acid mutation N311V or the amino acid mutations Y77H and N311V relative to wild-type PglB having the amino acid sequence of SEQ ID NO: 6.

Embodiment 4 is the method of embodiment 3, wherein the recombinant host cell further comprises a sequence encoding a GtrS having the amino acid sequence of SEQ ID NO: 4, and nucleotide sequences encoding a GtrA and a GtrB having the amino acid sequences of SEQ ID NOs: 7 and 8, respectively.

Embodiment 5 is the method of embodiment 1, wherein the $O_x$-antigen is O6A antigen polysaccharide, and the $PglB_y$ comprises the amino acid mutations of N311V, K482R, D483H, and A669V relative to wild-type PglB having the amino acid sequence of SEQ ID NO: 6.

Embodiment 6 is the method of embodiment 1, wherein the $O_x$-antigen is O8 antigen polysaccharide, and the $PglB_y$ comprises no amino acid mutations at positions 77, 80, 287, 289, 311, 482, 483 and 669 relative to wild-type PglB having the amino acid sequence of SEQ ID NO: 6.

Embodiment 7 is the method of embodiment 1, wherein the $O_x$-antigen is O15 antigen polysaccharide, and the $PglB_y$ comprises the amino acid mutations of N311V, K482R, D483H, and A669V relative to wild-type PglB having the amino acid sequence of SEQ ID NO: 6.

Embodiment 8 is the method of embodiment 1, wherein the $O_x$-antigen is O16 antigen polysaccharide, and the $PglB_y$ comprises the amino acid mutations of Y77H, S80R, Q287P, K289R, and N311V relative to wild-type PglB having the amino acid sequence of SEQ ID NO: 6.

Embodiment 9 is the method of embodiment 1, wherein the $O_x$-antigen is O18A antigen polysaccharide, and the $PglB_y$ comprises no amino acid mutations at positions 77, 80, 287, 289, 311, 482, 483 and 669 relative to wild-type PglB having the amino acid sequence of SEQ ID NO: 6.

Embodiment 10 is the method of embodiment 1, wherein the $O_x$-antigen is O75 antigen polysaccharide, and the $PglB_y$ comprises the amino acid mutation of N311V relative to wild-type PglB having the amino acid sequence of SEQ ID NO: 6.

Embodiment 11 is a method of preparing a bioconjugate of an *E. coli* $O_x$ antigen polysaccharide covalently linked to a carrier protein, the method comprising:

(i) providing a recombinant host cell comprising:

(a) a nucleotide sequence of an rfb gene cluster for the $O_x$-antigen polysaccharide;

(b) a nucleotide sequence encoding the carrier protein comprising at least one glycosylation site comprising a glycosylation consensus sequence having SEQ ID NO: 1, preferably having SEQ ID NO: 2; and (c) a nucleotide sequence encoding an oligosaccharyl transferase $PglB_y$; and (ii) culturing the recombinant host cell under conditions for production of the bioconjugate, wherein the $PglB_y$ comprises the amino acid mutation N311V relative to the wild-type PglB having the amino acid sequence of SEQ ID NO: 6, wherein the $O_x$-antigen is O1A antigen polysaccharide, glucosylated O4 antigen polysaccharide, O6A antigen polysaccharide, O15 antigen polysaccharide, O16 antigen polysaccharide, or O75 antigen polysaccharide, and when the $O_x$-antigen is glucosylated O4 antigen polysaccharide, the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8, respectively, wherein the translocase is capable of translocating bactoprenol linked glucose and the glycosyltransferase is capable of glucosylating bactoprenol, and wherein the O1A, glucosylated O4, O6A, O15, O16, and O75 antigen polysaccharides have the structures of Formulas (O1A), (O4-Glc+), (O6A), (O15), (O16), and (O75), respectively, as shown in Table 1, and each n is independently an integer of 1 to 100, preferably 3 to 50, e.g. 5 to 40, e.g. 7 to 25, e.g. 10 to 20.

Embodiment 12 is the method of any one of embodiments 1 to 11, further comprising isolating the bioconjugate from the recombinant host cell.

Embodiment 13 is the method of any one of embodiments 1 to 12, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae.*

Embodiment 14 is the method of embodiment 13, wherein the carrier protein is detoxified exotoxin A of *Pseudomonas aeruginosa* (EPA).

Embodiment 15 is the method of embodiment 14, wherein the EPA carrier protein comprises 1-10, preferably 2-4, more preferably 4, of the glycosylation sites.

Embodiment 16 is the method of embodiment 15, wherein each glycosylation site comprises a glycosylation consensus sequence having SEQ ID NO: 2.

Embodiment 17 is the method of embodiment 16, wherein the EPA carrier protein comprises SEQ ID NO: 3.

Embodiment 18 is the method of anyone of embodiments 1-17, wherein the recombinant host cell is an *E. coli* cell, e.g. an *E. coli* K-12 strain, such as strain W3110.

Embodiment 19 is a bioconjugate produced by the method of any one of embodiments 1-18.

Embodiment 20 is a composition comprising a bioconjugate of embodiment 19.

Embodiment 21 is a composition comprising at least 2, preferably at least 3, more preferably at least 5, still more preferably at least 7 bioconjugates of embodiment 19.

Embodiment 22 is a composition of embodiment 20 or 21, comprising a bioconjugate of *E. coli* glucosylated O4 antigen polysaccharide covalently linked to a carrier protein, wherein the glucosylated O4 antigen polysaccharide has the structure of Formula (O4-Glc+) as shown in Table 1, and n is an integer of 1 to 100, preferably 3 to 50, e.g. 5 to 40, e.g. 7 to 25, e.g. 10 to 20.

Embodiment 23 is a composition of any one of embodiments 20 to 22, further comprising at least a bioconjugate of *E. coli* O25B antigen polysaccharide covalently linked to a carrier protein, wherein the O25B antigen polysaccharide has the structure of Formula (O25B) as shown in Table 1, and n is an integer of 1 to 100, preferably 3 to 50, e.g. 5 to 40, e.g. 7 to 25, e.g. 10 to 20.

Embodiment 24 is a composition of any one of embodiments 20 to 23, further comprising at least a bioconjugate of *E. coli* O2 antigen polysaccharide covalently linked to a carrier protein, wherein the O2 antigen polysaccharide has the structure of Formula (O2) as shown in Table 1, and n is an integer of 1 to 100, preferably 3 to 50, e.g. 5 to 40, e.g. 7 to 25, e.g. 10 to 20.

Embodiment 25 is a composition of any one of embodiments 20 to 24, comprising: (i) bioconjugate of *E. coli* O1A antigen polysaccharide covalently coupled to a carrier protein, (ii) bioconjugate of *E. coli* O2 antigen polysaccharide covalently coupled to a carrier protein, (iii) bioconjugate of *E. coli* glucosylated O4 antigen polysaccharide covalently coupled to a carrier protein, (iv) bioconjugate of *E. coli* O6A antigen polysaccharide covalently coupled to a carrier protein, (v) bioconjugate of *E. coli* O8 antigen polysaccharide covalently coupled to a carrier protein, (vi) bioconjugate of *E. coli* O15 antigen polysaccharide covalently coupled to a carrier protein, (vii) bioconjugate of *E. coli* O16 antigen polysaccharide covalently coupled to a carrier protein, (viii) bioconjugate of *E. coli* O25B antigen polysaccharide covalently coupled to a carrier protein, and (ix) bioconjugate of *E. coli* O75 antigen polysaccharide covalently coupled to a carrier protein, wherein the O1A, O2, glucosylated O4, O6A, O8, O15, O16, O25B, and O75 antigen polysaccharides have the structures of Formulas (O1A), (O2), (O4-Glc+), (O6A), (O8), (O15), (O16), (O25B), and (O75), respectively, as shown in Table 1, and each n is independently an integer of 1 to 100, preferably 3 to 50, e.g. 5 to 40, e.g. 7 to 25, e.g. 10 to 20.

Embodiment 26 is a composition of embodiment 25, further comprising: (x) bioconjugate of *E. coli* O18A antigen polysaccharide covalently coupled to a carrier protein, wherein the O18A antigen polysaccharide has the structure of Formula (O18A) as shown in Table 1, and n is an integer of 1 to 100, preferably 3 to 50, e.g. 5 to 40, e.g. 7 to 25, e.g. 10 to 20.

Embodiment 27 is a composition of any one of embodiments 20 to 26, wherein the composition is an immunogenic composition.

Embodiment 28 is a method of vaccinating a subject against *E. coli*, in particular extra-intestinal pathogenic *E. coli* (ExPEC), comprising administering to the subject the bioconjugate of embodiment 19, or the composition or immunogenic composition of any one of embodiments 20 to 27.

Embodiment 29 is the bioconjugate of embodiment 19, or the composition or immunogenic composition of any one of embodiments 20 to 27 for use in vaccination against extra-intestinal pathogenic *E. coli* (ExPEC).

Embodiment 30 is a recombinant host cell for preparing a bioconjugate of an *E. coli* $O_x$ antigen polysaccharide covalently linked to a carrier protein, the recombinant host cell comprising:

(a) a nucleotide sequence of an rfb gene cluster for the $O_x$-antigen polysaccharide;

(b) a nucleotide sequence encoding the carrier protein comprising at least one glycosylation site comprising a glycosylation consensus sequence having SEQ ID NO: 1, preferably having SEQ ID NO: 2; and (c) a nucleotide sequence encoding an oligosaccharyl transferase $PglB_y$;

wherein:

when the $O_x$-antigen is O1A antigen polysaccharide, the $PglB_y$ comprises the amino acid mutations of N311V, K482R, D483H, and A669V;

when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a glucosyltransferase GtrS having at least 80% identity to SEQ ID NO: 4 and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having at least 80% sequence identity to SEQ ID NOs: 7 and 8 respectively, wherein the translocase is capable of translocating bactoprenol linked glucose and the glycosyltransferase is capable of glucosylating bactoprenol;

when the $O_x$-antigen is O6A antigen polysaccharide, the $PglB_y$ comprises the amino acid mutations of N311V, K482R, D483H, and A669V;

when the $O_x$-antigen is O8 antigen polysaccharide, the $PglB_y$ comprises no amino acid mutations at positions 77, 80, 287, 289, 311, 482, 483 and 669;

when the $O_x$-antigen is O15 antigen polysaccharide, the $PglB_y$ comprises the amino acid mutations of N311V, K482R, D483H, and A669V;

when the $O_x$-antigen is O16 antigen polysaccharide, the $PglB_y$ comprises the amino acid mutations of Y77H, S80R, Q287P, K289R, and N311V;

when the $O_x$-antigen is O18A antigen polysaccharide, the $PglB_y$ comprises no amino acid mutations at positions 77, 80, 287, 289, 311, 482, 483 and 669; and when the $O_x$-antigen is O75 antigen polysaccharide, the $PglB_y$ comprises the amino acid mutation of N311V;

wherein in each case the amino acid mutations are relative to the wild-type PglB having the amino acid sequence of SEQ ID NO: 6, and wherein the O1A, glucosylated O4, O6A, O8, O15, O16, O18A, and O75 antigen polysaccharides have the structures of Formulas (O1A), (O4-Glc+), (O6A), (O8), (O15), (O16), (O18A), and (O75), respectively, as shown in Table 1, and each n is independently an integer of 1 to 100, preferably 3 to 50, e.g. 5 to 40, e.g. 7 to 25, e.g. 10 to 20.

Embodiment 31 is the recombinant host cell of embodiment 30, wherein the $O_x$-antigen is O1A antigen polysaccharide, and the $PglB_y$ comprises the amino acid mutations of N311V, K482R, D483H, and A669V relative to wild-type PglB having the amino acid sequence of SEQ ID NO: 6.

Embodiment 32 is the recombinant host cell of embodiment 30, wherein the $O_x$-antigen is glucosylated O4 antigen polysaccharide, and the $PglB_y$ comprises the amino acid mutation N311V or the amino acid mutations Y77H and N311V relative to wild-type PglB having the amino acid sequence of SEQ ID NO: 6.

Embodiment 33 is the recombinant host cell of embodiment 32, wherein the recombinant host cell further comprises a sequence encoding a GtrS having the amino acid sequence of SEQ ID NO: 4, and nucleotide sequences encoding a GtrA and a GtrB having the amino acid sequences of SEQ ID NOs: 7 and 8, respectively.

Embodiment 34 is the recombinant host cell of embodiment 30, wherein the $O_x$-antigen is O6A antigen polysaccharide, and the $PglB_y$ comprises the amino acid mutations of N311V, K482R, D483H, and A669V relative to wild-type PglB having the amino acid sequence of SEQ ID NO: 6.

Embodiment 35 is the recombinant host cell of embodiment 30, wherein the $O_x$-antigen is O8 antigen polysaccharide, and the $PglB_y$ comprises no amino acid mutations at positions 77, 80, 287, 289, 311, 482, 483 and 669 relative to wild-type PglB having the amino acid sequence of SEQ ID NO: 6.

Embodiment 36 is the recombinant host cell of embodiment 30, wherein the $O_x$-antigen is O15 antigen polysaccharide, and the $PglB_y$ comprises the amino acid mutations of N311V, K482R, D483H, and A669V relative to wild-type PglB having the amino acid sequence of SEQ ID NO: 6.

Embodiment 37 is the recombinant host cell of embodiment 30, wherein the $O_x$-antigen is O16 antigen polysaccharide, and the $PglB_y$ comprises the amino acid mutations of Y77H, S80R, Q287P, K289R, and N311V relative to wild-type PglB having the amino acid sequence of SEQ ID NO: 6.

Embodiment 38 is the recombinant host cell of embodiment 30, wherein the $O_x$-antigen is O18A antigen polysaccharide, and the $PglB_y$ comprises no amino acid mutations at positions 77, 80, 287, 289, 311, 482, 483 and 669 relative to wild-type PglB having the amino acid sequence of SEQ ID NO: 6.

Embodiment 39 is the recombinant host cell of embodiment 30, wherein the $O_x$-antigen is O75 antigen polysaccharide, and the $PglB_y$ comprises the amino acid mutation of N311V relative to wild-type PglB having the amino acid sequence of SEQ ID NO: 6.

Embodiment 40 is the recombinant host cell of any one of embodiments 30 to 39, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

Embodiment 41 is the recombinant host cell of any one of embodiments 30-40, wherein the carrier protein is detoxified exotoxin A of *Pseudomonas aeruginosa* (EPA).

Embodiment 42 is the recombinant host cell of embodiment 41, wherein the EPA carrier protein comprises 1-10, preferably 2-4, more preferably 4, of the glycosylation sites.

Embodiment 43 is the recombinant host cell of embodiment 42, wherein each glycosylation site comprises a glycosylation consensus sequence having SEQ ID NO: 2.

Embodiment 44 is the recombinant host cell of embodiment 43, wherein the EPA carrier protein comprises SEQ ID NO: 3.

Embodiment 45 is the recombinant host cell of any one of embodiments 30 to 44, wherein the recombinant host cell is an *E. coli* cell, e.g. an *E. coli* K-12 strain, such as strain W3110.

Embodiment 46 is a bioconjugate according to embodiment 19, wherein the bioconjugate is a bioconjugate of *E. coli* glucosylated O4 antigen polysaccharide covalently linked to a carrier protein.

Embodiment 47 is a bioconjugate according to embodiment 46, wherein the carrier protein is an EPA carrier protein comprising SEQ ID NO: 3.

Embodiment 48 is a bioconjugate according to embodiment 46 or 47, wherein the glucosylated O4 antigen polysaccharide has the structures of Formula (O4-Glc+) as shown in Table 1, and n is an integer of 5 to 40.

Embodiment 49 is a composition comprising a bioconjugate according to any one of embodiments 46-48.

Embodiment 50 is a composition according to embodiment 49, further comprising one or more conjugates each comprising an *E. coli* antigen polysaccharide covalently coupled to a carrier protein.

Embodiment 51 is a composition according to embodiment 50, wherein the one or more conjugates comprise *E. coli* antigen polysaccharide of one or more of the following *E. coli* serotypes: O1A, O2, O6A, O8, O15, O16, O18A, O25B, and O75, wherein the O1A, O2, O6A, O8, O15, O16, O25B, and O75 antigen polysaccharides have the structures of Formulas (O1A), (O2), (O6A), (O8), (O15), (O16), (O18A), (O25B), and (O75), respectively, as shown in Table 1, and each n is independently an integer of 1 to 100, preferably 3 to 50, e.g. 5 to 40, e.g. 7 to 25, e.g. 10 to 20.

Embodiment 52 is a composition according to embodiment 51, comprising conjugates of *E. coli* serotypes: O1A, O2, O6A, O8, O15, O16, O18A, O25B, and O75.

Embodiment 53 is a composition according to embodiment 52, wherein each of the conjugates is a bioconjugate.

EXAMPLES

The following examples of the invention are to further illustrate the nature of the invention. It should be understood that the following examples do not limit the invention and the scope of the invention is to be determined by the appended claims.

Example 1: Epidemiological Data of *E. coli* Infections

To determine the O-serotype distribution of bacteremia-causing *E. coli*, global surveillance studies were performed. Between 2011 and 2017, more than 3200 *E. coli* bloodstream isolates were collected from patients≥60 years of age hospitalized in countries within North America, Europe, the Asia-Pacific region, and South America. Each strain was analyzed for O antigen serotype using classical agglutination techniques and sequence-based O-genotyping. See Table 2.

Isolated human blood samples were analyzed to determine the identity of pathogens therein and their antibiotic resistance patterns. *E. coli* isolates were obtained from the samples following the analysis. *E. coli* identity was verified by MALDI-TOF MS. Further analysis on the *E. coli* isolates was performed using an antisera-based agglutination assay to determine their O-antigen serotype (DebRoy et al. (2011) Animal health research reviews/Conference of Research Workers in Animal Diseases 12, 169-185). Isolates untypeable by the agglutination method, were further analyzed by whole-genome sequencing followed by O-genotyping based on O-serotype specific wzy and wzx gene sequences.

TABLE 2 distribution of the most common bacteremia-associated *E. coli* O-serotypes from a collection of 3217 blood isolates collected globally between 2011 and 2017, based on O-serotyping by agglutination plus O-genotyping of isolates un-typeable by agglutination. Subjects were hospitalized in the following countries: USA, Canada, Argentina, Brazil, UK, Germany, Spain, Italy, The Netherlands, France, Japan, Thailand, South Korea and Australia.

| O-serotype | Prevalence n (%) |
| --- | --- |
| O25 | 737 (22.9%) |
| O2 | 268 (8.3%) |
| O6 | 261 (8.1%) |
| O1 | 255 (7.9%) |
| O75 | 145 (4.5%) |
| O15 | 110 (3.4%) |
| O8 | 104 (3.2%) |
| O16 | 103 (3.2%) |
| O4 | 96 (3.0%) |
| O18 | 91 (2.8%) |

Stratification of on geographical location in the global set of bacteremia-associated *E. coli* showed a prevalence of the top 10 O-serotypes independent of location, suggesting these to be the predominant O-serotypes globally associated with bacteremia-causing *E. coli*.

In the global set of bacteremia-associated multi-drug resistant *E. coli* isolates (n=345), i.e. those strains that are resistant to at least three classes of clinically relevant antimicrobial drugs, the prevalence of the top 10 O-serotypes is 75.4%.

All information from epidemiology analysis taken together, the 10 predominant O-serotypes could cover an estimated 60-80% of *E. coli*-associated bacteremia infections, assuming coverage of subportions of the un-typeable strains.

A multivalent vaccine covering a significant proportion of bacteremia-causing *E. coli* serotypes would be very useful. The O-serotypes of Table 2 would thus be good candidates for an O-antigen based multivalent vaccine. Such a vaccine could beneficially be prepared using bioconjugation technology.

One of the serotypes in the top-10 (Table 2) is O4. It would thus be beneficial to prepare a bioconjugate vaccine that includes O-antigen polysaccharide of *E. coli* serotype O4 coupled to a carrier protein.

Example 2: Characterization of Contemporary O4 Clinical Isolates for Genes Encoding O-Antigen Modifying Enzymes Two variants of *E. coli* O4 antigen polysaccharide have been described (see, e.g. Jann B, et al., 1993, Carbohydr. Res. 248: 241-250), one having an unbranched structure (structure shown as (O4-Glc−) in Table 1) and another variant substituted with an additional glucose side-branch (structure shown as (O4-Glc+) in Table 1). The proportion in which these two variants are found in contemporary clinical isolates was not known. Although both variants react with O4 antisera, it was also not known whether immunological differences between these variants exist. Moreover, an enzyme responsible for attaching the glucose side-branch to generate the (O4-Glc+) antigen polysaccharide was hitherto not identified, and a putative coding sequence thereof is likely residing outside the O4 rfb gene cluster.

A set of 32 agglutination-confirmed *E. coli* O4 clinical isolates originally isolated during the period of 2011-2012 from subjects in the United States and the European Union were subjected to whole genome sequence analysis. Extracted rfb gene cluster sequences from the 32 sequenced O4 isolates were aligned with those of the reference strain and compared at the nucleotide level. Except for some naturally occurring single nucleotide polymorphisms, the characterized isolates all displayed an rfb cluster that was identical to the O4 reference strain, indicating that *E. coli* O4 strains, independent of their Glc-branching status, carry an identical rfb gene cluster. Thus, to generate the *E. coli* O4-Glc+ antigen polysaccharide, a gene with unknown sequence that encodes an *E. coli* O4-specific branching enzyme and that must reside somewhere outside of the *E. coli* O4 rfb gene cluster is likely needed. The sequence of this unknown gene needs to be identified and employed if one wants to produce bioconjugates with the *E. coli* O4-Glc+ antigen polysaccharides in a strain that would otherwise only produce bioconjugates with *E. coli* O4-Glc-antigen polysaccharides.

The whole-genome sequence data were then analyzed for the presence of genes outside of the rfb gene cluster that may encode O-antigen modifying enzymes. Homologs of gtrAB in *Shigella flexneri* were first identified in *E. coli* O4. An open reading frame downstream of gtrAB in *E. coli* was then putatively identified as the *E. coli* O4-specific gene gtrS, that could encode the putative *E. coli* O4 specific branching enzyme GtrS responsible for adding a glucose branch to the *E. coli* O4 antigen.

The amino acid sequence of the O4 specific GtrS enzyme is provided as SEQ ID NO: 4. An exemplary nucleic acid sequence encoding this protein is provided as SEQ ID NO: 5.

Of the characterized *E. coli* O4 isolates, approximately 80% were found to carry the here identified gtrS gene (26 out of 32). Prevalence of the *E. coli* O4-specific gtrS sequence was also determined by PCR using sequence specific primers in an independent set of 20 agglutination-confirmed *E. coli* O4 clinical isolates isolated during the period of 2014-2016 from subjects in the United States and the European Union. This analysis demonstrated that 17 out of 20 isolates carried the O4 gtrS sequence, which corresponds to a prevalence of 85%.

Example 3: Cloning of O4 gtrS into *E. coli* W3110, Production and Structural Confirmation of Glc-Modified O4 Bioconjugates To test whether bioconjugates comprising O4-antigen polysaccharide modified with a branching glucose could be prepared, *E. coli* O4-antigen EPA bioconjugate production strains with the putative branching enzyme were constructed. For this, the endogenous O16-gtrS gene was substituted by the putative O4-gtrS gene (SEQ ID NO: 5, see Example 2) and the O16 rfb cluster was replaced with the O4 rfb cluster in *E. coli* strain W3110 ΔwzzE-wecG ΔwaaL Δwbbl-J-K by homologous recombination. Alternatively, in some strains, the O4 rfb cluster was encoded on a plasmid.

Subsequently, plasmids encoding a detoxified exotoxin A of *Pseudomonas aeruginosa* (EPA) carrier protein (a variant either having 2 or 4 consensus glycosylation sites, referred to as 'EPA-2' and 'EPA-4', respectively), and oligosaccharyl transferase PglB were introduced into the strains. O4-EPA bioconjugates modified with Glc were produced by growing the *E. coli* production strains in bioreactor cultures, and induction of PglB and EPA expression by IPTG and arabinose, respectively. The O4-EPA bioconjugates were extracted from the biomass periplasmic extract.

To confirm the detailed polysaccharide composition and linkage of the O4-EPA bioconjugates, multiple NMR experiments were performed on the bioconjugates having EPA-4 carrier protein (data not shown). The assignments obtained agreed with literature published (Jansson, P. E., et al., 1984, Carbohydr. Res. 134(2): 283-291; Jann B, et al., 1993, Carbohydr. Res. 248: 241-250). The 1D spectrum recorded at 313K showed a large HOD signal and small sharp signals from the O4 pentasaccharide RU with five anomeric, two NAc and two H6 signals (Rha and FucNAc).

The 1D proton assignments were confirmed by use of 2D proton-proton and proton-carbon correlation NMR experiments. First, 2D TOCSY (120 ms) experiments demonstrated the expected cross peaks from H1 and H6 (for Rha and FucNAc) for the O4 pentasaccharide RU and small peaks from the terminal RU and EPA. In the methyl region, TOCSY showed cross peaks from H6 to H1 for α-Rha and H6 to H5 for α-FucNAc for the O4 RU. Other peaks observed were from EPA amino acids and terminal Rha (tRha). Second, a carbon NMR spectrum contained well-dispersed and diagnostic single peaks for the O4 RU. The carbons were profiled indirectly through the attached protons by use of the HSQC experiment. The HSQC-DEPT experiment gave inverted peaks for $CH_2$ groups. The HSQC gave cross peaks for the O4 pentasaccharide RU [5 anomeric, ring, two N-acetyl and two methyl (Rha & FucNAc)] groups as well as EPA amino acids in characteristic regions. Each of the proton/carbon pairs for the O4 could be assigned based on the proton assignments and literature.

The structural characterization experiments thus confirmed that Glc-branched O4 bioconjugates (comprising polysaccharide antigen structures as indicated by Formula (O4-Glc+) in Table 1) could be produced, using the putative *E. coli* O4-gtrS gene identified in Example 2.

Example 4: Immunogenicity of a Glc-Branched O4 Bioconjugate in Rabbits

Glc-modified O4 bioconjugates (i.e. having glycans with the structure of Formula (O4-Glc+) as shown in Table 1) were used for rabbit immunization by applying a speedy-rabbit protocol (Eurogentec). Sera from immunized rabbits were analyzed by ELISA for anti-O4 IgG titers against purified O4 lipopolysaccharide (LPS) with (Glc+; i.e. containing glucosylated O4 polysaccharide) or without Glc-branching (Glc−; i.e. containing non-glucosylated O4 polysaccharide). Immunization with the bioconjugate resulted in high IgG titers in both rabbits (FIG. 1). In both cases, antibody titers induced by the O4 bioconjugate were higher against Glc+ LPS as compared to Glc-LPS.

Figure 2:
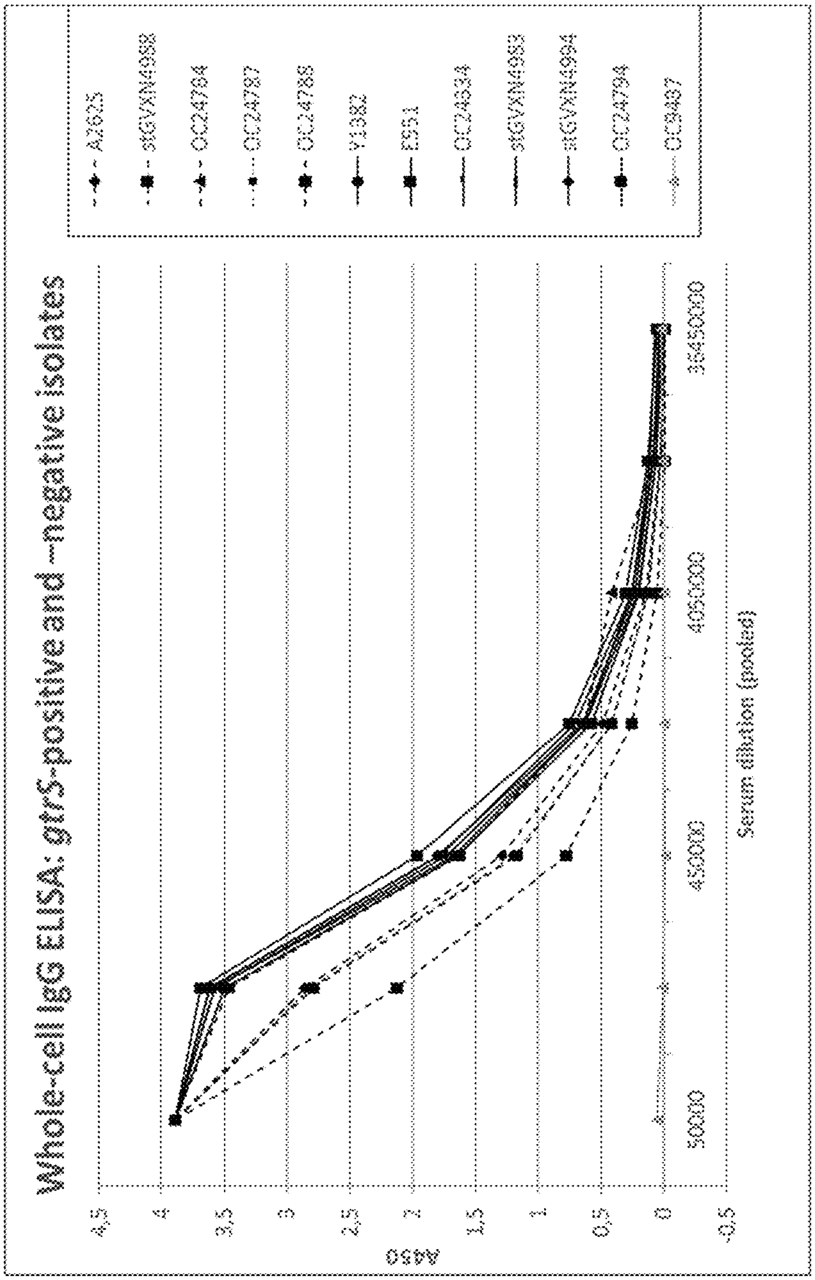
FIG. 2 shows IgG titers in whole cell ELISAs with pooled sera from rabbits immunized with a Glc-modified O4 bioconjugate against *E. coli* O4 isolates with characterized gtrS status as described in Example 4; the following isolates were gtrS-negative: A2625, stGVXN4988, OC24784, OC24787 and OC24788; the following isolates were gtrS-positive: Y1382, E551, OC24334, stGVXN4983, stGVXN4994 and OC24794; the negative control strain OC9487 (ATCC 35383; serotype O75) was also included.

Sera were also pooled and used in whole cell ELISA studies with test sets of *E. coli* O4 isolates with characterized gtrS status. Five gtrS-negative (no Glc-branching) and six gtrS-positive (Glc-branching) *E. coli* O4 isolates and a negative control strain were tested. Pooled sera from rabbits immunized with a Glc-modified O4 bioconjugate contained high titers of IgG specifically recognizing the tested O4 isolates (FIG. 2). In concordance with the LPS ELISA, all tested O4 isolates were recognized by the immune sera. The gtrS-positive isolates displayed an overall higher binding than the gtrS-negative isolates (FIG. 2). In particular, the following isolates were gtrS-positive: Y1382, E551, OC24334, stGVXN4983, stGVXN4994 and OC24794, and the following isolates were gtrS-negative: A2625, stGVXN4988, OC24784, OC24787, and OC24788. Immune sera did not bind the negative control strain of a non-related O-serotype, *E. coli* OC9487 (ATCC 35383).

The profiles of LPS extracted from the test set of gtrS-positive and -negative isolates in silver-stained polyacrylamide gels did not reveal marked differences between isolates expressing unmodified and modified forms of the O4 antigen confirming that the observed differences are not explained by quantitative differences in LPS expression levels (data not shown).

Figure 3:
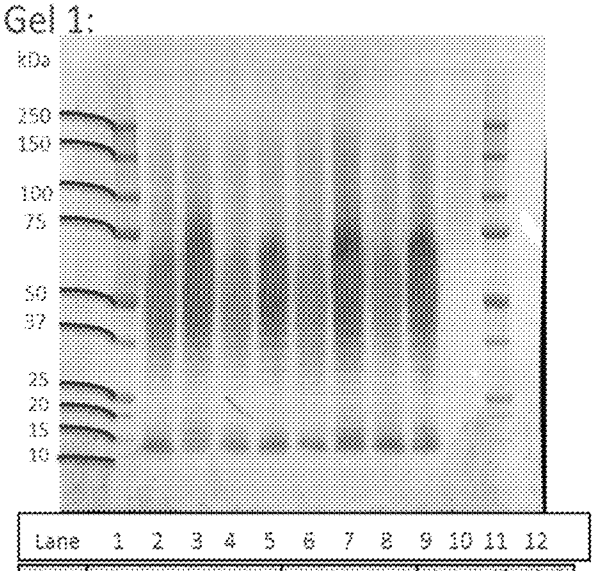
FIG. 3 shows Western blots of LPS extracted from gtrS-positive and -negative O4 isolates probed with pooled sera from rabbits immunized with modified O4 polysaccharide.
Figure 3:
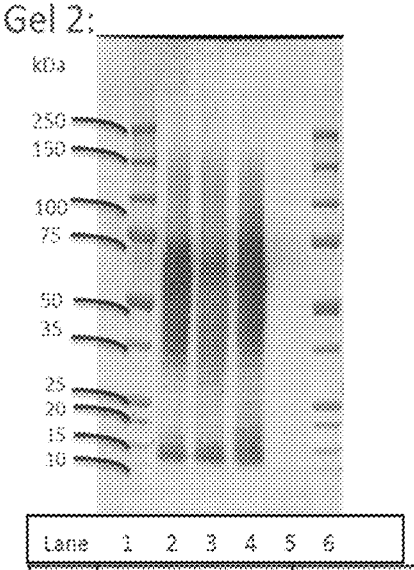

Western blots of extracted LPS using pooled immune sera were performed to assess recognition of O4 O-antigen by IgGs elicited in response to immunization with a Glc-modified O4 bioconjugate. Binding of both modified and unmodified O4 LPS by IgGs from modified O4 immunized rabbits was observed and included specific recognition of LPS bands spanning a wide range of sizes, including high molecular weight LPS bands (FIG. 3).

In the further experiments below, when reference is made to 'O4' bioconjugate or production strains or 'EcoO4', the bioconjugate or production strain of Glc-branched O4 (having glycan structure (O4-Glc+) in Table 1) is meant, unless specifically indicated otherwise (the terms 'O4' and 'O4-Glc+' are thus used interchangeably for bioconjugates or production strains in those experiments).

Example 5: Immunogenicity of a Glc-Branched O4 Bioconjugate in Rats

Sprague Dawley rats were immunized intramuscularly 3 times with formulation buffer or (O4-Glc+)-EPA bioconjugate (i.e. bioconjugate of glucosylated O4 antigen polysaccharide covalently coupled to EPA carrier protein; carrier protein was EPA-2 as described in Example 3 above) at 3 different doses (0.04 μg, 0.40 μg or 4.0 μg). Serum antibody levels were measured by ELISA at day 0, 14 and 42 post-immunization.

Figure 4A:
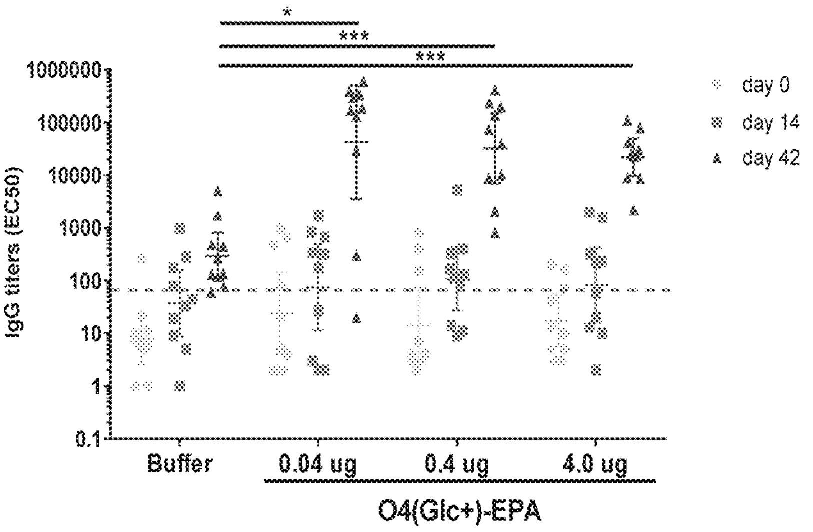
FIGS. 4A and 4B show antibody responses induced by glucosylated O4 (O4-Glc+)-EPA bioconjugates.
Figure 4B:
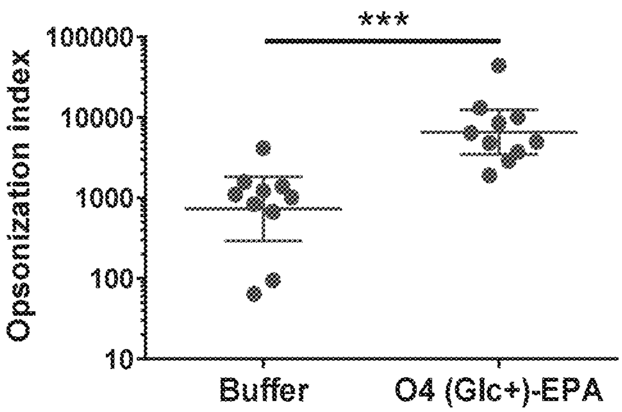

Immunization with 0.04 μg, 0.40 μg and 4.00 μg of (O4-Glc+)-EPA bioconjugate induced significant increase in the levels of IgG antibodies at day 42 post-immunization when compared to formulation buffer (FIG. 4A). The antibodies induced by (O4-Glc+)-conjugate were functional, i.e., capable of mediating killing of (O4-Glc+) *E. coli* strain (FIG. 4B).

Figure 5:
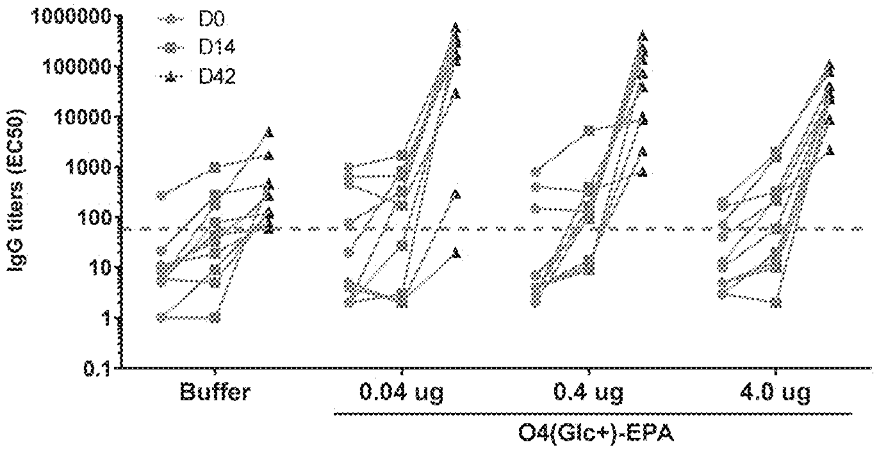
FIG. 5 shows the boost effect of glucosylated O4 (O4 Glc+)-EPA bioconjugate in Sprague Dawley rats immunized at 3 different doses as described in Example 4; serum antibody levels were measured by ELISA at day 0, 14 and 42 post-immunization; individual titers (log 10 EC50 titer) are shown for each animal; the lines between the data points connect IgG titers for each animal in time; the grey dotted line indicates the threshold above which the dilution curves of the samples have a 4PL fitting; statistical analysis was performed with Wilcoxon signed-rank test and Bonferroni correction for multiple comparisons (day 14 vs day 0, P=0.012 for 4.0 μg/dose; day 42 vs day 0, P=0.006 for all doses; day 42 vs day 14, P=0.006 for all doses)

Antibody levels induced by 0.04 μg, 0.40 μg and 4.0 μg of (O4-Glc+)-EPA bioconjugate were significantly increased at day 42 as compared to those detected at baseline (day 42 vs day 0, P=0.006 for all doses) and at day 14 post-immunization (day 42 vs day 14, P=0.006 for all doses) (FIG. 5). In the group that received 4.0 μg of bioconjugate, titers were also significantly increased at day 14 compared to day 0, indicating that a single dose of 4.0 μg of (O4-Glc+)-EPA bioconjugate induces significant increase in IgG titers (day 14 vs day 0, P=0.012). The significant increase in IgG titers observed between day 14 and 42, for all three concentrations of bioconjugate tested showed that a third dose of (O4-Glc+)-EPA bioconjugate is able to boost antibody responses (FIG. 5).

Figure 6:
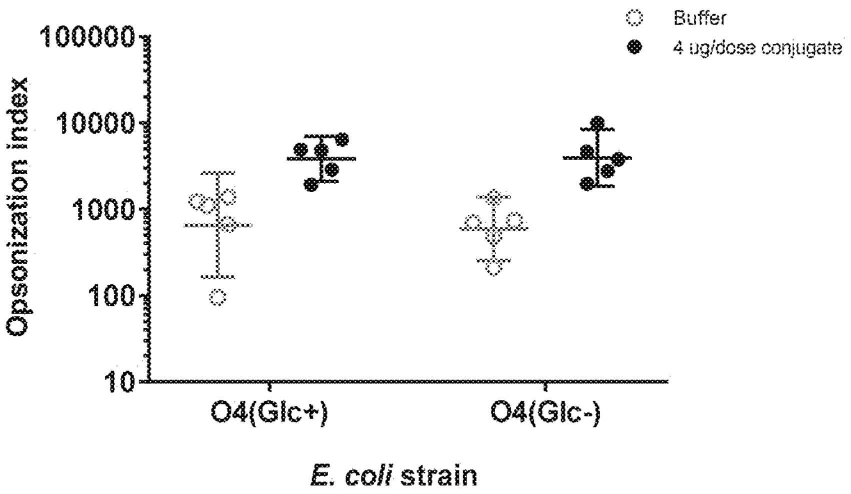
FIG. 6 shows the functionality of antibodies induced by O4-Glc+-EPA bioconjugate; Sprague Dawley rats were immunized intramuscularly 3 times with formulation buffer or O4(Glc+)-EPA bioconjugate at 4.00 μg/dose; functionality of the antibodies was determined by opsonophagocytic killing assay (OPKA) using O4(Glc+) and O4(Glc−) *E. coli* strains; individual opsonic titers (OI) and GMT±95% CI are shown.

Functionality of antibodies induced by O4-Glc+-EPA conjugate in the rats immunized intramuscularly 3 times with formulation buffer or the bioconjugate at 4.00 μg/dose was determined by opsonophagocytic killing assay (OPKA) using O4 (Glu+) and O4(Glu−) *E. coli* strains. The antibodies induced by (O4-Glc+)-EPA bioconjugate were functional, i.e., capable of mediating killing of an (O4-Glc+) *E. coli* strain (FIG. 4B, FIG. 6). Notably, antibodies induced by (O4-Glc+)-EPA bioconjugate were capable of mediating killing of both (O4-Glc+) and (O4-Glc−, i.e. having glycans with structure of Formula (O4-Glc−) in Table 1, i.e. O4 polysaccharide without Glc-branching) *E. coli* strains (FIG. 6).

In conclusion, antibodies induced by O4-Glc+-EPA bioconjugate are cross-reactive and capable of mediating killing of *E. coli* O4 strains with and without glucose branching.

Example 6: Production Strains for *E. coli* O-Antigen Bioconjugates and Resulting Bioconjugate Products In addition to (O4-Glc+)-EPA bioconjugates prepared as described above, nine (9) other bioconjugates were produced. In particular, the additionally produced bioconjugates included *E. coli* O1A-EPA bioconjugate, O2-EPA bioconjugate, O6A-EPA bioconjugate, O8-EPA bioconjugate, O15-EPA bioconjugate, O16-EPA bioconjugate, O18A-EPA bioconjugate, O25B-EPA bioconjugate, and O75-EPA bioconjugate. The chemical structures of the glycans of these conjugates can be seen in the respective Formulas in Table 1. A composition comprising the 10 bioconjugates is referred to herein as 'ExPEC10V'. A composition comprising the O1A-EPA, O2-EPA, O6A-EPA and O25B-EPA bioconjugates is referred to as 'ExPEC4V' (and was previously described in for instance WO 2015/124769 and WO 2017/035181).

*Escherichia coli* W3110 Parental Strain

The non-pathogenic *E. coli* K12 strain W3110 was used as the parental strain for the construction of all ten production strains. The *E. coli* K12 strain W3110 was obtained from the *coli* Genetic Stock Center (Yale University, New Haven (Conn.), USA, product number CGSC #4474). Its relevant genotype was previously described (*E. coli* W3110, F-, lambda-, IN(rrnD-rrnE)1, rph-1) and its genomic sequence was previously published (Hayashi K, et al., 2006, Mol. Syst. Biol. 2006.0007 (doi:10.1038/msb4100049). The *E. coli* W3110 strain was genetically modified to enable production of each of the *E. coli* O-antigen bioconjugates (Table 3).

Bioconjugate Production Strains

The "ExPEC4V" and "ExPEC10V" compositions both comprise the O2-EPA and O25B-EPA bioconjugates from the same production strains. The "ExPEC4V" composition comprises the O1A-EPA bioconjugate from the stGVXN4411 or stLMTB10217 production strains, while the "ExPEC10V" composition comprises the O1A-EPA bioconjugate from the stLMTB10217 production strain. The "ExPEC4V" composition comprises the O6A-EPA bioconjugate from the stGVXN4112 production strain, while the "ExPEC10V" composition comprises the O6A-EPA bioconjugate from the stLMTB10923 production strain. Furthermore, the "ExPEC10V" composition comprises the O4-EPA (i.e. (O4-Glc+)-EPA), O8-EPA, O15-EPA, O16-EPA, O18A-EPA, and O75-EPA bioconjugates from production strains that are not used for "ExPEC4V". Different production strains could vary in the plasmids for expression of the EPA carrier protein and/or the oligosaccharyl transferase PglB, as indicated below. An overview of several production strains is given in Table 3 below.

TABLE 3

Overview of genetic engineering of *E. coli* production strains for O-antigen bioconjugates for ExPEC4V and ExPEC10V vaccine compositions

| | | Genomic mutations | | | Plasmids | |
|---|---|---|---|---|---|---|
| Serotype | Strain name | rfb gene cluster | waaL | gtrABS | pglB | epa |
| O1A (ExPEC4V) | stGVXN4411 | Δrfb::O1A rfb upecGVXN_032 | ΔwaaL | — | pGVXN970 | pGVXN1076 |
| O1A (ExPEC4V; ExPEC10V) | stLMTB10217 | Δrfb::O1A rfb upecGVXN_032 | ΔwaaL | — | pGVXN1221 | pGVXN1076 |
| O2 | stGVXN4906 | Δrfb::O2 rfb upecGVXN_116 | ΔwaaL | — | pGVXN971 | pGVXN1076 |
| O4 | BVEC-L-00684 | Δrfb::O4 rfb CCUG11450 | ΔwaaL | ΔgtrS::gtrS O4 | pGVXN1217 | pGVXN1076 |
| O6A (ExPEC4V) | stGVXN4112 | Δrfb::O6A rfb CCUG11309 | ΔwaaL | — | pGVXN114 | pGVXN659 |
| O6A (ExPEC10V) | stLMTB10923 | Δrfb::O6A rfb CCUG11309 | ΔwaaL | — | pGVXN1221 | pGVXN1076 |
| O8 | stLMTB11734 | Δrfb::O8 rfb E2420 | ΔwaaL | ΔgtrABS | pGVXN970 | pGVXN1076 |
| O15 | stLMTB11738 | Δrfb::O15 rfb OC24891 | ΔwaaL | ΔgtrABS | pGVXN1221 | pGVXN1076 |
| O16 | stLMTB11739 | Δrfb::O16 rfb OC24208 | ΔwaaL | ΔgtrABS | pGVXN2381 | pGVXN1076 |
| O18A | BVEC-L-00559 | Δrfb::O18A rfb OC24255 | ΔwaaL | ΔgtrABS | pGVXN970 | pGVXN1076 |
| O25B | stGVXN4459 | Δrfb::O25B rfb upecGVXN_138 | ΔwaaL | ΔgtrABS | pGVXN970 | pGVXN1076 |
| O75 | stLMTB11737 | Δrfb::O75 rfb CCUG31 | ΔwaaL | ΔgtrABS | pGVXN1217 | pGVXN1076 |

O-Antigen Biosynthesis (Rib) Gene Cluster

In all *E. coli* O-antigen production strains, the naturally occurring. *E. coli* W3110 genomic O16::IS55-antigen biosynthesis (rfb) gene cluster was replaced by the selected O-antigen-specific biosynthesis clusters from *E. coli* strains of the selected serotype, encoding for the serotype-specific O-antigen structures (see Table 1 for these O-antigen structures). The ten donor rfb clusters were selected or confirmed after whole-genome analysis of *E. coli* blood isolates. Replacement of the W3110 O16::IS55rfb gene cluster, which is defective in O-antigen biosynthesis, has been achieved in a single homologous recombination event. In case of the O16 and O18A rfb gene clusters, the donor DNA recombined via the flanking gnd and rmlCA genes, while the rfb gene cluster for the other strains recombined via the flanking gnd and gaF genes. Sequences of the rfb clusters in the production strains are provided in SEQ ID NOs: 9 and 11-19.

O-Antigen Ligase (waaL) Gene

All *E. coli* O-antigen production strains carry an artificially introduced deletion of the *E. coli* W3110 genomic O-antigen ligase encoded by the waaL gene. In the ΔwaaL strains the transfer of the O-antigen to lipid A is disrupted, which instead directs transfer of the O-antigen to the carrier protein to increase product yield.

O-Antigen Glucosylation (gtrABS) Genes

In the *E. coli* O8, O15, O16, O18A, O25B, and O75 production strains the *E. coli* W3110 genomic gtrABS genes, which are responsible for O16 O-antigen glucosylation, have been deleted. While the gtrA and gtrB genes in different serotypes are highly homologous and interchangeable, the gtrS gene encodes a serotype-specific O-antigen glycosyl transferase. In *E. coli* W3110 GtrS can transfer a glucose (Glc) residue to the GlcNAc sugar in the α-L-Rha-(1→3)-D-GlcNAc motif of the *E. coli* O16 O-antigen. In the *E. coli* O1A, O2 and O6A production strains no deletion or replacement of the gtrABS gene has occurred. These O-antigens miss the α-L-Rha-(1→3)-D-GlcNAc motif that is the natural substrate for *E. coli* O16 gtrS. In the *E. coli* O4 production strain, the W3110 gtrS gene has been replaced with the *E. coli* O4 gtrS gene to accommodate proper glucosylation of the *E. coli* O4 O-antigen.

Oligosaccharyl Transferase PglB

All *E. coli* O-antigen production strains expressed a variant of the *C. jejuni* glycosyl transferase PglB, which can transfer the O-antigen onto an amino acid consensus sequence on a carrier protein by N-glycosylation. PglB has broad substrate recognition, but due to low product yields several production strains were prepared expressing a PglB variant having modified substrate specificities, which resulted in improved product yield (see e.g. WO 2016/107818, WO 2016/107819). The pglB gene was placed behind an Isopropyl β-*D*-1-thiogalactopyranoside (IPTG) inducible promoter on a plasmid. Table 4 below lists the PglB variants encoded by the plasmids used for production of the *E. coli* O-antigen production strains for the bioconjugates for the ExPEC4V and ExPEC10V compositions described above. Further plasmids with variation in vector backbone, antibiotic resistance marker, and/or alternative PglB variants have also been tested successfully for bioconjugate production.

strains for bioconjugates used in the "ExPEC4V" and "ExPEC10V" compositions described above. Plasmids with variation in vector backbone, antibiotic resistance marker, and/or EPA variants, e.g. varying in the number of consensus N-glycosylation site motifs (e.g. having two such motifs, EPA-2), have also been tested successfully for bioconjugate production.

Example 7: Optimizing the Oligosaccharyltransferase for Generation of Bioconjugates with Glucosylated O4 (O4-Glc+) Antigen Yield optimization for bioconjugate production can be achieved by modification of the *C. jejuni* oligosaccharyl transferase PglB, which can lead to a more efficient or higher degree of N-glycosylation of the O-antigen of interest to the EPA carrier protein. In an *E. coli* strain for production of bioconjugate with glucosylated O4 (O4-Glc+) O-antigen polysaccharide, such optimization strategy was applied and resulted in an (O4-Glc+)-specific optimized PglB variant improving bioconjugate product yield.

In this approach, an O4-Glc+O-antigen polysaccharide producing strain containing an EPA-expression plasmid was transformed with a variety of different PglB expression plasmids, each of which contained different amino acid substitutions in the PglB protein, altering substrate specificity. Bioconjugate production level and profile of each strain was assessed at shake-flask level in osmotic shock experiments, and readout was performed by capillary electrophoresis immunoassays on the periplasmic extract using O4-Glc+-specific monoclonal antibodies.

Figure 7:
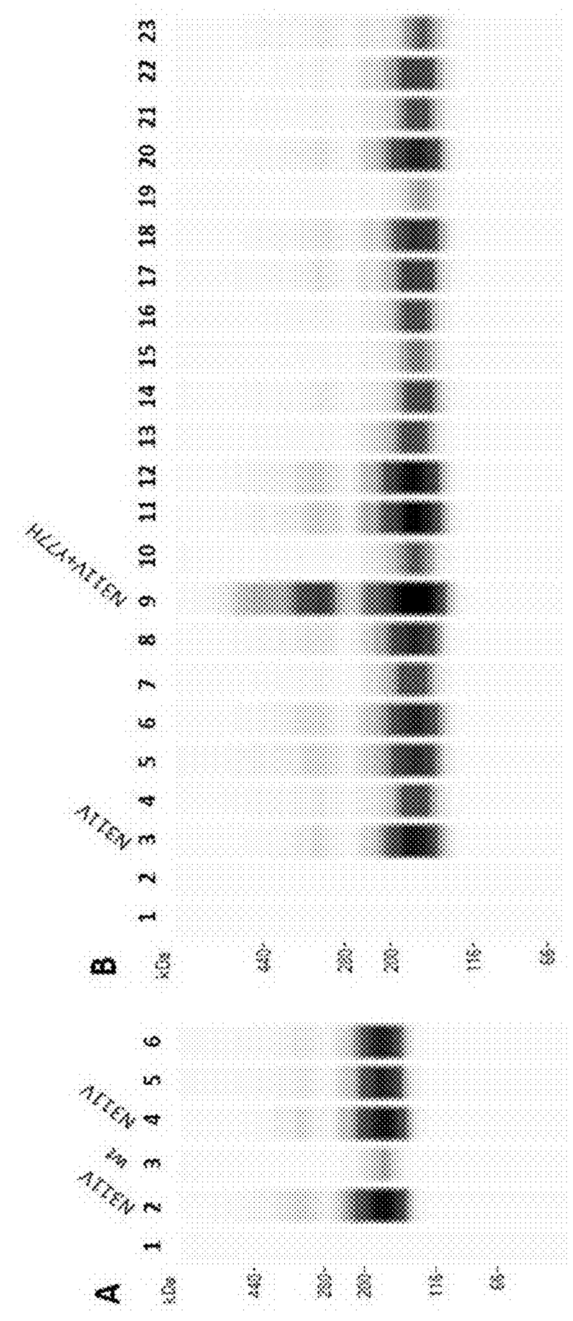
FIG. 7 shows capillary electrophoresis readout of PglB screen visualizing O4-Glc+ bioconjugate production for each tested strain in a blot-like image, using monoclonal antibodies to detect O4-Glc+ bioconjugate in the periplasmic fraction. Mono-glycosylated product approximately 180 kDa, di-glycosylated product approximately 320 kDa and tri-glycosylated product approximately 450 kDa. A) First screening round. Wt PglB in lane 3, N311V-PglB in lanes 2 and 4, empty control strain in lane 1 and other PglB variants in lanes 5 and 6. B) Second screening round. N311V PglB in lane 3, N311V+Y77H PglB in lane 9, empty control strain in lanes 1 and 2, other PglB variants in remaining lanes.

One of the tested PglB variants containing an N311V amino acid substitution was found to improve product yield of glucosylated O4 bioconjugates significantly (FIG. 7A).

TABLE 4

Pg1B and EPA plasmids used in *E. coli* O-antigen Production Strains

| Plasmid name | Gene | Description[1] |
|---|---|---|
| pGVXN114 | pg1B | *C. jejuni* codon usage; SpR |
| pGVXN970 | pg1B | *E. coli* codon usage optimized; SpR |
| pGVXN971 | pg1B$^{N534Q}$ | *E. coli* codon usage optimized; The natural glycosylation site of Pg1B was inactivated; SpR |
| pGVXN1217 | pg1B$^{N311V}$ | *E. coli* codon usage optimized; Substrate optimized Pg1B; SpR |
| pGVXN1221 | pg1B$^{N311V,K482R,D483H,A669V}$ | *E. coli* codon usage optimized; Substrate optimized Pg1B; SpR |
| pGVXN2381 | pg1B$^{Y77H,S80R,Q287P,K289R,N311V}$ | *E. coli* codon usage optimized; Substrate optimized Pg1B; SpR |
| pGVXN659 | EPA-4 | EPA with four bioconjugation sites; AmpR |
| pGVXN1076 | EPA-4 | EPA with four bioconjugation sites; KanR |

[1]SpR, spectinomycin resistant; AmpR, ampicillin resistant; KanR, kanamycin resistant Carrier Protein (EPA)

All *E. coli* O-antigen production strains expressed a genetically detoxified *P. aeruginosa* ADP-ribosyltransferase toxoid (EPA) as a carrier protein for the O-antigen. The EPA toxoid differs from wild-type EPA toxin in two residues: Leu552 was changed to Val and Glu553 (in the catalytic domain) was deleted. Glu553 deletions were reported to significantly reduce toxicity. In addition to the detoxification mutation, four (EPA-4) consensus N-glycosylation site motifs were introduced. The epa gene was placed behind a L-Arabinose (Ara) inducible promoter on a plasmid (Table 4). Table 4 is limited to the plasmids used in production In a further improvement where the N311V PglB-variant was further modified, an Y77H amino acid substitution further enhanced O4-Glc+-specific product yield and showed an increased degree of di- and tri-glycosylated product compared to the N311V PglB-variant, where other modifications were found to be neutral or had a negative effect on product yield (FIG. 7B). Plasmid pLMTB4008 (SpR) encodes *E. coli* codon usage optimized, (O4-Glc+)-substrate optimized, PglB variant with mutations Y77H and N311V.

The PglB variant with optimized substrate specificity for O4-Glc+O-antigen polysaccharide, containing N311V and Y77H amino acid substitutions relative to wild-type (wt) *C. jejuni* glycosyl transferase PglB, was found to double bioconjugate yield compared to the first round optimized PglB-N311V variant.

Similarly using screens, the most optimal yielding PglB variants were also determined for *E. coli* O-antigen bioconjugate production of the of the other nine serotypes in the ExPEC10V composition.

For bioconjugates having the O1A, O6A, or O15 antigen polysaccharide, PglB with amino acid mutations N311V, K482R, D483H, and A669V was found to give the highest yields.

For bioconjugates having the O2, O8, O18A, or O25B antigen polysaccharide, wild-type PglB (i.e. not having amino acid mutations at positions 77, 80, 287, 289, 311, 482, 483 and 669) was found to give the highest yields.

For bioconjugates having the O16 antigen polysaccharide, PglB with amino acid mutations Y77H, S80R, Q287P, K289R, and N311V was found to give the highest yields.

For bioconjugates having the O75 antigen polysaccharide, PglB with amino acid mutation N311V was found to give the highest yields.

It can be seen from these results that the optimal PglB variant is different for different O-antigens, and that the optimal PglB variant for producing a bioconjugate with a given O-antigen polysaccharide is unpredictable.

Example 8: Bioconjugates of O-Antigens from 10 *E. coli* Serotypes and their Quality Attributes O-glycan residues of the target O-antigens are structurally diverse and have variable repeating units. The specificity and affinity of the glycosyl transferase PglB is linked to the glycan structure. Thus, making a bioconjugate that has the desired quality attributes, e.g., purity, glycan/protein ratio, etc., is a challenging, non-straightforward, task. The right combination of PglB and EPA carrier protein determines the yield and may influence glycosylation efficiency. By optimizing the PglB and carrier proteins, bioconjugates having the desired quality attributes were produced. It may be also important to maintain a lower threshold value of total carrier protein, particularly when one or more O-antigen bioconjugates are combined together and administered in a single composition or vaccine, because very high amounts of carrier protein may lead to immunological interference. In order to avoid such a phenomenon, conjugates having a higher glycan/protein ratio are preferred. Hence, for ExPEC10V vaccine, bioconjugates with at least comparable (to the previously described ExPEC4V vaccine that has been subject to clinical trials) glycosylation ratio were developed.

The bioconjugates were each produced by culturing the respective host cells (Example 6, Table 3) in bioreactors (10 L and/or 200 L volumes) and expression of the bioconjugates, following methods previously described. Each drug substance was manufactured batch-wise by bacterial fed-batch fermentation to generate biomass containing the expressed bioconjugates of the corresponding polysaccharide serotype. Cells were cultured and induced with IPTG and arabinose. The bioconjugates were isolated from the periplasm of the cells in the bioreactor cultures by osmotic shock followed by chromatographic purification. This process was performed for each of the 10 bioconjugates.

The *E. coli* O-antigen bioconjugates thus prepared that are drug substances (DSs) for ExPEC10V and ExPEC4V showed comparable critical quality attributes: (1) process-related purity (measured by RP-HPLC) was higher than 95%, (2) polysaccharide/protein ratio ranged between about 0.1-0.5, mostly between 0.15 and 0.45, (3) bacterial endotoxin (Ph. Eur. 2.2.3) was less than 0.5 EU/μg polysaccharide. The average length of the individual polysaccharide chains was typically between about 10-20 repeating units (measured using high resolution SDS-PAGE).

The structures of the polysaccharide repeat units were confirmed (by NMR and MS/MS of the conjugates, intact or trypsin-digested) to be the ones shown in the Formulas for the corresponding serotypes in Table 1, for all ten bioconjugates that are DSs for the ExPEC10V composition described above.

The O18 serotype had the lowest yields of bioconjugate production amongst the ten serotypes of which bioconjugates were made for the ExPEC10V composition.

ExPEC10V drug product (DP) comprises a mixture of the ten monovalent DSs described above.

Example 9: Toxicology of ExPEC10V Vaccine

A single-dose pilot toxicity and local tolerance study (non-GLP) with ExPEC10V was conducted in female NZW rabbits. One group (n=2) received an intramuscular (IM) injection (on Day 0) of the control (saline), and a second group (n=4) received an IM injection of ExPEC10V at 105.6 μg total polysaccharide (PS)/dose (9.6:9.6:9.6:9.6:9.6:9.6:9.6:9.6:19.2:9.6 μg PS per dose, for respectively O-serotypes O1A, O2, O4, O6A, O8, O15, O16, O18A, O25B and O75) using a dosing volume of 0.6 mL (176 μg PS/mL). Necropsy was performed on Day 2.

There were no mortalities observed. In addition, there were no vaccine-related effects noted for clinical observations (including injection site effects using Draize scoring), body weight, food consumption, and body temperature. Histopathologically, there were no vaccine-related changes observed at the administration site or draining (iliac) lymph node. A minimal increase in germinal center formation in the spleen was observed in one out of four treated animals (Day 2), and was considered a normal, immunological response to the injected vaccine. Overall, the administration of a single IM dose of ExPEC10V to female rabbits was well-tolerated.

Example 10: Immunogenicity of ExPEC10V Blended Formulation in Rabbits

An ExPEC4V vaccine (comprising bioconjugates of *E.coli* O1A, 02, 06A, and 025B serotypes) has previously been shown to be immunogenic for these four serotypes in rats, rabbits, and humans (see e.g. WO 2015/124769: WO 2017/035181; Huttner et al, 2017, Lancet Infect Dis, hypertext transfer protocol://dx.doi.org/10.1016/S1473-3099(17)30108-1: RW Frenck Jr, et al, abstract 5587, ASM Microbe 2018). The novel bioconjugates of the invention having the *E. coli* glucosylated 04 serotype were shown to be immunogenic in Examples 4 and 5 above. Immunogenicity of the bioconjugates of *E. coli* serotypes 08, 015, 016, 018A, and 075 (all having EPA-2 as carrier protein in this experiment) when separately administered (monovalent) to rats confirmed that also each of these bioconjugates was immunogenic, since ELISA data indicated that each of these bioconjugates could elicit high levels of *E. coli* O-antigen specific antibodies (not shown).

Immunogenicity of the 10-valent vaccine that contained a mixture of the 10 bioconjugates as described above was also tested. New Zealand White (NZW) rabbits (female, 12-16 weeks old) received 3 intramuscular immunizations with ExPEC10V or saline administered 2 weeks apart (Table 5; administration at days 0, 14, and 27). The 10 polysaccharides that are part of the ExPEC10V vaccine used in these experiments were conjugated to the carrier protein EPA containing 4 sites of glycosylation (EPA-4). The vaccine was formulated in 3 different doses: Group 1 ('high dose'): 8 ug/dose of O1A, O2, O6A, O4, O8, O15, O16, O18 and O75 and 16 ug/dose of O25B; Group 2 ('medium dose'): 4 ug/dose of O2, O4, O8, O15, O16, O18 and O75, 8 ug/dose of O1A and O6A and 16 ug/dose of O25B; Group 3 ('low dose'): 0.4 ug/dose of O2, O4, O8, O15, O16, O18 and O75, 0.8 ug/dose of O1A and O6A and 1.6 ug/dose of O25B. Animals from the control group (Group 4) received only saline (0.9% (w/v) sodium chloride solution) (Table 5).

Antibody responses were evaluated at day 0 (pre-immunization) and days 14, 27 and 42 post-immunization. Serum antibody levels induced by each of the bioconjugates included in the vaccine and the carrier protein EPA were measured by ELISA (total IgG), using type-specific LPS as coating material. The antibody titers were reported as EC50 values that correspond to the half maximal effective concentration based on duplicates of 12-step titration curves plotted in a 4-parameter logistic nonlinear regression model. Functional activity was determined by OPK.

TABLE 5

Description of experimental groups.

| Experimental groups | Dosing (μg/PS) O1A:O2:O6A:O25B:O4:O8:O15:O16:O18A:O75 | Sample size |
|---|---|---|
| Group 1 (high dose) | 8:8:8:16:8:8:8:8:8:8 | 7 |
| Group 2 (medium dose) | 8:4:8:16:4:4:4:4:4:4 | 7 |
| Group 3 (low dose) | 0.8:0.4:0.8:1.6:0.4:0.4:0.4:0.4:0.4:0.4 | 7 |
| Group 4 (control) | 0.9% (w/v) sodium chloride solution | 7 |

Figure 8:
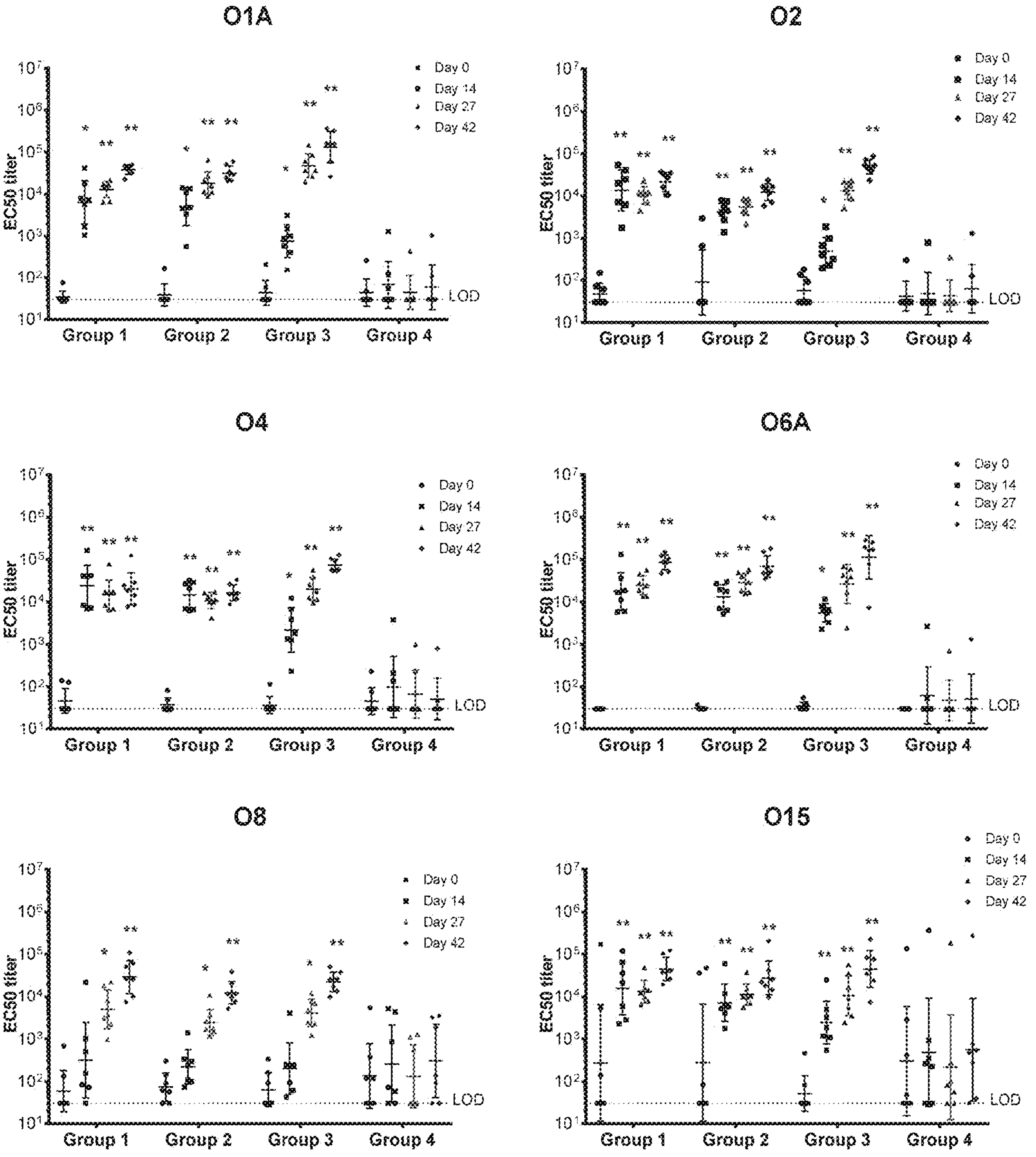
FIG. 8 shows antibody responses induced by ExPEC10V vaccine in New Zealand White rabbits. Animals received 3 intramuscular immunizations with ExPEC10V or saline administered 2 weeks apart. ExPEC10V vaccine was administered at 3 different concentrations (group 1: high dose, group 2: medium dose and group 3: low dose, Table 11) and a control group received only saline (group 4, 0.9% (w/v) sodium chloride solution). Antibody levels were measured by ELISA at day 0 (pre-vaccination) and days 14, 27 and 42 (post-vaccination). Individual titers (EC50 titer) and geometric mean titers (GMT) 95% CI are shown. Wilcoxon Rank Sum test with Bonferroni correction for multiple comparisons. Comparisons ExPEC10V vaccinated animals (group 1, 2 and 3) versus saline control (group 4). *p≤0.05, p≤0.01; *p≤0.001; ****p≤0.0001. LOD: limit of detection.

Results are shown in FIG. 8 and summarized in Table 6.

TABLE 6

Summary of *E. coli* O-antigen specific antibody responses induced by ExPEC10V in NZW rabbits.

| ExPEC10V | Antibody responses day 14 post-vaccination | | | | | | | | | |
|---|---|---|---|---|---|---|---|---|---|---|
| dose | O1A | O2 | O6A | O25B | O4 | O8 | O15[#] | O16 | O18A | O75 |
| High | * | ** | ** | * | ** | ns | ** | ** | * | ns |
| Mid | * | ** | ** | ** | ** | ns | ** | ** | ns | ns |
| Low | * | * | * | * | * | ns | ** | ** | ns | ns |
| **ExPEC10V** | **Antibody responses day 27 post-vaccination** | | | | | | | | | |
| dose | O1A | O2 | O6A | O25B | O4 | O8 | O15[#] | O16 | O18A | O75 |
| High | ** | ** | ** | ** | ** | * | ** | ** | ** | ** |
| Mid | ** | ** | ** | ** | ** | * | ** | ** | * | ** |
| Low | ** | ** | ** | ** | ** | * | ** | ** | ** | ** |
| **ExPEC10V** | **Antibody responses day 42 post-vaccination** | | | | | | | | | |
| dose | O1A | O2 | O6A | O25B | O4 | O8 | O15[#] | O16 | O18A | O75 |
| High | ** | ** | ** | ** | ** | ** | ** | ** | ** | ** |
| Mid | ** | ** | ** | ** | ** | ** | ** | ** | ** | ** |
| Low | ** | ** | ** | ** | ** | ** | ** | ** | ** | ** |

Serotype-specific antibody responses in which p values were statistically significant are shown by asterisks.

Serotype-specific antibody responses in which p values were not statistically significant are designated as ns.

Wilcoxon Rank Sum test with Bonferroni correction for multiple comparisons.

Comparisons ExPEC10V vaccinated animals (Group 1, 2 and 3) versus saline control (Group 4).

*$p \leq 0.05$, **$p \leq 0.01$.

[#]P values were statistically significant after excluding an outlier animal from the control group (sensitivity analysis).

The high dose of ExPEC10V (Group 1) induced significantly higher IgG antibody levels at all time-points investigated (Days 14, 27 and 42 post-immunization) when compared to saline control for O1A, O2, O4, O6A, O16, O18A and O25B (FIG. 8, Table 6). Significantly higher antibody titers induced by O8 and O75 conjugates when compared to saline control were observed at Days 27 and 42 post-immunization (FIG. 8, Table 6).

The medium dose of ExPEC10V (Group 2) and the low dose (Group 3) induced significantly higher antibody levels at all time-points investigated (Days 14, 27 and 42 post-immunization) when compared to saline control for O1A, O2, O4, O6A, O16 and O25B (FIG. 8, Table 6). Significantly higher antibody titers induced by O8, O18A and O75 conjugates when compared to saline control were observed at Days 27 and 42 post-immunization suggesting that the boost dose in rabbits increases the response to these O-serotypes (FIG. 8, Table 6).

For O15 conjugates, sensitivity analysis omitting an outlier animal from the control group showed that all three doses of ExPEC10V vaccine induced a significant increase in antibody responses when compared to saline control at Days 14, 27 and 42 post-immunization (FIG. 8, Table 6).

Antibodies induced by the carrier protein EPA were significantly higher than EPA antibody titers in the saline-treated (control) group for the three doses of ExPEC10V tested (high, medium and low) at all time points investigated (Days 14, 27 and 42) (FIG. 8).

Between dose comparisons (not shown) showed that at Day 14 post-vaccination, the high dose of ExPEC10V induced significantly higher antibody responses when compared to the low dose for most of the conjugates tested (O1A, O2, O4, O6A, O15, O16, O18A and O25B). The medium dose of ExPEC10V also induced significantly higher antibody responses compared to the low dose for O1A, O2, O4, O18A, O25B and O75. For O8 conjugate, all three formulations of ExPEC10V induced similar levels of antibodies at Day 14 post-vaccination.

The low dose of ExPEC10V induced a significant increase in antibody responses at Day 42 post vaccination (after a prime and two boost doses) when compared to the high and medium doses of ExPEC10V for O1A, O2, O4, O16, O25B and O75 conjugates. These findings are in line with other experiences with conjugate vaccines, where for instance no clear relationship between dose and the magnitude of the antibody response to primary vaccination was observed in infants vaccinated with pneumococcal conjugate vaccine (Poolman J T, et al. Expert Rev Vaccines. 2013, 12(12):1379-94).

There were no significant differences between the three doses of ExPEC10V tested at Day 42 post-vaccination for O6A, O8 and O15 conjugates. For the O18A conjugate, the high dose of ExPEC10V induced a significantly higher antibody response when compared to the medium dose at Day 42 post-vaccination.

For the carrier protein (EPA), the high and medium dose of ExPEC10V induced significantly higher antibody responses when compared to the low dose at day 14 post-vaccination. The high dose of the vaccine also induced significantly higher antibody responses when compared to the low dose at day 42 post-vaccination.

In conclusion, the three formulations of ExPEC10V (high, medium and low), administered via intramuscular injection on Days 0, 14, 27 are immunogenic in rabbits.

So far, functional antibodies capable of killing *E. coli* strains induced by this vaccine in rabbits were shown for serotypes O1A, O2, O4, O6A, O15, O16 and O25B.

In a further experiment, a GMP batch of the ExPEC10V vaccine (see Example 8 above for production) was prepared and injected into NZW rabbits as part of a toxicology study (Table 7). In this study, NZW rabbits (males and females) received 3 intramuscular injections (0.6 mL) of the ExPEC10V vaccine (day 1, 15 and 29) and a control group received 0.9% (w/v) sodium chloride solution (saline). Each dose of the vaccine contained 9.6 g polysaccharide (PS) for serotypes O1A, O2, O4, O6A, O8, O15, O16, O18A and O75 and 19.2 g PS for serotypes O25B, corresponding to 105.6 g total PS (176 g total PS/mL) and 382.8 g of total EPA (638 µg EPA/mL). IgG titers against O-antigens and carrier protein (EPA) were determined from samples collected during the pre-treatment period (day 1) and days 31 and 50 post-immunization.

Figure 9:
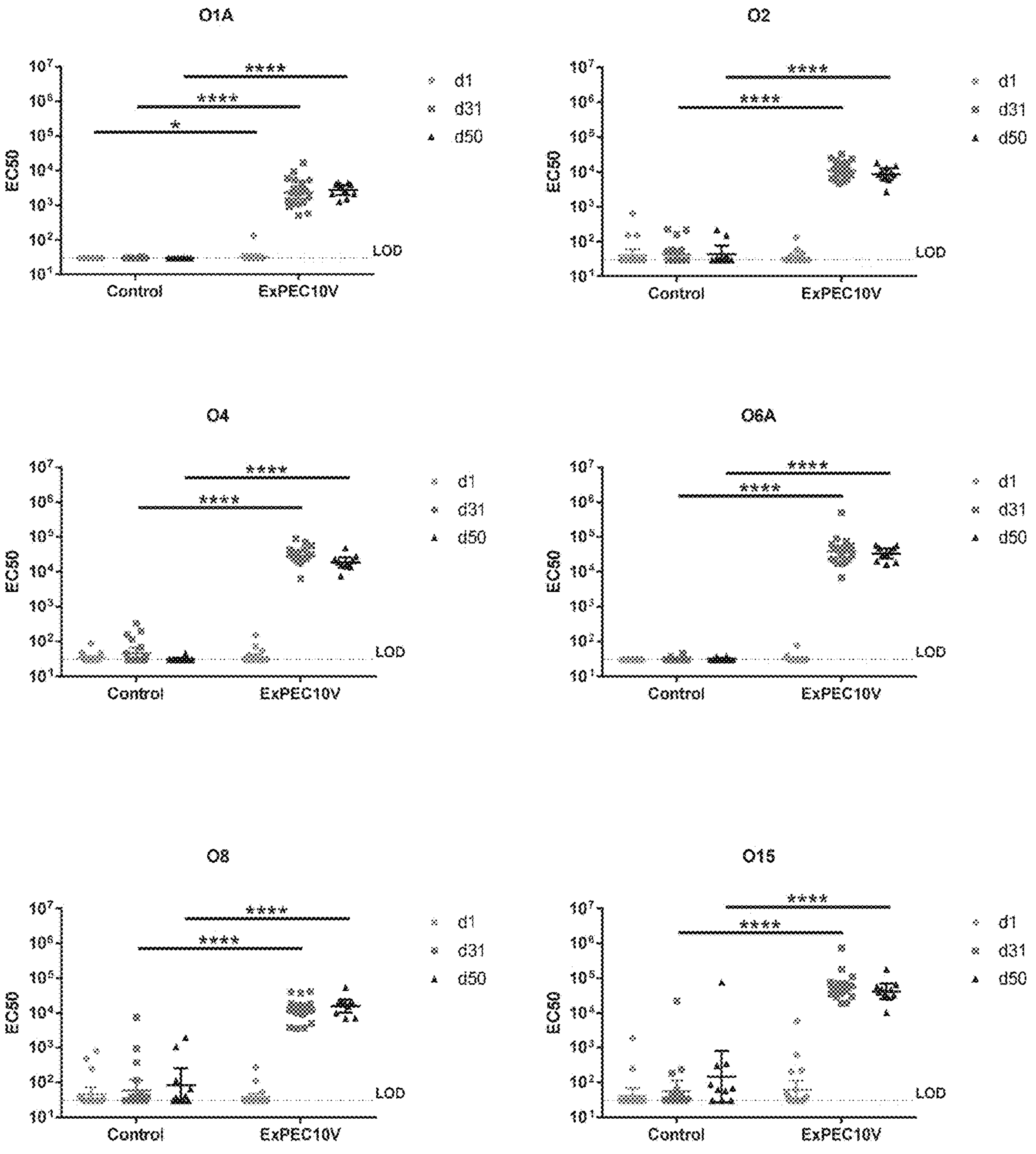
FIG. 9 shows antibody responses induced by ExPEC10V. New Zealand White rabbits received 3 intramuscular immunizations with ExPEC10V (105.6 g total polysaccharide) or 0.9% w/v sodium chloride solution (control). IgG titers were determined by ELISA at day 1 (pre-immunization, n=20/group), day 31 (post-immunization, n=20/group) and day 50 (post-immunization, n=10/group). Plots show individual titers and geometric mean 95% confidence interval for each group. Differences in IgG titers between the ExPEC10V and control group were analyzed using a Tobit model with a likelihood ratio test. P-values≤0.05 were considered significant. *P≤0.05, ****P≤0.0001.

A significant increase in antibody responses against all O-antigens and the carrier protein EPA were observed at day 31 and 50 post-vaccination in the group that received ExPEC10V when compared to the control group that received only saline (FIG. 9, Table 8). For O1A serotype, a significantly higher antibody response was also observed at day 1 (baseline) when vaccinated animals were compared with the controls. These results suggest that some animals were pre-exposed to *E. coli* or have antibodies that cross-react with O1A-LPS.

TABLE 7

Experimental groups and ExPEC10V dose used in NZW rabbits.

| Groups | Treatment | Dose | Dosing days | Main (day 31) (males/ females) | Recovery (day 50) (males/ females) |
|---|---|---|---|---|---|
| 1 | control | 0 | 1, 15, 29 | 10 | 10 |
| 2 | ExPEC10V | 105.6 µg PS* | 1, 15, 29 | 10 | 10 |

*Each dose (0.6 mL dosing volume) contains 9.6:9.6:9.6:9.6:9.6:9.6:9.6:9.6:19.2:9.6 µg polysaccharide (PS) for serotypes O1A, O2, O4, O6A, O8, O15, O16, O18A, O25B, O75, respectively (176 µg total PS/mL). Each dose contains 382.8 µg EPA protein (638 µg EPA/mL).

TABLE 8

Immunogencity of ExPEC10V in NZW rabbits as part to a toxicology study.

| Treatment | Antibody responses day 31 post-vaccination | | | | | | | | | |
|---|---|---|---|---|---|---|---|---|---|---|
| ExPEC10V | O1A | O2 | O6A | O25B | O4 | O8 | O15 | O16 | O18A | O75 |
| Day 31 | **** | **** | **** | **** | **** | **** | **** | **** | **** | **** |
| Day 50 | **** | **** | **** | **** | **** | **** | **** | **** | **** | **** |

Antibody responses induced by ExPEC10V.

Serotypes in which a significant increase in antibody responses was observed in the vaccine group compared to control are shown by asterisks.

Tobit model with a likelihood ratio test.

****P ≤ 0.0001.

Example 11: Phase 1/2a Trial with the ExPEC10V Vaccine in Humans

At present, there is no vaccine available to prevent IED. The serotypes comprising the ExPEC10V vaccine (O1A, O2, O4, O6A, O8, O15, O16, O18A, O25B and O75) were selected to address invasive disease caused by the majority of clinically relevant ExPEC strains that also represent the majority of ExPEC isolates causing antimicrobial resistant IED, including ST131. The selected serotypes are representative for the ten prevalent ExPEC O-serotypes causing bloodstream infections in the older population and responsible for approximately 70% of bloodstream infections caused by ExPEC.

Since the mechanism of action of conjugate vaccines in the prevention of invasive disease is not expected to be affected by antibiotic resistance mechanisms, it is believed that ExPEC10V vaccine provides protection against IED caused by drug-resistant- and drug-susceptible O1A, O2, O4, O6A, O8, O15, O16, O18A, O25B and O75 serotypes.

There is preceding clinical experience with ExPEC4V, an earlier vaccine candidate which comprised a subset of four of the *E. coli* O-antigen conjugates (O1A, O2, O6A and O25B) also found in ExPEC10V. Based on the results from four clinical studies (two completed phase 1 studies, one completed phase 2 study and an ongoing phase 2 study), ExPEC4V was well-tolerated by the study participants and no vaccine-related safety signals were observed at doses up to 16 μg polysaccharide (PS) per serotype (O1A, O2, O6A and O25B). Most adverse events (AEs) were Grade 1 and 2, very few Grade 3 AEs were reported. Late-onset solicited local AEs (AEs which start after Day 5 post-vaccination) were observed mainly with the higher doses of ExPEC4V. In each study, the ExPEC4V vaccine was shown to be immunogenic, demonstrating a dose-dependent vaccine immune response, and O-antigen specific Immunoglobulin G (IgG) titer increases, as measured by enzyme-linked immunosorbent assay (ELISA). Functional activity of the antibodies was demonstrated with an ExPEC4V-optimized opsonophagocytic killing assay (OPKA). Co-analysis of ELISA and OPKA test results showed correlation between the assay responses (Pearson correlation coefficients≥0.61 and ≥0.48 for Day 30 and Day 360, respectively in a Phase 2 clinical trial [study 4V-BAC2001]), substantiating the use of ELISA as a primary measure of ExPEC4V antibody titers and to predict functional antibody activity. Analysis of the immunogenicity data has demonstrated the durability of the immune response through three years after vaccination with ExPEC4V. It has now also been observed that sera from humans vaccinated with ExPEC4V and that had high titers of serotype-specific opsonophagocytic antibodies, when passively transferred into mice that were subsequently intraperitoneally challenged with *E. coli* strains of O25B or O2 serotype, were able to mediate protection in vivo (not shown). Hence, ExPEC4V-specific opsonophagocytic human antibodies mediate bacterial killing in vivo, which is in line with other conjugate vaccines in which the proposed mechanism of protection is by induction of opsonophagocytic antibodies that mediate bacterial killing.

ExPEC10V includes a total often serotypes and increases coverage from about 50% (ExPEC4V) to approximately 70% of bloodstream infections caused by ExPEC in adults aged 60 years and older. Based on the clinical experience with ExPEC4V, and on the pre-clinical data for ExPEC10V as discussed in the examples above, it is expected that administration of ExPEC10V will induce immune responses to *E. coli* serotypes O1A, O2, O4, O6A, O8, O15, O16, O18A, O25B and O75 also in humans.

A randomized, observer-blind, first-in-human phase 1/2a study to evaluate the safety, reactogenicity, and immunogenicity of three different doses of the ExPEC10V vaccine is conducted in humans aged 60 to 85 years in stable health (study 10V-BAC1001). The study design includes 2 cohorts: A total of 1,004 participants are enrolled in the study with 404 participants (100 participants/ExPEC10V dose) aged≥60 to ≤85 years in stable health in Cohort 1 and an additional of 600 participants aged≥60 years in stable health with a history of UTI in the past 5 years in Cohort 2.

ExPEC10V is a 10-valent vaccine candidate in development for the prevention of invasive extraintestinal pathogenic *Escherichia coli* (ExPEC) disease (IED) in adults 60 years of age and older. ExPEC10V consists of the O-antigen polysaccharides (PSs) of the ExPEC serotypes O1A, O2, O4, O6A, O8, O15, O16, O18A, O25B and O75 separately bioconjugated to the carrier protein, a genetically detoxified form of exotoxin A (EPA) derived from *Pseudomonas aeruginosa*, and its production has been described above. The O4 PS is the glucosylated form, having the structure of Formula (O4-Glc+) in Table 1.

Objectives and Endpoints

COHORT 1 - Phase 1/2a observer-blind period with open-label long-term follow-up period (N = 404):

| Objectives | Endpoints |
|---|---|
| **Primary** | |
| To evaluate the safety and reactogenicity of different doses of ExPEC10V in participants ≥60 to ≤85 years of age | Solicited local and systemic adverse events (AEs) collected for 14 days post-vaccination (from Day 1 to Day 15)<br>Unsolicited AEs collected from the administration of the study vaccine until 29 days post-vaccination (from Day 1 to Day 30)<br>Serious adverse events (SAEs) collected from the administration of the study vaccine until Day 181 |
| To evaluate the dose-dependent immunogenicity of ExPEC10V on Day 15 in participants ≥60 to ≤85 years of age | Antibody titers for ExPEC10V, as determined by multiplex electrochemiluminescent (ECL)-based immunoassay and multiplex opsonophagocytic assay (MOPA) on Day 15 |
| **Secondary** | |
| To evaluate the correlation between multiplex ECL-based immunoassay (total antibody) and MOPA (functional antibody) serum titers on Day 15 | Antibody titers for ExPEC10V, as determined by multiplex ECL-based immunoassay and MOPA on Day 15 |
| To evaluate the dose-dependent immunogenicity of ExPEC10V on Days 30 and 181 in participants ≥60 to ≤85 years of age | Antibody titers for ExPEC10V, as determined by multiplex ECL-based immunoassay and MOPA on Days 30 and 181 |
| To evaluate, in the long-term follow-up (LTFU) period, the safety of the ExPEC10V dose selected for further clinical development based on the Day 30 primary analysis in participants ≥60 to ≤85 years of age | SAEs related to the study vaccine or study procedures collected from Day 182 until the end of the study |
| To evaluate, in the LTFU period, the immunogenicity of the ExPEC10V dose selected for further clinical development based on the Day 30 primary analysis | Antibody titers for ExPEC10V, as determined by multiplex ECL-based immunoassay and MOPA at Year 1 (Day 366), Year 2 (Day 731) and Year 3 (Day 1096) |

| COHORT 2 - Double-blind period with double-blind long-term follow-up period (N = 600): | |
|---|---|
| Objectives | Endpoints |
| Primary | |
| To evaluate the safety and reactogenicity of the selected dose of ExPEC10V in participants ≥60 years of age with a history of UTI in the past 5 years | Solicited local and systemic AEs collected for 14 days post-vaccination (from Day 1 to Day 15)<br>Unsolicited AEs collected from the administration of the study vaccine until 29 days post-vaccination (from Day 1 to Day 30)<br>SAEs collected from the administration of the study vaccine until Day 181 |
| To evaluate the immunogenicity of the selected dose of ExPEC10V on Day 30 in participants ≥60 years of age with a history of UTI in the past 5 years | Antibody titers for ExPEC10V, as determined by multiplex ECL-based immunoassay and MOPA on Day 30 |
| Secondary | |
| To evaluate the correlation between multiplex ECL-based immunoassay (total antibody) and MOPA (functional antibody) serum titers on Day 30 in participants ≥60 years of age with a history of UTI in the past 5 years | Antibody titers for ExPEC10V, as determined by multiplex ECL-based immunoassay and MOPA on Day 30 |
| To evaluate the immunogenicity of the selected dose of ExPEC10V on Days 15 and 181 in participants ≥60 years of age with a history of UTI in the past 5 years | Antibody titers for ExPEC10V, as determined by multiplex ECL-based immunoassay and MOPA on Days 15 and 181 |
| To evaluate, in the LTFU period, the safety of the selected dose of ExPEC10V in participants ≥60 years of age with a history of UTI in the past 5 years | SAEs related to the study vaccine or study procedures collected from Day 182 until the end of the study |
| To evaluate, in the LTFU period, the immunogenicity of the selected dose of ExPEC10V in participants ≥60 years of age with a history of UTI in the past 5 years | Antibody titers for ExPEC10V, as determined by multiplex ECL-based immunoassay and MOPA at Year 1 (Day 366), Year 2 (Day 731), and Year 3 (Day 1096) |
| Exploratory | |
| To evaluate the effect of ExPEC10V on the intestinal (stool) microbiome by metagenomic analyses | Metagenomics of stool samples from a selected subset[1] of participants to evaluate the effect of ExPEC10V on:<br>Prevalence of pathogens (eg, *Clostridium difficile*) in the intestinal flora<br>Prevalence of ExPEC10V serotypes in the intestinal flora |

Overall Design

This is a randomized, multicenter, interventional study including two cohorts.

Figure 10A:
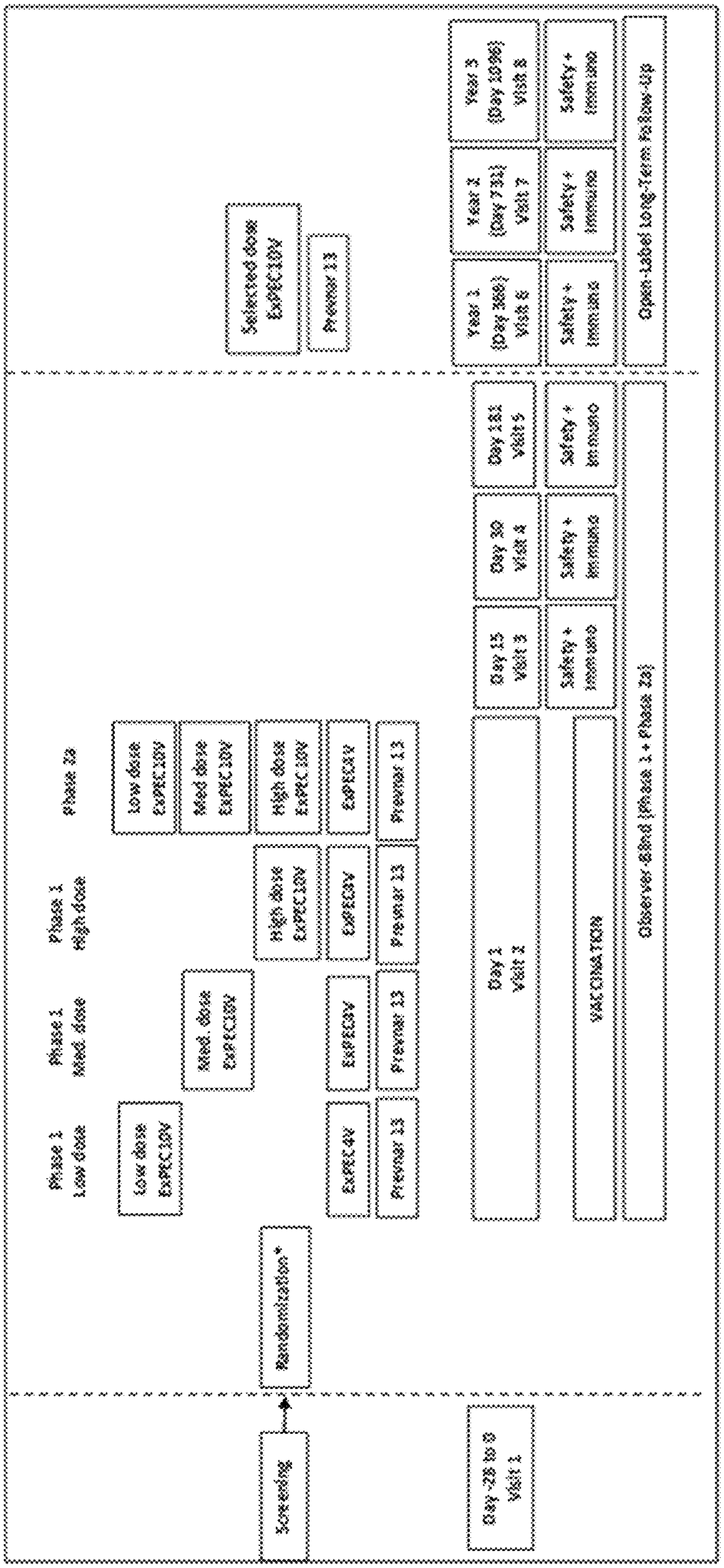
FIG. 10A shows the overall study design for Cohort 1.

For Cohort 1, the study has an observer-blind, active-controlled design, and a total of 404 adult participants aged≥60 to ≤85 years in stable health with or without a history of UTI are included. The study design for Cohort 1 is comprised of three periods: a maximum of 28-day screening period, an observer-blinded 181-day follow-up period with vaccination on Day 1 and an open-label LTFU period which lasts from Day 182 until 3 years (Day 1096) post-vaccination (FIG. 10A). Only participants from the ExPEC10V selected dose group (approximately 100 participants) and participants from the Prevnar 13 group progress to the LTFU period. The end of Cohort 1 is the last participant's Year 3 visit (Day 1096).

Figure 10B:
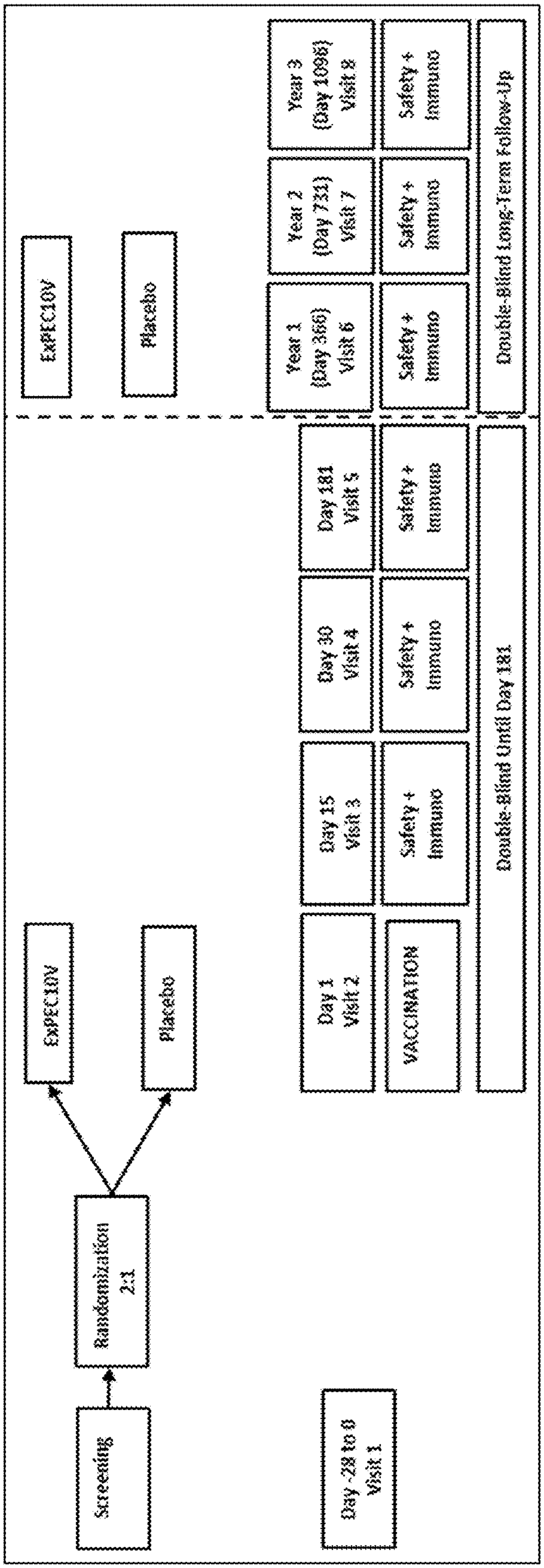
FIG. 10B shows the overall study design for Cohort 2. See Example 11 for details.

For Cohort 2, the study has a double-blind, placebo-controlled design, and a total of 600 adult participants aged≥60 years in stable health with a history of UTI in the past 5 years is included. Enrollment commences after completion of the Phase 1/2a primary analysis and ExPEC10V dose selection from Cohort 1. The study design for Cohort 2 is comprised of three periods: a maximum 28-day screening period, a double-blind 181-day follow-up period with vaccination on Day 1, and a double-blind LTFU period which lasts from Day 182 until 3 years (Day 1096) post-vaccination (FIG. 10B). All participants in Cohort 2 progress to the LTFU period. The end of study is the last participant's Year 3 visit (Day 1096) in Cohort 2.

Cohort 1: Phase 1

In Phase 1 of Cohort 1, a total of 84 participants are enrolled in a staggered approach following stepwise dose-escalating procedures with safety evaluations in place before progressing from one step to the next. An internal Data Review Committee (DRC) is commissioned for this study to review the physical examination data (baseline as well as targeted), baseline demographic data and the 14-day post-vaccination safety data (including solicited local and systemic AEs, unsolicited AEs, SAEs, clinical laboratory data and vital signs) of these 84 Phase 1 participants. In this phase of the study, participants were enrolled and randomized in six steps:

Step 1: Four sentinel participants were enrolled and randomized; two participants in the ExPEC10V low dose group (Table 11), and one participant each in the ExPEC4V and Prevnar 13 groups.

Step 2: Twenty-four participants were enrolled and randomized; 18 participants in the ExPEC10V low dose group (Table 11), and three participants each in the ExPEC4V and Prevnar 13 groups.

Step 3: Four sentinel participants were enrolled and randomized; two participants in the ExPEC10V medium dose group (Table 11), and one participant each in the ExPEC4V and Prevnar 13 groups.

Step 4: Twenty-four participants were enrolled and randomized; 18 participants in the ExPEC10V medium dose group (Table 11), and three participants each in the ExPEC4V and Prevnar 13 groups.

Step 5: Four sentinel participants were enrolled and randomized; two participants in the ExPEC10V high dose group (Table 11), and one participant each in the ExPEC4V and Prevnar 13 groups.

Step 6: Twenty-four participants were enrolled and randomized; 18 participants in the ExPEC10V high dose group (Table 11), and three participants each in the ExPEC4V and Prevnar 13 groups.

All participants received a single intramuscular (IM) injection of either ExPEC10V (1 of 3 doses), ExPEC4V or Prevnar 13 on Day 1 per the assigned study vaccination groups. The four sentinel participants at each of Steps 1, 3 and 5 were contacted by telephone 24 hours post-vaccination to collect safety information. The blinded 24-hour post-vaccination safety data in each group of four sentinel participants were reviewed by the principal investigator (PI), study responsible physician (SRP) and sponsor medical lead (SML). Randomization of additional participants for the next step was halted until this Day 2 sentinel safety evaluation was completed.

In the absence of any clinically significant findings, an additional 24 participants (for Steps 2, 4, and 6) were enrolled and randomized to one of three study vaccination groups (Table 11) to receive a single IM injection of either ExPEC10V (1 of 3 doses), ExPEC4V or Prevnar 13 on Day 1.

After vaccination of an additional 24 participants at each dose level (low dose in Step 2, medium dose in Step 4, and high dose in Step 6), 14-day post-vaccination safety data of all 28 (4+24) participants at each dose level was reviewed by the DRC before progressing to the next dose level or Phase 2a.

Cohort 1: Phase 2a

Based on acceptable safety and reactogenicity (in the absence of any safety concerns or any events meeting a specific study pausing rule) as determined by DRC after the review of 14-day post-vaccination safety data for the initial 84 participants, the remaining 320 participants from Cohort 1 are randomized and dosed in Phase 2a of the study. These additional 320 participants were enrolled and randomized in parall in a ratio of 2:2:2:1:1 to one of the five study vaccination groups to receive a single IM injection of either ExPEC10V (1 of 3 doses), ExPEC4V or Prevnar 13 on Day 1 (Table 11).

In addition to performing the 14-day safety review for the initial 84 participants, the DRC also evaluates safety data of Cohort 1 over the course of the study and review any events that meet a specific study vaccination pausing rule or any other safety issue that may arise.

For Cohort 1, the primary analysis occurs when all participants have completed the Day 30 visit (Visit 4) or have discontinued earlier. The final analysis occurs when all participants have completed the Day 181 visit or have discontinued earlier. For participants progressing to the open-label long-term follow-up (LTFU) period (ExPEC10V selected dose group and Prevnar 13 group), yearly follow-up analyses include safety and immunogenicity data (multiplex ECL-based immunoassay and MOPA) collected up to the time of the visit at Year 1 (Day 366), Year 2 (Day 731) and Year 3 (Day 1096) after vaccination.

Cohort 2

In Cohort 2, the safety, reactogenicity, and immunogenicity of the selected dose of ExPEC10V (based on the primary analysis results of Cohort 1) is evaluated in participants aged≥60 years in stable health with a history of UTI in the past 5 years. For Cohort 2, the study has a double-blind, placebo-controlled design, and a total of 600 participants are enrolled and randomized in parallel in a 2:1 ratio (400 participants in the ExPEC10V group and 200 in the placebo group).

All participants receive a single IM injection of either the selected dose of ExPEC10V or placebo on Day 1 per the assigned study vaccination groups (Table 11).

For Cohort 2, the primary analysis includes safety and immunogenicity data and occurs when all participants have completed the Day 30 visit (Visit 4) or have discontinued earlier. The final analysis occurs when all participants have completed the Day 181 visit or have discontinued earlier. For all participants, yearly follow-up analyses include safety and immunogenicity data (multiplex ECL-based immunoassay and MOPA) collected up to the time of the visit at Year 1 (Day 366), Year 2 (Day 731), and Year 3 (Day 1096) after vaccination.

A stool sample analysis is performed in a selected subset of participants to evaluate the effect of ExPEC10V on the prevalence of pathogens (eg, *Clostridium difficile*) and ExPEC10V serotypes in the intestinal flora using metagenomics.

Number of Participants

A total of 1004 participants is enrolled in the study; 404 participants in Cohort 1 and 600 participants in Cohort 2.

Intervention Groups

Description of Interventions

ExPEC10V: *E. coli* bioconjugate vaccine in phosphate buffered solution containing O-antigen PS of ExPEC serotypes O1A, O2, O4, O6A, O8, O15, O16, O18A, O25B and O75 separately bioconjugated to the EPA carrier protein. Single 0.5 mL IM (deltoid) injection of one of the three doses of ExPEC10V on Day 1.

ExPEC4V: *E. coli* bioconjugate vaccine in saline buffer solution containing O-antigen PS of ExPEC serotypes O1A, O2, O6A, O25B (4:4:4:8 μg PS/ExPEC serotypes) separately bioconjugated to the EPA carrier protein. Single 0.5 mL IM (deltoid) injection of ExPEC4V on Day 1.

Prevnar 13: Sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein. Single 0.5 mL IM (deltoid) injection on Day 1, supplied in a single-dose prefilled syringe.

Placebo: normal saline. Single 0.5 mL IM (deltoid) injection of placebo on Day 1.

The ExPEC study intervention materials are described in Table 9.

TABLE 9

BAC1001MV ExPEC Study Vaccines.

| Study Arm | O1A (μg) | O2 (μg) | O4 (μg) | O6A (μg) | O8 (μg) | O15 (μg) | O16 (μg) | O18A (μg) | O25B (μg) | O75 (μg) | EPA (μg) | PS (Total) (μg) |
|---|---|---|---|---|---|---|---|---|---|---|---|---|
| Low dose ExPEC10V | 4 | 4 | 4 | 4 | 4 | 4 | 4 | 4 | 8 | 4 | 160 | 44 |
| Medium dose ExPEC10V | 8 | 4 | 4 | 8 | 4 | 4 | 4 | 4 | 16 | 4 | 221 | 60 |
| High dose ExPEC10V | 8 | 8 | 8 | 8 | 8 | 8 | 8 | 8 | 16 | 8 | 320 | 88 |
| ExPEC4V | 4 | 4 | — | 4 | — | — | — | — | 8 | — | 72 | 20 |

EPA = a genetically detoxified form of exotoxin A derived from *Pseudomonas aeruginosa*;

PS = polysaccharide

ExPEC4V consists of the O-antigen polysaccharides (PSs) of the ExPEC serotypes O1A, O2, O6A, and O25B separately bioconjugated to the EPA carrier protein.

ExPEC10V consists of the O-antigen polysaccharides (PSs) of the ExPEC serotypes O1A, O2, O4, O6A, O8, O15, O16, O18A, O25B and O75 separately bioconjugated to the EPA carrier protein.

Dose is based on PS only.

The EPA (μg) are measured values.

ExPEC10V is composed of 10 monovalent drug substances (DSs). For this clinical study, 2 different concentrations (medium and high) of drug product (DP) are produced (Table 10). A third (low) concentration is obtained in the clinic by diluting the high concentration 1:1 with dilution buffer, which is the same as the formulation buffer. Each DP is formulated in Sodium/Potassium phosphate buffer at pH 7.0 (0.02% [w/w] Polysorbate 80, 5% [w/w] sorbitol, 10 mM methionine).

TABLE 10

Composition of ExPEC10V vaccine for phase 1/2a clinical study

| Ingredient Active[a] | Amount (μg/mL)[a] Low Concentration[b] | Medium Concentration | High Concentration |
|---|---|---|---|
| O-antigen polysaccharide | | | |
| EcoO1A | 8 | 16 | 16 |
| EcoO2 | 8 | 8 | 16 |
| EcoO4 | 8 | 8 | 16 |
| EcoO6A | 8 | 16 | 16 |
| EcoO8 | 8 | 8 | 16 |
| EcoO15 | 8 | 8 | 16 |
| EcoO16 | 8 | 8 | 16 |
| EcoO18A | 8 | 8 | 16 |
| EcoO25B | 16 | 32 | 32 |
| EcoO75 | 8 | 8 | 16 |
| Carrier protein | | | |
| EPA | 320 | 441 | 640 |
| Excipients | | | |
| $KH_2PO_4$ | | 6.19 mM | |
| $Na_2HPO_4$ | | 3.81 mM | |
| Sothitol | | 5% (w/w) | |
| Methionine | | 10 mM | |
| Polysorbate 80 | | 0.02% (w/w) | |

EPA = genetically detoxified *P. aeruginosa* exotoxin A used as carrier protein

[a]The active ingredient is a biologically synthesized conjugate composed of the PS antigen and a carrier protein (EPA); the dose is calculated on the PS moiety only.

[b]The "low concentration" is obtained in the clinic by diluting the "high concentration" 1:1 with dilution buffer Safety Evaluations Key safety assessments include solicited local and systemic AEs, unsolicited AEs, SAEs, physical examinations, vital sign measurements, and clinical laboratory tests.

Immunogenicity Evaluations

Key immunogenicity assessments of collected sera include the assessment of ExPEC10V and ExPEC4V serotype-specific total IgG antibody levels elicited by the vaccine as measured by a multiplex ECL-based immunoassay, and ExPEC10V and ExPEC4V serotype-specific functional antibodies as measured by an opsonophagocytic killing assay (OPKA) in multiplex format (MOPA). Immunogenicity assessments of pneumococcal antibody titers elicited by Prevnar 13 are not performed.

The levels of serum antibodies induced by ExPEC10V are measured by a multiplex electrochemiluminescent (ECL)-based immunoassay. This assay combines high binding carbon electrodes in a multi-spot 96-well format microplate that is coated with different *E. coli* O-LPS antigens or the carrier protein EPA. The levels of antigen-specific antibodies present in serum samples are detected using a secondary antibody (anti-human IgG) labeled with SULFO-TAG. The SULFO-TAG emits light in the presence of electrical stimulation at an intensity that increases proportionally to the amount of bound IgG antibodies. This assay was qualified according to International Conference on Harmonisation (ICH) recommendations.

The levels of functional antibodies induced by ExPEC10V are measured by a multiplex opsonophagocytic assay (MOPA). Briefly, heat-inactivated serum samples are serially diluted and incubated with different *E. coli* strains that are specifically resistant to different types of antibiotics. After that, human complement and phagocytic cells (HL60) are added to the reaction and, after a second incubation period, an aliquot of the reaction mix is transferred to different PVDF hydrophilic membrane filter plates containing media supplemented with specific antibiotic that selectively allow growth of a strain that is resistant to that particular antibiotic. After overnight grown, the colony forming units (CFUs) are counted to determine the number of surviving bacteria. This assay was qualified according to ICH recommendations.

For ExPEC10V serotype antibodies as measured by multiplex ECL-based immunoassay and MOPA, and EPA as measured by multiplex ECL-based immunoassay only, the following measures of immunogenicity are evaluated and tabulated by the study vaccination groups, for all immunogenicity time points:

- proportion of participants with a ≥2-fold and ≥4-fold increase in serum antibody titers from Day 1 (pre-vaccination)
- geometric mean titer (GMT)
- GMR: fold change from baseline, calculated from the post-baseline/baseline value.

For the LTFU period, descriptive summaries of immunogenicity are provided for each serotype.

Dose selection for later phases considers the totality of the evidence available at the time of the primary analysis of Cohort 1 (Day 30 results).

TABLE 11

Cohort 1: Vaccination Schedule

| Study Vaccination Group | Vaccination on Day 1 | Phase 1 Step 1 Sentinel participants (Low dose) | Step 2 Additional participants (Low dose) | Step 3 Sentinel participants (Medium dose) | Step 4 Additional participants (Medium dose) | Step 5 Sentinel participants (High dose) | Step 6 Additional participants (High dose) | Phase 2a Step 7 Additional Phase 2a Participants | Total |
|---|---|---|---|---|---|---|---|---|---|
| G1 | Low dose ExPEC10V* | 2 | 18 | | | | | 80 | 100 |
| G2 | Medium dose ExPEC10V* | | | 2 | 18 | | | 80 | 100 |
| G3 | High dose ExPEC10V* | | | | | 2 | 18 | 80 | 100 |

TABLE 11-continued

Cohort 1: Vaccination Schedule

| Study Vaccination Group | Vaccination on Day 1 | Phase 1 | | | | | | | Total |
|---|---|---|---|---|---|---|---|---|---|
| | | Step 1 Sentinel participants (Low dose) | Step 2 Additional participants (Low dose) | Step 3 Sentinel participants (Medium dose) | Step 4 Additional participants (Medium dose) | Step 5 Sentinel participants (High dose) | Step 6 Additional participants (High dose) | Phase 2a Step 7 Additional Phase 2a Participants | |
| G4 | ExPEC4V** | 1 | 3 | 1 | 3 | 1 | 3 | 40 | 52 |
| G5 | Prevnar 13*** | 1 | 3 | 1 | 3 | 1 | 3 | 40 | 52 |
| Total | | 4 | 24 | 4 | 24 | 4 | 24 | 320 | 404 |

*ExPEC10V consists of the O-antigen polysaccharides (PSs) of the ExPEC serotypes O1A, O2, O4, O6A, O8, O15, O16, O18A, O25B and O75 separately bioconjugated to the carrier protein, a genetically detoxified form of exotoxin A (EPA) derived from *Pseudomonas aeruginosa*.
**ExPEC4V consists of the O-antigen polysaccharides (PSs) of the ExPEC serotypes O1A, O2, O6A, and O25B separately bioconjugated to the carrier protein, a genetically detoxified form of exotoxin A (EPA) derived from *Pseudomonas aeruginosa*.
***Prevnar 13, Pneumococcal 13-valent conjugate vaccine (Diphtheria CRM197 protein) is a sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein.

TABLE 11

Cohort 2: Vaccination Schedule

| Study Vaccination Group | Vaccination on Day 1 | Total |
|---|---|---|
| G6 | ExPEC10V[a] | 400 |
| G7 | Placebo | 200 |
| Total | | 600 |

[a]ExPEC10V consists of the O-antigen polysaccharides (PSs) of the ExPEC serotypes O1A, O2, O4, O6A, O8, O15, O16, O18A, O25B, and O75 separately bioconjugated to the carrier protein, a genetically detoxified form of exotoxin A (EPA) derived from *Pseudomonas aeruginosa*.

The randomization ratio for the participants enrolled in Cohort 2 of the study is 2:1 (ExPEC10V:Placebo). The ExPEC1V dose used in Cohort 2 is based on the primary analysis (Day 30) results of Cohort 1.

Status

Enrollment and vaccination of Cohort 1 of the study described above was completed. The study is ongoing in a blinded manner. Based on ongoing review of the safety data, no major safety issues were identified, and the ExPEC10V vaccine has an acceptable safety profile.

The analysis of the immunogenicity of the Cohort 1 clinical samples is ongoing in a blinded fashion. The ECL data were 100% Acceptance Quality Limits (AQL) checked and uploaded for data management. Analysis of the MOPA samples is ongoing. Data unblinding and statistical analysis is performed by using a clinical research organization (CRO).

The Cohort 2 vaccinations are started once the ExPEC10V dose for that Cohort has been identified based on the finalized primary analysis of the Day 30 results from Cohort 1.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

SEQUENCES

SEQ ID NO: 1 (Glycosylation consensus sequence)
Asn-X-Ser(Thr), wherein X can be any amino acid except Pro SEQ ID NO: 2 (Optimized glycosylation consensus sequence)
Asp(Glu)-X-Asn-Z-Ser(Thr), wherein X and Z are independently selected from any amino acid except Pro SEQ ID NO: 3 (EPA carrier protein comprising 4 glycosylation consensus sequences (EPA-4))
G SGGGDQNATG SGGGKLAEEA FDLWNECAKA CVLDLKDGVR SSRMSVDPAI ADTNGQGVLH YSMVLEGGND
ALKLAIDNAL SITSDGLTIR LEGGVEPNKP VRYSYTRQAR GSWSLNWLVP IGHEKPSNIK VFIHELNAGN
QLSHMSPIYT IEMGDELLAK LARDATFFVR AHESNEMQPT LAISHAGVSV VMAQAQPRRE KRWSEWASGK
VLCLLDPLDG VYNYLAQQRC NLDDTWEGKI YRVLAGNPAK HDLDIKDNNN STPTVISHRL HFPEGGSLAA
LTAHQACHLP LEAFTRHRQP RGWEQLEQCG YPVQRLVALY LAARLSWNQV DQVIRNALAS PGSGGDLGEA
IREQPEQARL ALTLAAAESE RFVRQGTGND EAGAASADVV SLTCPVAKDQ NRTKGECAGP ADSGDALLER
NYPTGAEFLG DGGDVSFSTR GTQNWTVERL LQAHRQLEER GYVFVGYHGT FLEAAQSIVF GGVRARSQDL
DAIWRGFYIA GDPALAYGYA QDQEPDARGR IRNGALLRVY VPRWSLPGFY RTGLTLAAPE AAGEVERLIG
HPLPLRLDAI TGPEEEGGRV TILGWPLAER TVVIPSAIPT DPRNVGGDLD PSSIPDKEQA ISALPDYASQ
PGKPPREDLK LGSGGGDQNA T

SEQ ID NO: 4 (O4 GtrS amino acid sequence)
MNNLIMNNWCKLSIFIIAFILLWLRRPDILTNAQFWAEDSVFWYKDAYENGFLSSLTTPRNGYFQTVSTFI
VGLTALLNPDYAPFVSNFFGIMIRSVIIWFLFTERFNFLTLTTRIFLSIYFLCMPGLDEVHANITNAHWYL
SLYVSMILIARNPSSKSWRFHDIFFILLSGLSGPFIIFILAASCFKFINNCKDHISVRSFINFYLRQPYAL
MIVCALIQGTSIILTFNGTRSSAPLGFSFDVISSIISSNIFLFTFVPWDIAKAGWDNLLLSYFLSVSILSC
AAFVFVKGTWRMKVFATLPLLIIIFSMAKPQLTDSAPQLPTLINGQGSRYFVNIHIAIFSLLCVYLLECVR
GKVATLFSKIYLTILLFVMGCLNFVITPLPNMNWREGATLINNAKTGDVISIQVLPPGLTLELRKK -continued

| SEQUENCES |
| --- |

SEQ ID NO: 5 (Example O4 gtrS nucleic acid sequence)
ATGAATAATTTAATTATGAATAACTGGTGTAAATTATCTATATTTATTATTGCATTTATTTTGCTATGGCT
TAGAAGGCCGGATATACTCACAAACGCACAATTTTGGGCAGAAGATTCCGTTTTCTGGTATAAGGACGCCT
ATGAGAACGGATTCTTAAGTTCACTAACAACGCCTAGGAATGGGTATTTCCAGACTGTTTCTACATTTATA
GTTGGTCTGACTGCTTTATTAAATCCAGATTATGCACCTTTTGTTTCTAATTTTTTTGGCATAATGATTCG
CTCAGTAATTATATGGTTTTTATTTACAGAAAGATTCAACTTCCTCACATTGACTACTAGGATTTTCTTAT
CTATTTATTTTCTATGCATGCCTGGATTGGATGAAGTTCATGCAAATATAACAAATGCACATTGGTATTTG
TCATTATATGTATCAATGATCCTGATAGCTCGCAATCCAAGTTCAAAATCATGGAGGTTTCATGATATATT
CTTTATCTTGCTATCCGGGCTCAGTGGCCCATTTATAATTTTCATTTTAGCAGCTTCATGCTTTAAATTTA
TAAATAATTGTAAAGATCATATTAGTGTAAGATCTTTCATAAATTTCTACTTGCGTCAGCCATACGCATTA
ATGATTGTTTGCGCTTTAATTCAAGGAACTTCTATAATTCTAACTTTCAATGGCACACGTTCCTCAGCACC
GCTAGGATTCAGTTTTGATGTGATTTCGTCTATTATATCATCGAATATTTTTTTATTTACATTTGTCCCAT
GGGATATTGCAAAGGCTGGGTGGGATAATTTACTGTTATCTTATTTTTTGTCTGTTTCGATTTTGTCGTGT
GCGGCCTTTGTTTTTGTTAAAGGTACGTGGCGAATGAAAGTATTTGCAACTTTACCATTGCTAATTATAAT
ATTTTCAATGGCAAAACCACAATTGACAGACTCGGCACCTCAATTGCCAACACTTATTAATGGGCAAGGTT
CAAGATACTTCGTAAATATACATATTGCGATATTCTCTTTGCTATGTGTTTACTTACTTGAGTGCGTCAGG
GGGAAAGTGGCAACTTTATTTTCCAAAATATACTTAACAATTTTGCTATTCGTGATGGGATGTTTGAATTT
TGTTATCACCCCACTCCCAAACATGAACTGGAGGGAAGGTGCTACTTTGATTAATAATGCAAAAACTGGTG
ATGTCATTTCGATTCAAGTGCTACCACCTGGCCTAACACTTGAACTAAGGAAAAAATAA SEQ ID NO: 6 (Example PglB sequence (‘wild-type’))
MLKKEYLKNPYLVLFAMIILAYVFSVFCRFYWVWWASEFNEYFFNNQLMIISNDGYAFAEGARDMIAGFHQ
PNDLSYYGSSLSALTYWLYKITPFSFESIILYMSTFLSSLVVIPTILLANEYKRPLMGFVAALLASIANSY
YNRTMSGYYDTDMLVIVLPMFILFFMVRMILKKDFFSLIALPLFIGIYLWWYPSSYTLNVALIGLFLIYTL
IFHRKEKIFYIAVILSSLTLSNIAWFYQSAIIVILFALFALEQKRLNFMIIGILGSATLIFLILSGGVDPI
LYQLKFYIFRSDESANLTQGFMYFNVNQTIQEVENVDLSEFMRRISGSEIVFLFSLFGFVWLLRKHKSMIM
ALPILVLGFLALKGGLRFTIYSVPVMALGFGFLLSEFKAIMVKKYSQLTSNVCIVFATILTLAPVFIHIYN
YKAPTVFSQNEASLLNQLKNIANREDYVVTWWDYGYPVRYYSDVKTLVDGGKHLGKDNFFPSFALSKDEQA
AANMARLSVEYTEKSFYAPQNDILKTDILQAMMKDYNQSNVDLFLASLSKPDFKIDTPKTRDIYLYMPARM
SLIFSTVASFSFINLDTGVLDKPFTFSTAYPLDVKNGEIYLSNGVVLSDDFRSFKIGDNVVSVNSIVEINS
IKQGEYKITPIDDKAQFYIFYLKDSAIPYAQFILMDKTMFNSAYVQMFFLGNYDKNLFDLVINSRDAKVFK
LKI SEQ ID NO: 7 (example gtrA amino acid sequence; *E. coli* W3110 yfdG, GenBank: BAA16209.1)
MLKLFAKYTSIGVLNTLIHWVVFGVCIYVAHTNQALANFAGFVVAVSFSFFANAKFTFKASTTTMRYMLYV
GFMGTLSATVGWAADRCALPPMITLVTFSAISLVCGFVYSKFIVFRDAK SEQ ID NO: 8 (example gtrB amino acid sequence -*E. coli* W3110 yfdH, GenBank: BAA16210.1)
MKISLVVPVFNEEEAIPIFYKTVREFEELKSYEVEIVFINDGSKDATESIINALAVSDPLVVPLSFTRNFG
KEPALFAGLDHATGDAIIPIDVDLQDPIEVIPHLIEKWQAGADMVLAKRSDRSTDGRLKRKTAEWFYKLHN
KISNPKIEENVGDFRLMSRDVVENIKLMPERNLFMKGILSWVGGKTDIVEYVRAERIAGDTKFNGWKLWNL
ALEGITSFSTFPLRIWTYIGLVVASVAFIYGAWMILDTIIFGNAVRGYPSLLVSILFLGGIQMIGIGVLGE
YIGRTYIETKKRPKYIIKRVKK SEQ ID NO: 9 (example O4 rfb locus nucleotide sequence - O4-EPA production strain BVEC-L-00684f)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGTGAAAATACTT
GTTACTGGTGGCGCAGGATTTATTGGTTCAGCTGTAGTTCGTCACATTATAAATAATACGCAGGATAGTGT
TGTTAATGTCGATAAATTAACGTACGCCGGAAACCGGGAATCACTTGCTGATGTTTCTGATTCTGAACGCT
ATGTTTTTGAACATGCGGATATTTGCGATGCACCTGCAATGGCACGGATTTTTGCTCAGCATCAGCCGGAT
GCAGTGATGCACCTGGCTGCTGAAAGCCATGTTGACCGTTCAATTACAGGCCCTGCGGCATTTATTGAAAC
CAATATTGTTGGTACTTATGTCCTTTTGGAAGCCGCTCGCAATTACTGGTCTGCTCTTGATAGCGACAAGA
AAAATAGCTTCCGTTTTCATCATATTTCTACTGACGAAGTATATGGTGATTTGCCTCATCCTGACGAGGTA
AATAATACAGAAGAATTACCCTTATTTACTGAGACAACAGCTTACGCGCCAAGCAGCCCTTATTCCGCATC
CAAAGCATCCAGCGATCATTTAGTCCGCGCGTGGAAACGTACCTATGGTTTACCGACCATTGTGACTAATT
GCTCTAACAATTATGGTCCTTATCATTTCCCGGAAAAATTGATTCCATTGGTTATTCTCAATGCTCTGGAA
GGTAAAGCATTACCTATTTATGGTAAAGGGGATCAAATTCGCGACTGGCTGTATGTTGAAGATCATGCGCG
TGCGTTATATACCGTCGTAACCGAAGGTAAAGCGGGTGAAACTTATAACATTGGTGGGCACAACGAAAAGA
AAAACATAGATGTAGTGCTCACTATTTGTGATTTGCTGGATGAGATTGTACCGAAAGAGAAATCTTATCGT -continued

SEQUENCES

GAGCAAATCACTTATGTTGCCGATCGTCCGGGACACGATCGCCGTTATGCGATTGATGCTGAGAATATTGG
TCGCGAATTGGGATGGAAACCACAGGAAACGTTTGAGAGCGGGATTCGGAAGACAGTGGAATGGTATCTGT
CCAATACAAAATGGGTTGATAATGTGAAAAGTGGTGCCTATCAATCGTGGATTGAAGAGAACTATGAGGGC
CGCCAGTAATGAATATCCTCCTTTTTGGCAAAACAGGGCAGGTAGGTTGGGAACTACAGCGTGCTCTGGCA
CCTCTGGGTAACTTGATTGCTCTTGATGTTCATTCCACTGATTATTGTGGCGATTTCAGTAACCCCGAAGG
TGTGGCTGAAACCGTCAAAAAAATTCGCCCAGATGTTATTGTTAATGCTGCTGCTCATACCGCGGTAGATA
AGGCTGAGTCAGAACCAGAATTTGCACAATTACTCAATGCGACCAGCGTTGAAGCAATTGCAAAAGCGGCT
AATGAAGTTGGGGCTTGGGTAATTCATTACTCAACTGACTACGTCTTCCCTGGAAATGGCGACATGCCATG
GCTCGAGACTGATGTAACCGCTCCGCTCAATGTTTATGGCAAAACCAAATTGGCTGGAGAAAGAGCATTAC
AAGAACATTGCGCAAAGCATCTTATTTTCCGTACCAGCTGGGTATATGCAGGTAAAGGAAATAACTTTGCC
AAAACAATGTTACGTCTGGCAAAAGAGCGCGAAGAACTGGCTGTGATAAACGATCAGTTTGGCGCACCAAC
AGGTGCTGAATTGCTGGCTGATTGCACCGCTCATGCCATTCGCGTGGCATTAAAAAAACCAGAAGTTGCTG
GCTTGTACCATCTGGTAGCAAATGGCACAACAACCTGGCACGATTACGCCGCGCTAGTATTCGAAGAAGCC
CGTAAAGCAGGGATTGACCTTGCACTTAACAAACTCAACGCCGTACCAACAACGGCTTATCCTACTCCAGC
CCGCCGTCCTCATAATTCTCGCCTCAATACCGAAAAGTTTCAGCAGAACTTTGCGCTTGTCTTGCCTGACT
GGCAGGTGGGCGTGAAACGTATGCTCAACGAATTATTTACGACTACGGCAATTTAACAAATTTTTGCATCT
CGCTCATGATGCCAGAGCGGGATGAATTAAAAGGAATGGTGAAATGAAAACGCGTAAAGGTATTATTCTGG
CTGGTGGTTCCGGCACTCGTCTTTATCCTGTGACGATGGCAGTGAGTAAACAACTGCTGCCGATTTATGAT
AAGCCGATGATTTATTATCCGCTTTCAACGCTTATGTTAGCGGGTATTCGCGATATTCTTATTATCAGTAC
GCCACAGGATACACCGCGTTTCCAACAATTGTTGGGGGACGGGAGTCAGTGGGGGCTTAATCTACAGTATA
AAGTACAACCGAGTCCGGATGGCCTGGCGCAAGCGTTTATTATTGGTGAAGACTTTATTGGTGGTGATGAT
TGTGCACTCGTACTTGGCGATAATATCTTCTATGGACACGACTTGCCGAAATTAATGGAAGCTGCTGTTAA
CAAAGAAATCGGTGCAACGGTATTTGCTTATCACGTCAATGATCCTGAACGTTATGGTGTCGTGGAGTTTG
ATAATAACGGTACTGCAATTAGCCTGGAAGAAAAACCGCTGGAACCAAAAAGTAACTATGCGGTTACTGGG
CTTTATTTCTATGACAATGATGTTGTAGAAATGGCGAAAAACCTTAAGCCTTCTGCCCGTGGCGAACTGGA
AATTACCGATATTAACCGTATTTATATGGAGCAGGGACGTTTGTCTGTCGCTATGATGGGGCGTGGTTATG
CCTGGTTGGATACTGGTACACATCAAAGTCTTATTGAAGCAAGTAACTTCATTGCCACCATTGAAGAGCGT
CAGGGATTAAAGGTATCTTGCCCGGAAGAGATTGCTTACCGTAAAGGGTTTATTGATGCTGAGCAGGTGAA
AGTATTAGCCGAACCGCTGAAGAAAAATGATTATGGTCAGTATCTGCTAAAAATGATTAAAGGTTATTAAT
AAAATGAACGTAATTAAAACTGAAATTCCTGATGTGCTGATTTTTGAACCAAAAGTTTTTGGTGATGAACG
TGGCTTCTTTTTTGAGAGTTTTAACCAGAAAGTATTTGAAGAAGCTGTAGGACGGAAGGTTGAATTTGTTC
AGGATAACCATTCTAAGTCTAAAATAAATGTATTGCGTGGGATGCATTATCAAACACAAAATACTCAAGGA
AAACTGGTTCGGGTAATTTCTGGTTCAGTATATGATGTTGCCGTAGATTTAAGAGAAAAATCAAAGACATT
TGGCAAATGGGTGGGTGTAGAATTATCTGGGAATAATAAAAGACAATTGTGGATCCCCGAAGGTTTTGCCC
ATGGTTTTTATGTGTTGGAGGAGAATACCGAATTTGTTTATAAATGTACCGATACTTATAACCCTGCTCAT
GAACACACATTGCTATGGAATGATCCAACTATCAATATAAGTTGGCCAATCATACAAAACTGCAAGCCAAT
TATTTCTGAAAAAGATGCTAATGGACATCTTTTTTCACATAAAACCTATTTCTGAAATGCAATATTATGAG
TTTAATTAGAAACAGTTTCTATAATATTGCTGGTTTTGCTGTGCCGACATTAGTTGCAGTCCCTGCTTTGG
GGATTCTTGCCAGGCTGCTTGGACCGGAGAATTTTGGACTTTTCACACTAGCATTCGCTTTGATAGGATAT
GCAAGTATTTTCGACGCCGGGATTAGTCGAGCTGTAATCAGAGAAATCGCTCTTTATCGAGAAAGTGAAAA
AGAGCAAATACAAATTATTTCGACAGCAAGTGTAATCGTACTATTCTTAGGGGTGGTTGCAGCTTTGTTAC
TTTATTTTAGTAGTAATAAAGTTGTTGAGTTATTGAATGTTAGTTCCGTTTATATTGAAACAGCAGTGCGT
GCATTCTCTGTTATTTCATTTATAATACCTGTGTATCTGATTAACCAGATTTGGCTTGGTTATCTGGAAGG
GCTAGAAAAATTTGCAAATATAAATGTTCAGAGAATGATTTCTAGCACAAGCTTGGCTATATTACCAGTGA
TATTTTGTTATTACAATCCCTCGTTGCTTTATGCTATGTATGGGTTGGTGGTTGGGCGTGTGATTTCATTT
TTGATTAGCGCAATAATTTGTCGAGATATTATTCTTAAAAGTAAACTTTACTTTAATGTGGCAACTTGCAA
TCGTCTTATCTCTTTTGGTGGATGGATAACAGTTAGTAATATCATAAGCCCAATCATGGCATATTTCGACC
GCTTTATCATCTCTCATATTATGGGGGCTTCGAGAATTGCATTTTATACAGCGCCCTCAGAGGGTGTATCA
AGGTTAATTAATATCCCATATGCTTTGGCAAGAGCTCTATTTCCTAAATTGGCATATAGCAATAATGATGA
TGAACGAAAAAAATTACAACTACAGAGCTACGCAATTATAAGCATTGTATGTCTACCCATAGTTGTTATTG
GTGTCATTTTTGCCTCATTCATAATGACAACATGGATGGGACCTGATTATGCCTTAGAAGCAGCAACTATC
ATGAAAATACTTCTTGCTGGTTTTTTCTTTAACTCTTTAGCGCAAATACCTTATGCATACTTGCAATCTAT
CGGAAAGTCAAAAATTACCGCATTTGTGCATCTCATAGAACTTGCGCCATACTTATTATTATTGTATTACT
TCACAATGCATTTCGGCATAATTGGCACGGCAATCGCTTGGTCACTTAGAACATTTTGTGATTTTGTTATA
CTACTTTCGATATCGAGAAGAAAATGATTGCGGTTGATATTGCGCTTGCAACCTACAATGGTGCTAATTTT
ATTCGGCAACAGATTGAATCTATCCAGAAACAAACTTATAGAAATTGGCGTCTTATAATAAGTGATGATAA
CTCGAGTGATGATACTGTTGATATTATTAAGGATATGATGTCTAACGACAGTCGTATCTATTTGGTAGGAA
ATAAAAGACAAGGAGGGGTTATTCAGAACTTTAATTATGCTCTTTCACAAACTACATCTGAAATTGTGTTA
CTATGTGACCAGGATGACATTTGGCCGGAGGAGCGTCTGGAAATTCTTATAGATAAATTTAAGGCCTTGCA
GCGTAATGATTTTGTTCCGGCAATGATGTTTACTGATTTGAAATTAGTAGACGAAAATAATTGTTTGATTG
CAGAAAGTTTTTATCGAACGAATAATATTAATCCACAAGATAATCTGAAAAATAATAATCTTCTCTGGCGT
TCAACGGTATATGGCTGTACTTGCATCATGAATAAGAAACTTGTTGATATTGCATTGCCTATACCTACATA
TGCACATATGCATGATCAATGGTTGGCATTATTAGCGAAGCAATATGGTAACATTTTTTATTTCGACTATG
CGTCTGTTCGTTATAGGCAACATTCTACAAATGTTGTTGGTGGTAGAAATAAAACGCCATTTCAAAAATTT
AATTCCATACAAAAAAACCTAAAAAGGATTAATTTGCTAGTGGATAGAACTGTTGCTTTAATTAAATCAAA
TAACGATTTCTATCCAGGGAATAAAATGGAAAATAAAATTGATTACTTAAAATTTGGAGTGAATGAAGTAT
TACCTTATCTTTTTAAAGGAAACAAGAAAGTTTTTTCACTTTGTGTATTAATTAGTTTGGCATTACAAAAA
TGATATATTTATTATTTTTTTTTGCACTGTTTATGATCTGTACGTTTTTAACACACAGGCGACAGGCATTA
TATGTTGTATCTGCGTTAGTATTTCTTTTTTTGGCTTTAACCTATCCATCAGGAGGGGACTGGATAGGTTA
TTTTCTCCATTATGACTGCATGGTTAATGAGCAGTGTAATAATGGTTTTATAATGTTTGAACCTGGATATG
AATTAATTGTTTCCTTATTTGGATATTTGGGATTTCAGACAATTATTATTTTTATAGCCGCTGTAAATGTA
ATTCTAATATTAAATTTTGCAAAGCATTTTGAAAACGGAAGTTTTGTTATTGTTGCGATAATGTGCATGTT
CCTTTGGAGTGTTTATGTTGAGGCGATTAGACAGGCTCTGGCCTTATCTATAGTTATATTTGGGATTCATT
CTCTTTTTTTGGGTAGAAAAAGGAAATTTATAACATTAGTATTATTTGCGTCAACTTTCCATATAACTGCT
TTGATTTGTTTTCTTCTAATGACTCCTCTATTTTCAAAGAAATTAAGCAAGATAATAAGTTATAGCCTATT
AATTTTCAGTAGCTTCTTTTTCGCTTTTTCTGAAACCATATTAAGTGCACTCCTTGCAATTTTGCCAGAAG
GATCCATTGCCAGTGAAAAATTAAGTTTTTACTTAGCAACCGAGCAATACAGGCCACAGTTATCTATTGGG

-continued

| SEQUENCES |
| --- |
| AGTGGCACTATTCTTGACATTATACTTATTTTTCTGATATGTGTAAGTTTTAAACGAATAAAGAAATATAT<br>GCTCGCTAATTATAATGCTGCAAATGAGATATTGCTTATTGGTTGCTGTCTTTATATTTCTTTCGGTATTT<br>TTATCGGGAAAATGATGCCAGTTATGACTCGCATTGGTTGGTATGGTTTTCCATTTGTTATAGTACTTCTT<br>TATATTAACTTGGGTTATTCAGAATATTTTAAGAGGTATATAAATAAAAGAGGGTGTGGGTATAGCAAATT<br>ATTAATTGCTTTTTATTTTTTGCTACAAATTTTGCGACCATTAACATATGATTATAGCTATTATAATATAA<br>TGCACCAGGATACTTTGCTGAATAGGTTTGATGCATTAGATGATGCATCATTAAGACAATCAGCGAAGAGA<br>AAATGTTTCGATTTGGGAAAGATAGGATATGGTTTCTTATGTAGTATATAATATCCTGCATTCATTCGGAT<br>AATTTCCTATGGAAGTGTCCTTTGCTCTGTCTGTCCTCATTTGTTGAAATTTTATGTTAATAAGAAGCTTT<br>AGATAACCACTTAGGAACTGTATGTTTGATCTGTCCAAAAATTATATTATTGTAAGTGCGACGGCGCTGGC<br>TTCCGGAGGTGCATTAACTATATTAAAGCAATTTATAAAACATGCATCACAAAATTCAAATGACTATATTA<br>TGTTTGTATCTGCGGGATTGGAGTTGCCGGTCTGTGATAACATCATTTACATAGAAAACACACCAAAAGGA<br>TGGTTGAAAAGAATATATTGGGATTGGTTCGGTTGTCGGAAGTTTATCTCGGAACATAAGATTAACGTTAA<br>GAAAGTAATTTCTCTACAAAATTCCAGTTTGAATGTTCCTTACGAACAGATTATTTACTTGCACCAGCCAA<br>TTCCTTTTAGTAAAGTTGATTCTTTTTTAAAAAATATCACATCCGATAACGTAAAGCTTTTTTTATATAAA<br>AAGTTTTATTCCTATTTTATATTTAAATATGTGAATGCCAATACAACCATCGTAGTGCAAACGAATTGGAT<br>GAAAAAAGGAGTGCTGGAGCAATGTGATAAAATTAGTACCGAAAGGGTCCTTGTTATAAAACCTGATATCA<br>AAGCATTTAATAATACTAATTTTGATGTAGATATGGATGTATCTGCAAAAACACTCTTATATCCAGCGACA<br>CCACTTACCTATAAAAATCATTTGGTCATTCTGAAGGCGTTGGTTATTTTAAAGAAAAAGTATTTTATAGA<br>TGATCTGAAATTCCAAGTGACTTTTGAAAAGAATAGGTACAAAAATTTTGATAAGTTTGTGCAATTAAATA<br>ACTTAAGCAAAAACGTTGATTATCTCGGCGTTCTTTCATACTCGAACTTGCAAAAAAAATATATGGCGGCA<br>TCTTTAATCGTTTTTCCTAGCTATATCGAATCATATGGGTTACCACTCATCGAAGCTGCTAGTTTAGGAAA<br>AAAAATCATTAGTAGTGATCTTCCTTATGCCCGGGATGTTTTAAAGGATTATAGCGGCGTAGATTTTGTAA<br>TTTACAATAATGAAGATGGCTGGGCTAAGGCGTTGTTTAATGTTTTAAATGGCAATTCGAAGCTCAATTTT<br>AGGCCTTATGAAAAAGATAGTCGTTCATCTTGGCCACAGTTCTTCTCTATTTTGAAATAAGGTGTATTATG<br>TTTAATGGTAAAATATTGTTAATTACTGGTGGTACGGGGTCTTTCGGTAATGCTGTTCTAAGACGTTTTCT<br>TGACACTGATATCAAAGAAATACGTATTTTTTCCCGGGATGAAAAAAAACAAGATGACATGAGGAAAAAAT<br>ATAATAATCCGAAACTTAAGTTCTATATAGGTGATGTTCGCGACTATTCGAGTATCCTCAATGCTTCTCGA<br>GGTGTTGATTTTATTTATCATGCTGCAGCTCTGAAGCAAGTACCTTCCTGCGAATTCCACCCAATGGAAGC<br>TGTAAAAACGAATGTTTTAGGTACGGAAAACGTACTGGAAGCGGCAATAGCTAATGGAGTTAGGCGAATTG<br>TATGTTTGAGTACAGATAAAGCTGTATATCCTATCAATGCAATGGGTATTTCCAAAGCGATGATGGAAAAA<br>GTAATGGTAGCAAAATCGCGCAATGTTGACTGCTCTAAAACGGTTATTTGCGGTACACGTTATGGCAATGT<br>AATGGCATCTCGTGGTTCAGTTATCCCATTATTTGTCGATCTGATTAAATCAGGTAGACCAATGACGATAA<br>CAGACCCTAATATGACTCGTTTCATGATGACTCTCGAAGACGCTGTTGATTTGGTTCTTTACGCATTTGAA<br>CATGGCAATAATGGTGATATTTTTGTCCAAAAGGCACCTGCGGCTACCATCGAAACGTTGGCTATTGCACT<br>CAAAGAATTACTTAATGTAAACCAACACCCTGTAAATATAATCGGCACCCGACACGGGGAAAAACTGTACG<br>AAGCGTTATTGAGCCGAGAGGAAATGATTGCAGCGGAGGATATGGGTGATTATTATCGTGTTCCACCAGAT<br>CTCCGCGATTTGAACTATGGAAAATATGTGGAACATGGTGACCGTCGTATCTCGGAAGTGGAAGATTATAA<br>CTCTCATAATACTGATAGGTTAGATGTTGAGGGAATGAAAAAATTACTGCTAAAACTTCCTTTTATCCGGG<br>CACTTCGGTCTGGTGAAGATTATGAGTTGGATTCATAATATGAAAATTTTAGTTACTGGCGCTGCAGGGTT<br>TATCGGTCGAAATTTGGTATTCCGGCTTAAGGAAGCTGGATATAACGAACTCATTACGATAGATCGTAACT<br>CTTCTTTGGCGGATTTAGAGCAGGGACTTAAGCAGGCAGATTTTATTTTTCACCTTGCTGGGGTAAATCGT<br>CCCGTGAAGGAGTGTGAATTTGAAGAGGGAAATAGTAATCTAACTCAACAGATTGTTGATATCCTGAAAAA<br>AAACAATAAAAATACTCCTATCATGCTGAGTTCTTCCATCCAGGCTGAATGTGATAACGCTTATGGAAAGA<br>GTAAAGCAGCTGCGGAAAAAATCATTCAGCAGTATGGGGAAACGACAAACGCTAAATATTATATTTATCGC<br>TTGCCGAATGTATTCGGTAAGTGGTGTCGACCAAATTATAACTCCTTTATAGCAACTTTCTGCCATCGCAT<br>TGCAAATGATGAAGCTATTACAATTAATGATCCTTCAGCAGTTGTAAATCTGGTGTATATAGATGACTTTT<br>GTTCTGACATATTAAAGCTATTAGAAGGAGCGAACGAAACTGGTTACAGGACATTTGGTCCAATTTATTCT<br>GTTACTGTTGGTGAAGTGGCACAATTAATTTACCGGTTTAAAGAAAGTCGCCAAACATTAATCACCGAAGA<br>TGTAGGTAATGGATTTACACGTGCATTGTACTCAACATGGTTAAGTTACCTGTCTCCTGAACAGTTTGCGT<br>ATACGGTTCCTTCTTATAGTGATGACAGAGGGGTATTCTGTGAAGTATTGAAAACGAAAAACGCGGGCCAG<br>TTTTCGTTCTTTACTGCGCATCCAGGAATTACTCGGGGTGGTCATTATCATCATTCCAAAAATGAGAAATT<br>TATTGTCATCCGAGGAAGTGCTTGTTTCAAATTTGAAAATATTGTCACGAGTGAACGATATGAACTTAATG<br>TTTCCTCTGATGATTTTAAAATTGTTGAAACAGTTCCGGGATGGACGCATAACATTACTAATAATGGCTCG<br>GATGAGCTAGTTGTTATGCTTTGGGCAAATGAAATATTTAATCGTTCTGAACCAGATACTATAGCGAGAGT<br>TTTATCGTGAAAAAATTGAAAGTCATGTCGGTTGTTGGGACTCGTCCAGAAATTATTCGACTCTCGCGTGT<br>CCTTGCAAAATTAGATGAATATTGTGACCACCTTATTGTTCATACCGGGCAAAACTACGATTATGAACTGA<br>ATGAAGTTTTTTTCAAAGATTTGGGTGTTCGCAAACCTGATTATTTTCTTAATGCCGCAGGTAAAAATGCA<br>GCAGAGACTATTGGACAAGTTATCATTAAAGTTGATGAGGTCCTTGAACAGGAAAAACCAGAAGCCATGTT<br>AGTACTTGGCGATACTAACTCCTGTATTTCAGCAATACCAGCAAAGCGTCGAAGAATTCCGATCTTCCATA<br>TGGAGGCTGGGAATCGTTGTTTTGACCAACGCGTACCGGAAGAAACTAACAGAAAAATAGTTGATCATACC<br>GCTGATATCAATATGACATATAGTGATATCGCGCGTGAATATCTTCTGGCTGAAGGTGTACCAGCCGATAG<br>AATTATTAAAACCGGTAGCCCAATGTTTGAAGTACTCACTCATTATATGCCGCAGATTGATGGTTCCGATG<br>TACTTTCTCGCCTGAATTTAACACCTGGGAATTTCTTTGTGGTAAGTGCCCACAGAGAAGAAAATGTTGAT<br>ACCCCTAAACAACTTGTGAAACTGGCGAATATACTTAATACCGTGGCTGAAAAATATGATGTCCCGGTAGT<br>TGTTTCTACTCATCCTCGCACTCGTAACCGCATCAACGAAAACGGTATTCAATTCCATAAAAATATCTTGC<br>TTCTTAAGCCATTAGGATTTCACGATTACAACCATCTGCAAAAAAATGCACGTGCTGTTTTATCGGATAGT<br>GGGACTATTACAGAAGAGTCCTCCATTATGAACTTCCCTGCACTCAATATACGAGAAGCGCACGAACGCCC<br>GGAAGGCTTCGAAGAAGGGGCAGTAATGATGGTCGGTCTTGAATCTGATCGCGTTTTACAGGCATTAGAAA<br>TTATTGCAACACAGCCTCGTGGAGAAGTACGCTTACTTCGTCAGGTTAGTGACTATAGCATGCCAAATGTT<br>TCAGATAAAGTTCTGCGTATTATCCATTCATATACTGACTACGTTAAACGGGTTGTCTGGAAGCAATACTA<br>ATGAAACTTGCATTAATCATTGATGATTATTTGCCCCATAGCACACGCGTTGGGGCTAAAATGTTTCATGA<br>GTTAGGCCTTGAATTACTGAGCAGAGGCCATGATGTAACTGTAATTACGCCTGACATCTCATTACAAGCAA<br>TTTATTCTATTAGTATGATTGATGGTATAAAGGTTTGGCGTTTCAAAAGTGGACCTTTAAAGGATGTAGGT<br>AAGGCTAAACGTGCCATAAATGAAACTCTTTTATCTTTTCGCGCATGGCGCGCATTTAAGCACCTCATTCA<br>ACATGATACATTTGATGGTATCGTTTATTATTCCCCCTCTATTTTTTGGGGCGACTTGGTTAAAAAAATAA<br>AACAACGATGCCAGTGCCCAAGCTATCTGATCCTAAGGGATATGTTTCCACAGTGGGTCATTGATGCAGGT<br>ATGTTGAAAGCCGGTTCACCAATTGAAAAATATTTTAGGTATTTTGAAAAAAAGTCATATCAGCAGGCTGG |

-continued

SEQUENCES

CCGGATAGGGGTAATGTCTGATAAGAATCTTGAGATATTTCGCCAGACCAATAAAGGTTATCCGTGTGAAG
TTTTACGTAATTGGGCCTCAATGACTCCTGTGTCTGCCAGCGATGATTATCATTCACTTCGTCAAAAATAC
GATCTAAAAGATAAAGTCATTTTTTTCTATGGCGGTAATATTGGGCATGCTCAGGATATGGCAAACTTAAT
GCGCCTTGCGCGTAATATGATGCGTTATCATGATGCTCATTTCCTGTTTATAGGGCAGGGTGATGAAGTTG
AGCTGATAAAATCTCTTGCTGCAGAATGGAATTTAACTAATTTCACTCATCTACCTTCAGTGAACCAGGAA
GAGTTTAAATTAATTTTATCTGAAGTTGATGTCGGCCTGTTCTCCCTTTCATCTCGCCATTCTTCACATAA
TTTCCCCGGAAAATTACTAGGGTATATGGTTCAATCAATCCCGATCCTTGGGAGTGTGAATGGCGGCAATG
ATTTAATGGATGTAATTAATAAGCACAGAGCCGGTTTCATTCATGTTAATGGTGAAGATGATAAACTGTTT
GAATCTGCACAATTGCTTCTTAGTGATTCAGTTTTAAGAAAACAGCTAGGTCAGAACGCTAATGTGTTGTT
AAAGTCTCAATTTTCGGTTGAATCGGCGGCACATACTATCGAAGTCCGACTGGAGGCTGGAGAATGCGTTT
AGTTGATGACAATATTCTGGATGAACTTTTTCGCACTGCAGCAAATTCTGAACGTTTGCGCGCTCATTATT
TATTGCACGCATCTCATCAGGAGAAGGTTCAACGTTTACTTATTGCATTTGTACGCGACAGCTATGTTGAA
CCCCATTGGCATGAGTTACCGCATCAGTGGGAAATGTTTGTCGTCATGCAAGGGCAATTAGAAGTTTGTTT
GTATGAGCAAAATGGTGAGATCCAAAAACAGTTTGTTGTTGGAGACGGTACGGGAATAAGCGTCGTGGAAT
TTTCCCCAGGAGATATACATAGTGTCAAATGCCTGTCACCAAAAGCCCTTATGTTGGAGATAAAGGAGGGG
CCATTTGACCCACTCAAAGCTAAGGCTTTTTCTAAGTGGTTATAGGGCGATACACCACCGTTTATTCTTCT
ATCTTATTCTATACATGCTGGGTTACCATCTTAGCTTCTTCAAGCCGCGCAACCCCGCGGTGACCACCCCT
GACAGGAGTAGCTAGCATTTGACCACCCCTGACAGGATTAGCTAGCATATGAGCTCGAGGATATCTACTGT
GGGTACCCGGGATCCGTGTAGGCTGGAGCTGCTTCGAAGTTCCTATACTTTCTAGAGAATAGGAACTTCGG
AATAGGAACTAAGGAGGATATTCATAT

SEQ ID NO: 10 (example signal sequence for EPA carrier protein)
MKKIWLALAG LVLAFSASA SEQ ID NO: 11 (example O1A rfb locus nucleotide sequence - O1A-EPA production strain stGVXN4411 and stLMTB10217)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGCTAGCGTGAAG
ATACTTGTTACTAGGGGCGCAGGATTTATTGGTTCTGCTGTAGTTCGTCACATTATAAATAATACGCAGGA
TAGTGTTGTTAATGTCGATAAATTAACGTACGCCGGAAACCTGGAATCACTTGCTGATGTTTCTGACTCTG
AACGCTATGTTTTTGAACATGCGGATATTTGCGATGCTGCTGCAATGGCGCGGATTTTTGCTCAGCATCAG
CCGGATGCAGTGATGCACCTGGCTGCTGAAAGCCATGTGGATCGTTCAATTACAGGCCCTGCGGCATTTAT
TGAAACCAATATTGTTGGTACTTATGTCCTTTTGGAAGCGGCTCGCAATTACTGGTCTGCTCTTGATGGCG
ACAAGAAAAATAGCTTCCGTTTTCATCATATTTCTACTGACGAAGTCTATGGTGATTTGCCTCATCCTGAC
GAAGTAAATAATAAAGAACAATTACCCCTCTTTACTGAGACGACAGCTTACGCGCCTAGTAGTCCTTATTC
CGCATCAAAAGCATCCAGCGATCATTTAGTCCGCGCGTGGAAACGTACCTATGGTTTACCGACTATTGTGA
CTAACTGTTCGAATAACTACGGTCCTTATCACTTTCCGGAAAAATTGATTCCACTAGTAATTCTTAATGCT
CTGGAAGGTAAGGCATTACCTATTTATGGCAAAGGGGATCAAATTCGTGACTGGCTGTATGTTGAAGATCA
TGCGCGTGCGTTATATACCGTAGTTACTGAAGGTCAAGCGGGTGAAACCTATAACATTGGCGGACACAACG
AAAAGAAAAACATCGATGTTGTGCTGACTATTTGTGATTTGTTGGACGAGATAGTCCCGAAAGAGAAATCT
TATCGTGAGCAAATTACTTATGTTGCTGATCGCCCAGGGCATGATCGCCGTTATGCGATTGATGCTGAGAA
GATTGGTCGCGAATTGGGATGGAAACCACAGGAAACGTTTGAGAGTGGGATTCGTAAAACGGTGGAATGGT
ATTTGGCTAATGCAAAATGGGTTGATAATGTGAAAAGTGGTGCCTATCAATCGTGGATTGAACAGAACTAT
GAGGGCCGCCAGTAATGAATATCCTCCTTTTTGGCAAAACAGGGCAGGTAGGTTGGGAACTACAGCGTGCT
CTGGCACCTCTGGGTAATTTGATTGCTCTTGATGTTCACTCCACTGATTACTGTGGTGATTTTAGTAACCC
TGAAGGTGTGGCTGAAACAGTCAAAAGAATTCGACCTGATGTTATTGTTAATGCTGCGGCTCACACCGCAG
TAGATAAGGCTGAGTCAGAACCCGAATTTGCACAATTACTCAATGCGACTAGCGTTGAATCAATTGCAAAA
GCGGCAAATGAAGTTGGGGCTTGGGTAATTCATTACTCAACTGACTACGTATTCCCTGGAAATGGCGACAC
GCCATGGCTGGAGATGGATGCAACCGCACCGCTAAATGTTTACGGTGAAACCAAGTTAGCTGGAGAAAAAG
CATTACAAGAGCATTGTGCGAAGCACCTAATTTTCCGTACCAGCTGGGTCTATGCAGGTAAAGGAAATAAT
TTCGCCAAAACGATGTTGCGTCTGGCAAAAGAGCGTGAAGAACTAGCCGTTATTAATGATCAGTTTGGTGC
GCCAACAGGTGCTGAACTGCTGGCTGATTGTACGGCACATGCCATTCGTGTCGCACTGAATAAACCGGATG
TCGCAGGCTTGTACCATTTGGTAGCCAGTGGTACCACAACCTGGTACGATTATGCTGCGCTGGTTTTTGAA
GAGGCGCGCAATGCAGGCATTCCTCTTGCACTCAACAAGCTCAACGCAGTACCAACAACTGCCTATCCTAC
ACCAGCTCGTCGTCCACATAACTCTCGCCTTAATACAGAAAAATTTCAGCAGAATTTTGCGCTTGTATTGC
CTGACTGGCAGGTTGGTGTGAAACGCATGCTCAACGAATTATTTACGACTACAGCAATTTAATAGTTTTTG
CATCTTGTTCGTGATGGTGGAGCAAGATGAATTAAAAGGAATGATGAAATGAAAACGCGTAAAGGTATTAT
TTTAGCGGGTGGTTCTGGTACTCGTCTTTATCCTGTGACTATGGTCGTCAGTAAACAGCTATTACCTATAT
ATGATAAACCGATGATCTATTATCCGCTTTCTACACTGATGTTAGCGGGTATTCGCGATATTCTGATTATT
AGTACGCCACAGGATACTCCTCGTTTTCAACAACTGCTGGGTGACGGTAGCCAGTGGGGCCTGAATCTTCA
GTACAAAGTGCAACCGAGTCCGGATGGTCTTGCGCAGGCATTTATTATCGGTGAAGAGTTTATTGGTGGTG -continued

| SEQUENCES |
| --- |
| ATGATTGTGCTTTGGTACTTGGTGATAATATCTTCTACGGTCACGACCTGCCTAAGTTAATGGATGCCGCT<br>GTTAACAAAGAAAGTGGTGCAACGGTATTTGCCTATCACGTTAATGATCCTGAACGCTATGGTGTCGTTGA<br>GTTTGATAAAAACGGTACGGCGATCAGCCTGGAAGAAAAACCGCTACAACCAAAAAGTAATTATGCGGTAA<br>CCGGGCTTTATTTTTATGATAACGACGTTGTCGAAATGGCGAAAAATCTTAAGCCTTCTGCCCGCGGTGAA<br>CTGGAAATTACCGATATTAACCGTATCTATATGGAACAAGGGCGTTTATCTGTTGCCATGATGGGGCGTGG<br>TTATGCGTGGTTAGACACGGGGACACATCAGAGCCTGATTGAGGCAAGCAACTTTATTGCAACAATTGAAG<br>AGCGTCAGGGGCTGAAAGTTTCCTGCCCGGAAGAAATTGCTTACCGTAAAGGGTTTGTTGATGCTGAGCAG<br>GTGAAAGTATTAGCTGAACCTCTGAAAAAAAATGCTTATGGTCAGTATCTGCTGAAAATGATTAAAGGTTA<br>TTAATAAAATGAACGTAATTAAAACAGAAATTCCTGATGTACTGATTTTTGAACCGAAAGTTTTTGGTGAT<br>GAGCGTGGTTTCTTTTTTGAGAGCTTTAACCAGAAGGTTTTGAGGAAGCTGTAGGCCGCAAAGTTGAATT<br>TGTTCAGGATAACCATTCGAAGTCTAGTAAAGGTGTTTTACGCGGGCTGCATTATCAGTTGGAACCTTATG<br>CACAAGGAAAATTGGTGCGTTGCGTTGTCGGTGAAGTTTTTGACGTAGCTGTTGATATTCGTAAATCGTCA<br>TCGACTTTTGGCAAATGGGTTGGGGTGAATTTATCTGCTGAGAATAAGCGGCAATTGTGGATTCCTGAGGG<br>ATTTGCACATGGTTTTTTAGTGCTGAGTGAGACGGCGGAGTTTTTGTATAAGACGACAAATTATTATCATC<br>CTCAGAGTGATAGAGGAATAAAATGGGATGATCCAAGCATCAATATTTCATGGCCAGTCGATTCACAAGTG<br>CTGCTATCAGCTAAAGATAATAAGCATCCTCCATTAACAAAGATTGAAATGTATAGTTAAGATCACGATAA<br>ATCTTGGAAGGGTTGCAAAATTGAATAAAATAGTGAGCAAAAGTGAAATAAGGAACGTAATCCACAATGCT<br>GGCTATATGATGATTACTCAGATAGCTTTATATGTTGCACCATTATTTATACTGAGTTATCTGTTAAAAAC<br>ACTGGGGGTTGCACAGTTTGGTAATTATGCCTTAATACTATCAATCGTTGCATATTTACAGATTATAACGG<br>ATTATGGTTTTTCTTTTAGTGCAAGTCGTGCGATCTCACAGAATAGAGAGGACAAAGAATATATATCAAAA<br>ATTTATCTGTCAACTATGACTATCAAGTTGGCGATATGCGCTTTCTTATTCTTATTGCTCATGCTATTTTT<br>AAATCTTTTGCCTGTGCAAGCTGAATTAAAACAAGGAATATTATATGGATATCTTCTTGTAATAGGAAATA<br>CTTTCCAACCACAATGGTTTTTCCAAGGTATCGAAAAATTAAAAATCATAGCCCTTTCTAATGTTATATCA<br>AGATGCGCCGCGTGTTTACTTGTATTTATCTATGTGAGGAATAGCGAGGATTTACAAAAAGCACTTTTAGT<br>ACAGTCACTTCCATTAGTAATTTCTGCGATTGGATTAAATATATTTATATTGAAATATATCAATATTATTT<br>TTCCGGAAAAAAAATTATTTAAGGTAATTTTAAAAGAAGGTAAGGATTTTTTTCTTGCATCACTTTATTCT<br>GTTATTCTCAATAATAGTGGCATTTTTCTATTAGGGATTTTTACTAATCCTGTTATTGTTGGTGTATATGC<br>CGCCGCTGAAAAGATAGTCAAGGCCGTATTGTCGCTATTTACACCACTGACGCAAGCTATATATCCTTATA<br>ATTGTCGTAAGTTTTCACTATCCGTATTTGACGGCATTGAGGCAGCAAAAAAAAACTGGTATACCAATTATA<br>ATTTTAGCATTTATAGCTGCTGTTATCGTTGCAATTACCTTACCTGTTGCAATCGACTATCTTAATTTTCC<br>AAAAGAAACAATTTTTGTAGGTCAAATATTAAGTGCATGGATCTTTTTTGGTGTTCTTAATAATGTATTCG<br>GCATTCAGATATTGAGTGCATCAGGAAGAAGTAAAATATATAGTAGGATGGTATTCGTATCAGCGCTTATA<br>ACATTACTTTTGATTACTCTATTATTGCAGTTTTGTAACGCCACTGGAGTGGCATGTGCAATATTATTGGG<br>TGAAATGTTCTTATCAATATTGTTACTTAAGCGATATAAAAAAATAATTTAAGGAATAGTTATGAAGAAGT<br>TATTATTAGTGTTCGGTACTAGGCCTGAAGCAATAAAGATGGCCTCTATCATTGAATTATTAAAAAAAGAT<br>TGTAGATTCGAATATAAAATATGTGTGACAGGCCAACATAAAGAGATGCTTGATCAAGTTATGCAAGTATT<br>TGATGTTAAACCTGATTATAATTTACGGATTATGCAGCCTGGGCAAACATTAGTATCTATAGCAACAAATA<br>TACTCTCACGGTTAAGTGAAGTTTTAATTATAGAAAAGCCAGATATTATACTTGTGCATGGGGATACAACG<br>ACTACCCTTGCTGCTACTTTAGCTGGGTATTACCACCAAATAAAAGTTTGTCATGTGGAAGCAGGATTAAG<br>AACAGGGGATATTTACTCTCCTTGGCCTGAAGAGGGCAATCGTAAAGTTACAGGGGCATTAGCATGTATTC<br>ATTTCGCCCCAACAGAGAGATCAAAAGATAATCTCCTGAGGGAGGGGGTCAAAGTAAATAATATATTTGTA<br>ACGGGTAATACCGTCATCGACTCTTTATTTATTGCAAAAGATATCATAGATAATGACCCTAATATAAAGAA<br>CGCTTTACATAATAAATTTAATTTTCTTGATAAAAGCCGACGAGTAGTACTTATAACAGGTCATCGAAGAG<br>AAAATTTCGGGAAAGGTTTTGAAGATATATGCTTTGCAATAAAGGAATTAGCTTTCATTTATCCTAATGTA<br>GATTTTATTTATCCGGTGCATCTTAATCCCAATGTAATGGAACCAGTACATCGTATATTAGATAATATATG<br>TAATATTTACCTTATTGAGCCCTTGGATTATTTGCCTTTTGTTTATTTAATGAATGAGTCATATTTAATAT<br>TGACTGATTCAGGGGGGATACAAGAAGAAGCGCCTTCGTTAGGTAAACCGGTTTTGGTTATGCGTGATACT<br>ACTGAACGCCCTGAGGCGGTTGAGGCTGGTACTGTTGTATTAGTGGGGACTTCTAAGATAAAAATAGTAAA<br>TAAAGTAACGGAGCTATTAAACAATGCTGATATCTACAATGCTATGTCTCTGTTACATAATCCATATGGCG<br>ATGGAACAGCTGCTCAAAAAATTCTTAATGTGCTCGCCCAAGAGCTAATTTAATTTAAGCTAAAAATATGT<br>TATTAATTATTGCTGATTATCCAAACGAAATGAATATGCGCGAGGGAGCTATGCAACGAATAGATGCGATA<br>GACTCTCTCATTCGAGATCGCAAGCGAGTGTATTTGAATATTTCATTCAAAAAGCATCTAGTTCGCTCAAA<br>TAGTTCCTTTAATAATGTTATAGTTGAAAATCTAAATGCAATTATTCACAGAAACATCATAAAACAGTACA<br>TGCAAAAATCAACAACTATATATGTTCATTCTGTTTATAATTTATTAAAGGTTATAACGCTCATTGATCTA<br>AAAAAAACAATTCTTGATATACATGGTGTTGTACCGGAAGAACTTTTGGCAGATAATAAAAAATTACTTAG<br>TAAAGTATATAACATGGTGGAAAAAAAAGGTGTCCTTGGATGCAAAAAATTAATACACGTCAGTACAGAAA<br>TGCAAAAACACTATGAAGCAAAATATGGAGTAAACTTGGCTGAAAGGTCAATAGTGCTCCCGATTTTTGAA<br>TATAAAAATATAACCCAATCGCAAAACAAATGGACAGAAAATAAAATACGAAGTATCTATCTTGGAGGATT<br>ACAAACATGGCAAAATATTGATAAAATGATTCAAGTTTGTGATGACACAGTGATAAACAATGAAGCAGGTA<br>AGTATGAATTCAACTTTTTCATCCCACAGAGTAACTTGGAAGGGTTTATAGATAAATATTCGTTAAAATTA<br>CATAATATCAATGCTAATGCATCTACGCTATCACGTGATGAAGTAATTCCCTTTCTAAAAGAATGTCATAT<br>TGGTTTTGTATTGCGCGATGATATAATAGTAAACAGAGTTGCGTGCCCTACAAAATTGGTTGAATATTTAG<br>AGTGTGGTGTCGTTCCAGTTGTGCTCTCCCCACTTATAGGTGATTTTTATTCGATGGGATATCAATACATT<br>ACTACAGAGGAAATGGCTAACAGAAGTATAAGTTTGTTGGATCTTGAAAAAATGGCTGCACATAATTTACA<br>AATTTTGACTTCTTATCAGAAGAGAACCTACAAGGCACAGAAAGAACTTATTGCTCAACTGTGCTGAATTT<br>TTTACATATATAAAATTATGTAAGCATATCGCGGGTCAGGTAATTGTATGCGTATCAAATATAAAGATAAC<br>GGTTATATATTATGTTTTCTATTATGTTTCATTTTGAGCTACTTAGTTTTACTCAAATCTGACTACTTTCC<br>TGCTGATTTTCTGCCATATACAGAAATATACGATGGGACATACGGAGAAATCAATAATATTGAGCCTGCCT<br>TTTTATATTTAACACGGTTGTTTCATTATTTAAATTTCCCCTATATATTTTTTGCAATGTTAGTTTGTGCC<br>TTATGTTTAAGTTGGAAAATAAAATATGCAAGAAAAATAATTAAAGATAGTTATATATATTTGTTCTTGTA<br>TGTATATGTATCATTTTATGTGTTTTTGCATGAAATGACTCAATTGCGCATAGCAATTGCAGTCACTATGT<br>GCTATGTGTCGGTTTATTATTACTTTTATAAAAATTGTATTAAACATGCACTGCCATGGATGGTGTTGGCT<br>ATTTTGTTTCATTACAGCGCCTTGCTTTTATTTATGTCATTATTTATATACAGTTATAGGAGGTTATTAAT<br>AGTAATTATAGGGTTTGTAATATGTATGAGCTTTTTAAACGTGTATGCAGATACAATTGCACTATATTTGC<br>CAAATGAAAAAATAGTAAATTATTTATATAGTATTTCATCATCATTAGACAATAGAAATGATTTGGCAATA<br>TTCAACCTGAATAATATAATATTTTTATCAATATTTATTTTGATCTTTTATCTTAGCCGATATATAAAATT<br>AAATGATAATGAGGCGAAGTTTATTAAGTATGTGCAATGTTCAGGAATATTAGCCTTTTGTATTTTCTTTC |

-continued

SEQUENCES

TGGCTAGTGGAGTCCCGGTCATTGCTTATCGAACTGCAGAGTTGCTGCGAATATTTTATCCGATGGCTTTA
GTATTAATCCTTTCGCATATAAAAAATAATAATATGCGTTATTTTATTGCAGTCATTATAGTTATCCTTTC
AGGCTTAATGTTGTTTATAACACTAAGGGCTGTATCAATAGTTGGTCAAGGATTATAAAATGAATGTTGCT
ATTTTGTTGTCTACGTATAATGGCGAAAAATATTTAGAGGAACAACTGGATTCATTGCTGCTTCAAAGTTA
TCAGGATTTTGTAGTGTATATCCGTGATGACGGATCATCTGATAGAACTGTAAATATAATAAACCAATACG
TAATGAAAGATAACAGATTTATTAACGTGGGTAATTCAGAAAATCTTGGTTGTGCTGCTTCGTTTATTAAT
TTATTAAGAAATGCTTCAGCCGATATTTATATGTTTTGTGACCAAGATGATTATTGGCTTCCGAATAAATT
ACAGCGTGCTGTGGATTATTTTTCGGCTATTGATCCTTTACAACCTACCTTGTATCATTGCGATCTAAGCG
TTGTTGATGAAAAACTTAATATTATACAAAATTCATTTTTGCAGCATCAGAAAATGTCAGCGTATGATTCA
ATGAGAAAAAATAATCTTTTCATACAAAATTTTGTTGTTGGTTGTTCATGTGCTGTTAATGCTTCACTTGC
GGAATTTGTTCTTTCGCGAATTGGAGAGCAGCATGTAAAAATGATAGCTATGCATGACTGGTGGTTAGCCG
TGACTGCAAAACTTTTTGGTCGAATCCATTTTGATAATACTCAAACGATTCTTTATCGACAACATCAGGGC
AATGTATTAGGTGCAAAATCATCAGGTATGATGCGTTTTATTCGATTAGGATTAAATGGGCAAGGGATTTC
GCGAGTAGTATCTTTTAGAAAAAAAGTTTGTGCGCAAAATAAGCTTCTTTTAGATGTCTATGATAAAGATT
TAAATCTTGAGCAAAAAAAATCTATCAGGCTTGTAATTGAGGGCCTTAAAGAGAACTCTTCAATTGCTGAC
CTTTTAAAATGTTTCTATCATGGTAGCTATATGCAAGGTTTTAAACGTAATCTTGCCTTAATATATTCAGT
TCTTTACACAAAAAAAAGAAGATAGTGTATCCTTATGAAAAAAATTGCTATTATCGGTACTGTTGGCATAC
CAGCATCATATGGCGGATTTGAAACATTAGTTGAAAATTTAACAAGATACAATTCCTCGGGAGTTGAATAT
AATGTTTTTTGTTCATCGTTTCACTACAAATCCCACCAAAAAAAACATAATGGGGCCCGTTTAATTTATAT
TCCGCTTAAAGCCAATGGATGGCAGAGCATTGCGTATGACATAATTTCGTTAGCATATTCTATTTTTTTGA
AGCCTGATGTGATTCTGATTTTAGGGGTTTCTGGTTGTTCATTTTTGCCTTTCTTCAAACTCTTAACACGC
GCTAAGTTTATTACTAATATTGATGGCCTGGAATGGCGAAGAGATAAATGGAATTCAAAAGTGAAACGTTT
CTTAAAATTTTCAGAAAAAATCGCAGTTCAATATTCGGATGTCGTTATTACGGATAATGAGGCAATTTCTG
AGTACGTTTTTAACGAGTATAATAAAGATAGCCGAGTTATTGCCTATGGAGGGGATCATGCATGGTTAAAT
ACTGAGGATGTATTTACAACAAGAAATTATAAAAGCGATTACTACCTTTCTGTATGTCGTATCGAACCCGA
AAACAATGTAGAATTAATTTTAAAAACATTTTCAAAGCTAAAATATAAAATAAAATTTATTGGAAATTGGA
ATGGCAGCGAGTTTGGAAAGAAACTTAGGCTGCATTATTCTAACTATCCAAATATTGAAATGATTGATCCG
ATTTATGATCTTCAACAATTATTTCACTTACGAAATAATTGCATAGGATATATACATGGTCATTCGGCTGG
AGGAACAAACCCTTCTTTAGTCGAGGCAATGCATTTTAGTAAACCTATATTTGCATATGATTGTAAGTTTA
ATAGGTACACTACTGAAAATGAAGCATGTTATTTTTCTAATGAATCTGACCTCGCAGAGAAAATCATAATG
CATTGTGAGCTATCATTAGGTGTCTCTGGCACGAAAATGAAAGAAATTGCTAACCAGAAATACACTTGGAG
ACGAATAGCAGAAATGTATGAGGATTGCTATTAACTCTGTTAAACTTCAAATCTTTTACAATATATGGCAT
GACTATAAGCGCATTAATTGTTTTTCAAGCCGCTCTCGCGGTGACCACCCCCTGACAGGGGATCCGTGTAG
GCTGGAGCTGCTTCGAAGTTCCTATACTTTCTAGAGAATAGGAACTTCGGAATAGGAACTAAGGAGGATAT
TCATATGGATAAAGCCGTAAGCATATAAGCATGGATAAGCTATTTATACTTTAATAAGTACTTTGTATACT
TATTTGCGAACATTCCAGGCCGCGAGCATTCAGCGCGGTGATCACACCTGACAGGAGTATGTAATGTCCAA
GCAACAGATCGGCGTAGTCGGTATGGCAGTGATGGGACGCAACCTTGCGCTCAACATCGAAAGCCGTGGTT
ATACCGTCTCTATTTTCAACCGTTCCCGTGAGAAGACGGAAGAAGTGATTGCCGAAAATCCAGGCAAGAAA
CTGGTTCCTTACTATACGGTGAAAGAGTTTGTCGAATCTCTGGAAACGCCTCGTCGCATCCTGTTAATGGT
GAAAGCAGGTGCAGGCACGGATGCTGCTATTGATTCCCTCAAACCATATCTCGATAAAGGAGACATCATCA
TTGATGGTGGTAACACCTTCTTCCAGGACACTATTCGTCGTAATCGTGAGCTTTCAGCAGAGGGCTTTAAC
TTCATCGGTACCGGTGTTTCTGGCGGTGAAGAGGGGGCGCTGAAAGGTCCTTCTATTATGCCTGGTGGCCA
GAAAGAAGCCTATGAATTGGTAGCACCGATCCTGACCAAAATCGCCGCCGTAGCTGAAGACGGTGAACCAT
GCGTTACCTATATTGGTGCCGATGGCGCAGGTCACTATGTGAAGATGGTTCACAACGGTATTGAATACGGC
GATATGCAGCTGATTGCTGAAGCCTATTCTCTGCTTAAAGGTGGCCTGAACCTCACCAACGAAGAACTGGC
GCAGACCTTTACCGAGTGGAATAACGGTGAACTGAGCAGTTACCTGATCGACATCACCAAAGATATCTTCA
CCAAAAAAGATGAAGACGGTAACTACCTGGTTGATGTGATCCTGGATGAAGCGGCTAACAAAGGTACCGGT
AAATGGACCAGCCAGAGCGCGCTGGATCTCGGCGAACCGCTGTCGCTGATTACCGAGTCTGTGTTTGCACG
TTATATCTCTTCTCTGAAAGATCAGCGTGTTGCCGCATCTAAAGTTCTCTCTGGTCCGCAAGCACAGCCAG
CAGGCGACAAGGCTGAGTTCATCGAAAAAGTTCGTCGTGCGCTGTATCTGGGCAAAATCGTTTCTTACGCC
CAGGGCTTCTCTCAGCTGCGTGCTGCGTCTGAAGAGTACAACTGGGATCTGAACTACGGCGAAATCGCGAA
GATTTTCCGTGCTGGCTGCATCATCCGTGCGCAGTTCCTGCAGAAAATCACCGATGCTTATGCCGAAAATC
CACAGATCGCTAACCTGTTGCTGGCTCCGTACTTCAAGCAAATTGCCGATGACTACCAGCAGGCGCTGCGT
GATGTCGTTGCTTATGCAGTACAGAACGGTATTCCGGTTCCGACCTTCTCCGCAGCGGTTGCCTATTACGA
CAGCTACCGTGCTGCTGTTCTGCCTGCGAACCTGATCCAGGCACAGCGTGACTATTTTGGTGCGCATACTT
ATAAGCGTATCGATAAAGAAGGTGTGTTCCATACCGAATGGCTGGATTAA

SEQ ID NO: 12 (example O2 rfb locus nucleotide sequence - O2-EPA production strain stGVXN4906)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGTGAAAATACTT
GTTACTGGTGGCGCAGGATTTATTGGTTCAGCTGTAGTTCGTCACATTATAAATAATACGCAGGATAGTGT -continued

| SEQUENCES |
| --- |
| TGTTAATGTCGATAAATTAACGTACGCCGGAAACCGGGAATCACTTGCTGATGTTTCTGATTCTGAACGCT<br>ATGTTTTTGAACATGCGGATATTTGCGATGCACCTGCAATGGCACGGATTTTTGCTCAGCATCAGCCGGAT<br>GCAGTGATGCACCTGGCTGCTGAAAGCCATGTTGACCGTTCAATTACAGGCCCTGCGGCATTTATTGAAAC<br>CAATATTGTTGGTACTTATGTCCTTTTGGAAGCCGCTCGCAATTACTGGTCTGCTCTTGATAGCGACAAGA<br>AAAATAGCTTCCGTTTTCATCATATTTCTACTGACGAAGTCTATGGTGATTTGCCTCATCCAGATGAAGTA<br>AATAATACAGAAGAATTACCCTTATTTACTGAGACGACAGCTTACGCGCCAAGCAGCCCTTATTCCGCATC<br>CAAAGCATCCAGCGATCATTTAGTCCGCGCATGGAAACGTACGTATGGTTTACCGACCATTGTGACTAATT<br>GCTCGAACAACTATGGTCCGTATCACTTCCCGGAAAAGCTTATTCCATTGGTTATTCTTAATGCACTGGAA<br>GGTAAGGCATTACCTATTTATGGCAAAGGGGATCAAATTCGCGACTGGTTGTATGTAGAGGATCATGCTCG<br>TGCGTTATATACCGTCGTAACCGAAGGTAAAGCGGGTGAAACTTATAACATTGGCGGACACAACGAAAAGA<br>AAAACATCGATGTTGTGCTGACTATTTGTGATTTGTTGGATGAGATTGTACCGAAAGAGAAATCTTATCGT<br>GAGCAAATTACTTATGTTGCTGATCGCCCAGGGCATGATCGCCGTTATGCAATTGATGCCGATAAAATTAG<br>CCGCGAATTGGGCTGGAAACCACAGGAAACGTTTGAGAGCGGGATTCGCAAAACGGTGGAATGGTATCTGG<br>CTAATACAAATTGGGTTGAGAATGTGAAAAGCGGTGCTTATCAGTCATGGATCGAACAAAACTATGAGGGC<br>CGTCAGTAATGAATATCCTGCTTTTCGGCAAAACAGGGCAGGTGGGTTGGGAACTGCAGCGTGCTCTGGCG<br>CCGCTGGGTAATCTGATCGCTCTTGATGTTCACTCCACTAATTATTGTGGAGATTTCAGCAACCCCGAAGG<br>TGTGGCAGAAACCGTCAAAAAAATTCGTCCTGACGTTATTGTTAATGCTGCTGCTCACACTGCAGTAGATA<br>AAGCAGAATCAGAACCGGATTTCGCACAATTACTTAACGCGACAAGCGTCGAAGCGATTGCAAAAGCTGCT<br>AATGAAGTCGGGGCCTGGGTTATACACTACTCTACTGATTATGTTTTCCCAGGCAGTGGTGACGCGCCATG<br>GCTGGAAACGGATGCAACAGCACCGCTAAATGTTTACGGTGAAACAAAATTAGCTGGGGAAAAGGCATTAC<br>AAGAACATTGCGCAAAGCATCTTATTTTCCGTACCAGCTGGGTATACGCTGGTAAAGGAAATAACTTTGCT<br>AAAACGATGTTGCGTTTGGCAAAAGAACGCGAAGAACTGGCTGTGATAAACGATCAGTTTGGCGCACCAAC<br>AGGTGCTGAATTGCTGGCTGATTGCACCGCTCATGCCATTCGCGTGGCATTAAAAAAACCAGAAGTCGCTG<br>GCTTGTACCATCTGGTAGCAAGTGGCACAACAACCTGGCACGATTATGCTGCGCTGGTTTTTGAAGAGGCG<br>CGCAAAGCAGGGATTAATCTTGCACTTAACAAACTTAACGCCGTGCCAACAACGGCCTATCCCACACCAGC<br>CCGTCGACCCCATAACTCTCGCCTCAATACAGAAAAGTTTCAGCAGAACTTTGCGCTTGTCTTGCCTGACT<br>GGCAGGTGGGCGTGAAACGTATGCTCAACGAATTATTTACGACTACGGCAATTTAACAAATTTTTGCATCT<br>CGCTCATGATGCCAGAGCGGGATGAATTAAAAGGAATGGTGAAATGAAAACGCGTAAAGGTATTATTCTGG<br>CTGGTGGTTCCGGCACTCGTCTTTATCCTGTGACGATGGCAGTGAGTAAACAATTGCTGCCGATTTATGAT<br>AAGCCGATGATTTATTATCCGCTTTCAACGCTTATGTTAGCGGGTATTCGCGATATTCTTATTATTAGTAC<br>GCCACAGGATACACCGCGTTTCCAACAATTATTGGGGGACGGGAGCCAGTGGGGTCTTAATCTACAGTATA<br>AAGTACAACCGAGTCCGGATGGCCTGGCGCAAGCGTTTATTATTGGCGAAGACTTTATTGGTGGTGATGAT<br>TGTGCACTCGTACTTGGCGATAATATCTTCTATGGACACGACTTGCCGAAATTGATGGAAGCTGCTGTTAA<br>CAAAGAAAGCGGTGCAACGGTATTTGCTTATCACGTTAATGATCCTGAACGCTATGGTGTCGTGGAGTTTG<br>ATAATAACGGTACGGCAATTAGCCTGGAAGAAAAACCGCTGGAGCCAAAAAGCAACTATGCGGTTACTGGG<br>CTTTATTTCTATGACAATGACGTTGTGGAAATGGCTAAAAACCTTAAGCCTTCTGCCCGTGGCGAACTGGA<br>AATTACCGATATTAACCGTATTTATATGGAACAAGGACGTTTGTCTGTAGCCATGATGGGGCGTGGCTATG<br>CATGGTTGGATACAGGGACGCATCAAAGCCTTATTGAAGCAAGTAACTTCATTGCAACAATTGAAGAGCGT<br>CAGGGATTAAAGGTATCTTGCCCGGAAGAGATTGCTTACCGTAAAGGGTTTATTGATGCCGAGCAGGTGAA<br>AGTATTAGCCGAACCGCTTATCAAGAATCAATATGGTCAATATTTGCTGAAAATGATCAGCGAATAGTATA<br>TGGGAACTCAATGATGGATATTAAATTAATCTCTTTGCAAAAACATGGGGATGAGCGCGGTGCATTAATTG<br>CTCTTGAAGAGCAACGAAATATACCTTTCGAAGTCAAAAGAATATATTACATACTTGAGACTCTTAATGGA<br>GTAAGACGCGGATTTCATGCGCACAAGGTTACTCGTCAGTTAGCTATTGTAGTCAAGGGAGCTTGTAAATT<br>TCATCTGGATAATGGTAAAGAAACAAAGCAGGTGGAACTTAATGATCCAACAATTGCGTTGCTGATAGAAC<br>CCTATATATGGCATGAAATGTATGATTTTAGTGATGATTGTGTGCTGCTTGTAATTGCGGATGATTTCTAT<br>AAAGAGTCTGATTATATCCGCAATTATGATGATTTTATTAGAAGAGTAAATTCAATTGAGAATTCATAAGC<br>TAAGTGACGTCCAGACAACATCAATTGGTGATGGAACAACTATCTGGCAGTTTGTTGTGATACTAAAAGGT<br>GCTGTAATTGGTAATAATTGCAACATCTGTGCAAATACCTTAATTGAAAATAACGTTGTAATTGGTAACAA<br>TGTCACAGTCAAAAGCGGTGTGTATATTTGGGATGGCGTTAAAATAGAGGATAATGTTTTTATTGGTCCTT<br>GTGTAGCATTTACAAATGATAAGTATCCTCGCTCTAAAGTCTATCCTGATGAATTTTTGCAAACAATAATA<br>CGCAAAGGAGCATCAATAGGTGCTAACGCAACCATCCTGCCAGGAATTGAAATTGGTGAAAAAGCAATCGT<br>TGGTGCGGGGAGTGTTGTAACCAAAAATGTACCGCCATGCGCAATAGTAGTAGGTAATCCAGCTCGATTTA<br>TTAAATGGGTAGAGGATAATGAATAAAATTGATTTTTTAGATCTTTTTGCAATTAACCAGCGACAGCACAA<br>AGAATTAGTCTCTGCGTTTAGTAGGGTGCTAGATTCTGGTTGGTATATCATGGGCGAAGAACTTGAGCAGT<br>TCGAGAAAGAGTTCGCAGAATACTGTGGAGTTAAGTATTGCATTGGTGTAGCAAATGGCCTTGATGCGTTG<br>ATACTAGTATTGAGGGCATGGAAAGAACTTGGCTATCTTGAAGACGGTGACGAGGTATTAGTACCGGCAAA<br>TACATATATTGCTTCTATTCTTGCTATAACAGAGAACAAACTTGTTCCTGTTCTTGTTGAACCAGATATAG<br>AAACTTATAATATTAATCCTGCTTTAATTGAAAATTACATTACGGAAAAAACTAAAGCAATATTACCGGTT<br>CACTTATATGGTCTATTGTGCAATATGCCAGAAATTAGTGCAATCGCCAGAAAATATAATCTGTTGATTCT<br>TGAAGATTGTGCACAAGCACATGGTGCAATACGTGATGGTCGCAAAGCTGGAGCTTGGGGGGATGCTGCAG<br>GATTTAGTTTTTATCCAGGAAAAAACCTTGGAGCTTTGGGGGATGCGGGAGCTGTTACTACAAATAATGCA<br>GAATTATCCTCAACTATAAAAGCTTTGCGAAATTATGGGTCACATAAGAAATATGAAAATATTTATCAGGG<br>ATTGAATAGTCGATTGGATGAACTGCAAGCAGCCTTATTGCGTGTAAAAATCCATACATTACCGGAAGATA<br>CTGCGATTCGGCAAAGGATTGCTGAAAAATATATTCGTGAAATAAAAAACCCTGCGATTACGTTACCAGTG<br>TACGAAGGCCAAGGTGCGCATGTTTGGCATTTATTTGTAGTAAGAATCGCTAATCGTGAAAAATTCCAGTC<br>ATACTTATTAGAGAAGGGTATCAAAACCTTAATTCACTATCCATTACCACCCCATAAGCAGCAAGCATATC<br>AAAATATGTCTAGCCTTAGCCTTCCAATTACTGAGCAAATTCATGATGAAGTCATTTCTTTACCTATAAGT<br>CCGGTAATGAGTGAAGATGATGTCAATTATGTAATCAAAATGGTCAATGATTACAAGTAATGAAAAAATTT<br>CTTCAGGTAACTATATTATCCGCTATCTATACATTCATTAAAATGATTGCGGGTTTTATCATCGGTAAGGT<br>AGTAGCAATTTATACAGGGCCATCAGGGGTAGCAATGCTTGGCCAAGTGCAAAGTTTAATCACAATAGTTG<br>CAGGTACTACCTCTGCACCTGTAAGCACAGGCCTTGTTCGATATACTGCGGAAAATTGGCAAGAAGGACAA<br>GAAGCATGCGCGCCATGGTGGCGCGCATGCTTAAGGGTTACTCTGTTTTTATTCTTGCTTATTATTCCCGT<br>TGTTATTATATTGTCGAAAAATATTAGTGAGTTACTTTTTAGCGATGGACAATACACATGGTTAATCATTT<br>TCGCATGTTGTATATTGCCATTCTCCATTATAAATACATTGATCGCTTCAGTTTTAAATGGTCAACAATTT<br>TATAAGCAATATATATTGGTTGGGATGTTTTCTGTATTCATTTCTACTATGTTTATGATTTTGTTGATTGT<br>AGCTTATAATCTTAAAGGTGCATTGATTGCCACAGCTATAAATAGTGCTATTGCTGGTCTTGTATTGGTTT<br>TATTTTGTCTCAATAAATCTTGGTTTAGATTTAAATATTGGTGGGGTAAAACGGATAAAGACAAAATTATA |

-continued

| SEQUENCES |
| --- |
| AAAATTATTCATTATACTCTGATGGCTCTGGTTTCTGTTATCTCCATGCCTACAGCATTGATGTGTATTAG<br>AAAAATATTGATTGCTAAAACTGGTTGGGAGGATGCAGGGCAATGGCAGGCCGTATGGAAGATATCTGAGG<br>TTTATCTTGGTGTTGTGACAATTGCTTTGTCAACATATTTCTTACCAAGATTGACAATTATAAAAACAAGT<br>TTCCTTATAAAAAAAGAAGTAAATAGTACTATATTATACATAATATCTATTACTTCATTCATGGCGTTGAG<br>TATCTATTTATTCCGCGATTTGGTAATAACAGTTTTATTTACTGAACAGTTTCGCTCAGCTCGTGAATTAT<br>TTTTATTACAACTTATAGGGGATGTAATAAAAATTGCTGGGTTTCTTTATGCATACCCTCTTCAAAGTCAG<br>GGGCATACTAAACTATTCATCAGTTCAGAAGTGATTTTTTCTATGCTCTTTATCATTACCACCTATATTTT<br>TGTTGTAAATTATGGAGTACATGGTGCTAACATAAGTTATGTCATTACATATAGTTTATATTTTGTGTTTG<br>CATTTGTGTTTACTAATTTTATTAATGTTAGAAGAAATAATTAAAAACAGAGGTTGAATTTTGAAAATAAT<br>TATACCTGTCTTAGGATTTGGCAGGGCTGGTGGTGAAAGAGTTCTTTCTAAGCTGGCAACTGAATTGATGA<br>ATTATGGACATGATGTAAGTTTTGTTGTTCCAGATAATAGAACTAATCCATATTATGCTACCACAGCAAAA<br>ATTGTCACGAGTAAATCTAGTCAAAACCGTGTAAAAATATTGAGAATCATTAAAAATTACTATAATCTGTG<br>GCGTAAATGCATAGAGTTAAATCCTGATGCTGTAGTTGCTAGTTTTCATTTGACTGCCTATCTTGTCGCAT<br>TATTACCAATCACCCGTCGTAAGAAATATTATTATATTCAGGCGTATGAAGTTAATTTTTTTGATAATATA<br>ATATGGAAATTAATAGCGGGTTTAACATATTATTTACCGCTTAAAAAAATACTAAATAGTCCTAATTTGCT<br>TCCTCATAAACATGATGATTTTATAGGAGTAGTTCCTGCAGGAGTAGATTTAAACGTTTTCTATCCGAAAC<br>CATCAAATAGGTTATTAAATGGTCACACATCAATAGGGATTATTGGTAGAAAAGAGAAGCACAAAGGAACT<br>AGCGAAATTATTTCAGTATTGTGTTCACTGGAAAATAAAGCTGGAATTATAATCAATATTGCGATCTATCT<br>TGAAGAAGTTGATAAGCAGCGTTTAATCGCTGCCGGGTTTCAGGTTAATTTTTTTCCGATTACTTCTGATT<br>TAGAATTGGCATCCTTTTATCGAAGCAATGACATCATGATTGCTGTTGGGTTAATTGAAGATGGCGCTTTC<br>CATTATCCTTGTGCTGAATCAATGGCTTGTGGTTGTCTTGTTATTTCAAATTATGCGCCACTTACTGAAAC<br>TAACAGTGTACTTAAATTAGTCAAGTTTGATGCTTGCAAACTTGGTGAAGCAATTAATCTTTGTCTCAATC<br>TTGACCTAGAAGAAAAAAGCAAAGAAATCCAATCTAATATTTCTGTGTTGAATAAATATGACTGGAAAATT<br>GTTGGTGAAACTTTCAATAGTTTATTGTTAGATGCAAATAAATAGTATACGTTGATGGGGAAAATATGAAT<br>ATTGTTAAAACTGATATTCCAGATCTGATCGTTCTTGAACCAAAAGTGTTTAGTGATGAACGCGGCTTTTT<br>TATGGAGAGTTATAATCAGATTGAATTTGAGAAGGCAATAGGAAGGCACGTAAATTTTGTTCAGGATAATC<br>ATTCAAAATCTAGTAAAGGCGTACTACGTGGGTTGCATTATCAATTAGCACCGTATGCACAGGCTAAATTA<br>GTTCGATGTGTTGTAGGTCAGGTATTTGATGTTGCTGTTGATCTTAGAAAAAATTCACCAACGTTCAAAAA<br>ATGGTTTGGAATAACCCTTTCCGCAGAAAATAAACGACAATTATGGATACCCGAAGGATTTGCTCATGGTT<br>TCTTGGTGACCAGTGATGAAGCTGAGTTCATTTATAAGACAACTAACTACTATGCTCCTGGTCATCAGCAA<br>GCAATTATTTACAATGATCCTATTTTAAACATCGATTGGCCTTTCTGCAGTAGTGCTCTGTCATTATCACA<br>AAAAGATCAAGAAGCAAAATTATTTTCAGAATTATTGGACAGTGAACTGTTCTAATAAAGTGTGCCACCTT<br>ATCCGTCTGAAGGATAGGTGGTTGCTTATATTTTTTTGAGTATGTTTGTATAATGACAGAAAATAGTCCGA<br>AATATAAACACGATAAAAGCTTAATAAGTTTTATCTACTTATTTTTTATATTTACACTTATTGTAGGCTTT<br>ATTATCGCAAATACCCAGTTTTTGGGGCGAAGTAGAGACTATGATAATTATATACAGATCTTTTCTGGTAA<br>AGAAGGGGAGGGGGTTCTTGAATTATTTTATCGCGGATTGATGTTAATAACGACCAGCTATGAAACTATCA<br>TTTTTATAATTTTAACATGTTCTTTTTTTATAAAGGCAAGGTTTCTCGCTAACTATTCGCGTAATTTTTCA<br>GGCTTGACCTTATTCTTTATTTATTATGCAAGCGTTGCACTTTGGGTTTTAGATTATACTCAATTCAGAAA<br>TGGTCTATGTATTTCCATTTTAATGTTTTCCGTATACTATTTATTTATAAATAAACCGACTTATTTTTATT<br>TCTCGGTATTATGTGCAATTGCAACTCATTGGTCTGCTTTGCCTTTTTTGCTTTTATATCCTTTTGTCTAT<br>TCAACAAAAATAAGACGCCTTGGTTATTTTTGTTTCAGTATTCTTGTTTTGATTGCGATCTCAGGAGAAGG<br>AAAAGAGATCATATCTTTTATAAGAAATTTTGGAGTGGGACAAAAAATAGGAAATGAAGCTGGTGTAAATT<br>TAATAAATTCATTATCCCTTACCGCTATTTCCTGGTTTATTATTAGTTACATATCAAGCATTGGAAATGAA<br>AGGAGAAATTTAAGGCTTTTCTTTTGTTATGGTGTCATGCAATACGTGACTTTTAGCCTTTTCTCTCTACC<br>TGTTATGGCTTTCCGTATTTTGGAAATGTATTTTTTCCTTATGCTAACCATTGGGGTGTTTATTAAGCAAA<br>AAAAGAATTATTATTTTATTTTTTGCAAAGTGTTAATTTTATTGTATCTAACATACTATTATCATATGGTC<br>TTTGGAGTGATTAATGTGTAAGGCTAAGGTGTTGGCTATAATTGTTACTTACAACCCGGAAATTATTCGAT<br>TGACGGAATGTATTAACTCTTTAGCCCCACAAGTTGAGAGAATAATTCTTGTAGATAATGGCTCAAATAAT<br>AGTGATTTGATAAAAAAATATCAGTATTAATAACCTTGAAATTATTTTACTTTCGGAAAACAAAGGCATTGC<br>ATTTGCTCAGAACCATGGTGTTAAGAAGGGCCTGGAAGCAAAAGAGTTTGACTATTTATTTTTCTCAGATC<br>AGGATACTTGCTTTCCTAGCGATGTTATTGAAAAACTTAAGAGTACATTTACGAAAAATAATAAAAAAGGT<br>AAAAATGTTGCTTGTGCTTCTCCTTTTTTTAAAGACCATCGTTCAAATTATATGCATCCGTCAGTCAGCCT<br>AAATATTTTTACGAGTACAAAAGTTATATGTAGTGAAGTAGACGATGATCTTTATCCCTCGCATGTTATTG<br>CTTCTGGGATGTTAATGTCTCGTGAAGCATGGCGCGTCGTCGGACCATTTTGTGAAAAACTCTTTATAGAC<br>TGGGTTGATACAGAATGGTGTTGGCGTGCATTAGCTAATAATATGATTATTGTTCAGACACCATCAGTCAT<br>CATTTCTCATGAACTTGGGTATGGGCAGAAAATTTTTGCTGGTCGATCTGTTACAATACATAATTCTTTCA<br>GAAATTTTTATAAAATACGCAATGCAATATACTTAATGCTGCATTCAAATTATAGCTTCAAGTATCGTTAT<br>CATGCTTTTTTTCATGCGACAAAGAATGTTGTATTTGAAATTTTATATTCGAAAGAAAAATTAAATTCACT<br>GAAGGTTTGTTTTAAAGCTGTACGTGATGGTATGTTCAATAATTTTTAATACGAAAATAGTTAGGCTCAAG<br>GTGTTTAAATGGAAGAAAATAATATGAAGACGGTCGCTGTAGTTGGCACAGTGGGTGTTCCTGCTTGTTAT<br>GGTGGGTTCGAATCACTTGTTCAGAATCTAATTGATTATCAATCTGATGGTATACAATATCAGATATTTTG<br>CTCTTCAAAAAAATATGATAAAAAATTTAAAAATTATAAAAATGCAGAATTAATCTATTTGCCGATAAATG<br>CCAATGGCGTCTCTAGCATAATTTATGATATTATGTGTTTAATTATTTGTTTATTCAAAAGGCCAGATGTT<br>GTTTTAATATTGGGGGTGTCTGGTTGTTTATTTCTACCAATTTATAAACTATTTTCAAAATCAAAGATTAT<br>TGTCAATATTGATGGGCTTGAATGGCGTAGAAATAAATGGGGAACGTTTGCTAAGAAATTTCTTAAAATAT<br>CTGAGGCGATATCTATTAGAATAGCTGATATTATCATTTCAGATAATCAAGCAATAGCTGATTATGTGGAA<br>AATAAGTACAAGAAAAAAAGTGTAGTTATAGCTTATGGCGGAGATCATGCCACTAATCTTAGTACACCGAT<br>AGACAATGATCAAAAAAAAGAAGGTTATTATTTGGGGCTTTGTAGGATAGAGCCTGAGAATAATATAGAAA<br>TGATTCTGAATGCCTTCATTAATACAGATAAAAAAATTAAATTTATGGGTAATTGGGATAACAGCGAGTAT<br>GGACGCCAGCTAAAAAAATATTATTCAAACTATCCAAATATCACCCTACTAGAACCTAACTATAATATTGA<br>AGAGCTTTATAAACTAAGAAAAAATTGTCTTGCATACATTCATGGACACTCGGCTGGTGGAACAAACCCTT<br>CTTTAGTTGAAGCGATGCATTTTAATATTCCTATTTTTGCTTTCGATTGTGACTTTAATCGTTACACAACT<br>AACAATTTAGCTCATTACTTTAATGATTCTGAACAACTTAGCTTATTAGCAGAAAGTTTGTCTTTTGGAAA<br>TCTTAAATGTCGAGTATTAGATTTAAAAAATTATGCTGAAGATATGTATAACTGGAGGCATATAGCTGCTA<br>TGTATGAATCTATTTATTAAACGCATTAACAATAATATAATTGACCTTATATAGCAGGGAAAGATCACGTA<br>ACGCTGCGGCGCGCCGATCCCCATATGAATATCCTCCTTAGTTCCTATTCCGAAGTTCCTATTCTTTCTAG<br>AGAATAGGAACTTCGGAATAGGAACTAAGGAGGATATTCATATGGATAAAGCCGTAAGCATATAAGCATGG |

-continued

| SEQUENCES |
|---|
| ATAAGCTATTTATACTTTAATAAGTACTTTGTATACTTATTTGCGAACATTCCAGGCCGCGAGCATTCAGC<br>GCGGTGATCACACCTGACAGGAGTATGTAATGTCCAAGCAACAGATCGGCGTAGTCGGTATGGCAGTGATG<br>GGACGCAACCTTGCGCTCAACATCGAAAGCCGTGGTTATACCGTCTCTATTTTCAACCGTTCCCGTGAGAA<br>GACGGAAGAAGTGATTGCCGAAAATCCAGGCAAGAAACTGGTTCCTTACTATACGGTGAAAGAGTTTGTCG<br>AATCTCTGGAAACGCCTCGTCGCATCCTGTTAATGGTGAAAGCAGGTGCAGGCACGGATGCTGCTATTGAT<br>TCCCTCAAACCATATCTCGATAAAGGAGACATCATCATTGATGGTGGTAACACCTTCTTCCAGGACACTAT<br>TCGTCGTAATCGTGAGCTTTCAGCAGAGGGCTTTAACTTCATCGGTACCGGTGTTTCTGGCGGTGAAGAGG<br>GGGCGCTGAAAGGTCCTTCTATTATGCCTGGTGGCCAGAAAGAAGCCTATGAATTGGTAGCACCGATCCTG<br>ACCAAAATCGCCGCCGTAGCTGAAGACGGTGAACCATGCGTTACCTATATTGGTGCCGATGGCGCAGGTCA<br>CTATGTGAAGATGGTTCACAACGGTATTGAATACGGCGATATGCAGCTGATTGCTGAAGCCTATTCTCTGC<br>TTAAAGGTGGCCTGAACCTCACCAACGAAGAACTGGCGCAGACCTTTACCGAGTGGAATAACGGTGAACTG<br>AGCAGTTACCTGATCGACATCACCAAAGATATCTTCACCAAAAAAGATGAAGACGGTAACTACCTGGTTGA<br>TGTGATCCTGGATGAAGCGGCTAACAAAGGTACCGGTAAATGGACCAGCCAGAGCGCGCTGGATCTCGGCG<br>AACCGCTGTCGCTGATTACCGAGTCTGTGTTTGCACGTTATATCTCTTCTCTGAAAGATCAGCGTGTTGCC<br>GCATCTAAAGTTCTCTCTGGTCCGCAAGCACAGCCAGCAGGCGACAAGGCTGAGTTCATCGAAAAAGTTCG<br>TCGTGCGCTGTATCTGGGCAAAATCGTTTCTTACGCCCAGGGCTTCTCTCAGCTGCGTGCTGCGTCTGAAG<br>AGTACAACTGGGATCTGAACTACGGCGAAATCGCGAAGATTTTCCGTGCTGGCTGCATCATCCGTGCGCAG<br>TTCCTGCAGAAAATCACCGATGCTTATGCCGAAAATCCACAGATCGCTAACCTGTTGCTGGCTCCGTACTT<br>CAAGCAAATTGCCGATGACTACCAGCAGGCGCTGCGTGATGTCGTTGCTTATGCAGTACAGAACGGTATTC<br>CGGTTCCGACCTTCTCCGCAGCGGTTGCCTATTACGACAGCTACCGTGCTGCTGTTCTGCCTGCGAACCTG<br>ATCCAGGCACAGCGTGACTATTTTGGTGCGCATACTTATAAGCGTATCGATAAAGAAGGTGTGTTCCATAC<br>CGAATGGCTGGATTAA |
| SEQ ID NO: 13 (example O6A rfb locus nucleotide sequence - O6A-EPA production strain stGVXN4112 and stLMTB10923)<br>ATGACGAATTTAAAAGCAGTTATTCCTGTAGCGGGTCTCGGGATGCATATGTTGCCTGCCACTAAGGCGAT<br>ACCCAAAGAGATGCTACCAATCGTCGACAAGCCAATGATTCAGTACATTGTTGACGAGATTGTGGCTGCAG<br>GGATCAAAGAAATCCTCCTGGTAACTCACGCGTCCAAGAACGCGGTCGAAAACCACTTCGACACCTCTTAT<br>GAGTTAGAATCACTCCTTGAGCAGCGCGTGAAGCGTCAACTGCTGGCGGAAGTACAGTCCATTTGCCCGCC<br>GGGCGTGACAATTATGAACGTGCGTCAGGGCGAACCTTTAGGTTTGGGCCACTCCATTTTATGTGCACGAC<br>CTGCCATTGGTGACAATCCATTTGTCGTGGTGCTGCCAGACGTTGTGATCGACGACGCCAGCGCCGACCCG<br>CTGCGCTACAACCTTGCTGCCATGATTGCGCGCTTCAACGAAACGGGCCGCAGCCAGGTGCTGGCAAAACG<br>TATGCCGGGTGACCTCTCTGAATACTCTGTCATCCAGACCAAAGAGCCGCTGGACCGCGAAGGTAAAGTCA<br>GCCGCATTGTTGAATTCATCGAAAAACCGGATCAGCCGCAGACGCTGGACTCAGACATCATGGCCGTTGGT<br>CGCTATGTGCTTTCTGCCGATATTTGGCCGGAACTTGAACGCACTCAGCCTGGTGCATGGGGGCGTATTCA<br>GCTGACTGATGCCATTGCCGAACTGGCGAAAAAACAGTCCGTTGATGCCATGCTGATGACCGGCGACAGCT<br>ACGACTGCGGTAAAAAAATGGGTTATATGCAAGCGTTCGTGAAGTATGGACTACGCAACCTCAAAGAAGGG<br>GCGAAGTTCCGTAAAGGGATTGAGAAGCTGTTAAGCGAATAATGAAAATCTGACCGGATGTAACGGTTGAT<br>AAGAAAATTATAACGGCAGTGAAGATTAGCGGCGAAAGTAATTTGTTGCGAATTTTCCTGCCGTTGTTTTA<br>TATAAACAATCAGAATAACAACGACTTAGCAATAGGATTTTCGTCAAAGTTTTCCAGGATTTTCCTTGTTT<br>CCAGAGCGGATTGGTAAGACAATTAGCATTTGAATTTTACGGGTTTAGCGCGAGTGGGTAACGCTCGTCAC<br>ATCGTAGACATGCATGCAGTGCTCTGGTAGCTGTAAAGCCAGGGGCGGTAGCGTGCTGAAATTATAAAGTC<br>ATTCTTATAGAACATCGCATTTCAATAATATAATTACACCTAAATGAATAGGATACAACGTGTGCACAATT<br>ATTTAAGGCTTAAAGATAAAATAAAAAACGTATTTTTAGGGTTGTATATATTGCAGTTATTTAATTATATC<br>GCGCCATTGGTAATTATCCCTATCCTGATAAAATATATTGGGTTGGGGGAATATGGGGAATTGGTCTATAT<br>TACATCTATTTATCAAATAGTGGCTTTGATTATTGATTTTGGCTTTACTTACACAGGACCTGTGGTTGCTG<br>CGAGACATAGATGTGAGACCCAAAATTTACAGCGCTATTACTCAATAGTTGTTCTTTTAAAATCATTGCTT<br>TTTATAATTGCATTAACATGTGTATTTTTATTGTGCAGATTAAATATAGTCCACTTGTCATTTTTTGGGTT<br>TTTGTCAATTTTTCTATGCACTATTGGTAATATATTATCGCCCAATTGGTTTTTGCAGGGGATTGGTGATT<br>TTAAAAAACTTTCATACTCACAAGTAATAGTGAGAATAACATTGTTTATCATACTTCTTGTTTATGTCTGT<br>AGTGGCGGAGATAATGTTTTTATCCTAAGTTTTTTGCAAAATGCAACATTACTCATATGCTGTATATACTT<br>ATGGCCAAATATTCATATTAGCCATGTTGTTCATCTTAAACCTAATGAATGCATTGTGGAATTTAAGAAGG<br>CAGGAAATGTTTTTATTGGCGTAATAGGTACGATTGGTTACAATGGTCTAATTCCTGTGTTAATTGGAAAC<br>CTTTGCGGTAATACGAGTCTTGGTGTTTTTTCAATCGTTCAAAAAATGACAACAGCATGTCAAAGTCTAAT<br>TAATCCAATATCACAGTATATGTTATCTCAAGTTTCAGAAATTAAACCTCAAGATAAACTGTTTTATTATA<br>GAATTAAAAAAAGTTTTTTTGTGCATTTAACAATTAGCATAATTGCATGTTTATGTTATATGGGGTTAGGG<br>CAATATGTGGCGACTTTTATAGGTAAAGTTGACGTTTCATTTGTTATTATTTTATTTGCGTCAATAATTAC<br>CATTTTTTCATCTTTAAATAATGTCCTTGGTATACAGTTTCTTATACCGACAGATAATGTAAAAATACTAC<br>GAAGTATAAATGTTATGGCGGGAATTATTGTTGTTAGTTTGTCCTGGCTGTTAATATCACGCTTTGACATT<br>CTGGGGGGGGTTTATTAAACCTAATTGGTGAGTTTCTTGTATTCAGTATGCTAGCTTTTATTGCCCATCG<br>AAAGTGGGGAGCGAGAGTATAATGAAAGTGAAGGCGGTTCCTGCTATTACATTCTATTTAAGTTTAATGCT<br>GACAATTTTAGTGTTACTGTTTGGTAATGAACCAAATAAATCACAATATATCCTTGTTATAGCAACGATAA<br>CAGTTTTTTATATCGCATATATCACTAATAAAATAACTTCTCCGGCCAGCCTTCTCGTTATATCATCTTTT<br>GTGTTTTTAGGTTGTCGCCCTTTATTATCTTTGTTTGCAAACTATGATTATAGGATTGCCGATTGGTTTAT<br>TGAAGGATATATGGATGACGATGTGATTTTGGCTAACTATGCTATAACACTAATGTATTATGGTTATACAT<br>TGGGACTAATTCTATGCAAAAATACTGAAAAATTTTATCCGCATGGTCCTTATCCTGAAAAACAATTGCTA<br>AAAATAAAGTTTCTTTTGACTTTATTTTTTCTGGGTTCGATAGGTATGGTTGTAAAAGGGATATTCTTTTT<br>TAACTTTATAGAATCTAATAGTTATGTTGATATTTATCAATCAAATATAACAACGCCAATAGGTTATGATT<br>TTCTATCTTATTTATTTTATTGTTCTTTTTTCCTTATATGTGCGTTTCATATACAGTTCAGAACAAATAAA<br>AAATTTCTTTTTATTGCGATATGCATTGCTGCATTTAGCACCTTGAAGGGTAGTCGTAGTGAAGCTATAAC<br>GTTTCTTTTAACGGTTACATGTATATATTTTAATGAAGTAAAGACAAGAAACTTACGTCTGCTGATTACAA<br>TGATTTTTGTTTTTAGCGTCATTTTTGTGATTAGTGAATTTATCTCAATGTGGCGCACTGGAGGGAGTTTT<br>TTTCAATTAATGCAGGGTAATAATCCTGTTATAAACTTTGTATACGGCATGGAGTATCATATCTTTCCAT<br>TTATCAATCAGTAAAACTACAACTATTGTCAGGGGGATATAATGTTACCTATCTATTCAGCCAGTTAATAA<br>TAACTTGCTCGTCAATATTTAATGTCAAATTGAGCTTGCCGGAAATAAGCTATAGCCATTTGGCCTCATAC<br>ACAGCAAACCCAGAACTATATAATCTTGGGTTCGGACTTGGGGGGAGTTATTTAGCAGAATCGTTTTTAGC<br>ATTTGGTCTGATTGGATGTTTCATTATACCCTTTTTACTTTTACTTAATTTAAATGTATTGGAAAAATATA |

-continued

| SEQUENCES |
| --- |
| CAAAAAACAAACCAATTATATATTTTGTTTATTATAGTGTGTTGCCACCTATATTATTCACACCAAGAGAG<br>ACTTTGTTCTATTTCTTCCCCTATCTTGTCAAAAGTATATTTGTTGCTTTTTTAGTTACATTATACATCCA<br>GTATAAAAAGGATTGACCAAAATGTCAGAAAAAAATGTCAGCATAATAATCCCAAGTTATAACAGGGCTCA<br>TATTCTTAAGGAGGTCATACCAAGTTATTTTCAGGATGAGACTTTAGAGGTTATAGTTATCAATGATGGAT<br>CAACAGATAATACAAATAGTGTATTAGCTGAACTGAAGGAAAAATATTCTCAGTTAGTTATTTTAGAAAAT<br>GAAACGAATAAAAAACAGATGTATTCTAAAAACCGAGGGATTGAAATAGCCAAAGGGAAATATATTTTTTT<br>TGGTGATGATGACTCTTACCTCTTACCCGGTGTTATATCTCGGTTATTGGCTACAAAATATGAGACAGGCG<br>CTGATGTAATCGGCGCAAGAATACTTTATATGAATAATAACGAGAAAACAATTGAAGATTGCATAAATCGA<br>CATAAAAAAGAGGGGCGTTTTGTTAGTGATCTAAATAGATTGGATTTTAGTTATACATGTGATTTGGACCA<br>TCCGATTGAATGTTTTTATGCACAGCCTTTTGTTCTAGCTGAAAGGGAACTAATATCGAAATATCGATTTG<br>ATATATCTTATACGGGAAACTGCTATCGTGAGGAAACTGATTTCATGCTATCTCTATTTATTAAAAATAAA<br>AAATTTATATATGATTCAAAGGCTTTGTTAATAAATTTACCTCCAAGAAAAGCGACGGGAGGGGCAAGAAC<br>AGCTAATCGATTAAAATATCATTACGAAAGTTGCATAAATAATTATAGATTTTTAAAAAAATATAATGATA<br>ATTTGAATCTTCTTTCAGGACAAAAGCATGCTATATTTTACCGACAGTGTCAATTCGTTCTGCTAAAAATG<br>AAGTCGTTTATCGGGAAGTTTTTAAAATGATTATATATATCGCCGCGTATAATGGTTCAGGAGGGCAAGGT<br>GGGGTGGAAAGGGTTGTTGCCCAACAATGTAACATTCTTAAAAATTTGGGGGTTAAAGTCATTATACTTGA<br>TAAAACATACTTCAAAATTTCTAACAAAATTCGTAACAAAAAAATACAAGTAGCACTTTATCCAATATTAG<br>TTTCTCTTTATTTAACCTTACAAAAATTACGTGGCGTGACGTTTAAAGTTATTGCACATGGCTATTGTTCT<br>CCTTTTTATAGGAATGACATCTTAATAGCTCATGGCAATATGAAATGTTATTTTCAAACAGTCATGAATAA<br>AAAACCTAATCGGTTGTCTGGCAGTGGTCTTTTATCTTTCTATGAGCGTTGGGCTGGAGCATTTTCAAAAA<br>ATATCTGGGCTGTTTCAAATAAGGTTAAAAGTGAATGGAATGAGCTTTACAATATTAATTCACATAAAATC<br>AAAGTTGTTCGAAATTTTATAAATCTTGCACAATTTGATTACACTGATGTTAATGAAGCAGAATATGTGAC<br>ATTTGTCGGGCGATTGGAAAAAGGAAAAGGAATAGATGATCTGTATTACATATGTAAAAATCTGCCAGATA<br>CTTCCTTCCATTTAGTTTCAAGTATTCCCGCCCCACAAAATTTTGCTTCGCTAAATAATGTTCTGACCAGC<br>ATTGCTGTCCCCTATGCGAAAATGCCAGAAATATTTAAGAAATCCAGAGTACTTATTTTACCGTCCTATTA<br>TGAAGGATATGAGCTGGTTACTATTGAAGCGCTATGCTGTGGTTGCCCTGTGATAGGCTATAATGTTGGTG<br>CAATTAGAGAGTTGTATGCAGAAAGTTTTCCTGGCGTATTTATTGCCAATAATAAAGAAGATTTAGCACAA<br>GTAGCCTACAAATTAATTAGTCTTGATAATGAAAAATATTATCATTTGAGACAAACTATTTATAGCAAGCG<br>TGAGCTTTTTTCTGAAGAGAGATATGCGGAAATTTTAACGGCGGCATTTAATGAAAAAAAATAAGAAACTC<br>TGTCTCATTTCAATTAACTCATATAATGAACTTACCGGAGGAGGAGTATATTTACGTACGCTTGTTAGTTT<br>TCTACAAAAACAGAATGTTAATTTAACACTTATTGATAAAAAATCCTCAGGTAAACTATTCGAAGACAATA<br>CTTTTCAACATATATCATTTATTAAAGGTAAACGTCAGGATATAATATCCAGGCTTTTTTTTATACCATCA<br>TTTTATGTCCCTTATATTTTCTCAATAATTAAAATTTTACGGAAGCAAGATATTCTTGCTTTTCACAACTC<br>TCGGCTTGGATTGTTATGTCTGCTTTTTAGAATACTCATGCCCCACAAAAAGATCATATTGTTTACGGATA<br>ACTTCGAATATGACTTAATAAGACAAAAAGATAAAAACATAACTACTTTTATTGAAAAATTAATTGTTTAT<br>CTCAATGAATTTATCGGGCTTAAGAATTCAGATTTAGTTAGCTATATTACCCGGCAAGATAAAAATGCAAT<br>GGATAAATTTTATGGGATTAAAAAAAGCAGAAATTTAATTCTCCCTGTGATATTTAGTAGAGAAAAACCAA<br>CTGATGTATTGTCAGCTCACTTTATTAATGAGTATAATCGATTGAATAATGATAATAGGAAAAAAGTAGTA<br>TTTACTGCATCTTTTGATTTTTTTCCAAATATAGATGCTGCCAACTATGTTTTAAATGCAGCAAAGTCTAA<br>TAATGATTATTGCTATATTTTGGCAGGTAGGAAAAGTACTACTTTGAATCTTCCTGATTTGGATAATTTAT<br>TTTTTTTCGATAATCTATCTAATAGTGAAATGTCATATTTATTATCTGCTTGTGATGTTTTTTATTCTCCT<br>ATAGTTTTAGGAAGTGGAATGAAAACAAAAATTGCAGAAGCACTATCATATGGATTATATATTTATGCGAC<br>AGAGCATTCCTTAATCGGCTATGATGAAATTATACACAATAAGGAGTGTGTTAAAAAAATCTCACATTTGG<br>ATGAGGAATTTCCTAAAGATTTCAAGATGAAAAGTATCAATAAACAGCTAATAATGTCTTATCAGCAAAAA<br>TATTATTCACATTATCGGTTTAATGGCCATGAACTTGATATAATAAATTTTGACGATTAGTTAGTGGAGAT<br>ATAATATGAACATATTAGTAACTGGTGGTGCTGGATATATCGGATCTCATACGGCTATTGAATTACTGAAT<br>GCAGGTCATGAGATTATCGTTCTGGACAATTTCAGTAATGCTTCATACAAGTGTATCGAAAAAATAAAAGA<br>AATTACTCGACGTGATTTTATAACAATTACTGGAGATGCTGGGTGTAGGAAGACACTCTCCGCTATTTTCG<br>AGAAACACGCCATAGATATAGTTATTCATTTTGCTGGCTTTAAATCTGTTTCAGAGTCTAAAAGTGAACCC<br>TTAAAGTATTACCAGAATAATGTTGGAGTGACCATTACTTTATTACAGGTAATGGAAGAGTACAGAATTAA<br>AAAATTTATCTTTAGTTCATCTGCGACAGTCTATGGTGAACCAGAGATAATTCCAATTCCAGAAACAGCTA<br>AAATTGGAGGAACTACGAATCCATATGGCACATCGAAGTATTTTGTTGAAAAAATTCTAGAGGATGTTAGT<br>TCCACGGGAAAACTGGATATAATTTGCTTGAGATATTTTAATCCTGTCGGTGCTCATTCTAGTGGTAAAAT<br>AGGTGAGGCTCCATCTGGTATCCCTAATAATCTTGTTCCTTATTTATTGGATGTTGCGAGTGGTAAACGTG<br>ATAAATTATTTATTTATGGCAATGATTACCCTACTAATGATGGAACAGGTGTAAGGGATTTTATTCATGTT<br>GTTGACTTAGCGAAAGGTCATTTGGCTGCAATGAATTATTTAAGTATCAATTCGGGATATAATATCTTTAA<br>TCTTGGTACAGGAAAAGGTTATTCGGTACTTGAATTAATCACTACATTTGAAAAATTAACAAACATTAAGG<br>TCAATAAATCTTTTATAGAGAGAAGGGCAGGGGATGTTGCGTCTTGTTGGGCTGATGCAGATAAAGCTAAT<br>TCTTTATTGGACTGGCAAGCCGAACAAACTCTAGAACAGATGTTATTGGACTCGTGGCGTTGGAAAAAAAA<br>TTATCCAGACGGATTCTGAATATAAAAGGTTTCAGTTTTATGAATCAATCAGAGCAGAGAAAAAAAATACT<br>GGTTCTTACACCTCGCTTTCCCTACCCTGTCATTGGAGGGGATAGATTAAGAGTCTATATGTTATGTAAAG<br>AACTTTCCAAAAAATATGATCTTATTCTTCTGAGCTTATGTGATCAACCACTAGAACTTGAAATAAATATA<br>AATGACTCGGTCTTCAAAGAAATTCATCGTGTCTATCTACCAAAATATAAATCATATTATAATGTATTAAA<br>AGCTTTGGTTACGCAAAAACCGTTGCAAATTGCTTATTATCAATCGGACACATTTAAGAATAAATACAATA<br>AATTAATTAAACAATGCGATGCAGTATTTTGTCATCTGATAAGAGTTGCTGATTATGTTAAGGATACAGAC<br>AAGTTCAAAATTCTTGATATGACAGATGCAATATCTTTGAATTACAGTCGCGTTAAAAAATTAGCAAGTAA<br>AAAAAGTTTGCGTGCAATTATTTATTCTCTGGAACAAAAAAGATTAGAATCATATGAACGTTCTGTGGCGA<br>ATCTTTTTGATTTGACCACTTTTATTTCATCCGTAGACCGTGACTATCTCTACCCTAATCTGGGCAGTAAT<br>ATCCATATAGTCAATAATGGGGTTGATACATCAGCCTTGAGATATATAAAAAGAGAAATAAAAATCGATAA<br>GCCTGTGGAACTTATATTTATCGGAAATATGTATTCTTTACAAAATATGGATGCTGCAAAACATTTTGCTA<br>AGAATATTTTACCTTGCTTGTATGATGAGTTTAATATTATTTTTAAAGTGATTGGTAAGATCTCAGAAACT<br>AATAAAAATATATTAAATTCATTTAAAAATACAATTGCTTTAGGTACTGTTGATGATATCAATTCTTCCGC<br>TTCTACAGGGCATATAGGTATATGTCCTGTTCGTCTTGGAGCAGGCGTACAAAATAAAATTCTTGAATACA<br>TGGCTTTAGGTTTACCATGTATTACATCTAGCATTGGTTATGAAGGTATTAATGCAAAATCAGGTAGCGAA<br>ATTTTTGTTGCAGATACAGTAGAGCAATATAAAAACGTACTAAGAGAAATAATTTACGATTATAATCGTTA<br>TACTGAAGTGGCTGAAAATGCCCGTAGTTTTGTAGAAAATAATTTTTCTTGGGAATCAAAAGTTGCCAATT<br>TAATGAATACATTAGATGAGAAATTATATGAACAATAATAAAATTATTACACCTATCATTATGGCTGGTGG |

-continued

SEQUENCES

TTCAGGCAGTCGGTTGTGGCCACTATCAAGAATTCTCTATCCGAAACAATTTCTTAGCCTAATCGGTAGTC
ATACCATGCTTCAAACAACGGCTAATCGTCTGGATGGTTTGGATTGTACCAACCCTTATGTCATTTGTAAT
GAACAATACCGCTTTATAGTTGCTGAACAGCTTAGAAAAATCGATAGATTGACTTCAAAGAATATCATCCT
TGAGCCTGTTGGGCGTAACACTGCCCCTGCAATTGCATTAGCGGCGTTGCTGATGTCTAAGTCTGATAAAA
GTGCAGATGATCTTATGCTCGTACTGGCTGCAGATCACGTTATACACGATGAAGAAAAATTTTGTAACGCT
GTTAGATCGGCAATTCCATACGCTGCTGATGGGAAATTGGTAACATTTGGTATAATTCCAGACAAAGCAGA
AACTGGTTATGGTTATATACATCGAGGACAATATATTAATCAGGAAGATTCGGATGCATTTATAGTGTCAT
CATTTGTTGAAAAGCCAAATCATGAGACAGCCACTAAATATCTTGCTTCCGGTGAGTATTATTGGAATAGC
GGTATGTTTTTGTTTAGTGCAAATCGTTATATAGAGGAACTTAAACAATTTCGGCCTGATATTTTATCCGC
TTGTGAAAAAGCAATTGCTTCAGCGAACTTTGACCTTGATTTTGTGCGTTTAGATGAAAGTTCTTTCTCTA
AGTGCCCTGAAGAATCAATTGATTACGCTGTAATGGAAAAAACAAAAGACGCAATTGTTATTCCAATGGAT
GCTGGCTGGAGTGATGTCGGTTCATGGTCTTCTCTTTGGGAAATTAATGATAAAGACTCAGACGGCAACGT
AATAGTTGGGGATATTTTCTCTCATGAAACAAAGAATTCTTTCATATATGCCGAATCGGGAATTGTTGCTA
CAGTTGGAGTGGAAAATTTAGTTGTTGTCCAAACAAAGGATGCTGTTCTTGTCTCAGAGAGAAATAAAGTT
CAGGATGTAAAGAAAATAGTAGAACAAATTAAAAATTCAGGTCGTAGCGAGCATTATGTTCATCGCGAAGT
ATATCGTCCTTGGGGTAAATATGATTCCATTGACACAGGGGAGCGTTATCAGGTCAAACGTATAACAGTAA
ATCCTGGTGAAGGACTTTCTTTACAAATGCACCATCATAGGGCAGAACATTGGATCATAGTTTCTGGAACT
GCAAGGGTGACTATAGGTTCTGAAACTAAGATTCTTAGCGAAAATGAATCTGTTTACATACCTCTTGGTGT
AATACACTGCTTGGAAAATCCAGGGAAAATTCCTCTTGATTTAATTGAAGTTCGTTCTGGATCTTATTTAG
AAGAAGACGATGTTATCCGTTTTCAGGACCGATATGGTCGTAGCTAAATTTTTGATAATGTAACGTTAGTA
GAAGAGCGCTAATATTTTTAGTTAATCTGTAATAAGTATTATTTGTTTAAGGTATATCATGTCGAGTTTAC
CCTGCTTTAAAGCCTATGATATTCGCGGGAAATTAGGCGAAGAACTGAATGAAGATATTGCCTGGCGCATT
GGTCGCGCTTATGGCGAATTTCTCAAACCGAAAACCATTGTGTTAGGCGGTGACGTCCGACTCACCAGCGA
AACCTTAAAACTGGCGCTGGCGAAGGGGTTACAGGATGCGGGCGTCGATGTGCTGGATATTGGCATGTCCG
GCACCGAAGAGATCTATTTCGCCACGTTCCATCTCGGCGTGGATGGCGGCATCGAAGTTACCGCCAGCCAT
AACCCGATGGATTACAACGGCATGAAACTGGTGCGCGAAGGGGCTCGCCCGATCAGCGGTGATACCGGACT
GCGCGACATCCAGCGTCTGGCAGAAGCCAACGACTTTCCTCCCGTTGATGAAACCAAACGCGGTCGCTATC
AGCAAATCAATCTGCGTGACGCTTACGTTGATCACCTGTTCGGTTATATCAACGTCAAAAACCTCACGCCG
CTCAAGCTGGTGATTAACTCCGGGAACGGCGCGGCGGGTCCGGTGGTGGACGCCATTGAAGCCCGCTTTAA
AGCCCTCGGCGCACCCGTGGAATTAATCAAAGTGCACAACACGCCGGACGGCAATTTCCCCAACGGTATTC
CTAACCCGCTACTGCCGGAATGTCGCGACGACACCCGCAATGCGGTCATCAAACACGGCGCGGATATGGGC
ATTGCCTTTGATGGCGATTTTGACCGCTGTTTCCTGTTTGACGAAAAAGGGCAGTTTATTGAGGGCTACTA
CATTGTCGGCCTGCTGGCAGAAGCGTTCCTCGAAAAAAATCCCGGCGCGAAGATCATCCACGATCCACGTC
TCTCCTGGAACACCGTTGATGTGGTGACTGCCGCAGGCGGCACCCCGGTAATGTCGAAAACCGGACACGCC
TTTATTAAAGAACGTATGCGCAAGGAAGACGCTATCTACGGTGGCGAAATGAGCGCCCACCATTACTTCCG
TGATTTCGCTTACTGCGACAGCGGCATGATCCCGTGGCTGCTGGTCGCCGAACTGGTGTGCCTGAAAGGAA
AAACGCTGGGCGAACTGGTGCGCGACCGGATGGCAGCGTTTCCGGCAAGCGGTGAGATCAACAGCAAACTG
GCACACCCCGTTGAGGCGATTAACCGCGTGGAACAGCACTTTAGCCGCGAGGCGCTGGCGGTGGATCGCAC
CGATGGCATCAGCATGACCTTTGCCGACTGGCGCTTTAACCTGCGCTCCTCTAACACCGAACCGGTGGTGC
GGTTGAATGTGGAATCGCGCGGCGATGTACCGCTGATGGAAGAAAAGACAAAACTTATCCTTGAGTTACTG
AACAAGTAATTCAGTAATTTCATATAAATGGGTTTTAAAAAACGGAAAAGATGAGATATCCGGTGTGGTAT
ATCCAAGGTAATGCTATTCAGTATCTCTATGAGTGAGTTAACATCTATACCACATTTAAGCCGCACACTTC
GGGATCCCCATATGAATATCCTCCTTAGTTCCTATTCCGAAGTTCCTATTCTTTCTAGAGAATAGGAACTT
CGGAATAGGAACTAAGGAGGATATTCATATGGATAAAGCCGTAAGCATATAAGCATGGATAAGCTATTTAT
ACTTTAATAAGTACTTTGTATACTTATTTGCGAACATTCCAGGCCGCGAGCATTCAGCGCGGTGATCACAC
CTGACAGGAGTATGTAATGTCCAAGCAACAGATCGGCGTAGTCGGTATGGCAGTGATGGGACGCAACCTTG
CGCTCAACATCGAAAGCCGTGGTTATACCGTCTCTATTTTCAACCGTTCCCGTGAGAAGACGGAAGAAGTG
ATTGCCGAAAATCCAGGCAAGAAACTGGTTCCTTACTATACGGTGAAAGAGTTTGTCGAATCTCTGGAAAC
GCCTCGTCGCATCCTGTTAATGGTGAAAGCAGGTGCAGGCACGGATGCTGCTATTGATTCCCTCAAACCAT
ATCTCGATAAAGGAGACATCATCATTGATGGTGGTAACACCTTCTTCCAGGACACTATTCGTCGTAATCGT
GAGCTTTCAGCAGAGGGCTTTAACTTCATCGGTACCGGTGTTTCTGGCGGTGAAGAGGGGGCGCTGAAAGG
TCCTTCTATTATGCCTGGTGGCCAGAAAGAAGCCTATGAATTGGTAGCACCGATCCTGACCAAAATCGCCG
CCGTAGCTGAAGACGGTGAACCATGCGTTACCTATATTGGTGCCGATGGCGCAGGTCACTATGTGAAGATG
GTTCACAACGGTATTGAATACGGCGATATGCAGCTGATTGCTGAAGCCTATTCTCTGCTTAAAGGTGGCCT
GAACCTCACCAACGAAGAACTGGCGCAGACCTTTACCGAGTGGAATAACGGTGAACTGAGCAGTTACCTGA
TCGACATCACCAAAGATATCTTCACCAAAAAAGATGAAGACGGTAACTACCTGGTTGATGTGATCCTGGAT
GAAGCGGCTAACAAAGGTACCGGTAAATGGACCAGCCAGAGCGCGCTGGATCTCGGCGAACCGCTGTCGCT
GATTACCGAGTCTGTGTTTGCACGTTATATCTCTTCTCTGAAAGATCAGCGTGTTGCCGCATCTAAAGTTC
TCTCTGGTCCGCAAGCACAGCCAGCAGGCGACAAGGCTGAGTTCATCGAAAAAGTTCGTCGTGCGCTGTAT
CTGGGCAAAATCGTTTCTTACGCCCAGGGCTTCTCTCAGCTGCGTGCTGCGTCTGAAGAGTACAACTGGGA
TCTGAACTACGGCGAAATCGCGAAGATTTTCCGTGCTGGCTGCATCATCCGTGCGCAGTTCCTGCAGAAAA
TCACCGATGCTTATGCCGAAAATCCACAGATCGCTAACCTGTTGCTGGCTCCGTACTTCAAGCAAATTGCC
GATGACTACCAGCAGGCGCTGCGTGATGTCGTTGCTTATGCAGTACAGAACGGTATTCCGGTTCCGACCTT
CTCCGCAGCGGTTGCCTATTACGACAGCTACCGTGCTGCTGTTCTGCCTGCGAACCTGATCCAGGCACAGC
GTGACTATTTTGGTGCGCATACTTATAAGCGTATCGATAAAGAAGGTGTGTTCCATACCGAATGGCTGGAT
TAA

SEQ ID NO: 14 (example O8 rfb locus nucleotide sequence - O8-EPA production strain stLMTB11734)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA -continued

| SEQUENCES |
|---|
| GCCGCATTGTTGAATTTATCGAAAAACCGGATCAGCCGCAGACGCTGGACTCAGACATCATGGCCGTAGGT<br>CGCTATGTGCTTTCTGCCGATATTTGGCCGGAACTGGAACGTACTCAGCCTGGTGCATGGGGACGTATTCA<br>GCTGACTGATGCTATTGCCGAGCTGGCGAAAAAACAATCCGTTGATGCAATGCTGATGACCGGCGACAGTT<br>ACGACTGCGGCAAAAAAATGGGCTATATGCAGGCGTTTGTGAAGTATGGCCTACGCAACCTGAAAGAAGGG<br>GCGAAGTTCCGTAAAGGTATTGAGAAGCTGTTAAGCGAATAATGAAAATCTGACCGGATGTAACGGTTGAT<br>AAGAAAATTATAACGGCAGTGAAAATTCGCAGCAAAAGTAATTTGTTGCGAATCTTCCTGCCGTTGTTTTA<br>TATAAACCATCAGAATAACAACGAGTTAGCAGTAGGGTTTTATTCAAAGTTTTCCAGGATTTTCCTTGTTT<br>CCAGAGCGGATTGGTAAGACAATTAGCGTTTGAATTTTTCGGGTTTAGCGCGAGTGGGTAACGCTCGTCAC<br>ATCATAGGCATGCATGCAGTGCTCTGGTAGCTGTAAAGCCAGGGGCGGTAGCGTGCATTAATACCTCTATT<br>AATCAAACTGAGAGCCGCTTATTTCACAGCATGCTCTGAAGTAATATGGAATAAATTAAGCTAGCGATCGC<br>TTAAGATCTAGGATTTCATTATGTTACTTCCTGTAATTATGGCTGGTGGTACCGGCAGTCGTCTCTGGCCG<br>ATGTCACGCGAGCTTTATCCGAAACAGTTCCTCCGCCTGTTCGGGCAGAACTCCATGCTGCAGGAAACCAT<br>CACCCGACTCTCGGGCCTTGAAATCCATGAACCGATGGTCATCTGTAACGAAGAGCACCGCTTCCTGGTGG<br>CTGAACAGCTACGCCAGCTCAATAAGCTGTCGAATAATATTATTCTTGAGCCGGTCGGGCGCAACACCGCC<br>CCGGCCATCGCCCTGGCAGCCCTTCAGGCCACCCGCGACGGCGACGACCCGCTGATGCTGGTTCTCGCCGC<br>TGACCATATCATCAATAACCAGTCGGCCTTCCACGACGCCATCCGGGTCGCCGAGCAGTATGCTGATGAAG<br>GTCATCTGGTCACCTTCGGTATCGTGCCGAATGCCCCGGAAACTGGCTACGGTTACATTCAGCGCGGCGTG<br>GCGCTCACCGATAGTGCCCATTCCGCGTACCAGGTGGCCCGCTTTGTGGAGAAGCCGGATCGCGAGCGCGC<br>CGAGGCTTACCTCGCCTCCGGGGAGTACTACTGGAACAGCGGCATGTTTATGTTCCGCGCCAAGAAATACC<br>TCATCGAGCTGGCCAAATACCGTCCGGATATCCTGGAAGCCTGCCAGGCTGCGGTGAATGCCGCCGATAAT<br>GGCAGCGATTTCATCAATATCCCGCATGATATTTTCTGCGAGTGCCCGGATGAGTCCGTGGACTATGCCGT<br>TATGGAGAAAACCGCCGATGCGGTGGTGGTCGGTCTCGATGCTGACTGGAGCGACGTCGGCTCCTGGTCCG<br>CACTATGGGAGGTCAGCCCGAAAGACGAGCAGGGCAATGTCCTCAGCGGTGACGCGTGGGTACACAACAGC<br>GAAAACTGCTACATCAACAGCGACGAGAAGCTAGTGGCGGCCATTGGCGTAGAGAATCTGGTGATTGTCAG<br>CACTAAGGACGCCGTGCTGGTGATGAATCGCGAGCGTTCCCAGGACGTGAAGAAGGCGGTCGAGTTCCTCA<br>AGCAGAACCAGCGCAGCGAGTACAAGCGCCACCGTGAGATTTACCGCCCCTGGGGCCGTTGCGACGTAGTG<br>GTCCAGACCCCGCGCTTCAACGTCAACCGCATCACGGTGAAACCAGGCGGTGCCTTCTCGATGCAGATGCA<br>CCACCATCGCGCCGAGCATTGGGTTATTCTCGCCGGCACCGGTCAGGTGACTGTCAACGGTAAGCAGTTCC<br>TGTTGTCCGAGAACCAGTCCACCTTTATTCCGATTGGCGCCGAGCACTGCCTGGAAAACCCTGGCTGTATT<br>CCGCTGGAAGTGCTGGAGATCCAGTCGGGGGCGTACCTTGGCGAGGACGACATTATTCGTATTAAAGACCA<br>GTATGGTCGTTGCTAATTATTTTCGGGACAAGACGCAGAATGACACAGTTAACTTGTTTTAAAGCTTATGA<br>CATCCGTGGTGAACTGGGTGAGGAACTGAACGAGGACATCGCCTACCGTATCGGTCGCGCCTACGGCGAAT<br>TTCTGAAACCCGGGAAGATAGTGGTGGGGGGCGATGTGCGCCTCACAAGCGAGTCGCTGAAGCTGGCGCTG<br>GCCCGCGGGTTAATGGACGCCGGTACCGACGTGCTGGACATCGGCCTGAGCGGTACCGAAGAGATTTACTT<br>TGCCACCTTCCACCTTGGGGTAGATGGTGGCATCGAGGTGACCGCGAGCCACAATCCTATGAACTACAACG<br>GCATGAAGCTGGTGCGCGAGAATGCGAAGCCCATCAGCGGCGACACCGGCCTGCGGGATATCCAGCGCCTG<br>GCGGAGGAAAACCAGTTCCCGCCAGTGGACCCGGCGCGTCGCGGGACCCTGAGCAAGATATCGGTACTGAA<br>GGAGTATGTTGACCATCTGATGAGCTACGTGGACTTCTCGAACTTCACCCGTCCACTGAAGTTGGTGGTGA<br>ACTCCGGAAACGGGGCTGCGGGGCACGTGATTGATGAGGTGGAGAAACGCTTCGCGGCGGCTGGGGTGCCG<br>GTAACCTTTATCAAGGTGCATCACCAGCCGGATGGCCATTTCCCTAACGGTATCCCGAATCCGCTGCTGCC<br>GGAGTGCCGCCAGGATACCGCCGACGCGGTGCGCGAGCATCAGGCCGACATGGGGATTGCCTTTGACGGCG<br>ACTTCGATCGCTGCTTCCTGTTCGATGACGAAGCTTCGTTTATCGAGGGGTATTACATTGTCGGCCTGCTG<br>GCTGAGGCGTTCCTGCAGAAGCAGCCGGGAGCGAAAATCATTCACGACCCGCGCTTGACGTGGAACACGGT<br>AGACATCGTGACCCGCAACGGCGGCCAGCCGGTGATGTCGAAGACGGGGCATGCGTTCATCAAGGAGCGGA<br>TGCGTCAGGAAGACGCTATCTACGGCGGGGAGATGAGTGCGCACCATTACTTCCGCGATTTCGCCTACTGC<br>GATAGCGGGATGATCCCGTGGCTGCTGGTGGCGGAGCTGCTGTGTCTGAAGAACAGCTCGCTGAAATCGCT<br>GGTGGCGGACCGCCAGAAGGCGTTCCCTGCGTCGGGAGAGATCAACCGCAAGCTAAGTAATGCTGCTGAGG<br>CGATCGCCCGCATCCGGGCGCAGTATGAGCCGGCGGCTGCACACATCGACACAACGGACGGGATCAGTATT<br>GAATACCCTGAATGGCGCTTTAACCTGCGCACGTCTAACACCGAGCCGGTGGTGCGTCTGAACGTTGAGTC<br>CAGAGCTGATGTGGCGCTTATGAATGAAAAAACGACCGAGCTGTTACACCTGTTAAGCGGGGAATAAGGTG<br>AGAGATTTACTAACGACGATTTATCGTTATCGGGGATTTATCTGGAGCAGTGTTAAACGTGATTTTCAGGC<br>ACGCTATCAAACTAGTATGCTGGGCGCACTATGGCTCGTTTTACAACCGCTCTCTATGATTCTGGTCTATA<br>CCCTGGTTTTTTCCGAGGTGATGAAGGCAAGAATGCCCGATAATACCGGGTCGTTTGCCTATAGTATTTAT<br>CTCTGTTCCGGGGTACTGACCTGGGGATTATTTACTGAGATGCTGGATAAAGGTCAGAGCGTATTTATTAA<br>CAATGCTAATCTGATCAAGAAACTCAGTTTTCCGAAAATCTGTCTGCCGATCATCGTGACGTTATCGGCGG<br>TGCTAAATTTCGCGATTATTTTCAGTCTGTTTCTAATTTTTATCATTGTCACCGGTAACTTCCCCGGCTGG<br>CTCTTTCTCTCGGTGATACCGGTCCTGCTTTTGCAGATCCTGTTTGCCGGTGGGCTGGGGATGATCCTTGG<br>TGTCATGAACGTCTTTTTCAGGGATGTGGGGCAACTGGTTGGCGTTGCGCTGCAATTCTGGTTTTGGTTCA<br>CACCCATTGTTTATGTACTGAATTCATTACCTGCATGGGCAAAAAATCTGATGATGTATAACCCGATGACT<br>CGGATCATGCAATCTTATCAGTCCATCTTCGCCTATCATCTGGCCCCCAACTGGTATTCGCTATGGCCAGT<br>ATTGGCTCTCGCCATTATTTTCTGCGTCATCGGTTTCAGGATGTTCCGCAAGCATGCGGCGGATATGGTGG<br>ATGAATTATAATGAGTTATATCAGAGTAAATAATGTCGGTAAGGCGTATCGCCAGTATCACTCAAAGACCG<br>GGAGACTGATCGAATGGTTATCCCCTCTGAATACCAAACGCCATAATTTGAAATGGATCCTCCGCGATATT<br>AATTTCGAAGTCGCTCCGGGCGAGGCTGTCGGTATTATCGGTATCAACGGTGCAGGCAAGAGTACCCTGCT<br>TAAACTCATAACCGGGACGTCCAGGCCGACGACTGGAGAAATTGAAATCTCCGGACGTGTCGCTGCATTAC<br>TCGAATTGGGGATGGGGTTTCATTCTGATTTCACTGGTCGGCAGAATGTTTATATGTCTGGGCAACTGTTG<br>GGGTTATCGTCAGAGAAAATAACTGAACTGATGCCGCAAATTGAAGAGTTTGCTGAGATTGGGGACTATAT<br>CGATCAACCTGTGCGCGTCTACTCCAGTGGGATGCAAGTTCGATTAGCTTTTAGTGTAGCGACGGCTATCC<br>GTCCTGATGTGCTAATTATCGATGAGGCATTATCTGTTGGGGATGCATATTTCCAGCATAAAAGCTTTGAG<br>CGTATTCGAAAATTTCGTCAGGAAGGGACCACGCTGTTGCTGGTATCCCATGATAAACAAGCGATCCAAAG<br>CATTTGCGACCGGGCCATTTTATTGAATAAAGGCCAAATTGAAATGGAAGGTGAACCTGAAGCAGTGATGG<br>ATTATTACAATGCTCTTCTGGCCGATAAACAAAATCAGTCCATTAAACAAGTTGAGCATAATGGTAAAACG<br>CAAACTGTTTCAGGCACTGGTGAGGTGACTATCTCTGAGGTTCATCTTCTCGATGAACAGGGCAATGTGAC<br>TGAATTTGTTTCGGTAGGGCATCGTGTCAGCTTGCAGGTCAACGTTGAGGTCAAGGACGATATTCCTGAGC<br>TTGTTGTCGGATATATGATTAAGGATCGACTTGGGCAGCCGATTTTCGGGACCAATACGTACCATCTCAAT<br>CAGACACTCACCTCCCTGAAAAAAGGAGAAAAGCGTTCGTTCTTATTTTCTTTCGATGCGAGATTGGGGGT<br>TGGCTCCTATTCTGTCGCTGTCGCGTTGCATACTTCCAGTACGCACCTCGGCAAAAACTATGAATGGCGCG |

-continued

| SEQUENCES |
|---|
| ATCTGGCCGTGGTATTCAACGTCGTTAACACGGAACAACAAGAGTTTGTCGGCGTGTCCTGGTTGCCGCCT<br>GAACTGGAGATTTCTTAATGGGTTCGTCGTTTTATCGTTCATTTGAAGAACGACACAGAGGTTCGGTTGAA<br>GAAATCAAGCGCCGCTTGAGTTTTTATTTACCTTTTCTTGCAGGTCTGAAGGACATTTATCCTGATGGCGT<br>GATTGCGGATATTGGTTGCGGACGTGGCGAATGGTTGGAGATCCTGACTGAAAATGGCATTGCGAACATCG<br>GCGTCGATCTCGATGATGGCATGCTGGCGCGCGCCAGGGAGGCCGGACTGAATGTGCAGAAAATGGATTGT<br>CTGCAGTTTTTGCAAAGTCAGGCGGATCAGAGCCTGATAGCGTTGACCGGTTTTCATATTGCTGAGCATTT<br>GCCGTTTGAGGTCCTGCAGCAACTCGCCATGCATACCCTACGGGTGCTGAAACCAGGTGGTTTGCTGATCC<br>TCGAAACGCCGAACCCGGAGAATGTAAGCGTCGGCACCTGTTCATTTTATATGGATCCAACGCATAATCAT<br>CCTCTGCCACCGCCACTGCTTGAGTTTTTACCTATTCATTATGGTTTTACCCGAGCAATTACCGTTCGTCT<br>GCAGGAAAAAGAGGTTCTTCAATCTCCGGATGCAGCCGTTAATTTGGTCGATGTACTCAAAGGGGTGAGCC<br>CCGACTACAGCATCATTGCTCAGAAAGCAGCGCCAACAGATATTCTTGAACGCTTTGACACCCTGTTTACC<br>CAGCAGTACGGTCTGACGCTGGATGCTCTGAGCAACCGTTACGATGCGATTTTGCGCCAACAGTTTTCGTC<br>CGTTGTCTCACGGCTGGAGACGTTGAACCAAACCTATATGCAACAGATAAGCCAAATGTCAGAGACTATTC<br>AGACGTTGCAAGGTGAGGTTGACGATCTGAGTCATGTCATCGATCAGAACCATCAGCTTCATCAGCAAATG<br>GCGGATTTACATAACAGTCGTTCATGGCGTATTACTCAACCACTACGCTGGTTGTCTTTGCAACGTCAATT<br>ATTACGTCAGGAAGGGGCTAAAGTGCGAGCCCGTAGGGCTGGAAAAAAATATTGCGCAAAGGGATGGCGC<br>TCTCGCTGGTCTTTTTCCATCGTTACCCTAAGTCTAAGGTTTATCTGTTTAAGGTTCTGAGAAAAACTGGC<br>TGCTATACATTGCTACAACGTTTGTTCCAACGCGTAATGCTGGTGCAATCTGACACGATGATGATGCAGTC<br>CAGAAGATATGATGTGGGTACTGAAGAAATGACAAGTCGCGCGATGAGTATTTATAACGAATTAAAAAATA<br>AAAATACGGAGAAATAACGATGCGTATTGTCATAGATTTACAAGGCGCACAGACGGAAAGCCGCTTTCGTG<br>GCATCGGTCGTTATAGTATCGCAATCGCCAGAGGCATAATCAGAAATAACAGCCGGCATGAGATTTTCATC<br>GCGCTATCCGCCATGCTGGATGAGTCGATTGCAAATATTAAGGCGCAATTTGCCGATCTCCTGCCGGCAGA<br>AAATATAGTCGTATGGCATGCCGTAGGCCCTGTTCGTGCGATGGACCAAGGTAATGAATGGCGTCGGGAGA<br>GCGCAGAACTGATTCGGGAAGCGTTTCTTGAATCATTGTGTCCAGATGTCGTTTTCATTACGAGTTTGTTT<br>GAAGGTCATGTCGACGATGCGGCTACATCGGTACACAAATTTAGTCGTCAGTATAAAGTAGCCGTACTGCA<br>CCACGATCTTATCCCCCTCGTGCAGGCGGAAACCTATCTGCAGGACGATGTATACAAACCCTACTATTTAC<br>AGAAAGTTGAGTGGTTAAAAAACGCTGACCTTTTGTTGACTAACTCTGCTTATACCGCACAGGAAGCGATC<br>GAGCATCTGCATTTACAGGGCGATCATGTGCAGAATATTGCAGCCGCAGTCGATTCTCAGTTTTGTATGGC<br>GGAGGTGGCAGCGAGCGAAAAAGAGACCGTCCTTGGCCATTACGGTATTCAGCGCGAGTTCATGTTGTATG<br>CGCCCGGAGGATTTGACTCAAGGAAAAACTTTAAACGGTTGATTGAGGCCTATGCCGGGCTCAGTGATGCC<br>TTACGTCGCAGTCATCAACTGGTCATCGTCAGTAAGCTTTCCATCGGTGATCGTCAGTATCTGGAATCCCT<br>TGCGTCAGGTAATGGTTTACAGCAGGGCGAACTGGTACTCACTGGTTATGTGCCGGAAGATGAGCTGATCC<br>AGCTCTATCGCCTATGTAAGCTGTTCATCTTTGCTTCACTACATGAAGGTTTTGGGTTGCCGGTTCTGGAA<br>GCAATGTCGTGCGGTGCGCCGGTGATTGGCTCAAATGTCACCAGTATTCCTGAAGTCATCGGTAATCCTGA<br>GGCATTATTCGACCCGTATTCTGTCTCTTCCATGAGGGATAAGATCGCGCAATGTTTGACTGATGATACCT<br>TCCTCGCGCGTCTGAAAGAAATGGCGCAGCAGCAAGCGCGTAATTTCTCTTGGGATAAAGCTGCGGTGACT<br>GCTCTGGAAGCTTTCGAAAAGATCGCGGTAGAAGACACCGGTACTGCGCAGGTTTTGCCTGAAGCTTTGAT<br>TCAGAAGATCCTTGCTATCTCACAAGGGCAGCCAGATGACCGCGATCTGCGCTTGTGCGCAACGGCCATTG<br>ATTACAATCTGAAAACGGCAGAACTTTATCAAATCGACGATAAATCGCTGAACTGGCGTGTGGAAGGCCCA<br>TTCGATAGCTCATATAGTCTGGCGTTGGTCAACCGCGAATTTGCCCGGGCACTCTCAGCCGATGGTGTAGA<br>GGTTTTATTGCATTCCACTGAAGGACCAGGTGATTTTGCCCCAGATGCCTCGTTTATGGCACAGTCGGAAA<br>ATAGTGATCTTCTGGCATTTTATAATCAATGTCAGACCCGCAAGAGTAACGAAAAGATAGATATTATTAGC<br>AGAAATATCTATCCACCGCGGGTTACCAAAATGGATGCCAAAGTAAAATTCCTTCATTGTTATGCTTGGGA<br>AGAAACGGGCTTTCCGCAACCGTGGATCAATGAATTTAATCGGGAACTTGACGGAGTGCTGTGTACTTCGG<br>AACATGTTCGTAAAATACTGATTGATAACGGACTGAATGTGCCCGCATTTGTTGTTGGCAATGGCTGTGAC<br>CATTGGCTCAATATCCCAGCCGAGACGACAAAAGATGTGGATCACGGAACATTCCGTTTCCTGCACGTCTC<br>TTCTTGTTTCCCACGCAAAGGGATACAGGCAATGCTTCAGGCTTGGGGGAAGGCGTTCACTCGTCGTGACA<br>ATGTTATCTTAATCATTAAGACTTTTAACAATCCGCACAATGAAATTGACGCATGGCTGGCTCAGGCCCAG<br>GCTCAATTCATAGACTATCCCAAAGTTGAAGTGATCAAAGAGGATATGTCAGCCACCGAGCTTAAAGGGCT<br>TTATGAAAGCTGTGATGTTTTGGTTGCTCCAGGTTGCGCTGAAGGCTTTGGTTTACCTATTGCTGAAGCAA<br>TGCTGAGTGGGCTACCGGCTATCGTCACCAATTGGAGCGGGCAACTTGATTTTGTTAATTCACAAAATTCA<br>TGGCTGGTTGACTATCAGTTCACTCGGGTAAAAACGCACTTTGGTCTGTTTTCCTCAGCCTGGGCCAGTGT<br>GGATATTGACAACTTAACAGATGCATTAAAAGCGGCAGCCTCAACCGATAAATCAGTGCTGCGTGACATGG<br>CCAATGCTGGTCGCGAGCTTCTTCTGCAGCAGTTTACCTGGAAAGCGGTGGCTGATCGTTCTTGCCAGGCG<br>GTCAAGACTCTGCGTGCGCATATTGATATTGCACAGCATCGGGCGCGCATTGGCTGGGTGACGACCTGGAA<br>CACGAAATGTGGGATCGCAACCTATTCCCAGCATCTGGTGGAAAGCGCACCTCATGGCGCGGATGTTGTTT<br>TTGCTCCCCAGGTCAGCGCTGGCGATCTTGTGTGTGCAGACGAAGAGTTTGTACTTCGCAACTGGATTGTA<br>GGTAAAGAGAGCAACTATCTGGAAAACCTCCAGCCACACATTGATGCTCTGAGACTCGATGTCATTGTGAT<br>CCAATTCAACTATGGATTCTTTAATCATCGAGAACTGTCGGCGTTTATTCGTCGCCAGCATGACGCCGGTC<br>GTTCAGTTGTTATGACGATGCACTCAACTGTGGATCCGCTGGAAAAAGAGCCGAGCTGGAATTTCCGTCTT<br>GCTGAAATGAAAGAGGCGCTGGCACTTTGCGACCGGTTGTTGGTGCATTCGATTGCCGATATGAACCGCCT<br>TAAAGATTTAGGCTTAACTGCGAATGTTGCTTTATTCCCGCACGGTGTTATCAACTACTCCGCAGCGAGCG<br>TCACACGTCAACAGCAGTCTTTACCGCTAATTGCGAGCTATGGCTTCTGCTTACCGCATAAGGGCCTGATG<br>GAACTAGTAGAATCCGTCCATAGACTCAAGCAAGCCGGTAAACCGGTTCGTTTACGACTGGTGAACGCAGA<br>GTATCCTGTTGGGGAGTCACGCGATCTGGTGGCAGAGCTTAAAGCTGCTGCTCAGCGGTTAGGTGTTACCG<br>ATCTGATTGAGATGCATAATGATTTCCTACCTGATGCGGAGAGTCTGCGGTTGCTTTCAGAAGCCGATCTT<br>CTGATTTTTGCTTATCAGAATACTGGGGAGTCTGCTAGCGGGGCGGTACGTTATGGTATGGCGACTCAAAA<br>ACCTGTTGCGGTAACGCCCCTGGCGATATTTGATGATTTGGACGATGCCGTCTTTAAATTTGATGGATGCA<br>GCGTCGATGATATCAGTCAGGGGATTGACCGGATCCTGAATTCCATCCGTGAACAGAACTCTTGGGCAACC<br>AGGACTCAACAACGTGCCGATGCATGGCGGGAACAACATGATTATCAAGCTGTTTCACGCCGTCTGGTTAA<br>TATGTGTCAAGGCTTAGCTAAAGCTAAATATTTAAATAAAAATATCTCTCTTGTATTTTTTGCCTTTGAA<br>TACAAGAGGGGTTAGATAATGTGTCATTTATTATGAAAATTATTTTTGCTACTGAGCCAATTAAATACCCA<br>TTAACGGGCATCGGTCGGTATTCCCTGGAGCTGGTTAAGCGGCTGGCGGTCGCCCGCGAAATTGAAGAATT<br>AAAGCTATTTCACGGTGCGTCGTTTATAGAACAGATCCCTTTGGTGGAGAATAAAAGCGATACCAAAGCCA<br>GCAATCATGGTCGTCTGTCGGCGTTTCTACGCCGACAGACGCTGTTGATTGAGGCTTATCGCTTGCTGCAT<br>CCGCGGCGCCAGGCGTGGGCATTGCGCGACTATAAGGATTATATCTACCATGGCCCCAATTTTTATCTGCC<br>GCATAAACTGGAACGCGCCGTGACCACGTTTCATGACATATCCATTTTTACCTGCCCGGAATATCATCCAA |

-continued

| SEQUENCES |
|---|

AAGATCGGGTTCGCTATATGGAGAAGTCCCTGCATGAGAGTCTGGATTCGGCAAAGCTGATCCTGACCGTT
TCTGATTTCTCGCGCAGTGAAATTATCCGCTTGTTCAACTATCCGGCGGAGCGGATCGTAACCACCAAGCT
AGCCTGCAGCAGTGACTATATCCCACGCAGCCCGGCAGAGTGTCTGCCGGTACTGCAGAAATATCAGCTGG
CGTGGCAGGCCTACGCGCTATATATCGGCACTATGGAGCCACGTAAAAATATCCGAGGCCTGCTGCATGCC
TATCAGCTGCTACCGATGGAGATCCGCATGCGCTATCCGCTAATCCTTAGCGGCTATCGCGGCTGGGAAGA
CGATGTGCTGTGGCAGTTAGTCGAGCGCGGTACTCGGGAAGGCTGGATCCGTTACCTCGGATATGTTCCGG
ATGAAGACCTGCCGTATCTGTACGCAGCGGCCAGAGTCTTTGTTTATCCCTCCTTCTACGAGGGATTCGGT
TTACCTATTCTTGAAGCGATGTCTTGCGGTGTGCCGGTAGTATGCTCCAATGTCACCTCTTTGCCTGAGGT
TGTTGGCGATGCCGGCCTCGTTGCCGATCCTAATGATATAGACGCGATTAGCGCGCAAATTTTGCAGAGCC
TGCAAGATGATAGCTGGCGGGAAATCGCCACCGCGCGCGGTCTTGCTCAGGCGAAACAGTTTTCGTGGGAG
AACTGTGCGACACAGACCATTAACGCCTATAAATTACTCTAAGGGTGTCAGTTGAGAGTTCTACACGTCTA
TAAGACTTACTATCCCGATACCTACGGCGGTATTGAGCAGGTCATTTATCAGCTAAGTCAGGGCTGCGCCC
GCCGGGGAATCGCAGCCGATGTTTTCACTTTTAGCCCGGACAAAGATACAGGTCCTGTCGCTTACGAAGAT
CATCGGGTCATTTATAATAAACAGCTTTTTGAAATTGCCTCCACGCCGTTTTCGCTGAAAGCGTTAAAGCG
TTTTAAGCTGATTAAAGATGACTACGATATCATCAACTACCATTTTCCGTTTCCCTTTATGGATATGCTGC
ATCTTTCGGCGCGGCCTGACGCCAGGACTGTGGTGACCTATCACTCTGATATAGTGAAACAAAAACGGTTA
ATGAAGCTGTACCAGCCGCTGCAGGAGCGATTTCTCAGCGGCGTAGATTGCATCGTTGCCTCGTCGCCCAA
TTACGTGGCTTCCAGCCAGACCCTGAAAAAATATCTGGATAAAACGGTGGTGATCCCGTTTGGTCTGGAGC
AGCAGGACGTGCAGCACGATCCGCAGAGGGTCGCGCACTGGCGGGAAACTGTCGGCGATAAGTTCTTTCTC
TTCGTCGGCACTTTCCGCTACTACAAAGGGCTGCATATTCTGATGGATGCCGCTGAGCGTAGCCGACTGCC
AGTGGTGGTTGTAGGGGGCGGGCCGCTGGAATCGGAAGTGCGGCGTGAAGCGCAGCAGCGCGGGCTGAGCA
ATGTGATGTTTACCGGCATGCTCAACGACGAAGATAAGTACATTCTCTTCCAGCTCTGCCGGGGCGTGGTA
TTCCCCTCGCATCTGCGCTCTGAGGCGTTTGGCATTACGTTATTGGAAGGCGCACGCTTTGCAAGGCCGCT
GATCTCTTGCGAGATCGGTACAGGTACCTCTTTCATTAACCAGGACAAAGTGAGTGGTTGCGTGATTCCGC
CGAATGATAGCCAGGCGCTGGTGGAGGCGATGAATGAGCTCTGGAATAACGAGGAAACCTCCAACCGCTAT
GGCGAAAACTCGCGTCGTCGTTTGAAGAGATGTTTACTGCCGACCATATGATTGACGCCTATGTCAATCT
CTACACTACATTGCTGGAAAGCAAATCCTGAGCGGCCGCGAGCTCGTCGACTCGAGGATCCGTGTAGGCTG
GAGCTGCTTCGAAGTTCCTATACTTTCTAGAGAATAGGAACTTCGGAATAGGAACTAAGGAGGATATTCAT
ATGGATAAAGCCGTAAGCATATAAGCATGGATAAGCTATTTATACTTTAATAAGTACTTTGTATACTTATT
TGCGAACATTCCAGGCCGCGAGCATTCAGCGCGGTGATCACACCTGACAGGAGTATGTAATGTCCAAGCAA
CAGATCGGCGTAGTCGGTATGGCAGTGATGGGACGCAACCTTGCGCTCAACATCGAAAGCCGTGGTTATAC
CGTCTCTATTTTCAACCGTTCCCGTGAGAAGACGGAAGAAGTGATTGCCGAAAATCCAGGCAAGAAACTGG
TTCCTTACTATACGGTGAAAGAGTTTGTCGAATCTCTGGAAACGCCTCGTCGCATCCTGTTAATGGTGAAA
GCAGGTGCAGGCACGGATGCTGCTATTGATTCCCTCAAACCATATCTCGATAAAGGAGACATCATCATTGA
TGGTGGTAACACCTTCTTCCAGGACACTATTCGTCGTAATCGTGAGCTTTCAGCAGAGGGCTTTAACTTCA
TCGGTACCGGTGTTTCTGGCGGTGAAGAGGGGGCGCTGAAAGGTCCTTCTATTATGCCTGGTGGCCAGAAA
GAAGCCTATGAATTGGTAGCACCGATCCTGACCAAAATCGCCGCCGTAGCTGAAGACGGTGAACCATGCGT
TACCTATATTGGTGCCGATGGCGCAGGTCACTATGTGAAGATGGTTCACAACGGTATTGAATACGGCGATA
TGCAGCTGATTGCTGAAGCCTATTCTCTGCTTAAAGGTGGCCTGAACCTCACCAACGAAGAACTGGCGCAG
ACCTTTACCGAGTGGAATAACGGTGAACTGAGCAGTTACCTGATCGACATCACCAAAGATATCTTCACCAA
AAAAGATGAAGACGGTAACTACCTGGTTGATGTGATCCTGGATGAAGCGGCTAACAAAGGTACCGGTAAAT
GGACCAGCCAGAGCGCGCTGGATCTCGGCGAACCGCTGTCGCTGATTACCGAGTCTGTGTTTGCACGTTAT
ATCTCTTCTCTGAAAGATCAGCGTGTTGCCGCATCTAAAGTTCTCTCTGGTCCGCAAGCACAGCCAGCAGG
CGACAAGGCTGAGTTCATCGAAAAAGTTCGTCGTGCGCTGTATCTGGGCAAAATCGTTTCTTACGCCCAGG
GCTTCTCTCAGCTGCGTGCTGCGTCTGAAGAGTACAACTGGGATCTGAACTACGGCGAAATCGCGAAGATT
TTCCGTGCTGGCTGCATCATCCGTGCGCAGTTCCTGCAGAAAATCACCGATGCTTATGCCGAAAATCCACA
GATCGCTAACCTGTTGCTGGCTCCGTACTTCAAGCAAATTGCCGATGACTACCAGCAGGCGCTGCGTGATG
TCGTTGCTTATGCAGTACAGAACGGTATTCCGGTTCCGACCTTCTCCGCAGCGGTTGCCTATTACGACAGC
TACCGTGCTGCTGTTCTGCCTGCGAACCTGATCCAGGCACAGCGTGACTATTTTGGTGCGCATACTTATAA
GCGTATTGATAAAGAAGGTGTGTTCCATACCGAATGGCTGGATTAA

SEQ ID NO: 15 (example O15 rfb locus nucleotide sequence - O15-EPA production strain stLMTB11738)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGCTAGCATGAGC
AAAACTAAACTAAATGTTCTTTACCTTGCAATAAGTCAGGGTGCCAATTACCTACTGCCATTATTAATTTT
TCCTTATCTTGTTAGAGTCATTGGTGTATCGAATTTTGGTGATCTGAGTTTTTCATTGATAACTATACAAG
TGTTGTTAATGGTTGTTGAATATGGTTTTGGATATAGTGGGACAAGAGAAATAGCACTAAATAACGATAAA
AAATACCATTCTGAATTTTTTTGCGGTGTGGTGCTTGCTCGTTTTATATTAATGCTAATTGCAGCTATAAT
ACTCATAATACTCTGTTTTTTTATGTTTTAACGACGTTAAGTCTTTGTTATGTGTTGGTTTTCTGTCCG
TAATTGCAGGTGTTTTCAATCCAAATTGGTTTTTGCAAGGTAAGGAAATGATGAGTGTGATGGCTGTGCTG -continued

| SEQUENCES |
| --- |
| TCACTATTTTCACGAGGCATAGCAGTCGTTGCAGTTTATCTAATTATAAAACCCGCAACGCCGATGTACAT<br>CAGTGCCTTATTATTGAGCATGCCATATATTTTGTATTCATTCTGTGGCGTTGCCTACTTACTTATTATCA<br>AGGAGATTTTTTTATGTAGGCCACCGATAAAGAAAATTCAAGTAATTTTAAAAAATGGATTTCATTTTTTT<br>TGTTCAACACTTGCGACTAGTGCATACACAATGTTGACCCCTCTTGTATTGGGTGGCGTATCTGGAAAGTT<br>TGATGTAGGCATCTTTAACTCAGCTAACATGATCAAACAAGGTTTGGCTGGACTTGCATCACCATTAGTCC<br>AAGCTTTTTATCCAAGAATTAACATTTTGCAAAGAGAGAATCCATATATTGCAAACTTAAAATCTAGAATG<br>ATTCTTAAATACTTGCTTGTTTTTTACATGGCTTTAGCAATACCATTTTTACTTTTTGCCAACCAATTATC<br>ATTATTAATATTCGGCATGAAAGGTGAAGTAATTGCAGGTGCAATGCAATTAATGACATTGCTTCCTATAT<br>TCATAGGTTTTAATACAGTTGTCGGGTTACTTGTATTAGTACCTAATGGGATGCAAAAACAGTATTTCAAA<br>TCTATTTTCCTAGGAACTATTACTTGTTTAAGCATAGTTTATCCAGCATGTAAATATTATGGAGCAACGGG<br>TGCGATTGTGAGTCTTATTGTAGCTGAAATTTTCGTTGGCATGGGAATGCTTAAACAATTCATTAAAGTAA<br>ATAAAACCGTATGTAGGCCTCATAAATTATGAATATCTCGGTAATAATATCTGTTTGGAAACGCCCAGTTC<br>AATTAGAATTGATTCTCTCTGAGCTCGATTCTCAGGCTAAAGACAATAGTCTACACCTAGAAGTAATTGTT<br>TCCGATAGTCATAGTGGTAAAGAAATTGATGATGTAGTTGCTGATAATATTCATAAAAAGAAAAATATTAA<br>TATTATCCATCAACATACTAAAAATATACTCTCCGCTAAGCGCAATTTCGGAGCATCCCTAGCCCATGGGG<br>ATTATTTAATATTTCTTGATGATGATTGTATACCCGCAAGTGGATATATATCATCGTTGCTGAACTATTTA<br>AAAAAAATGAATAGTAAAAGCGTTTTATGTGGGGAAGTTAGATTCGAAAATGAACTCATTGAGACCAGCAA<br>TTACTATCGCTACAGGAACTCTTTACACCCTAAGTTTAGTGATAGTCCTGATATCTCTATGAATGCCTGGA<br>CTTTTGTCGCAATGAATTGTGTTCTTGATAGAAAGGCATTTTCATCAGGTATAGTTTCATATAATGAAAAT<br>TTTATTGGTTATGGTTGTGAAGATCATGAGTTTGGGTGGCAACTTGAAAAAAATGACTTCAAAATTATTTT<br>TGCTGATTTTAAAATATTACATCACGAATACAGTGGCGATATAGAAGGATATACAAAAAAAATTCGTGCTA<br>CAGCACGTGATGGTATGAATGTATTAAGCAAAGTAAGGCCTGAAATGTTTTCTACTAATAAAAAATTATTC<br>CTAGTTGAGAAAATATTTAGTAAACACAAAACGTTTAGTAAAATATGCCAATCAATATTTTTCAATAAATT<br>TATTTTTAAAAAAATAATACAATTTTTAAAAAAAACAGATGCAAATAAAAAACTCTATTTCCCAATTCTTT<br>ACAGATATGTGTTGATTTCGGCATATATACATGGTATTGGAGAGCGTGGCACCTCAAAAACAGATGATTTG<br>CTTAAGAACTGGTATATATAGATGATGCTATCTTCATTTATTAAGACATTTGTATGGAAGGTAAAAAACAA<br>TGAAGTATAATGCATTGATGGCTTTTTTATTATTTTTTGTTGTTTTTTTTAGATTGTCGCTGATAATACCT<br>TTCTTATATTTGGCATTATTCCTGCATTTTTTGGTATTATGTATTTAGTGCGTAATTTTATGATTACTAT<br>GGGCAATGGATTGGTATCTATAGATCGTAAAAATTTGTTGCTGTTATCTATATTCATAATTATTTTTTTAT<br>TTTGTTTGGTTTTCGATTTGTTTCAAAAAAGCCATTCTTTTCAAAGTTATTTTACCGTTAGATTATTTATG<br>TTGTTTTTATTTTCATTTGTTCCTGCGTATTATTTAGTAAATAGATTCATAAAGGGTGACTTGAAATTAAT<br>GGAGCGAATATTAGTGTATTCTCTCTGGGTTCAAATAGTTATTTTTTTTGGTATGTATATAAGTCCAGAGT<br>TAAAAAGATTGTTATATACTTTCTTTGGTATGTCTGACTCTGTTAATCTTTGGGAACAAAATGCTAAAGTA<br>AGAGGATTTGGGTTGTCGGGTGAAATAAATTTCATGACACCATTTTTGATGATCTATATGTCATTTTTTAT<br>GATGAAAAGGCGTTATGCTTTAATTACTTTAATTTGTCTGACTCAAATCGTAAATTCTAACATGGCTGTGA<br>TTGCAGCCATTATTGGTATCGGTTGCTCTAGACTTAATATTAATATAAAAATTGCAACAGTATTGATTTTG<br>GGAGTTTTAGTTTATAGCTTAGGAGCGGTGTTCTTTCCTCGATTTTATGATGAGTTCGTTTCTGGAGATGG<br>CACAAGAACTCTGGATATCTTATTACAGCAACATGTGTTTGTTGTAGGTAATTTAGATTTTTTTAATATTA<br>TATTTGGATTACAGCAAAACATATCTTCATCAATCCCCGATATTAAACAAAGTTCGGATATGGGCTGGGTT<br>ATACTGTTTAATTACGGTGGGTTAACATTTATTACACTCTTTTTATTTTTAATCTTTACTATTTCTATTGC<br>GACATTTGGAATGACATATCAAGCAATTATATGGATGTTAATTGGGATAATTTTCAATACCAAAGGTTTAG<br>TTTTAGGATCTAACGGCTATTTCTTTCTATCTTTTATATATATGTTTTTGAATAGAGTAACACTTAGTGGA<br>CAGAGTTCAATTACTAATAAGTTAGGTCAAGTAAGTAAATAGCTTCCAGAGTATATTTGTCAATGATTTGA<br>GGTTCGGTTATTATGTTTTCATCTAAAACACTGTTAATTACTGGTGGTACTGGCTCTTTCGGGAATGCTGT<br>ATTAAATAGATTTCTTGATACAGATATTGCAGAAATCCGTATATTTAGTCGTGATGAAAAAAAACAAGATG<br>ATATGCGGAAAAAATACAATAATCAAAAATTAAAGTTCTATATTGGTGATGTCAGAGATTACCGTAGTATT<br>TTGAATGCGACTCGCGGTGTTGATTTTATATATCATGCAGCGGCACTTAAGCAAGTTCCATCATGTGAATT<br>TCATCCTATGGAAGCCGTTAAAACTAATATCCTTGGTACGGAAAATGTTCTTGAAGCAGCTATAGCGAATG<br>AAGTGAAGAGGGTTGTATGCCTAAGTACTGATAAAGCTGTATACCCGATTAACGCAATGGGTATTTCAAAA<br>GCTATGATGGAAAAGGTCATGGTCGCGAAATCCCGTAATGTTGATCGCAATAAAACAGTAATATGTGGTAC<br>CCGTTATGGGAATGTTATGGCATCTCGCGGTTCAGTTATTCCATTATTTGTTGATCTTATTAGAGCGGGCA<br>AGCCACTCACAATAACTGATCCTAATATGACCCGCTTTATGATGACTCTTGAGGATGCGGTAGATTTAGTT<br>CTTTATGCGTTTGAACATGGTAATAATGGTGATATCTTTGTGCAAAAAGCACCTGCAGCAACTATTGACAC<br>ATTAGCTATTGCTTTAAAGGAATTACTAAATGTTCCTGACCATCCGGTAAATGTCATTGGAACGCGTCATG<br>GCGAGAAATTATATGAAGCTCTACTTAGTCGTGAGGAAATGATCGCTGCTATAGATATGGGCGATTATTAC<br>CGTGTCCCGCCAGATCTTCGTGACCTTAATTATGGCAAATATGTTGAGCAAGGTGATAGCCGAATATCTGA<br>AATAGAAGATTATAACTCTCATAATACTCAACGGTTAGATGTTGAAGGCATGAAAGAGCTCTTGCTAAAAT<br>TAGCCTTTATTCGAGCAATTCGTGCTGGTGAAAAATATAATCTGGATTCATGATATGAAAATATTAGTTAC<br>TGGTGCAAATGGTTTTATTGGTCGTAATTTATGTTTGAGGCTTGAGGAACTTGGTTATAAAGATCTTATTA<br>GAATTGATCGAGAATCAACGAAGCAAGATCTTGAACAAGGCTTACAGGATGCCGATTTTATTTATCACTTA<br>GCTGGTATCAATAGACCTAAGACTGATGATGAGTTTATTTCTGGAAACAGTGATTTAACAAAGCATATAGT<br>TGAGTATCTCCTTTCTATTGGTAAGAATACACCAATTATGCTAAGTTCTTCGATACAAGCTGAACTTAATA<br>ATGCTTATGGGGTTAGCAAAGCTGTAGCTGAAAGCTATGTCGAAAAATATGCTGCTGCTAGTGGTTCTTCG<br>TATTATATTTTCAGATATCCAAACGTTTTTGGTAAATGGTGTAAGCCAAACTATAATTCTTTTATAGCAAC<br>TTTTTGCTACAATATTTCCAATGATATTGAGATTACTATCAATGATGCAGCAGCGCCAGTCAATCTGGTCT<br>ATATTGATGATGTTTGTACTGATGCTATAGCTCTTCTCTCTGGGACGGTTGAAAGTGGATATAAAGTTGTT<br>GCACCAATTTATTCAACAACAGTTGGTGAAGTTGCAGAATTAATTTATAGCTTCAAAAATAGCCGTTCCAC<br>CCTGATCACAGAGGCTGTCGGGGCGGGATTTACCCGTGCATTGTATTCTACATGGCTGAGTTATTTACCAG<br>CAGAGAAGTTTGCGTACAAGGTACCTTTTTATGGGGATGCCCGCGGAGTCTTTTGTGAGATGTTGAAAACG<br>CCTTCAGCGGGGCAGTTTTCATTTTTTACTGCTCACCCTGGTATTACGCGTGGCGGACATTACCATCACAG<br>TAAAAATGAGAAGTTTTTGGTCATTCGAGGTCAGGCATGCTTTAAATTTGAACATGTGATTACCGGTGAGC<br>GATATGAACTGAAAGTTTCATCGGGTGAGTTTAAGATTGTTGAAACAGTTCCTGGTTGGACACATGACATT<br>ACAAATATTGGAACTGATGAATTAATAGTCATGCTCTGGGCAAATGAAATTTTCAACCGTGATGAGCCCGA<br>TACTATTGCGAGACCTCTATAATGAAAAAATTAAAAGTTATGTCTGTTGTTGGAACCCGTCCTGAGATTAT<br>CCGTTTGTCGAGGGTTCTTGCTAAGTTTGATGAATACTGCGAGCATATTATTGTCCATACTGGTCAAAATT<br>ATGATTACGAATTAAATGAAGTGTTCTTCAATGACTTGGGTGTTCGAAAACCTGATTATTTTTTAAATGCA<br>GCGGGTAAAAATGCGGCGGAAACCATTGGTCAGGTTATTATTAAGGTAGATGAAGTATTAGAAATCGAAAA |

-continued

SEQUENCES

ACCTGAAGCAATACTGGTATTGGGCGATACGAATTCATGTATTTCTGCCATTCCGGCCAAACGCCGTAAAG
TGCCTATATTTCATATGGAAGCAGGTAACCGTTGTTTCGATCAACGCGTGCCTGAAGAAACCAACAGACGT
ATTGTTGACCATACGGCTGATATCAATATGACCTACAGTGATATTGCTCGTGAATATCTCTTGGCTGAAGG
TATCCCAGCTGATCGGATCATAAAAACTGGTAGCCCTATGTTTGAGGTTCTTTCATATTATATGCCCCAAA
TTGATGGTTCAGATGTGCTATCGCGTTTGAATCTACAGTCTGGTGAGTTTTTTGTAGTAAGTGCGCATCGT
GAAGAGAATGTTGATTCTCCAAAACAGCTCGTAAAGCTTGCGAACATTCTAAATACTGTTGCTGAAAAATA
TAATCTTCCAGTTATTGTCTCCACACACCCAAGGACACGTAACCGAATCCGTGAGCAAGGAATTGAATTTC
ATTCAAATATAAATCTACTGAAACCATTGGGTTTCCATGATTATAACCACTTGCAGAAGAACTCACGAGCT
GTGCTTTCAGATAGCGGTACTATCACTGAAGAGTCATCCATCATGAATTTCCCAGCGGTAAACATCCGGGA
AGCGCATGAGCGTCCGGAAGGCTTTGAGGAAGCATCCGTCATGATGGTGGGGTTAGAGTGTGAACGCGTAT
TACAAGCGCTGGATATTCTGGCAACACAACCGCGAGGTGAAGTCCGTCTTTTACGTCAGGTTAGTGATTAC
AGCATGCCAAATGTGTCGGATAAAGTTGTCAGAATTGTTCACTCTTACACAGATTATGTTAAGAGAGTCGT
CTGGAAAGAATATTGATGAAACTTGCTTTAATCATAGATGATTACCTGCCCAACAGTACTCGTGTTGGTGC
AAAAATGTTTCATGAACTTGCTCAAGAATTTATCCAGCGTGGGCACGATGTTACGGTAATTACTCCTGGTA
CGGGCATGCAAGAAGAGATTTCTTTTGATACCTTTCAGGGGGTAAAAACATGGCGTTTTAAAAGCGGGCCG
CTCAAGGATGTAAGTAAAATTCAGCGAGCGGTCAATGAAACGCTTTTGTCCTATCGGGCGTGGAAAGCCAT
CAAAAAATGGGTAAAAAAAGAGACCTTTGAGGGGGTGATTTATTATTCACCTTCCATATTCTGGGGGCCTT
TAGTTAAAAAAATTAAAGCTCGTTGCCAATGTCCTGCTTATCTTATTTTAAGAGATATGTTTCCACAATGG
GTAATTGATGCAGGAATGCTTAATGCTGGTTCCCCAATAGAACGCTACTTTCGTCTTTTTGAAAAAATATC
TTATCGTCAGGCAAATCGTATTGGACTTATGTCTGATAAGAATCTTGATGTTTTTCGGAAAGATAATAAAG
GCTATCCGTGCGAAGTTTTGCGTAATTGGGCATCCCTAACACCAACGATCATACCCAAGGATTATATACCA
CTACGTAAGCGACTTGGCCTAGAGGATAAAACCATTTTCTTCTATGGTGGAAACATAGGTCATGCACAGGA
CATGACAAACTTGATGCGACTTGTGAGAAACATGGCAGCATATCCTCAAGCTCATTTCCTATTTATTGGCC
AGGGGGATGAAGTTGAATTAATTAATTCATTAGCATCTGAGTGGGCATTGACGAATTTCACCTATTTGCCC
TCGGTTAACCAAGATGAATTTAAGTTCATTTTGTCGGAAATGGATATCGGCTTGTTTTCTCTTTCCGCTAG
ACACTCTTCCCATAATTTTCCTGGTAAGTTATTAGGCTATATGGTTCAGTCGCTACCTATTTTAGGTAGCG
TAAATGCCGGAAATGATTTGCTCGACATTGTCAATCAAAATAATGCGGGATTAATCCATGTCAATGGTGAG
GACGATAAATTATGTCAATCTGCGCTATTAATGTTGCATGATATTGATGTGCGCCGGCAACTTGGTTCGGG
GGCGAATATATTGTTGAAAGAACAATTCTCCGTTGAGTCTGCGGCACAGACGATAGAAATGAGGTTGGAGG
CATGCAATGCGATTAATTGATAATGACCAACTCGACGAATTATATGATCAAGCCGGGCAATCGGAACGTTT
ACGTTCCCACCTTATGATGCACGGCTCGCATCAAGAAAAGGTACAGCGTTTACTTATTGCATTAGTAAAGG
GCAGCTATGTTGAACCGCATTATCACGAACTTCCTCATCAGTGGGAAATGTTCATTGTTATGGAGGGGCAA
CTTCAGGTTTGTTTGTATGGTAGAAATGGTGAGGTTATAAAGCAATTTATAGCAGGAGATAATACTGGAAT
GAGCATTGTGGAGTTTTCTCCGGGCGATATACACAGTGTCGAATGCCTATCTCCGCGTGCTCTTATGGTGG
AAGTTAAGGAGGGGCCATTTGACCCTTCTTTTGCAAAATCGTTCGTGTGAGCGGCCGCGAGCTCGTCGACT
CGAGGATCCGTGTAGGCTGGAGCTGCTTCGAAGTTCCTATACTTTCTAGAGAATAGGAACTTCGGAATAGG
AACTAAGGAGGATATTCATATGGATAAAGCCGTAAGCATATAAGCATGGATAAGCTATTTATACTTTAATA
AGTACTTTGTATACTTATTTGCGAACATTCCAGGCCGCGAGCATTCAGCGCGGTGATCACACCTGACAGGA
GTATGTAATGTCCAAGCAACAGATCGGCGTAGTCGGTATGGCAGTGATGGGACGCAACCTTGCGCTCAACA
TCGAAAGCCGTGGTTATACCGTCTCTATTTTCAACCGTTCCCGTGAGAAGACGGAAGAAGTGATTGCCGAA
AATCCAGGCAAGAAACTGGTTCCTTACTATACGGTGAAAGAGTTTGTCGAATCTCTGGAAACGCCTCGTCG
CATCCTGTTAATGGTGAAAGCAGGTGCAGGCACGGATGCTGCTATTGATTCCCTCAAACCATATCTCGATA
AAGGAGACATCATCATTGATGGTGGTAACACCTTCTTCCAGGACACTATTCGTCGTAATCGTGAGCTTTCA
GCAGAGGGCTTTAACTTCATCGGTACCGGTGTTTCTGGCGGTGAAGAGGGGGCGCTGAAAGGTCCTTCTAT
TATGCCTGGTGGCCAGAAAGAAGCCTATGAATTGGTAGCACCGATCCTGACCAAAATCGCCGCCGTAGCTG
AAGACGGTGAACCATGCGTTACCTATATTGGTGCCGATGGCGCAGGTCACTATGTGAAGATGGTTCACAAC
GGTATTGAATACGGCGATATGCAGCTGATTGCTGAAGCCTATTCTCTGCTTAAAGGTGGCCTGAACCTCAC
CAACGAAGAACTGGCGCAGACCTTTACCGAGTGGAATAACGGTGAACTGAGCAGTTACCTGATCGACATCA
CCAAAGATATCTTCACCAAAAAAGATGAAGACGGTAACTACCTGGTTGATGTGATCCTGGATGAAGCGGCT
AACAAAGGTACCGGTAAATGGACCAGCCAGAGCGCGCTGGATCTCGGCGAACCGCTGTCGCTGATTACCGA
GTCTGTGTTTGCACGTTATATCTCTTCTCTGAAAGATCAGCGTGTTGCCGCATCTAAAGTTCTCTCTGGTC
CGCAAGCACAGCCAGCAGGCGACAAGGCTGAGTTCATCGAAAAAGTTCGTCGTGCGCTGTATCTGGGCAAA
ATCGTTTCTTACGCCCAGGGCTTCTCTCAGCTGCGTGCTGCGTCTGAAGAGTACAACTGGGATCTGAACTA
CGGCGAAATCGCGAAGATTTTCCGTGCTGGCTGCATCATCCGTGCGCAGTTCCTGCAGAAAATCACCGATG
CTTATGCCGAAAATCCACAGATCGCTAACCTGTTGCTGGCTCCGTACTTCAAGCAAATTGCCGATGACTAC
CAGCAGGCGCTGCGTGATGTCGTTGCTTATGCAGTACAGAACGGTATTCCGGTTCCGACCTTCTCCGCAGC
GGTTGCCTATTACGACAGCTACCGTGCTGCTGTTCTGCCTGCGAACCTGATCCAGGCACAGCGTGACTATT
TTGGTGCGCATACTTATAAGCGTATTGATAAAGAAGGTGTGTTCCATACCGAATGGCTGGATTAA

SEQ ID NO: 16 (example O16 rfb locus nucleotide sequence -O16-EPA production strain stLMTB11739)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC -continued

| SEQUENCES |
| --- |
| ATCATAGGCATGCATGCAGTGCTCTGGTAGCTGTAAAGCCAGGGGCGGTAGCGTGCATTAATACCTCTATT<br>AATCAAACTGAGAGCCGCTTATTTCACAGCATGCTCTGAAGTAATATGGAATAAATTAAGTGAAAATACTT<br>GTTACTGGTGGCGCAGGATTTATTGGTTCAGCTGTAGTTCGTCACATTATAAATAATACGCAGGATAGTGT<br>TGTTAATGTCGATAAATTAACGTACGCCGGAAACCGGGAATCACTTGCTGATGTTTCTGATTCTGAACGCT<br>ATGTTTTTGAACATGCGGATATTTGCGATGCACCTGCAATGGCACGGATTTTTGCTCAGCATCAGCCGGAT<br>GCAGTGATGCACCTGGCTGCTGAAAGCCATGTTGACCGTTCAATTACAGGCCCTGCGGCATTTATTGAAAC<br>CAATATTGTTGGTACTTATGTCCTTTTGGAAGCCGCTCGCAATTACTGGTCTGCTCTTGATAGCGACAAGA<br>AAAATAGCTTCCGTTTTCATCATATTTCTACTGACGAAGTCTATGGTGATTTGCCTCATCCAGATGAAGTA<br>AATAATACAGAAGAATTACCCTTATTTACTGAGACGACAGCTTACGCGCCAAGCAGCCCTTATTCCGCATC<br>CAAAGCATCCAGCGATCATTTAGTCCGCGCGTGGAAACGTACATATGGTTTACCGACAATTGTGACTAATT<br>GCTCGAACAACTATGGTCCTTATCATTTCCCGGAAAAGCTTATTCCACTGGTTATTCTTAATGCACTGGAA<br>GGTAAGGCATTACCTATTTATGGCAAAGGAGATCAGATCCGCGACTGGTTGTATGTTGAAGATCATGCGCG<br>TGCGTTATATACCGTCGTAACCGAAGGTAAAGCGGGTGAAACTTATAACATTGGTGGGCACAACGAAAAGA<br>AAAACATCGATGTAGTGCTCACTATTTGTGATTTGCTGGATGAGATTGTACCGAAAGAGAAATCTTATCGT<br>GAGCAAATCACTTATGTTGCTGATCGTCCGGGACACGATCGCCGCTATGCTATTGATGCTGAGAAGATTGG<br>TCGCGCATTGGGATGGAAACCACAGGAAACGTTTGAGAGCGGGATTCGTAAAACGGTGGAATGGTACCTGT<br>CCAATACAAAATGGGTTGATAATGTGAAAAGTGGTGCCTATCAATCGTGGATTGAACAGAACTATGAGGGC<br>CGCCAGTAATGAATATCCTCCTTTTTGGCAAAACAGGGCAGGTAGGTTGGGAACTACAGCGTGCTCTGGCA<br>CCTTTGGGTAATTTGATTGCTTTTGATGTTCACTCTACTGATTATTGCGGTGATTTTAGTAATCCTGAAGG<br>TGTAGCTGAAACCGTAAGAAGCATTCGGCCGGATATTATTGTCAATGCAGCCGCTCACACCGCAGTAGACA<br>AAGCAGAATCAGAACCGGAGTTTGCACAATTAATTAACGCAACAAGTGTCGAAGCGATTGCGAAAGCAGCA<br>AATGAAGTTGGAGCCTGGGTTATCCATTACTCGACTGATTACGTCTTCCCTGGAAATGGCGATATGCCATG<br>GCTGGAGACGGATGCAACCGCACCACTAAATGTTTACGGTGAAACCAAGTTAGCCGGAGAAAAAGCGTTAC<br>AGGAATATTGCGCGAAGCATCTTATTTTCCGGACCAGCTGGGTCTATGCAGGAAAAGGAAATAACTTCGCC<br>AAAACGATGTTACGTCTGGCAAAAGAGCGTGAAGAATTAGCGGTTATTAACGATCAGTTTGGTGCGCCAAC<br>AGGTGCTGAACTGCTGGCTGATTGTACAGCACATGCCATTCGTGTCGCACTGAATAAACCGGATGTCGCAG<br>GCTTGTACCATTTGGTAGCCAGTGGTACCACAACCTGGTACGATTATGCTGCGCTGGTTTTTGAAGAGGCG<br>CGCAAAGCAGGCATTCCCCTTGCACTCAACAAGCTCAACGCAGTACCAACAACAGCCTATCCTACACCAGC<br>TCGTCGTCCACATAACTCTCGCCTTAATACAGAAAAATTTCAGCAGAACTTTGCGCTTGTCTTGCCTGACT<br>GGCAGGTTGGCGTGAAACGAATGCTCAATGAATTATTTACGACTACAGCAATTTAATAGTTTTTGCATCTT<br>GTTCGTGATGGTGGAGCAAGATGAATTAAAAGGAATGATGAAATGAAAATGCGTAAAGGTATTATTTTAGC<br>GGGTGGTTCTGGTACACGTCTTTATCCTGTGACTATGGCTGTCAGTAAACAGCTATTACCTATTTATGATA<br>AACCGATGATCTATTACCCGCTCTCTACACTGATGTTGGCGGGTATTCGCGATATTTTGATTATCAGTACA<br>CCTCAGGATACTCCTCGTTTTCAACAATTGCTGGGTGACGGTAGCCAGTGGGGCCTGAATCTTCAGTACAA<br>AGTGCAACCTAGCCCAGATGGCCTCGCGCAGGCATTTATCATCGGTGAAGAGTTTATTGGTGGTGATGATT<br>GTGCTTTGGTTCTTGGTGATAATATCTTTTACGGTCACGATCTGCCGAAGCTAATGGAGGCCGCTGTTAAC<br>AAAGAAAGTGGTGCAACGGTATTTGCCTATCACGTTAATGATCCAGAACGCTATGGTGTCGTTGAGTTTGA<br>TAAAAACGGTACGGCAATCAGTCTGGAAGAAAAACCGTTAGAACCAAAGAGTAATTACGCCGTTACAGGTC<br>TGTACTTTTATGATAACGACGTGGTTCAGATGGCGAAAAACTTGAAGCCGTCTGCACGTGGTGAGTTAGAA<br>ATTACAGATATTAACCGTATTTATCTTGAGCAGGGACGTCTGTCTGTCGCGATGATGGGGCGTGGCTACGC<br>GTGGCTGGACACGGGGACTCATCAGAGTCTGATAGAAGCAAGTAATTTTATTGCGACAATTGAAGAGCGCC<br>AGGGATTGAAGGTTTCCTGTCCTGAAGAGATTGCATTTCGTAAAGGTTTTATTGATGTTGAGCAAGTAAGA<br>AAATTAGCTGTACCACTAATAAAGAATAATTATGGGCAGTATCTTTATAAAATGACGAAGGATTCAAATTA<br>ATGAATGTGATTAGAACTGAAATTGAAGATGTGCTAATTCTGGAGCCAAGAGTATTTGGTGATGATAGAGG<br>TTTCTTTTATGAGAGCTTTAATCAATCAGCATTTGAACATATTCTAGGCTATCCGGTCAGCTTTGTTCAAG<br>ACAATCACTCACGTTCATCAAAAAATGTACTCAGAGGCCTTCACTTTCAACGCGGCGAGTACGCACAAGAT<br>AAACTTGTACGCTGCACTCATGGAGCAGTTTTTGATGTTGCTGTTGATATTCGACCCAATTCGGTATCCTT<br>TGGTAAATGGGTTGGTGTTCTGCTTTCAGCTGATAATAAGCAGCAGTTGTGGATACCAAAAGGGTTTGCTC<br>ATGGCTTTTTGGTTCTGTCTGATATCGCTGAATTTCAATATAAAACTACAAACTATTATCATCCTGAAAGC<br>GATTGTGGAATATGTTGGAATGATGAACGCATTGCAATTGATTGGCCCCAAACATCAGGGTTAATCCTTTC<br>GCCAAAAGATGAAAGGCTCTTTACGTTAGATGAGCTTATCAGATTAAAATTAATTGCATGAATACGAATAA<br>ATTATCTTTAAGAAGAAACGTTATATATCTGGCTGTCGTTCAAGGTAGCAATTATCTTTTACCATTGCTTA<br>CATTTCCATATCTTGTAAGAACACTTGGTCCTGAAAATTTCGGTATATTCGGTTTTTGCCAAGCGACTATG<br>CTATATATGATAATGTTTGTTGAATATGGTTTCAATCTCACAGCAACTCAGAGTATTGCCAAAGCAGCAGA<br>TAGTAAAGATAAAGTAACGTCTATTTTTTGGGCGGTGATATTTTCAAAAATAGTTCTTATCGTCATTACAT<br>TGATTTTCTTAACGTCGATGACCTTGCTTGTTCCTGAATATAACAAGCATGCCGTAATTATATGGTCGTTT<br>GTTCCTGCATTAGTCGGGAATTTAATCTACCCTATCTGGCTGTTTCAGGGAAAAGAAAAAATGAAATGGCT<br>GACTTTAAGTAGTATTTTATCCCGCTTGGCTATTATCCCTCTAACATTTATTTTTGTGAACACAAAGTCAG<br>ATATAGCAATTGCCGGTTTTATTCAGTCAAGTGCAAATCTGGTTGCTGGAATTATTGCACTAGCTATCGTT<br>GTTCATGAAGGTTGGATTGGTAAAGTTACGCTATCATTACATAATGTGCGTCGATCTTTAGCAGACGGTTT<br>TCATGTTTTTATTTCCACATCTGCTATTAGTTTATATTCTACGGGAATAGTTATTATCCTGGGATTTATAT<br>CTGGACCAACGTCCGTAGGGAATTTTAATGCGGCCAATACTATAAGAAACGCGCTTCAAGGGCTATTAAAT<br>CCTATCACCCAAGCAATATACCCAAGAATATCAAGTACGCTTGTTCTTAATCGTGTGAAGGGTGTGATTTT<br>AATTAAAAAATCATTGACCTGCTTGAGTTTGATTGGTGGTGCTTTTTCATTAATTCTGCTCTTGGGTGCAT<br>CTATACTAGTAAAAATAAGTATAGGGCCGGGATATGATAATGCAGTGATTGTGCTAATGATTATATCGCCT<br>CTGCCTTTTCTTATTTCATTAAGTAATGTCTATGGCATTCAAGTTATGCTGACCCATAATTATAAGAAAGA<br>ATTCAGTAAGATTTTAATCGCTGCGGGTTTGTTGAGTTTGTTGTTGATTTTTCCGCTAACAACTCTTTTTA<br>AAGAGATTGGTGCAGCAATAACATTGCTTGCAACAGAGTGCTTAGTTACGTCACTCATGCTGATGTTCGTA<br>AGAAATAATAAATTACTGGTTTGCTGAGGATTTTATGTACGATTATATCATTGTTGGTTCTGGTTTGTTTG<br>GTGCCGTTTGTGCGAATGAGTTAAAAAAGCTAAACAAAAAAGTTTTAGTGATTGAGAAAAGAAATCATATC<br>GGTGGAAATGCGTACACAGAGGACTGTGAGGGTATCCAGATTCATAAATATGGTGCACATATTTTTCATAC<br>CAATGATAAATATATATGGGATTACGTTAATGATTTAGTAGAATTTAATCGTTTTACTAATTCTCCACTGG<br>CGATTTATAAAGACAAATTATTCAACCTTCCTTTTAATATGAATACTTTCCACCAAATGTGGGGAGTTAAA<br>GATCCTCAAGAAGCTCAAAATATCATTAATGCTCAGAAAAAAAAGTATGGTGACAAGGTACCTGAAAATTT<br>GGAGGAGCAGGCGATTTCATTAGTTGGGGAGGACTTATACCAAGCATTGATAAAGGGTTATACGGAGAAGC<br>AGTGGGGAAGAAGTGCAAAAGAATTGCCTGCATTTATTATTAAGCGAATCCCAGTGAGATTTACGTTTGAT<br>AACAATTATTTTTCCGATCGCTATCAAGGTATTCCGGTGGGAGGCTACACTAAGCTTATTGAAAAAATGCT |

-continued

SEQUENCES

TGAAGGTGTGGACGTAAAATTAGGCATTGATTTTTTGAAAGACAAAGATTCTCTAGCGAGTAAAGCCCATA
GAATCATCTACACTGGACCCATTGATCAGTACTTCGACTATAGGTTTGGAGCGTTAGAATATCGCTCTTTA
AAATTTGAGACGGAACGCCATGAATTTCCAAACTTCCAAGGGAATGCAGTAATAAATTTCACTGATGCTAA
TGTACCATATACCAGAATAATTGAGCATAAACATTTTGACTATGTTGAGACAAAGCATACGGTTGTTACAA
AAGAATATCCATTAGAGTGGAAAGTTGGCGACGAACCCTACTATCCAGTTAATGATAATAAAAACATGGAG
CTTTTTAAGAAATATAGAGAGTTAGCTAGCAGAGAAGACAAGGTTATATTTGGCGGGCGTTTGGCCGAGTA
TAAATATTATGATATGCATCAAGTGATATCTGCCGCTCTTTATCAAGTGAAAAATATAATGAGTACGGATT
AATGATCTATCTTGTAATTAGTGTCTTTCTCATTACAGCATTTATCTGTTTATATCTTAAGAAGGATATAT
TTTATCCAGCCGTATGCGTTAATATCATCTTCGCACTGGTCTTATTGGGATATGAAATAACGTCAGATATA
TATGCTTTTCAGTTAAATGACGCTACGTTGATTTTTCTACTTTGCAATGTTTTGACATTTACCCTGTCATG
TTTATTGACGGAAAGTGTATTAGATCTAAATATCAGAAAAGTCAATAATGCTATTTATAGCATACCATCGA
AGAAAGTGCATAATGTAGGCTTGTTAGTTATTTCTTTTTCGATGATATATATATGCATGAGGTTAAGTAAC
TACCAGTTCGGGACTAGCTTACTTAGCTATATGAATTTGATAAGAGATGCTGATGTTGAAGACACATCAAG
AAATTTCTCAGCATACATGCAGCCAATCATTCTAACTACTTTTGCTTTATTTATTTGGTCTAAAAAATTTA
CTAATACAAAGGTAAGTAAAACATTTACTTTACTTGTTTTTATTGTATTCATCTTTGCAATTATACTGAAT
ACTGGTAAGCAAATTGTCTTTATGGTTATCATCTCTTATGCATTCATCGTAGGTGTTAATAGAGTAAAACA
TTATGTTTATCTTATTACAGCTGTAGGTGTTCTATTCTCCTTGTATATGCTCTTTTTACGTGGACTGCCTG
GGGGGATGGCATATTATCTATCCATGTATTTGGTCAGCCCTATAATCGCGTTTCAGGAGTTTTATTTTCAG
CAAGTATCTAACTCTGCCAGTTCTCATGTCTTTTGGTTTTTTGAAAGGCTGATGGGGCTATTAACAGGTGG
AGTCTCTATGTCGTTGCATAAAGAATTTGTGTGGGTGGGTTTGCCAACAAATGTTTATACTGCTTTTTCGG
ATTATGTTTATATTTCCGCGGAGCTAAGCTATTTGATGATGGTTATTCATGGCTGTATTTCAGGTGTTTTA
TGGAGATTGTCTCGAAATTACATATCTGTGAAAATATTTTATTCATATTTTATTTATACCTTTTCTTTCAT
TTTTTATCATGAAAGCTTCATGACTAATATTAGCAGTTGGATACAAATAACTCTTTGTATCATAGTATTCT
CTCAATTTCTTAAGGCCCAGAAAATAAAGTGAAAATGTATTTTTTGAATGATTTAAATTTCTCTAGACGCG
ATGCTGGATTTAAAGCAAGAAAAGATGCACTGGACATTGCTTCAGATTATGAAAACATTTCTGTTGTTAAC
ATTCCTCTATGGGGTGGAGTAGTCCAGAGAATTATTAGTTCTGTTAAGCTTAGTACATTTCTCTGCGGTCT
TGAAAATAAAGATGTTTTAATTTTCAATTTCCCGATGGCCAAACCATTTTGGCATATATTGTCATTCTTTC
ACCGCCTTCTAAAATTTAGAATAGTACCTCTGATTCATGATATTGATGAATTAAGAGGAGGAGGGGGTAGT
GATTCTGTGCGGCTTGCTACCTGTGATATGGTCATAAGTCACAATCCACAAATGACAAAGTACCTTAGTAA
ATATATGTCTCAGGATAAAATCAAAGACATAAAAATATTTGATTACCTCGTCTCATCTGATGTGGAGCATC
GAGATGTTACGGATAAGCAACGAGGGGTCATATATGCTGGCAACCTTTCTAGGCATAAATGTTCTTTCATA
TATACTGAAGGATGCGATTTTACTCTCTTTGGTGTCAACTATGAAAATAAAGATAATCCTAAATATCTTGG
AAGTTTTGATGCTCAATCTCCGGAAAAGATTAACCTCCCAGGCATGCAATTTGGACTCATTTGGGATGGAG
ATTCTGTCGAAACCTGTAGTGGTGCCTTTGGCGACTATTTAAAGTTTAATAACCCTCATAAGACATCTCTT
TATCTTTCAATGGAACTTCCAGTATTTATATGGGATAAAGCCGCCCTTGCGGATTTCATTGTAGATAATAG
AATAGGATATGCAGTGGGATCAATCAAAGAAATGCAAGAGATTGTTGACTCCATGACAATAGAAACTTATA
AGCAAATTAGTGAGAATACAAAAATTATTTCTCAGAAAATTCGAACAGGAAGTTACTTCAGGGATGTTCTT
GAAGAGGTGATCGATGATCTTAAAACTCGCTAAACGATATGGTCTCTGTGGTTTTATTCGGCTTGTTAGAG
ATGTCTTATTGACTCGTGTATTTTACCGGAACTGTAGAATTATTCGATTTCCCTGCTATATTCGCAATGAT
GGTAGCATTAATTTTGGTGAAAATTTCACAAGTGGAGTCGGTCTCAGGCTGGATGCATTTGGACGTGGCGT
GATTTTTTTTTCCGATAATGTGCAAGTTAACGACTATGTTCATATCGCCTCAATTGAGAGCGTTACGATAG
GTCGGGATACGCTTATTGCAAGTAAAGTATTTATTACCGATCATAATCACGGTTCCTTTAAGCACTCTGAT
CCAATGAGTTCGCCAAATATACCTCCAGACATGCGCACGTTGGAATCTTCAGCTGTTGTAATTGGCCAGAG
GGTTTGGTTGGGTGAGAATGTGACGGTTTTGCCTGGAACAATTATTGGTAATGGAGTCGTAGTCGGCGCCA
ATTCTGTTGTTAGAGGTTCTATTCCCGAAAATACTGTCATTGCGGGAGTACCAGCAAAAATCATAAAGAAA
TACAATCATGAGACCAAATTATGGGAAAAAGCATAGTCGTTGTTTCTGCGGTCAATTTTACCACTGGCGGT
CCATTTACCATTTTGAAAAAATTTTTGGCAGCAACTAATAATAAAGAAAATGTCAGTTTTATCGCATTAGT
CCATTCTGCTAAAGAGTTAAAAGAAAGTTATCCATGGGTTAAATTCATTGAGTTTCCTGAGGTTAAAGGGT
CGTGGCTAAAACGTTTGCACTTTGAATATGTAGTTTGTAAAAAACTTTCAAAAGAGCTGAATGCTACGCAT
TGGATTTGTCTGCATGATATTACGGCCAATGTCGTCACTAAAAAAAGATATGTGTATTGTCATAACCCTGC
CCCTTTTTATAAAGGAATTTTATTCCGTGAAATTCTTATGGAGCCTAGCTTTTTCTTATTTAAAATGCTAT
ACGGGCTGATATATAAAATAAACATTAAAAAAAATACTGCAGTGTTTGTTCAACAATTCTGGATGAAAGAA
AAATTTATCAAGAAATATTCTATAAATAACATCATTGTCAGTCGGCCAGAAATTAAATTATCTGATAAAAG
CCAACTTACTGATGATGATTCTCAATTTAAGAATAACCCTTCTGAGTTGACAATATTTTACCCTGCTGTTC
CACGAGTATTTAAAAATTACGAGCTTATTATTAGTGCAGCAAGGAAATTGAAAGAACAATCCAATATTAAA
TTTCTGCTTACTATCAGTGGTACAGAAAATGCGTATGCAAAATATATTATCAGTCTTGCAGAAGGACTGGA
TAATGTTCATTTCCTCGGGTACTTGGATAAAGAAAAAATCGATCATTGTTATAATATTTCAGATATAGTTT
GTTTTCCCTCTAGGTTAGAAACATGGGGATTGCCGTTGTCTGAGGCTAAAGAGCGAGGTAAGTGGGTATTA
GCATCAGATTTCCCATTTACTAGAGAAACTCTTGGTAGTTATGAAAAGAAAGCTTTTTTTGATTCTAATAA
CGATGACATGTTAGTTAAACTTATTATTGACTTCAAAAAAGGTAACCTCAAAAAAGATATCTCTGATGCAA
ATTTCATTTATCGTAATGAAAATGTATTAGTTGGGTTTGATGAACTAGTTAATTTTATTACTGAAGAACAT
TGAAATGGTATATATAATAATCGTTTCCCACGGACATGAAGACTACATCAAAAAATTACTCGAAAATCTTA
ATGCTGACGATGAGCACTACAAGATTATCGTACGCGACAACAAAGACTCTCTATTATTGAAACAAATATGC
CAGCATTATGCAGGCCTGGACTATATTAGTGGAGGTGTATACGGCTTTGGTCATAATAATAATATTGCGGT
GGCGTATGTAAAGGAAAAATATAGACCCGCAGATGATGATTACATTTTGTTTTTGAATCCCGATATCATCA
TGAAGCATGATGATTTGCTGACATATATTAAATATGTCGAAAGTAAGCGTTATGCTTTTAGTACATTATGC
CTGTTCCGAGATGAAGCGAAATCTTTACATGATTATTCCGTAAGAAAATTTCCTGTGCTTTCTGATTTTAT
TGTGTCATTTATGTTAGGGATTAATAAAACAAAAATTCCTAAAGAAAGTATCTATTCTGATACGGTTGTTG
ATTGGTGCGCAGGATCATTTATGCTGGTACGTTTTTCAGATTTTGTGCGTGTAAATGGCTTCGATCAAGGT
TACTTTATGTACTGTGAAGATATTGACCTGTGCTTGAGGCTTAGCCTGGCTGGTGTCAGACTTCATTATGT
TCCCGCTTTTCATGCGATACATTATGCTCATCATGACAATCGAAGTTTTTTTTCAAAAGCCTTCAGATGGC
ACTTAAAAAGTACTTTTAGATATTTAGCCAGAAAACGTATTTTATCAAATCGCAACTTTGATCGAATTTCA
TCAGTTTTTCACCCGTAAGAGCTCGGTACCCGGGCCTAGGGTGTAGGCTGGAGCTGCTTCGAAGTTCCTAT
ACTTTCTAGAGAATAGGAACTTCGGAATAGGAACTAAGGAGGATATTCATATCCGTCGACGGCGGCCGCCC
TGCAGGCATGCAAGCTTGATCCATATGGATCGCTAGCTTAATTAAATAAAGCCGTAAGCATATAAGCATGG
ATAAGCTATTTATACTTTAATAAGTACTTTGTATACTTATTTGCGAACATTCCAGGCCGCGAGCATTCAGC
GCGGTGATCACACCTGACAGGAGTATGTAATGTCCAAGCAACAGATCGGCGTAGTCGGTATGGCAGTGATG

-continued

SEQUENCES

GGACGCAACCTTGCGCTCAACATCGAAAGCCGTGGTTATACCGTCTCTATTTTCAACCGTTCCCGTGAGAA
GACGGAAGAAGTGATTGCCGAAAATCCAGGCAAGAAACTGGTTCCTTACTATACGGTGAAAGAGTTTGTCG
AATCTCTGGAAACGCCTCGTCGCATCCTGTTAATGGTGAAAGCAGGTGCAGGCACGGATGCTGCTATTGAT
TCCCTCAAACCATATCTCGATAAAGGAGACATCATCATTGATGGTGGTAACACCTTCTTCCAGGACACTAT
TCGTCGTAATCGTGAGCTTTCAGCAGAGGGCTTTAACTTCATCGGTACGGGTGTTTCTGGCGGTGAAGAGG
GGGCGCTGAAAGGTCCTTCTATTATGCCTGGTGGCCAGAAAGAAGCCTATGAATTGGTAGCACCGATCCTG
ACCAAAATCGCCGCCGTAGCTGAAGACGGTGAACCATGCGTTACCTATATTGGTGCCGATGGCGCAGGTCA
CTATGTGAAGATGGTTCACAACGGTATTGAATACGGCGATATGCAGCTGATTGCTGAAGCCTATTCTCTGC
TTAAAGGTGGCCTGAACCTCACCAACGAAGAACTGGCGCAGACCTTTACCGAGTGGAATAACGGTGAACTG
AGCAGTTACCTGATCGACATCACCAAAGATATCTTCACCAAAAAAGATGAAGACGGTAACTACCTGGTTGA
TGTGATCCTGGATGAAGCGGCTAACAAAGGTACGGGTAAATGGACCAGCCAGAGCGCGCTGGATCTCGGCG
AACCGCTGTCGCTGATTACCGAGTCTGTGTTTGCACGTTATATCTCTTCTCTGAAAGATCAGCGTGTTGCC
GCATCTAAAGTTCTCTCTGGTCCGCAAGCACAGCCAGCAGGCGACAAGGCTGAGTTCATCGAAAAAGTTCG
TCGTGCGCTGTATCTGGGCAAAATCGTTTCTTACGCCCAGGGCTTCTCTCAGCTGCGTGCTGCGTCTGAAG
AGTACAACTGGGATCTGAACTACGGCGAAATCGCGAAGATTTTCCGTGCTGGCTGCATCATCCGTGCGCAG
TTCCTGCAAAAAATCACCGATGCTTATGCCGAAAATCCACAGATCGCTAACCTGTTGCTGGCTCCGTACTT
CAAGCAAATTGCCGATGACTACCAGCAGGCGCTGCGTGATGTCGTTGCTTATGCAGTACAGAACGGTATTC
CGGTTCCGACCTTCTCCGCAGCGGTTGCCTATTACGACAGCTACCGTGCTGCTGTTCTGCCTGCGAACCTG
ATCCAGGCACAGCGTGACTATTTTGGTGCGCATACTTATAAGCGTATTGATAAAGAAGGTGTGTTCCATAC
CGAATGGCTGGATTAA

SEQ ID NO: 17 (example O18A rfb locus nucleotide sequence - O18A-EPA production strain BVEC-L-00559)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGTGAAAATACTT
GTTACTGGTGGCGCAGGATTTATTGGTTCAGCTGTAGTTCGTCACATTATAAATAATACGCAGGATAGTGT
TGTTAATGTCGATAAATTAACGTACGCCGGAAACCGGGAATCACTTGCTGATGTTTCTGATTCTGAACGCT
ATGTTTTTGAACATGCGGATATTTGCGATGCACCTGCAATGGCACGGATTTTTGCTCAGCATCAGCCGGAT
GCAGTGATGCACCTGGCTGCTGAAAGCCATGTTGACCGTTCAATTACAGGCCCTGCGGCATTTATTGAAAC
CAATATTGTTGGTACTTATGTCCTTTTGGAAGCCGCTCGCAATTACTGGTCTGCTCTTGATAGCGACAAGA
AAAATAGCTTCCGTTTTCATCATATTTCTACTGACGAAGTCTATGGTGATTTGCCTCATCCAGATGAAGTA
AATAATACAGAAGAATTACCCTTATTTACTGAGACGACAGCTTACGCGCCAAGCAGCCCTTATTCCGCATC
CAAAGCATCCAGCGATCATTTAGTCCGCGCGTGGAAACGTACATATGGTTTACCGACAATTGTGACTAATT
GCTCGAACAACTATGGTCCTTATCATTTCCCGGAAAAGCTTATTCCACTGGTTATTCTTAATGCACTGGAA
GGTAAGGCATTACCTATTTATGGCAAAGGAGATCAGATCCGCGACTGGTTGTATGTTGAAGATCATGCGCG
TGCGTTATATACCGTCGTAACCGAAGGTAAAGCGGGTGAAACTTATAACATTGGTGGGCACAACGAAAAGA
AAAACATCGATGTAGTGCTCACTATTTGTGATTTGCTGGATGAGATTGTACCGAAAGAGAAATCTTATCGT
GAGCAAATCACTTATGTTGCTGATCGTCCGGGACACGATCGCCGCTATGCTATTGATGCTGAGAAGATTGG
TCGCGCATTGGGATGGAAACCACAGGAAACGTTTGAGAGCGGGATTCGTAAAACGGTGGAATGGTACCTGT
CCAATACAAAATGGGTTGATAATGTGAAAAGTGGTGCCTATCAATCGTGGATTGAACAGAACTATGAGGGC
CGCCAGTAATGAATATCCTCCTTTTTGGCAAAACAGGGCAGGTAGGTTGGGAACTACAGCGTGCTCTGGCA
CCTTTGGGTAATTTGATTGCTTTTGATGTTCACTCTACTGATTATTGCGGTGATTTTAGTAATCCTGAAGG
TGTAGCTGAAACCGTAAGAAGCATTCGGCCGGATATTATTGTCAATGCAGCCGCTCACACCGCAGTAGACA
AAGCAGAATCAGAACCGGAGTTTGCACAATTAATTAACGCAACAAGTGTCGAAGCGATTGCGAAAGCAGCA
AATGAAGTTGGAGCCTGGGTTATCCATTACTCGACTGATTACGTCTTCCCTGGAAATGGCGATATGCCATG
GCTGGAGACGGATGCAACCGCACCACTAAATGTTTACGGTGAAACCAAGTTAGCCGGAGAAAAAGCGTTAC
AGGAATATTGCGCGAAGCATCTTATTTTCCGGACCAGCTGGGTCTATGCAGGAAAAGGAAATAACTTCGCC
AAAACGATGTTACGTCTGGCAAAAGAGCGTGAAGAATTAGCGGTTATTAACGATCAGTTTGGTGCGCCAAC
AGGTGCTGAACTGCTGGCTGATTGTACAGCACATGCCATTCGTGTCGCACTGAATAAACCGGATGTCGCAG
GCTTGTACCATTTGGTAGCCAGTGGTACCACAACCTGGTACGATTATGCTGCGCTGGTTTTTGAAGAGGCG
CGCAAAGCAGGCATTCCCCTTGCACTCAACAAGCTCAACGCAGTACCAACAACAGCCTATCCTACACCAGC
TCGTCGTCCACATAACTCTCGCCTTAATACAGAAAAATTTCAGCAGAACTTTGCGCTTGTCTTGCCTGACT
GGCAGGTTGGCGTGAAACGAATGCTCAATGAATTATTTACGACTACAGCAATTTAATAGTTTTTGCATCTT
GTTCGTGATGGTGGAGCAAGATGAATTAAAAGGAATGATGAAATGAAAATGCGTAAAGGTATTATTTTAGC
GGGTGGTTCTGGTACACGTCTTTATCCTGTGACTATGGCTGTCAGTAAACAGCTATTACCTATTTATGATA
AACCGATGATCTATTACCCGCTCTCTACACTGATGTTGGCGGGTATTCGCGATATTTTGATTATCAGTACA
CCTCAGGATACTCCTCGTTTTCAACAATTGCTGGGTGACGGTAGCCAGTGGGGCCTGAATCTTCAGTACAA
AGTGCAACCTAGCCCAGATGGCCTCGCGCAGGCATTTATCATCGGTGAAGAGTTTATTGGTGGTGATGATT
GTGCTTTGGTTCTTGGTGATAATATCTTTTACGGTCACGATCTGCCGAAGCTAATGGAGGCCGCTGTTAAC
AAAGAAAGTGGTGCAACGGTATTTGCCTATCACGTTAATGATCCAGAACGCTATGGTGTCGTTGAGTTTGA
TAAAAACGGTACGGCAATCAGTCTGGAAGAAAAACCGTTAGAACCAAAGAGTAATTACGCCGTTACAGGTC -continued

| SEQUENCES |
| --- |
| TGTACTTTTATGATAACGACGTGGTTCAGATGGCGAAAAACTTGAAGCCGTCTGCACGTGGTGAGTTAGAA<br>ATTACAGATATTAACCGTATTTATCTTGAGCAGGGACGTCTGTCTGTCGCGATGATGGGGCGTGGCTACGC<br>GTGGCTGGACACGGGGACTCATCAGAGTCTGATAGAAGCAAGTAATTTTATTGCGACAATTGAAGAGCGCC<br>AGGGATTGAAGGTTTCCTGTCCTGAAGAGATTGCATTTCGTAAAGGTTTTATTGATGTTGAGCAAGTAAGA<br>AAATTAGCTGTACCACTAATAAAGAATAATTATGGGCAGTATCTTTATAAAATGACGAAGGATTCAAATTA<br>ATGAATGTGATTAGAACTGAAATTGAAGATGTGCTAATTCTGGAGCCAAGAGTATTTGGTGATGATAGAGG<br>TTTCTTTTATGAGAGCTTTAATCAATCAGCATTTGAACATATTCTAGGCTATCCGGTCAGCTTTGTTCAAG<br>ACAATCACTCACGTTCATCAAAAAATGTACTCAGAGGCCTTCACTTTCAACGCGGCGAGTACGCACAAGAT<br>AAACTTGTACGCTGCACTCATGGAGCAGTTTTTGATGTTGCTGTTGATATTCGACCCAATTCGGTATCCTT<br>TGGTAAATGGGTTGGTGTTCTGCTTTCAGCTGATAATAAGCAGCAGTTGTGGATACCAAAAGGGTTTGCTC<br>ATGGCTTTTTGGTTCTGTCTGATATCGCTGAATTTCAATATAAAACTACAAACTATTATCATCCTGAAAGC<br>GATTGTGGAATATGTTGGAATGATGAACGCATTGCAATTGATTGGCCCCAAACATCAGGGTTAATCCTTTC<br>GCCAAAAGATGAAAGGCTCTTTACGTTAGATGAGCTTATCAGATTAAAATTAATTGCATGAGGCCGGCCTT<br>AAGGAGGACTAGTCCCGGCGCGCCATGAGTTTAATCAAAAACAGTTTTTGGAACCTTTGCGGGTATGTACT<br>TCCAGCTATTGTGACACTACCAGCTTTGGGTATTATGGGGCGAAAATTAGGCCCAGAATTATTTGGTGTAT<br>TCACTTTGGCATTAGCTGTTGTGGGTTATGCAAGCATTTTTGATGCAGGCCTTACTCGCGCAGTGATACGA<br>GAAGTCGCAATTGAAAAAGATAATGAAGAAAATAAGTTGAAAATTATTTCTTCAGCGACAGTTGTAATTAT<br>TTATTTGAGTTTGGCCGCCTCACTCTTATTATTTTTTTTTAGTGGTCATATCGCATTGCTACTGAACATTA<br>GTGAGACTTTTTTTCATAATGTAAGTGTCTCGCTTAAAATTCTCGCAGCATCCATACCATTATTTTTGATT<br>ACTCAAATATGGTTGTCAATTTTAGAAGGTGAAGAAAGATTTGGTTTACTTAATATCTACAAATCAATTAC<br>GGGAGTGATATTAGCAATCTCACCGGCATTATTTATACTTATTAAACCCTCTTTGATGTATGCGATAATAG<br>GCTTAGTTCTAGCAAGGTTTTTATGTTTTATTTTGGCTTTTATAATTTGTCACGATAAAGTGCTTAAAGCT<br>AAACTAACAATCGATATACCAACAATTAAAAGATTGTTTATGTTCGGTGGTTGGATTACAGTAAGTAATAT<br>CATCAGCCCTGTGCTATCATATTTGATAGGTTTATTGTTTCAAATCAACTTGGGGCTGCTAATGTTGCTT<br>TTTATACTGCACCATCAGAAATTATTTCTCGGCTTAGTATAATTCCAGGTGCGTTTTCAAGAGCCTTATTT<br>CCAAGATTAGCTAATGCAAATAATTCCGCTGAAAGATATAAAACGAAAAGATTAATTACAATTTCACTTTT<br>AATAATCATCACCCCTATTTTTTGTATTGGCGTGTTATTTTCAGAGAAGATAATGGTTTTATGGATGGGGG<br>CATCATTTTTTGGTGAGCCTGGTTTGGTATTATCAATATTACTGATTGGCTTTATTTTTAATGGATTGGCA<br>CAAGTACCATTTGCCAGTATTCAATCCCGAGGTCATGCTAAGATAACTGCATTTGTTCATCTCTTAGAGTT<br>GTTTCCTTATTTATTACTTTTATTTTACCTCATAAAAGCACATGGGGTTGTTGGCGCGGGTATTGCGTGGT<br>CAGTGAGGATGATAGTAGATTATATAGCATTAAGTCTTTTGGACGGTAAGTATATTAATAAATAAAATTCA<br>AAATGCAAGTTAATAACTCATGGCTTTATTTGGGTAGGTGACAATTTATAATGATATATATATTAACTTTA<br>ACTCTTCTTCTAGTTATAGCCATAATGTTTTCTCTTCTCGGCACAAAAAGTAGGATCACATCTCCATTACC<br>TTTGCATTTTTTACCATGGTTACTAACTTTAATTGTCGGGATAAGTAATTACGATCAATTTTACGAGTTTA<br>ATGAAAGAAGCTTTTACTCTTTGTTGATTTGGTTTACAGTTATTTTTATATTTTATTTCATAGGGGAACTG<br>GTTAATTATAAACGTGAAAATATAAATGTTTATTATGGTCTTTCACATATTAAATATGAATGTAAAAAATA<br>TTGGATCATTGTCATCCCAATTTCATTATATACCATTTTCGAAATATATATGGTTGGTATGGGGGGAGCAG<br>ATGGATTCTTTCTCAATTTACGTCTTGCAAATACATTGGAGGGCTATACGGGTAAAAAATTTATCTTAATG<br>CCTGCTGTATATCCTCTAATGATGGCTATGTTCGCAATTGTTTGTCTAACAAAAACTTCCAAATTAAATAA<br>ATACTCCATTTATTTCTGGATGTTTTTGTATTGTATTGGCACAATGGGAAAATTTTCAATATTAACGCCAA<br>TATTGACATATTTAATTATTTATGACTTCAAACATAGATTAAAAGTAAAAAAAACAATAAAGTTTACATTG<br>TTGATAATTATATTAGCTTTAACTTTGCATTTTACACGTATGGCTGAGAATGACCACTCAACATTTTTATC<br>TATTTTAGGGCTCTATATTTATTCACCAATAATTGCTTTAGGCCAGTTGAATGAAGTAAATAGTAGTCATT<br>TTGGTGAGTATACGTTTAGATTCATATATGCTATAACTAATAAAATTGGCCTTATTAAAGAATTGCCAGTA<br>AATACTATTCTTGACTATTCATACGTTCCTGTACCAACAAATGTATATACTGCACTTCAACCATTTTACCA<br>GGATTTTGGTTATACTGGCATCATATTTGGAGCAGTATTATACGGACTAATATATGTGAGTTTATACACGG<br>CCGGTGTTCGTGGAAATAATACACAGGCATTACTGATTTACGCATTGTTTTCAGTTAGCAGTGCAACGGCT<br>TTCTTCGCTGAAACGCTAGTAACGAATTTAGCTGGAAATGTGATGTTAGTATTATGTACCATCTTACTATG<br>GCGATTTACAGTAATATGCAAACCAGTACAGTAACCATTCTAATGGCCACCTACAATGGCGAGGCCTTCAT<br>CAAAAATCAGATTTTGTCACTACAACAACAAACATTTTCTAACTGGCGGTTATTTATTCAGGATGATGGGT<br>CTACAGACAATACTATATCTATAATAAAAAACTTCCAAAAATCTGACTCCAGAATTCGGCTAGTTGATGAT<br>AATTTGAAAGGTCAAGGTGCAGGAAAAAATTTTTATCGCTGATAAAGTACAGCGAGACAGATTATACAAT<br>TTATTGTGACCAAGATGATATTTGGTTAGAAAACAAAATATTTGAATTAGTAAAGTATGCAAATGAAATTA<br>AATTGAATGTATCAGATGCGCCTTCGCTAGTTTATGCTGATGGCTATGCTTATATGGATGGTGAGGGTACA<br>ATCGATTTTTCTGGGATATCTAACAATCATGCTGATCAATTAAAGGATTTTCTTTTTTTTAATGGTGGATA<br>CCAAGGATGTTCTATTATGTTCAATCGTGCAATGACCAAATTTCTTCTGAATTATCGAGGATTTGTATATC<br>TACATGACGATATCACAACATTAGCTGCATACGCTCTTGGTAAAGTTTATTTTCTCCCGAAATACCTTATG<br>TTATATAGACAGCACACGAATGCGGTAACTGGTATCAAAACATTCCGCAATGGATTGACTTCTAAATTTAA<br>ATCACCAGTAAACTATCTTTTATCACGAAAACATTATCAGGTAAAAAAATCTTTTTTTGAATGTAACAGCT<br>CTATCTTATCAGAGACGAATAAAAAAGTTTTTTTGGATTTTATTTCATTTTGTGAATCAAATAATAAATTT<br>ACAGATTTTTTTAAGTTATGGCGAGGTGGGTTTAGATTAAATAACAGTAGAACTAAATTATTATTAAAATT<br>CTTAATACGGAGAAAATTTAGCGAATGATTTCAATACTTACACCTACTTTTAATCGGCAACATACTTTATC<br>AAGGCTATTCAATTCTCTTATATTACAAACTGATAAAGATTTTGAGTGGATAATAATTGATGATGGTAGTA<br>TAGATGCAACAGCGGTACTTGTAGAAGATTTTAGAAAAAAATGTGATTTTGACTTGATTTATTGCTATCAG<br>GAAAATAATGGTAAGCCCATGGCTTTAAACGCTGGTGTTAAAGCTTGTAGAGGCGATTATATCTTTATTGT<br>TGACAGTGATGATGCACTAACTCCCGATGCCATAAAATTAATTAAAGAATCAATACATGATTGCTTATCTG<br>AGAAGGAAAGTTTCAGCGGAGTCGGTTTTAGAAAAGCATATATAAAAGGGGGGATTATTGGTAATGATTTA<br>AATAATTCTTCAGAACATATATACTATTTAAATGCGACTGAGATTAGCAATTTAATAAATGGTGATGTTGC<br>ATATTGTTTTAAAAAAGAAAGTTTGGTAAAAAAATCCATTCCCCCGTATAGAAGATGAAAAATTTGTTCCAG<br>AATTATATATTTGGAATAAAATAACTGACAAGGCGAAGATTCGATTTAACATAAGCAAAGTTATATATCTT<br>TGTGAGTATCTTGATGATGGTCTTTCTAAAAATTTCCATAACCAGCTTAAAAAATACCCAAAGGGGTTTAA<br>GATTTATTACAAAGATCAAAGAAAACGAGAGAAAACTTATATAAAAAAAACAAAGATGCTAATTAGATATT<br>TGCAATGTTGTTATTATGAGAAAATAAAATGAAAATACTATTTGTCATTACAGGTTTAGGCCTTGGAGGTG<br>CTGAGAAGCAGGTTTGTCTTTTAGCTGATAAATTAAGTTTAAGCGGGCACCATGTAAAGATTATTTCACTT<br>GGACATATGTCTAATAATAAAGTCTTTCCTAGCGAAAATAATGTTAATGTCATTAATGTAAATATGTCAAA<br>AAACATTTCTGGAGTTATAAAAGGTTGTGTCAGAATTAGAGATGTTATAGCTAATTTCAAACCAGACATTG<br>TACACAGTCATATGTTTCATGCAAACATTATCACTAGATTGTCTGTAATTGGAATCAAAAACAGACCTGGT |

-continued

SEQUENCES

ATTATATCAACTGCACATAATAAAAATGAAGGTGGGTATTTCAGAATGCTCACATATAGAATAACCGATTG
TTTAAGTGATTGTTGTACAAATGTTAGCAAAGAAGCAGTGGATGAGTTTTTACGGATAAAAGCCTTTAATC
CCGCTAAAGCAATTACTATGTATAATGGGATAGATACCAATAAATTTAAATTTGATTTATTGGCAAGGAGG
GAAATTCGAGACGGTATTAATATAAAAAATGATGATATATTATTACTTGCTGCAGGTCGTTTAACGTTAGC
TAAAGATTATCCTAATTTATTGAATGCAATGACTCTGCTTCCTGAACACTTTAAACTTATTATTATTGGTG
ATGGTGAATTGCGTGACGAAATTAATATGCTTATAAAAAAATTGCAATTATCTAATAGGGTGTCCTTGTTG
GGAGTTAAAAAAAATATTGCTCCCTATTTTTCTGCATGTGATATTTTTGTTCTCTCTTCTCGTTGGGAAGG
ATTTGGATTAGTCGTGGCAGAAGCTATGTCATGTGAGCGAATTGTTGTTGGCACGGATTCAGGGGGAGTAA
GAGAAGTTATTGGTGACGATGATTTTCTTGTACCCATATCTGATTCAACACAACTTGCAAGCAAAATTGAA
AAATTGTCTTTGAGCCAGATACGTGATCACATTGGTTTTCGGAATCGTGAGCGTATTTTAAAAAATTTCTC
AATAGATACTATTATTATGCAGTGGCAAGAACTCTATGGAACTATAATTTGCTCAAAACATGAAAGGTAGA
TTTATATTTGGAACGTGTCTTTTGTTTGAATTTAATTCAATCTCAATTGAGATTTTTGTATTTCAAAAATA
CCATCATAGCTAACGATGATTGGTATTTATTTTAAGATGCTTTCTATAAATATATTGACGTTTTTAATGCG
CCGAAACGATTGGGCTGGGAACAGAGAAGTAAAACTGTTTTGAGAATGAAGAGTTTTTGAGATGTTTATGG
ATATTAAAAATTGATCCAGTGAATTAATTATTTATAATAAATCAAGATTTAATGTTAATAAATGATAATCT
TTTCTGACACTCATATTAATTATGAGTGGTACGTTTGGTAAACGGTAAACTATTATATGACAGCTAGAACA
ACTAAAGTTTTGCACTTACAATTACTCCCACTCTTAAGTGGCGTTCAAAGGGTAACATTAAACGAAATTAG
TGCGTTATATACTGATTATGATTATACACTAGTTTGCTCAAAAAAAGGTCCACTAACAAAAGCATTGCTGG
AATATGATGTCGATTGTCATTGTATCCCCGAACTTACGAGAGAAATTACCGTAAAGAATGATTTTAAAGCA
TTGTTCAAGCTTTATAAGTTCATAAAAAAAGAAAAATTTGACATTGTGCATACACATTCTTCAAAAACAGG
TATTTTGGGGCGAGTTGCTGCCAAATTAGCACGTGTTGGAAAGGTGATCCACACTGTACATGGTTTTTCTT
TTCCAGCCGCATCTAGTAAAAAAAGTTATTACCTTTATTTTTTCATGGAATGGATAGCAAAGTTCTTTACG
GATAAGTTAATCGTCTTGAATGTAGATGATGAATATATAGCAATAAACAAATTAAAATTCAAGCGGGATAA
AGTTTTTTTAATTCCTAATGGAGTAGACACTGATAAGTTTTCTCCTTTAGAAAATAAAATTTATAGTAGCA
CCTTGAATCTAGTAATGGTTGGTAGATTATCCAAGCAAAAAGATCCTGAGACATTATTGCTTGCTGTTGAA
AAACTGCTGAATGAAAATGTTAATGTTAAGCTGACACTTGTAGGAGATGGTGAACTAAAAGAACAGTTAGA
AAGCAGGTTCAAACGGCAAGATGGACGTATAATTTTTCATGGATGGTCAGATAACATTGTTAATATTTTAA
AAGTTAATGATCTTTTTATATTACCTTCTCTTTGGGAGGGTATGCCATTAGCAATTTTAGAAGCATTGAGC
TGTGGACTTCCATGTATAGTCACTAATATTCCAGGTAATAATAGCTTAATAGAAGATGGCTATAATGGTTG
TTTGTTTGAAATTAGAGATTGTCAGTTATTATCTCAAAAAATCATGTCATATGTTGGTAAGCCAGAACTGA
TTGCACAGCAATCTACCAATGCACGATCATTTATTCTGAAAAATTATGGATTAGTTAAAAGAAATAATAAG
GTCAGACAGCTATATGATAATTAAGAGCTCGGTACCCGGGCCTAGGGTGTAGGCTGGAGCTGCTTCGAAGT
TCCTATACTTTCTAGAGAATAGGAACTTCGGAATAGGAACTAAGGAGGATATTCATATCCGTCGACGGCGG
CCGCCCTGCAGGCATGCAAGCTTGATCCATATGGATCGCTAGCTTAATTAAATAAAGCCGTAAGCATATAA
GCATGGATAAGCTATTTATACTTTAATAAGTACTTTGTATACTTATTTGCGAACATTCCAGGCCGCGAGCA
TTCAGCGCGGTGATCACACCTGACAGGAGTATGTAATGTCCAAGCAACAGATCGGCGTAGTCGGTATGGCA
GTGATGGGACGCAACCTTGCGCTCAACATCGAAAGCCGTGGTTATACCGTCTCTATTTTCAACCGTTCCCG
TGAGAAGACGGAAGAAGTGATTGCCGAAAATCCAGGCAAGAAACTGGTTCCTTACTATACGGTGAAAGAGT
TTGTCGAATCTCTGGAAACGCCTCGTCGCATCCTGTTAATGGTGAAAGCAGGTGCAGGCACGGATGCTGCT
ATTGATTCCCTCAAACCATATCTCGATAAAGGAGACATCATCATTGATGGTGGTAACACCTTCTTCCAGGA
CACTATTCGTCGTAATCGTGAGCTTTCAGCAGAGGGCTTTAACTTCATCGGTACCGGTGTTTCTGGCGGTG
AAGAGGGGGCGCTGAAAGGTCCTTCTATTATGCCTGGTGGCCAGAAAGAAGCCTATGAATTGGTAGCACCG
ATCCTGACCAAAATCGCCGCCGTAGCTGAAGACGGTGAACCATGCGTTACCTATATTGGTGCCGATGGCGC
AGGTCACTATGTGAAGATGGTTCACAACGGTATTGAATACGGCGATATGCAGCTGATTGCTGAAGCCTATT
CTCTGCTTAAAGGTGGCCTGAACCTCACCAACGAAGAACTGGCGCAGACCTTTACCGAGTGGAATAACGGT
GAACTGAGCAGTTACCTGATCGACATCACCAAAGATATCTTCACCAAAAAAGATGAAGACGGTAACTACCT
GGTTGATGTGATCCTGGATGAAGCGGCTAACAAAGGTACGGGTAAATGGACCAGCCAGAGCGCGCTGGATC
TCGGCGAACCGCTGTCGCTGATTACCGAGTCTGTGTTTGCACGTTATATCTCTTCTCTGAAAGATCAGCGT
GTTGCCGCATCTAAAGTTCTCTCTGGTCCGCAAGCACAGCCAGCAGGCGACAAGGCTGAGTTCATCGAAAA
AGTTCGTCGTGCGCTGTATCTGGGCAAAATCGTTTCTTACGCCCAGGGCTTCTCTCAGCTGCGTGCTGCGT
CTGAAGAGTACAACTGGGATCTGAACTACGGCGAAATCGCGAAGATTTTCCGTGCTGGCTGCATCATCCGT
GCGCAGTTCCTGCAAAAAATCACCGATGCTTATGCCGAAAATCCACAGATCGCTAACCTGTTGCTGGCTCC
GTACTTCAAGCAAATTGCCGATGACTACCAGCAGGCGCTGCGTGATGTCGTTGCTTATGCAGTACAGAACG
GTATTCCGGTTCCGACCTTCTCCGCAGCGGTTGCCTATTACGACAGCTACCGTGCTGCTGTTCTGCCTGCG
AACCTGATCCAGGCACAGCGTGACTATTTTGGTGCGCATACTTATAAGCGTATTGATAAAGAAGGTGTGTT
CCATACCGAATGGCTGGATTAA

SEQ ID NO: 18 (example O25B rfb locus nucleotide sequence - O25B-EPA production strain stGVXN4459)
ATGACGAATTTAAAAGCAGTTATTCCTGTAGCGGGTCTCGGGATGCATATGTTGCCTGCCACTAAGGCGAT
ACCCAAAGAGATGCTACCAATCGTCGACAAGCCAATGATTCAGTACATTGTTGACGAGATTGTGGCTGCAG
GGATCAAAGAAATCCTCCTGGTAACTCACGCGTCCAAGAACGCGGTCGAAAACCACTTCGACACCTCTTAT
GAGTTAGAATCACTCCTTGAGCAGCGCGTGAAGCGTCAACTGCTGGCGGAAGTACAGTCCATCTGTCCGCC
GGGCGTGACCATTATGAACGTGCGTCAGGGCGAACCTTTAGGTTTAGGCCACTCCATTTTGTGTGCGCGAC
CTGCCATTGGTGACAACCCATTTGTCGTGGTACTGCCAGACGTTGTGATCGACGATGCCAGCGCCGACCCG
CTACGTTACAACCTTGCTGCCATGATTGCACGTTTCAACGAAACGGGCCGCAGCCAGGTGCTGGCAAAACG
TATGCCGGGTGACCTCTCTGAATACTCCGTCATCCAGACTAAAGAGCCGCTGGACCGTGAGGGTAAAGTCA
GCCGCATTGTTGAATTTATCGAAAAACCGGATCAGCCGCAGACGCTGGACTCAGACATCATGGCCGTAGGT
CGCTATGTGCTTTCTGCCGATATTTGGCCGGAACTGGAACGTACTCAGCCTGGTGCATGGGGACGTATTCA
GCTGACTGATGCTATTGCCGAGCTGGCGAAAAAACAATCCGTTGATGCAATGCTGATGACCGGCGACAGTT
ACGACTGCGGCAAAAAAATGGGCTATATGCAGGCGTTTGTGAAGTATGGCCTACGCAACCTGAAAGAAGGG
GCGAAGTTCCGTAAAGGTATTGAGAAGCTGTTAAGCGAATAATGAAAATCTGACCGGATGTAACGGTTGAT
AAGAAAATTATAACGGCAGTGAAAATTCGCAGCAAAAGTAATTTGTTGCGAATCTTCCTGCCGTTGTTTTA
TATAAACCATCAGAATAACAACGAGTTAGCAGTAGGGTTTTATTCAAAGTTTTCCAGGATTTTCCTTGTTT
CCAGAGCGGATTGGTAAGACAATTAGCGTTTGAATTTTTCGGGTTTAGCGCGAGTGGGTAACGCTCGTCAC
ATCATAGGCATGCATGCAGTGCTCTGGTAGCTGTAAAGCCAGGGGCGGTAGCGTGCATTAATACCTCTATT
AATCAAACTGAGAGCCGCTTATTTCACAGCATGCTCTGAAGTAATATGGAATAAATTAAGCTAGCAGTGAA -continued

| SEQUENCES |
|---|
| GATACTTGTTACTGGTGGCGCAGGATTTATTGGTTCTGCTGTTGTTCGTCACATAATAAATAATACGCAAG<br>ATAGTGTTGTTAATGTCGATAAATTAACATACGCCGGAAACCTGGAATCACTTGCAGATGTTTCTGATTCT<br>GAACGCTATTTCTTTGAACATGCGGATATTTGTGATGCAGCTGCAATGGCACGGATTTTTGCTCAGCATCA<br>GCCGGATGCAGTGATGCACCTGGCAGCTGAAAGCCATGTTGACCGTTCAATTACAGGCCCTGCGGCATTTA<br>TTGAAACCAATATTGTGGGTACTTATGTCCTTTTAGAAGCGGCTCGGAATTATTGGTCTGGTCTGGATGAT<br>GAAAAGAAAAAAAACTTCCGTTTTCATCATATTTCTACTGATGAGGTGTATGGTGACTTACCCCATCCGGA<br>TGAAGTAAATAGCAATGAAACGTTGCCGCTATTTACGGAAACGACAGCATACGCGCCAAGTAGTCCATATT<br>CTGCTTCTAAAGCTTCCAGCGATCATTTGGTTCGCGCATGGAAACGTACTTATGGTTTACCGACCATTGTG<br>ACTAATTGCTCGAACAACTATGGTCCTTATCATTTCCCGGAAAAGCTTATTCCACTGGTTATTCTTAATTC<br>ACTGGAAGGTAAGGCATTACCTATTTATGGCAAAGGAGATCAGATCCGCGACTGGTTGTATGTAGAGGATC<br>ATGCTCGAGCGTTATATACCGTCGTAACCGAAGGTAAAGCGGGCGAAACTTATAACATTGGTGGACACAAC<br>GAAAAGAAAAACATCGACGTAGTGTTCACTATTTGTGATTTGTTGGATGAGATAGTCCCGAAAGAGAAATC<br>TTACCGCGAGCAAATTACTTATGTTACCGATCGTCCGGGACACGATCGCCGTTATGCGATTGATGCTGAGA<br>AGATTGGTCGCGAATTGGGATGGAAACCACAGGAAACGTTTGAGAGTGGGATTCGTAAAACGGTGGAATGG<br>TACCTGTCCAATACAAAATGGGTTGATAATGTGAAAAGTGGTGCCTATCAATCGTGGATTGAACAGAACTA<br>TGAGGGCCGCCAGTAATGAATATCCTCCTTTTTGGCAAAACAGGGCAGGTAGGTTGGGAACTACAGCGTGC<br>TCTGGCACCTCTGGGTAATTTGATTGCTCTTGATGTTCACTCCACTGATTACTGTGGTGATTTTAGTAATC<br>CTGAAGGTGTAGCTGAAACCGTAAGAAGCATTCGGCCTGATATTATTGTCAACGCAGCCGCTCACACCGCA<br>GTAGACAAAGCAGAATCAGAACCGAAGTTTGCACAATTACTGAACGCGACGAGTGTCGAAGCGATCGCGAA<br>AGCAGCCAATGAAGTCGGCGCCTGGGTTATTCACTACTCTACTGACTACGTATTTCCGGGGACCGGTGAAA<br>TACCATGGCAGGAGGAGGATGCAACCGCACCGCTAAATGTTTACGGTGAAACCAAGTTAGCGGGAGAAAAA<br>GCATTACAAGAGCATTGTGCGAAGCACCTTATTTTCCGGACCAGCTGGGTCTATGCAGGTAAAGGAAATAA<br>CTTCGCCAAAACAATGTTGCGTCTGGCAAAAGAGCGTGAAGAATTAGCCGTTATTAATGATCAGTTTGGTG<br>CGCCAACTGGCGCAGAGTTACTGGCTGATTGTACGGCACATGCTATTCGTGTGGCACTGAATAAACCGGAA<br>GTCGCAGGCTTGTACCATCTGGTAGCTAGTGGTACCACAACGTGGCACGATTATGCTGCGCTGGTTTTTGA<br>AGAGGCGCGCAAAGCAGGCATTCCCCTTGCACTCAACAAGCTCAACGCAGTACCAACAACAGCCTATCCTA<br>CACCAGCTCGTCGTCCACATAACTCTCGCCTTAATACAGAAAAATTTCAGCAGAACTTTGCGCTTGTCTTG<br>CCTGACTGGCAGGTTGGCGTGAAACGAATGCTTAACGAATTATTTACGACTACAGCAATTTAATAGTTTTT<br>GCATCTTGTTCGTAATGGTGGAGCAAGATGTATTAAAAGGAATGATGAAATGAAAACGCGTAAAGGTATTA<br>TTTTGGCGGGTGGTTCTGGTACTCGTCTTTATCCTGTGACGATGGCCGTCAGTAAACAGCTGTTACCGATT<br>TATGATAAACCGATGATCTATTACCCGCTCTCTACACTGATGTTAGCGGGTATTCGCGATATTCTGATTAT<br>CAGTACACCACAGGATACTCCTCGTTTTCAACAACTGCTGGGTGACGGGAGCCAGTGGGGCCTGAATCTTC<br>AGTACAAAGTGCAACCGAGTCCGGATGGTCTTGCGCAGGCGTTTATTATCGGTGAAGAGTTTATTGGTGGT<br>GATGATTGTGCTTTGGTACTTGGTGATAATATCTTCTACGGCCACGACCTGCCGAAGTTAATGGACGTAGC<br>TGTTAACAAAGAAAGTGGTGCAACGGTATTTGCCTATCACGTTAATGATCCTGAACGTTATGGTGTCGTGG<br>AGTTTGATAATAACGGTACTGCAATTAGCCTGGAAGAAAAACCGCTGGAACCAAAAAGTAACTATGCGGTT<br>ACTGGGCTTTATTTCTATGACAATGACGTTGTGGAAATGGCGAAAAACCTTAAGCCTTCTGCCCGAGGTGA<br>ACTGGAAATTACCGATATTAACCGTATTTATATGGAACAAGGACGTTTGTCTGTCGCTATGATGGGGCGTG<br>GCTATGCATGGCTGGATACAGGGACGCATCAAAGTCTTATTGAAGCAAGCAACTTCATTGCCACCATTGAA<br>GAGCGCCAGGGACTAAAGGTTTCCTGTCCGGAAGAAATTGCTTATCGTAAAGGGTTTATTGATGCTGAGCA<br>GGTAAAAGTATTAGCCGAACCGTTGAAGAAAAATGCTTATGGTCAGTATCTGCTCAAAATGATTAAAGGTT<br>ATTAATAAGATGAACGTAATTAAAACTGAAATTCCTGATGTGCTGATTTTTGAACCAAAAGTTTTTGGGGA<br>TGAACGTGGCTTCTTTTTTGAGAGTTTTAATCAGAGGATTTTTGAAGAAGCAGTAGGTCGTAAGGTTGAGT<br>TTGTTCAGGATAACCATTCTAAGTCCAGTAAAGGTGTTTTACGTGGTCTTCATTATCAGTTAGAACCTTAT<br>GCTCAAGGAAAACTGGTGCGCTGTGTTGTTGGCGAGGTTTTTGATGTTGCGGTTGATATTCGTAAATCGTC<br>ACCTACATTTGGGAAATGGGTTGGGGTGAATTTGTCTGCTGAGAATAAGCGTCAGTTGTGGATTCCTGAGG<br>GATTTGCACATGGTTTTTTGGTGCTGAGTGATTTAGCAGAAGTTTTATATAAAACGAATCAATATTATGCT<br>CCATCACATGAAAAAAATATTATATGGAATGACCTCTTGCTTAATATTAAATGGCCGAGCACAGCACTGAT<br>CACTCTGTCTGATAAGGATGCAAATGGGGAAAGATTTGAACTAAGTGAGTTTTGAAATGTCTCTCTTAAAA<br>CATAGTATATGGAATGTTGCGGGCTACTTTATACCAACATTAATTGCAATTCCCGCCTTTGGATTAATTGC<br>GAGGAAAATTGGTGTAGAACTATTTGGTTTGTATACGTTAGCAATGATTTTTATAGGGTATGCAAGTATAT<br>TTGATGCTGGGTTAACAAGAGCTGTTGTGCGTGAAATAGCATTACTAAAAAACAGAGTGGACGATTGTAAT<br>ACGATAATAGTAACTTCTATTATCGCTGTGATATTTTTAGGGTTTATCGGAGGCGGGGGAGTGTTTCTGCT<br>TAAAGGCGATATTATTGAACTGTTAAATATCTCACCAATATATTACGCCGATTCGATAAAGTCTCTAGTAT<br>TATTATCATCTCTGATACCTGTATTCTTAGTCACGCAAATACTATTAGCAGAGCTTGAGGGTCGGGAATAT<br>TTTGGGATTCTAAATATACAAAAAAGTGTAGGGAATTCTTTAATTGCAGGGTTACCTGCATTATTTGTTTT<br>AATTAATCAAACGCTTTTTTCTGCAATTATTGGTGTAGCGATTGCAAGAGTTATATGCTTGTGGTTAAGCT<br>ACATTATGAGCAGGGAAAGAATAACTATCGATATCTCATTTTTTTCAATAACTGTTTTAAAGCGGTTATTT<br>AGATATGGCGGGTGGGTAACTATAAGTAACATAATATCTCCTATATTAGCGAGTATGGATAGATTTATTCT<br>ATCCCATATCCAGGGAGCATCAAAAATATCATTCTATACAGTCCCTAATGAGCTGGTAACTAGGCTTGGAA<br>TAGTTCCAGGCTCTCTTGGGAAAGCTGTTTTTCCAAAATTAAGTCATGCAAGGAATTTTACAGCGTCATAT<br>GCAGAGCAAAAAAAAGCTTATATATTAATGACTGTCATTGTAATGCCTTTGGTTTTATTTGTATATTATTA<br>CGCAAAGTTTATTTTAACATTGTGGATGGGGGCTGAGTATGCAGGGATTTCGGTCGAAATATTACGGATTA<br>TGCTTATAGGGTATATTTTTAACTGTTATTCACAAATCTCTTTTGCCAACATACAGGCCTTTGGAAAAGCA<br>AAATACACTGCATACATCCATATGATGGAATTTATTCCTTATTTGATAATGTTATATATAATTTCAAAGGA<br>ATATGGGGTTATTGGTGTTGCGTGGTTATGGACAATTCGAGTAATAATTGATTTTTTGATGCTTTTATATA<br>TGAGTTATCGTTGTAATAATCTTATGAAAAAAGGGTAGCCTGATGATATATATTGTGGTATTAAATTGGAA<br>TGGGGCTATAGATACCATTAATTGTGTTAAAAGTTTAATGGATTTAAATGTTAGCGATTATAAAATTATCA<br>TTGTTGATAACTGTTCTATGGATAACTCATATGATACTATAAAAGAAAATCTTAATTCATTATATATTGCT<br>GATAAAAGTATCATTGAGGTGAAGTATGAGGATAGAAATAAATATAAAACCTTAGAAAACGATAAAATCAT<br>ATTAATACAATCTCCGCAAAATAATGGGTACGCAAGTGGTAATAATATTGGCATAGAGTTCGCTCTTAATC<br>AGGAGAATATGAAATACGTCTGGGTTCTGAATAATGATACTGAAGTGGATAAAGAGGCTTTAACTCATTTA<br>ATTAGTAAATGTGATTCAGATAAAAGTATAGGGATTTGCGGTTCTCGTTTAGTCTATTTTGCCGACAGAGA<br>GATGCAGCAAGGACTAGGTGGGGTGCATAACAAATGGTTATGCACTACAAAAAATTATGAAATGGGAAGAT<br>TAGTTTCCAAAAAATATGATGATGAAGTCATTAGTAATGATATAGATTATATAATTGGCGCATCGATGTTT<br>TTCTCTAGAGAATGTTTGGAAACAGTTGGATTGATGAATGAAGAATATTTTTTATACTATGAAGAGTTAGA<br>TATTTGCCTCAGAGCAAAAGCAAAGAACTTTAAATTAGGTATTTGCTCAGAAAGTTTGGTTTATCATAAAA |

-continued

| SEQUENCES |
|---|
| TAGGTGCAAGTACTGATGGGGGAAAGAGCATGATGGCTGATCTTTGCTCAATAAAAAATAGGCTGGTCATT<br>ACAGAAAGGTTTTATCCCCAATATTATTGGACGGTATGGTTGTCACTTTTTGTTGTAGCATTTAACCGTGC<br>TAGAAGAGGTGAGTTTAATAAGATGAAAAGATGTTTGAATGTTATGTTTAACTTCAAACGAAACAAAGGTA<br>GCAAATGCCATTAGAATATGCACTTAATCATGGTGTTAATAAATCTATAGTTTGATATGTTATTAAAGGGT<br>ATTTAATGAAAGTGGCTTTTTATCTGCTTATGATCCACTATCTACATCCAGTTGGTCTGGCACACCTTAT<br>TATATGCTAAAGGCATTATCGAAGAGAAATATTTCCATTGAAATATTAGGACCGGTAAATAGCTATATGAT<br>ATACATGTTAAAAGTATATAAATTAATATTAAGGTGTTTCGGAAAAGAATATGATTATAGTCATTCGAAGT<br>TGCTTTCCAGGTATTACGGTAGAATATTCGGTAGGAAATTAAAAAAAATTGATGGTTTGGATTTTATTATC<br>GCACCTGCAGGTTCCTCACAAATTGCTTTTTTAAAAACAACCATACCAATAATATATCTATCGGATACAAC<br>ATATGATCAATTAAAAAGCTATTATCCGAATTTAAATAAAAAAACAATTATAAATGATGAGGATGCAAGTT<br>TAATCGAACGCAAGGCTATTGAAAAAGCAACAGTAGTATCTTTCCCATCTAAATGGGCAATGGATTTTTGC<br>AGGAATTATTACAGATTAGATTTTGATAAATTAGTTGAAATACCATGGGGGGCTAATTTATTTGATGATAT<br>TCACTTTGCTAATAAAAATATAATTCAAAAGAATAGTTATACTTGTCTTTTCTTGGGAGTTGATTGGGAAA<br>GAAAAGGTGGGAAAACAGCCTTGAAAGCAATTGAATATGTAAGGCAGTTATATGGGATCGATGTTAGACTA<br>AAAATTTGTGGATGTACTCCGAATCAAAAGATTTTACCTACTTGGGTTGAATTAATTGATAAAGTAGATAA<br>AAATAACGTTGACGAATATCAGAAATTCATCGATGTGTTATCTAACGCTGATATACTTCTTTTACCAACCA<br>TTGCTGAATGTTATGGAATGGTATTTTGTGAAGCTGCTGCTTTTGGATTGCCTGTTGTCGCTACAGATACA<br>GGTGGAGTCAGTTCTATAGTTATCAACGAAAGGACGGGGATATTAATTAAAGACCCGTTAGACTATAAGCA<br>CTTTGGAAATGCAATTCATAAAATAATTAGTTCCGTAGAGACTTATCAAAACTACTCCCAAAACGCAAGAA<br>TTAGATATAATAATATATTGCATTGGGACAATTGGGCTAAAAAGATAATTGAGATTATGTATGAGCATAAG<br>AATAGAAGAATCAAATAGCACAAAAAGAATTATATGTTTATTTATACTTTTTCTTGTTTTCCCTGATTTTT<br>TGTTTTATACATTAGGGGTTGATAATTTTAGCATTTCAACGATAATCTCAATTACATTGCTTTTTGTTTTT<br>TTAAGAGCTAAAAATATTTGCAAAGATAATTTTCTAATAATAGTAGCGTTATTCATATTGTTGTGTTTTAA<br>CTGTTTGTTAAGTATGCTATTTAATATTGAACAGGCTTTAACATTTAAAGTTGTACTTTCAATATATAGCA<br>TCTTAATAATGGCATACGTCTCCTCTTGTTATGCACAGACGTTGTGGTTATGTTCTGAAGAAATACTTAAG<br>AGATCCGTCTTTTATTTGTTCGCATTTCTTTGCCTTATTGGCATTATAAGTATTCTTTTACAGAAGACTGA<br>GATTATACATGATAAAAGTATGATTCTTTTTCCTGAACCATCAGCATTTGCATTGGTTTTTATACCTATCT<br>TTTCATTTTGTTTATACTATACAAGAGGGGGGGGGCTACTATTGCTCTATATATTATCTTTGGGTATTGCG<br>TTAGGTATCCAGAATTTAACAATGTTGGTAGGCATTGTGATTAGTGTTTTTGTGATGAAAAAAATAACTAT<br>AAGGCAAACTATTGTTATACTTTTGGGGGCATGGATTTTTTCCATGATATTAAGTGATTTAGACATTTCTT<br>ACTATACATCGCGGCTTGATTTTAAAAATACTACGAACCTATCAGTGCTTGTATATCTTTCAGGAATTGAA<br>AGAGCTTTCTTGAATTTTATTACAAGTTATGGTCTTGGTATTGGTTTTCAACAAATGGGAGTGAATGGGGA<br>GATAGGAATATATCAACAAATTTTAGCTGAACTTGATGCCCCTATGTTAAATATATACGATGGCTCATTTA<br>TTTCTTCTAAGTTAATATCTGAGTTTGGGGTTATTGGTGCATTAATGTGTATTTTCTATTTTTTTTATTTT<br>TCCCGATTTTATCTGCGTTTCAAAAAAAGTAAGAGATATTCACCGCAGTATATTTTAGCATATAGCTTCTA<br>CATGTGTTTCTTCATCCCTCTTTTTATACGTGGTGCTGGTTATATAAACCCCTATGTGTTTATGTTATTTT<br>CATCAATATTTTTGTGCAAATATCACGCTAAAAATATCTTGATGAAATCTAATGTCCAGATAGCTATATAA<br>TAGTAGATTATATTATCATTATCACGTAAATTACATATTAATAGCATATATGATAACTAGGACATAAATAA<br>TGTGCATTAAAAAAAAACTTAAGTTAATTAAACGATATGGCCTTTATGGTGGTCTTAGGCTTCTTAAAGAT<br>ATATTCTTAACAAAATTTTTATTTTGTTCAAATGTTAGGATTATTAGATTTCCATGTTATATTAGAAAAGA<br>TGGAAGTGTTAGTTTTGGAAAAGGTTTTACATCAGGTGTAGGATTACGAGTTGATGCATTTATGGATGCCG<br>TAGTTTCCATTGGAGAAAATGTTCAAATTAATGACTATGTTCACATCGCGGCTATTAATAATGTCATTATT<br>GGTAGAGATACATTAATAGCAAGTAAAGTATTTATTAGTGATCATAATCATGGTATTTTTTTCTAAATCCGA<br>TATCCATAGTTCACCAACTATTATTCCTTCGTCTAGGCCCCTTGAATCTGCACCTGTGTATATTGGAGAGC<br>GTGTGTGGATTGGCGAAAATGTGACAATATTACCAGGTGCGTGTATAGGTAATGGTGTAGTTATTGGCGCA<br>AACAGTGTTGTTCGTGGTGAGATTCCTAATAATGTGATCATTGCTGGTGTTCCAGCTAAAATTGTTAAAAA<br>ATATAACTATGAGCGTATGCAATGGGAAAGAATATAGTTGTAATATCGGCTGTTAATTTTACAACCGGAGG<br>CCCCTTTACCGTACTAAAAAATGTGCTTACAGCAACTAAAGATAGAGCCGAATGTAAATTTATTGCACTGG<br>TTCATAGCTCTGCTGAACTAATGGAATTATTTCCGTGGGTTGAATTTATAGAGTATCCAGAAGTCAAGTCT<br>TCGTGGGTTAAAAGATTATATTTCGAATATATAACTTGCAATAGATTATCTAAGGTGATTAAGGCAACTCA<br>TTGGGTATGCTTACATGATATTACAGCAAATGTTAGTGTACCCTATAGATTTGTTTATTGCCACAATCCTG<br>CACCGTTCTATAAATATTTAAGCTATCGAGATATTATAGGAGAACCTAAATTTTATCTTTTTTATCTTTTT<br>TATGGGCTTTTATACAATATCAATATAAAAAAGAACACAGCAGTTTTTGTTCAGCAGCAGTGGCTAAAAAA<br>AGAATTCGAAAAAAAATATAAGTTAAAGAATGTTGTTGTTAGTCGCCCTGAAGATATTTGCCCTTTTGAAA<br>GTGATGGTTTGGTAAGAAATAATAATAAAAAGGATGTGAGGATATTTTACCCAGCAGTGCCCCGTATATTT<br>AAAAACTTTGAAGTTATCATACGTGCTGCACAAATATTACAAGATAAAAATATTCATTTTTATCTTACTTT<br>TGATGGTACTGAAAATAAGTATGCAAAAAGAATATATAAATTAGCTTCCGAACTGAAAAATGTACATTTCC<br>TCGGTTACCTTAATGCAACCGAGATGGTTAACTTTTATCAAGATTCAGATATTATTTGTTTCCCATCGAAA<br>CTAGAAACGTGGGGATTACCATTATCAGAAGCTAAAACATACAAAAAATGGATATTTGCGGCAGACTTACC<br>TTATGCTCATGAAGTTTTATATAACTATTCAAAACTAGATATTTTCCATTTGACGATGAGAAAATACTTG<br>TTCGCTACATATTAGAGTACACAAGTAAAAATATGCATGAAGATATAAAAAATAGTAGGGTGAATTTTAAT<br>AATGATGCATTGACTGGTTTTGAACAGTTTATTGAATATATCCTCAAGGGGAACTGACGTGGTTTATATTA<br>TAATCGTTTCACATGGCCATGATGACTATATAGAAAATCTTTTATTAAATTTAAAGTTGCCCTCTGGAAGA<br>TTTAAAATAATAGTTCGTGATAACAAAAGTTCAATGGTTTTAAAAAAAACATGCGAAAAAAATTGCGTAAC<br>CTATTTGCATGGAGGGCAATATGGATTTGGACATAATAATAACATAGCAGTGTCATATATAATTAATAACT<br>TCATGATTATGAATAATGATTATTTTCTCTTTCTTAACCCCGATGTATTCATAACCAGTGAAAGTTTGATT<br>AATTATGTTGATTATATAATTAGTAATGATTATAAGTTTAGCACATTATGTCTTTATCGAGATTTTACTAA<br>AAGCAAACATGATTATTCAATACGGAGTTTTCCAACTTTATATGATTTTCTTTGTTCTTTTTTATTGGGGG<br>TGAATAAAAGTAAAATTAAGAAGGAAAATATACTTTCTGATACTGTAGTTGATTGGTGTGCTGGCTCATTT<br>ATGCTTATTCATGCTTTAAGTTTCTTAAATGTGAATGGTTTTGATCAAAAATATTTTATGTATTGTGAAGA<br>TATTGACCTTTGTATGCGTTTAAAATTAAGTGGAGTAGATCTTTACTATACTCCCCATTTTGATGCTATTC<br>ATTATGCGCAGCATGAAAATAGAAGAATATTTACTAAAGCATTTCGATGGCATATAAGGAGTATTACGCGC<br>TACATATTACGGAAACCAATTCTTTCTTATAAAAACTATAGAAAAATTACATCCGAACTGGTAAAGTGATT<br>AAGGATCCGTGTAGGCTGGAGCTGCTTCGAAGTTCCTATACTTTCTAGAGAATAGGAACTTCGGAATAGGA<br>ACTAAGGAGGATATTCATATGGATAAAGCCGTAAGCATATAAGCATGGATAAGCTATTTATACTTTAATAA<br>GTACTTTGTATACTTATTTGCGAACATTCCAGGCCGCGAGCATTCAGCGCGGTGATCACACCTGACAGGAG<br>TATGTAATGTCCAAGCAACAGATCGGCGTAGTCGGTATGGCAGTGATGGGACGCAACCTTGCGCTCAACAT |

-continued

| SEQUENCES |
|---|
| CGAAAGCCGTGGTTATACCGTCTCTATTTTCAACCGTTCCCGTGAGAAGACGGAAGAAGTGATTGCCGAAA<br>ATCCAGGCAAGAAACTGGTTCCTTACTATACGGTGAAAGAGTTTGTCGAATCTCTGGAAACGCCTCGTCGC<br>ATCCTGTTAATGGTGAAAGCAGGTGCAGGCACGGATGCTGCTATTGATTCCCTCAAACCATATCTCGATAA<br>AGGAGACATCATCATTGATGGTGGTAACACCTTCTTCCAGGACACTATTCGTCGTAATCGTGAGCTTTCAG<br>CAGAGGGCTTTAACTTCATCGGTACCGGTGTTTCTGGCGGTGAAGAGGGGGCGCTGAAAGGTCCTTCTATT<br>ATGCCTGGTGGCCAGAAAGAAGCCTATGAATTGGTAGCACCGATCCTGACCAAAATCGCCGCCGTAGCTGA<br>AGACGGTGAACCATGCGTTACCTATATTGGTGCCGATGGCGCAGGTCACTATGTGAAGATGGTTCACAACG<br>GTATTGAATACGGCGATATGCAGCTGATTGCTGAAGCCTATTCTCTGCTTAAAGGTGGCCTGAACCTCACC<br>AACGAAGAACTGGCGCAGACCTTTACCGAGTGGAATAACGGTGAACTGAGCAGTTACCTGATCGACATCAC<br>CAAAGATATCTTCACCAAAAAAGATGAAGACGGTAACTACCTGGTTGATGTGATCCTGGATGAAGCGGCTA<br>ACAAAGGTACCGGTAAATGGACCAGCCAGAGCGCGCTGGATCTCGGCGAACCGCTGTCGCTGATTACCGAG<br>TCTGTGTTTGCACGTTATATCTCTTCTCTGAAAGATCAGCGTGTTGCCGCATCTAAAGTTCTCTCTGGTCC<br>GCAAGCACAGCCAGCAGGCGACAAGGCTGAGTTCATCGAAAAAGTTCGTCGTGCGCTGTATCTGGGCAAAA<br>TCGTTTCTTACGCCCAGGGCTTCTCTCAGCTGCGTGCTGCGTCTGAAGAGTACAACTGGGATCTGAACTAC<br>GGCGAAATCGCGAAGATTTTCCGTGCTGGCTGCATCATCCGTGCGCAGTTCCTGCAGAAAATCACCGATGC<br>TTATGCCGAAAATCCACAGATCGCTAACCTGTTGCTGGCTCCGTACTTCAAGCAAATTGCCGATGACTACC<br>AGCAGGCGCTGCGTGATGTCGTTGCTTATGCAGTACAGAACGGTATTCCGGTTCCGACCTTCTCCGCAGCG<br>GTTGCCTATTACGACAGCTACCGTGCTGCTGTTCTGCCTGCGAACCTGATCCAGGCACAGCGTGACTATTT<br>TGGTGCGCATACTTATAAGCGTATTGATAAAGAAGGTGTGTTCCATACCGAATGGCTGGATTAA<br><br>SEQ ID NO: 19 (example O75 rfb locus nucleotide sequence - O75-EPA production strain stLMTB11737)<br>ATGACGAATTTAAAAGCAGTTATTCCTGTAGCGGGTCTCGGGATGCATATGTTGCCTGCCACTAAGGCGAT<br>ACCCAAAGAGATGCTACCAATCGTCGACAAGCCAATGATTCAGTACATTGTTGACGAGATTGTGGCTGCAG<br>GGATCAAAGAAATCCTCCTGGTAACTCACGCGTCCAAGAACGCGGTCGAAAACCACTTCGACACCTCTTAT<br>GAGTTAGAATCACTCCTTGAGCAGCGCGTGAAGCGTCAACTGCTGGCGGAAGTACAGTCCATCTGTCCGCC<br>GGGCGTGACCATTATGAACGTGCGTCAGGGCGAACCTTTAGGTTTAGGCCACTCCATTTTGTGTGCGCGAC<br>CTGCCATTGGTGACAACCCATTTGTCGTGGTACTGCCAGACGTTGTGATCGACGATGCCAGCGCCGACCCG<br>CTACGTTACAACCTTGCTGCCATGATTGCACGTTTCAACGAAACGGGCCGCAGCCAGGTGCTGGCAAAACG<br>TATGCCGGGTGACCTCTCTGAATACTCCGTCATCCAGACTAAAGAGCCGCTGGACCGTGAGGGTAAAGTCA<br>GCCGCATTGTTGAATTTATCGAAAAACCGGATCAGCCGCAGACGCTGGACTCAGACATCATGGCCGTAGGT<br>CGCTATGTGCTTTCTGCCGATATTTGGCCGGAACTGGAACGTACTCAGCCTGGTGCATGGGGACGTATTCA<br>GCTGACTGATGCTATTGCCGAGCTGGCGAAAAAACAATCCGTTGATGCAATGCTGATGACCGGCGACAGTT<br>ACGACTGCGGCAAAAAAATGGGCTATATGCAGGCGTTTGTGAAGTATGGCCTACGCAACCTGAAAGAAGGG<br>GCGAAGTTCCGTAAAGGTATTGAGAAGCTGTTAAGCGAATAATGAAAATCTGACCGGATGTAACGGTTGAT<br>AAGAAAATTATAACGGCAGTGAAAATTCGCAGCAAAAGTAATTTGTTGCGAATCTTCCTGCCGTTGTTTTA<br>TATAAACCATCAGAATAACAACGAGTTAGCAGTAGGGTTTTATTCAAAGTTTTCCAGGATTTTCCTTGTTT<br>CCAGAGCGGATTGGTAAGACAATTAGCGTTTGAATTTTTCGGGTTTAGCGCGAGTGGGTAACGCTCGTCAC<br>ATCATAGGCATGCATGCAGTGCTCTGGTAGCTGTAAAGCCAGGGGCGGTAGCGTGCATTAATACCTCTATT<br>AATCAAACTGAGAGCCGCTTATTTCACAGCATGCTCTGAAGTAATATGGAATAAATTAAGCTAGCAGTGAA<br>GATACTTGTTACTGGTGGCGCAGGATTTATTGGTTCTGCTGTTGTTCGTCACATAATAAATAATACGCAAG<br>ATAGTGTTGTTAATGTCGATAAATTAACATACGCCGGAAACCTGGAATCGCTCGCTGAAATTTCTGATTCT<br>GAACGTTATTCATTTGAGCATGCAGATATCTGCGATGCCGAAGCGATGGCTCGTATTTTCGCACAGCACCA<br>GCCAGACGCGGTGATGCACCTGGCAGCAGAGAGCCACGTTGACCGCTCAATAACTGGCCCTGCGGCATTTA<br>TTGAAACCAATATTGTGGGTACTTATGTTCTTTTAGAAGCGGCGCGCAATTATTGGTCTGGTCTGGATGAT<br>GAAAAGAAAAAAAACTTCCGCTTTCATCATATTTCTACTGATGAGGTGTATGGTGACTTACCCCATCCGGA<br>TGAAGTAAATAGCAATGAAACGTTGCCGCTATTTACGGAAATGACAGCATACGCGCCAAGTAGTCCATATT<br>CTGCTTCTAAAGCTTCCAGCGATCATTTGGTTCGCGCATGGAAACGTACTTATGGTTTACCGACCATTGTG<br>ACTAATTGCTCGAACAACTATGGTCCTTATCATTTCCCGGAAAAGCTTATTCCACTGGTTATTCTTAATGC<br>ACTGGAAGGTAAGGCATTACCTATTTATGGCAAAGGAGATCAGATCCGCGACTGGTTGTATGTAGAGGATC<br>ATGCTCGAGCGTTATATACCGTCGTAACCGAAGGTAAAGCGGGCGAAACTTATAACATTGGTGGACACAAC<br>GAAAAGAAAAACATCGACGTAGTGTTCACTATTTGTGATTTGTTGGATGAGATAGTCCCGAAAGAGAAATC<br>TTATCGTGAGCAAATTACCTATGTTGCTGATCGCCCAGGGCATGATCGCCGTTATGCAATTGATGCCGATA<br>AAATTAGCCGCGAATTGGGCTGGAAACCACAGGAAACGTTTGAGAGCGGGATTCGTAAAACTGTGGAATGG<br>TATCTGTCCAATACAAAATGGGTTGATAATGTGAAAAGTGGTGCCTATCAATCGTGGATTGAACAGAACTA<br>TGGGGGCCGCCACTAATGAATATCCTCCTTTTTGGCAAAACAGGGCAGGTTGGTTGGGAACTACAGCGTGC<br>TCTGGCACCTCTGGGTAATTTGATTGCTCTTGATGTTCACTCCACTGATTACTGTGGTGATTTTAGTAACC<br>CTGAAGGTGTGGCTGAAACCGTTAGAAGCATTCGGCCTGATATTATTGTCAACGCAGCCGCTCACACCGCA<br>GTAGACAAAGCAGAATCAGAACCGGAGTTTGCACAATTACTGAACGCGACGAGTGTCGAAGCGATCGCGAA<br>AGCAGCCAATGAAGTCGGCGCTTGGGTTATTCACTACTCTACTGACTACGTATTTCCGGGGACCGGTGAAA<br>TACCATGGCAGGAGGAGGATGCAACCGCACCGCTAAATGTTTACGGTGAAACCAAGTTAGCAGGAGAAAAA<br>GCATTACAAGAGCATTGTGCGAAGCACCTTATTTTCCGGACCAGCTGGGTCTATGCAGGTAAAGGAAATAA<br>CTTCGCCAAAACGATGTTGCGTCTGGCAAAAGAGCGTGAAGAATTAGCCGTTATTAATGATCAGTTTGGTG<br>CGCCAACTGGCGCAGAGTTGCTGGCTGATTGTACGGCACATGCCATTCGTGTGGCACTGAATAAACCGGAA<br>GTCGCAGGTTTGTACCATCTGGTAGCCAGTGGTACCACAACCTGGCACGATTATGCTGCGCTGGTTTTTGA<br>AGAGGCGCGCAAAGCAGGCATTCCCCTTGCACTCAACAAGCTCAACGCAGTACCAACAACAGTCTATCCTA<br>CACCAGCTCGTCGTCCACATAACTCTCGCCTTAATACAGAAAAATTTCAGCAGAACTTTGCGCTTGTCTTG<br>CCTGACTGGCAGGTTGGTGTGAAACGCATGCTCAACGAATTATTTACGACTACAGCAATTTAATAGTTTTT<br>GCATCTTGTTCGTGATGGTGGAACAAGATGAATTAAAAGGAATGATGGAATGAATACGCGTAAAGGTATTA<br>TTTTAGCGGGTGGTTCTGGTACACGTCTTTATCCTGTGACTATGGCTGTCAGTAAACAGCTGTTACCGATT<br>TATGATAAACCGATGATCTATTACCCGCTCTCTACACTGATGTTGGCGGGTATTCGCGATATTTTGATTAT<br>CAGCACGCCACAGGATACTCCTCGTTTTCAACAACTGCTGGGTGATGGGAGCCAGTGGGGGCTAAATCTTC<br>ACTACAAAGTGCAACCGAGTCCGGATGGTCTTGCGCAGGCATTTATCATCGGTGAAGAGTTTATCGGTGGT<br>GATGATTGTGCTTTGGTACTTGGTGATAATATCTTCTACGGTCACGACCTGCCTAAGTTAATGGATGCCGC<br>TGTTAACAAAGAAAGTGGTGCAACGGTATTTGCCTATCACGTTAATGATCCTGAACGCTATGGTGTCGTTG<br>AGTTTGATAAAAACGGTACTGCAATCAGCCTGGAAGAAAAACCGTTACAACCAAAAGTAATTATGCGGTA<br>ACCGGGCTTTATTTCTATGATAACTACGTTGTGGAAATGGCGAAAATCTTAAGCCTTCTGCCCGCGGTGA |

-continued

| SEQUENCES |
|---|
| ACTGGAAATTACCGATATTAACCGTATCTATATGGAACAGGGGCATTTATCTGTTGCCATGATGGGACGTG<br>GATATGCCTGGCTGGACACGGGGACACATCAAAGTCTTATTGAAGCAAGCAACTTCATTGCCACCATTGAA<br>GAGCGCCAGGGCTTGAAAGTTTCCTGCCCGGAAGAAATTGCTTACCGTAAAGGGTTTATTGATGCTGAGCA<br>GGTGAAAGTATTAGCTAAACCGCTGAAAAAAAATGCTTATGGTCAGTATCTGCTAAAAATGATTAAAGGTT<br>ATTAATAAAATGAATGTTATTAAAACAGAAATTCCAGATGTACTGATTTTTGAACCGAAAGTTTTTGGTGA<br>TGAGCGTGGTTTCTTTATGGAAAGCTTTAATCAGAAAGTTTTCGAAGAGGCTGTAGGGCGGAAGGTTGAAT<br>TTGTTCAGGATAATCATTCTAAATCGTGTAAAGGTGTACTTAGAGGTTTACACTTTCAGCTTCCTCCCTTT<br>GAGCAGGCAAAATTAGTAAGGTGTATAGTTGGCGAGGTATTTGATGTTGCAGTAGACATTAGACCTAATTC<br>TGAAACATTTGGTTCATGGGTTGGAGTAACTCTTTCGTCAGAAAATAAAAGGCAGCTATGGATTCCAGAAG<br>GATTCGCCCATGGTTTTTAACTTTAAGTGATATTGCAGAGTTTGTTTATAAAACTAACAACTATTATTCT<br>TTAAATCATGAAAGGGGAGTCATTTGGAACGATGAGGAAATTAACATTGCCTGGCCCTCTCAATCAGAGAA<br>GATTCTGTCACAGAAAGATATTAATTTACCATCATTTAGATTTGTTCAAATGTTTAGCAAGTAGTGTTATC<br>TTTACACTGCACATAGTCATCATTTTTTATGCTTTAAGTAAATTATATTGCACATCTATAACACAAAGCGC<br>AATAATATTTCGACCTGATGAAGGTTTGTGGTTATTTATCTTTCTAGGCGTTTTTTATGACTAAAATAGTT<br>GTGGTTTCTACAGCTCCAATATTCCCGACAAATAATGGGTACAAAAGTTCTGTATTAGGAAGAATTGATGA<br>GTTATTAAATGAGGATAATGAGGTCGTTTGATTGAAATAAACCTTGAAAATGTTACGGAAAAGAAAGATG<br>AATTAATACCAACAAGATTTAATAATATTCAAAGATATGAAGTAAAAAAAATATCTAGATCATTTATTGCC<br>GAGTTACAAATATTATTTGATATCAGAACTCGGTATGAACAATTATTTTCTTCTGCTGACATTAGAGATAA<br>CATAAAAAAGATAATTGATTTAGAAAAACCTTCTATTATTATTGCTGAGTCTATATGGGCGTTGCAAGCAT<br>TGCCTATTGAAATTAGTGCGAGAATACACTGTGTTATTCATGATGTGGCAACTGATTTCTTTAAAGAAATG<br>TTTGTATCTCATAATGAGGTTGTACGAAAAATTTTGTTTTTTAATGATTACCTAAAGTTGAAAATTACTGA<br>AGAAAATATTATCAAACGTTTGAGAGTTGAGCAATTTATCTTTCTGACAGAAGAAGATAAATGTTGGTATA<br>AAACAAGATACAATATTGATGAGGGTTGTTGTTCCTTAGCGAGCAATCATCTTTATGTAGAAAAGATTAAG<br>AGAACTATCAATTTCCAAACCCCTTTCCTGCTTATTCCCGGTAGCATTGAATTTTCACAAAATTTTTACGG<br>CTTAAATTGGTTTATAAAAAATATATATCCTGGATTAAATAGGAAAATAAGAATAGTTGTAACAGGAAAGG<br>CATCAGATAAAAAAATAAAGATGTTAAACTGTGGAGAGGAAATTACCTTTACGGGAGAGCTTGACTTTTCC<br>ACATATAATAAACTTAGCTCAACATGCTTGTGTGTTATTGCACCGATTACAACGGGCACTGGAATTAAAAT<br>AAAAATATTAGAAGCTGTACAAAAAGGTATTCCTGTACTTACAACAAAATTTGCTTCAAAAGGAATATGTT<br>CCGATTTATGTTTTTATTGCGAGGAGGATACTGACACAAACTTTGTCAATTTAATTAACAGTTTTCTTGAA<br>ACGACATTAAGAGTCCAAGAATGAATTTATTGCTTTTTTCAGTCCTTGCGTTTGGTTTAATATTGGCTTTG<br>GCCCATAATAATAAAAGTGGAGATATTAACGCATACTTAATGTTTTTTCTCGTGGTCCTAATGGTATTAAT<br>ATCAGGGCTGCGTATGAATGATAGTGATTATATCGAATACAGGAAAATGTATAATGAAGTGCCTATTTTAT<br>GTGACTTTAGTCTCGCATCTATAAGAGATATACATGGGGAGGTAGGCTATCTATTCTTATCATCAATCTTT<br>AAAACTTTATGCTTGCCATTTCAATTATTTCTTTTTTTTATTGCTTTTTTATCACTCCTGCTTACATATTT<br>TTCATTCAGAAAAATAAGTTTAATACCGATACTATCGTTAGTTTTTTATTTAAGCCATGCTTTTATAGTTA<br>GAGATTTGATTCAAATTAGGGCAGGATTAGCTGTTAGCATATCATTATATTCAATAATTAAATTTAAAGGA<br>AATAAAAGTATAATTACAGGAGTTTTATTTGCTTCTTTGATTCATTCTGGGGCGCTTATTATTGCTCTTTG<br>TTATCCTTTTTTCAAAAAAAAATACATAACATTAAAAATGATGTTGTTTTATTTTTAGTGTCAATTATTT<br>TTTCTTATTTGAATGGGCTTAATTTATCGATACAACTCTTATCTCAATATAGTTTGCTTCCAACTGCAATT<br>TCGAATTATGTTGGTTGGGAAGAATATGATTATCGGGTGAGTATATTTACTAATCCGGTTTTTATTAAAGG<br>TGTTTTTTTAATTGTCTTAATGCACAAATATGTACTTTCAGATATTAAAAATGAGAAAATTATAGTGCTTT<br>ATAACTTATATGTTTTAGGTGTATTAGCTATGGTTGCATTGAGTGGGATGGCTATTCTTTCAGGCCGTCTT<br>TCATCCTTTCTGACACTAGGTGAAAGCATTTTAATTGTATATGCTCTGTTCTACAAAAGAAATACACCTCT<br>GGCGTTTCTAATTTTTTCTTTTTTAACAATTGTGCAATTAGGATATGATCTATTTATTTCTAATGTGCATC<br>CTGAGCTTACTCTGATTATATTTGGGTGAATCTAAGTGAAAAATAATAAAATAGGCATACTTATCTCTAAA<br>ATACAAAATCTTGGACCTGTGAATGTAGTACGAGGATTGATAAAAGAAAATAAAAAATATGCTTTTACTGT<br>TTTTTGTTTAACAAATAGCGTAGATAAAAATATATATGATGAGTTATGCTGTTTAGGAGCCAAGGTTATAT<br>TAATACCAGATGGTACTTGGTTCAGCAAAATTTTATTTGTGAGAAGTTTTTAAAGGAACATCCACATAAT<br>ATCTTACATTCACATGGGATCACGGCCGATATGTTTTCTTACTTTCTGAATGGCGTGAAAATATCTACTAT<br>TCACAATAGACTAGATGAGGATTATATCCCATTATTTGGCGCGGTTAAAGGGAATGCTATATATTATCTTC<br>ATCGTTTTATATTACGAAGATTTAATCATATCGTTGCTTGCTCAGCAGCGGTCCAATCAAAACTGAAACAA<br>TCGAAAGTAAAAACTAAAATAACCACCATCCAGAATGGGATTGATATAACTAGGTTTAAGACACTTGAGTC<br>TGATAAAAAAAAATTATTGAGGGAAAAACACGGATTTGATAGTGAAAAAAGAATATTTATATATTGTGGCT<br>CGTTATCATTAAGGAAAAATATTGCTTACCTCTTGGAACACTTAGCCATCGAAGAAAATGATATATTTTTA<br>ATTCTAGGTGATGGTGAACTTTTTAGATATTGTAAGGATAAATATTCTAAAGATTTACGGTATATATTTAT<br>GGGGAAAGTTGAATGCCCTCTTGAATATTATCAATTATCAGATATTTTTGTTTCCGCTTCTTTATCGGAAG<br>GGCTCCCCCTTGGCACTATTAGAAGCTGCCTCTACTGGGTGCTATTTATATGTTAGCGATATAGAGCCCCAT<br>AGAGAAATTGCATCTCTATTAGGAGAGGAAAATATTTCTATGTTTAAAATTAAGGATGGATCATATAATTA<br>TTTGCAACCTAAAATAAAAAAAGCTGACTATAACGCTCTTTCTGACGATAAACTTTACAATATATCCGATA<br>AAAAAATGTCAAATCTTTATGACAAACTTTTTGTTTCTTTATTAGAGCAGAGGCACTAATATAATGATTTA<br>TGTTTCGGTAATTTCTCATGGTCATTTCAAAACTCTTAAGGAATTAGGAGCAGTATCAAAATTAAATAATC<br>ACAGCAGAATTAAAGTTATCATCAAAGATAATTTAGGAGAGAGCGAGCTTTTGGATTTTTGTCAGGAAAAC<br>AAAATAACTTATTTAAGGTCTAAAGAGAAAAAAGGATTTGGAGAGAATAATAATGAAGTTTTTTCCTCTAT<br>ATCCTCCTTAATTACTAAGGAAGATTTTTTTGTGGTTATGAATCCTGATATATATATTGAGTGCTCTGATC<br>TATTAGATGTCGTAGATGAGTGTGGTTCAGCGAATGTTAATCTAGCAACGATAAATTTATACAGGGATTTT<br>GATAAAAAAACATATGATAACTCAGTAAGGAAATTTCCCTCGGCAATTGATTTTTTTATGTCATTTTTATT<br>TAAGAAAAATGACTGTGTAGTAAATAAGAACAAAATAACGAAACCAACATATGTTGATTGGGCTGCAGGTT<br>CTTTTCTAATATTTAATGCCTTCTTTTATTCAAAACTCAACGGATTCAACGAAAAGTATTTTATGTATTGC<br>GAAGATATTGATATATGTTGGCGAGCTAAAAAACACTTCAATACTTCAGTTTTATACTATCCATGCTATGC<br>AGCAATTCATTTGGCACAATTTAACAATCGTAGGATTTTTAGTAGACATTTCATTTGGCATATAAAAAGTA<br>TTATCCTTTTTTTATTATATAAAAATGGTATGCTGCGTTCTAGTAAGTTGCTTTAATGCTAATATTCTTTT<br>AAGAGGTGAGAATGATACCTGTTATTTTGGCTGGTGGTTCGGGAAGTCGCTTGTGGCCACTTTCACGAGAA<br>AAGTTCCCCAAGCAGTTTTTAAAGTTGACTGGCAGTTTGACAATGTTGCAGTCAACATTGTCACGTCTTAA<br>TAATTTAAATGCTGATGATTCAATAGTTATATGCAACGAAGAGCATAGATTTATTGTTGCAGAACAATTAA<br>GAGAGTTAGGCAAACTTTCAAATAACATTATTCTTGAACCCAAAGGTCGTAATACAGCCCCTGCTATAACA<br>CTCGCAGCATTAGCAGCAAAAAGAAAATTCGCTGATGAAGATCCATTGATTCTTATTTAGCTGCAGATCA<br>CAACATCCAAGACGAACATGTTTTCTGTGAGGCAATTAATAAGGCGTCATCTTTAGCTAGTTATGGAAAAC |

-continued

| SEQUENCES |
| --- |
| TAGTGACTTTTGGTATCGTTCCATTCAAACCTGAAACTGGGTATGGCTATATTCGTCGCGGTGATGAAGTG<br>CCTGTAGATGAGCAGCATGCGGTGGCCTTTGAAGTGGCGCAGTTTGTCGAAAAACCGAATCTGGAAACCGC<br>GCAGGCCTATGTGGCAAGCGGCGAATATTACTGGAACAGCGGTATGTTCCTGTTCCGTGCCGGACGCTATC<br>TCGAAGAACTGAAAAAGTATCGTCCGGATATTCTCGATGCCTGTGAAAAAGCGATGAGCGCCGTCGATCCG<br>GATCTCGATTTTATTCGTGTGGATGAAGAGGCGTTTCTCGCTTGTCCGGAAGAGTCGGTGGATTACGCGGT<br>CATGGAATGCACGGCAGATGCCGTTGTGGTGCCGATGGATGCGGGCTGGAGCGATGTCGGTTCCTGGTCTT<br>CATTATGGGAGATCAGCGCCCACACCGCCGAGGGCAACGTTTGCCACGGCGATGTGATTAATCACAAAACT<br>GAAAACAGCTATGTGTACGCCGAATCTGGCCTGGTCACCACCGTCGGGGTGAAAGATTTGGTGGTAGTGCA<br>GACCAAAGATGCAGTGCTGATTGCCGACCGTAATGCGGTGCAGGATGTGAAGAAAGTGGTCGAGCAGATCA<br>AAGCTGATGGTCGCCATGAGCATCGGGTGCATCGCGAAGTGTATCGTCCGTGGGGCAAATATGACTCTATC<br>GACGCGGGCGACCGCTACCAGGTGAAACGCATCACCGTGAAACCGGGCGAAGGTTTGTCGGTACAGATGCA<br>TTATCATCGCGCGGAACACTGGGTGGTTGTCGCGGGAACGGCAAAAGTCACTATCAACGGTGATATCAAAC<br>TGCTTGGTGAAAACGAGTCCATTTATATTCCGCTGGGGGCGATGCACTGCCTGGAAAACCCGGGGAAAATA<br>GATTTAGAATTAATTGAAGTTCGCTCTGGTGCATATCTTGAAGAAGATGATGTTATTAGATGTTATGATCG<br>CTATGGACGAAAGTAATATATAATAATTATTTCAGAATTAGAAATGATAATTATAAGTTTTCGTCTGGATA<br>AACAATAGATAGTATGGGTTGGAAAATATGAGTTCTTTAACTTGTTTTAAAGCTTACGACATTCGCGGGAA<br>ATTAGGTGAAGAACTGAATGAAGATATCGCCTGGCGCATTGGTCGCGCCTATGGCGAATTTCTCAAACCGA<br>AAACCATTGTGTTAGGCGGTGATGTCCGTCTCACCAGCGAAACCTTAAAACTGGCGCTGGCAAAAGGTTTA<br>CAGGATGCGGGCGTCGATGTGCTGGATATTGGCATGTCCGGCACCGAAGAGATTTATTTCGCCACGTTCCA<br>TCTCGGCGTGGATGGCGGCATTGAAGTTACCGCCAGCCATAATCCGATGGATTACAACGGCATGAAGCTGG<br>TGCGCGAAGGGGCTCGCCCGATCAGCGGTGATACCGGACTGCGCGACGTCCAGCGTCTGGCAGAAGCTAAC<br>GACTTTCCTCCCGTCGATGAAACCAAACGCGGTCGCTATCAGCAAATCAATCTGCGTGACGCTTACGTTGA<br>TCACCTGTTCGGTTATATCAATGTCAAAAACCTTACGCCGCTCAAGCTGGTGATCAACTCCGGGAATGGCG<br>CAGCGGGTCCGGTGGTGGACGCTATCGAAGCCCGCTTTAAAGCCCTCGGCGCACCGGTGGAGTTAATCAAA<br>GTGCATAACACGCCGGACGGCAATTTCCCCAACGGTATTCCTAACCCGTTGCTGCCGGAATGTCGCGACGA<br>CACCCGCAATGCGGTCATCAAACACGGCGCGGATATGGGCATTGCCTTTGATGGCGATTTTGACCGCTGTT<br>TCCTGTTTGACGAAAAAGGGCAGTTTATTGAGGGCTACTACATTGTCGGCCTGCTGGCAGAAGCGTTCCTC<br>GAAAAAAATCCCGGCGCGAAGATCATCCACGATCCACGTCTCTCCTGGAACACCATTGATGTGGTGACGGC<br>CGCGGGCGGCACGCCGGTGATGTCGAAAACAGGACACGCCTTTATTAAAGAACGTATGCGCAAGGAAGACG<br>CCATCTACGGTGGCGAAATGAGCGCTCACCATTACTTCCGCGATTTCGCTTACTGTGACAGCGGCATGATC<br>CCGTGGCTGCTGGTCGCCGAACTGGTGTGCCTGAAAGGAAAAACGCTGGGCGAACTGGTGCGCGACCGGAT<br>GGCGGCGTTTCCGGCAAGCGGTGAGATCAACAGAAAACTGGCGCACCCTGTTGAGGCGATTAACCGCGTGG<br>AACAGCATTTTAGCCGTGAGGTGCTGGCGGTGGATCGCACCGATGGCATCAGCATGACCTTTGCCGACTGG<br>CGCTTTAACCTGCGCTCTTCCAACACCGAACCGGTGGTGCGCCTGAATGTGGAATCTCGCGGTGATGTTCA<br>GGTTATGGTAATCCATACTCAAGAAATATTATCAATTTTGACGTCATAAAGAATAAGCCCTGACAAGTTAG<br>GGCTTAATTAATATATATTTTTTTGAATTGGGGATTTGTGGTAAGATTTTTAATATGTTATTTAATGTGG<br>TTGAATTAATGTTGACTGGAAAATAATAATGAGAACGAAAAAAGCATTACACAACTTTAAAGTTGATTTAT<br>TAATTACTTTTTTATTGGTTTTGCTAGGGTTTATATTCGAACTGTTTTTGTTTCAAAAATGGGAAGTGAT<br>ATTACTGGAGTGATGTTACTATTCACACAGTTGACAGCATATCTCAATTTGGCAGAATTAGGTATTGGAAT<br>TGCAGCTGCCAGCGTATTATATAAACCGCTCAGCGAGAATGAATACAATAAAATAACTTACATAATATCTT<br>TGCTCTCAGTCATATACAAATATATATTTGTGTTTGTTTTGATTCTTGGCGTTGTTATAGGTATCTGTATT<br>TATTACTTTATTGATTCTGTAAAGGTTGTAAATGGCGTTTTTTTATATTGGGCTTTGTTCGTTTTTAATAC<br>ATCGTTGACATATAGTTATGCTAAATACTCCACATTATTAACTGCTAATCAGCGGTACTCAGCAGTAAGAA<br>AAATTCAAGGTGGCGGAAAAGTTATAATAATTGTATTTCAGATATTAATTTTGTGCTTTACGCAAAGTTTC<br>ATACTTTATTTGTTAGTTGAGACTTTAGGTATTTTTTCTCAATATTTGATTTTTAAAAAAATAATTGGGAA<br>CGGAAATCAATATCTCAGTAATGAGGTTTTACTTATTGAAAGCGATAAACTTTTGATAAAAAAAGAATTAA<br>AAATAAGAATAAAAAAATATGTTCTTCCATAAAATAGGTGCTGTGCTTGTCCTTAATACAGACTACCTGCTT<br>GTATCAAAGTTTCTGACATTAAGTTATGTGACAATTTTTGGCAGCTATATGATGGTATTTCAGATAGTAAC<br>TGTTTTGATGTCAAGTTTTGTTAATGCTATTACTGCAGGAATGGGTAATTACTTAATTAATAAAAGTAATT<br>TAGAAATTAAGGAAATTACACGTCAATTTTATGTGATATTTATCGCCTTTGCAACATTCATATCACTAAAT<br>ATGTTTTTTCTTGTTAATGATTTTATCGCAAAATGGATAGGTGTTAATTATACATTAAGTAACACCCTAGT<br>TGCATTAATGATTGTTAACGTATTCATTAGTGTTGTCAGGGTACCTTCTGATATATTAAAAAACGCAAGTG<br>GACATTTTGGTGATATTTATTATCCATTATTAGAAGGTGTGCTGAATATTACGATATCCATCATTTTGGCT<br>ATCATTATTGGATTACCTGGCATTATTATAGGGACAATAGTATCTAACTTAATAGTAATAATGCTTGCGAA<br>ACCATTATATCTTTACTCTAAGTTATTTAATCTTAGAAATCCGACGAGGGTTTATTTTGAATTTATTTCTC<br>GGCCTATGTTATATTCATTATGTGTGATTGGGGTGAGCTATTTATTGCGCGATGAAATATATTCATTTAAA<br>GTAAGTACATGGTTGGATTTTATTAACAAGCTACTCTTAGTCTCTACTCCTAGCATATTGGTAATATGTGC<br>TATTTTCTCTACGGATAGTGACTTTAGATTATTTTTCAGAAAAATTATATATGTGATTATGAAGAAATAAA<br>AATTTCGAAAATGTATTAATCGAAATTATGCAACGAGCTTTATTTTTATAAATGATATGTGATCTTTTCGC<br>GAATAGGAGTAAGGATCCGTGTAGGCTGGAGCTGCTTCGAAGTTCCTATACTTTCTAGAGAATAGGAACTT<br>CGGAATAGGAACTAAGGAGGATATTCATATGGATAAAGCCGTAAGCATATAAGCATGGATAAGCTATTTAT<br>ACTTTAATAAGTACTTTGTATACTTATTTGCGAACATTCCAGGCCGCGAGCATTCAGCGCGGTGATCACAC<br>CTGACAGGAGTATGTAATGTCCAAGCAACAGATCGGCGTAGTCGGTATGGCAGTGATGGGACGCAACCTTG<br>CGCTCAACATCGAAAGCCGTGGTTATACCGTCTCTATTTTCAACCGTTCCCGTGAGAAGACGGAAGAAGTG<br>ATTGCCGAAAATCCAGGCAAGAAACTGGTTCCTTACTATACGGTGAAAGAGTTTGTCGAATCTCTGGAAAC<br>GCCTCGTCGCATCCTGTTAATGGTGAAAGCAGGTGCAGGCACGGATGCTGCTATTGATTCCCTCAAACCAT<br>ATCTCGATAAAGGAGACATCATCATTGATGGTGGTAACACCTTCTTCCAGGACACTATTCGTCGTAATCGT<br>GAGCTTTCAGCAGAGGGCTTTAACTTCATCGGTACCGGTGTTTCTGGCGGTGAAGAGGGGGCGCTGAAAGG<br>TCCTTCTATTATGCCTGGTGGCCAGAAAGAAGCCTATGAATTGGTAGCACCGATCCTGACCAAAATCGCCG<br>CCGTAGCTGAAGACGGTGAACCATGCGTTACCTATATTGGTGCCGATGGCGCAGGTCACTATGTGAAGATG<br>GTTCACAACGGTATTGAATACGGCGATATGCAGCTGATTGCTGAAGCCTATTCTCTGCTTAAAGGTGGCCT<br>GAACCTCACCAACGAAGAACTGGCGCAGACCTTTACCGAGTGGAATAACGGTGAACTGAGCAGTTACCTGA<br>TCGACATCACCAAAGATATCTTCACCAAAAAAGATGAAGACGGTAACTACCTGGTTGATGTGATCCTGGAT<br>GAAGCGGCTAACAAAGGTACCGGTAAATGGACCAGCCAGAGCGCGCTGGATCTCGGCGAACCGCTGTCGCT<br>GATTACCGAGTCTGTGTTTGCACGTTATATCTCTTCTCTGAAAGATCAGCGTGTTGCCGCATCTAAAGTTC<br>TCTCTGGTCCGCAAGCACAGCCAGCAGGCGACAAGGCTGAGTTCATCGAAAAAGTTCGTCGTGCGCTGTAT<br>CTGGGCAAAATCGTTTCTTACGCCCAGGGCTTCTCTCAGCTGCGTGCTGCGTCTGAAGAGTACAACTGGGA |

-continued

| SEQUENCES |
|---|
| TCTGAACTACGGCGAAATCGCGAAGATTTTCCGTGCTGGCTGCATCATCCGTGCGCAGTTCCTGCAGAAAA<br>TCACCGATGCTTATGCCGAAAATCCACAGATCGCTAACCTGTTGCTGGCTCCGTACTTCAAGCAAATTGCC<br>GATGACTACCAGCAGGCGCTGCGTGATGTCGTTGCTTATGCAGTACAGAACGGTATTCCGGTTCCGACCTT<br>CTCCGCAGCGGTTGCCTATTACGACAGCTACCGTGCTGCTGTTCTGCCTGCGAACCTGATCCAGGCACAGC<br>GTGACTATTTTGGTGCGCATACTTATAAGCGTATTGATAAAGAAGGTGTGTTCCATACCGAATGGCTGGAT<br>TAA |

The invention claimed is:

1. A method of preparing a bioconjugate of an *E. coli* $O_x$ antigen polysaccharide covalently linked to a carrier protein, the method comprising:

(i) providing a recombinant host cell comprising:

a. a nucleotide sequence of an rfb gene cluster for the $O_x$-antigen polysaccharide;

b. a nucleotide sequence encoding the carrier protein comprising at least one glycosylation site comprising a glycosylation consensus sequence having SEQ ID NO: 1; and c. a nucleotide sequence encoding an oligosaccharyl transferase $PglB_y$; and (ii) culturing the recombinant host cell under conditions for production of the bioconjugate, wherein:

the $O_x$-antigen is O1A antigen polysaccharide, the $PglB_y$ comprises the amino acid mutations of N311V, K482R, D483H, and A669V;

wherein the amino acid mutations are relative to the wild-type PglB having the amino acid sequence of SEQ ID NO: 6, and wherein the O1A antigen polysaccharide has the structure of:

[→3)-α-L-Rhap-(1→3)-α-L-Rhap-(1→3)-β-L-Rhap-(1→4)-
2
↑
1
β-D-ManpNAc
-β-D-GlcpNAc-(1→]$_n$, and n is an integer of 1 to 100.

2. The method of claim 1, further comprising isolating the bioconjugate from the recombinant host cell.

3. The method of claim 1, wherein the recombinant host cell is an *E. coli* cell.

4. The method of claim 1, wherein the carrier protein is detoxified Exotoxin A of *P. aeruginosa* (EPA) comprising SEQ ID NO: 3.

5. The method of claim 1, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified *E. coli* heat labile enterotoxin, Cholera toxin B subunit (CTB), cholera toxin, detoxified cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

6. The method of claim 1, wherein the $PglB_y$ consists of the amino acid mutations of N311V, K482R, D483H, and A669V.

* * * * *

SEQUENCE LISTING

<160> NUMBER OF SEQ ID NOS: 19

<210> SEQ ID NO 1
<211> LENGTH: 3
<212> TYPE: PRT
<213> ORGANISM: Artificial Sequence
<220> FEATURE:
<223> OTHER INFORMATION: glycosylation consensus sequence
<220> FEATURE:
<221> NAME/KEY: VARIANT
<222> LOCATION: (2)..(2)
<223> OTHER INFORMATION: any amino acid residue except Pro
<220> FEATURE:
<221> NAME/KEY: VARIANT
<222> LOCATION: (3)..(3)
<223> OTHER INFORMATION: Ser or Thr

<400> SEQUENCE: 1

Asn Xaa Xaa
1

<210> SEQ ID NO 2
<211> LENGTH: 5
<212> TYPE: PRT
<213> ORGANISM: Artificial Sequence
<220> FEATURE:
<223> OTHER INFORMATION: optimized glycosylation consensus sequence
<220> FEATURE:
<221> NAME/KEY: VARIANT
<222> LOCATION: (1)..(1)
<223> OTHER INFORMATION: Asp or Glu
<220> FEATURE:
<221> NAME/KEY: VARIANT
<222> LOCATION: (2)..(2)
<223> OTHER INFORMATION: any amino acid residue except Pro
<220> FEATURE:
<221> NAME/KEY: VARIANT
<222> LOCATION: (4)..(4)
<223> OTHER INFORMATION: any amino acid residue except Pro
<220> FEATURE:
<221> NAME/KEY: VARIANT
<222> LOCATION: (5)..(5)
<223> OTHER INFORMATION: Ser or Thr

<400> SEQUENCE: 2

Xaa Xaa Asn Xaa Xaa
1               5

<210> SEQ ID NO 3
<211> LENGTH: 652
<212> TYPE: PRT
<213> ORGANISM: Artificial Sequence
<220> FEATURE:
<223> OTHER INFORMATION: EPA carrier protein comprising 4 glycosylation
      consensus sequences (EPA-4)

<400> SEQUENCE: 3

Gly Ser Gly Gly Gly Asp Gln Asn Ala Thr Gly Ser Gly Gly Gly Lys
1               5                   10                  15

-continued

```
Leu Ala Glu Glu Ala Phe Asp Leu Trp Asn Glu Cys Ala Lys Ala Cys
            20                  25                  30

Val Leu Asp Leu Lys Asp Gly Val Arg Ser Ser Arg Met Ser Val Asp
        35                  40                  45

Pro Ala Ile Ala Asp Thr Asn Gly Gln Gly Val Leu His Tyr Ser Met
    50                  55                  60

Val Leu Glu Gly Gly Asn Asp Ala Leu Lys Leu Ala Ile Asp Asn Ala
65                  70                  75                  80

Leu Ser Ile Thr Ser Asp Gly Leu Thr Ile Arg Leu Glu Gly Gly Val
                85                  90                  95

Glu Pro Asn Lys Pro Val Arg Tyr Ser Tyr Thr Arg Gln Ala Arg Gly
            100                 105                 110

Ser Trp Ser Leu Asn Trp Leu Val Pro Ile Gly His Glu Lys Pro Ser
        115                 120                 125

Asn Ile Lys Val Phe Ile His Glu Leu Asn Ala Gly Asn Gln Leu Ser
    130                 135                 140

His Met Ser Pro Ile Tyr Thr Ile Glu Met Gly Asp Glu Leu Leu Ala
145                 150                 155                 160

Lys Leu Ala Arg Asp Ala Thr Phe Phe Val Arg Ala His Glu Ser Asn
                165                 170                 175

Glu Met Gln Pro Thr Leu Ala Ile Ser His Ala Gly Val Ser Val Val
            180                 185                 190

Met Ala Gln Ala Gln Pro Arg Arg Glu Lys Arg Trp Ser Glu Trp Ala
        195                 200                 205

Ser Gly Lys Val Leu Cys Leu Leu Asp Pro Leu Asp Gly Val Tyr Asn
    210                 215                 220

Tyr Leu Ala Gln Gln Arg Cys Asn Leu Asp Asp Thr Trp Glu Gly Lys
225                 230                 235                 240

Ile Tyr Arg Val Leu Ala Gly Asn Pro Ala Lys His Asp Leu Asp Ile
                245                 250                 255

Lys Asp Asn Asn Asn Ser Thr Pro Thr Val Ile Ser His Arg Leu His
            260                 265                 270

Phe Pro Glu Gly Gly Ser Leu Ala Ala Leu Thr Ala His Gln Ala Cys
        275                 280                 285

His Leu Pro Leu Glu Ala Phe Thr Arg His Arg Gln Pro Arg Gly Trp
    290                 295                 300

Glu Gln Leu Glu Gln Cys Gly Tyr Pro Val Gln Arg Leu Val Ala Leu
305                 310                 315                 320

Tyr Leu Ala Ala Arg Leu Ser Trp Asn Gln Val Asp Gln Val Ile Arg
                325                 330                 335

Asn Ala Leu Ala Ser Pro Gly Ser Gly Gly Asp Leu Gly Glu Ala Ile
            340                 345                 350

Arg Glu Gln Pro Glu Gln Ala Arg Leu Ala Leu Thr Leu Ala Ala Ala
        355                 360                 365

Glu Ser Glu Arg Phe Val Arg Gln Gly Thr Gly Asn Asp Glu Ala Gly
    370                 375                 380

Ala Ala Ser Ala Asp Val Val Ser Leu Thr Cys Pro Val Ala Lys Asp
385                 390                 395                 400

Gln Asn Arg Thr Lys Gly Glu Cys Ala Gly Pro Ala Asp Ser Gly Asp
                405                 410                 415

Ala Leu Leu Glu Arg Asn Tyr Pro Thr Gly Ala Glu Phe Leu Gly Asp
            420                 425                 430
```

-continued

Gly Gly Asp Val Ser Phe Ser Thr Arg Gly Thr Gln Asn Trp Thr Val
        435                 440                 445

Glu Arg Leu Leu Gln Ala His Arg Gln Leu Glu Glu Arg Gly Tyr Val
    450                 455                 460

Phe Val Gly Tyr His Gly Thr Phe Leu Glu Ala Ala Gln Ser Ile Val
465                 470                 475                 480

Phe Gly Gly Val Arg Ala Arg Ser Gln Asp Leu Asp Ala Ile Trp Arg
                485                 490                 495

Gly Phe Tyr Ile Ala Gly Asp Pro Ala Leu Ala Tyr Gly Tyr Ala Gln
            500                 505                 510

Asp Gln Glu Pro Asp Ala Arg Gly Arg Ile Arg Asn Gly Ala Leu Leu
        515                 520                 525

Arg Val Tyr Val Pro Arg Trp Ser Leu Pro Gly Phe Tyr Arg Thr Gly
    530                 535                 540

Leu Thr Leu Ala Ala Pro Glu Ala Ala Gly Glu Val Glu Arg Leu Ile
545                 550                 555                 560

Gly His Pro Leu Pro Leu Arg Leu Asp Ala Ile Thr Gly Pro Glu Glu
                565                 570                 575

Glu Gly Gly Arg Val Thr Ile Leu Gly Trp Pro Leu Ala Glu Arg Thr
            580                 585                 590

Val Val Ile Pro Ser Ala Ile Pro Thr Asp Pro Arg Asn Val Gly Gly
        595                 600                 605

Asp Leu Asp Pro Ser Ser Ile Pro Asp Lys Glu Gln Ala Ile Ser Ala
    610                 615                 620

Leu Pro Asp Tyr Ala Ser Gln Pro Gly Lys Pro Pro Arg Glu Asp Leu
625                 630                 635                 640

Lys Leu Gly Ser Gly Gly Gly Asp Gln Asn Ala Thr
                645                 650

<210> SEQ ID NO 4
<211> LENGTH: 421
<212> TYPE: PRT
<213> ORGANISM: Artificial Sequence
<220> FEATURE:
<223> OTHER INFORMATION: O4 GtrS amino acid sequence

<400> SEQUENCE: 4

Met Asn Asn Leu Ile Met Asn Asn Trp Cys Lys Leu Ser Ile Phe Ile
1               5                   10                  15

Ile Ala Phe Ile Leu Leu Trp Leu Arg Arg Pro Asp Ile Leu Thr Asn
            20                  25                  30

Ala Gln Phe Trp Ala Glu Asp Ser Val Phe Trp Tyr Lys Asp Ala Tyr
        35                  40                  45

Glu Asn Gly Phe Leu Ser Ser Leu Thr Thr Pro Arg Asn Gly Tyr Phe
    50                  55                  60

Gln Thr Val Ser Thr Phe Ile Val Gly Leu Thr Ala Leu Leu Asn Pro
65                  70                  75                  80

Asp Tyr Ala Pro Phe Val Ser Asn Phe Phe Gly Ile Met Ile Arg Ser
                85                  90                  95

Val Ile Ile Trp Phe Leu Phe Thr Glu Arg Phe Asn Phe Leu Thr Leu
            100                 105                 110

Thr Thr Arg Ile Phe Leu Ser Ile Tyr Phe Leu Cys Met Pro Gly Leu
        115                 120                 125

Asp Glu Val His Ala Asn Ile Thr Asn Ala His Trp Tyr Leu Ser Leu
    130                 135                 140

-continued

```
Tyr Val Ser Met Ile Leu Ile Ala Arg Asn Pro Ser Ser Lys Ser Trp
145                 150                 155                 160

Arg Phe His Asp Ile Phe Phe Ile Leu Leu Ser Gly Leu Ser Gly Pro
                165                 170                 175

Phe Ile Ile Phe Ile Leu Ala Ala Ser Cys Phe Lys Phe Ile Asn Asn
            180                 185                 190

Cys Lys Asp His Ile Ser Val Arg Ser Phe Ile Asn Phe Tyr Leu Arg
        195                 200                 205

Gln Pro Tyr Ala Leu Met Ile Val Cys Ala Leu Ile Gln Gly Thr Ser
    210                 215                 220

Ile Ile Leu Thr Phe Asn Gly Thr Arg Ser Ser Ala Pro Leu Gly Phe
225                 230                 235                 240

Ser Phe Asp Val Ile Ser Ser Ile Ile Ser Ser Asn Ile Phe Leu Phe
                245                 250                 255

Thr Phe Val Pro Trp Asp Ile Ala Lys Ala Gly Trp Asp Asn Leu Leu
            260                 265                 270

Leu Ser Tyr Phe Leu Ser Val Ser Ile Leu Ser Cys Ala Ala Phe Val
        275                 280                 285

Phe Val Lys Gly Thr Trp Arg Met Lys Val Phe Ala Thr Leu Pro Leu
    290                 295                 300

Leu Ile Ile Ile Phe Ser Met Ala Lys Pro Gln Leu Thr Asp Ser Ala
305                 310                 315                 320

Pro Gln Leu Pro Thr Leu Ile Asn Gly Gln Gly Ser Arg Tyr Phe Val
                325                 330                 335

Asn Ile His Ile Ala Ile Phe Ser Leu Leu Cys Val Tyr Leu Leu Glu
            340                 345                 350

Cys Val Arg Gly Lys Val Ala Thr Leu Phe Ser Lys Ile Tyr Leu Thr
        355                 360                 365

Ile Leu Leu Phe Val Met Gly Cys Leu Asn Phe Val Ile Thr Pro Leu
    370                 375                 380

Pro Asn Met Asn Trp Arg Glu Gly Ala Thr Leu Ile Asn Asn Ala Lys
385                 390                 395                 400

Thr Gly Asp Val Ile Ser Ile Gln Val Leu Pro Pro Gly Leu Thr Leu
                405                 410                 415

Glu Leu Arg Lys Lys
            420


<210> SEQ ID NO 5
<211> LENGTH: 1266
<212> TYPE: DNA
<213> ORGANISM: Artificial Sequence
<220> FEATURE:
<223> OTHER INFORMATION: Example O4 gtrS nucleic acid sequence

<400> SEQUENCE: 5

atgaataatt taattatgaa taactggtgt aaattatcta tatttattat tgcatttatt      60

ttgctatggc ttagaaggcc ggatatactc acaaacgcac aattttgggc agaagattcc     120

gttttctggt ataaggacgc ctatgagaac ggattcttaa gttcactaac aacgcctagg     180

aatgggtatt tccagactgt ttctacattt atagttggtc tgactgcttt attaaatcca     240

gattatgcac cttttgtttc taattttttt ggcataatga ttcgctcagt aattatatgg     300

tttttattta cagaaagatt caacttcctc acattgacta ctaggatttt cttatctatt     360

tattttctat gcatgcctgg attggatgaa gttcatgcaa atataacaaa tgcacattgg     420

tatttgtcat tatatgtatc aatgatcctg atagctcgca atccaagttc aaaatcatgg     480
```

```
aggtttcatg atatattctt tatcttgcta tccgggctca gtggcccatt tataattttc    540

attttagcag cttcatgctt taaatttata aataattgta aagatcatat tagtgtaaga    600

tctttcataa atttctactt gcgtcagcca tacgcattaa tgattgtttg cgctttaatt    660

caaggaactt ctataattct aactttcaat ggcacacgtt cctcagcacc gctaggattc    720

agttttgatg tgatttcgtc tattatatca tcgaatattt ttttatttac atttgtccca    780

tgggatattg caaaggctgg gtgggataat ttactgttat cttatttttt gtctgtttcg    840

attttgtcgt gtgcggcctt tgtttttgtt aaaggtacgt ggcgaatgaa agtatttgca    900

actttaccat tgctaattat aatattttca atggcaaaac cacaattgac agactcggca    960

cctcaattgc caacacttat taatgggcaa ggttcaagat acttcgtaaa tatacatatt   1020

gcgatattct ctttgctatg tgtttactta cttgagtgcg tcagggggaa agtggcaact   1080

ttattttcca aaatatactt aacaattttg ctattcgtga tgggatgttt gaattttgtt   1140

atcaccccac tcccaaacat gaactggagg gaaggtgcta ctttgattaa taatgcaaaa   1200

actggtgatg tcatttcgat tcaagtgcta ccacctggcc taacacttga actaaggaaa   1260

aaataa                                                               1266


<210> SEQ ID NO 6
<211> LENGTH: 713
<212> TYPE: PRT
<213> ORGANISM: Artificial Sequence
<220> FEATURE:
<223> OTHER INFORMATION: Example PglB sequence ('wild-type')

<400> SEQUENCE: 6

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
```

```
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
        355                 360                 365

Gly Gly Leu Arg Phe Thr Ile Tyr Ser Val Pro Val Met Ala Leu Gly
    370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
    450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640
```

```
Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710


<210> SEQ ID NO 7
<211> LENGTH: 120
<212> TYPE: PRT
<213> ORGANISM: Escherichia coli

<400> SEQUENCE: 7

Met Leu Lys Leu Phe Ala Lys Tyr Thr Ser Ile Gly Val Leu Asn Thr
1               5                   10                  15

Leu Ile His Trp Val Val Phe Gly Val Cys Ile Tyr Val Ala His Thr
            20                  25                  30

Asn Gln Ala Leu Ala Asn Phe Ala Gly Phe Val Val Ala Val Ser Phe
        35                  40                  45

Ser Phe Phe Ala Asn Ala Lys Phe Thr Phe Lys Ala Ser Thr Thr Thr
    50                  55                  60

Met Arg Tyr Met Leu Tyr Val Gly Phe Met Gly Thr Leu Ser Ala Thr
65                  70                  75                  80

Val Gly Trp Ala Ala Asp Arg Cys Ala Leu Pro Pro Met Ile Thr Leu
                85                  90                  95

Val Thr Phe Ser Ala Ile Ser Leu Val Cys Gly Phe Val Tyr Ser Lys
            100                 105                 110

Phe Ile Val Phe Arg Asp Ala Lys
        115                 120


<210> SEQ ID NO 8
<211> LENGTH: 306
<212> TYPE: PRT
<213> ORGANISM: Escherichia coli

<400> SEQUENCE: 8

Met Lys Ile Ser Leu Val Val Pro Val Phe Asn Glu Glu Glu Ala Ile
1               5                   10                  15

Pro Ile Phe Tyr Lys Thr Val Arg Glu Phe Glu Glu Leu Lys Ser Tyr
            20                  25                  30

Glu Val Glu Ile Val Phe Ile Asn Asp Gly Ser Lys Asp Ala Thr Glu
        35                  40                  45

Ser Ile Ile Asn Ala Leu Ala Val Ser Asp Pro Leu Val Val Pro Leu
    50                  55                  60

Ser Phe Thr Arg Asn Phe Gly Lys Glu Pro Ala Leu Phe Ala Gly Leu
65                  70                  75                  80

Asp His Ala Thr Gly Asp Ala Ile Ile Pro Ile Asp Val Asp Leu Gln
                85                  90                  95

Asp Pro Ile Glu Val Ile Pro His Leu Ile Glu Lys Trp Gln Ala Gly
            100                 105                 110

Ala Asp Met Val Leu Ala Lys Arg Ser Asp Arg Ser Thr Asp Gly Arg
        115                 120                 125
```

```
Leu Lys Arg Lys Thr Ala Glu Trp Phe Tyr Lys Leu His Asn Lys Ile
    130                 135                 140

Ser Asn Pro Lys Ile Glu Glu Asn Val Gly Asp Phe Arg Leu Met Ser
145                 150                 155                 160

Arg Asp Val Val Glu Asn Ile Lys Leu Met Pro Glu Arg Asn Leu Phe
                165                 170                 175

Met Lys Gly Ile Leu Ser Trp Val Gly Gly Lys Thr Asp Ile Val Glu
            180                 185                 190

Tyr Val Arg Ala Glu Arg Ile Ala Gly Asp Thr Lys Phe Asn Gly Trp
        195                 200                 205

Lys Leu Trp Asn Leu Ala Leu Glu Gly Ile Thr Ser Phe Ser Thr Phe
    210                 215                 220

Pro Leu Arg Ile Trp Thr Tyr Ile Gly Leu Val Val Ala Ser Val Ala
225                 230                 235                 240

Phe Ile Tyr Gly Ala Trp Met Ile Leu Asp Thr Ile Ile Phe Gly Asn
                245                 250                 255

Ala Val Arg Gly Tyr Pro Ser Leu Leu Val Ser Ile Leu Phe Leu Gly
            260                 265                 270

Gly Ile Gln Met Ile Gly Ile Gly Val Leu Gly Glu Tyr Ile Gly Arg
        275                 280                 285

Thr Tyr Ile Glu Thr Lys Lys Arg Pro Lys Tyr Ile Ile Lys Arg Val
    290                 295                 300

Lys Lys
305
```

<210> SEQ ID NO 9
<211> LENGTH: 14440
<212> TYPE: DNA
<213> ORGANISM: Artificial Sequence
<220> FEATURE:
<223> OTHER INFORMATION: example O4 rfb locus nucleotide sequence - O4-
      EPA production strain BVEC-L-00684f

<400> SEQUENCE: 9

```
atgacgaatt taaaagcagt tattcctgta gcgggtctcg ggatgcatat gttgcctgcc      60

actaaggcga tacccaaaga gatgctacca atcgtcgaca agccaatgat tcagtacatt     120

gttgacgaga ttgtggctgc agggatcaaa gaaatcctcc tggtaactca cgcgtccaag     180

aacgcggtcg aaaaccactt cgacacctct tatgagttag aatcactcct tgagcagcgc     240

gtgaagcgtc aactgctggc ggaagtacag tccatctgtc cgccgggcgt gaccattatg     300

aacgtgcgtc agggcgaacc tttaggttta ggccactcca ttttgtgtgc gcgacctgcc     360

attggtgaca acccatttgt cgtggtactg ccagacgttg tgatcgacga tgccagcgcc     420

gacccgctac gttacaacct tgctgccatg attgcacgtt tcaacgaaac gggccgcagc     480

caggtgctgg caaaacgtat gccgggtgac ctctctgaat actccgtcat ccagactaaa     540

gagccgctgg accgtgaggg taaagtcagc cgcattgttg aatttatcga aaaaccggat     600

cagccgcaga cgctggactc agacatcatg gccgtaggtc gctatgtgct ttctgccgat     660

atttggccgg aactggaacg tactcagcct ggtgcatggg gacgtattca gctgactgat     720

gctattgccg agctggcgaa aaaacaatcc gttgatgcaa tgctgatgac cggcgacagt     780

tacgactgcg gcaaaaaaat gggctatatg caggcgtttg tgaagtatgg cctacgcaac     840

ctgaaagaag ggcgaagtt ccgtaaaggt attgagaagc tgttaagcga ataatgaaaa     900

tctgaccgga tgtaacggtt gataagaaaa ttataacggc agtgaaaatt cgcagcaaaa     960
```

-continued gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagtga aaatacttgt tactggtggc gcaggattta ttggttcagc tgtagttcgt 1320
cacattataa ataatacgca ggatagtgtt gttaatgtcg ataaattaac gtacgccgga 1380
aaccgggaat cacttgctga tgtttctgat tctgaacgct atgtttttga acatgcggat 1440
atttgcgatg cacctgcaat ggcacggatt tttgctcagc atcagccgga tgcagtgatg 1500
cacctggctg ctgaaagcca tgttgaccgt tcaattacag gccctgcggc atttattgaa 1560
accaatattg ttggtactta tgtccttttg gaagccgctc gcaattactg gtctgctctt 1620
gatagcgaca agaaaaatag cttccgtttt catcatattt ctactgacga agtatatggt 1680
gatttgcctc atcctgacga ggtaaataat acagaagaat taccccttatt tactgagaca 1740 acagcttacg cgccaagcag cccttattcc gcatccaaag catccagcga tcatttagtc 1800
cgcgcgtgga aacgtaccta tggtttaccg accattgtga ctaattgctc taacaattat 1860
ggtccttatc atttcccgga aaaattgatt ccattggtta ttctcaatgc tctggaaggt 1920
aaagcattac ctatttatgg taaaggggat caaattcgcg actggctgta tgttgaagat 1980
catgcgcgtg cgttatatac cgtcgtaacc gaaggtaaag cgggtgaaac ttataacatt 2040
ggtgggcaca acgaaaagaa aaacatagat gtagtgctca ctatttgtga tttgctggat 2100
gagattgtac cgaaagagaa atcttatcgt gagcaaatca cttatgttgc cgatcgtccg 2160
ggacacgatc gccgttatgc gattgatgct gagaatattg gtcgcgaatt gggatggaaa 2220
ccacaggaaa cgtttgagag cgggattcgg aagacagtgg aatggtatct gtccaataca 2280
aaatgggttg ataatgtgaa aagtggtgcc tatcaatcgt ggattgaaga gaactatgag 2340
ggccgccagt aatgaatatc ctcctttttg gcaaaacagg gcaggtaggt tgggaactac 2400
agcgtgctct ggcacctctg ggtaacttga ttgctcttga tgttcattcc actgattatt 2460
gtggcgattt cagtaacccc gaaggtgtgg ctgaaaccgt caaaaaaatt cgcccagatg 2520
ttattgttaa tgctgctgct cataccgcgg tagataaggc tgagtcagaa ccagaatttg 2580
cacaattact caatgcgacc agcgttgaag caattgcaaa agcggctaat gaagttgggg 2640
cttgggtaat tcattactca actgactacg tcttccctgg aaatggcgac atgccatggc 2700
tcgagactga tgtaaccgct ccgctcaatg tttatggcaa aaccaaattg gctggagaaa 2760
gagcattaca agaacattgc gcaaagcatc ttattttccg taccagctgg gtatatgcag 2820
gtaaaggaaa taactttgcc aaaacaatgt tacgtctggc aaaagagcgc gaagaactgg 2880
ctgtgataaa cgatcagttt ggcgcaccaa caggtgctga attgctggct gattgcaccg 2940
ctcatgccat tcgcgtggca ttaaaaaaac cagaagttgc tggcttgtac catctggtag 3000
caaatggcac aacaacctgg cacgattacg ccgcgctagt attcgaagaa gcccgtaaag 3060
cagggattga ccttgcactt aacaaactca acgccgtacc aacaacggct tatcctactc 3120
cagcccgccg tcctcataat tctcgcctca ataccgaaaa gtttcagcag aactttgcgc 3180
ttgtcttgcc tgactggcag gtgggcgtga aacgtatgct caacgaatta tttacgacta 3240
cggcaattta acaaattttt gcatctcgct catgatgcca gagcgggatg aattaaaagg 3300
aatggtgaaa tgaaaacgcg taaaggtatt attctggctg gtggttccgg cactcgtctt 3360
tatcctgtga cgatggcagt gagtaaacaa ctgctgccga tttatgataa gccgatgatt 3420
tattatccgc tttcaacgct tatgttagcg ggtattcgcg atattcttat tatcagtacg 3480
ccacaggata caccgcgttt ccaacaattg ttgggggacg ggagtcagtg gggcttaat 3540
ctacagtata aagtacaacc gagtccggat ggcctggcgc aagcgtttat tattggtgaa 3600
gactttattg gtggtgatga ttgtgcactc gtacttggcg ataatatctt ctatggacac 3660
gacttgccga aattaatgga agctgctgtt aacaaagaaa tcggtgcaac ggtatttgct 3720
tatcacgtca atgatcctga acgttatggt gtcgtggagt ttgataataa cggtactgca 3780
attagcctgg aagaaaaacc gctggaacca aaaagtaact atgcggttac tgggctttat 3840
ttctatgaca atgatgttgt agaaatggcg aaaaacctta agccttctgc ccgtggcgaa 3900
ctggaaatta ccgatattaa ccgtatttat atggagcagg gacgtttgtc tgtcgctatg 3960
atggggcgtg gttatgcctg gttggatact ggtacacatc aaagtcttat tgaagcaagt 4020
aacttcattg ccaccattga agagcgtcag ggattaaagg tatcttgccc ggaagagatt 4080
gcttaccgta aagggtttat tgatgctgag caggtgaaag tattagccga accgctgaag 4140
aaaaatgatt atggtcagta tctgctaaaa atgattaaag gttattaata aaatgaacgt 4200
aattaaaact gaaattcctg atgtgctgat tttgaacca aaagtttttg gtgatgaacg 4260
tggcttcttt tttgagagtt ttaaccagaa agtatttgaa gaagctgtag gacggaaggt 4320
tgaatttgtt caggataacc attctaagtc taaaataaat gtattgcgtg ggatgcatta 4380
tcaaacacaa aatactcaag gaaaactggt tcgggtaatt tctggttcag tatatgatgt 4440
tgccgtagat ttaagagaaa aatcaaagac atttggcaaa tgggtgggtg tagaattatc 4500
tgggaataat aaaagacaat tgtggatccc cgaaggtttt gcccatggtt tttatgtgtt 4560
ggaggagaat accgaatttg tttataaatg taccgatact tataaccctg ctcatgaaca 4620
cacattgcta tggaatgatc caactatcaa tataagttgg ccaatcatac aaaactgcaa 4680
gccaattatt tctgaaaaag atgctaatgg acatcttttt tcacataaaa cctatttctg 4740
aaatgcaata ttatgagttt aattagaaac agtttctata atattgctgg ttttgctgtg 4800
ccgacattag ttgcagtccc tgctttgggg attcttgcca ggctgcttgg accggagaat 4860
tttggacttt tcacactagc attcgctttg ataggatatg caagtatttt cgacgccggg 4920
attagtcgag ctgtaatcag agaaatcgct ctttatcgag aaagtgaaaa agagcaaata 4980
caaattattt cgacagcaag tgtaatcgta ctattcttag ggtggttgc agctttgtta 5040
ctttatttta gtagtaataa agttgttgag ttattgaatg ttagttccgt ttatattgaa 5100
acagcagtgc gtgcattctc tgttatttca tttataatac ctgtgtatct gattaaccag 5160
atttggcttg gttatctgga agggctagaa aaatttgcaa atataaatgt tcagagaatg 5220
atttctagca caagcttggc tatattacca gtgatatttt gttattacaa tccctcgttg 5280
ctttatgcta tgtatgggtt ggtggttggg cgtgtgattt catttttgat tagcgcaata 5340
atttgtcgag atattattct taaaagtaaa ctttacttta atgtggcaac ttgcaatcgt 5400
cttatctctt ttggtggatg gataacagtt agtaatatca taagcccaat catggcatat 5460
ttcgaccgct ttatcatctc tcatattatg gggcttcga gaattgcatt ttatacagcg 5520
ccctcagagg gtgtatcaag gttaattaat atcccatatg ctttggcaag agctctattt 5580
cctaaattgg catatagcaa taatgatgat gaacgaaaaa aattacaact acagagctac 5640
gcaattataa gcattgtatg tctacccata gttgttattg gtgtcatttt tgcctcattc 5700

-continued

```
ataatgacaa catggatggg acctgattat gccttagaag cagcaactat catgaaaata   5760
cttcttgctg gttttttctt taactcttta gcgcaaatac cttatgcata cttgcaatct   5820
atcggaaagt caaaaattac cgcatttgtg catctcatag aacttgcgcc atacttatta   5880
ttattgtatt acttcacaat gcatttcggc ataattggca cggcaatcgc ttggtcactt   5940
agaacatttt gtgattttgt tatactactt tcgatatcga gaagaaaatg attgcggttg   6000
atattgcgct tgcaacctac aatggtgcta attttattcg gcaacagatt gaatctatcc   6060
agaaacaaac ttatagaaat tggcgtctta taataagtga tgataactcg agtgatgata   6120
ctgttgatat tattaaggat atgatgtcta acgacagtcg tatctatttg gtaggaaata   6180
aaagacaagg aggggttatt cagaacttta attatgctct ttcacaaact acatctgaaa   6240
ttgtgttact atgtgaccag gatgacattt ggccggagga gcgtctggaa attcttatag   6300
ataaatttaa ggccttgcag cgtaatgatt ttgttccggc aatgatgttt actgatttga   6360
aattagtaga cgaaaataat tgtttgattg cagaaagttt ttatcgaacg aataatatta   6420
atccacaaga taatctgaaa aataataatc ttctctggcg ttcaacggta tatggctgta   6480
cttgcatcat gaataagaaa cttgttgata ttgcattgcc tatacctaca tatgcacata   6540
tgcatgatca atggttggca ttattagcga agcaatatgg taacattttt tatttcgact   6600
atgcgtctgt tcgttatagg caacattcta caaatgttgt tggtggtaga aataaaacgc   6660
catttcaaaa atttaattcc atacaaaaaa acctaaaaag gattaatttg ctagtggata   6720
gaactgttgc tttaattaaa tcaaataacg atttctatcc agggaataaa atggaaaata   6780
aaattgatta cttaaaattt ggagtgaatg aagtattacc ttatcttttt aaaggaaaca   6840
agaaagtttt ttcactttgt gtattaatta gtttggcatt acaaaaatga tatatttatt   6900
attttttttt gcactgttta tgatctgtac gtttttaaca cacaggcgac aggcattata   6960
tgttgtatct gcgttagtat ttcttttttt ggctttaacc tatccatcag gaggggactg   7020
gataggttat tttctccatt atgactgcat ggttaatgag cagtgtaata atggttttat   7080
aatgtttgaa cctggatatg aattaattgt ttccttattt ggatatttgg gatttcagac   7140
aattattatt tttatagccg ctgtaaatgt aattctaata ttaaattttg caaagcattt   7200
tgaaaacgga agttttgtta ttgttgcgat aatgtgcatg ttcctttgga gtgtttatgt   7260
tgaggcgatt agacaggctc tggccttatc tatagttata tttgggattc attctctttt   7320
tttgggtaga aaaaggaaat ttataacatt agtattattt gcgtcaactt tccatataac   7380
tgctttgatt tgttttcttc taatgactcc tctattttca aagaaattaa gcaagataat   7440
aagttatagc ctattaattt tcagtagctt ctttttcgct ttttctgaaa ccatattaag   7500
tgcactcctt gcaattttgc cagaaggatc cattgccagt gaaaaattaa gtttttactt   7560
agcaaccgag caatacaggc cacagttatc tattgggagt ggcactattc ttgacattat   7620
acttatttt ctgatatgtg taagttttaa acgaataaag aaatatatgc tcgctaatta   7680
taatgctgca aatgagatat tgcttattgg ttgctgtctt tatatttctt tcggtatttt   7740
tatcgggaaa atgatgccag ttatgactcg cattggttgg tatggttttc catttgttat   7800
agtacttctt tatattaact tgggttattc agaatatttt aagaggtata taaataaaag   7860
agggtgtggg tatagcaaat tattaattgc tttttatttt ttgctacaaa ttttgcgacc   7920
attaacatat gattatagct attataatat aatgcaccag gatactttgc tgaataggtt   7980
tgatgcatta gatgatgcat cattaagaca atcagcgaag agaaaatgtt tcgatttggg   8040
```

-continued aaagatagga tatggtttct tatgtagtat ataatatcct gcattcattc ggataatttc 8100
ctatggaagt gtcctttgct ctgtctgtcc tcatttgttg aaattttatg ttaataagaa 8160
gctttagata accacttagg aactgtatgt ttgatctgtc caaaaattat attattgtaa 8220
gtgcgacggc gctggcttcc ggaggtgcat taactatatt aaagcaattt ataaaacatg 8280
catcacaaaa ttcaaatgac tatattatgt ttgtatctgc gggattggag ttgccggtct 8340
gtgataacat catttacata gaaaacacac caaaaggatg gttgaaaaga atatattggg 8400
attggttcgg ttgtcggaag tttatctcgg aacataagat taacgttaag aaagtaattt 8460
ctctacaaaa ttccagtttg aatgttcctt acgaacagat tatttacttg caccagccaa 8520
ttccttttag taaagttgat tcttttttaa aaaatatcac atccgataac gtaaagcttt 8580
ttttatataa aaagttttat tcctatttta tatttaaata tgtgaatgcc aatacaacca 8640
tcgtagtgca aacgaattgg atgaaaaaag gagtgctgga gcaatgtgat aaaattagta 8700
ccgaaagggt ccttgttata aaacctgata tcaaagcatt taataatact aattttgatg 8760
tagatatgga tgtatctgca aaaacactct tatatccagc gacaccactt acctataaaa 8820
atcatttggt cattctgaag gcgttggtta ttttaaagaa aaagtatttt atagatgatc 8880
tgaaattcca agtgactttt gaaaagaata ggtacaaaaa ttttgataag tttgtgcaat 8940
taaataactt aagcaaaaac gttgattatc tcggcgttct ttcatactcg aacttgcaaa 9000
aaaaatatat ggcggcatct ttaatcgttt ttcctagcta tatcgaatca tatgggttac 9060
cactcatcga agctgctagt ttaggaaaaa aaatcattag tagtgatctt ccttatgccc 9120
gggatgtttt aaaggattat agcggcgtag attttgtaat ttacaataat gaagatggct 9180
gggctaaggc gttgtttaat gttttaaatg gcaattcgaa gctcaatttt aggccttatg 9240
aaaaagatag tcgttcatct tggccacagt tcttctctat tttgaaataa ggtgtattat 9300
gtttaatggt aaaatattgt taattactgg tggtacgggg tctttcggta atgctgttct 9360
aagacgtttt cttgacactg atatcaaaga aatacgtatt ttttcccggg atgaaaaaaa 9420
acaagatgac atgaggaaaa aatataataa tccgaaactt aagttctata taggtgatgt 9480
tcgcgactat tcgagtatcc tcaatgcttc tcgaggtgtt gattttattt atcatgctgc 9540
agctctgaag caagtacctt cctgcgaatt ccacccaatg gaagctgtaa aaacgaatgt 9600
tttaggtacg gaaaacgtac tggaagcggc aatagctaat ggagttaggc gaattgtatg 9660
tttgagtaca gataaagctg tatatcctat caatgcaatg ggtatttcca aagcgatgat 9720
ggaaaaagta atggtagcaa aatcgcgcaa tgttgactgc tctaaaacgg ttatttgcgg 9780
tacacgttat ggcaatgtaa tggcatctcg tggttcagtt atcccattat ttgtcgatct 9840
gattaaatca ggtagaccaa tgacgataac agaccctaat atgactcgtt tcatgatgac 9900
tctcgaagac gctgttgatt tggttcttta cgcatttgaa catggcaata atggtgatat 9960
ttttgtccaa aaggcacctg cggctaccat cgaaacgttg gctattgcac tcaaagaatt 10020
acttaatgta aaccaacacc ctgtaaatat aatcggcacc cgacacgggg aaaaactgta 10080
cgaagcgtta ttgagccgag aggaaatgat tgcagcggag gatatgggtg attattatcg 10140
tgttccacca gatctccgcg atttgaacta tggaaaatat gtggaacatg gtgaccgtcg 10200
tatctcggaa gtggaagatt ataactctca taatactgat aggttagatg ttgagggaat 10260
gaaaaaatta ctgctaaaac ttccttttat ccgggcactt cggtctggtg aagattatga 10320
gttggattca taatatgaaa attttagtta ctggcgctgc agggtttatc ggtcgaaatt 10380
tggtattccg gcttaaggaa gctggatata acgaactcat tacgatagat cgtaactctt 10440

```
ctttggcgga tttagagcag ggacttaagc aggcagattt tatttttcac cttgctgggg  10500
taaatcgtcc cgtgaaggag tgtgaatttg aagagggaaa tagtaatcta actcaacaga  10560
ttgttgatat cctgaaaaaa aacaataaaa atactcctat catgctgagt tcttccatcc  10620
aggctgaatg tgataacgct tatggaaaga gtaaagcagc tgcggaaaaa atcattcagc  10680
agtatgggga aacgacaaac gctaaatatt atatttatcg cttgccgaat gtattcggta  10740
agtggtgtcg accaaattat aactccttta tagcaacttt ctgccatcgc attgcaaatg  10800
atgaagctat tacaattaat gatccttcag cagttgtaaa tctggtgtat atagatgact  10860
tttgttctga catattaaag ctattagaag gagcgaacga aactggttac aggacatttg  10920
gtccaattta ttctgttact gttggtgaag tggcacaatt aatttaccgg tttaaagaaa  10980
gtcgccaaac attaatcacc gaagatgtag gtaatggatt tacacgtgca ttgtactcaa  11040
catggttaag ttacctgtct cctgaacagt ttgcgtatac ggttccttct tatagtgatg  11100
acagaggggt attctgtgaa gtattgaaaa cgaaaaacgc gggccagttt tcgttcttta  11160
ctgcgcatcc aggaattact cggggtggtc attatcatca ttccaaaaat gagaaattta  11220
ttgtcatccg aggaagtgct tgtttcaaat ttgaaaatat tgtcacgagt gaacgatatg  11280
aacttaatgt ttcctctgat gattttaaaa ttgttgaaac agttccggga tggacgcata  11340
acattactaa taatggctcg gatgagctag ttgttatgct ttgggcaaat gaaatattta  11400
atcgttctga accagatact atagcgagag ttttatcgtg aaaaaattga aagtcatgtc  11460
ggttgttggg actcgtccag aaattattcg actctcgcgt gtccttgcaa aattagatga  11520
atattgtgac caccttattg ttcataccgg gcaaaactac gattatgaac tgaatgaagt  11580
tttttcaaa gatttgggtg ttcgcaaacc tgattatttt cttaatgccg caggtaaaaa  11640
tgcagcagag actattggac aagttatcat taaagttgat gaggtccttg aacaggaaaa  11700
accagaagcc atgttagtac ttggcgatac taactcctgt atttcagcaa taccagcaaa  11760
gcgtcgaaga attccgatct tccatatgga ggctgggaat cgttgttttg accaacgcgt  11820
accggaagaa actaacagaa aaatagttga tcataccgct gatatcaata tgacatatag  11880
tgatatcgcg cgtgaatatc ttctggctga aggtgtacca gccgatagaa ttattaaaac  11940
cggtagccca atgtttgaag tactcactca ttatatgccg cagattgatg gttccgatgt  12000
actttctcgc ctgaatttaa cacctgggaa tttctttgtg gtaagtgccc acagagaaga  12060
aaatgttgat accccctaaac aacttgtgaa actggcgaat atacttaata ccgtggctga  12120
aaaatatgat gtcccggtag ttgtttctac tcatcctcgc actcgtaacc gcatcaacga  12180
aaacggtatt caattccata aaaatatctt gcttcttaag ccattaggat ttcacgatta  12240
caaccatctg caaaaaaatg cacgtgctgt tttatcggat agtgggacta ttacagaaga  12300
gtcctccatt atgaacttcc ctgcactcaa tatacgagaa gcgcacgaac gcccggaagg  12360
cttcgaagaa ggggcagtaa tgatggtcgg tcttgaatct gatcgcgttt tacaggcatt  12420
agaaattatt gcaacacagc ctcgtggaga agtacgctta cttcgtcagg ttagtgacta  12480
tagcatgcca aatgtttcag ataaagttct gcgtattatc cattcatata ctgactacgt  12540
taaacgggtt gtctggaagc aatactaatg aaacttgcat taatcattga tgattatttg  12600
ccccatagca cacgcgttgg ggctaaaatg tttcatgagt taggccttga attactgagc  12660
agaggccatg atgtaactgt aattacgcct gacatctcat tacaagcaat ttattctatt  12720
agtatgattg atggtataaa ggtttggcgt ttcaaaagtg gacctttaaa ggatgtaggt  12780
```

```
aaggctaaac gtgccataaa tgaaactctt ttatcttttc gcgcatggcg cgcatttaag  12840

cacctcattc aacatgatac atttgatggt atcgtttatt attccccctc tatttttttgg 12900

ggcgacttgg ttaaaaaaat aaaacaacga tgccagtgcc caagctatct gatcctaagg  12960

gatatgtttc cacagtgggt cattgatgca ggtatgttga aagccggttc accaattgaa  13020

aaatatttta ggtattttga aaaaaagtca tatcagcagg ctggccggat aggggtaatg  13080

tctgataaga atcttgagat atttcgccag accaataaag gttatccgtg tgaagtttta  13140

cgtaattggg cctcaatgac tcctgtgtct gccagcgatg attatcattc acttcgtcaa  13200

aaatacgatc taaaagataa agtcattttt ttctatggcg gtaatattgg gcatgctcag  13260

gatatggcaa acttaatgcg ccttgcgcgt aatatgatgc gttatcatga tgctcatttc  13320

ctgtttatag ggcagggtga tgaagttgag ctgataaaat ctcttgctgc agaatggaat  13380

ttaactaatt tcactcatct accttcagtg aaccaggaag agtttaaatt aattttatct  13440

gaagttgatg tcggcctgtt ctccctttca tctcgccatt cttcacataa tttccccgga  13500

aaattactag ggtatatggt tcaatcaatc ccgatccttg ggagtgtgaa tggcggcaat  13560

gatttaatgg atgtaattaa taagcacaga gccggtttca ttcatgttaa tggtgaagat  13620

gataaactgt ttgaatctgc acaattgctt cttagtgatt cagttttaag aaaacagcta  13680

ggtcagaacg ctaatgtgtt gttaaagtct caattttcgg ttgaatcggc ggcacatact  13740

atcgaagtcc gactggaggc tggagaatgc gtttagttga tgacaatatt ctggatgaac  13800

tttttcgcac tgcagcaaat tctgaacgtt tgcgcgctca ttatttattg cacgcatctc  13860

atcaggagaa ggttcaacgt ttacttattg catttgtacg cgacagctat gttgaacccc  13920

attggcatga gttaccgcat cagtgggaaa tgtttgtcgt catgcaaggg caattagaag  13980

tttgtttgta tgagcaaaat ggtgagatcc aaaaacagtt tgttgttgga gacggtacgg  14040

gaataagcgt cgtggaattt tccccaggag atatacatag tgtcaaatgc ctgtcaccaa  14100

aagcccttat gttggagata aaggaggggc catttgaccc actcaaagct aaggcttttt  14160

ctaagtggtt atagggcgat acaccaccgt ttattcttct atcttattct atacatgctg  14220

ggttaccatc ttagcttctt caagccgcgc aaccccgcgg tgaccacccc tgacaggagt  14280

agctagcatt tgaccacccc tgacaggatt agctagcata tgagctcgag gatatctact  14340

gtgggtaccc gggatccgtg taggctggag ctgcttcgaa gttcctatac tttctagaga  14400

ataggaactt cggaatagga actaaggagg atattcatat                        14440
```

<210> SEQ ID NO 10
<211> LENGTH: 19
<212> TYPE: PRT
<213> ORGANISM: Artificial Sequence
<220> FEATURE:
<223> OTHER INFORMATION: example signal sequence for EPA carrier protein

<400> SEQUENCE: 10

```
Met Lys Lys Ile Trp Leu Ala Leu Ala Gly Leu Val Leu Ala Phe Ser
1               5                   10                  15

Ala Ser Ala
```

<210> SEQ ID NO 11
<211> LENGTH: 13043
<212> TYPE: DNA
<213> ORGANISM: Artificial Sequence
<220> FEATURE:
<223> OTHER INFORMATION: example O1A rfb locus nucleotide sequence - O1A-EPA production strain stGVXN4411 and stLMTB10217

<400> SEQUENCE: 11

```
atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag ggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat tttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagcta gcgtgaagat acttgttact aggggcgcag gatttattgg ttctgctgta   1320
gttcgtcaca ttataaataa tacgcaggat agtgttgtta atgtcgataa attaacgtac   1380
gccggaaacc tggaatcact tgctgatgtt tctgactctg aacgctatgt ttttgaacat   1440
gcggatattt gcgatgctgc tgcaatggcg cggatttttg ctcagcatca gccggatgca   1500
gtgatgcacc tggctgctga aagccatgtg gatcgttcaa ttacaggccc tgcggcattt   1560
attgaaacca atattgttgg tacttatgtc cttttggaag cggctcgcaa ttactggtct   1620
gctcttgatg gcgacaagaa aaatagcttc cgttttcatc atatttctac tgacgaagtc   1680
tatggtgatt tgcctcatcc tgacgaagta aataataaag aacaattacc cctctttact   1740
gagacgacag cttacgcgcc tagtagtcct tattccgcat caaaagcatc cagcgatcat   1800
ttagtccgcg cgtggaaacg tacctatggt ttaccgacta ttgtgactaa ctgttcgaat   1860
aactacggtc cttatcactt tccggaaaaa ttgattccac tagtaattct taatgctctg   1920
gaaggtaagg cattacctat ttatggcaaa ggggatcaaa ttcgtgactg gctgtatgtt   1980
gaagatcatg cgcgtgcgtt atataccgta gttactgaag gtcaagcggg tgaaacctat   2040
aacattggcg gacacaacga aaagaaaaac atcgatgttg tgctgactat ttgtgatttg   2100
ttggacgaga tagtcccgaa agagaaatct tatcgtgagc aaattactta tgttgctgat   2160
cgcccagggc atgatcgccg ttatgcgatt gatgctgaga agattggtcg cgaattggga   2220
tggaaaccac aggaaacgtt tgagagtggg attcgtaaaa cggtggaatg gtatttggct   2280
```

-continued

```
aatgcaaaat gggttgataa tgtgaaaagt ggtgcctatc aatcgtggat tgaacagaac   2340
tatgagggcc gccagtaatg aatatcctcc tttttggcaa aacagggcag gtaggttggg   2400
aactacagcg tgctctggca cctctgggta atttgattgc tcttgatgtt cactccactg   2460
attactgtgg tgattttagt aaccctgaag gtgtggctga aacagtcaaa agaattcgac   2520
ctgatgttat tgttaatgct gcggctcaca ccgcagtaga taaggctgag tcagaacccg   2580
aatttgcaca attactcaat gcgactagcg ttgaatcaat tgcaaaagcg gcaaatgaag   2640
ttggggcttg ggtaattcat tactcaactg actacgtatt ccctggaaat ggcgacacgc   2700
catggctgga gatggatgca accgcaccgc taaatgttta cggtgaaacc aagttagctg   2760
gagaaaaagc attacaagag cattgtgcga agcacctaat tttccgtacc agctgggtct   2820
atgcaggtaa aggaaataat ttcgccaaaa cgatgttgcg tctggcaaaa gagcgtgaag   2880
aactagccgt tattaatgat cagtttggtg cgccaacagg tgctgaactg ctggctgatt   2940
gtacggcaca tgccattcgt gtcgcactga ataaaccgga tgtcgcaggc ttgtaccatt   3000
tggtagccag tggtaccaca acctggtacg attatgctgc gctggttttt gaagaggcgc   3060
gcaatgcagg cattcctctt gcactcaaca agctcaacgc agtaccaaca actgcctatc   3120
ctacaccagc tcgtcgtcca cataactctc gccttaatac agaaaaattt cagcagaatt   3180
ttgcgcttgt attgcctgac tggcaggttg gtgtgaaacg catgctcaac gaattattta   3240
cgactacagc aatttaatag tttttgcatc ttgttcgtga tggtggagca agatgaatta   3300
aaaggaatga tgaaatgaaa acgcgtaaag gtattatttt agcgggtggt tctggtactc   3360
gtctttatcc tgtgactatg gtcgtcagta aacagctatt acctatatat gataaaccga   3420
tgatctatta tccgctttct acactgatgt tagcgggtat tcgcgatatt ctgattatta   3480
gtacgccaca ggatactcct cgttttcaac aactgctggg tgacggtagc cagtggggcc   3540
tgaatcttca gtacaaagtg caaccgagtc cggatggtct tgcgcaggca tttattatcg   3600
gtgaagagtt tattggtggt gatgattgtg ctttggtact tggtgataat atcttctacg   3660
gtcacgacct gcctaagtta atggatgccg ctgttaacaa agaaagtggt gcaacggtat   3720
ttgcctatca cgttaatgat cctgaacgct atggtgtcgt tgagtttgat aaaaacggta   3780
cggcgatcag cctggaagaa aaaccgctac aaccaaaaag taattatgcg gtaaccgggc   3840
tttattttta tgataacgac gttgtcgaaa tggcgaaaaa tcttaagcct tctgcccgcg   3900
gtgaactgga aattaccgat attaaccgta tctatatgga acaagggcgt ttatctgttg   3960
ccatgatggg gcgtggttat gcgtggttag acacggggac acatcagagc ctgattgagg   4020
caagcaactt tattgcaaca attgaagagc gtcaggggct gaaagtttcc tgcccggaag   4080
aaattgctta ccgtaaaggg tttgttgatg ctgagcaggt gaaagtatta gctgaacctc   4140
tgaaaaaaaa tgcttatggt cagtatctgc tgaaaatgat taaaggttat taataaaatg   4200
aacgtaatta aaacagaaat tcctgatgta ctgatttttg aaccgaaagt ttttggtgat   4260
gagcgtggtt tctttttga gagctttaac cagaaggttt ttgaggaagc tgtaggccgc   4320
aaagttgaat ttgttcagga taaccattcg aagtctagta aaggtgtttt acgcgggctg   4380
cattatcagt tggaacctta tgcacaagga aaattggtgc gttgcgttgt cggtgaagtt   4440
tttgacgtag ctgttgatat tcgtaaatcg tcatcgactt ttggcaaatg ggttggggtg   4500
aatttatctg ctgagaataa gcggcaattg tggattcctg agggatttgc acatggtttt   4560
ttagtgctga gtgagacggc ggagtttttg tataagacga caaattatta tcatcctcag   4620
agtgatagag gaataaaatg ggatgatcca agcatcaata tttcatggcc agtcgattca   4680
```

caagtgctgc tatcagctaa agataataag catcctccat taacaaagat tgaaatgtat 4740
agttaagatc acgataaatc ttggaagggt tgcaaaattg aataaaatag tgagcaaaag 4800
tgaaataagg aacgtaatcc acaatgctgg ctatatgatg attactcaga tagctttata 4860
tgttgcacca ttatttatac tgagttatct gttaaaaaca ctgggggttg cacagtttgg 4920
taattatgcc ttaatactat caatcgttgc atatttacag attataacgg attatggttt 4980
ttcttttagt gcaagtcgtg cgatctcaca gaatagagag gacaaagaat atatatcaaa 5040
aatttatctg tcaactatga ctatcaagtt ggcgatatgc gctttcttat tcttattgct 5100
catgctattt ttaaatcttt tgcctgtgca agctgaatta aaacaaggaa tattatatgg 5160
atatcttctt gtaataggaa atactttcca accacaatgg tttttccaag gtatcgaaaa 5220
attaaaaatc atagcccttt ctaatgttat atcaagatgc gccgcgtgtt tacttgtatt 5280
tatctatgtg aggaatagcg aggatttaca aaaagcactt ttagtacagt cacttccatt 5340
agtaatttct gcgattggat taaatatatt tatattgaaa tatatcaata ttatttttcc 5400
ggaaaaaaaa ttatttaagg taattttaaa agaaggtaag gatttttttc ttgcatcact 5460
ttattctgtt attctcaata atagtggcat ttttctatta gggattttta ctaatcctgt 5520
tattgttggt gtatatgccg ccgctgaaaa gatagtcaag gccgtattgt cgctatttac 5580
accactgacg caagctatat atccttataa ttgtcgtaag ttttcactat ccgtatttga 5640
cggcattgag gcagcaaaaa aaactggtat accaattata attttagcat ttatagctgc 5700
tgttatcgtt gcaattacct tacctgttgc aatcgactat cttaattttc caaaagaaac 5760
aatttttgta ggtcaaatat taagtgcatg gatctttttt ggtgttctta ataatgtatt 5820
cggcattcag atattgagtg catcaggaag aagtaaaata tatagtagga tggtattcgt 5880
atcagcgctt ataacattac ttttgattac tctattattg cagttttgta acgccactgg 5940
agtggcatgt gcaatattat tgggtgaaat gttcttatca atattgttac ttaagcgata 6000
taaaaaaata atttaaggaa tagttatgaa gaagttatta ttagtgttcg gtactaggcc 6060
tgaagcaata aagatggcct ctatcattga attattaaaa aaagattgta gattcgaata 6120
taaaatatgt gtgacaggcc aacataaaga gatgcttgat caagttatgc aagtatttga 6180
tgttaaacct gattataatt tacggattat gcagcctggg caaacattag tatctatagc 6240
aacaaatata ctctcacggt taagtgaagt tttaattata gaaaagccag atattatact 6300
tgtgcatggg gatacaacga ctacccttgc tgctacttta gctgggtatt accaccaaat 6360
aaaagtttgt catgtggaag caggattaag aacaggggat atttactctc cttggcctga 6420
agagggcaat cgtaaagtta caggggcatt agcatgtatt catttcgccc caacagagag 6480
atcaaaagat aatctcctga gggagggggt caaagtaaat aatatatttg taacgggtaa 6540
taccgtcatc gactctttat ttattgcaaa agatatcata gataatgacc ctaatataaa 6600
gaacgcttta cataataaat ttaattttct tgataaaagc cgacgagtag tacttataac 6660
aggtcatcga agagaaaatt tcgggaaagg ttttgaagat atatgctttg caataaagga 6720
attagctttc atttatccta atgtagattt tatttatccg gtgcatctta atcccaatgt 6780
aatggaacca gtacatcgta tattagataa tatatgtaat atttacctta ttgagccctt 6840
ggattatttg ccttttgttt atttaatgaa tgagtcatat ttaatattga ctgattcagg 6900
ggggatacaa gaagaagcgc cttcgttagg taaaccggtt ttggttatgc gtgatactac 6960
tgaacgccct gaggcggttg aggctggtac tgttgtatta gtggggactt ctaagataaa 7020

-continued

```
aatagtaaat aaagtaacgg agctattaaa caatgctgat atctacaatg ctatgtctct   7080
gttacataat ccatatggcg atggaacagc tgctcaaaaa attcttaatg tgctcgccca   7140
agagctaatt taatttaagc taaaaatatg ttattaatta ttgctgatta tccaaacgaa   7200
atgaatatgc gcgagggagc tatgcaacga atagatgcga tagactctct cattcgagat   7260
cgcaagcgag tgtatttgaa tatttcattc aaaaagcatc tagttcgctc aaatagttcc   7320
tttaataatg ttatagttga aaatctaaat gcaattattc acagaaacat cataaaacag   7380
tacatgcaaa aatcaacaac tatatatgtt cattctgttt ataatttatt aaaggttata   7440
acgctcattg atctaaaaaa aacaattctt gatatacatg gtgttgtacc ggaagaactt   7500
ttggcagata ataaaaaatt acttagtaaa gtatataaca tggtggaaaa aaaaggtgtc   7560
cttggatgca aaaaattaat acacgtcagt acagaaatgc aaaaacacta tgaagcaaaa   7620
tatggagtaa acttggctga aaggtcaata gtgctcccga tttttgaata taaaaatata   7680
acccaatcgc aaaacaaatg gacagaaaat aaaatacgaa gtatctatct tggaggatta   7740
caaacatggc aaaatattga taaaatgatt caagtttgtg atgacacagt gataaacaat   7800
gaagcaggta agtatgaatt caactttttc atcccacaga gtaacttgga agggtttata   7860
gataaatatt cgttaaaatt acataaatatc aatgctaatg catctacgct atcacgtgat   7920
gaagtaattc cctttctaaa agaatgtcat attggttttg tattgcgcga tgatataata   7980
gtaaacagag ttgcgtgccc tacaaaattg gttgaatatt tagagtgtgg tgtcgttcca   8040
gttgtgctct ccccacttat aggtgatttt tattcgatgg gatatcaata cattactaca   8100
gaggaaatgg ctaacagaag tataagtttg ttggatcttg aaaaaatggc tgcacataat   8160
ttacaaattt tgacttctta tcagaagaga acctacaagg cacagaaaga acttattgct   8220
caactgtgct gaattttta catatataaa attatgtaag catatcgcgg gtcaggtaat   8280
tgtatgcgta tcaaatataa agataacggt tatatattat gttttctatt atgtttcatt   8340
ttgagctact tagttttact caaatctgac tactttcctg ctgattttct gccatataca   8400
gaaatatacg atgggacata cggagaaatc aataatattg agcctgcctt tttatattta   8460
acacggttgt ttcattattt aaatttcccc tatatatttt ttgcaatgtt agtttgtgcc   8520
ttatgtttaa gttggaaaat aaaatatgca agaaaaaataa ttaaagatag ttatatatat   8580
ttgttcttgt atgtatatgt atcattttat gtgtttttgc atgaaatgac tcaattgcgc   8640
atagcaattg cagtcactat gtgctatgtg tcggtttatt attactttta taaaaattgt   8700
attaaacatg cactgccatg gatggtgttg gctattttgt ttcattacag cgccttgctt   8760
ttatttatgt cattatttat atacagttat aggaggttat taatagtaat tatagggttt   8820
gtaaatatgta tgagcttttt aaacgtgtat gcagatacaa ttgcactata tttgccaaat   8880
gaaaaaatag taaattattt atatagtatt tcatcatcat tagacaatag aaatgatttg   8940
gcaatattca acctgaataa tataatattt ttatcaatat ttattttgat cttttatctt   9000
agccgatata taaaattaaa tgataatgag gcgaagttta ttaagtatgt gcaatgttca   9060
ggaatattag ccttttgtat tttctttctg gctagtggag tcccggtcat tgcttatcga   9120
actgcagagt tgctgcgaat attttatccg atggctttag tattaatcct ttcgcatata   9180
aaaaataata atatgcgtta ttttattgca gtcattatag ttatcctttc aggcttaatg   9240
ttgtttataa cactaagggc tgtatcaata gttggtcaag gattataaaa tgaatgttgc   9300
tattttgttg tctacgtata atggcgaaaa atatttagag gaacaactgg attcattgct   9360
gcttcaaagt tatcaggatt ttgtagtgta tatccgtgat gacggatcat ctgatagaac   9420
```

-continued

```
tgtaaatata ataaaccaat acgtaatgaa agataacaga tttattaacg tgggtaattc   9480
agaaaatctt ggttgtgctg cttcgtttat taatttatta agaaatgctt cagccgatat   9540
ttatatgttt tgtgaccaag atgattattg gcttccgaat aaattacagc gtgctgtgga   9600
ttatttttcg gctattgatc ctttacaacc taccttgtat cattgcgatc taagcgttgt   9660
tgatgaaaaa cttaatatta tacaaaattc atttttgcag catcagaaaa tgtcagcgta   9720
tgattcaatg agaaaaaata atcttttcat acaaaatttt gttgttggtt gttcatgtgc   9780
tgttaatgct tcacttgcgg aatttgttct ttcgcgaatt ggagagcagc atgtaaaaat   9840
gatagctatg catgactggt ggttagccgt gactgcaaaa ctttttggtc gaatccattt   9900
tgataatact caaacgattc tttatcgaca acatcagggc aatgtattag gtgcaaaatc   9960
atcaggtatg atgcgtttta ttcgattagg attaaatggg caagggattt cgcgagtagt  10020
atcttttaga aaaaaagttt gtgcgcaaaa taagcttctt ttagatgtct atgataaaga  10080
tttaaatctt gagcaaaaaa aatctatcag gcttgtaatt gagggcctta aagagaactc  10140
ttcaattgct gaccttttaa aatgtttcta tcatggtagc tatatgcaag gttttaaacg  10200
taatcttgcc ttaatatatt cagttcttta cacaaaaaaa agaagatagt gtatccttat  10260
gaaaaaaatt gctattatcg gtactgttgg cataccagca tcatatggcg gatttgaaac  10320
attagttgaa aatttaacaa gatacaattc ctcgggagtt gaatataatg tttttttgttc  10380
atcgtttcac tacaaatccc accaaaaaaa acataatggg gcccgtttaa tttatattcc  10440
gcttaaagcc aatggatggc agagcattgc gtatgacata atttcgttag catattctat  10500
tttttgaag cctgatgtga ttctgatttt aggggtttct ggttgttcat ttttgccttt  10560
cttcaaactc ttaacacgcg ctaagtttat tactaatatt gatggcctgg aatggcgaag  10620
agataaatgg aattcaaaag tgaaacgttt cttaaaattt tcagaaaaaa tcgcagttca  10680
atattcggat gtcgttatta cggataatga ggcaatttct gagtacgttt ttaacgagta  10740
taataaagat agccgagtta ttgcctatgg aggggatcat gcatggttaa atactgagga  10800
tgtatttaca acaagaaatt ataaaagcga ttactacctt tctgtatgtc gtatcgaacc  10860
cgaaaacaat gtagaattaa ttttaaaaac attttcaaag ctaaaatata aaataaaatt  10920
tattggaaat tggaatggca gcgagtttgg aaagaaactt aggctgcatt attctaacta  10980
tccaaatatt gaaatgattg atccgattta tgatcttcaa caattatttc acttacgaaa  11040
taattgcata ggatatatac atggtcattc ggctggagga acaaaccctt ctttagtcga  11100
ggcaatgcat tttagtaaac ctatatttgc atatgattgt aagtttaata ggtacactac  11160
tgaaaatgaa gcatgttatt tttctaatga atctgacctc gcagagaaaa tcataatgca  11220
ttgtgagcta tcattaggtg tctctggcac gaaaatgaaa gaaattgcta accagaaata  11280
cacttggaga cgaatagcag aaatgtatga ggattgctat taactctgtt aaacttcaaa  11340
tcttttacaa tatatggcat gactataagc gcattaattg tttttcaagc cgctctcgcg  11400
gtgaccaccc cctgacaggg gatccgtgta ggctggagct gcttcgaagt tcctatactt  11460
tctagagaat aggaacttcg gaataggaac taaggaggat attcatatgg ataaagccgt  11520
aagcatataa gcatggataa gctatttata ctttaataag tactttgtat acttatttgc  11580
gaacattcca ggccgcgagc attcagcgcg gtgatcacac ctgacaggag tatgtaatgt  11640
ccaagcaaca gatcggcgta gtcggtatgg cagtgatggg acgcaacctt gcgctcaaca  11700
tcgaaagccg tggttatacc gtctctattt tcaaccgttc ccgtgagaag acggaagaag  11760
```

```
tgattgccga aaatccaggc aagaaactgg ttccttacta tacggtgaaa gagtttgtcg  11820
aatctctgga aacgcctcgt cgcatcctgt taatggtgaa agcaggtgca ggcacggatg  11880
ctgctattga ttccctcaaa ccatatctcg ataaaggaga catcatcatt gatggtggta  11940
acaccttctt ccaggacact attcgtcgta atcgtgagct ttcagcagag ggctttaact  12000
tcatcggtac cggtgtttct ggcggtgaag agggggcgct gaaaggtcct tctattatgc  12060
ctggtggcca gaaagaagcc tatgaattgg tagcaccgat cctgaccaaa atcgccgccg  12120
tagctgaaga cggtgaacca tgcgttacct atattggtgc cgatggcgca ggtcactatg  12180
tgaagatggt tcacaacggt attgaatacg gcgatatgca gctgattgct gaagcctatt  12240
ctctgcttaa aggtggcctg aacctcacca acgaagaact ggcgcagacc tttaccgagt  12300
ggaataacgg tgaactgagc agttacctga tcgacatcac caaagatatc ttcaccaaaa  12360
aagatgaaga cggtaactac ctggttgatg tgatcctgga tgaagcggct aacaaaggta  12420
ccggtaaatg gaccagccag agcgcgctgg atctcggcga accgctgtcg ctgattaccg  12480
agtctgtgtt tgcacgttat atctcttctc tgaaagatca gcgtgttgcc gcatctaaag  12540
ttctctctgg tccgcaagca cagccagcag gcgacaaggc tgagttcatc gaaaaagttc  12600
gtcgtgcgct gtatctgggc aaaatcgttt cttacgccca gggcttctct cagctgcgtg  12660
ctgcgtctga agagtacaac tgggatctga actacggcga aatcgcgaag attttccgtg  12720
ctggctgcat catccgtgcg cagttcctgc agaaaatcac cgatgcttat gccgaaaatc  12780
cacagatcgc taacctgttg ctggctccgt acttcaagca aattgccgat gactaccagc  12840
aggcgctgcg tgatgtcgtt gcttatgcag tacagaacgg tattccggtt ccgaccttct  12900
ccgcagcggt tgcctattac gacagctacc gtgctgctgt tctgcctgcg aacctgatcc  12960
aggcacagcg tgactatttt ggtgcgcata cttataagcg tatcgataaa gaaggtgtgt  13020
tccataccga atggctggat taa                                          13043
```

<210> SEQ ID NO 12
<211> LENGTH: 13790
<212> TYPE: DNA
<213> ORGANISM: Artificial Sequence
<220> FEATURE:
<223> OTHER INFORMATION: example O2 rfb locus nucleotide sequence - O2-
EPA production strain stGVXN4906

<400> SEQUENCE: 12

```
atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
```

-continued

```
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagtga aaatacttgt tactggtggc gcaggattta ttggttcagc tgtagttcgt   1320
cacattataa ataatacgca ggatagtgtt gttaatgtcg ataaattaac gtacgccgga   1380
aaccgggaat cacttgctga tgtttctgat tctgaacgct atgtttttga acatgcggat   1440
atttgcgatg cacctgcaat ggcacggatt tttgctcagc atcagccgga tgcagtgatg   1500
cacctggctg ctgaaagcca tgttgaccgt tcaattacag gccctgcggc atttattgaa   1560
accaatattg ttggtactta tgtccttttg gaagccgctc gcaattactg gtctgctctt   1620
gatagcgaca agaaaaatag cttccgtttt catcatattt ctactgacga agtctatggt   1680
gatttgcctc atccagatga agtaaataat acagaagaat taccccttatt tactgagacg   1740
acagcttacg cgccaagcag cccttattcc gcatccaaag catccagcga tcatttagtc   1800
cgcgcatgga aacgtacgta tggtttaccg accattgtga ctaattgctc gaacaactat   1860
ggtccgtatc acttcccgga aaagcttatt ccattggtta ttcttaatgc actggaaggt   1920
aaggcattac ctatttatgg caaaggggat caaattcgcg actggttgta tgtagaggat   1980
catgctcgtg cgttatatac cgtcgtaacc gaaggtaaag cgggtgaaac ttataacatt   2040
ggcggacaca acgaaaagaa aaacatcgat gttgtgctga ctatttgtga tttgttggat   2100
gagattgtac cgaaagagaa atcttatcgt gagcaaatta cttatgttgc tgatcgccca   2160
gggcatgatc gccgttatgc aattgatgcc gataaaatta gccgcgaatt gggctggaaa   2220
ccacaggaaa cgtttgagag cgggattcgc aaaacggtgg aatggtatct ggctaataca   2280
aattgggttg agaatgtgaa aagcggtgct tatcagtcat ggatcgaaca aaactatgag   2340
ggccgtcagt aatgaatatc ctgcttttcg gcaaaacagg gcaggtgggt tgggaactgc   2400
agcgtgctct ggcgccgctg ggtaatctga tcgctcttga tgttcactcc actaattatt   2460
gtggagattt cagcaacccc gaaggtgtgg cagaaaccgt caaaaaaatt cgtcctgacg   2520
ttattgttaa tgctgctgct cacactgcag tagataaagc agaatcagaa ccggatttcg   2580
cacaattact taacgcgaca agcgtcgaag cgattgcaaa agctgctaat gaagtcgggg   2640
cctgggttat acactactct actgattatg ttttcccagg cagtggtgac gcgccatggc   2700
tggaaacgga tgcaacagca ccgctaaatg tttacggtga aacaaaatta gctggggaaa   2760
aggcattaca agaacattgc gcaaagcatc ttattttccg taccagctgg gtatacgctg   2820
gtaaaggaaa taactttgct aaaacgatgt tgcgtttggc aaaagaacgc gaagaactgg   2880
ctgtgataaa cgatcagttt ggcgcaccaa caggtgctga attgctggct gattgcaccg   2940
ctcatgccat tcgcgtggca ttaaaaaaac cagaagtcgc tggcttgtac catctggtag   3000
caagtggcac aacaacctgg cacgattatg ctgcgctggt ttttgaagag gcgcgcaaag   3060
cagggattaa tcttgcactt aacaaactta acgccgtgcc aacaacggcc tatcccacac   3120
```

cagcccgtcg accccataac tctcgcctca atacagaaaa gtttcagcag aactttgcgc 3180
ttgtcttgcc tgactggcag gtgggcgtga aacgtatgct caacgaatta tttacgacta 3240
cggcaattta acaaattttt gcatctcgct catgatgcca gagcgggatg aattaaaagg 3300
aatggtgaaa tgaaaacgcg taaaggtatt attctggctg gtggttccgg cactcgtctt 3360
tatcctgtga cgatggcagt gagtaaacaa ttgctgccga tttatgataa gccgatgatt 3420
tattatccgc tttcaacgct tatgttagcg ggtattcgcg atattcttat tattagtacg 3480
ccacaggata caccgcgttt ccaacaatta ttgggggacg ggagccagtg ggtcttaat 3540
ctacagtata aagtacaacc gagtccggat ggcctggcgc aagcgtttat tattggcgaa 3600
gactttattg gtggtgatga ttgtgcactc gtacttggcg ataatatctt ctatggacac 3660
gacttgccga aattgatgga agctgctgtt aacaaagaaa gcggtgcaac ggtatttgct 3720
tatcacgtta atgatcctga acgctatggt gtcgtggagt ttgataataa cggtacggca 3780
attagcctgg aagaaaaacc gctggagcca aaaagcaact atgcggttac tgggctttat 3840
ttctatgaca atgacgttgt ggaaatggct aaaaacctta agccttctgc ccgtggcgaa 3900
ctggaaatta ccgatattaa ccgtatttat atggaacaag gacgtttgtc tgtagccatg 3960
atggggcgtg gctatgcatg gttggataca gggacgcatc aaagccttat tgaagcaagt 4020
aacttcattg caacaattga agagcgtcag ggattaaagg tatcttgccc ggaagagatt 4080
gcttaccgta aagggtttat tgatgccgag caggtgaaag tattagccga accgcttatc 4140
aagaatcaat atggtcaata tttgctgaaa atgatcagcg aatagtatat gggaactcaa 4200
tgatggatat taaattaatc tctttgcaaa aacatgggga tgagcgcggt gcattaattg 4260
ctcttgaaga gcaacgaaat atacctttcg aagtcaaaag aatatattac atacttgaga 4320
ctcttaatgg agtaagacgc ggatttcatg cgcacaaggt tactcgtcag ttagctattg 4380
tagtcaaggg agcttgtaaa tttcatctgg ataatggtaa agaaacaaag caggtggaac 4440
ttaatgatcc aacaattgcg ttgctgatag aaccctatat atggcatgaa atgtatgatt 4500
ttagtgatga ttgtgtgctg cttgtaattg cggatgattt ctataaagag tctgattata 4560
tccgcaatta tgatgatttt attagaagag taaattcaat tgagaattca taagctaagt 4620
gacgtccaga caacatcaat tggtgatgga acaactatct ggcagtttgt tgtgatacta 4680
aaaggtgctg taattggtaa taattgcaac atctgtgcaa ataccttaat tgaaaataac 4740
gttgtaattg gtaacaatgt cacagtcaaa agcggtgtgt atatttggga tggcgttaaa 4800
atagaggata atgtttttat tggtccttgt gtagcattta caaatgataa gtatcctcgc 4860
tctaaagtct atcctgatga atttttgcaa acaataatac gcaaaggagc atcaataggt 4920
gctaacgcaa ccatcctgcc aggaattgaa attggtgaaa aagcaatcgt tggtgcgggg 4980
agtgttgtaa ccaaaaatgt accgccatgc gcaatagtag taggtaatcc agctcgattt 5040
attaaatggg tagaggataa tgaataaaat tgattttta gatcttttg caattaacca 5100
gcgacagcac aaagaattag tctctgcgtt tagtagggtg ctagattctg gttggtatat 5160
catgggcgaa gaacttgagc agttcgagaa agagttcgca gaatactgtg gagttaagta 5220
ttgcattggt gtagcaaatg gccttgatgc gttgatacta gtattgaggg catggaaaga 5280
acttggctat cttgaagacg gtgacgaggt attagtaccg gcaaatacat atattgcttc 5340
tattcttgct ataacagaga acaaacttgt tcctgttctt gttgaaccag atatagaaac 5400
ttataatatt aatcctgctt taattgaaaa ttacattacg gaaaaaacta aagcaatatt 5460

-continued

```
accggttcac ttatatggtc tattgtgcaa tatgccagaa attagtgcaa tcgccagaaa   5520
atataatctg ttgattcttg aagattgtgc acaagcacat ggtgcaatac gtgatggtcg   5580
caaagctgga gcttgggggg atgctgcagg atttagtttt tatccaggaa aaaaccttgg   5640
agctttgggg gatgcgggag ctgttactac aaataatgca gaattatcct caactataaa   5700
agctttgcga aattatgggt cacataagaa atatgaaaat atttatcagg gattgaatag   5760
tcgattggat gaactgcaag cagccttatt gcgtgtaaaa atccatacat taccggaaga   5820
tactgcgatt cggcaaagga ttgctgaaaa atatattcgt gaaataaaaa accctgcgat   5880
tacgttacca gtgtacgaag gccaaggtgc gcatgtttgg catttatttg tagtaagaat   5940
cgctaatcgt gaaaaattcc agtcatactt attagagaag ggtatcaaaa ccttaattca   6000
ctatccatta ccaccccata agcagcaagc atatcaaaat atgtctagcc ttagccttcc   6060
aattactgag caaattcatg atgaagtcat ttctttacct ataagtccgg taatgagtga   6120
agatgatgtc aattatgtaa tcaaaatggt caatgattac aagtaatgaa aaaatttctt   6180
caggtaacta tattatccgc tatctataca ttcattaaaa tgattgcggg ttttatcatc   6240
ggtaaggtag tagcaattta tacagggcca tcaggggtag caatgcttgg ccaagtgcaa   6300
agtttaatca caatagttgc aggtactacc tctgcacctg taagcacagg ccttgttcga   6360
tatactgcgg aaaattggca agaaggacaa gaagcatgcg cgccatggtg gcgcgcatgc   6420
ttaagggtta ctctgttttt attcttgctt attattcccg ttgttattat attgtcgaaa   6480
aatattagtg agttactttt tagcgatgga caatacacat ggttaatcat tttcgcatgt   6540
tgtatattgc cattctccat tataaataca ttgatcgctt cagttttaaa tggtcaacaa   6600
ttttataagc aatatatatt ggttgggatg ttttctgtat tcatttctac tatgtttatg   6660
attttgttga ttgtagctta taatcttaaa ggtgcattga ttgccacagc tataaatagt   6720
gctattgctg gtcttgtatt ggttttattt tgtctcaata aatcttggtt tagatttaaa   6780
tattggtggg gtaaaacgga taaagacaaa attataaaaa ttattcatta tactctgatg   6840
gctctggttt ctgttatctc catgcctaca gcattgatgt gtattagaaa aatattgatt   6900
gctaaaactg gttgggagga tgcagggcaa tggcaggccg tatggaagat atctgaggtt   6960
tatcttggtg ttgtgacaat tgctttgtca acatatttct taccaagatt gacaattata   7020
aaaacaagtt tccttataaa aaaagaagta aatagtacta tattatacat aatatctatt   7080
acttcattca tggcgttgag tatctattta ttccgcgatt tggtaataac agttttattt   7140
actgaacagt ttcgctcagc tcgtgaatta tttttattac aacttatagg ggatgtaata   7200
aaaattgctg ggtttcttta tgcataccct cttcaaagtc aggggcatac taaactattc   7260
atcagttcag aagtgatttt ttctatgctc tttatcatta ccacctatat ttttgttgta   7320
aattatggag tacatggtgc taacataagt tatgtcatta catatagttt atattttgtg   7380
tttgcatttg tgtttactaa ttttattaat gttagaagaa ataattaaaa acagaggttg   7440
aattttgaaa ataattatac ctgtcttagg atttggcagg gctggtggtg aaagagttct   7500
ttctaagctg gcaactgaat tgatgaatta tggacatgat gtaagttttg ttgttccaga   7560
taatagaact aatccatatt atgctaccac agcaaaaatt gtcacgagta aatctagtca   7620
aaaccgtgta aaaatattga gaatcattaa aaattactat aatctgtggc gtaaatgcat   7680
agagttaaat cctgatgctg tagttgctag ttttcatttg actgcctatc ttgtcgcatt   7740
attaccaatc acccgtcgta agaaatatta ttatattcag gcgtatgaag ttaatttttt   7800
tgataaatata atatggaaat taatagcggg tttaacatat tatttaccgc ttaaaaaaat   7860
```

-continued

```
actaaatagt cctaatttgc ttcctcataa acatgatgat tttataggag tagttcctgc   7920
aggagtagat ttaaacgttt tctatccgaa accatcaaat aggttattaa atggtcacac   7980
atcaataggg attattggta gaaaagagaa gcacaaagga actagcgaaa ttatttcagt   8040
attgtgttca ctggaaaata aagctggaat tataatcaat attgcgatct atcttgaaga   8100
agttgataag cagcgtttaa tcgctgccgg gtttcaggtt aattttttc cgattacttc    8160
tgatttagaa ttggcatcct tttatcgaag caatgacatc atgattgctg ttgggttaat   8220
tgaagatggc gctttccatt atccttgtgc tgaatcaatg gcttgtggtt gtcttgttat   8280
ttcaaattat gcgccactta ctgaaactaa cagtgtactt aaattagtca agtttgatgc   8340
ttgcaaactt ggtgaagcaa ttaatctttg tctcaatctt gacctagaag aaaaaagcaa   8400
agaaatccaa tctaatattt ctgtgttgaa taaatatgac tggaaaattg ttggtgaaac   8460
tttcaatagt ttattgttag atgcaaataa atagtatacg ttgatgggga aaatatgaat   8520
attgttaaaa ctgatattcc agatctgatc gttcttgaac caaaagtgtt tagtgatgaa   8580
cgcggctttt ttatggagag ttataatcag attgaatttg agaaggcaat aggaaggcac   8640
gtaaattttg ttcaggataa tcattcaaaa tctagtaaag gcgtactacg tgggttgcat   8700
tatcaattag caccgtatgc acaggctaaa ttagttcgat gtgttgtagg tcaggtattt   8760
gatgttgctg ttgatcttag aaaaaattca ccaacgttca aaaaatggtt tggaataacc   8820
ctttccgcag aaaataaacg acaattatgg atacccgaag gatttgctca tggtttcttg   8880
gtgaccagtg atgaagctga gttcatttat aagacaacta actactatgc tcctggtcat   8940
cagcaagcaa ttatttacaa tgatcctatt ttaaacatcg attggccttt ctgcagtagt   9000
gctctgtcat tatcacaaaa agatcaagaa gcaaaattat tttcagaatt attggacagt   9060
gaactgttct aataaagtgt gccaccttat ccgtctgaag gataggtggt tgcttatatt   9120
tttttgagta tgtttgtata atgacagaaa atagtccgaa atataaacac gataaaagct   9180
taataagttt tatctactta ttttttatat ttacacttat tgtaggcttt attatcgcaa   9240
atacccagtt tttggggcga agtagagact atgataatta tatacagatc ttttctggta   9300
aagaagggga gggggttctt gaattatttt atcgcggatt gatgttaata acgaccagct   9360
atgaaactat catttttata attttaacat gttctttttt tataaaggca aggtttctcg   9420
ctaactattc gcgtaatttt tcaggcttga ccttattctt tatttattat gcaagcgttg   9480
cactttgggt tttagattat actcaattca gaaatggtct atgtatttcc attttaatgt   9540
tttccgtata ctatttattt ataaataaac cgacttattt ttatttctcg gtattatgtg   9600
caattgcaac tcattggtct gctttgcctt ttttgctttt atatcctttt gtctattcaa   9660
caaaaataag acgccttggt tatttttgtt tcagtattct tgttttgatt gcgatctcag   9720
gagaaggaaa agagatcata tcttttataa gaaattttgg agtgggacaa aaaataggaa   9780
atgaagctgg tgtaaattta ataaattcat tatcccttac cgctatttcc tggtttatta   9840
ttagttacat atcaagcatt ggaaatgaaa ggagaaattt aaggcttttc ttttgttatg   9900
gtgtcatgca atacgtgact tttagccttt tctctctacc tgttatggct ttccgtattt   9960
tggaaatgta ttttttcctt atgctaacca ttggggtgtt tattaagcaa aaaaagaatt  10020
attattttat tttttgcaaa gtgttaattt tattgtatct aacatactat tatcatatgg  10080
tctttggagt gattaatgtg taaggctaag gtgttggcta taattgttac ttacaacccg  10140
gaaattattc gattgacgga atgtattaac tctttagccc cacaagttga gagaataatt  10200
```

```
cttgtagata atggctcaaa taatagtgat ttgataaaaa atatcagtat taataacctt  10260
gaaattattt tactttcgga aaacaaaggc attgcatttg ctcagaacca tggtgttaag  10320
aagggcctgg aagcaaaaga gtttgactat ttatttttct cagatcagga tacttgcttt  10380
cctagcgatg ttattgaaaa acttaagagt acatttacga aaaataataa aaaaggtaaa  10440
aatgttgctt gtgcttctcc ttttttttaaa gaccatcgtt caaattatat gcatccgtca  10500
gtcagcctaa atatttttac gagtacaaaa gttatatgta gtgaagtaga cgatgatctt  10560
tatccctcgc atgttattgc ttctgggatg ttaatgtctc gtgaagcatg gcgcgtcgtc  10620
ggaccatttt gtgaaaaact ctttatagac tgggttgata cagaatggtg ttggcgtgca  10680
ttagctaata atatgattat tgttcagaca ccatcagtca tcatttctca tgaacttggg  10740
tatgggcaga aaatttttgc tggtcgatct gttacaatac ataattcttt cagaaatttt  10800
tataaaatac gcaatgcaat atacttaatg ctgcattcaa attatagctt caagtatcgt  10860
tatcatgctt tttttcatgc gacaaagaat gttgtatttg aaattttata ttcgaaagaa  10920
aaattaaatt cactgaaggt ttgttttaaa gctgtacgtg atggtatgtt caataatttt  10980
taatacgaaa atagttaggc tcaaggtgtt taaatggaag aaaataatat gaagacggtc  11040
gctgtagttg gcacagtggg tgttcctgct tgttatggtg ggttcgaatc acttgttcag  11100
aatctaattg attatcaatc tgatggtata caatatcaga tattttgctc ttcaaaaaaa  11160
tatgataaaa aatttaaaaa ttataaaaat gcagaattaa tctatttgcc gataaatgcc  11220
aatggcgtct ctagcataat ttatgatatt atgtgtttaa ttatttgttt attcaaaagg  11280
ccagatgttg ttttaatatt gggggtgtct ggttgtttat ttctaccaat ttataaacta  11340
ttttcaaaat caaagattat tgtcaatatt gatgggcttg aatggcgtag aaataaatgg  11400
ggaacgtttg ctaagaaatt tcttaaaata tctgaggcga tatctattag aatagctgat  11460
attatcattt cagataatca agcaatagct gattatgtgg aaaataagta caagaaaaaa  11520
agtgtagtta tagcttatgg cggagatcat gccactaatc ttagtacacc gatagacaat  11580
gatcaaaaaa aagaaggtta ttatttgggg ctttgtagga tagagcctga gaataatata  11640
gaaatgattc tgaatgcctt cattaataca gataaaaaaa ttaaatttat gggtaattgg  11700
gataacagcg agtatggacg ccagctaaaa aaatattatt caaactatcc aaatatcacc  11760
ctactagaac ctaactataa tattgaagag ctttataaac taagaaaaaa ttgtcttgca  11820
tacattcatg gacactcggc tggtggaaca aacccttctt tagttgaagc gatgcatttt  11880
aatattccta tttttgcttt cgattgtgac tttaatcgtt acacaactaa caatttagct  11940
cattacttta atgattctga acaacttagc ttattagcag aaagtttgtc ttttggaaat  12000
cttaaatgtc gagtattaga tttaaaaaat tatgctgaag atatgtataa ctggaggcat  12060
atagctgcta tgtatgaatc tatttattaa acgcattaac aataatataa ttgaccttat  12120
atagcaggga aagatcacgt aacgctgcgg cgcgccgatc cccatatgaa tatcctcctt  12180
agttcctatt ccgaagttcc tattctttct agagaatagg aacttcggaa taggaactaa  12240
ggaggatatt catatggata aagccgtaag catataagca tggataagct atttatactt  12300
taataagtac tttgtatact tatttgcgaa cattccaggc cgcgagcatt cagcgcggtg  12360
atcacacctg acaggagtat gtaatgtcca agcaacagat cggcgtagtc ggtatggcag  12420
tgatgggacg caaccttgcg ctcaacatcg aaagccgtgg ttataccgtc tctattttca  12480
accgttcccg tgagaagacg gaagaagtga ttgccgaaaa tccaggcaag aaactggttc  12540
cttactatac ggtgaaagag tttgtcgaat ctctggaaac gcctcgtcgc atcctgttaa  12600
```

```
tggtgaaagc aggtgcaggc acggatgctg ctattgattc cctcaaacca tatctcgata  12660

aaggagacat catcattgat ggtggtaaca ccttcttcca ggacactatt cgtcgtaatc  12720

gtgagctttc agcagagggc tttaacttca tcggtaccgg tgtttctggc ggtgaagagg  12780

gggcgctgaa aggtccttct attatgcctg gtggccagaa agaagcctat gaattggtag  12840

caccgatcct gaccaaaatc gccgccgtag ctgaagacgg tgaaccatgc gttacctata  12900

ttggtgccga tggcgcaggt cactatgtga agatggttca caacggtatt gaatacggcg  12960

atatgcagct gattgctgaa gcctattctc tgcttaaagg tggcctgaac ctcaccaacg  13020

aagaactggc gcagaccttt accgagtgga ataacggtga actgagcagt tacctgatcg  13080

acatcaccaa agatatcttc accaaaaaag atgaagacgg taactacctg gttgatgtga  13140

tcctggatga agcggctaac aaaggtaccg gtaaatggac cagccagagc gcgctggatc  13200

tcggcgaacc gctgtcgctg attaccgagt ctgtgtttgc acgttatatc tcttctctga  13260

aagatcagcg tgttgccgca tctaaagttc tctctggtcc gcaagcacag ccagcaggcg  13320

acaaggctga gttcatcgaa aaagttcgtc gtgcgctgta tctgggcaaa atcgtttctt  13380

acgcccaggg cttctctcag ctgcgtgctg cgtctgaaga gtacaactgg gatctgaact  13440

acggcgaaat cgcgaagatt ttccgtgctg gctgcatcat ccgtgcgcag ttcctgcaga  13500

aaatcaccga tgcttatgcc gaaaatccac agatcgctaa cctgttgctg gctccgtact  13560

tcaagcaaat tgccgatgac taccagcagg cgctgcgtga tgtcgttgct tatgcagtac  13620

agaacggtat tccggttccg accttctccg cagcggttgc ctattacgac agctaccgtg  13680

ctgctgttct gcctgcgaac ctgatccagg cacagcgtga ctattttggt gcgcatactt  13740

ataagcgtat cgataaagaa ggtgtgttcc ataccgaatg gctggattaa             13790
```

<210> SEQ ID NO 13
<211> LENGTH: 13777
<212> TYPE: DNA
<213> ORGANISM: Artificial Sequence
<220> FEATURE:
<223> OTHER INFORMATION: example O6A rfb locus nucleotide sequence - O6A-EPA production strain stGVXN4112 and stLMTB10923

<400> SEQUENCE: 13

```
atgacgaatt taaaagcagt tattcctgta gcgggtctcg ggatgcatat gttgcctgcc     60

actaaggcga tacccaaaga gatgctacca atcgtcgaca agccaatgat tcagtacatt    120

gttgacgaga ttgtggctgc agggatcaaa gaaatcctcc tggtaactca cgcgtccaag    180

aacgcggtcg aaaaccactt cgacacctct tatgagttag aatcactcct tgagcagcgc    240

gtgaagcgtc aactgctggc ggaagtacag tccatttgcc cgccgggcgt gacaattatg    300

aacgtgcgtc agggcgaacc tttaggtttg ggccactcca ttttatgtgc acgacctgcc    360

attggtgaca atccatttgt cgtggtgctg ccagacgttg tgatcgacga cgccagcgcc    420

gacccgctgc gctacaacct tgctgccatg attgcgcgct tcaacgaaac gggccgcagc    480

caggtgctgg caaaacgtat gccgggtgac ctctctgaat actctgtcat ccagaccaaa    540

gagccgctgg accgcgaagg taaagtcagc cgcattgttg aattcatcga aaaaccggat    600

cagccgcaga cgctggactc agacatcatg gccgttggtc gctatgtgct ttctgccgat    660

atttggccgg aacttgaacg cactcagcct ggtgcatggg ggcgtattca gctgactgat    720

gccattgccg aactggcgaa aaaacagtcc gttgatgcca tgctgatgac cggcgacagc    780

tacgactgcg gtaaaaaaat gggttatatg caagcgttcg tgaagtatgg actacgcaac    840
```

```
ctcaaagaag gggcgaagtt ccgtaaaggg attgagaagc tgttaagcga ataatgaaaa    900
tctgaccgga tgtaacggtt gataagaaaa ttataacggc agtgaagatt agcggcgaaa    960
gtaatttgtt gcgaattttc ctgccgttgt tttatataaa caatcagaat aacaacgact   1020
tagcaatagg attttcgtca aagttttcca ggattttcct tgtttccaga gcggattggt   1080
aagacaatta gcatttgaat tttacgggtt tagcgcgagt gggtaacgct cgtcacatcg   1140
tagacatgca tgcagtgctc tggtagctgt aaagccaggg gcggtagcgt gctgaaatta   1200
taaagtcatt cttatagaac atcgcatttc aataatataa ttacacctaa atgaatagga   1260
tacaacgtgt gcacaattat ttaaggctta aagataaaat aaaaaacgta tttttagggt   1320
tgtatatatt gcagttattt aattatatcg cgccattggt aattatccct atcctgataa   1380
aatatattgg gttgggggaa tatggggaat tggtctatat tacatctatt tatcaaatag   1440
tggctttgat tattgatttt ggctttactt acacaggacc tgtggttgct gcgagacata   1500
gatgtgagac ccaaaattta cagcgctatt actcaatagt tgttctttta aaatcattgc   1560
tttttataat tgcattaaca tgtgtatttt tattgtgcag attaaatata gtccacttgt   1620
catttttgg gtttttgtca atttttctat gcactattgg taatatatta tcgcccaatt    1680
ggtttttgca ggggattggt gattttaaaa aactttcata ctcacaagta atagtgagaa   1740
taacattgtt tatcatactt cttgtttatg tctgtagtgg cggagataat gtttttatcc   1800
taagtttttt gcaaaatgca acattactca tatgctgtat atacttatgg ccaaatattc   1860
atattagcca tgttgttcat cttaaaccta atgaatgcat tgtggaattt aagaaggcag   1920
gaaatgtttt tattggcgta ataggtacga ttggttacaa tggtctaatt cctgtgttaa   1980
ttggaaacct ttgcggtaat acgagtcttg gtgtttttc aatcgttcaa aaaatgacaa    2040
cagcatgtca aagtctaatt aatccaatat cacagtatat gttatctcaa gtttcagaaa   2100
ttaaacctca agataaactg ttttattata gaattaaaaa aagttttttt gtgcatttaa   2160
caattagcat aattgcatgt ttatgttata tggggttagg gcaatatgtg gcgactttta   2220
taggtaaagt tgacgtttca tttgttatta ttttatttgc gtcaataatt accatttttt   2280
catctttaaa taatgtcctt ggtatacagt ttcttatacc gacagataat gtaaaaaatac  2340
tacgaagtat aaatgttatg gcgggaatta ttgttgttag tttgtcctgg ctgttaatat   2400
cacgctttga cattctgggg ggggttttat taaacctaat tggtgagttt cttgtattca   2460
gtatgctagc ttttattgcc catcgaaagt ggggagcgag agtataatga aagtgaaggc   2520
ggttcctgct attacattct atttaagttt aatgctgaca atttagtgt tactgtttgg    2580
taatgaacca aataaatcac aatatatcct tgttatagca acgataacag ttttttatat   2640
cgcatatatc actaataaaa taacttctcc ggccagcctt ctcgttatat catcttttgt   2700
gtttttaggt tgtcgccctt tattatcttt gtttgcaaac tatgattata ggattgccga   2760
ttggtttatt gaaggatata tggatgacga tgtgattttg gctaactatg ctataacact   2820
aatgtattat ggttatacat tgggactaat tctatgcaaa aatactgaaa aattttatcc   2880
gcatggtcct tatcctgaaa aacaattgct aaaaataaag tttcttttga ctttattttt   2940
tctgggttcg ataggtatgg ttgtaaaagg gatattcttt tttaacttta tagaatctaa   3000
tagttatgtt gatatttatc aatcaaatat aacaacgcca ataggttatg attttctatc   3060
ttatttattt tattgttctt ttttccttat atgtgcgttt catatacagt tcagaacaaa   3120
taaaaaattt ctttttattg cgatatgcat tgctgcattt agcaccttga agggtagtcg   3180
```

-continued

```
tagtgaagct ataacgtttc ttttaacggt tacatgtata tattttaatg aagtaaagac   3240
aagaaactta cgtctgctga ttacaatgat ttttgttttt agcgtcattt ttgtgattag   3300
tgaatttatc tcaatgtggc gcactggagg gagttttttt caattaatgc agggtaataa   3360
tcctgttata aactttgtat acggcatggg agtatcatat ctttccattt atcaatcagt   3420
aaaactacaa ctattgtcag gggatataa tgttacctat ctattcagcc agttaataat   3480
aacttgctcg tcaatattta atgtcaaatt gagcttgccg gaaataagct atagccattt   3540
ggcctcatac acagcaaacc cagaactata taatcttggg ttcggacttg gggggagtta   3600
tttagcagaa tcgtttttag catttggtct gattggatgt ttcattatac ccttttttact   3660
tttacttaat ttaaatgtat tggaaaaata tacaaaaaac aaaccaatta tatattttgt   3720
ttattatagt gtgttgccac ctatattatt cacaccaaga gagactttgt tctatttctt   3780
cccctatctt gtcaaaagta tatttgttgc ttttttagtt acattataca tccagtataa   3840
aaaggattga ccaaaatgtc agaaaaaaat gtcagcataa taatcccaag ttataacagg   3900
gctcatattc ttaaggaggt cataccaagt tattttcagg atgagacttt agaggttata   3960
gttatcaatg atggatcaac agataataca aatagtgtat tagctgaact gaaggaaaaa   4020
tattctcagt tagttatttt agaaaatgaa acgaataaaa aacagatgta ttctaaaaac   4080
cgagggattg aaatagccaa agggaaatat atttttttttg gtgatgatga ctcttacctc   4140
ttacccggtg ttatatctcg gttattggct acaaaatatg agacaggcgc tgatgtaatc   4200
ggcgcaagaa tactttatat gaataataac gagaaaacaa ttgaagattg cataaatcga   4260
cataaaaaag aggggcgttt tgttagtgat ctaaatagat tggattttag ttatacatgt   4320
gatttggacc atccgattga atgtttttat gcacagcctt ttgttctagc tgaaagggaa   4380
ctaatatcga aatatcgatt tgatatatct tatacgggaa actgctatcg tgaggaaact   4440
gatttcatgc tatctctatt tattaaaaat aaaaaattta tatatgattc aaaggctttg   4500
ttaataaatt tacctccaag aaaagcgacg ggaggggcaa gaacagctaa tcgattaaaa   4560
tatcattacg aaagttgcat aaataattat agatttttaa aaaaatataa tgataatttg   4620
aatcttcttt caggacaaaa gcatgctata ttttaccgac agtgtcaatt cgttctgcta   4680
aaaatgaagt cgtttatcgg gaagttttta aaatgattat atatatcgcc gcgtataatg   4740
gttcaggagg gcaaggtggg gtggaaaggg ttgttgccca acaatgtaac attcttaaaa   4800
atttgggggt taaagtcatt atacttgata aaacatactt caaaatttct aacaaaattc   4860
gtaacaaaaa aatacaagta gcactttatc caatattagt ttctctttat ttaaccttac   4920
aaaaattacg tggcgtgacg tttaaagtta ttgcacatgg ctattgttct cctttttata   4980
ggaatgacat cttaatagct catggcaata tgaaatgtta ttttcaaaca gtcatgaata   5040
aaaaacctaa tcggttgtct ggcagtggtc ttttatcttt ctatgagcgt tgggctggag   5100
cattttcaaa aaatatctgg gctgtttcaa ataaggttaa aagtgaatgg aatgagcttt   5160
acaatattaa ttcacataaa atcaaagttg ttcgaaattt tataaatctt gcacaatttg   5220
attacactga tgttaatgaa gcagaatatg tgacatttgt cgggcgattg gaaaaaggaa   5280
aaggaataga tgatctgtat tacatatgta aaaatctgcc agatacttcc ttccatttag   5340
tttcaagtat tcccgcccca caaaattttg cttcgctaaa taatgttctg accagcattg   5400
ctgtccccta tgcgaaaatg ccagaaatat ttaagaaatc cagagtactt attttaccgt   5460
cctattatga aggatatgag ctggttacta ttgaagcgct atgctgtggt tgccctgtga   5520
taggctataa tgttggtgca attagagagt tgtatgcaga aagttttcct ggcgtattta   5580
```

ttgccaataa taaagaagat ttagcacaag tagcctacaa attaattagt cttgataatg 5640
aaaaatatta tcatttgaga caaactattt atagcaagcg tgagcttttt tctgaagaga 5700
gatatgcgga aattttaacg gcggcattta atgaaaaaaa ataagaaact ctgtctcatt 5760
tcaattaact catataatga acttaccgga ggaggagtat atttacgtac gcttgttagt 5820
tttctacaaa aacagaatgt taatttaaca cttattgata aaaaatcctc aggtaaacta 5880
ttcgaagaca atacttttca acatatatca tttattaaag gtaaacgtca ggatataata 5940
tccaggcttt tttttatacc atcattttat gtcccttata ttttctcaat aattaaaatt 6000
ttacggaagc aagatattct tgcttttcac aactctcggc ttggattgtt atgtctgctt 6060
tttagaatac tcatgcccca caaaaagatc atattgttta cggataactt cgaatatgac 6120
ttaataagac aaaaagataa aaacataact acttttattg aaaaattaat tgtttatctc 6180
aatgaattta tcgggcttaa gaattcagat ttagttagct atattacccg gcaagataaa 6240
aatgcaatgg ataaatttta tggattaaa aaaagcagaa atttaattct ccctgtgata 6300
tttagtagag aaaaaccaac tgatgtattg tcagctcact ttattaatga gtataatcga 6360
ttgaataatg ataataggaa aaaagtagta tttactgcat cttttgattt ttttccaaat 6420
atagatgctg ccaactatgt tttaaatgca gcaaagtcta ataatgatta ttgctatatt 6480
ttggcaggta ggaaaagtac tactttgaat cttcctgatt tggataattt attttttttc 6540
gataatctat ctaatagtga aatgtcatat ttattatctg cttgtgatgt tttttattct 6600
cctatagttt taggaagtgg aatgaaaaca aaaattgcag aagcactatc atatggatta 6660
tatatttatg cgacagagca ttccttaatc ggctatgatg aaattataca caataaggag 6720
tgtgttaaaa aaatctcaca tttggatgag gaatttccta aagatttcaa gatgaaaagt 6780
atcaataaac agctaataat gtcttatcag caaaaatatt attcacatta tcggtttaat 6840
ggccatgaac ttgatataat aaattttgac gattagttag tggagatata atatgaacat 6900
attagtaact ggtggtgctg gatatatcgg atctcatacg gctattgaat tactgaatgc 6960
aggtcatgag attatcgttc tggacaattt cagtaatgct tcatacaagt gtatcgaaaa 7020
aataaaagaa attactcgac gtgattttat aacaattact ggagatgctg ggtgtaggaa 7080
gacactctcc gctattttcg agaaacacgc catagatata gttattcatt ttgctggctt 7140
taaatctgtt tcagagtcta aaagtgaacc cttaaagtat taccagaata atgttggagt 7200
gaccattact ttattacagg taatggaaga gtacagaatt aaaaaattta tctttagttc 7260
atctgcgaca gtctatggtg aaccagagat aattccaatt ccagaaacag ctaaaattgg 7320
aggaactacg aatccatatg gcacatcgaa gtattttgtt gaaaaaattc tagaggatgt 7380
tagttccacg ggaaaactgg atataatttg cttgagatat tttaatcctg tcggtgctca 7440
ttctagtggt aaaataggtg aggctccatc tggtatccct aataatcttg ttccttattt 7500
attggatgtt gcgagtggta aacgtgataa attatttatt tatggcaatg attaccctac 7560
taatgatgga acaggtgtaa gggattttat tcatgttgtt gacttagcga aaggtcattt 7620
ggctgcaatg aattatttaa gtatcaattc gggatataat atctttaatc ttggtacagg 7680
aaaaggttat tcggtacttg aattaatcac tacatttgaa aaattaacaa acattaaggt 7740
caataaatct tttatagaga gaagggcagg ggatgttgcg tcttgttggg ctgatgcaga 7800
taaagctaat tctttattgg actggcaagc cgaacaaact ctagaacaga tgttattgga 7860
ctcgtggcgt tggaaaaaaa attatccaga cggattctga atataaaagg tttcagtttt 7920

-continued

```
atgaatcaat cagagcagag aaaaaaaata ctggttctta cacctcgctt tccctaccct   7980
gtcattggag ggatagatt aagagtctat atgttatgta aagaactttc caaaaaatat   8040
gatcttattc ttctgagctt atgtgatcaa ccactagaac ttgaaataaa tataaatgac   8100
tcggtcttca aagaaattca tcgtgtctat ctaccaaaat ataaatcata ttataatgta   8160
ttaaaagctt tggttacgca aaaaccgttg caaattgctt attatcaatc ggacacattt   8220
aagaataaat acaataaatt aattaaacaa tgcgatgcag tattttgtca tctgataaga   8280
gttgctgatt atgttaagga tacagacaag ttcaaaattc ttgatatgac agatgcaata   8340
tctttgaatt acagtcgcgt taaaaaatta gcaagtaaaa aaagtttgcg tgcaattatt   8400
tattctctgg aacaaaaaag attagaatca tatgaacgtt ctgtggcgaa tctttttgat   8460
ttgaccactt ttatttcatc cgtagaccgt gactatctct accctaatct gggcagtaat   8520
atccatatag tcaataatgg ggttgataca tcagccttga gatatataaa aagagaaata   8580
aaaatcgata agcctgtgga acttatattt atcggaaata tgtattcttt acaaaatatg   8640
gatgctgcaa aacattttgc taagaatatt ttaccttgct tgtatgatga gtttaatatt   8700
atttttaaag tgattggtaa gatctcagaa actaataaaa atatattaaa ttcatttaaa   8760
aatacaattg ctttaggtac tgttgatgat atcaattctt ccgcttctac agggcatata   8820
ggtatatgtc ctgttcgtct tggagcaggc gtacaaaata aaattcttga atacatggct   8880
ttaggtttac catgtattac atctagcatt ggttatgaag gtattaatgc aaaatcaggt   8940
agcgaaattt ttgttgcaga tacagtagag caatataaaa acgtactaag agaaataatt   9000
tacgattata atcgttatac tgaagtggct gaaaatgccc gtagttttgt agaaaataat   9060
ttttcttggg aatcaaaagt tgccaattta atgaatacat tagatgagaa attatatgaa   9120
caataataaa attattacac ctatcattat ggctggtggt tcaggcagtc ggttgtggcc   9180
actatcaaga attctctatc cgaaacaatt tcttagccta atcggtagtc ataccatgct   9240
tcaaacaacg gctaatcgtc tggatggttt ggattgtacc aacccttatg tcatttgtaa   9300
tgaacaatac cgctttatag ttgctgaaca gcttagaaaa atcgatagat tgacttcaaa   9360
gaatatcatc cttgagcctg ttgggcgtaa cactgcccct gcaattgcat tagcggcgtt   9420
gctgatgtct aagtctgata aaagtgcaga tgatcttatg ctcgtactgg ctgcagatca   9480
cgttatacac gatgaagaaa aattttgtaa cgctgttaga tcggcaattc catacgctgc   9540
tgatgggaaa ttggtaacat ttggtataat tccagacaaa gcagaaactg gttatggtta   9600
tatacatcga ggacaatata ttaatcagga agattcggat gcatttatag tgtcatcatt   9660
tgttgaaaag ccaaatcatg agacagccac taaatatctt gcttccggtg agtattattg   9720
gaatagcggt atgtttttgt ttagtgcaaa tcgttatata gaggaactta aacaatttcg   9780
gcctgatatt ttatccgctt gtgaaaaagc aattgcttca gcgaactttg accttgattt   9840
tgtgcgttta gatgaaagtt ctttctctaa gtgccctgaa gaatcaattg attacgctgt   9900
aatggaaaaa acaaaagacg caattgttat tccaatggat gctggctgga gtgatgtcgg   9960
ttcatggtct tctctttggg aaattaatga taaagactca gacggcaacg taatagttgg  10020
ggatattttc tctcatgaaa caaagaattc tttcatatat gccgaatcgg gaattgttgc  10080
tacagttgga gtggaaaatt tagttgttgt ccaaacaaag gatgctgttc ttgtctcaga  10140
gagaaataaa gttcaggatg taaagaaaat agtagaacaa attaaaaatt caggtcgtag  10200
cgagcattat gttcatcgcg aagtatatcg tccttggggt aaatatgatt ccattgacac  10260
aggggagcgt tatcaggtca aacgtataac agtaaatcct ggtgaaggac tttctttaca  10320
```

aatgcaccat catagggcag aacattggat catagtttct ggaactgcaa gggtgactat 10380
aggttctgaa actaagattc ttagcgaaaa tgaatctgtt tacatacctc ttggtgtaat 10440
acactgcttg gaaaatccag ggaaaattcc tcttgattta attgaagttc gttctggatc 10500
ttatttagaa gaagacgatg ttatccgttt tcaggaccga tatggtcgta gctaaatttt 10560
tgataatgta acgttagtag aagagcgcta atatttttag ttaatctgta ataagtatta 10620
tttgtttaag gtatatcatg tcgagtttac cctgctttaa agcctatgat attcgcggga 10680
aattaggcga agaactgaat gaagatattg cctggcgcat tggtcgcgct tatggcgaat 10740
ttctcaaacc gaaaaccatt gtgttaggcg gtgacgtccg actcaccagc gaaaccttaa 10800
aactggcgct ggcgaagggg ttacaggatg cgggcgtcga tgtgctggat attggcatgt 10860
ccggcaccga agagatctat ttcgccacgt tccatctcgg cgtggatggc ggcatcgaag 10920
ttaccgccag ccataacccg atggattaca acggcatgaa actggtgcgc gaaggggctc 10980
gcccgatcag cggtgatacc ggactgcgcg acatccagcg tctggcagaa gccaacgact 11040
ttcctcccgt tgatgaaacc aaacgcggtc gctatcagca aatcaatctg cgtgacgctt 11100
acgttgatca cctgttcggt tatatcaacg tcaaaaacct cacgccgctc aagctggtga 11160
ttaactccgg gaacggcgcg gcgggtccgg tggtggacgc cattgaagcc cgctttaaag 11220
ccctcggcgc acccgtggaa ttaatcaaag tgcacaacac gccggacggc aatttcccca 11280
acggtattcc taacccgcta ctgccggaat gtcgcgacga cacccgcaat gcggtcatca 11340
aacacggcgc ggatatgggc attgcctttg atggcgattt tgaccgctgt ttcctgtttg 11400
acgaaaaagg gcagtttatt gagggctact acattgtcgg cctgctggca gaagcgttcc 11460
tcgaaaaaaa tcccggcgcg aagatcatcc acgatccacg tctctcctgg aacaccgttg 11520
atgtggtgac tgccgcaggc ggcacccccgg taatgtcgaa aaccggacac gcctttatta 11580
aagaacgtat gcgcaaggaa gacgctatct acggtggcga aatgagcgcc caccattact 11640
tccgtgattt cgcttactgc gacagcggca tgatcccgtg gctgctggtc gccgaactgg 11700
tgtgcctgaa aggaaaaacg ctgggcgaac tggtgcgcga ccggatggca gcgtttccgg 11760
caagcggtga gatcaacagc aaactggcac accccgttga ggcgattaac cgcgtggaac 11820
agcactttag ccgcgaggcg ctggcggtgg atcgcaccga tggcatcagc atgacctttg 11880
ccgactggcg ctttaacctg cgctcctcta acaccgaacc ggtggtgcgg ttgaatgtgg 11940
aatcgcgcgg cgatgtaccg ctgatggaag aaaagacaaa acttatcctt gagttactga 12000
acaagtaatt cagtaatttc atataaatgg gttttaaaaa acggaaaaga tgagatatcc 12060
ggtgtggtat atccaaggta atgctattca gtatctctat gagtgagtta acatctatac 12120
cacatttaag ccgcacactt cgggatcccc atatgaatat cctccttagt tcctattccg 12180
aagttcctat tctttctaga gaataggaac ttcggaatag gaactaagga ggatattcat 12240
atggataaag ccgtaagcat ataagcatgg ataagctatt tatactttaa taagtacttt 12300
gtatacttat ttgcgaacat tccaggccgc gagcattcag cgcggtgatc acacctgaca 12360
ggagtatgta atgtccaagc aacagatcgg cgtagtcggt atggcagtga tgggacgcaa 12420
ccttgcgctc aacatcgaaa gccgtggtta taccgtctct attttcaacc gttcccgtga 12480
gaagacggaa gaagtgattg ccgaaaatcc aggcaagaaa ctggttcctt actatacggt 12540
gaaagagttt gtcgaatctc tggaaacgcc tcgtcgcatc ctgttaatgg tgaaagcagg 12600
tgcaggcacg gatgctgcta ttgattccct caaaccatat ctcgataaag gagacatcat 12660

```
cattgatggt ggtaacacct tcttccagga cactattcgt cgtaatcgtg agctttcagc  12720
agagggcttt aacttcatcg gtaccggtgt ttctggcggt gaagaggggg cgctgaaagg  12780
tccttctatt atgcctggtg gccagaaaga agcctatgaa ttggtagcac cgatcctgac  12840
caaaatcgcc gccgtagctg aagacggtga accatgcgtt acctatattg gtgccgatgg  12900
cgcaggtcac tatgtgaaga tggttcacaa cggtattgaa tacggcgata tgcagctgat  12960
tgctgaagcc tattctctgc ttaaaggtgg cctgaacctc accaacgaag aactggcgca  13020
gacctttacc gagtggaata acggtgaact gagcagttac ctgatcgaca tcaccaaaga  13080
tatcttcacc aaaaaagatg aagacggtaa ctacctggtt gatgtgatcc tggatgaagc  13140
ggctaacaaa ggtaccggta aatggaccag ccagagcgcg ctggatctcg gcgaaccgct  13200
gtcgctgatt accgagtctg tgtttgcacg ttatatctct tctctgaaag atcagcgtgt  13260
tgccgcatct aaagttctct ctggtccgca agcacagcca gcaggcgaca aggctgagtt  13320
catcgaaaaa gttcgtcgtg cgctgtatct gggcaaaatc gtttcttacg cccagggctt  13380
ctctcagctg cgtgctgcgt ctgaagagta caactgggat ctgaactacg gcgaaatcgc  13440
gaagattttc cgtgctggct gcatcatccg tgcgcagttc ctgcagaaaa tcaccgatgc  13500
ttatgccgaa aatccacaga tcgctaacct gttgctggct ccgtacttca agcaaattgc  13560
cgatgactac cagcaggcgc tgcgtgatgt cgttgcttat gcagtacaga acggtattcc  13620
ggttccgacc ttctccgcag cggttgccta ttacgacagc taccgtgctg ctgttctgcc  13680
tgcgaacctg atccaggcac agcgtgacta ttttggtgcg catacttata agcgtatcga  13740
taaagaaggt gtgttccata ccgaatggct ggattaa                           13777
```

```
<210> SEQ ID NO 14
<211> LENGTH: 15027
<212> TYPE: DNA
<213> ORGANISM: Artificial Sequence
<220> FEATURE:
<223> OTHER INFORMATION: example O8 rfb locus nucleotide sequence - O8-
      EPA production strain stLMTB11734

<400> SEQUENCE: 14

atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag ggcgaagtt ccgtaaaggt attgagaagc tgttaagcga ataatgaaaa    900
```

-continued

```
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagcta gcgatcgctt aagatctagg atttcattat gttacttcct gtaattatgg   1320
ctggtggtac cggcagtcgt ctctggccga tgtcacgcga gctttatccg aaacagttcc   1380
tccgcctgtt cgggcagaac tccatgctgc aggaaaccat cacccgactc tcgggccttg   1440
aaatccatga accgatggtc atctgtaacg aagagcaccg cttcctggtg gctgaacagc   1500
tacgccagct caataagctg tcgaataata ttattcttga gccggtcggg cgcaacaccg   1560
ccccggccat cgccctggca gcccttcagg ccacccgcga cggcgacgac ccgctgatgc   1620
tggttctcgc cgctgaccat atcatcaata accagtcggc cttccacgac gccatccggg   1680
tcgccgagca gtatgctgat gaaggtcatc tggtcacctt cggtatcgtg ccgaatgccc   1740
cggaaactgg ctacggttac attcagcgcg gcgtggcgct caccgatagt gcccattccg   1800
cgtaccaggt ggcccgcttt gtggagaagc cggatcgcga gcgcgccgag gcttacctcg   1860
cctccgggga gtactactgg aacagcggca tgtttatgtt ccgcgccaag aaatacctca   1920
tcgagctggc caaataccgt ccggatatcc tggaagcctg ccaggctgcg gtgaatgccg   1980
ccgataatgg cagcgatttc atcaatatcc cgcatgatat tttctgcgag tgcccggatg   2040
agtccgtgga ctatgccgtt atggagaaaa ccgccgatgc ggtggtggtc ggtctcgatg   2100
ctgactggag cgacgtcggc tcctggtccg cactatggga ggtcagcccg aaagacgagc   2160
agggcaatgt cctcagcggt gacgcgtggg tacacaacag cgaaaactgc tacatcaaca   2220
gcgacgagaa gctagtggcg gccattggcg tagagaatct ggtgattgtc agcactaagg   2280
acgccgtgct ggtgatgaat cgcgagcgtt cccaggacgt gaagaaggcg gtcgagttcc   2340
tcaagcagaa ccagcgcagc gagtacaagc gccaccgtga gatttaccgc ccctggggcc   2400
gttgcgacgt agtggtccag accccgcgct tcaacgtcaa ccgcatcacg gtgaaaccag   2460
gcggtgcctt ctcgatgcag atgcaccacc atcgcgccga gcattgggtt attctcgccg   2520
gcaccggtca ggtgactgtc aacggtaagc agttcctgtt gtccgagaac cagtccacct   2580
ttattccgat tggcgccgag cactgcctgg aaaaccctgg ctgtattccg ctggaagtgc   2640
tggagatcca gtcgggggcg taccttggcg aggacgacat tattcgtatt aaagaccagt   2700
atggtcgttg ctaattattt tcgggacaag acgcagaatg acacagttaa cttgttttaa   2760
agcttatgac atccgtggtg aactgggtga ggaactgaac gaggacatcg cctaccgtat   2820
cggtcgcgcc tacggcgaat ttctgaaacc cgggaagata gtggtggggg gcgatgtgcg   2880
cctcacaagc gagtcgctga agctggcgct ggcccgcggg ttaatggacg ccggtaccga   2940
cgtgctggac atcggcctga gcggtaccga agagatttac tttgccacct tccaccttgg   3000
ggtagatggt ggcatcgagg tgaccgcgag ccacaatcct atgaactaca acggcatgaa   3060
gctggtgcgc gagaatgcga agcccatcag cggcgacacc ggcctgcggg atatccagcg   3120
cctggcggag gaaaaccagt tcccgccagt ggacccggcg cgtcgcggga ccctgagcaa   3180
gatatcggta ctgaaggagt atgttgacca tctgatgagc tacgtggact tctcgaactt   3240
cacccgtcca ctgaagttgg tggtgaactc cggaaacggg gctgcggggc acgtgattga   3300
```

-continued

```
tgaggtggag aaacgcttcg cggcggctgg ggtgccggta acctttatca aggtgcatca   3360
ccagccggat ggccatttcc ctaacggtat cccgaatccg ctgctgccgg agtgccgcca   3420
ggataccgcc gacgcggtgc gcgagcatca ggccgacatg gggattgcct ttgacggcga   3480
cttcgatcgc tgcttcctgt tcgatgacga agcttcgttt atcgaggggt attacattgt   3540
cggcctgctg gctgaggcgt tcctgcagaa gcagccggga gcgaaaatca ttcacgaccc   3600
gcgcttgacg tggaacacgg tagacatcgt gacccgcaac ggcggccagc cggtgatgtc   3660
gaagacgggg catgcgttca tcaaggagcg gatgcgtcag gaagacgcta tctacggcgg   3720
ggagatgagt gcgcaccatt acttccgcga tttcgcctac tgcgatagcg ggatgatccc   3780
gtggctgctg gtggcggagc tgctgtgtct gaagaacagc tcgctgaaat cgctggtggc   3840
ggaccgccag aaggcgttcc ctgcgtcggg agagatcaac cgcaagctaa gtaatgctgc   3900
tgaggcgatc gcccgcatcc gggcgcagta tgagccggcg gctgcacaca tcgacacaac   3960
ggacgggatc agtattgaat accctgaatg gcgctttaac ctgcgcacgt ctaacaccga   4020
gccggtggtg cgtctgaacg ttgagtccag agctgatgtg gcgcttatga atgaaaaaac   4080
gaccgagctg ttacacctgt taagcgggga ataaggtgag agatttacta acgacgattt   4140
atcgttatcg gggatttatc tggagcagtg ttaaacgtga ttttcaggca cgctatcaaa   4200
ctagtatgct gggcgcacta tggctcgttt tacaaccgct ctctatgatt ctggtctata   4260
ccctggtttt ttccgaggtg atgaaggcaa gaatgcccga taataccggg tcgtttgcct   4320
atagtattta tctctgttcc ggggtactga cctggggatt atttactgag atgctggata   4380
aaggtcagag cgtatttatt aacaatgcta atctgatcaa gaaactcagt tttccgaaaa   4440
tctgtctgcc gatcatcgtg acgttatcgg cggtgctaaa tttcgcgatt attttcagtc   4500
tgtttctaat ttttatcatt gtcaccggta acttccccgg ctggctcttt ctctcggtga   4560
taccggtcct gcttttgcag atcctgtttg ccggtgggct ggggatgatc cttggtgtca   4620
tgaacgtctt tttcagggat gtggggcaac tggttggcgt tgcgctgcaa ttctggtttt   4680
ggttcacacc cattgtttat gtactgaatt cattacctgc atgggcaaaa aatctgatga   4740
tgtataaccc gatgactcgg atcatgcaat cttatcagtc catcttcgcc tatcatctgg   4800
cccccaactg gtattcgcta tggccagtat tggctctcgc cattattttc tgcgtcatcg   4860
gtttcaggat gttccgcaag catgcggcgg atatggtgga tgaattataa tgagttatat   4920
cagagtaaat aatgtcggta aggcgtatcg ccagtatcac tcaaagaccg ggagactgat   4980
cgaatggtta tcccctctga ataccaaacg ccataatttg aaatggatcc tccgcgatat   5040
taatttcgaa gtcgctccgg gcgaggctgt cggtattatc ggtatcaacg gtgcaggcaa   5100
gagtaccctg cttaaactca taaccgggac gtccaggccg acgactggag aaattgaaat   5160
ctccggacgt gtcgctgcat tactcgaatt ggggatgggg tttcattctg atttcactgg   5220
tcggcagaat gtttatatgt ctgggcaact gttggggtta tcgtcagaga aaataactga   5280
actgatgccg caaattgaag agtttgctga gattggggac tatatcgatc aacctgtgcg   5340
cgtctactcc agtgggatgc aagttcgatt agcttttagt gtagcgacgg ctatccgtcc   5400
tgatgtgcta attatcgatg aggcattatc tgttggggat gcatatttcc agcataaaag   5460
ctttgagcgt attcgaaaat ttcgtcagga agggaccacg ctgttgctgg tatcccatga   5520
taaacaagcg atccaaagca tttgcgaccg ggccatttta ttgaataaag gccaaattga   5580
aatggaaggt gaacctgaag cagtgatgga ttattacaat gctcttctgg ccgataaaca   5640
```

-continued

```
aaatcagtcc attaaacaag ttgagcataa tggtaaaacg caaactgttt caggcactgg   5700
tgaggtgact atctctgagg ttcatcttct cgatgaacag ggcaatgtga ctgaatttgt   5760
ttcggtaggg catcgtgtca gcttgcaggt caacgttgag gtcaaggacg atattcctga   5820
gcttgttgtc ggatatatga ttaaggatcg acttgggcag ccgattttcg ggaccaatac   5880
gtaccatctc aatcagacac tcacctccct gaaaaaagga gaaaagcgtt cgttcttatt   5940
ttctttcgat gcgagattgg gggttggctc ctattctgtc gctgtcgcgt tgcatacttc   6000
cagtacgcac ctcggcaaaa actatgaatg gcgcgatctg gccgtggtat tcaacgtcgt   6060
taacacggaa caacaagagt ttgtcggcgt gtcctggttg ccgcctgaac tggagatttc   6120
ttaatgggtt cgtcgtttta tcgttcattt gaagaacgac acagaggttc ggttgaagaa   6180
atcaagcgcc gcttgagttt ttatttacct tttcttgcag gtctgaagga catttatcct   6240
gatggcgtga ttgcggatat tggttgcgga cgtggcgaat ggttggagat cctgactgaa   6300
aatggcattg cgaacatcgg cgtcgatctc gatgatggca tgctggcgcg cgccagggag   6360
gccggactga atgtgcagaa aatggattgt ctgcagtttt tgcaaagtca ggcggatcag   6420
agcctgatag cgttgaccgg ttttcatatt gctgagcatt tgccgtttga ggtcctgcag   6480
caactcgcca tgcataccct acgggtgctg aaaccaggtg gtttgctgat cctcgaaacg   6540
ccgaacccgg agaatgtaag cgtcggcacc tgttcatttt atatggatcc aacgcataat   6600
catcctctgc caccgccact gcttgagttt ttacctattc attatggttt tacccgagca   6660
attaccgttc gtctgcagga aaaagaggtt cttcaatctc cggatgcagc cgttaatttg   6720
gtcgatgtac tcaaaggggt gagccccgac tacagcatca ttgctcagaa agcagcgcca   6780
acagatattc ttgaacgctt tgacaccctg tttacccagc agtacggtct gacgctggat   6840
gctctgagca accgttacga tgcgattttg cgccaacagt tttcgtccgt tgtctcacgg   6900
ctggagacgt tgaaccaaac ctatatgcaa cagataagcc aaatgtcaga gactattcag   6960
acgttgcaag gtgaggttga cgatctgagt catgtcatcg atcagaacca tcagcttcat   7020
cagcaaatgg cggatttaca taacagtcgt tcatggcgta ttactcaacc actacgctgg   7080
ttgtctttgc aacgtcaatt attacgtcag gaaggggcta aagtgcgagc ccgtagggct   7140
gggaaaaaaa tattgcgcaa agggatggcg ctctcgctgg tctttttcca tcgttaccct   7200
aagtctaagg tttatctgtt taaggttctg agaaaaactg gctgctatac attgctacaa   7260
cgtttgttcc aacgcgtaat gctggtgcaa tctgacacga tgatgatgca gtccagaaga   7320
tatgatgtgg gtactgaaga aatgacaagt cgcgcgatga gtatttataa cgaattaaaa   7380
aataaaaata cggagaaata acgatgcgta ttgtcataga tttacaaggc gcacagacgg   7440
aaagccgctt tcgtggcatc ggtcgttata gtatcgcaat cgccagaggc ataatcagaa   7500
ataacagccg gcatgagatt ttcatcgcgc tatccgccat gctggatgag tcgattgcaa   7560
atattaaggc gcaatttgcc gatctcctgc cggcagaaaa tatagtcgta tggcatgccg   7620
taggccctgt tcgtgcgatg gaccaaggta atgaatggcg tcgggagagc gcagaactga   7680
ttcgggaagc gtttcttgaa tcattgtgtc cagatgtcgt tttcattacg agtttgtttg   7740
aaggtcatgt cgacgatgcg gctacatcgg tacacaaatt tagtcgtcag tataaagtag   7800
ccgtactgca ccacgatctt atccccctcg tgcaggcgga aacctatctg caggacgatg   7860
tatacaaacc ctactattta cagaaagttg agtggttaaa aaacgctgac cttttgttga   7920
ctaactctgc ttataccgca caggaagcga tcgagcatct gcatttacag ggcgatcatg   7980
tgcagaatat tgcagccgca gtcgattctc agttttgtat ggcggaggtg gcagcgagcg   8040
```

aaaaagagac cgtccttggc cattacggta ttcagcgcga gttcatgttg tatgcgcccg 8100
gaggatttga ctcaaggaaa aactttaaac ggttgattga ggcctatgcc gggctcagtg 8160
atgccttacg tcgcagtcat caactggtca tcgtcagtaa gctttccatc ggtgatcgtc 8220
agtatctgga atcccttgcg tcaggtaatg gtttacagca gggcgaactg gtactcactg 8280
gttatgtgcc ggaagatgag ctgatccagc tctatcgcct atgtaagctg ttcatctttg 8340
cttcactaca tgaaggtttt gggttgccgg ttctggaagc aatgtcgtgc ggtgcgccgg 8400
tgattggctc aaatgtcacc agtattcctg aagtcatcgg taatcctgag gcattattcg 8460
acccgtattc tgtctcttcc atgagggata agatcgcgca atgtttgact gatgatacct 8520
tcctcgcgcg tctgaaagaa atggcgcagc agcaagcgcg taatttctct tgggataaag 8580
ctgcggtgac tgctctggaa gctttcgaaa agatcgcggt agaagacacc ggtactgcgc 8640
aggttttgcc tgaagctttg attcagaaga tccttgctat ctcacaaggg cagccagatg 8700
accgcgatct gcgcttgtgc gcaacggcca ttgattacaa tctgaaaacg gcagaacttt 8760
atcaaatcga cgataaatcg ctgaactggc gtgtggaagg cccattcgat agctcatata 8820
gtctggcgtt ggtcaaccgc gaatttgccc gggcactctc agccgatggt gtagaggttt 8880
tattgcattc cactgaagga ccaggtgatt ttgccccaga tgcctcgttt atggcacagt 8940
cggaaaatag tgatcttctg gcattttata atcaatgtca gacccgcaag agtaacgaaa 9000
agatagatat tattagcaga aatatctatc caccgcgggt taccaaaatg gatgccaaag 9060
taaaattcct tcattgttat gcttgggaag aaacgggctt tccgcaaccg tggatcaatg 9120
aatttaatcg ggaacttgac ggagtgctgt gtacttcgga acatgttcgt aaaatactga 9180
ttgataacgg actgaatgtg cccgcatttg ttgttggcaa tggctgtgac cattggctca 9240
atatcccagc cgagacgaca aaagatgtgg atcacggaac attccgtttc ctgcacgtct 9300
cttcttgttt cccacgcaaa gggatacagg caatgcttca ggcttggggg aaggcgttca 9360
ctcgtcgtga caatgttatc ttaatcatta agacttttaa caatccgcac aatgaaattg 9420
acgcatggct ggctcaggcc caggctcaat tcatagacta tcccaaagtt gaagtgatca 9480
aagaggatat gtcagccacc gagcttaaag ggctttatga aagctgtgat gttttggttg 9540
ctccaggttg cgctgaaggc tttggtttac ctattgctga agcaatgctg agtgggctac 9600
cggctatcgt caccaattgg agcgggcaac ttgattttgt taattcacaa aattcatggc 9660
tggttgacta tcagttcact cgggtaaaaa cgcactttgg tctgttttcc tcagcctggg 9720
ccagtgtgga tattgacaac ttaacagatg cattaaaagc ggcagcctca accgataaat 9780
cagtgctgcg tgacatggcc aatgctggtc gcgagcttct tctgcagcag tttacctgga 9840
aagcggtggc tgatcgttct tgccaggcgg tcaagactct gcgtgcgcat attgatattg 9900
cacagcatcg ggcgcgcatt ggctgggtga cgacctggaa cacgaaatgt gggatcgcaa 9960
cctattccca gcatctggtg gaaagcgcac ctcatggcgc ggatgttgtt tttgctcccc 10020
aggtcagcgc tggcgatctt gtgtgtgcag acgaagagtt tgtacttcgc aactggattg 10080
taggtaaaga gagcaactat ctggaaaacc tccagccaca cattgatgct ctgagactcg 10140
atgtcattgt gatccaattc aactatggat tctttaatca tcgagaactg tcggcgttta 10200
ttcgtcgcca gcatgacgcc ggtcgttcag ttgttatgac gatgcactca actgtggatc 10260
cgctggaaaa agagccgagc tggaatttcc gtcttgctga aatgaaagag gcgctggcac 10320
tttgcgaccg gttgttggtg cattcgattg ccgatatgaa ccgccttaaa gatttaggct 10380

-continued

```
taactgcgaa tgttgcttta ttcccgcacg gtgttatcaa ctactccgca gcgagcgtca  10440
cacgtcaaca gcagtcttta ccgctaattg cgagctatgg cttctgctta ccgcataagg  10500
gcctgatgga actagtagaa tccgtccata gactcaagca agccggtaaa ccggttcgtt  10560
tacgactggt gaacgcagag tatcctgttg gggagtcacg cgatctggtg gcagagctta  10620
aagctgctgc tcagcggtta ggtgttaccg atctgattga gatgcataat gatttcctac  10680
ctgatgcgga gagtctgcgg ttgctttcag aagccgatct tctgattttt gcttatcaga  10740
atactgggga gtctgctagc ggggcggtac gttatggtat ggcgactcaa aaacctgttg  10800
cggtaacgcc cctggcgata tttgatgatt tggacgatgc cgtctttaaa tttgatggat  10860
gcagcgtcga tgatatcagt caggggattg accggatcct gaattccatc cgtgaacaga  10920
actcttgggc aaccaggact caacaacgtg ccgatgcatg gcgggaacaa catgattatc  10980
aagctgtttc acgccgtctg gttaatatgt gtcaaggctt agctaaagct aaatatttta  11040
aataaaaata tctctcttgt attttttgcc tttgaataca agaggggtta gataatgtgt  11100
catttattat gaaaattatt tttgctactg agccaattaa atacccatta acgggcatcg  11160
gtcggtattc cctggagctg gttaagcggc tggcggtcgc ccgcgaaatt gaagaattaa  11220
agctatttca cggtgcgtcg tttatagaac agatcccttt ggtggagaat aaaagcgata  11280
ccaaagccag caatcatggt cgtctgtcgg cgtttctacg ccgacagacg ctgttgattg  11340
aggcttatcg cttgctgcat ccgcggcgcc aggcgtgggc attgcgcgac tataaggatt  11400
atatctacca tggccccaat ttttatctgc cgcataaact ggaacgcgcc gtgaccacgt  11460
ttcatgacat atccattttt acctgcccgg aatatcatcc aaaagatcgg gttcgctata  11520
tggagaagtc cctgcatgag agtctggatt cggcaaagct gatcctgacc gtttctgatt  11580
tctcgcgcag tgaaattatc cgcttgttca actatccggc ggagcggatc gtaaccacca  11640
agctagcctg cagcagtgac tatatcccac gcagcccggc agagtgtctg ccggtactgc  11700
agaaatatca gctggcgtgg caggcctacg cgctatatat cggcactatg gagccacgta  11760
aaaatatccg aggcctgctg catgcctatc agctgctacc gatggagatc cgcatgcgct  11820
atccgctaat ccttagcggc tatcgcggct gggaagacga tgtgctgtgg cagttagtcg  11880
agcgcggtac tcgggaaggc tggatccgtt acctcggata tgttccggat gaagacctgc  11940
cgtatctgta cgcagcggcc agagtctttg tttatccctc cttctacgag ggattcggtt  12000
tacctattct tgaagcgatg tcttgcggtg tgccggtagt atgctccaat gtcacctctt  12060
tgcctgaggt tgttggcgat gccggcctcg ttgccgatcc taatgatata gacgcgatta  12120
gcgcgcaaat tttgcagagc ctgcaagatg atagctggcg ggaaatcgcc accgcgcgcg  12180
gtcttgctca ggcgaaacag ttttcgtggg agaactgtgc gacacagacc attaacgcct  12240
ataaattact ctaagggtgt cagttgagag ttctacacgt ctataagact tactatcccg  12300
atacctacgg cggtattgag caggtcattt atcagctaag tcagggctgc gcccgccggg  12360
gaatcgcagc cgatgttttc acttttagcc cggacaaaga tacaggtcct gtcgcttacg  12420
aagatcatcg ggtcatttat aataaacagc tttttgaaat tgcctccacg ccgttttcgc  12480
tgaaagcgtt aaagcgtttt aagctgatta aagatgacta cgatatcatc aactaccatt  12540
ttccgtttcc ctttatggat atgctgcatc tttcggcgcg gcctgacgcc aggactgtgg  12600
tgacctatca ctctgatata gtgaaacaaa aacggttaat gaagctgtac cagccgctgc  12660
aggagcgatt tctcagcggc gtagattgca tcgttgcctc gtcgcccaat tacgtggctt  12720
ccagccagac cctgaaaaaa tatctggata aaacggtggt gatcccgttt ggtctggagc  12780
```

-continued

```
agcaggacgt gcagcacgat ccgcagaggg tcgcgcactg gcgggaaact gtcggcgata  12840
agttctttct cttcgtcggc actttccgct actacaaagg gctgcatatt ctgatggatg  12900
ccgctgagcg tagccgactg ccagtggtgg ttgtaggggg cgggccgctg gaatcggaag  12960
tgcggcgtga agcgcagcag cgcgggctga gcaatgtgat gtttaccggc atgctcaacg  13020
acgaagataa gtacattctc ttccagctct gccggggcgt ggtattcccc tcgcatctgc  13080
gctctgaggc gtttggcatt acgttattgg aaggcgcacg ctttgcaagg ccgctgatct  13140
cttgcgagat cggtacaggt acctctttca ttaaccagga caaagtgagt ggttgcgtga  13200
ttccgccgaa tgatagccag gcgctggtgg aggcgatgaa tgagctctgg aataacgagg  13260
aaacctccaa ccgctatggc gaaaactcgc gtcgtcgttt tgaagagatg tttactgccg  13320
accatatgat tgacgcctat gtcaatctct acactacatt gctggaaagc aaatcctgag  13380
cggccgcgag ctcgtcgact cgaggatccg tgtaggctgg agctgcttcg aagttcctat  13440
actttctaga gaataggaac ttcggaatag gaactaagga ggatattcat atggataaag  13500
ccgtaagcat ataagcatgg ataagctatt tatactttaa taagtacttt gtatacttat  13560
ttgcgaacat tccaggccgc gagcattcag cgcggtgatc acacctgaca ggagtatgta  13620
atgtccaagc aacagatcgg cgtagtcggt atggcagtga tgggacgcaa ccttgcgctc  13680
aacatcgaaa gccgtggtta taccgtctct attttcaacc gttcccgtga gaagacggaa  13740
gaagtgattg ccgaaaatcc aggcaagaaa ctggttcctt actatacggt gaaagagttt  13800
gtcgaatctc tggaaacgcc tcgtcgcatc ctgttaatgg tgaaagcagg tgcaggcacg  13860
gatgctgcta ttgattccct caaaccatat ctcgataaag gagacatcat cattgatggt  13920
ggtaacacct tcttccagga cactattcgt cgtaatcgtg agctttcagc agagggcttt  13980
aacttcatcg gtaccggtgt ttctggcggt gaagaggggg cgctgaaagg tccttctatt  14040
atgcctggtg gccagaaaga agcctatgaa ttggtagcac cgatcctgac caaaatcgcc  14100
gccgtagctg aagacggtga accatgcgtt acctatattg gtgccgatgg cgcaggtcac  14160
tatgtgaaga tggttcacaa cggtattgaa tacggcgata tgcagctgat tgctgaagcc  14220
tattctctgc ttaaaggtgg cctgaacctc accaacgaag aactggcgca gacctttacc  14280
gagtggaata acggtgaact gagcagttac ctgatcgaca tcaccaaaga tatcttcacc  14340
aaaaaagatg aagacggtaa ctacctggtt gatgtgatcc tggatgaagc ggctaacaaa  14400
ggtaccggta aatggaccag ccagagcgcg ctggatctcg gcgaaccgct gtcgctgatt  14460
accgagtctg tgtttgcacg ttatatctct tctctgaaag atcagcgtgt tgccgcatct  14520
aaagttctct ctggtccgca agcacagcca gcaggcgaca aggctgagtt catcgaaaaa  14580
gttcgtcgtg cgctgtatct gggcaaaatc gtttcttacg cccagggctt ctctcagctg  14640
cgtgctgcgt ctgaagagta caactgggat ctgaactacg gcgaaatcgc gaagattttc  14700
cgtgctggct gcatcatccg tgcgcagttc ctgcagaaaa tcaccgatgc ttatgccgaa  14760
aatccacaga tcgctaacct gttgctggct ccgtacttca agcaaattgc cgatgactac  14820
cagcaggcgc tgcgtgatgt cgttgcttat gcagtacaga acggtattcc ggttccgacc  14880
ttctccgcag cggttgccta ttacgacagc taccgtgctg ctgttctgcc tgcgaacctg  14940
atccaggcac agcgtgacta ttttggtgcg catacttata agcgtattga taaagaaggt  15000
gtgttccata ccgaatggct ggattaa                                      15027
```

<210> SEQ ID NO 15

<211> LENGTH: 11283
<212> TYPE: DNA
<213> ORGANISM: Artificial Sequence
<220> FEATURE:
<223> OTHER INFORMATION: example O15 rfb locus nucleotide sequence - O15-EPA production strain stLMTB11738

<400> SEQUENCE: 15
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctgg caaaacgtat gccgggtgac ctctctgaat actccgtcat ccagactaaa 540
gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccgg aactggaacg tactcagcct ggtgcatggg gacgtattca gctgactgat 720
gctattgccg agctggcgaa aaaacaatcc gttgatgcaa tgctgatgac cggcgacagt 780
tacgactgcg gcaaaaaaat gggctatatg caggcgtttg tgaagtatgg cctacgcaac 840
ctgaaagaag ggcgaagtt ccgtaaaggt attgagaagc tgttaagcga ataatgaaaa 900
tctgaccgga tgtaacggtt gataagaaaa ttataacggc agtgaaaatt cgcagcaaaa 960
gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagcta gcatgagcaa aactaaacta aatgttcttt accttgcaat aagtcagggt 1320
gccaattacc tactgccatt attaattttt ccttatcttg ttagagtcat tggtgtatcg 1380
aattttggtg atctgagttt ttcattgata actatacaag tgttgttaat ggttgttgaa 1440
tatggttttg gatatagtgg gacaagagaa atagcactaa ataacgataa aaaataccat 1500
tctgaatttt tttgcggtgt ggtgcttgct cgttttatat taatgctaat tgcagctata 1560
atactcataa tactctgttt tttttatgtt tttaacgacg ttaagtcttt gttatgtgtt 1620
ggttttctgt ccgtaattgc aggtgttttc aatccaaatt ggtttttgca aggtaaggaa 1680
atgatgagtg tgatggctgt gctgtcacta ttttcacgag gcatagcagt cgttgcagtt 1740
tatctaatta taaaacccgc aacgccgatg tacatcagtg ccttattatt gagcatgcca 1800
tatattttgt attcattctg tggcgttgcc tacttactta ttatcaagga gattttttta 1860
tgtaggccac cgataaagaa aattcaagta attttaaaaa atggatttca tttttttgt 1920 tcaacacttg cgactagtgc atacacaatg ttgacccctc ttgtattggg tggcgtatct 1980
ggaaagtttg atgtaggcat ctttaactca gctaacatga tcaaacaagg tttggctgga 2040
cttgcatcac cattagtcca agctttttat ccaagaatta acattttgca aagagagaat 2100

-continued

```
ccatatattg caaacttaaa atctagaatg attcttaaat acttgcttgt tttttacatg   2160
gctttagcaa taccattttt actttttgcc aaccaattat cattattaat attcggcatg   2220
aaaggtgaag taattgcagg tgcaatgcaa ttaatgacat tgcttcctat attcataggt   2280
tttaatacag ttgtcgggtt acttgtatta gtacctaatg ggatgcaaaa acagtatttc   2340
aaatctattt tcctaggaac tattacttgt ttaagcatag tttatccagc atgtaaatat   2400
tatggagcaa cgggtgcgat tgtgagtctt attgtagctg aaattttcgt tggcatggga   2460
atgcttaaac aattcattaa agtaaataaa accgtatgta ggcctcataa attatgaata   2520
tctcggtaat aatatctgtt tggaaacgcc cagttcaatt agaattgatt ctctctgagc   2580
tcgattctca ggctaaagac aatagtctac acctagaagt aattgtttcc gatagtcata   2640
gtggtaaaga aattgatgat gtagttgctg ataatattca taaaaagaaa aatattaata   2700
ttatccatca acatactaaa aatatactct ccgctaagcg caatttcgga gcatccctag   2760
cccatgggga ttatttaata tttcttgatg atgattgtat acccgcaagt ggatatatat   2820
catcgttgct gaactattta aaaaaaatga atagtaaaag cgttttatgt ggggaagtta   2880
gattcgaaaa tgaactcatt gagaccagca attactatcg ctacaggaac tctttacacc   2940
ctaagtttag tgatagtcct gatatctcta tgaatgcctg gacttttgtc gcaatgaatt   3000
gtgttcttga tagaaaggca ttttcatcag gtatagtttc atataatgaa aattttattg   3060
gttatggttg tgaagatcat gagtttgggt ggcaacttga aaaaaatgac ttcaaaatta   3120
tttttgctga ttttaaaata ttacatcacg aatacagtgg cgatatagaa ggatatacaa   3180
aaaaaattcg tgctacagca cgtgatggta tgaatgtatt aagcaaagta aggcctgaaa   3240
tgttttctac taataaaaaa ttattcctag ttgagaaaat atttagtaaa cacaaaacgt   3300
ttagtaaaat atgccaatca atatttttca ataaatttat ttttaaaaaa ataatacaat   3360
ttttaaaaaa aacagatgca aataaaaaac tctatttccc aattctttac agatatgtgt   3420
tgatttcggc atatatacat ggtattggag agcgtggcac ctcaaaaaca gatgatttgc   3480
ttaagaactg gtatatatag atgatgctat cttcatttat taagacattt gtatggaagg   3540
taaaaaacaa tgaagtataa tgcattgatg gctttttat tatttttgt tgttttttt   3600
agattgtcgc tgataatacc tttcttatat ttggcattta ttcctgcatt ttttggtatt   3660
atgtatttag tgcgtaattt tatgattact atgggcaatg gattggtatc tatagatcgt   3720
aaaaatttgt tgctgttatc tatattcata attattttt tattttgttt ggttttcgat   3780
ttgtttcaaa aaagccattc ttttcaaagt tattttaccg ttagattatt tatgttgttt   3840
ttattttcat ttgttcctgc gtattattta gtaaatagat tcataaaggg tgacttgaaa   3900
ttaatggagc gaatattagt gtattctctc tgggttcaaa tagttatttt ttttggtatg   3960
tatataagtc cagagttaaa aagattgtta tatactttct ttggtatgtc tgactctgtt   4020
aatctttggg aacaaaatgc taaagtaaga ggatttgggt tgtcgggtga aataaatttc   4080
atgacaccat ttttgatgat ctatatgtca ttttttatga tgaaaaggcg ttatgcttta   4140
attactttaa tttgtctgac tcaaatcgta aattctaaca tggctgtgat tgcagccatt   4200
attggtatcg gttgctctag acttaatatt aatataaaaa ttgcaacagt attgattttg   4260
ggagttttag tttatagctt aggagcggtg ttctttcctc gattttatga tgagttcgtt   4320
tctggagatg gcacaagaac tctggatatc ttattacagc aacatgtgtt tgttgtaggt   4380
aatttagatt tttttaatat tatatttgga ttacagcaaa acatatcttc atcaatcccc   4440
gatattaaac aaagttcgga tatgggctgg gttatactgt ttaattacgg tgggttaaca   4500
```

-continued

```
tttattacac tctttttatt tttaatcttt actatttcta ttgcgacatt tggaatgaca   4560
tatcaagcaa ttatatggat gttaattggg ataattttca ataccaaagg tttagtttta   4620
ggatctaacg gctatttctt tctatctttt atatatatgt ttttgaatag agtaacactt   4680
agtggacaga gttcaattac taataagtta ggtcaagtaa gtaaatagct tccagagtat   4740
atttgtcaat gatttgaggt tcggttatta tgttttcatc taaaacactg ttaattactg   4800
gtggtactgg ctctttcggg aatgctgtat taaatagatt tcttgataca gatattgcag   4860
aaatccgtat atttagtcgt gatgaaaaaa aacaagatga tatgcggaaa aaatacaata   4920
atcaaaaatt aaagttctat attggtgatg tcagagatta ccgtagtatt ttgaatgcga   4980
ctcgcggtgt tgattttata tatcatgcag cggcacttaa gcaagttcca tcatgtgaat   5040
ttcatcctat ggaagccgtt aaaactaata tccttggtac ggaaaatgtt cttgaagcag   5100
ctatagcgaa tgaagtgaag agggttgtat gcctaagtac tgataaagct gtatacccga   5160
ttaacgcaat gggtatttca aaagctatga tggaaaaggt catggtcgcg aaatcccgta   5220
atgttgatcg caataaaaca gtaatatgtg gtacccgtta tgggaatgtt atggcatctc   5280
gcggttcagt tattccatta tttgttgatc ttattagagc gggcaagcca ctcacaataa   5340
ctgatcctaa tatgacccgc tttatgatga ctcttgagga tgcggtagat ttagttcttt   5400
atgcgtttga acatggtaat aatggtgata tctttgtgca aaaagcacct gcagcaacta   5460
ttgacacatt agctattgct ttaaaggaat tactaaatgt tcctgaccat ccggtaaatg   5520
tcattggaac gcgtcatggc gagaaattat atgaagctct acttagtcgt gaggaaatga   5580
tcgctgctat agatatgggc gattattacc gtgtcccgcc agatcttcgt gaccttaatt   5640
atggcaaata tgttgagcaa ggtgatagcc gaatatctga aatagaagat tataactctc   5700
ataatactca acggttagat gttgaaggca tgaaagagct cttgctaaaa ttagccttta   5760
ttcgagcaat tcgtgctggt gaaaaatata atctggattc atgatatgaa aatattagtt   5820
actggtgcaa atggttttat tggtcgtaat ttatgtttga ggcttgagga acttggttat   5880
aaagatctta ttagaattga tcgagaatca acgaagcaag atcttgaaca aggcttacag   5940
gatgccgatt ttatttatca cttagctggt atcaatagac ctaagactga tgatgagttt   6000
atttctggaa acagtgattt aacaaagcat atagttgagt atctcctttc tattggtaag   6060
aatacaccaa ttatgctaag ttcttcgata caagctgaac ttaataatgc ttatggggtt   6120
agcaaagctg tagctgaaag ctatgtcgaa aaatatgctg ctgctagtgg ttcttcgtat   6180
tatattttca gatatccaaa cgtttttggt aaatggtgta agccaaacta taattctttt   6240
atagcaactt tttgctacaa tatttccaat gatattgaga ttactatcaa tgatgcagca   6300
gcgccagtca atctggtcta tattgatgat gtttgtactg atgctatagc tcttctctct   6360
gggacggttg aaagtggata taaagttgtt gcaccaattt attcaacaac agttggtgaa   6420
gttgcagaat taatttatag cttcaaaaat agccgttcca ccctgatcac agaggctgtc   6480
ggggcgggat ttacccgtgc attgtattct acatggctga gttatttacc agcagagaag   6540
tttgcgtaca aggtaccttt ttatggggat gcccgcggag tcttttgtga gatgttgaaa   6600
acgccttcag cggggcagtt ttcatttttt actgctcacc ctggtattac gcgtggcgga   6660
cattaccatc acagtaaaaa tgagaagttt ttggtcattc gaggtcaggc atgctttaaa   6720
tttgaacatg tgattaccgg tgagcgatat gaactgaaag tttcatcggg tgagtttaag   6780
attgttgaaa cagttcctgg ttggacacat gacattacaa atattggaac tgatgaatta   6840
```

-continued

```
atagtcatgc tctgggcaaa tgaaattttc aaccgtgatg agcccgatac tattgcgaga   6900
cctctataat gaaaaaatta aaagttatgt ctgttgttgg aacccgtcct gagattatcc   6960
gtttgtcgag ggttcttgct aagtttgatg aatactgcga gcatattatt gtccatactg   7020
gtcaaaatta tgattacgaa ttaaatgaag tgttcttcaa tgacttgggt gttcgaaaac   7080
ctgattattt tttaaatgca gcgggtaaaa atgcggcgga aaccattggt caggttatta   7140
ttaaggtaga tgaagtatta gaaatcgaaa aacctgaagc aatactggta ttgggcgata   7200
cgaattcatg tatttctgcc attccggcca aacgccgtaa agtgcctata tttcatatgg   7260
aagcaggtaa ccgttgtttc gatcaacgcg tgcctgaaga aaccaacaga cgtattgttg   7320
accatacggc tgatatcaat atgacctaca gtgatattgc tcgtgaatat ctcttggctg   7380
aaggtatccc agctgatcgg atcataaaaa ctggtagccc tatgtttgag gttctttcat   7440
attatatgcc ccaaattgat ggttcagatg tgctatcgcg tttgaatcta cagtctggtg   7500
agtttttgt agtaagtgcg catcgtgaag agaatgttga ttctccaaaa cagctcgtaa   7560
agcttgcgaa cattctaaat actgttgctg aaaaatataa tcttccagtt attgtctcca   7620
cacacccaag gacacgtaac cgaatccgtg agcaaggaat tgaatttcat tcaaatataa   7680
atctactgaa accattgggt ttccatgatt ataaccactt gcagaagaac tcacgagctg   7740
tgctttcaga tagcggtact atcactgaag agtcatccat catgaatttc ccagcggtaa   7800
acatccggga agcgcatgag cgtccggaag gctttgagga agcatccgtc atgatggtgg   7860
ggttagagtg tgaacgcgta ttacaagcgc tggatattct ggcaacacaa ccgcgaggtg   7920
aagtccgtct tttacgtcag gttagtgatt acagcatgcc aaatgtgtcg gataaagttg   7980
tcagaattgt tcactcttac acagattatg ttaagagagt cgtctggaaa gaatattgat   8040
gaaacttgct ttaatcatag atgattacct gcccaacagt actcgtgttg gtgcaaaaat   8100
gtttcatgaa cttgctcaag aatttatcca gcgtgggcac gatgttacgg taattactcc   8160
tggtacgggc atgcaagaag agatttcttt tgataccttt caggggggtaa aaacatggcg   8220
ttttaaaagc gggccgctca aggatgtaag taaaattcag cgagcggtca atgaaacgct   8280
tttgtcctat cgggcgtgga aagccatcaa aaaatgggta aaaaaagaga cctttgaggg   8340
ggtgatttat tattcacctt ccatattctg ggggccttta gttaaaaaaa ttaaagctcg   8400
ttgccaatgt cctgcttatc ttattttaag agatatgttt ccacaatggg taattgatgc   8460
aggaatgctt aatgctggtt ccccaataga acgctacttt cgtctttttg aaaaaatatc   8520
ttatcgtcag gcaaatcgta ttggacttat gtctgataag aatcttgatg tttttcggaa   8580
agataataaa ggctatccgt gcgaagtttt gcgtaattgg gcatccctaa caccaacgat   8640
catacccaag gattatatac cactacgtaa gcgacttggc ctagaggata aaaccatttt   8700
cttctatggt ggaaacatag gtcatgcaca ggacatgaca aacttgatgc gacttgtgag   8760
aaacatggca gcatatcctc aagctcattt cctatttatt ggccaggggg atgaagttga   8820
attaattaat tcattagcat ctgagtgggc attgacgaat ttcacctatt tgccctcggt   8880
taaccaagat gaatttaagt tcattttgtc ggaaatggat atcggcttgt tttctctttc   8940
cgctagacac tcttcccata attttcctgg taagttatta ggctatatgg ttcagtcgct   9000
acctatttta ggtagcgtaa atgccggaaa tgatttgctc gacattgtca atcaaaataa   9060
tgcgggatta atccatgtca atggtgagga cgataaatta tgtcaatctg cgctattaat   9120
gttgcatgat attgatgtgc gccggcaact tggttcgggg gcgaatatat tgttgaaaga   9180
acaattctcc gttgagtctg cggcacagac gatagaaatg aggttggagg catgcaatgc   9240
```

```
gattaattga taatgaccaa ctcgacgaat tatatgatca agccgggcaa tcggaacgtt   9300
tacgttccca ccttatgatg cacggctcgc atcaagaaaa ggtacagcgt ttacttattg   9360
cattagtaaa gggcagctat gttgaaccgc attatcacga acttcctcat cagtgggaaa   9420
tgttcattgt tatggagggg caacttcagg tttgtttgta tggtagaaat ggtgaggtta   9480
taaagcaatt tatagcagga gataatactg gaatgagcat tgtggagttt tctccgggcg   9540
atatacacag tgtcgaatgc ctatctccgc gtgctcttat ggtggaagtt aaggaggggc   9600
catttgaccc ttcttttgca aaatcgttcg tgtgagcggc cgcgagctcg tcgactcgag   9660
gatccgtgta ggctggagct gcttcgaagt tcctatactt tctagagaat aggaacttcg   9720
gaataggaac taaggaggat attcatatgg ataaagccgt aagcatataa gcatggataa   9780
gctatttata ctttaataag tactttgtat acttatttgc gaacattcca ggccgcgagc   9840
attcagcgcg gtgatcacac ctgacaggag tatgtaatgt ccaagcaaca gatcggcgta   9900
gtcggtatgg cagtgatggg acgcaacctt gcgctcaaca tcgaaagccg tggttatacc   9960
gtctctattt tcaaccgttc ccgtgagaag acggaagaag tgattgccga aaatccaggc  10020
aagaaactgg ttccttacta tacggtgaaa gagtttgtcg aatctctgga aacgcctcgt  10080
cgcatcctgt taatggtgaa agcaggtgca ggcacggatg ctgctattga ttccctcaaa  10140
ccatatctcg ataaaggaga catcatcatt gatggtggta acaccttctt ccaggacact  10200
attcgtcgta atcgtgagct ttcagcagag ggctttaact tcatcggtac cggtgtttct  10260
ggcggtgaag agggggcgct gaaaggtcct tctattatgc ctggtggcca gaaagaagcc  10320
tatgaattgg tagcaccgat cctgaccaaa atcgccgccg tagctgaaga cggtgaacca  10380
tgcgttacct atattggtgc cgatggcgca ggtcactatg tgaagatggt tcacaacggt  10440
attgaatacg gcgatatgca gctgattgct gaagcctatt ctctgcttaa aggtggcctg  10500
aacctcacca acgaagaact ggcgcagacc tttaccgagt ggaataacgg tgaactgagc  10560
agttacctga tcgacatcac caaagatatc ttcaccaaaa aagatgaaga cggtaactac  10620
ctggttgatg tgatcctgga tgaagcggct aacaaaggta ccggtaaatg gaccagccag  10680
agcgcgctgg atctcggcga accgctgtcg ctgattaccg agtctgtgtt tgcacgttat  10740
atctcttctc tgaaagatca gcgtgttgcc gcatctaaag ttctctctgg tccgcaagca  10800
cagccagcag gcgacaaggc tgagttcatc gaaaaagttc gtcgtgcgct gtatctgggc  10860
aaaatcgttt cttacgccca gggcttctct cagctgcgtg ctgcgtctga agagtacaac  10920
tgggatctga actacggcga aatcgcgaag attttccgtg ctggctgcat catccgtgcg  10980
cagttcctgc agaaaatcac cgatgcttat gccgaaaatc cacagatcgc taacctgttg  11040
ctggctccgt acttcaagca aattgccgat gactaccagc aggcgctgcg tgatgtcgtt  11100
gcttatgcag tacagaacgg tattccggtt ccgaccttct ccgcagcggt tgcctattac  11160
gacagctacc gtgctgctgt tctgcctgcg aacctgatcc aggcacagcg tgactatttt  11220
ggtgcgcata cttataagcg tattgataaa gaaggtgtgt tccataccga atggctggat  11280
taa                                                                11283
```

<210> SEQ ID NO 16
<211> LENGTH: 13435
<212> TYPE: DNA
<213> ORGANISM: Artificial Sequence
<220> FEATURE:
<223> OTHER INFORMATION: example O16 rfb locus nucleotide sequence - O16-EPA production strain stLMTB11739

<400> SEQUENCE: 16

```
atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagtga aaatacttgt tactggtggc gcaggattta ttggttcagc tgtagttcgt   1320
cacattataa ataatacgca ggatagtgtt gttaatgtcg ataaattaac gtacgccgga   1380
aaccgggaat cacttgctga tgtttctgat tctgaacgct atgtttttga acatgcggat   1440
atttgcgatg cacctgcaat ggcacggatt tttgctcagc atcagccgga tgcagtgatg   1500
cacctggctg ctgaaagcca tgttgaccgt tcaattacag gccctgcggc atttattgaa   1560
accaatattg ttggtactta tgtccttttg gaagccgctc gcaattactg gtctgctctt   1620
gatagcgaca agaaaaatag cttccgtttt catcatattt ctactgacga agtctatggt   1680
gatttgcctc atccagatga agtaaataat acagaagaat tacccttatt tactgagacg   1740
acagcttacg cgccaagcag cccttattcc gcatccaaag catccagcga tcatttagtc   1800
cgcgcgtgga aacgtacata tggtttaccg acaattgtga ctaattgctc gaacaactat   1860
ggtccttatc atttcccgga aaagcttatt ccactggtta ttcttaatgc actggaaggt   1920
aaggcattac ctatttatgg caaaggagat cagatccgcg actggttgta tgttgaagat   1980
catgcgcgtg cgttatatac cgtcgtaacc gaaggtaaag cgggtgaaac ttataacatt   2040
ggtgggcaca acgaaaagaa aaacatcgat gtagtgctca ctatttgtga tttgctggat   2100
gagattgtac cgaaagagaa atcttatcgt gagcaaatca cttatgttgc tgatcgtccg   2160
ggacacgatc gccgctatgc tattgatgct gagaagattg gtcgcgcatt gggatggaaa   2220
ccacaggaaa cgtttgagag cgggattcgt aaaacggtgg aatggtacct gtccaataca   2280
```

-continued

```
aaatgggttg ataatgtgaa aagtggtgcc tatcaatcgt ggattgaaca gaactatgag   2340
ggccgccagt aatgaatatc ctcctttttg gcaaaacagg gcaggtaggt tgggaactac   2400
agcgtgctct ggcacctttg ggtaatttga ttgcttttga tgttcactct actgattatt   2460
gcggtgattt tagtaatcct gaaggtgtag ctgaaaccgt aagaagcatt cggccggata   2520
ttattgtcaa tgcagccgct cacaccgcag tagacaaagc agaatcagaa ccggagtttg   2580
cacaattaat taacgcaaca agtgtcgaag cgattgcgaa agcagcaaat gaagttggag   2640
cctgggttat ccattactcg actgattacg tcttccctgg aaatggcgat atgccatggc   2700
tggagacgga tgcaaccgca ccactaaatg tttacggtga aaccaagtta gccggagaaa   2760
aagcgttaca ggaatattgc gcgaagcatc ttattttccg gaccagctgg gtctatgcag   2820
gaaaaggaaa taacttcgcc aaaacgatgt tacgtctggc aaaagagcgt gaagaattag   2880
cggttattaa cgatcagttt ggtgcgccaa caggtgctga actgctggct gattgtacag   2940
cacatgccat tcgtgtcgca ctgaataaac cggatgtcgc aggcttgtac catttggtag   3000
ccagtggtac cacaacctgg tacgattatg ctgcgctggt ttttgaagag gcgcgcaaag   3060
caggcattcc ccttgcactc aacaagctca acgcagtacc aacaacagcc tatcctacac   3120
cagctcgtcg tccacataac tctcgcctta atacagaaaa atttcagcag aactttgcgc   3180
ttgtcttgcc tgactggcag gttggcgtga aacgaatgct caatgaatta tttacgacta   3240
cagcaattta atagtttttg catcttgttc gtgatggtgg agcaagatga attaaaagga   3300
atgatgaaat gaaaatgcgt aaaggtatta ttttagcggg tggttctggt acacgtcttt   3360
atcctgtgac tatggctgtc agtaaacagc tattacctat ttatgataaa ccgatgatct   3420
attacccgct ctctacactg atgttggcgg gtattcgcga tattttgatt atcagtacac   3480
ctcaggatac tcctcgtttt caacaattgc tgggtgacgg tagccagtgg ggcctgaatc   3540
ttcagtacaa agtgcaacct agcccagatg gcctcgcgca ggcatttatc atcggtgaag   3600
agtttattgg tggtgatgat tgtgctttgg ttcttggtga taatatcttt tacggtcacg   3660
atctgccgaa gctaatggag gccgctgtta acaaagaaag tggtgcaacg gtatttgcct   3720
atcacgttaa tgatccagaa cgctatggtg tcgttgagtt tgataaaaac ggtacggcaa   3780
tcagtctgga agaaaaaccg ttagaaccaa agagtaatta cgccgttaca ggtctgtact   3840
tttatgataa cgacgtggtt cagatggcga aaaacttgaa gccgtctgca cgtggtgagt   3900
tagaaattac agatattaac cgtatttatc ttgagcaggg acgtctgtct gtcgcgatga   3960
tggggcgtgg ctacgcgtgg ctggacacgg ggactcatca gagtctgata gaagcaagta   4020
attttattgc gacaattgaa gagcgccagg gattgaaggt ttcctgtcct gaagagattg   4080
catttcgtaa aggttttatt gatgttgagc aagtaagaaa attagctgta ccactaataa   4140
agaataatta tgggcagtat ctttataaaa tgacgaagga ttcaaattaa tgaatgtgat   4200
tagaactgaa attgaagatg tgctaattct ggagccaaga gtatttggtg atgatagagg   4260
tttcttttat gagagcttta atcaatcagc atttgaacat attctaggct atccggtcag   4320
ctttgttcaa gacaatcact cacgttcatc aaaaaatgta ctcagaggcc ttcactttca   4380
acgcggcgag tacgcacaag ataaacttgt acgctgcact catggagcag tttttgatgt   4440
tgctgttgat attcgaccca attcggtatc ctttggtaaa tgggttggtg ttctgctttc   4500
agctgataat aagcagcagt tgtggatacc aaaagggttt gctcatggct tttggttct    4560
gtctgatatc gctgaatttc aatataaaac tacaaactat tatcatcctg aaagcgattg   4620
tggaatatgt tggaatgatg aacgcattgc aattgattgg ccccaaacat cagggttaat   4680
```

```
cctttcgcca aaagatgaaa ggctctttac gttagatgag cttatcagat taaaattaat   4740
tgcatgaata cgaataaatt atctttaaga agaaacgtta tatatctggc tgtcgttcaa   4800
ggtagcaatt atcttttacc attgcttaca tttccatatc ttgtaagaac acttggtcct   4860
gaaaatttcg gtatattcgg tttttgccaa gcgactatgc tatatatgat aatgtttgtt   4920
gaatatggtt tcaatctcac agcaactcag agtattgcca aagcagcaga tagtaaagat   4980
aaagtaacgt ctatttttg ggcggtgata ttttcaaaaa tagttcttat cgtcattaca   5040
ttgattttct taacgtcgat gaccttgctt gttcctgaat ataacaagca tgccgtaatt   5100
atatggtcgt ttgttcctgc attagtcggg aatttaatct accctatctg gctgtttcag   5160
ggaaaagaaa aaatgaaatg gctgacttta agtagtattt tatcccgctt ggctattatc   5220
cctctaacat ttatttttgt gaacacaaag tcagatatag caattgccgg ttttattcag   5280
tcaagtgcaa atctggttgc tggaattatt gcactagcta tcgttgttca tgaaggttgg   5340
attggtaaag ttacgctatc attacataat gtgcgtcgat ctttagcaga cggttttcat   5400
gtttttattt ccacatctgc tattagttta tattctacgg gaatagttat tatcctggga   5460
tttatatctg gaccaacgtc cgtagggaat tttaatgcgg ccaatactat aagaaacgcg   5520
cttcaagggc tattaaatcc tatcacccaa gcaatatacc caagaatatc aagtacgctt   5580
gttcttaatc gtgtgaaggg tgtgatttta attaaaaaat cattgacctg cttgagtttg   5640
attggtggtg ctttttcatt aattctgctc ttgggtgcat ctatactagt aaaaataagt   5700
atagggccgg gatatgataa tgcagtgatt gtgctaatga ttatatcgcc tctgcctttt   5760
cttatttcat taagtaatgt ctatggcatt caagttatgc tgacccataa ttataagaaa   5820
gaattcagta agattttaat cgctgcgggt ttgttgagtt tgttgttgat ttttccgcta   5880
acaactcttt ttaaagagat tggtgcagca ataacattgc ttgcaacaga gtgcttagtt   5940
acgtcactca tgctgatgtt cgtaagaaat aataaattac tggtttgctg aggattttat   6000
gtacgattat atcattgttg gttctggttt gtttggtgcc gtttgtgcga atgagttaaa   6060
aaagctaaac aaaaaagttt tagtgattga gaaaagaaat catatcggtg gaaatgcgta   6120
cacagaggac tgtgagggta tccagattca taaatatggt gcacatattt ttcataccaa   6180
tgataaatat atatgggatt acgttaatga tttagtagaa tttaatcgtt ttactaattc   6240
tccactggcg atttataaag acaaattatt caaccttcct tttaatatga atactttcca   6300
ccaaatgtgg ggagttaaag atcctcaaga agctcaaaat atcattaatg ctcagaaaaa   6360
aaagtatggt gacaaggtac ctgaaaattt ggaggagcag gcgatttcat tagttgggga   6420
ggacttatac caagcattga taaagggtta tacggagaag cagtggggaa gaagtgcaaa   6480
agaattgcct gcatttatta ttaagcgaat cccagtgaga tttacgtttg ataacaatta   6540
tttttccgat cgctatcaag gtattccggt gggaggctac actaagctta ttgaaaaaat   6600
gcttgaaggt gtggacgtaa aattaggcat tgattttttg aaagacaaag attctctagc   6660
gagtaaagcc catagaatca tctacactgg acccattgat cagtacttcg actataggtt   6720
tggagcgtta gaatatcgct ctttaaaatt tgagacggaa cgccatgaat ttccaaactt   6780
ccaagggaat gcagtaataa atttcactga tgctaatgta ccatatacca gaataattga   6840
gcataaacat tttgactatg ttgagacaaa gcatacggtt gttacaaaag aatatccatt   6900
agagtggaaa gttggcgacg aaccctacta tccagttaat gataataaaa acatggagct   6960
ttttaagaaa tatagagagt tagctagcag agaagacaag gttatatttg gcgggcgttt   7020
```

-continued

```
ggccgagtat aaatattatg atatgcatca agtgatatct gccgctcttt atcaagtgaa   7080
aaatataatg agtacggatt aatgatctat cttgtaatta gtgtctttct cattacagca   7140
tttatctgtt tatatcttaa gaaggatata ttttatccag ccgtatgcgt taatatcatc   7200
ttcgcactgg tcttattggg atatgaaata acgtcagata tatatgcttt tcagttaaat   7260
gacgctacgt tgatttttct actttgcaat gttttgacat ttaccctgtc atgtttattg   7320
acggaaagtg tattagatct aaatatcaga aaagtcaata atgctattta tagcatacca   7380
tcgaagaaag tgcataatgt aggcttgtta gttatttctt tttcgatgat atatatatgc   7440
atgaggttaa gtaactacca gttcgggact agcttactta gctatatgaa tttgataaga   7500
gatgctgatg ttgaagacac atcaagaaat ttctcagcat acatgcagcc aatcattcta   7560
actacttttg ctttatttat ttggtctaaa aaatttacta atacaaaggt aagtaaaaca   7620
tttactttac ttgtttttat tgtattcatc tttgcaatta tactgaatac tggtaagcaa   7680
attgtcttta tggttatcat ctcttatgca ttcatcgtag gtgttaatag agtaaaacat   7740
tatgtttatc ttattacagc tgtaggtgtt ctattctcct tgtatatgct ctttttacgt   7800
ggactgcctg gggggatggc atattatcta tccatgtatt tggtcagccc tataatcgcg   7860
tttcaggagt tttattttca gcaagtatct aactctgcca gttctcatgt cttttggttt   7920
tttgaaaggc tgatggggct attaacaggt ggagtctcta tgtcgttgca taaagaattt   7980
gtgtgggtgg gtttgccaac aaatgtttat actgcttttt cggattatgt ttatatttcc   8040
gcggagctaa gctatttgat gatggttatt catggctgta tttcaggtgt tttatggaga   8100
ttgtctcgaa attacatatc tgtgaaaata ttttattcat atttatttta taccttttct   8160
ttcatttttt atcatgaaag cttcatgact aatattagca gttggataca aataactctt   8220
tgtatcatag tattctctca atttcttaag gcccagaaaa taaagtgaaa atgtattttt   8280
tgaatgattt aaatttctct agacgcgatg ctggatttaa agcaagaaaa gatgcactgg   8340
acattgcttc agattatgaa aacatttctg ttgttaacat tcctctatgg ggtggagtag   8400
tccagagaat tattagttct gttaagctta gtacatttct ctgcggtctt gaaaataaag   8460
atgttttaat tttcaatttc ccgatggcca aaccattttg gcatatattg tcattctttc   8520
accgccttct aaaatttaga atagtacctc tgattcatga tattgatgaa ttaagaggag   8580
gagggggtag tgattctgtg cggcttgcta cctgtgatat ggtcataagt cacaatccac   8640
aaatgacaaa gtaccttagt aaatatatgt ctcaggataa aatcaaagac ataaaaaatat   8700
ttgattacct cgtctcatct gatgtggagc atcgagatgt tacggataag caacgagggg   8760
tcatatatgc tggcaacctt tctaggcata aatgttcttt catatatact gaaggatgcg   8820
attttactct ctttggtgtc aactatgaaa ataaagataa tcctaaatat cttggaagtt   8880
ttgatgctca atctccggaa aagattaacc tcccaggcat gcaatttgga ctcatttggg   8940
atggagattc tgtcgaaacc tgtagtggtg cctttggcga ctatttaaag tttaataacc   9000
ctcataagac atctctttat ctttcaatgg aacttccagt atttatatgg gataaagccg   9060
cccttgcgga tttcattgta gataatagaa taggatatgc agtgggatca atcaaagaaa   9120
tgcaagagat tgttgactcc atgacaatag aaacttataa gcaaattagt gagaatacaa   9180
aaattatttc tcagaaaatt cgaacaggaa gttacttcag ggatgttctt gaagaggtga   9240
tcgatgatct taaaactcgc taaacgatat ggtctctgtg gttttattcg gcttgttaga   9300
gatgtcttat tgactcgtgt attttaccgg aactgtagaa ttattcgatt tccctgctat   9360
attcgcaatg atggtagcat taattttggt gaaaatttca caagtggagt cggtctcagg   9420
```

```
ctggatgcat ttggacgtgg cgtgattttt ttttccgata atgtgcaagt taacgactat   9480
gttcatatcg cctcaattga gagcgttacg ataggtcggg atacgcttat tgcaagtaaa   9540
gtatttatta ccgatcataa tcacggttcc tttaagcact ctgatccaat gagttcgcca   9600
aatatacctc cagacatgcg cacgttggaa tcttcagctg ttgtaattgg ccagagggtt   9660
tggttgggtg agaatgtgac ggttttgcct ggaacaatta ttggtaatgg agtcgtagtc   9720
ggcgccaatt ctgttgttag aggttctatt cccgaaaata ctgtcattgc gggagtacca   9780
gcaaaaatca taaagaaata caatcatgag accaaattat gggaaaaagc atagtcgttg   9840
tttctgcggt caattttacc actggcggtc catttaccat tttgaaaaaa tttttggcag   9900
caactaataa taaagaaaat gtcagtttta tcgcattagt ccattctgct aaagagttaa   9960
aagaaagtta tccatgggtt aaattcattg agtttcctga ggttaaaggg tcgtggctaa  10020
aacgtttgca ctttgaatat gtagtttgta aaaaactttc aaaagagctg aatgctacgc  10080
attggatttg tctgcatgat attacggcca atgtcgtcac taaaaaaaga tatgtgtatt  10140
gtcataaccc tgcccctttt tataaaggaa ttttattccg tgaaattctt atggagccta  10200
gctttttctt atttaaaatg ctatacgggc tgatatataa aataaacatt aaaaaaaata  10260
ctgcagtgtt tgttcaacaa ttctggatga aagaaaaatt tatcaagaaa tattctataa  10320
ataacatcat tgtcagtcgg ccagaaatta aattatctga taaaagccaa cttactgatg  10380
atgattctca atttaagaat aacccttctg agttgacaat attttaccct gctgttccac  10440
gagtatttaa aaattacgag cttattatta gtgcagcaag gaaattgaaa gaacaatcca  10500
atattaaatt tctgcttact atcagtggta cagaaaatgc gtatgcaaaa tatattatca  10560
gtcttgcaga aggactggat aatgttcatt tcctcgggta cttggataaa gaaaaaatcg  10620
atcattgtta taatatttca gatatagttt gttttccctc taggttagaa acatggggat  10680
tgccgttgtc tgaggctaaa gagcgaggta agtgggtatt agcatcagat ttcccattta  10740
ctagagaaac tcttggtagt tatgaaaaga aagctttttt tgattctaat aacgatgaca  10800
tgttagttaa acttattatt gacttcaaaa aaggtaacct caaaaaagat atctctgatg  10860
caaatttcat ttatcgtaat gaaaatgtat tagttgggtt tgatgaacta gttaatttta  10920
ttactgaaga acattgaaat ggtatatata ataatcgttt cccacggaca tgaagactac  10980
atcaaaaaat tactcgaaaa tcttaatgct gacgatgagc actacaagat tatcgtacgc  11040
gacaacaaag actctctatt attgaaacaa atatgccagc attatgcagg cctggactat  11100
attagtggag gtgtatacgg ctttggtcat aataataata ttgcggtggc gtatgtaaag  11160
gaaaaatata gacccgcaga tgatgattac attttgtttt tgaatcccga tatcatcatg  11220
aagcatgatg atttgctgac atatattaaa tatgtcgaaa gtaagcgtta tgcttttagt  11280
acattatgcc tgttccgaga tgaagcgaaa tctttacatg attattccgt aagaaaattt  11340
cctgtgcttt ctgattttat tgtgtcattt atgttaggga ttaataaaac aaaaattcct  11400
aaagaaagta tctattctga tacggttgtt gattggtgcg caggatcatt tatgctggta  11460
cgtttttcag attttgtgcg tgtaaatggc ttcgatcaag gttactttat gtactgtgaa  11520
gatattgacc tgtgcttgag gcttagcctg gctggtgtca gacttcatta tgttcccgct  11580
tttcatgcga tacattatgc tcatcatgac aatcgaagtt ttttttcaaa agccttcaga  11640
tggcacttaa aaagtacttt tagatattta gccagaaaac gtattttatc aaatcgcaac  11700
tttgatcgaa tttcatcagt tttcacccg taagagctcg gtacccgggc ctagggtgta  11760
```

-continued ggctggagct gcttcgaagt tcctatactt tctagagaat aggaacttcg gaataggaac 11820
taaggaggat attcatatcc gtcgacggcg gccgccctgc aggcatgcaa gcttgatcca 11880
tatggatcgc tagcttaatt aaataaagcc gtaagcatat aagcatggat aagctattta 11940
tactttaata agtactttgt atacttattt gcgaacattc caggccgcga gcattcagcg 12000
cggtgatcac acctgacagg agtatgtaat gtccaagcaa cagatcggcg tagtcggtat 12060
ggcagtgatg ggacgcaacc ttgcgctcaa catcgaaagc cgtggttata ccgtctctat 12120
tttcaaccgt tcccgtgaga agacggaaga agtgattgcc gaaaatccag gcaagaaact 12180
ggttccttac tatacggtga aagagtttgt cgaatctctg gaaacgcctc gtcgcatcct 12240
gttaatggtg aaagcaggtg caggcacgga tgctgctatt gattccctca aaccatatct 12300
cgataaagga gacatcatca ttgatggtgg taacaccttc ttccaggaca ctattcgtcg 12360
taatcgtgag ctttcagcag agggctttaa cttcatcggt acgggtgttt ctggcggtga 12420
agagggggcg ctgaaaggtc cttctattat gcctggtggc cagaaagaag cctatgaatt 12480
ggtagcaccg atcctgacca aaatcgccgc cgtagctgaa gacggtgaac catgcgttac 12540
ctatattggt gccgatggcg caggtcacta tgtgaagatg gttcacaacg gtattgaata 12600
cggcgatatg cagctgattg ctgaagccta ttctctgctt aaaggtggcc tgaacctcac 12660
caacgaagaa ctggcgcaga cctttaccga gtggaataac ggtgaactga gcagttacct 12720
gatcgacatc accaaagata tcttcaccaa aaaagatgaa gacggtaact acctggttga 12780
tgtgatcctg gatgaagcgg ctaacaaagg tacgggtaaa tggaccagcc agagcgcgct 12840
ggatctcggc gaaccgctgt cgctgattac cgagtctgtg tttgcacgtt atatctcttc 12900
tctgaaagat cagcgtgttg ccgcatctaa agttctctct ggtccgcaag cacagccagc 12960
aggcgacaag gctgagttca tcgaaaaagt tcgtcgtgcg ctgtatctgg gcaaaatcgt 13020
ttcttacgcc cagggcttct ctcagctgcg tgctgcgtct gaagagtaca actgggatct 13080
gaactacggc gaaatcgcga agattttccg tgctggctgc atcatccgtg cgcagttcct 13140
gcaaaaaatc accgatgctt atgccgaaaa tccacagatc gctaacctgt tgctggctcc 13200
gtacttcaag caaattgccg atgactacca gcaggcgctg cgtgatgtcg ttgcttatgc 13260
agtacagaac ggtattccgg ttccgacctt ctccgcagcg gttgcctatt acgacagcta 13320
ccgtgctgct gttctgcctg cgaacctgat ccaggcacag cgtgactatt ttggtgcgca 13380
tacttataag cgtattgata aagaaggtgt gttccatacc gaatggctgg attaa 13435

<210> SEQ ID NO 17
<211> LENGTH: 13228
<212> TYPE: DNA
<213> ORGANISM: Artificial Sequence
<220> FEATURE:
<223> OTHER INFORMATION: example O18A rfb locus nucleotide sequence - O18A-EPA production strain BVEC-L-00559

<400> SEQUENCE: 17
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360

-continued

```
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagtga aaatacttgt tactggtggc gcaggattta ttggttcagc tgtagttcgt   1320
cacattataa ataatacgca ggatagtgtt gttaatgtcg ataaattaac gtacgccgga   1380
aaccgggaat cacttgctga tgtttctgat tctgaacgct atgtttttga acatgcggat   1440
atttgcgatg cacctgcaat ggcacggatt tttgctcagc atcagccgga tgcagtgatg   1500
cacctggctg ctgaaagcca tgttgaccgt tcaattacag gccctgcggc atttattgaa   1560
accaatattg ttggtactta tgtccttttg gaagccgctc gcaattactg gtctgctctt   1620
gatagcgaca agaaaaatag cttccgtttt catcatattt ctactgacga agtctatggt   1680
gatttgcctc atccagatga agtaaataat acagaagaat tacccttatt tactgagacg   1740
acagcttacg cgccaagcag cccttattcc gcatccaaag catccagcga tcatttagtc   1800
cgcgcgtgga aacgtacata tggtttaccg acaattgtga ctaattgctc gaacaactat   1860
ggtccttatc atttcccgga aaagcttatt ccactggtta ttcttaatgc actggaaggt   1920
aaggcattac ctatttatgg caaaggagat cagatccgcg actggttgta tgttgaagat   1980
catgcgcgtg cgttatatac cgtcgtaacc gaaggtaaag cgggtgaaac ttataacatt   2040
ggtgggcaca acgaaaagaa aaacatcgat gtagtgctca ctatttgtga tttgctggat   2100
gagattgtac cgaaagagaa atcttatcgt gagcaaatca cttatgttgc tgatcgtccg   2160
ggacacgatc gccgctatgc tattgatgct gagaagattg gtcgcgcatt gggatggaaa   2220
ccacaggaaa cgtttgagag cgggattcgt aaaacggtgg aatggtacct gtccaataca   2280
aaatgggttg ataatgtgaa aagtggtgcc tatcaatcgt ggattgaaca gaactatgag   2340
ggccgccagt aatgaatatc ctcctttttg gcaaaacagg gcaggtaggt tgggaactac   2400
agcgtgctct ggcacctttg ggtaatttga ttgcttttga tgttcactct actgattatt   2460
gcggtgattt tagtaatcct gaaggtgtag ctgaaaccgt aagaagcatt cggccggata   2520
ttattgtcaa tgcagccgct cacaccgcag tagacaaagc agaatcagaa ccggagtttg   2580
cacaattaat taacgcaaca agtgtcgaag cgattgcgaa agcagcaaat gaagttggag   2640
cctgggttat ccattactcg actgattacg tcttccctgg aaatggcgat atgccatggc   2700
tggagacgga tgcaaccgca ccactaaatg tttacggtga aaccaagtta gccggagaaa   2760
```

-continued

```
aagcgttaca ggaatattgc gcgaagcatc ttattttccg gaccagctgg gtctatgcag   2820
gaaaaggaaa taacttcgcc aaaacgatgt tacgtctggc aaaagagcgt gaagaattag   2880
cggttattaa cgatcagttt ggtgcgccaa caggtgctga actgctggct gattgtacag   2940
cacatgccat tcgtgtcgca ctgaataaac cggatgtcgc aggcttgtac catttggtag   3000
ccagtggtac cacaacctgg tacgattatg ctgcgctggt tttgaagag gcgcgcaaag   3060
caggcattcc ccttgcactc aacaagctca acgcagtacc aacaacagcc tatcctacac   3120
cagctcgtcg tccacataac tctcgcctta atacagaaaa atttcagcag aactttgcgc   3180
ttgtcttgcc tgactggcag gttggcgtga aacgaatgct caatgaatta tttacgacta   3240
cagcaattta atagtttttg catcttgttc gtgatggtgg agcaagatga attaaaagga   3300
atgatgaaat gaaaatgcgt aaaggtatta ttttagcggg tggttctggt acacgtcttt   3360
atcctgtgac tatggctgtc agtaaacagc tattacctat ttatgataaa ccgatgatct   3420
attacccgct ctctacactg atgttggcgg gtattcgcga tattttgatt atcagtacac   3480
ctcaggatac tcctcgtttt caacaattgc tgggtgacgg tagccagtgg ggcctgaatc   3540
ttcagtacaa agtgcaacct agcccagatg gcctcgcgca ggcatttatc atcggtgaag   3600
agtttattgg tggtgatgat tgtgctttgg ttcttggtga taatatcttt tacggtcacg   3660
atctgccgaa gctaatggag gccgctgtta acaaagaaag tggtgcaacg gtatttgcct   3720
atcacgttaa tgatccagaa cgctatggtg tcgttgagtt tgataaaaac ggtacggcaa   3780
tcagtctgga agaaaaaccg ttagaaccaa agagtaatta cgccgttaca ggtctgtact   3840
tttatgataa cgacgtggtt cagatggcga aaaacttgaa gccgtctgca cgtggtgagt   3900
tagaaattac agatattaac cgtatttatc ttgagcaggg acgtctgtct gtcgcgatga   3960
tggggcgtgg ctacgcgtgg ctggacacgg ggactcatca gagtctgata gaagcaagta   4020
attttattgc gacaattgaa gagcgccagg gattgaaggt ttcctgtcct gaagagattg   4080
catttcgtaa aggttttatt gatgttgagc aagtaagaaa attagctgta ccactaataa   4140
agaataatta tgggcagtat ctttataaaa tgacgaagga ttcaaattaa tgaatgtgat   4200
tagaactgaa attgaagatg tgctaattct ggagccaaga gtatttggtg atgatagagg   4260
tttcttttat gagagcttta atcaatcagc atttgaacat attctaggct atccggtcag   4320
ctttgttcaa gacaatcact cacgttcatc aaaaaatgta ctcagaggcc ttcactttca   4380
acgcggcgag tacgcacaag ataaacttgt acgctgcact catggagcag tttttgatgt   4440
tgctgttgat attcgaccca attcggtatc ctttggtaaa tgggttggtg ttctgctttc   4500
agctgataat aagcagcagt tgtggatacc aaaagggttt gctcatggct tttggttct   4560
gtctgatatc gctgaatttc aatataaaac tacaaactat tatcatcctg aaagcgattg   4620
tggaatatgt tggaatgatg aacgcattgc aattgattgg ccccaaacat cagggttaat   4680
cctttcgcca aaagatgaaa ggctctttac gttagatgag cttatcagat taaaattaat   4740
tgcatgaggc cggccttaag gaggactagt cccggcgcgc catgagttta atcaaaaaca   4800
gtttttggaa cctttgcggg tatgtacttc cagctattgt gacactacca gctttgggta   4860
ttatggggcg aaaattaggc ccagaattat ttggtgtatt cactttggca ttagctgttg   4920
tgggttatgc aagcattttt gatgcaggcc ttactcgcgc agtgatacga gaagtcgcaa   4980
ttgaaaaaga taatgaagaa aataagttga aaattatttc ttcagcgaca gttgtaatta   5040
tttatttgag tttggccgcc tcactcttat tattttttt tagtggtcat atcgcattgc   5100
```

-continued

```
tactgaacat tagtgagact ttttttcata atgtaagtgt ctcgcttaaa attctcgcag   5160
catccatacc attattttg attactcaaa tatggttgtc aattttagaa ggtgaagaaa   5220
gatttggttt acttaatatc tacaaatcaa ttacgggagt gatattagca atctcaccgg   5280
cattatttat acttattaaa ccctctttga tgtatgcgat aataggctta gttctagcaa   5340
ggtttttatg ttttattttg gcttttataa tttgtcacga taaagtgctt aaagctaaac   5400
taacaatcga tataccaaca attaaaagat tgtttatgtt cggtggttgg attacagtaa   5460
gtaatatcat cagccctgtg ctatcatatt ttgataggtt tattgtttca aatcaacttg   5520
gggctgctaa tgttgctttt tatactgcac catcagaaat tatttctcgg cttagtataa   5580
ttccaggtgc gttttcaaga gccttatttc caagattagc taatgcaaat aattccgctg   5640
aaagatataa aacgaaaaga ttaattacaa tttcactttt aataatcatc acccctattt   5700
tttgtattgg cgtgttattt tcagagaaga taatggtttt atggatgggg gcatcatttt   5760
ttggtgagcc tggtttggta ttatcaatat tactgattgg ctttattttt aatggattgg   5820
cacaagtacc atttgccagt attcaatccc gaggtcatgc taagataact gcatttgttc   5880
atctcttaga gttgtttcct tatttattac ttttatttta cctcataaaa gcacatgggg   5940
ttgttggcgc gggtattgcg tggtcagtga ggatgatagt agattatata gcattaagtc   6000
ttttggacgg taagtatatt aataaataaa attcaaaatg caagttaata actcatggct   6060
ttatttgggt aggtgacaat ttataatgat atatatatta actttaactc ttcttctagt   6120
tatagccata atgttttctc ttctcggcac aaaaagtagg atcacatctc cattaccttt   6180
gcatttttta ccatggttac taactttaat tgtcgggata agtaattacg atcaatttta   6240
cgagtttaat gaaagaagct tttactcttt gttgatttgg tttacagtta tttttatatt   6300
ttatttcata ggggaactgg ttaattataa acgtgaaaat ataaatgttt attatggtct   6360
ttcacatatt aaatatgaat gtaaaaaata ttggatcatt gtcatcccaa tttcattata   6420
taccattttc gaaatatata tggttggtat ggggggagca gatggattct ttctcaattt   6480
acgtcttgca aatacattgg agggctatac gggtaaaaaa tttatcttaa tgcctgctgt   6540
atatcctcta atgatggcta tgttcgcaat tgtttgtcta acaaaaactt ccaaattaaa   6600
taaatactcc atttatttct ggatgttttt gtattgtatt ggcacaatgg gaaaattttc   6660
aatattaacg ccaatattga catatttaat tatttatgac ttcaaacata gattaaaagt   6720
aaaaaaaaca ataaagttta cattgttgat aattatatta gctttaactt tgcattttac   6780
acgtatggct gagaatgacc actcaacatt tttatctatt ttagggctct atatttattc   6840
accaataatt gctttaggcc agttgaatga agtaaatagt agtcattttg gtgagtatac   6900
gtttagattc atatatgcta taactaataa aattggcctt attaaagaat tgccagtaaa   6960
tactattctt gactattcat acgttcctgt accaacaaat gtatatactg cacttcaacc   7020
attttaccag gattttggtt atactggcat catatttgga gcagtattat acggactaat   7080
atatgtgagt ttatacacgg ccggtgttcg tggaaataat acacaggcat tactgattta   7140
cgcattgttt tcagttagca gtgcaacggc tttcttcgct gaaacgctag taacgaattt   7200
agctggaaat gtgatgttag tattatgtac catcttacta tggcgattta cagtaatatg   7260
caaaccagta cagtaaccat tctaatggcc acctacaatg gcgaggcctt catcaaaaat   7320
cagattttgt cactacaaca acaaacattt tctaactggc ggttatttat tcaggatgat   7380
gggtctacag acaatactat atctataata aaaaacttcc aaaaatctga ctccagaatt   7440
cggctagttg atgataattt gaaaggtcaa ggtgcaggaa aaaatttttt atcgctgata   7500
```

aagtacagcg agacagatta tacaatttat tgtgaccaag atgatatttg gttagaaaac 7560
aaaatatttg aattagtaaa gtatgcaaat gaaattaaat tgaatgtatc agatgcgcct 7620
tcgctagttt atgctgatgg ctatgcttat atggatggtg agggtacaat cgatttttct 7680
gggatatcta acaatcatgc tgatcaatta aaggattttc ttttttttaa tggtggatac 7740
caaggatgtt ctattatgtt caatcgtgca atgaccaaat ttcttctgaa ttatcgagga 7800
tttgtatatc tacatgacga tatcacaaca ttagctgcat acgctcttgg taaagtttat 7860
tttctcccga aataccttat gttatataga cagcacacga atgcggtaac tggtatcaaa 7920
acattccgca atggattgac ttctaaattt aaatcaccag taaactatct tttatcacga 7980
aaacattatc aggtaaaaaa atcttttttt gaatgtaaca gctctatctt atcagagacg 8040
aataaaaaag tttttttgga ttttatttca ttttgtgaat caaataataa atttacagat 8100
ttttttaagt tatggcgagg tgggtttaga ttaaataaca gtagaactaa attattatta 8160
aaattcttaa tacggagaaa atttagcgaa tgatttcaat acttacacct acttttaatc 8220
ggcaacatac tttatcaagg ctattcaatt ctcttatatt acaaactgat aaagattttg 8280
agtggataat aattgatgat ggtagtatag atgcaacagc ggtacttgta gaagatttta 8340
gaaaaaaatg tgattttgac ttgatttatt gctatcagga aaataatggt aagcccatgg 8400
ctttaaacgc tggtgttaaa gcttgtagag gcgattatat ctttattgtt gacagtgatg 8460
atgcactaac tcccgatgcc ataaaattaa ttaaagaatc aatacatgat tgcttatctg 8520
agaaggaaag tttcagcgga gtcggtttta gaaaagcata tataaaaggg gggattattg 8580
gtaatgattt aaataattct tcagaacata tatactattt aaatgcgact gagattagca 8640
atttaataaa tggtgatgtt gcatattgtt ttaaaaaaga aagtttggta aaaaatccat 8700
tcccccgtat agaagatgaa aaatttgttc cagaattata tatttggaat aaaataactg 8760
acaaggcgaa gattcgattt aacataagca aagttatata tctttgtgag tatcttgatg 8820
atggtctttc taaaaatttc cataaccagc ttaaaaaata cccaaagggg tttaagattt 8880
attacaaaga tcaaagaaaa cgagagaaaa cttatataaa aaaaacaaag atgctaatta 8940
gatatttgca atgttgttat tatgagaaaa taaaatgaaa atactatttg tcattacagg 9000
tttaggcctt ggaggtgctg agaagcaggt ttgtctttta gctgataaat taagtttaag 9060
cgggcaccat gtaaagatta tttcacttgg acatatgtct aataataaag tctttcctag 9120
cgaaaataat gttaatgtca ttaatgtaaa tatgtcaaaa aacatttctg gagttataaa 9180
aggttgtgtc agaattagag atgttatagc taatttcaaa ccagacattg tacacagtca 9240
tatgtttcat gcaaacatta tcactagatt gtctgtaatt ggaatcaaaa acagacctgg 9300
tattatatca actgcacata ataaaaatga aggtgggtat ttcagaatgc tcacatatag 9360
aataaccgat tgtttaagtg attgttgtac aaatgttagc aaagaagcag tggatgagtt 9420
tttacggata aaagccttta atcccgctaa agcaattact atgtataatg ggatagatac 9480
caataaattt aaatttgatt tattggcaag gagggaaatt cgagacggta ttaatataaa 9540
aaatgatgat atattattac ttgctgcagg tcgtttaacg ttagctaaag attatcctaa 9600
tttattgaat gcaatgactc tgcttcctga acactttaaa cttattatta ttggtgatgg 9660
tgaattgcgt gacgaaatta atatgcttat aaaaaaattg caattatcta atagggtgtc 9720
cttgttggga gttaaaaaaa atattgctcc ctatttttct gcatgtgata tttttgttct 9780
ctcttctcgt tgggaaggat ttggattagt cgtggcagaa gctatgtcat gtgagcgaat 9840

-continued

```
tgttgttggc acggattcag gggagtaag agaagttatt ggtgacgatg attttcttgt   9900
acccatatct gattcaacac aacttgcaag caaaattgaa aaattgtctt tgagccagat   9960
acgtgatcac attggttttc ggaatcgtga gcgtatttta aaaaatttct caatagatac  10020
tattattatg cagtggcaag aactctatgg aactataatt tgctcaaaac atgaaaggta  10080
gatttatatt tggaacgtgt cttttgtttg aatttaattc aatctcaatt gagatttttg  10140
tatttcaaaa ataccatcat agctaacgat gattggtatt tattttaaga tgctttctat  10200
aaatatattg acgtttttaa tgcgccgaaa cgattgggct gggaacagag aagtaaaact  10260
gttttgagaa tgaagagttt ttgagatgtt tatggatatt aaaaattgat ccagtgaatt  10320
aattatttat aataaatcaa gatttaatgt taataaatga taatcttttc tgacactcat  10380
attaattatg agtggtacgt ttggtaaacg gtaaactatt atatgacagc tagaacaact  10440
aaagttttgc acttacaatt actcccactc ttaagtggcg ttcaaagggt aacattaaac  10500
gaaattagtg cgttatatac tgattatgat tatacactag tttgctcaaa aaaaggtcca  10560
ctaacaaaag cattgctgga atatgatgtc gattgtcatt gtatccccga acttacgaga  10620
gaaattaccg taaagaatga ttttaaagca ttgttcaagc tttataagtt cataaaaaaa  10680
gaaaaatttg acattgtgca tacacattct tcaaaaacag gtattttggg gcgagttgct  10740
gccaaattag cacgtgttgg aaaggtgatc cacactgtac atggtttttc ttttccagcc  10800
gcatctagta aaaaaagtta ttacctttat tttttcatgg aatggatagc aaagttcttt  10860
acggataagt taatcgtctt gaatgtagat gatgaatata tagcaataaa caaattaaaa  10920
ttcaagcggg ataaagtttt tttaattcct aatggagtag acactgataa gttttctcct  10980
ttagaaaata aaatttatag tagcaccttg aatctagtaa tggttggtag attatccaag  11040
caaaaagatc ctgagacatt attgcttgct gttgaaaaac tgctgaatga aaatgttaat  11100
gttaagctga cacttgtagg agatggtgaa ctaaaagaac agttagaaag caggttcaaa  11160
cggcaagatg gacgtataat ttttcatgga tggtcagata acattgttaa tattttaaaa  11220
gttaatgatc tttttatatt accttctctt tgggagggta tgccattagc aattttagaa  11280
gcattgagct gtggacttcc atgtatagtc actaatattc caggtaataa tagcttaata  11340
gaagatggct ataatggttg tttgtttgaa attagagatt gtcagttatt atctcaaaaa  11400
atcatgtcat atgttggtaa gccagaactg attgcacagc aatctaccaa tgcacgatca  11460
tttattctga aaaattatgg attagttaaa agaaataata aggtcagaca gctatatgat  11520
aattaagagc tcggtacccg ggcctagggt gtaggctgga gctgcttcga agttcctata  11580
ctttctagag aataggaact tcggaatagg aactaaggag gatattcata tccgtcgacg  11640
gcggccgccc tgcaggcatg caagcttgat ccatatggat cgctagctta attaaataaa  11700
gccgtaagca tataagcatg gataagctat ttatacttta ataagtactt tgtatactta  11760
tttgcgaaca ttccaggccg cgagcattca gcgcggtgat cacacctgac aggagtatgt  11820
aatgtccaag caacagatcg gcgtagtcgg tatggcagtg atgggacgca accttgcgct  11880
caacatcgaa agccgtggtt ataccgtctc tattttcaac cgttcccgtg agaagacgga  11940
agaagtgatt gccgaaaatc caggcaagaa actggttcct tactatacgg tgaaagagtt  12000
tgtcgaatct ctggaaacgc ctcgtcgcat cctgttaatg gtgaaagcag gtgcaggcac  12060
ggatgctgct attgattccc tcaaaccata tctcgataaa ggagacatca tcattgatgg  12120
tggtaacacc ttcttccagg acactattcg tcgtaatcgt gagctttcag cagagggctt  12180
taacttcatc ggtaccggtg tttctggcgg tgaagagggg gcgctgaaag gtccttctat  12240
```

tatgcctggt ggccagaaag aagcctatga attggtagca ccgatcctga ccaaaatcgc 12300
cgccgtagct gaagacggtg aaccatgcgt tacctatatt ggtgccgatg gcgcaggtca 12360
ctatgtgaag atggttcaca acggtattga atacggcgat atgcagctga ttgctgaagc 12420
ctattctctg cttaaaggtg gcctgaacct caccaacgaa gaactggcgc agacctttac 12480
cgagtggaat aacggtgaac tgagcagtta cctgatcgac atcaccaaag atatcttcac 12540
caaaaaagat gaagacggta actacctggt tgatgtgatc ctggatgaag cggctaacaa 12600
aggtacgggt aaatggacca gccagagcgc gctggatctc ggcgaaccgc tgtcgctgat 12660
taccgagtct gtgtttgcac gttatatctc ttctctgaaa gatcagcgtg ttgccgcatc 12720
taaagttctc tctggtccgc aagcacagcc agcaggcgac aaggctgagt tcatcgaaaa 12780
agttcgtcgt gcgctgtatc tgggcaaaat cgtttcttac gcccagggct tctctcagct 12840
gcgtgctgcg tctgaagagt acaactggga tctgaactac ggcgaaatcg cgaagatttt 12900
ccgtgctggc tgcatcatcc gtgcgcagtt cctgcaaaaa atcaccgatg cttatgccga 12960
aaatccacag atcgctaacc tgttgctggc tccgtacttc aagcaaattg ccgatgacta 13020
ccagcaggcg ctgcgtgatg tcgttgctta tgcagtacag aacggtattc cggttccgac 13080
cttctccgca gcggttgcct attacgacag ctaccgtgct gctgttctgc ctgcgaacct 13140
gatccaggca cagcgtgact attttggtgc gcatacttat aagcgtattg ataaagaagg 13200
tgtgttccat accgaatggc tggattaa 13228

<210> SEQ ID NO 18
<211> LENGTH: 13554
<212> TYPE: DNA
<213> ORGANISM: Artificial Sequence
<220> FEATURE:
<223> OTHER INFORMATION: example O25B rfb locus nucleotide sequence - O25B-EPA production strain stGVXN4459

<400> SEQUENCE: 18
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctgg caaaacgtat gccgggtgac ctctctgaat actccgtcat ccagactaaa 540
gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccgg aactggaacg tactcagcct ggtgcatggg gacgtattca gctgactgat 720
gctattgccg agctggcgaa aaaacaatcc gttgatgcaa tgctgatgac cggcgacagt 780
tacgactgcg gcaaaaaaat gggctatatg caggcgtttg tgaagtatgg cctacgcaac 840
ctgaaagaag ggcgaagttt ccgtaaaggt attgagaagc tgttaagcga ataatgaaaa 900
tctgaccgga tgtaacggtt gataagaaaa ttataacggc agtgaaaatt cgcagcaaaa 960
gtaatttgtt gcgaatcttc ctgccgttgt tttatataaa ccatcagaat aacaacgagt 1020

-continued

```
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagcta gcagtgaaga tacttgttac tggtggcgca ggatttattg gttctgctgt   1320
tgttcgtcac ataataaata atacgcaaga tagtgttgtt aatgtcgata aattaacata   1380
cgccggaaac ctggaatcac ttgcagatgt ttctgattct gaacgctatt tctttgaaca   1440
tgcggatatt tgtgatgcag ctgcaatggc acggattttt gctcagcatc agccggatgc   1500
agtgatgcac ctggcagctg aaagccatgt tgaccgttca attacaggcc ctgcggcatt   1560
tattgaaacc aatattgtgg gtacttatgt cctttttagaa gcggctcgga attattggtc  1620
tggtctggat gatgaaaaga aaaaaaactt ccgttttcat catatttcta ctgatgaggt   1680
gtatggtgac ttaccccatc cggatgaagt aaatagcaat gaaacgttgc cgctatttac   1740
ggaaacgaca gcatacgcgc caagtagtcc atattctgct tctaaagctt ccagcgatca   1800
tttggttcgc gcatggaaac gtacttatgg tttaccgacc attgtgacta attgctcgaa   1860
caactatggt ccttatcatt tcccggaaaa gcttattcca ctggttattc ttaattcact   1920
ggaaggtaag gcattaccta tttatggcaa aggagatcag atccgcgact ggttgtatgt   1980
agaggatcat gctcgagcgt tatataccgt cgtaaccgaa ggtaaagcgg gcgaaactta   2040
taacattggt ggacacaacg aaaagaaaaa catcgacgta gtgttcacta tttgtgattt   2100
gttggatgag atagtcccga aagagaaatc ttaccgcgag caaattactt atgttaccga   2160
tcgtccggga cacgatcgcc gttatgcgat tgatgctgag aagattggtc gcgaattggg   2220
atggaaacca caggaaacgt ttgagagtgg gattcgtaaa acggtggaat ggtacctgtc   2280
caatacaaaa tgggttgata atgtgaaaag tggtgcctat caatcgtgga ttgaacagaa   2340
ctatgagggc cgccagtaat gaatatcctc ctttttggca aaacagggca ggtaggttgg   2400
gaactacagc gtgctctggc acctctgggt aatttgattg ctcttgatgt tcactccact   2460
gattactgtg gtgattttag taatcctgaa ggtgtagctg aaaccgtaag aagcattcgg   2520
cctgatatta ttgtcaacgc agccgctcac accgcagtag acaaagcaga atcagaaccg   2580
aagtttgcac aattactgaa cgcgacgagt gtcgaagcga tcgcgaaagc agccaatgaa   2640
gtcggcgcct gggttattca ctactctact gactacgtat ttccggggac cggtgaaata   2700
ccatggcagg aggaggatgc aaccgcaccg ctaaatgttt acggtgaaac caagttagcg   2760
ggagaaaaag cattacaaga gcattgtgcg aagcacctta ttttccggac cagctgggtc   2820
tatgcaggta aaggaaataa cttcgccaaa acaatgttgc gtctggcaaa agagcgtgaa   2880
gaattagccg ttattaatga tcagtttggt gcgccaactg gcgcagagtt actggctgat   2940
tgtacggcac atgctattcg tgtggcactg aataaaccgg aagtcgcagg cttgtaccat   3000
ctggtagcta gtggtaccac aacgtggcac gattatgctg cgctggtttt tgaagaggcg   3060
cgcaaagcag gcattcccct tgcactcaac aagctcaacg cagtaccaac aacagcctat   3120
cctacaccag ctcgtcgtcc acataactct cgccttaata cagaaaaatt tcagcagaac   3180
tttgcgcttg tcttgcctga ctggcaggtt ggcgtgaaac gaatgcttaa cgaattattt   3240
acgactacag caatttaata gtttttgcat cttgttcgta atggtggagc aagatgtatt   3300
aaaaggaatg atgaaatgaa aacgcgtaaa ggtattattt tggcgggtgg ttctggtact   3360
```

-continued

```
cgtctttatc ctgtgacgat ggccgtcagt aaacagctgt taccgattta tgataaaccg   3420
atgatctatt acccgctctc tacactgatg ttagcgggta ttcgcgatat tctgattatc   3480
agtacaccac aggatactcc tcgttttcaa caactgctgg gtgacgggag ccagtggggc   3540
ctgaatcttc agtacaaagt gcaaccgagt ccggatggtc ttgcgcaggc gtttattatc   3600
ggtgaagagt ttattggtgg tgatgattgt gctttggtac ttggtgataa tatcttctac   3660
ggccacgacc tgccgaagtt aatggacgta gctgttaaca aagaaagtgg tgcaacggta   3720
tttgcctatc acgttaatga tcctgaacgt tatggtgtcg tggagtttga taataacggt   3780
actgcaatta gcctggaaga aaaaccgctg gaaccaaaaa gtaactatgc ggttactggg   3840
ctttatttct atgacaatga cgttgtggaa atggcgaaaa accttaagcc ttctgcccga   3900
ggtgaactgg aaattaccga tattaaccgt atttatatgg aacaaggacg tttgtctgtc   3960
gctatgatgg ggcgtggcta tgcatggctg gatacaggga cgcatcaaag tcttattgaa   4020
gcaagcaact tcattgccac cattgaagag cgccagggac taaaggtttc ctgtccggaa   4080
gaaattgctt atcgtaaagg gtttattgat gctgagcagg taaaagtatt agccgaaccg   4140
ttgaagaaaa atgcttatgg tcagtatctg ctcaaaatga ttaaaggtta ttaataagat   4200
gaacgtaatt aaaactgaaa ttcctgatgt gctgattttt gaaccaaaag tttttgggga   4260
tgaacgtggc ttcttttttg agagttttaa tcagaggatt tttgaagaag cagtaggtcg   4320
taaggttgag tttgttcagg ataaccattc taagtccagt aaaggtgttt tacgtggtct   4380
tcattatcag ttagaacctt atgctcaagg aaaactggtg cgctgtgttg ttggcgaggt   4440
tttgatgtt gcggttgata ttcgtaaatc gtcacctaca tttgggaaat gggttggggt   4500
gaatttgtct gctgagaata agcgtcagtt gtggattcct gagggatttg cacatggttt   4560
tttggtgctg agtgatttag cagaagtttt atataaaacg aatcaatatt atgctccatc   4620
acatgaaaaa aatattatat ggaatgacct cttgcttaat attaaatggc cgagcacagc   4680
actgatcact ctgtctgata aggatgcaaa tggggaaaga tttgaactaa gtgagttttg   4740
aaatgtctct cttaaaacat agtatatgga atgttgcggg ctactttata ccaacattaa   4800
ttgcaattcc cgcctttgga ttaattgcga ggaaaattgg tgtagaacta tttggtttgt   4860
atacgttagc aatgattttt atagggtatg caagtatatt tgatgctggg ttaacaagag   4920
ctgttgtgcg tgaaatagca ttactaaaaa acagagtgga cgattgtaat acgataatag   4980
taacttctat tatcgctgtg atatttttag ggtttatcgg aggcggggga gtgtttctgc   5040
ttaaaggcga tattattgaa ctgttaaata tctcaccaat atattacgcc gattcgataa   5100
agtctctagt attattatca tctctgatac ctgtattctt agtcacgcaa atactattag   5160
cagagcttga gggtcgggaa tattttggga ttctaaatat acaaaaaagt gtagggaatt   5220
ctttaattgc agggttacct gcattatttg ttttaattaa tcaaacgctt ttttctgcaa   5280
ttattggtgt agcgattgca agagttatat gcttgtggtt aagctacatt atgagcaggg   5340
aaagaataac tatcgatatc tcattttttt caataactgt tttaaagcgg ttatttagat   5400
atggcgggtg ggtaactata agtaacataa tatctcctat attagcgagt atggatagat   5460
ttattctatc ccatatccag ggagcatcaa aaatatcatt ctatacagtc cctaatgagc   5520
tggtaactag gcttggaata gttccaggct ctcttgggaa agctgttttt ccaaaattaa   5580
gtcatgcaag gaattttaca gcgtcatatg cagagcaaaa aaaagcttat atattaatga   5640
ctgtcattgt aatgcctttg gttttatttg tatattatta cgcaaagttt attttaacat   5700
tgtggatggg ggctgagtat gcagggattt cggtcgaaat attacggatt atgcttatag   5760
```

```
ggtatatttt taactgttat tcacaaatct cttttgccaa catacaggcc tttggaaaag   5820
caaaatacac tgcatacatc catatgatgg aatttattcc ttatttgata atgttatata   5880
taatttcaaa ggaatatggg gttattggtg ttgcgtggtt atggacaatt cgagtaataa   5940
ttgatttttt gatgctttta tatatgagtt atcgttgtaa taatcttatg aaaaaagggt   6000
agcctgatga tatatattgt ggtattaaat tggaatgggg ctatagatac cattaattgt   6060
gttaaaagtt taatggattt aaatgttagc gattataaaa ttatcattgt tgataactgt   6120
tctatggata actcatatga tactataaaa gaaaatctta attcattata tattgctgat   6180
aaaagtatca ttgaggtgaa gtatgaggat agaaataaat ataaaacctt agaaaacgat   6240
aaaatcatat taatacaatc tccgcaaaat aatgggtacg caagtggtaa taatattggc   6300
atagagttcg ctcttaatca ggagaatatg aaatacgtct gggttctgaa taatgatact   6360
gaagtggata aagaggcttt aactcattta attagtaaat gtgattcaga taaaagtata   6420
gggatttgcg gttctcgttt agtctatttt gccgacagag agatgcagca aggactaggt   6480
ggggtgcata acaaatggtt atgcactaca aaaaattatg aaatgggaag attagtttcc   6540
aaaaaatatg atgatgaagt cattagtaat gatatagatt atataattgg cgcatcgatg   6600
tttttctcta gagaatgttt ggaaacagtt ggattgatga atgaagaata tttttatac    6660
tatgaagagt tagatatttg cctcagagca aaagcaaaga actttaaatt aggtatttgc   6720
tcagaaagtt tggtttatca taaaataggt gcaagtactg atgggggaaa gagcatgatg   6780
gctgatcttt gctcaataaa aaataggctg gtcattacag aaaggtttta tccccaatat   6840
tattggacgg tatggttgtc actttttgtt gtagcattta accgtgctag aagaggtgag   6900
tttaataaga tgaaaagatg tttgaatgtt atgtttaact tcaaacgaaa caaaggtagc   6960
aaatgccatt agaatatgca cttaatcatg gtgttaataa atctatagtt tgatatgtta   7020
ttaaagggta tttaatgaaa gtggcttttt tatctgctta tgatccacta tctacatcca   7080
gttggtctgg cacaccttat tatatgctaa aggcattatc gaagagaaat atttccattg   7140
aaatattagg accggtaaat agctatatga tatacatgtt aaaagtatat aaattaatat   7200
taaggtgttt cggaaaagaa tatgattata gtcattcgaa gttgctttcc aggtattacg   7260
gtagaatatt cggtaggaaa ttaaaaaaaa ttgatggttt ggattttatt atcgcacctg   7320
caggttcctc acaaattgct tttttaaaaa caaccatacc aataatatat ctatcggata   7380
caacatatga tcaattaaaa agctattatc cgaatttaaa taaaaaaaca attataaatg   7440
atgaggatgc aagtttaatc gaacgcaagg ctattgaaaa agcaacagta gtatctttcc   7500
catctaaatg ggcaatggat ttttgcagga attattacag attagatttt gataaattag   7560
ttgaaatacc atgggggggct aatttatttg atgatattca ctttgctaat aaaaatataa   7620
ttcaaaagaa tagttatact tgtcttttct tgggagttga ttgggaaaga aaaggtggga   7680
aaacagcctt gaaagcaatt gaatatgtaa ggcagttata tgggatcgat gttagactaa   7740
aaatttgtgg atgtactccg aatcaaaaga ttttacctac ttgggttgaa ttaattgata   7800
aagtagataa aaataacgtt gacgaatatc agaaattcat cgatgtgtta tctaacgctg   7860
atatacttct tttaccaacc attgctgaat gttatggaat ggtattttgt gaagctgctg   7920
cttttggatt gcctgttgtc gctacagata caggtggagt cagttctata gttatcaacg   7980
aaaggacggg gatattaatt aaagacccgt tagactataa gcactttgga aatgcaattc   8040
ataaaaataat tagttccgta gagacttatc aaaactactc ccaaaacgca agaattagat   8100
```

-continued

```
ataataatat attgcattgg gacaattggg ctaaaaagat aattgagatt atgtatgagc   8160
ataagaatag aagaatcaaa tagcacaaaa agaattatat gtttatttat actttttctt   8220
gttttccctg attttttgtt ttatacatta ggggttgata attttagcat ttcaacgata   8280
atctcaatta cattgctttt tgttttttta agagctaaaa atatttgcaa agataatttt   8340
ctaataatag tagcgttatt catattgttg tgttttaact gtttgttaag tatgctattt   8400
aatattgaac aggctttaac atttaaagtt gtactttcaa tatatagcat cttaataatg   8460
gcatacgtct cctcttgtta tgcacagacg ttgtggttat gttctgaaga aatacttaag   8520
agatccgtct tttatttgtt cgcatttctt tgccttattg gcattataag tattctttta   8580
cagaagactg agattataca tgataaaagt atgattcttt ttcctgaacc atcagcattt   8640
gcattggttt ttatacctat cttttcattt tgtttatact atacaagagg ggggggggcta   8700
ctattgctct atatattatc tttgggtatt gcgttaggta tccagaattt aacaatgttg   8760
gtaggcattg tgattagtgt ttttgtgatg aaaaaaataa ctataaggca aactattgtt   8820
atacttttgg gggcatggat tttttccatg atattaagtg atttagacat ttcttactat   8880
acatcgcggc ttgattttaa aaatactacg aacctatcag tgcttgtata tctttcagga   8940
attgaaagag ctttcttgaa ttttattaca agttatggtc ttggtattgg ttttcaacaa   9000
atgggagtga atggggagat aggaatatat caacaaattt tagctgaact tgatgcccct   9060
atgttaaata tatacgatgg ctcatttatt tcttctaagt taatatctga gtttggggtt   9120
attggtgcat taatgtgtat tttctatttt ttttattttt cccgatttta tctgcgtttc   9180
aaaaaaagta agagatattc accgcagtat attttagcat atagcttcta catgtgtttc   9240
ttcatccctc tttttatacg tggtgctggt tatataaacc cctatgtgtt tatgttattt   9300
tcatcaatat ttttgtgcaa atatcacgct aaaaatatct tgatgaaatc taatgtccag   9360
atagctatat aatagtagat tatattatca ttatcacgta aattacatat taatagcata   9420
tatgataact aggacataaa taatgtgcat taaaaaaaaa cttaagttaa ttaaacgata   9480
tggcctttat ggtggtctta ggcttcttaa agatatattc ttaacaaaat ttttattttg   9540
ttcaaatgtt aggattatta gatttccatg ttatattaga aaagatggaa gtgttagttt   9600
tggaaaaggt tttacatcag gtgtaggatt acgagttgat gcatttatgg atgccgtagt   9660
ttccattgga gaaaatgttc aaattaatga ctatgttcac atcgcggcta ttaataatgt   9720
cattattggt agagatacat taatagcaag taaagtattt attagtgatc ataatcatgg   9780
tatttttttct aaatccgata tccatagttc accaactatt attccttcgt ctaggcccct   9840
tgaatctgca cctgtgtata ttggagagcg tgtgtggatt ggcgaaaatg tgacaatatt   9900
accaggtgcg tgtataggta atggtgtagt tattggcgca aacagtgttg ttcgtggtga   9960
gattcctaat aatgtgatca ttgctggtgt tccagctaaa attgttaaaa aatataacta  10020
tgagcgtatg caatgggaaa gaatatagtt gtaatatcgg ctgttaattt tacaaccgga  10080
ggcccccttta ccgtactaaa aaatgtgctt acagcaacta aagatagagc cgaatgtaaa  10140
tttattgcac tggttcatag ctctgctgaa ctaatggaat tatttccgtg ggttgaattt  10200
atagagtatc cagaagtcaa gtcttcgtgg gttaaaagat tatatttcga atatataact  10260
tgcaatagat tatctaaggt gattaaggca actcattggg tatgcttaca tgatattaca  10320
gcaaatgtta gtgtacccta tagatttgtt tattgccaca atcctgcacc gttctataaa  10380
tatttaagct atcgagatat tataggagaa cctaaatttt atctttttta tcttttttat  10440
gggcttttat acaatatcaa tataaaaaag aacacagcag tttttgttca gcagcagtgg  10500
```

```
ctaaaaaaag aattcgaaaa aaaatataag ttaaagaatg ttgttgttag tcgccctgaa  10560
gatatttgcc cttttgaaag tgatggtttg gtaagaaata ataataaaaa ggatgtgagg  10620
atattttacc cagcagtgcc ccgtatattt aaaaactttg aagttatcat acgtgctgca  10680
caaatattac aagataaaaa tattcatttt tatcttactt ttgatggtac tgaaaataag  10740
tatgcaaaaa gaatatataa attagcttcc gaactgaaaa atgtacattt cctcggttac  10800
cttaatgcaa ccgagatggt taacttttat caagattcag atattatttg tttcccatcg  10860
aaactagaaa cgtggggatt accattatca gaagctaaaa catacaaaaa atggatattt  10920
gcggcagact taccttatgc tcatgaagtt ttatataact attcaaaaac tagatatttt  10980
ccatttgacg atgagaaaat acttgttcgc tacatattag agtacacaag taaaaatatg  11040
catgaagata taaaaaatag tagggtgaat tttaataatg atgcattgac tggttttgaa  11100
cagtttattg aatatatcct caaggggaac tgacgtggtt tatattataa tcgtttcaca  11160
tggccatgat gactatatag aaaatctttt attaaattta aagttgccct ctggaagatt  11220
taaaataata gttcgtgata acaaaagttc aatggtttta aaaaaaacat gcgaaaaaaa  11280
ttgcgtaacc tatttgcatg gagggcaata tggatttgga cataataata acatagcagt  11340
gtcatatata attaataact tcatgattat gaataatgat tattttctct ttcttaaccc  11400
cgatgtattc ataaccagtg aaagtttgat taattatgtt gattatataa ttagtaatga  11460
ttataagttt agcacattat gtctttatcg agattttact aaaagcaaac atgattattc  11520
aatacggagt tttccaactt tatatgattt tctttgttct tttttattgg gggtgaataa  11580
aagtaaaatt aagaaggaaa atatactttc tgatactgta gttgattggt gtgctggctc  11640
atttatgctt attcatgctt taagtttctt aaatgtgaat ggttttgatc aaaaatattt  11700
tatgtattgt gaagatattg acctttgtat gcgtttaaaa ttaagtggag tagatcttta  11760
ctatactccc cattttgatg ctattcatta tgcgcagcat gaaaatagaa gaatatttac  11820
taaagcattt cgatggcata taaggagtat tacgcgctac atattacgga aaccaattct  11880
ttcttataaa aactatagaa aaattacatc cgaactggta aagtgattaa ggatccgtgt  11940
aggctggagc tgcttcgaag ttcctatact ttctagagaa taggaacttc ggaataggaa  12000
ctaaggagga tattcatatg gataaagccg taagcatata agcatggata agctatttat  12060
actttaataa gtactttgta tacttatttg cgaacattcc aggccgcgag cattcagcgc  12120
ggtgatcaca cctgacagga gtatgtaatg tccaagcaac agatcggcgt agtcggtatg  12180
gcagtgatgg gacgcaacct tgcgctcaac atcgaaagcc gtggttatac cgtctctatt  12240
ttcaaccgtt cccgtgagaa gacggaagaa gtgattgccg aaaatccagg caagaaactg  12300
gttccttact atacggtgaa agagtttgtc gaatctctgg aaacgcctcg tcgcatcctg  12360
ttaatggtga aagcaggtgc aggcacggat gctgctattg attccctcaa accatatctc  12420
gataaaggag acatcatcat tgatggtggt aacaccttct tccaggacac tattcgtcgt  12480
aatcgtgagc tttcagcaga gggctttaac ttcatcggta ccggtgtttc tggcggtgaa  12540
gagggggcgc tgaaaggtcc ttctattatg cctggtggcc agaaagaagc ctatgaattg  12600
gtagcaccga tcctgaccaa aatcgccgcc gtagctgaag acggtgaacc atgcgttacc  12660
tatattggtg ccgatggcgc aggtcactat gtgaagatgg ttcacaacgg tattgaatac  12720
ggcgatatgc agctgattgc tgaagcctat tctctgctta aaggtggcct gaacctcacc  12780
aacgaagaac tggcgcagac ctttaccgag tggaataacg gtgaactgag cagttacctg  12840
```

atcgacatca ccaaagatat cttcaccaaa aaagatgaag acggtaacta cctggttgat 12900
gtgatcctgg atgaagcggc taacaaaggt accggtaaat ggaccagcca gagcgcgctg 12960
gatctcggcg aaccgctgtc gctgattacc gagtctgtgt ttgcacgtta tatctcttct 13020
ctgaaagatc agcgtgttgc cgcatctaaa gttctctctg gtccgcaagc acagccagca 13080
ggcgacaagg ctgagttcat cgaaaaagtt cgtcgtgcgc tgtatctggg caaaatcgtt 13140
tcttacgccc agggcttctc tcagctgcgt gctgcgtctg aagagtacaa ctgggatctg 13200
aactacggcg aaatcgcgaa gattttccgt gctggctgca tcatccgtgc gcagttcctg 13260
cagaaaatca ccgatgctta tgccgaaaat ccacagatcg ctaacctgtt gctggctccg 13320
tacttcaagc aaattgccga tgactaccag caggcgctgc gtgatgtcgt tgcttatgca 13380
gtacagaacg gtattccggt tccgaccttc tccgcagcgg ttgcctatta cgacagctac 13440
cgtgctgctg ttctgcctgc gaacctgatc caggcacagc gtgactattt tggtgcgcat 13500
acttataagc gtattgataa agaaggtgtg ttccataccg aatggctgga ttaa 13554

<210> SEQ ID NO 19
<211> LENGTH: 15197
<212> TYPE: DNA
<213> ORGANISM: Artificial Sequence
<220> FEATURE:
<223> OTHER INFORMATION: example O75 rfb locus nucleotide sequence - O75-EPA production strain stLMTB11737

<400> SEQUENCE: 19
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctgg caaaacgtat gccgggtgac ctctctgaat actccgtcat ccagactaaa 540
gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccgg aactggaacg tactcagcct ggtgcatggg gacgtattca gctgactgat 720
gctattgccg agctggcgaa aaaacaatcc gttgatgcaa tgctgatgac cggcgacagt 780
tacgactgcg gcaaaaaaat gggctatatg caggcgtttg tgaagtatgg cctacgcaac 840
ctgaaagaag ggcgaagtt ccgtaaaggt attgagaagc tgttaagcga ataatgaaaa 900
tctgaccgga tgtaacggtt gataagaaaa ttataacggc agtgaaaatt cgcagcaaaa 960
gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagcta gcagtgaaga tacttgttac tggtggcgca ggatttattg gttctgctgt 1320

```
tgttcgtcac ataataaata atacgcaaga tagtgttgtt aatgtcgata aattaacata   1380
cgccggaaac ctggaatcgc tcgctgaaat ttctgattct gaacgttatt catttgagca   1440
tgcagatatc tgcgatgccg aagcgatggc tcgtattttc gcacagcacc agccagacgc   1500
ggtgatgcac ctggcagcag agagccacgt tgaccgctca ataactggcc ctgcggcatt   1560
tattgaaacc aatattgtgg gtacttatgt tcttttagaa gcggcgcgca attattggtc   1620
tggtctggat gatgaaaaga aaaaaaactt ccgctttcat catatttcta ctgatgaggt   1680
gtatggtgac ttaccccatc cggatgaagt aaatagcaat gaaacgttgc cgctatttac   1740
ggaaatgaca gcatacgcgc caagtagtcc atattctgct tctaaagctt ccagcgatca   1800
tttggttcgc gcatggaaac gtacttatgg tttaccgacc attgtgacta attgctcgaa   1860
caactatggt ccttatcatt tcccggaaaa gcttattcca ctggttattc ttaatgcact   1920
ggaaggtaag gcattaccta tttatggcaa aggagatcag atccgcgact ggttgtatgt   1980
agaggatcat gctcgagcgt tatataccgt cgtaaccgaa ggtaaagcgg gcgaaactta   2040
taacattggt ggacacaacg aaaagaaaaa catcgacgta gtgttcacta tttgtgattt   2100
gttggatgag atagtcccga aagagaaatc ttatcgtgag caaattacct atgttgctga   2160
tcgcccaggg catgatcgcc gttatgcaat tgatgccgat aaaattagcc gcgaattggg   2220
ctggaaacca caggaaacgt ttgagagcgg gattcgtaaa actgtggaat ggtatctgtc   2280
caatacaaaa tgggttgata atgtgaaaag tggtgcctat caatcgtgga ttgaacagaa   2340
ctatgggggc cgccactaat gaatatcctc ctttttggca aaacagggca ggttggttgg   2400
gaactacagc gtgctctggc acctctgggt aatttgattg ctcttgatgt tcactccact   2460
gattactgtg gtgattttag taaccctgaa ggtgtggctg aaaccgttag aagcattcgg   2520
cctgatatta ttgtcaacgc agccgctcac accgcagtag acaaagcaga atcagaaccg   2580
gagtttgcac aattactgaa cgcgacgagt gtcgaagcga tcgcgaaagc agccaatgaa   2640
gtcggcgctt gggttattca ctactctact gactacgtat ttccggggac cggtgaaata   2700
ccatggcagg aggaggatgc aaccgcaccg ctaaatgttt acggtgaaac caagttagca   2760
ggagaaaaag cattacaaga gcattgtgcg aagcacctta ttttccggac cagctgggtc   2820
tatgcaggta aaggaaataa cttcgccaaa acgatgttgc gtctggcaaa agagcgtgaa   2880
gaattagccg ttattaatga tcagtttggt gcgccaactg gcgcagagtt gctggctgat   2940
tgtacggcac atgccattcg tgtggcactg aataaaccgg aagtcgcagg tttgtaccat   3000
ctggtagcca gtggtaccac aacctggcac gattatgctg cgctggtttt tgaagaggcg   3060
cgcaaagcag gcattcccct tgcactcaac aagctcaacg cagtaccaac aacagtctat   3120
cctacaccag ctcgtcgtcc acataactct cgccttaata cagaaaaatt tcagcagaac   3180
tttgcgcttg tcttgcctga ctggcaggtt ggtgtgaaac gcatgctcaa cgaattattt   3240
acgactacag caatttaata gtttttgcat cttgttcgtg atggtggaac aagatgaatt   3300
aaaaggaatg atggaatgaa tacgcgtaaa ggtattattt tagcgggtgg ttctggtaca   3360
cgtctttatc ctgtgactat ggctgtcagt aaacagctgt taccgattta tgataaaccg   3420
atgatctatt acccgctctc tacactgatg ttggcgggta ttcgcgatat tttgattatc   3480
agcacgccac aggatactcc tcgttttcaa caactgctgg gtgatgggag ccagtggggg   3540
ctaaatcttc actacaaagt gcaaccgagt ccggatggtc ttgcgcaggc atttatcatc   3600
ggtgaagagt ttatcggtgg tgatgattgt gctttggtac ttggtgataa tatcttctac   3660
ggtcacgacc tgcctaagtt aatggatgcc gctgttaaca aagaaagtgg tgcaacggta   3720
```

```
tttgcctatc acgttaatga tcctgaacgc tatggtgtcg ttgagtttga taaaaacggt   3780
actgcaatca gcctggaaga aaaaccgtta caaccaaaaa gtaattatgc ggtaaccggg   3840
ctttatttct atgataacta cgttgtggaa atggcgaaaa atcttaagcc ttctgcccgc   3900
ggtgaactgg aaattaccga tattaaccgt atctatatgg aacaggggca tttatctgtt   3960
gccatgatgg gacgtggata tgcctggctg gacacgggga cacatcaaag tcttattgaa   4020
gcaagcaact tcattgccac cattgaagag cgccagggct tgaaagtttc ctgcccggaa   4080
gaaattgctt accgtaaagg gtttattgat gctgagcagg tgaaagtatt agctaaaccg   4140
ctgaaaaaaa atgcttatgg tcagtatctg ctaaaaatga ttaaaggtta ttaataaaat   4200
gaatgttatt aaaacagaaa ttccagatgt actgattttt gaaccgaaag tttttggtga   4260
tgagcgtggt ttctttatgg aaagctttaa tcagaaagtt ttcgaagagg ctgtagggcg   4320
gaaggttgaa tttgttcagg ataatcattc taaatcgtgt aaaggtgtac ttagaggttt   4380
acactttcag cttcctccct ttgagcaggc aaaattagta aggtgtatag ttggcgaggt   4440
atttgatgtt gcagtagaca ttagacctaa ttctgaaaca tttggttcat gggttggagt   4500
aactctttcg tcagaaaata aaaggcagct atggattcca gaaggattcg cccatggttt   4560
tttaacttta agtgatattg cagagtttgt ttataaaact aacaactatt attctttaaa   4620
tcatgaaagg ggagtcattt ggaacgatga ggaaattaac attgcctggc cctctcaatc   4680
agagaagatt ctgtcacaga aagatattaa tttaccatca tttagatttg ttcaaatgtt   4740
tagcaagtag tgttatcttt acactgcaca tagtcatcat tttttatgct ttaagtaaat   4800
tatattgcac atctataaca caaagcgcaa taatatttcg acctgatgaa ggtttgtggt   4860
tatttatctt tctaggcgtt ttttatgact aaaatagttg tggtttctac agctccaata   4920
ttcccgacaa ataatgggta caaaagttct gtattaggaa gaattgatga gttattaaat   4980
gaggataatg aggtcgtttt gattgaaata aaccttgaaa atgttacgga aaagaaagat   5040
gaattaatac caacaagatt taataatatt caaagatatg aagtaaaaaa aatatctaga   5100
tcatttattg ccgagttaca aatattattt gatatcagaa ctcggtatga acaattattt   5160
tcttctgctg acattagaga taacataaaa aagataattg atttagaaaa accttctatt   5220
attattgctg agtctatatg ggcgttgcaa gcattgccta ttgaaattag tgcgagaata   5280
cactgtgtta ttcatgatgt ggcaactgat ttctttaaag aaatgtttgt atctcataat   5340
gaggttgtac gaaaaatttt gtttttttaat gattacctaa agttgaaaat tactgaagaa   5400
aatattatca aacgtttgag agttgagcaa tttatctttc tgacagaaga agataaatgt   5460
tggtataaaa caagatacaa tattgatgag ggttgttgtt ccttagcgag caatcatctt   5520
tatgtagaaa agattaagag aactatcaat ttccaaaccc ctttcctgct tattcccggt   5580
agcattgaat tttcacaaaa tttttacggc ttaaattggt ttataaaaaa tatatatcct   5640
ggattaaata ggaaaataag aatagttgta acaggaaagg catcagataa aaaaataaag   5700
atgttaaact gtggagagga aattaccttt acgggagagc ttgacttttc cacatataat   5760
aaacttagct caacatgctt gtgtgttatt gcaccgatta caacgggcac tggaattaaa   5820
ataaaaatat tagaagctgt acaaaaaggt attcctgtac ttacaacaaa atttgcttca   5880
aaaggaatat gttccgattt atgtttttat tgcgaggagg atactgacac aaactttgtc   5940
aatttaatta acagttttct tgaaacgaca ttaagagtcc aagaatgaat ttattgcttt   6000
tttcagtcct tgcgtttggt ttaatattgg ctttggccca taataataaa agtggagata   6060
```

```
ttaacgcata cttaatgttt tttctcgtgg tcctaatggt attaatatca gggctgcgta   6120
tgaatgatag tgattatatc gaatacagga aaatgtataa tgaagtgcct attttatgtg   6180
actttagtct cgcatctata agagatatac atggggaggt aggctatcta ttcttatcat   6240
caatctttaa aactttatgc ttgccatttc aattatttct ttttttattt gctttttat    6300
cactcctgct tacatatttt tcattcagaa aaataagttt aataccgata ctatcgttag   6360
tttttatttt aagccatgct tttatagtta gagatttgat tcaaattagg gcaggattag   6420
ctgttagcat atcattatat tcaataatta aatttaaagg aaataaaagt ataattacag   6480
gagttttatt tgcttctttg attcattctg gggcgcttat tattgctctt tgttatcctt   6540
ttttcaaaaa aaaatacata acattaaaaa tgatgttgtt tttattttta gtgtcaatta   6600
ttttttctta tttgaatggg cttaatttat cgatacaact cttatctcaa tatagtttgc   6660
ttccaactgc aatttcgaat tatgttggtt gggaagaata tgattatcgg gtgagtatat   6720
ttactaatcc ggtttttatt aaaggtgttt ttttaattgt cttaatgcac aaatatgtac   6780
tttcagatat taaaaatgag aaaattatag tgctttataa cttatatgtt ttaggtgtat   6840
tagctatggt tgcattgagt gggatggcta ttctttcagg ccgtctttca tcctttctga   6900
cactaggtga aagcatttta attgtatatg ctctgttcta caaaagaaat acacctctgg   6960
cgtttctaat tttttctttt ttaacaattg tgcaattagg atatgatcta tttatttcta   7020
atgtgcatcc tgagcttact ctgattatat ttgggtgaat ctaagtgaaa aataataaaa   7080
taggcatact tatctctaaa atacaaaatc ttggacctgt gaatgtagta cgaggattga   7140
taaaagaaaa taaaaaatat gcttttactg tttttgttt aacaaatagc gtagataaaa    7200
atatatatga tgagttatgc tgtttaggag ccaaggttat attaatacca gatggtactt   7260
ggttcagcaa aattttattt gtgagaagtt ttttaaagga acatccacat aatatcttac   7320
attcacatgg gatcacggcc gatatgtttt cttactttct gaatggcgtg aaaatatcta   7380
ctattcacaa tagactagat gaggattata tcccattatt tggcgcggtt aaagggaatg   7440
ctatatatta tcttcatcgt tttatattac gaagatttaa tcatatcgtt gcttgctcag   7500
cagcggtcca atcaaaactg aaacaatcga aagtaaaaac taaaataacc accatccaga   7560
atgggattga tataactagg tttaagacac ttgagtctga taaaaaaaaa ttattgaggg   7620
aaaaacacgg atttgatagt gaaaaaagaa tatttatata ttgtggctcg ttatcattaa   7680
ggaaaaatat tgcttacctc ttggaacact tagccatcga agaaaatgat atatttttaa   7740
ttctaggtga tggtgaactt tttagatatt gtaaggataa atattctaaa gatttacggt   7800
atatatttat ggggaaagtt gaatgccctc ttgaatatta tcaattatca gatattttg    7860
tttccgcttc tttatcggaa gggctcccct tggcactatt agaagctgcc tctactgggt   7920
gctatttata tgttagcgat atagagcccc atagagaaat tgcatctcta ttaggagagg   7980
aaaatatttc tatgtttaaa attaaggatg gatcatataa ttatttgcaa cctaaaataa   8040
aaaaagctga ctataacgct ctttctgacg ataaacttta caatatatcc gataaaaaaa   8100
tgtcaaatct ttatgacaaa ctttttgttt ctttattaga gcagaggcac taatataatg   8160
atttatgttt cggtaatttc tcatggtcat ttcaaaactc ttaaggaatt aggagcagta   8220
tcaaaattaa ataatcacag cagaattaaa gttatcatca aagataattt aggagagagc   8280
gagcttttgg atttttgtca ggaaaacaaa ataacttatt taaggtctaa agagaaaaaa   8340
ggatttggag agaataataa tgaagttttt tcctctatat cctccttaat tactaaggaa   8400
gatttttttg tggttatgaa tcctgatata tatattgagt gctctgatct attagatgtc   8460
```

```
gtagatgagt gtggttcagc gaatgttaat ctagcaacga taaatttata cagggatttt   8520
gataaaaaaa catatgataa ctcagtaagg aaatttccct cggcaattga ttttttttatg   8580
tcatttttat ttaagaaaaa tgactgtgta gtaaataaga acaaaataac gaaaccaaca   8640
tatgttgatt gggctgcagg ttcttttcta atatttaatg ccttctttta ttcaaaactc   8700
aacggattca acgaaaagta ttttatgtat tgcgaagata ttgatatatg ttggcgagct   8760
aaaaaacact tcaatacttc agttttatac tatccatgct atgcagcaat tcatttggca   8820
caatttaaca atcgtaggat ttttagtaga catttcattt ggcatataaa aagtattatc   8880
cttttttttat tatataaaaa tggtatgctg cgttctagta agttgcttta atgctaatat   8940
tcttttaaga ggtgagaatg atacctgtta ttttggctgg tggttcggga agtcgcttgt   9000
ggccactttc acgagaaaag ttccccaagc agtttttaaa gttgactggc agtttgacaa   9060
tgttgcagtc aacattgtca cgtcttaata atttaaatgc tgatgattca atagttatat   9120
gcaacgaaga gcatagattt attgttgcag aacaattaag agagttaggc aaactttcaa   9180
ataacattat tcttgaaccc aaaggtcgta atacagcccc tgctataaca ctcgcagcat   9240
tagcagcaaa aagaaaattc gctgatgaag atccattgat tcttatttta gctgcagatc   9300
acaacatcca agacgaacat gttttctgtg aggcaattaa taaggcgtca tctttagcta   9360
gttatggaaa actagtgact tttggtatcg ttccattcaa acctgaaact gggtatggct   9420
atattcgtcg cggtgatgaa gtgcctgtag atgagcagca tgcggtggcc tttgaagtgg   9480
cgcagtttgt cgaaaaaccg aatctggaaa ccgcgcaggc ctatgtggca agcggcgaat   9540
attactggaa cagcggtatg ttcctgttcc gtgccggacg ctatctcgaa gaactgaaaa   9600
agtatcgtcc ggatattctc gatgcctgtg aaaaagcgat gagcgccgtc gatccggatc   9660
tcgattttat tcgtgtggat gaagaggcgt ttctcgcttg tccggaagag tcggtggatt   9720
acgcggtcat ggaatgcacg gcagatgccg ttgtggtgcc gatggatgcg ggctggagcg   9780
atgtcggttc ctggtcttca ttatgggaga tcagcgccca caccgccgag ggcaacgttt   9840
gccacggcga tgtgattaat cacaaaactg aaaacagcta tgtgtacgcc gaatctggcc   9900
tggtcaccac cgtcggggtg aaagatttgg tggtagtgca gaccaaagat gcagtgctga   9960
ttgccgaccg taatgcggtg caggatgtga agaaagtggt cgagcagatc aaagctgatg  10020
gtcgccatga gcatcgggtg catcgcgaag tgtatcgtcc gtggggcaaa tatgactcta  10080
tcgacgcggg cgaccgctac caggtgaaac gcatcaccgt gaaaccgggc gaaggtttgt  10140
cggtacagat gcattatcat cgcgcggaac actgggtggt tgtcgcggga acggcaaaag  10200
tcactatcaa cggtgatatc aaactgcttg gtgaaaacga gtccatttat attccgctgg  10260
gggcgatgca ctgcctggaa aacccgggga aaatagattt agaattaatt gaagttcgct  10320
ctggtgcata tcttgaagaa gatgatgtta ttagatgtta tgatcgctat ggacgaaagt  10380
aatatataat aattatttca gaattagaaa tgataattat aagttttcgt ctggataaac  10440
aatagatagt atgggttgga aaatatgagt tctttaactt gttttaaagc ttacgacatt  10500
cgcgggaaat taggtgaaga actgaatgaa gatatcgcct ggcgcattgg tcgcgcctat  10560
ggcgaatttc tcaaaccgaa aaccattgtg ttaggcggtg atgtccgtct caccagcgaa  10620
accttaaaac tggcgctggc aaaaggttta caggatgcgg gcgtcgatgt gctggatatt  10680
ggcatgtccg gcaccgaaga gatttatttc gccacgttcc atctcggcgt ggatggcggc  10740
attgaagtta ccgccagcca taatccgatg gattacaacg gcatgaagct ggtgcgcgaa  10800
```

```
ggggctcgcc cgatcagcgg tgataccgga ctgcgcgacg tccagcgtct ggcagaagct  10860
aacgactttc ctcccgtcga tgaaaccaaa cgcggtcgct atcagcaaat caatctgcgt  10920
gacgcttacg ttgatcacct gttcggttat atcaatgtca aaaaccttac gccgctcaag  10980
ctggtgatca actccgggaa tggcgcagcg ggtccggtgg tggacgctat cgaagcccgc  11040
tttaaagccc tcggcgcacc ggtggagtta atcaaagtgc ataacacgcc ggacggcaat  11100
ttccccaacg gtattcctaa cccgttgctg ccggaatgtc gcgacgacac ccgcaatgcg  11160
gtcatcaaac acggcgcgga tatgggcatt gcctttgatg gcgattttga ccgctgtttc  11220
ctgtttgacg aaaaagggca gtttattgag ggctactaca ttgtcggcct gctggcagaa  11280
gcgttcctcg aaaaaaatcc cggcgcgaag atcatccacg atccacgtct ctcctggaac  11340
accattgatg tggtgacggc cgcgggcggc acgccggtga tgtcgaaaac aggacacgcc  11400
tttattaaag aacgtatgcg caaggaagac gccatctacg gtggcgaaat gagcgctcac  11460
cattacttcc gcgatttcgc ttactgtgac agcggcatga tcccgtggct gctggtcgcc  11520
gaactggtgt gcctgaaagg aaaaacgctg ggcgaactgg tgcgcgaccg gatggcggcg  11580
tttccggcaa gcggtgagat caacagaaaa ctggcgcacc ctgttgaggc gattaaccgc  11640
gtggaacagc attttagccg tgaggtgctg gcggtggatc gcaccgatgg catcagcatg  11700
acctttgccg actggcgctt taacctgcgc tcttccaaca ccgaaccggt ggtgcgcctg  11760
aatgtggaat ctcgcggtga tgttcaggtt atggtaatcc atactcaaga aatattatca  11820
attttgacgt cataaagaat aagccctgac aagttagggc ttaattaata tatatttttt  11880
ttgaattggg gatttgtggt aagattttta atatgttatt taatgtggtt gaattaatgt  11940
tgactggaaa ataataatga gaacgaaaaa agcattacac aactttaaag ttgatttatt  12000
aattactttt ttattggttt tgctagggtt ttatattcga actgtttttg tttcaaaaat  12060
gggaagtgat attactggag tgatgttact attcacacag ttgacagcat atctcaattt  12120
ggcagaatta ggtattggaa ttgcagctgc cagcgtatta tataaaccgc tcagcgagaa  12180
tgaatacaat aaaataactt acataaatatc tttgctctca gtcatataca aatatatatt  12240
tgtgtttgtt ttgattcttg gcgttgttat aggtatctgt atttattact ttattgattc  12300
tgtaaaggtt gtaaatggcg tttttttata ttgggctttg ttcgttttta atacatcgtt  12360
gacatatagt tatgctaaat actccacatt attaactgct aatcagcggt actcagcagt  12420
aagaaaaatt caaggtggcg gaaaagttat aataattgta tttcagatat taattttgtg  12480
ctttacgcaa agtttcatac tttatttgtt agttgagact ttaggtattt tttctcaata  12540
tttgattttt aaaaaaataa ttgggaacgg aaatcaatat ctcagtaatg aggttttact  12600
tattgaaagc gataaacttt tgataaaaaa agaattaaaa ataagaataa aaaatatgtt  12660
cttccataaa ataggtgctg tgcttgtcct taatacagac tacctgcttg tatcaaagtt  12720
tctgacatta agttatgtga caatttttgg cagctatatg atggtatttc agatagtaac  12780
tgttttgatg tcaagttttg ttaatgctat tactgcagga atgggtaatt acttaattaa  12840
taaaagtaat ttagaaatta aggaaattac acgtcaattt tatgtgatat ttatcgcctt  12900
tgcaacattc atatcactaa atatgttttt tcttgttaat gattttatcg caaaatggat  12960
aggtgttaat tatacattaa gtaacaccct agttgcatta atgattgtta acgtattcat  13020
tagtgttgtc agggtacctt ctgatatatt aaaaaacgca agtggacatt ttggtgatat  13080
ttattatcca ttattagaag gtgtgctgaa tattacgata tccatcattt tggctatcat  13140
tattggatta cctggcatta ttatagggac aatagtatct aacttaatag taataatgct  13200
```

-continued

```
tgcgaaacca ttatatcttt actctaagtt atttaatctt agaaatccga cgagggttta  13260
ttttgaattt atttctcggc ctatgttata ttcattatgt gtgattgggg tgagctattt  13320
attgcgcgat gaaatatatt catttaaagt aagtacatgg ttggatttta ttaacaagct  13380
actcttagtc tctactccta gcatattggt aatatgtgct attttctcta cggatagtga  13440
ctttagatta tttttcagaa aaattatata tgtgattatg aagaaataaa aatttcgaaa  13500
atgtattaat cgaaattatg caacgagctt tatttttata aatgatatgt gatcttttcg  13560
cgaataggag taaggatccg tgtaggctgg agctgcttcg aagttcctat actttctaga  13620
gaataggaac ttcggaatag gaactaagga ggatattcat atggataaag ccgtaagcat  13680
ataagcatgg ataagctatt tatactttaa taagtacttt gtatacttat ttgcgaacat  13740
tccaggccgc gagcattcag cgcggtgatc acacctgaca ggagtatgta atgtccaagc  13800
aacagatcgg cgtagtcggt atggcagtga tgggacgcaa ccttgcgctc aacatcgaaa  13860
gccgtggtta taccgtctct attttcaacc gttcccgtga gaagacggaa gaagtgattg  13920
ccgaaaatcc aggcaagaaa ctggttcctt actatacggt gaaagagttt gtcgaatctc  13980
tggaaacgcc tcgtcgcatc ctgttaatgg tgaaagcagg tgcaggcacg gatgctgcta  14040
ttgattccct caaaccatat ctcgataaag gagacatcat cattgatggt ggtaacacct  14100
tcttccagga cactattcgt cgtaatcgtg agctttcagc agagggcttt aacttcatcg  14160
gtaccggtgt ttctggcggt gaagaggggg cgctgaaagg tccttctatt atgcctggtg  14220
gccagaaaga agcctatgaa ttggtagcac cgatcctgac caaaatcgcc gccgtagctg  14280
aagacggtga accatgcgtt acctatattg gtgccgatgg cgcaggtcac tatgtgaaga  14340
tggttcacaa cggtattgaa tacggcgata tgcagctgat tgctgaagcc tattctctgc  14400
ttaaaggtgg cctgaacctc accaacgaag aactggcgca gacctttacc gagtggaata  14460
acggtgaact gagcagttac ctgatcgaca tcaccaaaga tatcttcacc aaaaaagatg  14520
aagacggtaa ctacctggtt gatgtgatcc tggatgaagc ggctaacaaa ggtaccggta  14580
aatggaccag ccagagcgcg ctggatctcg gcgaaccgct gtcgctgatt accgagtctg  14640
tgtttgcacg ttatatctct tctctgaaag atcagcgtgt tgccgcatct aaagttctct  14700
ctggtccgca agcacagcca gcaggcgaca aggctgagtt catcgaaaaa gttcgtcgtg  14760
cgctgtatct gggcaaaatc gtttcttacg cccagggctt ctctcagctg cgtgctgcgt  14820
ctgaagagta caactgggat ctgaactacg gcgaaatcgc gaagattttc cgtgctggct  14880
gcatcatccg tgcgcagttc ctgcagaaaa tcaccgatgc ttatgccgaa aatccacaga  14940
tcgctaacct gttgctggct ccgtacttca agcaaattgc cgatgactac cagcaggcgc  15000
tgcgtgatgt cgttgcttat gcagtacaga acggtattcc ggttccgacc ttctccgcag  15060
cggttgccta ttacgacagc taccgtgctg ctgttctgcc tgcgaacctg atccaggcac  15120
agcgtgacta ttttggtgcg catacttata agcgtattga taaagaaggt gtgttccata  15180
ccgaatggct ggattaa                                                 15197
```